US012758641B2

(12) United States Patent
Basch et al.

(10) Patent No.: US 12,758,641 B2
(45) Date of Patent: Oct. 13, 2026

(54) BRM TARGETING COMPOUNDS AND ASSOCIATED METHODS OF USE

(71) Applicant: Prelude Therapeutics Incorporated, Wilmington, DE (US)

(72) Inventors: Corey Howard Basch, Delmar, DE (US); Song Mei, Wilmington, DE (US); Liang Liu, Hockessin, DE (US); Artem Shvartsbart, Kennett Square, PA (US); Andrew Paul Combs, Kennett Square, PA (US); John A. Rose, Newark, DE (US); Klare L. Bersch, Glen Mills, PA (US); Sina Rezazadeh, Newark, DE (US); Vijayarajan Devannah, Newark, DE (US); Danielle Beam Roth, Wilmington, DE (US)

(73) Assignee: Prelude Therapeutics Incorporated, Wilmington, DE (US)

( * ) Notice: Subject to any disclaimer, the term of this patent is extended or adjusted under 35 U.S.C. 154(b) by 345 days.

(21) Appl. No.: 18/467,790

(22) Filed: Sep. 15, 2023

(65) Prior Publication Data

US 2024/0165244 A1 May 23, 2024

Related U.S. Application Data

(60) Provisional application No. 63/375,739, filed on Sep. 15, 2022.

(51) Int. Cl.
*A61K 47/55* (2017.01)
*A61K 47/54* (2017.01)

(52) U.S. Cl.
CPC ............ *A61K 47/55* (2017.08); *A61K 47/545* (2017.08)

(58) Field of Classification Search
CPC .............................. A61K 47/55; A61K 47/545
See application file for complete search history.

(56) References Cited

U.S. PATENT DOCUMENTS

| | | | |
|---|---|---|---|
| 3,657,744 | A | 4/1972 | Ersek |
| 4,739,762 | A | 4/1988 | Palmaz |
| 4,992,445 | A | 2/1991 | Lawter |
| 5,001,139 | A | 3/1991 | Lawter |
| 5,023,252 | A | 6/1991 | Hseih |
| 5,040,548 | A | 8/1991 | Yock |
| 5,061,273 | A | 10/1991 | Yock |
| 5,195,984 | A | 3/1993 | Schatz |
| 5,292,331 | A | 3/1994 | Boneau |
| 5,451,233 | A | 9/1995 | Yock |
| 5,496,346 | A | 3/1996 | Horzewski |
| 5,674,278 | A | 10/1997 | Boneau |
| 5,879,382 | A | 3/1999 | Boneau |
| 6,344,053 | B1 | 2/2002 | Boneau |

FOREIGN PATENT DOCUMENTS

WO WO-2022099117 A1 * 5/2022 ........... C07D 487/14

* cited by examiner

*Primary Examiner* — Kamal A Saeed
*Assistant Examiner* — Jalisa Holmes Ferguson
(74) *Attorney, Agent, or Firm* — BakerHostetler

(57) ABSTRACT

The disclosure is directed to compounds of Formula I (I)

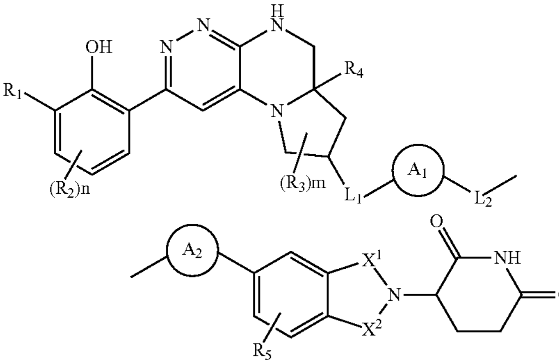

Pharmaceutical compositions comprising compounds of Formula I, as well as methods of their use and preparation, are also described.

66 Claims, No Drawings

BRM TARGETING COMPOUNDS AND ASSOCIATED METHODS OF USE

CROSS REFERENCE TO RELATED APPLICATIONS

This application claims the benefit of U.S. Provisional Application Nos. 63/375,739, filed Sep. 15, 2022, the entirety of which is incorporated by reference herein.

TECHNICAL FIELD

The description provides bifunctional compounds comprising a target protein binding moiety and a E3 ubiquitin ligase binding moiety, and associated methods of use. The bifunctional compounds are useful as modulators of targeted ubiquitination, especially with respect to Switch/Sucrose Non-Fermentable (SWI/SNF)-Related, Matrix-Associated, Actin-Dependent Regulator of Chromatin, Subfamily A, Member 2 (SMARCA2) (i.e., BRAHMA or BRM), which are degraded and/or otherwise inhibited by bifunctional compounds according to the present disclosure.

BACKGROUND

The human SWItch/Sucrose Non-Fermentable (SWI/SNF) complexes are ATP-dependent chromatin remodelers. These large complexes play important roles in essential cellular processes, such as transcription, DNA repair and replication by regulating DNA accessibility.

Mutations in the genes encoding up to 20 canonical SWI/SNF subunits are observed in nearly 20% of all human cancers with the highest frequency of mutations observed in rhabdoid tumors, female cancers (including ovarian, uterine, cervical and endometrial), lung adenocarcinoma, gastric adenocarcinoma, melanoma, esophageal, and renal clear cell carcinoma.

SMARCA2 (BRM) and SMARCA4 (BRG1) are the subunits containing catalytic ATPase domains and they are essential for the function of SWI/SNF in perturbation of histone-DNA contacts, thereby providing access points to transcription factors and cognate DNA elements that facilitate gene activation and repression.

SMARCA2 and SMARCA4 shares a high degree of homology (up to 75%). SMARCA4 is frequently mutated in primary tumors (i.e., deleted or inactivated), particularly in lung cancer (12%), melanoma, liver cancer and pancreatic cancer. SMARCA2 is one of the top essential genes in SMARCA4-mutant (deleted) cancer cell line. This is because SMARCA4 deleted cancer cells exclusively rely on SMARCA2 ATPase activity for their chromatin remodeling activity for cellular functions such as cell proliferation, survival and growth. Thus, targeting SMARCA2 may be promising therapeutic approach in SMARCA4-related or deficient cancers (genetic synthetic lethality).

Previous studies have demonstrated the strong synthetic lethality using gene expression manipulation such as RNAi; downregulating SMARCA2 gene expression in SMARCA4 mutated cancer cells results in suppression of cancer cell proliferation. However, SMARCA2/4 bromodomain inhibitors (e.g., PFI-3) exhibit none to minor effects on cell proliferation inhibition [Vangamudi et al. Cancer Res 2015]. This phenotypic discrepancy between gene expression downregulation and small molecule-based approach lead us to investigating protein degradation bispecific molecules in SMARCA4 deficient cancers.

SMARCA2 is also reported to play roles in multiple myeloma expressing t(4;14) chromosomal translocation [Chooi et al. Cancer Res abstract 2018]. SMARCA2 interacts with NSD2 and regulates gene expression such as PRL3 and CCND1. SMARCA2 gene expression downregulation with shRNA reduces cell cycle S phase and suppresses cell proliferation of t(4;14) MINI cells.

Therapeutic compounds that inhibit SMARCA2 and/or SMARCA4 are needed.

SUMMARY

The present disclosure is directed to compounds of Formula (I):

(I)

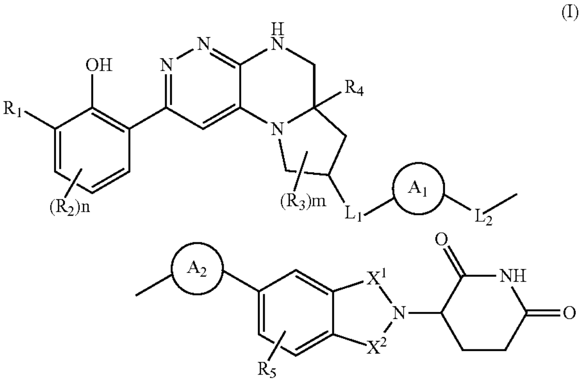

or a pharmaceutically acceptable salt thereof; wherein $R_1$ is halo, $C_{1-6}$ alkyl, or haloalkyl;

each $R_2$ is independently H, D, or F;

each $R_3$ is independently H, D, $C_{1-6}$ alkyl, haloalkyl, $C_{3-6}$ heterocycloalkyl or $C_{3-6}$ cycloalkyl;

n is 1, 2 or 3;

m is 1, 2, 3, or 4;

$R_4$ is H, D, $C_{1-6}$ alkyl, $C_{1-6}$ alkoxyalkyl, $C_{3-6}$ cycloalkyl, or $C_{1-6}$ haloalkyl;

$R_5$ is H, D, or F;

$L_1$ is a bond, O, S, S(O), $SO_2$, $NR_3$, $C(R_3)_2$ or CO;

$L_2$ is a bond, O, S, S(O), $SO_2$, $NR_3$, $C(R_3)_2$ or CO;

ring $A_1$ is a 6 membered aryl group or a 5-6 membered heteroaryl group;

ring $A_2$ is a 3-7 membered cycloalkyl group or a 4-7-membered heterocycloalkyl group;

$X_1$ is $CH_2$, CO, CH═CH (when $X_2$═CO), or N═CH (when $X_2$═CO);

$X_2$ is $CH_2$, CO, CH═CH (when $X_1$═CO), or N═CH (when $X_1$═CO);

wherein the alkyl group, haloalkyl group, cycloalkyl group, alkoxyalkyl group, aryl group, heteroaryl group or heterocycloalkyl group is optionally substituted by one or more $R^f$ groups;

each $R^f$ is independently D, oxo, halogen, $C_1$-$C_8$ alkoxy, $C_1$-$C_8$ alkyl, $C_{1-6}$ haloalkyl, $C_{1-6}$ haloalkoxy, —OH, —CN, —$NO_2$, —$C_2$-$C_6$ alkenyl, —$C_2$-$C_6$ alkynyl, $C_{6-10}$ aryl, $C_{5-12}$ heteroaryl, $C_{3-8}$ cycloalkyl, $C_{3-8}$ cycloalkenyl, $C_{3-8}$ heterocycloalkyl, $C_{3-8}$ heterocycloalkenyl, —$OR^a$, —$SR^a$, —$NR^cR^d$, —$NR^aR^c$, —$C(O)R^b$, —$OC(O)R^b$, —C(O)OR, —$C(O)NR^cR^d$, —$S(O)R^b$, —$S(O)_2NR^cR^d$, —$S(O)({=}NR)R^b$, —$SF_5$, —$P(O)R^bR^b$, —$P(O)R^cR^d$, —$P(O)(OR^b)(OR^b)$, —$B(OR^c)(OR^d)$, —$S(O)_2R^b$, —$C(O)NR^bOR$, —$S(O)_2$ OR, —$OS(O)_2OR$, or —$OPO(OR^b)(OR^b)$; wherein said $C_1$-$C_8$ alkyl is optionally substituted by 1-6 groups selected from D, halogen, —OH, —CN, —$OR^a$, —$SR^a$, —$NR^aR^d$, or $NR^cR^d$;

each $R^a$ is independently H, D, —$C(O)R^b$, —$C(O)OR^c$, —$C(O)NR^cR^d$, —$C({=}NR)NR^cR^d$, —$C({=}NOR^b)NR^cR^d$, —$C({=}NCN)NR^bR^c$, —$P(OR^c)_2$, —$P(O)R^cR^b$, —$P(O)R^cR^d$, —$P(O)OR^cOR^b$, —$S(O)R^b$, —$S(O)NR^cR^d$, —$S(O)_2R^b$, —$S(O)_2NR^cR^d$, $SiR_3$, —$C_1$-$C_{10}$ alkyl, —$C_2$-$C_{10}$ alkenyl, —$C_2$-$C_{10}$ alkynyl, $C_{6-10}$ aryl, $C_{3-8}$ cycloalkyl, $C_{3-8}$ cycloalkenyl, $C_{5-12}$ heteroaryl, $C_{3-8}$ heterocycloalkyl, or $C_{3-8}$ heterocycloalkenyl;

each $R^b$, is independently H, D, —$C_1$-$C_6$ alkyl, —$C_2$-$C_6$ alkenyl, —$C_2$-$C_6$ alkynyl, $C_{6-10}$ aryl, $C_{3-8}$ cycloalkyl, $C_{3-8}$ cycloalkenyl, $C_{5-12}$ heteroaryl, $C_{3-8}$ heterocycloalkyl, or $C_{3-8}$ heterocycloalkenyl; and each $R^c$ or $R^d$ is independently H, D, —$C_1$-$C_{10}$ alkyl, —$C_2$-$C_6$ alkenyl, —$C_2$-$C_6$ alkynyl, —$OC_1$-$C_6$alkyl, —O-cycloalkyl, $C_{6-10}$ aryl, $C_{5-12}$ heteroaryl, $C_{3-8}$ cycloalkyl, $C_{3-8}$ cycloalkenyl, $C_{3-8}$ heterocycloalkyl, or $C_{3-8}$ heterocycloalkenyl;

or $R^c$ and $R^d$, together with the atom to which they are both attached, form a monocyclic or multicyclic heterocycloalkyl, or a monocyclic or multicyclic heterocycloalkenyl group.

Stereoisomers of the compounds of Formula I, and the pharmaceutical salts and stereoisomers thereof, are also contemplated, described, and encompassed herein. Methods of using compounds of Formula I are described, as well as pharmaceutical compositions including the compounds of Formula I.

DETAILED DESCRIPTION OF ILLUSTRATIVE EMBODIMENTS

Unless otherwise defined, all technical and scientific terms used herein have the same meaning as commonly understood by one of ordinary skill in the art to which this disclosure pertains. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range.

Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (e.g., to at least one) of the grammatical object of the article unless the context clearly indicates otherwise. By way of example, "an element" means one element or more than one element.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are co-administered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder.

The term "ubiquitin ligase" refers to a family of proteins that facilitate the transfer of ubiquitin to a specific substrate protein, targeting the substrate protein for degradation. For example, an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

As used herein, "Cereblon (CRBN) E3 Ubiquitin Ligase" refers to the substrate recognition subunit of the Cullin RING E3 ubiquitin ligase complexes. CRBN are one of the most popular E3 ligases recruited by bifunctional Proteolysis-targeting chimeras (PROTACs) to induce ubiquitination and subsequent proteasomal degradation of a target protein (Maniaci C. et al., *Bioorg Med Chem.* 2019, 27(12): 2466-2479).

As used herein, the term "alkyl", by itself or as part of another substituent, means, unless otherwise stated, a straight or branched chain hydrocarbon radical having up to twelve carbon atoms. In some embodiments, the number of carbon atoms is designated (i.e., $C_1$-$C_8$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. Alkyl groups may be optionally substituted as provided herein. In some embodiments, the alkyl group is a $C_1$-$C_6$ alkyl; in some embodiments, it is a $C_1$-$C_4$ alkyl.

When a range of carbon atoms is used herein, for example, $C_1$-$C_6$, all ranges, as well as individual numbers of carbon atoms are encompassed. For example, "$C_1$-$C_3$" includes $C_1$-$C_3$, $C_1$-$C_2$, $C_2$-$C_3$, $C_1$, $C_2$, and $C_3$.

The term "optionally substituted", as used in combination with a substituent defined herein, means that the substituent may, but is not required to, have one or more hydrogens replaced with one or more suitable functional groups or other substituents as provided herein. For example, a substituent may be optionally substituted with one or more of: halo, cyano, $C_{1-6}$ alkyl, $C_{3-6}$ cycloalkyl, $C_{2-6}$ alkenyl, $C_{2-6}$ alkynyl, halo($C_{1-6}$)alkyl, $C_{1-6}$ alkoxy, halo($C_{1-6}$ alkoxy), $C_{1-6}$ alkylthio, $C_{1-6}$ alkylamino, $NH_2$, NH($C_{1-6}$ alkyl), N($C_{1-6}$ alkyl)$_2$, NH($C_{1-6}$alkoxy), N($C_{1-6}$ alkoxy)$_2$, C(O)NH$C_{1-6}$ alkyl, C(O)N($C_{1-6}$ alkyl)$_2$, C(O)$NH_2$, C(O)$C_{1-6}$ alkyl, C(O)$_2$$C_{1-6}$ alkyl, NHCO($C_{1-6}$ alkyl), N($C_{1-6}$ alkyl)CO ($C_{1-6}$ alkyl), S(O)$C_{1-6}$ alkyl, S(O)$_2$$C_{1-6}$ alkyl, oxo, 6-12 membered aryl, benzyl, pyridinyl, pyrazolyl, thiazolyl, isothiazolyl, or other 5 to 12 membered heteroaryl groups. In some embodiments, each of the above optional substituents are themselves optionally substituted by one or two groups.

The term "optionally substituted —$CH_2$—," refers to "—$CH_2$—" or substituted —$CH_2$—." A substituted —$CH_2$— may also be referred to as —CH(substituent)- or —C(substituent)(substituent)-, wherein each substituent is independently selected from the optional substituents described herein.

The term "cycloalkyl" as used herein refers to a 3-12 membered cyclic alkyl group, and includes bridged and spirocycles (e.g., adamantine). Cycloalkyl groups may be fully saturated or partially unsaturated. The term "cycloalkyl" also includes multiple condensed ring systems (e.g., ring systems comprising 2, 3 or 4 rings) wherein a single cycloalkyl ring (as defined above) can be condensed with one or more groups selected from heterocycles, carbocycles, aryls, or heteroaryls to form the multiple condensed ring system. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a cycloalkyl) can be at any position of the cycloalkylic ring. Examples of cycloalkyl groups include cyclopropyl, cyclobutyl, cyclopentyl, cycloheptyl, cyclohexyl, cycloheptyl, cyclooctyl, indenyl, bicyclo[2.2.1]heptanyl, bicyclo[3.1.1]heptanyl, bicyclo[4.1.0]heptanyl, spiro[3.3]heptanyl, and spiro[3.4]octanyl. In some embodiments, the cycloalkyl group is a 3-7 membered cycloalkyl.

The term "cycloalkenyl" when used alone or as part of a substituent group refers to monocyclic or multicyclic, partially saturated ring structure having from 3 to 10 carbon atoms ("$C_3$-$C_{10}$"), preferably from 3 to 6 carbon atoms ("$C_3$-$C_6$"). Cycloalkenyl groups of the disclosure include monocyclic groups, as well as multicyclic groups such as bicyclic and tricyclic groups. In those embodiments having at least one multicyclic cycloalkenyl group, the cyclic groups can share one common atom (i.e., spirocyclic). In other embodiments having at least one multicyclic cycloalkenyl group, the cyclic groups share two common atoms (e.g., fused or bridged). The term —$C_3$-$C_6$ cycloalkenyl refers to a cycloalkenyl group having between three and six carbon atoms. The cycloalkenyl group may be attached at any carbon atom of the partially saturated ring such that the result is a stable structure. Cycloalkenyl groups include groups in which the partially saturated ring is fused to an aryl group. Examples of cycloalkenyl groups include, for example, cyclopropenyl ($C_3$), cyclobutenyl ($C_4$), cyclopropenylmethyl ($C_4$), cyclopentenyl ($C_5$), cyclohexenyl ($C_6$), 1-methylcyclopropenyl ($C_4$), 2-methylcyclopentenyl ($C_4$), adamantenyl ($C_{10}$), spiro[3.3]heptenyl, bicyclo[3.3.0]octenyl, indanyl, and the like. In some embodiments, cycloalkenyl groups of the disclosure are optionally substituted. Unless otherwise specified, in those embodiments wherein the cycloalkenyl group is substituted, the cycloalkenyl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy, —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$. In other embodiments, the cycloalkenyl group is optionally substituted by 1-6 groups selected from D, halogen, —OH, —CN, —$OR^a$, —$SR^a$, —$NR^aR^d$, or $NR^cR^d$; or the cycloalkenyl group is optionally substituted by one or more R groups.

The term "alkenyl" as used herein refers to $C_2$-$C_{12}$ alkyl group that contains at least one carbon-carbon double bond. In some embodiments, the alkenyl group is optionally substituted. In some embodiments, the alkenyl group is a $C_2$-$C_6$ alkenyl.

The term "akynyl" as used herein refers to $C_2$-$C_{12}$ alkyl group that contains at least one carbon-carbon triple bond. In some embodiments, the alkenyl group is optionally substituted. In some embodiments, the alkynyl group is a $C_2$-$C_6$ alkynyl.

The terms "alkoxy," "alkylamino" and "alkylthio", are used in their conventional sense, and refer to those alkyl groups attached to the remainder of the molecule via an oxygen atom ("oxy"), an amino group ("amino") or thio group. The term "alkylamino" includes mono- di-alkylamino groups, the alkyl portions can be the same or different.

The term "alkoxyalkyl" as used herein refers to a linear monovalent hydrocarbon radical of one to six carbon atoms or a branched monovalent hydrocarbon radical of three to six carbons substituted with an alkoxy group, as defined above, e.g., 2-methoxyethyl, 1-, 2-, or 3-methoxypropyl, 2-ethoxyethyl, and the like.

The terms "halo" or "halogen", by itself or as part of another substituent, means a fluorine, chlorine, bromine, or iodine atom.

The term "haloalkyl" as used herein refers to any alkyl radical having one or more hydrogen atoms replaced by a halogen atom.

The term "heteroalkyl" refers to an alkyl group in which one or more carbon atom has been replaced by a heteroatom selected from S, O, P and N. Exemplary heteroalkyls include alkyl ethers, secondary and tertiary alkyl amines, alkyl amides, alkyl sulfides, and the like. The group may be a terminal group or a bridging group. As used herein reference to the normal chain when used in the context of a bridging group refers to the direct chain of atoms linking the two terminal positions of the bridging group.

The term "aryl" as used herein refers to a single, all carbon aromatic ring or a multiple condensed all carbon ring system wherein at least one of the rings is aromatic. For example, in certain embodiments, an aryl group has 6 to 12 carbon atoms. Aryl includes a phenyl radical. Aryl also includes multiple condensed ring systems (e.g., ring systems comprising 2, 3 or 4 rings) having about 9 to 12 carbon atoms in which at least one ring is aromatic and wherein the other rings may be aromatic or not aromatic. Such multiple condensed ring systems are optionally substituted with one or more (e.g., 1, 2 or 3) oxo groups on any carbocycle portion of the multiple condensed ring system.

The rings of the multiple condensed ring system can be connected to each other via fused, spiro and bridged bonds when allowed by valency requirements. It is to be understood that the point of attachment of a multiple condensed ring system, as defined above, can be at any position of the aromatic ring. Non-limiting examples of aryl groups include, but are not limited to, phenyl, indenyl, naphthyl, 1, 2, 3,4-tetrahydronaphth-yl, and the like.

The term "heteroaryl" as used herein refers to a single aromatic ring that has at least one atom other than carbon in the ring, wherein the atoms are selected from the group consisting of oxygen, nitrogen and sulfur; "heteroaryl" also includes multiple condensed ring systems that have at least one such aromatic ring, which multiple condensed ring systems are further described below.

Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetra-hydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. A heteroaryl (a single aromatic ring or multiple condensed ring system) can also have about 5 to 12 or about 5 to 10 members within the heteroaryl ring. Multiple condensed ring systems may be optionally substituted with one or more (e.g., 1, 2, 3 or 4) oxo groups on the carbocycle or heterocycle portions of the condensed ring. The rings of a multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the heteroaryl ring. It is also to be understood that the point of attachment for a heteroaryl or heteroaryl multiple condensed ring system can be at any suitable atom of the heteroaryl ring including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclo-penta[1,2-c]pyrazole. In one embodiment the term "heteroaryl" refers to a single aromatic ring containing at least one heteroatom. For example, the term includes 5-membered and 6-membered monocyclic aromatic rings that include one or more heteroatoms. Non-limiting examples of heteroaryl include but are not limited to pyridyl, furyl, thiazole, pyrimidine, oxazole, and thiadiazole.

The term "heterocycloalkyl" when used alone or as part of a substituent group refers to any three to twelve membered monocyclic or multicyclic, saturated ring structure containing at least one heteroatom selected from the group consisting of O, N, P, B and S. Heterocycloalkyl groups of the disclosure include monocyclic groups, as well as multicyclic groups such as bicyclic and tricyclic groups. In those embodiments having at least one multicyclic heterocycloalkyl group, the cyclic groups can share one common atom (i.e., spirocyclic). In other embodiments having at least one multicyclic heterocycloalkyl group, the cyclic groups share two common atoms (e.g., fused or bridged). The term —$C_3$-$C_6$ heterocycloalkyl refers to a heterocycloalkyl group having between three and six carbon ring atoms. The heterocycloalkyl group may be attached at any heteroatom or carbon atom of the group such that the result is a stable structure. Examples of heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, azepanyl, diazepanyl, oxepanyl, dioxepanyl, azocanyl, diazocanyl, oxocanyl, dioxocanyl, azaspiro[2.2]pentanyl, oxaazaspiro[3.3]heptanyl, oxaspiro[3.3]heptanyl, dioxaspiro[3.3]heptanyl, 3-azabicyclo[3.1.0]hexanyl,

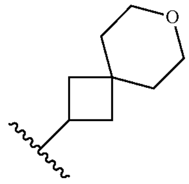, and the like. In some embodiments, heterocycloalkyl groups of the disclosure are optionally substituted. Unless otherwise specified, in those embodiments wherein the heterocycloalkyl group is substituted, the heterocycloalkyl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy, —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$. In other embodiments, the heterocycloalkyl group is optionally substituted by 1-6 groups selected from D, halogen, —OH, —CN, —OR$^a$, —SR$^a$, —NR$^a$R$^d$, or NR$^c$R$^d$; or the heterocycloalkyl group is optionally substituted by one or more R$^f$ groups.

The term "heterocycloalkenyl" when used alone or as part of a substituent group refers to any three to twelve membered monocyclic or multicyclic, partially saturated ring structure containing at least one heteroatom selected from the group consisting of O, N, P, B and S. Heterocycloalkenyl groups of the disclosure include monocyclic groups, as well as multicyclic groups such as bicyclic and tricyclic groups. In those embodiments having at least one multicyclic heterocycloalkenyl group, the cyclic groups can share one common atom (i.e., spirocyclic). In other embodiments having at least one multicyclic heterocycloalkenyl group, the cyclic groups share two common atoms (e.g., fused or bridged). The term —$C_3$-$C_6$ heterocycloalkenyl refers to a heterocycloalkenyl group having between three and six carbon atoms. The heterocycloalkenyl group may be attached at any heteroatom or carbon atom of the partially saturated ring such that the result is a stable structure. Heterocycloalkenyl groups include groups in which the partially saturated ring is fused to an aryl group, such as, for example isoindoline,

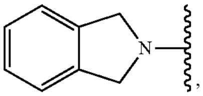 [SMILES: *N1Cc2ccccc2C1]

, or in which the partially saturated ring is fused to a heteroaryl group, such as, for example, 6,7-dihydro-5H-pyrrolo[3,4-b]pyridine,

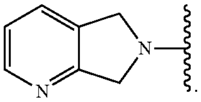 [SMILES: *N1Cc2cccnc2C1]

.

In some embodiments, heterocycloalkenyl groups of the disclosure are optionally substituted. Unless otherwise specified, in those embodiments wherein the heterocycloalkenyl group is substituted, the heterocycloalkenyl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy, —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$. In other embodiments, the heterocycloalkenyl group is optionally substituted by 1-6 groups selected from D, halogen, —OH, —CN, —OR$^a$, —SR$^a$, —NR$^a$R$^d$, or NR$^c$R$^d$; or the heterocycloalkenyl group is optionally substituted by one or more R$^f$ groups.

As used herein, the phrase "one or more R$^f$ groups" is meant to include 1, 2, 3, 4, 5, 6, 7 or 8 R$^f$ groups. In some embodiments, "one or more R$^f$ groups" is meant to include 1 R$^f$ group. In some embodiments, "one or more R$^f$ groups" is meant to include up to 2 R$^f$ groups. In some embodiments, "one or more R$^f$ groups" is meant to include up to 3 R$^f$ groups. In some embodiments, "one or more R$^f$ groups" is meant to include up to 4 R$^f$ groups. In some embodiments, "one or more R$^f$ groups" is meant to include up to 5 R$^f$ groups. In some embodiments, "one or more R$^f$ groups" is meant to include up to 6 R$^f$ groups. In some embodiments, "one or more R$^f$ groups" is meant to include up to 7 R$^f$ groups. In some embodiments, "one or more R$^f$ groups" is meant to include up to 8 R$^f$ groups.

As used herein, the term "heteroatom" is meant to include oxygen (O), nitrogen (N), sulfur (S), phosphorus (P), boron (B), and silicon (Si). The nitrogen and sulfur can be in an oxidized form when feasible.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution but differ with regard to the arrangement of the atoms or groups in space, e.g., enantiomers, diastereomers, tautomers.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, e.g., in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I with one or more solvent molecules.

"Treating" or "treatment" of any disease or disorder refers, in one embodiment, to ameliorating the disease or disorder (e.g., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In one aspect, the disclosure is directed to a compound of Formula (I):

$L_2$ is a bond, O, S, S(O), $SO_2$, $NR_3$, $C(R_3)_2$ or CO;

ring $A_1$ is a 6 membered aryl group or a 5-6 membered heteroaryl group;

ring $A_2$ is a 3-7 membered cycloalkyl group or a 4-7-membered heterocycloalkyl group;

$X_1$ is $CH_2$, CO, CH═CH (when $X_2$═CO), or N═CH (when $X_2$═CO);

$X_2$ is $CH_2$, CO, CH═CH (when $X_1$═CO), or N═CH (when $X_1$═CO);

wherein the alkyl group, haloalkyl group, cycloalkyl group, alkoxyalkyl group, aryl group, heteroaryl group or heterocycloalkyl group is optionally substituted by one or more $R^f$ groups;

each $R^f$ is independently D, oxo, halogen, $C_1$-$C_8$ alkoxy, $C_1$-$C_8$ alkyl, $C_{1-6}$ haloalkyl, $C_{1-6}$ haloalkoxy, —OH, —CN, —$NO_2$, —$C_2$-$C_6$ alkenyl, —$C_2$-$C_6$ alkynyl, $C_{6-10}$ aryl, $C_{5-12}$ heteroaryl, $C_{3-8}$ cycloalkyl, $C_{3-8}$ cycloalkenyl, $C_{3-8}$ heterocycloalkyl, $C_{3-8}$ heterocycloalkenyl, —$OR^a$, —$SR^a$, —$NR^cR^d$, —$NR^aR^c$, —$C(O)R^b$, —$OC(O)R^b$, —C(O)OR, —$C(O)NR^cR^d$, —$S(O)R^b$, —$S(O)_2NR^cR^d$, —S(O)(═NR)$R^b$, —$SF_5$, —$P(O)R^bR^b$, —$P(O)R^cR^d$, —$P(O)(OR^b)(OR^b)$, —$B(OR^c)(OR^d)$, —$S(O)_2R^b$, —$C(O)NR^bOR$, —$S(O)_2$ OR, —$OS(O)_2OR^b$, or —$OPO(OR^b)(OR^b)$; wherein said $C_1$-$C_8$ alkyl is optionally substituted by 1-6 groups selected from D, halogen, —OH, —CN, —$OR^a$, —$SR^a$, —$NR^aR^d$, or $NR^cR^d$;

each $R^a$ is independently H, D, —$C(O)R^b$, —$C(O)OR^c$, —$C(O)NR^cR^d$, —C(═NR)$NR^bR^c$, —C(═$NOR^b$)$NR^b$ $R^c$, —C(═NCN)$NR^bR^c$, —$P(OR^c)_2$, —$P(O)R^cR^b$, —$P(O)R^cR^d$, —$P(O)OR^cR^b$, —$S(O)R^b$, —$S(O)NR^c$ $R^d$, —$S(O)_2R^b$, —$S(O)_2NR^cR^d$, $SiR_3$, —$C_1$-$C_{10}$ alkyl, —$C_2$-$C_{10}$ alkenyl, —$C_2$-$C_{10}$ alkynyl, $C_{6-10}$ aryl, $C_{3-8}$ cycloalkyl, $C_{3-8}$ cycloalkenyl, $C_{5-12}$ heteroaryl, $C_{3-8}$ heterocycloalkyl, or $C_{3-8}$ heterocycloalkenyl;

each $R^b$, is independently H, D, —$C_1$-$C_6$ alkyl, —$C_2$-$C_6$ alkenyl, —$C_2$-$C_6$ alkynyl, $C_{6-10}$ aryl, $C_{3-8}$ cycloalkyl, $C_{3-8}$ cycloalkenyl, $C_{5-12}$ heteroaryl, $C_{3-8}$ heterocycloalkyl, or $C_{3-8}$ heterocycloalkenyl;

(I)

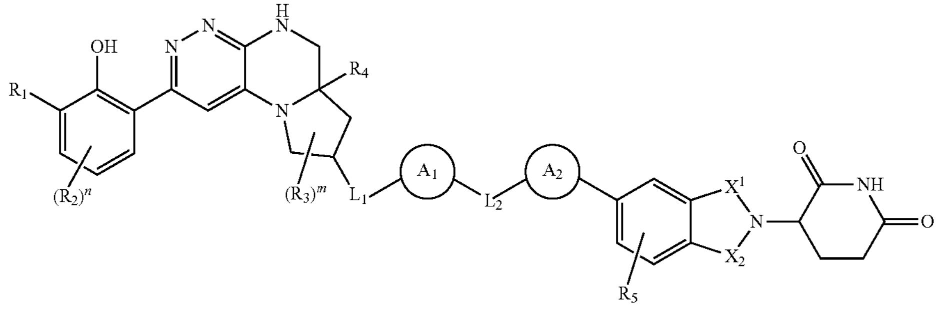

or a pharmaceutically acceptable salt thereof; wherein $R_1$ is halo, $C_{1-6}$ alkyl, or $C_{1-6}$ haloalkyl;

each $R_2$ is independently H, D, or F;

each $R_3$ is independently H, D, $C_{1-6}$ alkyl, $C_{1-6}$ haloalkyl, $C_{3-6}$ heterocycloalkyl or $C_{3-6}$ cycloalkyl;

n is 1, 2 or 3;

m is 1, 2, 3, or 4;

$R_4$ is H, D, $C_{1-6}$ alkyl, $C_{1-6}$ alkoxyalkyl, $C_{3-6}$ cycloalkyl, or $C_{1-6}$ haloalkyl;

$R_5$ is H, D, or F;

$L_1$ is a bond, O, S, S(O), $SO_2$, $NR_3$, $C(R_3)_2$ or CO;

each $R^c$ or $R^d$ is independently H, D, —$C_1$-$C_{10}$ alkyl, —$C_2$-$C_6$ alkenyl, —$C_2$-$C_6$ alkynyl, —$OC_1$-$C_6$alkyl, —O-cycloalkyl, $C_{6-10}$ aryl, $C_{5-12}$ heteroaryl, $C_{3-8}$ cycloalkyl, $C_{3-8}$ cycloalkenyl, $C_{3-8}$ heterocycloalkyl, or $C_{3-8}$ heterocycloalkenyl;

or $R^c$ and $R^d$, together with the atom to which they are both attached, form a monocyclic or multicyclic heterocycloalkyl, or a monocyclic or multicyclic heterocycloalkenyl group.

In some embodiments, $R^1$ in Formula I is halo, $C_{1-6}$ alkyl, or $C_{1-6}$ haloalkyl. In some embodiments, $R^1$ in Formula I is halo. In some embodiments, $R^1$ in Formula I is $C_{1-6}$ alkyl. In some embodiments, $R^1$ in Formula I is $C_{1-6}$ haloalkyl.

In other embodiments, $R^1$ in Formula I is F. In other embodiments, $R^1$ in Formula I is Cl. In other embodiments, $R^1$ in Formula I is methyl.

In some embodiments, each $R_2$ in Formula I is independently H, D, or F. In some embodiments, each $R_2$ in Formula I is H. In some embodiments, each $R_2$ in Formula I is D. In some embodiments, each $R_2$ in Formula I is F.

In other embodiments, at least one $R_2$ in Formula I is H. In other embodiments, at least one $R_2$ in Formula I is D. In other embodiments, at least one $R_2$ in Formula I is F.

In some embodiments, n in Formula (I) is 1, 2 or 3. In some embodiments, n in Formula (I) is 1. In other embodiments, n in Formula (I) is 2. In yet other embodiments, n in Formula (I) is 3.

In some embodiments, each $R_3$ in Formula I is independently H, D, $C_{1-6}$ alkyl, $C_{1-6}$ haloalkyl, $C_{3-6}$ heterocycloalkyl or $C_{3-6}$ cycloalkyl. In some embodiments, each $R_3$ in Formula I is H. In some embodiments, each $R_3$ in Formula I is D. In some embodiments, each $R_3$ in Formula I is $C_{1-6}$ alkyl.

In some embodiments, each $R_3$ in Formula I is $C_{1-6}$ haloalkyl. In some embodiments, each $R_3$ in Formula I is $C_{3-6}$ heterocycloalkyl. In some embodiments, each $R_3$ in Formula I is $C_{3-6}$ cycloalkyl.

In other embodiments, at least one $R_3$ in Formula I is H. In other embodiments, at least one $R_3$ in Formula I is D. In other embodiments, at least one $R_3$ in Formula I is $C_{1-6}$ alkyl. In other embodiments, at least one $R_3$ in Formula I is haloalkyl. In other embodiments, at least one $R_3$ in Formula I is $C_{3-6}$ cycloalkyl.

In some embodiments, m in Formula (I) is 1, 2, 3 or 4. In some embodiments, m in Formula (I) is 1. In some embodiments, m in Formula (I) is 2. In other embodiments, m in Formula (I) is 3. In other embodiments, m in Formula (I) is 4.

In some embodiments, $R_4$ in Formula I is independently H, D, $C_{1-6}$ alkyl, $C_{1-6}$ alkoxyalkyl, haloalkyl, or $C_{3-6}$ cycloalkyl. In some embodiments, $R_4$ in Formula I is H. In some embodiments, $R_4$ in Formula I is D. In other embodiments, $R_4$ in Formula I is $C_{1-6}$ alkyl. In other embodiments, $R_4$ in Formula I is $C_{1-6}$ alkoxyalkyl. In other embodiments, $R_4$ in Formula I is $C_{1-6}$ haloalkyl. In yet other embodiments, $R_4$ in Formula I is $C_{3-6}$ cycloalkyl.

In some embodiments, $R_5$ in Formula I is independently H, D, or F. In some embodiments, $R_5$ in Formula I is H. In other embodiments, $R_5$ in Formula I is D. In other embodiments, $R_5$ in Formula I is F.

In some embodiments, $L_1$ in Formula I is a bond, O, S, S(O), $SO_2$, $NR_3$, $C(R_3)_2$ or CO. In some embodiments, $L_1$ in Formula (I) is a bond. In some embodiments, $L_1$ in Formula (I) is O. In some embodiments, $L_1$ in Formula (I) is S. In other embodiments, $L_1$ in Formula (I) is S(O). In other embodiments, $L_1$ in Formula (I) is $SO_2$. In other embodiments, $L_1$ in Formula (I) is $NR_3$. In yet other embodiments, $L_1$ in Formula (I) is $C(R_3)_2$. In yet other embodiments, $L_1$ in Formula (I) is CO. In yet other embodiments, $L_1$ in Formula (I) is methylene.

In some embodiments, $L_2$ in Formula I is a bond, O, S, S(O), $SO_2$, $NR_3$, $C(R_3)_2$ or CO. In some embodiments, $L_2$ in Formula (I) is a bond. In some embodiments, $L_2$ in Formula (I) is O. In some embodiments, $L_2$ in Formula (I) is S. In other embodiments, $L_2$ in Formula (I) is S(O). In other embodiments, $L_2$ in Formula (I) is $SO_2$. In other embodiments, $L_2$ in Formula (I) is $NR_3$. In yet other embodiments, $L_2$ in Formula (I) is $C(R_3)_2$. In yet other embodiments, $L_2$ in Formula (I) is CO. In yet other embodiments, $L_2$ in Formula (I) is methylene.

In some embodiments, ring $A_1$ in Formula (I) is a 6 membered aryl group or a 5-6 membered heteroaryl group. In some embodiments, ring $A_1$ in Formula (I) is a 6 membered aryl group. In some embodiments, ring $A_1$ in Formula (I) is a phenyl group. In other embodiments, ring $A_1$ is a 5-6 membered heteroaryl group. In other embodiments, ring $A_1$ is a pyridine group. In other embodiments, ring $A_1$ is a pyrimidine group.

In some embodiments, ring $A_2$ in Formula (I) is a 3-7 membered cycloalkyl group or a 4-7-membered heterocycloalkyl group. In some embodiments, ring $A_2$ in Formula (I) is a 3-7 membered cycloalkyl group. In some embodiments, ring $A_2$ in Formula (I) is a cyclohexyl group. In some embodiments, ring $A_2$ is a 4-7-membered heterocycloalkyl group. In some embodiments, ring $A_2$ in Formula (I) is a piperazine group, a morpholine group, a piperidine group, a pyrrolidine group, an azetidine group or an azabicyclo-hexane group.

In some embodiments, ring $A_2$ in Formula (I) is a piperazine group. In some embodiments, ring $A_2$ in Formula (I) is a morpholine group. In other embodiments, ring $A_2$ in Formula (I) is a piperidine group. In other embodiments, ring $A_2$ in Formula (I) is a pyrrolidine group. In yet other embodiments, ring $A_2$ in Formula (I) is an azetidine group. In yet other embodiments, ring $A_2$ in Formula (I) is an azabicyclo-hexane group.

In some embodiments, $X_1$ in Formula (I) is $CH_2$, CO, CH═CH (when $X_2$═CO), or N═CH (when $X_2$═CO). In some embodiments, $X_1$ in Formula (I) is $CH_2$. In some embodiments, $X_1$ is CO.

In other embodiments, $X_1$ is CH═CH (when $X_2$═CO). In other embodiments, $X_1$ is N═CH (when $X_2$═CO).

In some embodiments, $X_2$ in Formula (I) is $CH_2$, CO, CH═CH (when $X_2$═CO), or N═CH (when $X_2$═CO). In some embodiments, $X_2$ in Formula (I) is $CH_2$. In some embodiments, $X_2$ is CO.

In other embodiments, $X_2$ is CH═CH (when $X_1$═CO). In other embodiments, $X_2$ is N═CH (when $X_1$═CO).

In some embodiments, each $R^f$ in Formula I is independently D, oxo, halogen, $C_1$-$C_8$ alkoxy, $C_1$-$C_8$ alkyl, $C_{1-6}$ haloalkyl, $C_{1-6}$ haloalkoxy, —OH, —CN, —$NO_2$, —$C_2$-$C_6$ alkenyl, —$C_2$-$C_6$ alkynyl, $C_{6-10}$ aryl, $C_{5-12}$ heteroaryl, $C_{3-8}$ cycloalkyl, $C_{3-8}$ cycloalkenyl, $C_{3-8}$ heterocycloalkyl, $C_{3-8}$ heterocycloalkenyl, —$OR^a$, —$SR^a$, —$NR^cR^d$, —$NR^aR^c$, —$C(O)R^b$, —$OC(O)R^b$, —C(O)OR, —$C(O)NR^cR^d$, —$S(O)R^b$, —$S(O)_2NR^cR^d$, —$S(O)(═NR)R^b$, —$SF_5$, —$P(O)R^bR^b$, —$P(O)R^cR^d$, —$P(O)(OR^b)(OR)$, —$B(OR^c)(OR^d)$, —$S(O)_2R^b$, —$C(O)NR^bOR^b$, —$S(O)_2OR^b$, —$OS(O)_2OR^b$, or —$OPO(OR^b)(OR^b)$; wherein said $C_1$-$C_8$ alkyl is optionally substituted by 1-6 groups selected from D, halogen, —OH, —CN, —$OR^a$, —$SR^a$, —$NR^aR^d$, or $NR^cR^d$.

In some embodiments, at least one $R^f$ in Formula I is D. In some embodiments, at least one $R^f$ in Formula I is oxo. In some embodiments, at least one $R^f$ in Formula I is halogen. In some embodiments, at least one $R^f$ in Formula I is $C_1$-$C_8$ alkoxy. In some embodiments, at least one $R^f$ in Formula I is $C_1$-$C_8$ alkyl. In some embodiments, the $C_1$-$C_8$ alkyl is optionally substituted by 1-6 groups selected from D, halogen, —OH, —CN, —$OR^a$, —$SR^a$, —$NR^aR^d$, or $NR^cR^d$. In some embodiments, at least one $R^f$ in Formula I is haloalkyl. In some embodiments, at least one $R^f$ in Formula I is —OH.

In some embodiments, $R^f$ in Formula I is —CN. In some embodiments, at least one $R^f$ in Formula I is —$NO_2$. In some embodiments, at least one $R^f$ in Formula I is —$C_2$-$C_6$ alkenyl. In some embodiments, at least one $R^f$ in Formula I is —$C_2$-$C_6$ alkynyl. In some embodiments, at least one $R^f$ in Formula I is $C_6$. 10 aryl. In some embodiments, at least one $R^f$ in Formula I is $C_{5-12}$ heteroaryl. In some embodiments, at least one $R^f$ in Formula I is $C_{3-8}$ cycloalkyl. In other embodiments, at least one $R^f$ in Formula I is $C_{3-8}$ cycloalkenyl. In other embodiments, at least one $R^f$ in Formula I is $C_{3-8}$ heterocycloalkyl. In other embodiments, at least one $R^f$ in Formula I is $C_{3-8}$ heterocycloalkenyl. In other embodiments, at least one $R^f$ in Formula I is —$OR^a$. In other embodiments, at least one $R^f$ in Formula I is —$SR^a$. In other embodiments, at least one $R^f$ in Formula I is —$NR^cR^d$. In other embodiments, at least one $R^f$ in Formula I is —$NR^aR^c$. In other embodiments, at least one $R^f$ in Formula I is —$C(O)R^b$. In other embodiments, at least one $R^f$ in Formula I is —$OC(O)R^b$. In other embodiments, at least one $R^f$ in Formula I is —C(O)OR. In other embodiments, at least one $R^f$ in Formula I is —$C(O)NR^cR^d$. In yet other embodiments, at least one $R^f$ in Formula I is —$S(O)R^b$. In yet other embodiments, at least one $R^f$ in Formula I is —$S(O)_2NR^cR^d$. In yet other embodiments, at least one $R^f$ in Formula I is —$S(O)({=}NR)R^b$. In yet other embodiments, at least one $R^f$ in Formula I is —$SF_5$. In yet other embodiments, at least one $R^f$ in Formula I is —$P(O)R^bR^b$. In yet other embodiments, at least one $R^f$ in Formula I is —$P(O)(OR^b)(OR^b)$. In yet other embodiments, at least one $R^f$ in Formula I is —$B(OR^c)(OR^d)$. In yet other embodiments, at least one $R^f$ in Formula I is —$S(O)_2R^b$. In yet other embodiments, at least one $R^f$ in Formula I is —$C(O)NR^bOR$. In yet other embodiments, at least one $R^f$ in Formula I is —$S(O)_2OR$. In yet other embodiments, at least one $R^f$ in Formula I is —$OS(O)_2OR$. In yet other embodiments, at least one $R^f$ in Formula I is —$OPO(OR^b)(OR)$.

In some embodiments, each $R^a$ in Formula I is independently H, D, —$C(O)R^b$, —$C(O)OR^c$, —$C(O)NR^cR^d$, —$C({=}NR)NR^bR^c$, —$C({=}NOR)NR^bR^c$, —$C({=}NCN)NR^bR^c$, —$P(OR^c)_2$, —P(O)RR, —$P(O)OR^cOR^b$, —$S(O)R^b$, —$S(O)NR^cR^d$, —$S(O)_2R^b$, —$S(O)_2NR^cR^d$, $SiR_3$, —$C_1$-$C_{10}$alkyl, —$C_2$-$C_{10}$ alkenyl, —$C_2$-$C_{10}$ alkynyl, $C_{6-10}$ aryl, $C_{3-8}$ cycloalkyl, $C_{3-8}$ cycloalkenyl, $C_{5-12}$ heteroaryl, $C_{3-8}$ heterocycloalkyl, or $C_{3-8}$ heterocycloalkenyl.

In some embodiments, at least one $R^a$ in Formula I is H. In some embodiments, at least one $R^a$ in Formula I is D. In some embodiments, at least one $R^a$ in Formula I is —$C(O)R^b$. In some embodiments, at least one $R^a$ in Formula I is —$C(O)OR^c$. In some embodiments, at least one $R^a$ in Formula I is —$C(O)NR^cR^d$. In some embodiments, at least one $R^a$ in Formula I is —$C({=}NR)NR^bR^c$. In some embodiments, at least one $R^a$ in Formula I is $C({=}NOR^b)NR^c$. In some embodiments, at least one $R^a$ in Formula I is —$C({=}NCN)NR^bR^c$.

In other embodiments, at least one $R^a$ in Formula I is —$P(OR^c)_2$, —$P(O)R^cR^b$, —$P(O)OR^cR^b$, —$S(O)R^b$, —$S(O)NR^cR^d$, —$S(O)_2R^b$, —$S(O)_2NR^cR^d$, $SiR_3$, and the like. In yet other embodiments, at least one $R^a$ in Formula I is —$C_1$-$C_{10}$ alkyl, —$C_2$-$C_{10}$ alkenyl, —$C_2$-$C_{10}$ alkynyl, $C_{6-10}$ aryl, $C_{3-8}$ cycloalkyl, $C_{3-8}$ cycloalkenyl, $C_{5-12}$ heteroaryl, $C_{3-8}$ heterocycloalkyl, $C_{3-8}$ heterocycloalkenyl, and the like.

In some embodiments, each $R^b$ in Formula I is independently H, D, —$C_1$-$C_6$ alkyl, —$C_2$-$C_6$ alkenyl, —$C_2$-$C_6$ alkynyl, $C_{6-10}$ aryl, $C_{3-8}$ cycloalkyl, $C_{3-8}$ cycloalkenyl, $C_{5-12}$ heteroaryl, $C_{3-8}$ heterocycloalkyl, or $C_{3-8}$ heterocycloalkenyl.

In some embodiments, at least one $R^b$ in Formula I is H. In some embodiments, at least one $R^b$ in Formula I is D. In some embodiments, at least one $R^b$ in Formula I is —$C_1$-$C_6$ alkyl. In some embodiments, at least one $R^b$ in Formula I is —$C_2$-$C_6$ alkenyl. In some embodiments, at least one $R^b$ in Formula I is —$C_2$-$C_6$ alkynyl. In other embodiments, at least one $R^b$ in Formula I is $C_{6-10}$ aryl. In other embodiments, at least one $R^b$ in Formula I is $C_{3-8}$ cycloalkyl. In other embodiments, at least one $R^b$ in Formula I is $C_{3-8}$ cycloalkenyl. In other embodiments, at least one $R^b$ in Formula I is $C_{5-12}$ heteroaryl. In other embodiments, at least one $R^b$ in Formula I is $C_{3-8}$ heterocycloalkyl. In other embodiments, at least one $R^b$ in Formula I is $C_{3-8}$ heterocycloalkenyl.

In some embodiments, each $R^c$ or $R^d$ in Formula I is independently H, D, —$C_1$-$C_6$ alkyl, —$C_2$-$C_6$ alkenyl, —$C_2$-$C_6$ alkynyl, $C_{6-10}$ aryl, $C_{3-8}$ cycloalkyl, $C_{3-8}$ cycloalkenyl, $C_{5-12}$ heteroaryl, $C_{3-8}$ heterocycloalkyl, or $C_{3-8}$ heterocycloalkenyl.

In some embodiments, $R^c$ or $R^d$ in Formula I is H. In some embodiments, $R^c$ or $R^d$ in Formula I is D. In some embodiments, $R^c$ or $R^d$ in Formula I is —$C_1$-$C_{10}$ alkyl. In some embodiments, $R^c$ or $R^d$ in Formula I is —$C_2$-$C_6$ alkenyl. In some embodiments, $R^c$ or $R^d$ in Formula I is —$C_2$-$C_6$ alkynyl. In other embodiments, $R^c$ or $R^d$ in Formula I is —$OC_1$-$C_6$alkyl. In other embodiments, $R^c$ or $R^d$ in Formula I is —O-cycloalkyl. In other embodiments, $R^c$ or $R^d$ in Formula I is $C_{6-10}$ aryl. In other embodiments, $R^c$ or $R^d$ in Formula I is $C_{3-8}$ cycloalkyl. In other embodiments, $R^c$ or $R^d$ in Formula I is $C_{3-8}$ cycloalkenyl. In other embodiments, $R^c$ or $R^d$ in Formula I is $C_{5-12}$ heteroaryl. In other embodiments, $R^c$ or $R^d$ in Formula I is $C_{3-8}$ heterocycloalkyl. In other embodiments, $R^c$ or $R^d$ in Formula I is $C_{3-8}$ heterocycloalkenyl.

In yet other embodiments, $R^c$ and $R^d$ in Formula I, together with the atom to which they are both attached, form a monocyclic or multicyclic heterocycloalkyl, or a monocyclic or multicyclic heterocycloalkenyl group. In yet other embodiments, $R^c$ and $R^d$ in Formula I form a monocyclic heterocycloalkyl. In yet other embodiments, $R^c$ and $R^d$ in Formula I form a multicyclic heterocycloalkyl. In yet other embodiments, $R^c$ and $R^d$ in Formula I form a monocyclic heterocycloalkenyl group. In yet other embodiments, $R^c$ and $R^d$ in Formula I form a multicyclic heterocycloalkenyl group.

In some embodiments, the compounds of Formula (I) are the pharmaceutically acceptable salts. In some embodiments, the compounds of Formula (I) are solvates. In some embodiments, the compounds of Formula (I) are N-oxides. In some embodiments, the compounds of Formula (I) are stereoisomers.

In some embodiments, the compounds of Formula (I) are represented by compounds of Formula IIa and Formula IIb:

(IIa)

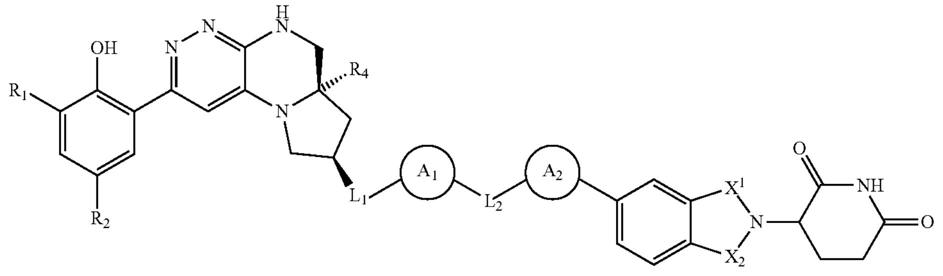

(IIb)

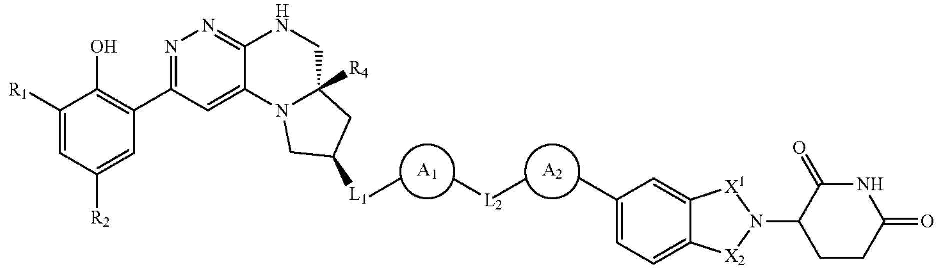

or a pharmaceutically acceptable salt thereof; wherein each $R_1$, $R_2$, $R_4$, $L_1$, Ring $A_1$, $L_2$, ring $A_2$, $X_1$, and $X_2$ are defined above with respect to Formula (I).

In some embodiments, the compounds of Formula (I) are represented by compounds of Formula IIIa and Formula IIIb:

(IIIa)

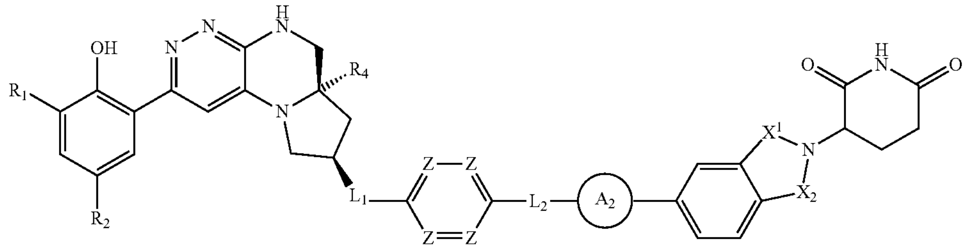

(IIIb)

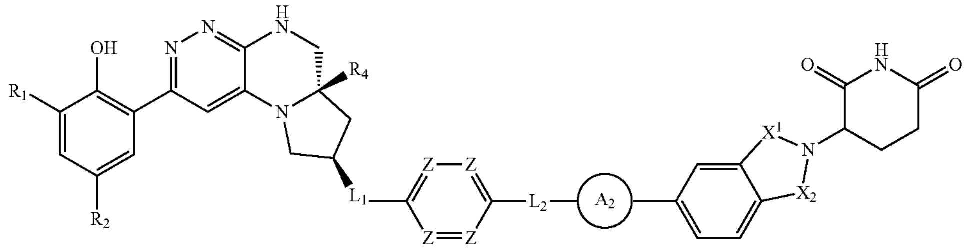

or a pharmaceutically acceptable salt thereof; wherein each $R_1$, $R_2$, $R_4$, $L_1$, $L_2$, ring $A_2$, $X_1$, and $X_2$ are defined above with respect to Formula (I);

each Z is independently N or $CR_6$; wherein $R_6$ is the same as $R^f$.

In some embodiments of Formula IIIa or Formula IIIb, each $R_6$ is independently H, D, halo, $C_{1-6}$ alkyl, $C_{1-6}$ alkoxy, $C_{1-6}$ haloalkyl, $C_{1-6}$ haloalkoxy, or $C_{3-6}$ cycloalkyl.

In some embodiments of Formula IIIa or Formula IIIb, each $R_6$ is independently H, D, halo, —CN, $C_{1-6}$ alkyl, $C_{1-6}$ alkoxy, $C_{1-6}$ haloalkyl, $C_{1-6}$ haloalkoxy, or $C_{3-6}$ cycloalkyl.

In some embodiments, each Z in Formula IIIa or Formula IIIb is independently N or $CR_6$. In some embodiments, each Z in Formula IIIa or Formula IIIb is N. In some embodiments, each Z in Formula IIIa or Formula IIIb is $CR_6$. In other embodiments, at least one Z in Formula IIIa or Formula IIIb is N. In other embodiments, at least two Z in Formula IIIa or Formula IIIb are N. In other embodiments, at least one Z in Formula IIIa or Formula IIIb is $CR_6$. In other embodiments, at least two Z in Formula IIIa or Formula IIIb are $CR_6$.

In some embodiments, each $R_6$ in Formula IIIa or Formula IIIb is independently H, D, halo, —CN, $C_{1-6}$ alkyl, $C_{1-6}$ alkoxy, $C_{1-6}$ haloalkyl, or $C_{3-6}$ cycloalkyl. In some embodiments, each $R_6$ in Formula IIIa or Formula IIIb is H. In some embodiments, each $R_6$ in Formula IIIa or Formula IIIb is D. In some embodiments, each $R_6$ in Formula IIIa or Formula IIIb is halo. In some embodiments, each $R_6$ in Formula IIIa or Formula IIIb is —CN. In other embodiments, each $R_6$ in Formula IIIa or Formula IIIb is $C_{1-6}$ alkyl. In other embodiments, each $R_6$ in Formula IIIa or Formula IIIb is $C_{1-6}$ alkoxy. In other embodiments, each $R_6$ in Formula IIIa or Formula IIIb is $C_{1-6}$ haloalkyl. In other embodiments, each $R_6$ in Formula IIIa or Formula IIIb is $C_{1-6}$ haloalkoxy. In other embodiments, each $R_6$ in Formula IIIa or Formula IIIb is $C_{3-6}$ cycloalkyl.

In other embodiments, at least one $R_6$ in Formula IIIa or Formula IIIb is H. In other embodiments, at least one $R_6$ in Formula IIIa or Formula IIIb is D. In other embodiments, at least one $R_6$ in Formula IIIa or Formula IIIb is halo. In other embodiments, at least one $R_6$ in Formula IIIa or Formula IIIb is —CN. In other embodiments, at least one $R_6$ in Formula IIIa or Formula IIIb is $C_{1-6}$ alkyl. In other embodiments, at least one $R_6$ in Formula IIIa or Formula IIIb is $C_{1-6}$ haloalkyl. In other embodiments, at least one $R_6$ in Formula IIIa or Formula IIIb is $C_{3-6}$ cycloalkyl.

In some embodiments, the compounds of Formula (I) are represented by compounds of Formula IVa and Formula IVb (IVa)

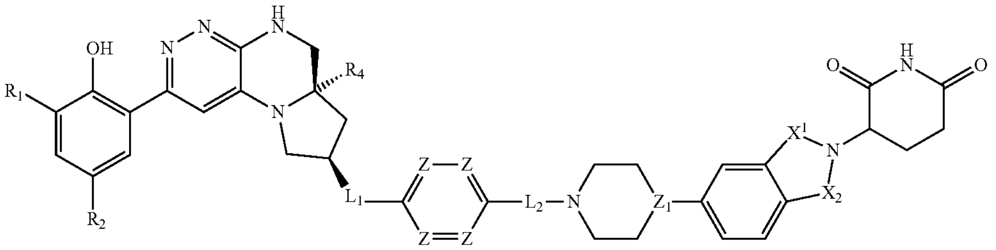

(IVb)

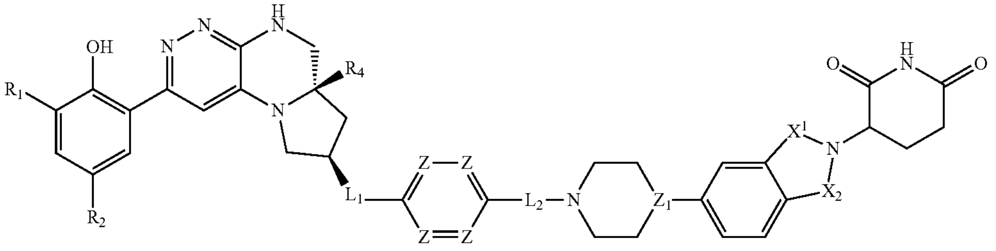

or a pharmaceutically acceptable salt thereof; wherein each $R_1$, $R_2$, $R_4$, $L_1$, $L_2$, $X_1$, and $X_2$ are defined above with respect to Formula (I); each Z and $R_6$ are defined above with respect to Formula IIIa or Formula IIIb; and $Z_1$ is N or $CR_6$.

In some embodiments, $Z_1$ in Formula IVa or Formula IVb is N or $CR_6$. In some embodiments, $Z_1$ in Formula IVa or Formula IVb is N. In some embodiments, $Z_1$ in Formula IVa or Formula IVb is $CR_6$.

In some embodiments, the compounds of Formula (I) are represented by compounds of Formula Va and Formula Vb (Va)

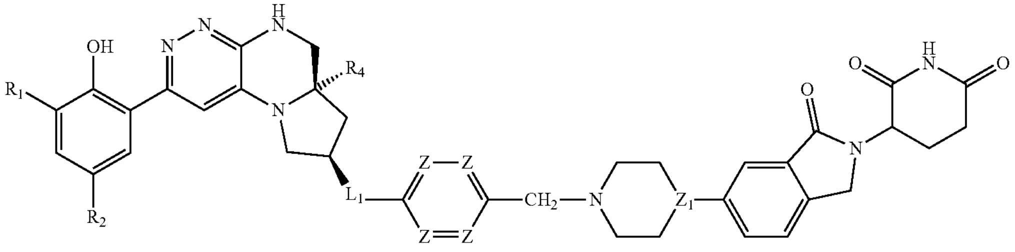

(Vb)

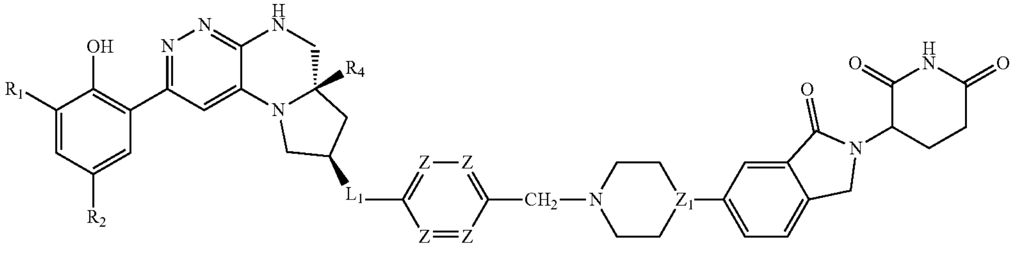

or a pharmaceutically acceptable salt thereof; wherein each $R_1$, $R_2$, $R_4$, and $L_1$ are defined above with respect to Formula (I); each Z and $R_6$ are defined above with respect to Formula IIIa or Formula IIIb; and $Z_1$ is defined above with respect to Formula IVa or Formula IVb.

In some embodiments, the compounds of Formula (I) are represented by compounds of Formula VIa and Formula VIb or a pharmaceutically acceptable salt thereof; wherein each $R_2$, $R_4$, and $L_1$ are defined above with respect to Formula (I); each Z and $R_6$ are defined above with respect to Formula IIIa or Formula IIIb; and $Z_1$ is defined above with respect to Formula VIa or Formula VIb.

In yet further embodiments, the compounds of Formula (I) are:

(VIa)

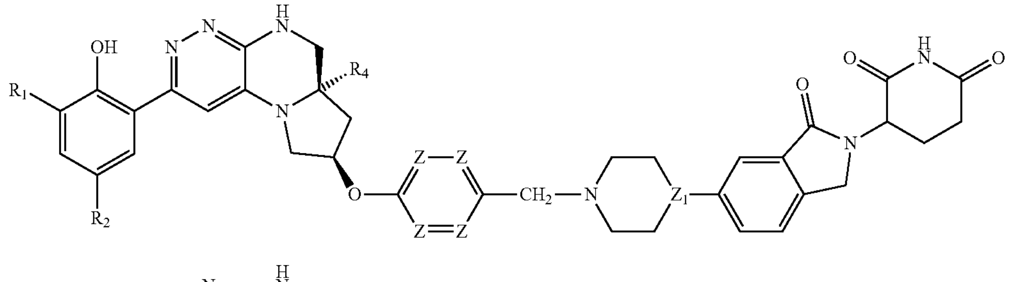

(VIb)

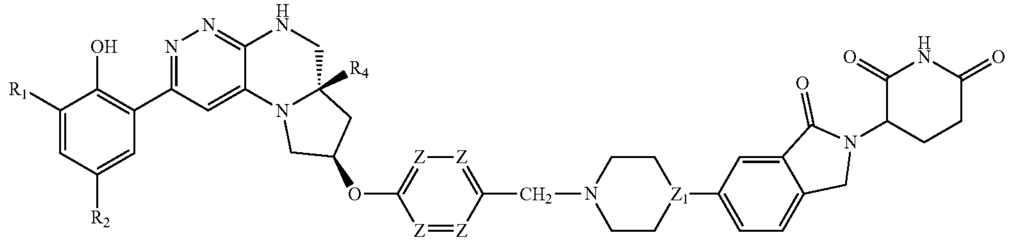

or a pharmaceutically acceptable salt thereof; wherein each $R_1$, $R_2$, and $R_4$, are defined above with respect to Formula (I); each Z and $R_6$ are defined above with respect to Formula IIIa or Formula IIIb; and $Z_1$ is defined above with respect to Formula VIa or Formula VIb.

In some embodiments, the compounds of Formula (I) are represented by compounds of Formula VIIa and Formula VIIb 3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)benzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-3-methylbenzyl)piperazin-1-yl)-1-oxoisoindolin-2-yl)piperidine-2,6-dione;

(VIIa)

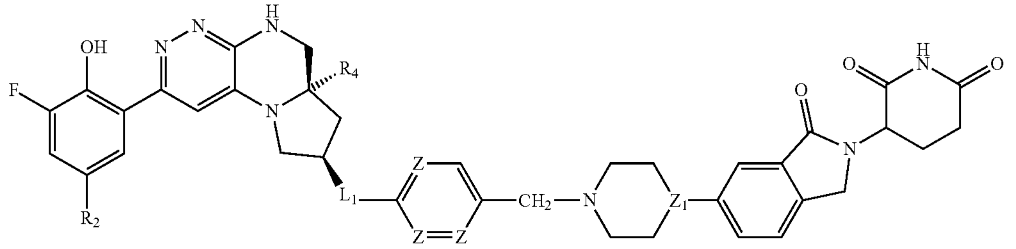

(VIIb)

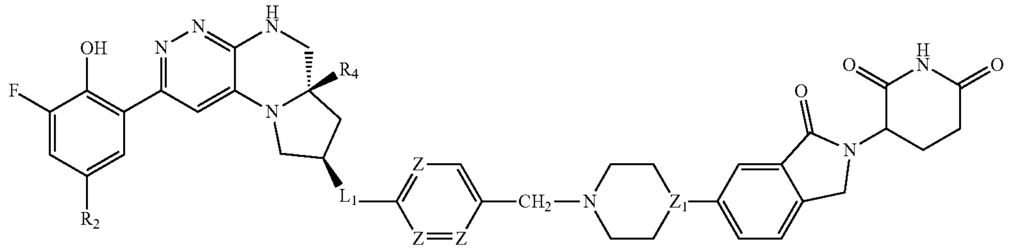

3-(6-(4-((5-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy) pyridin-2-yl)methyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[11,2':4,5]pyrazino[2,3-c]pyridazin-8-yl)oxy)-3-fluorobenzyl)piperazin-1-yl)-1-oxoisoindolin-2-yl)piperidine-2,6-dione;

3-(6-(4-(4-(((6aR,8R)-2-(3-fluoro-2-hydroxyphenyl)-5,6,6a,7,8,9-hexahydro-pyrrolo[1',2':4,5]pyrazino[2,3-c]pyridazin-8-yl)oxy)benzyl)piperazin-1-yl)-1-oxoisoindolin-2-yl)piperidine-2,6-dione;

3-(6-(4-(3-chloro-4-(((6aR,8R)-2-(3,5-difluoro-2-hydroxyphenyl)-5,6,6a, 7,8,9-hexahydropyrrolo[1',2':4,5]pyrazino[2,3-c]pyridazin-8-yl)oxy)benzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[11,2':4,5]pyrazino[2,3-c]pyridazin-8-yl)oxy)-2-methylbenzyl)piperazin-1-yl)-1-oxoisoindolin-2-yl)piperidine-2,6-dione;

3-(6-(4-(4-(((6aR,8R)-2-(3-chloro-2-hydroxyphenyl)-5,6,6a,7,8,9-hexahydro-pyrrolo[11,2':4,5]pyrazino[2,3-c]pyridazin-8-yl)oxy)benzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-2,5-dimethylbenzyl)piperazin-1-yl)-1-oxoisoindolin-2-yl)piperidine-2,6-dione;

3-(6-(4-(4-(((6aR,8R)-2-(3-chloro-2-hydroxyphenyl)-5,6,6a,7,8,9-hexahydro-pyrrolo[11,2':4,5]pyrazino[2,3-c]pyridazin-8-yl)oxy)-2-methylbenzyl)piperazin-1-yl)-1-oxoisoindolin-2-yl)piperidine-2,6-dione;

3-(6-(4-(4-(((6aR,8R)-2-(3-fluoro-2-hydroxyphenyl)-5,6,6a,7,8,9-hexahydro-pyrrolo[1',2':4,5]pyrazino[2,3-c]pyridazin-8-yl)oxy)-2-methylbenzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[11,2':4,5]pyrazino[2,3-c]pyridazin-8-yl)oxy)-2-methoxybenzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[11,2':4,5]pyrazino[2,3-c]pyridazin-8-yl)oxy)-2-fluorobenzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-3-isopropylbenzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-2-(trifluoromethyl)benzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-2-isopropylbenzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-2,6-dimethylbenzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-2,3-dimethylbenzyl)piperazin-1-yl)-1-oxoisoindolin-2-yl)piperidine-2,6-dione;

3-(6-(4-(4-(((6aR,8R)-2-(3-chloro-5-fluoro-2-hydroxyphenyl)-5,6,6a,7,8,9-hexahydro-pyrrolo[1',2':4,5]pyrazino[2,3-c]pyridazin-8-yl)oxy)-2-methylbenzyl)piperazin-1-yl)-1-oxoisoindolin-2-yl)piperidine-2,6-dione;

3-(6-(4-(4-(((6aR,8R)-2-(2-hydroxy-3-methylphenyl)-5,6,6a,7,8,9-hexahydro-pyrrolo[11,2':4,5]pyrazino[2,3-c]pyridazin-8-yl)oxy)-2-methylbenzyl)piperazin-1-yl)-1-oxoisoindolin-2-yl)piperidine-2,6-dione;

3-(6-(4-(4-(((6aR,8R)-2-(3-chloro-2-hydroxyphenyl)-5,6,6a,7,8,9-hexahydro-pyrrolo[11,2':4,5]pyrazino[2,3-c]pyridazin-8-yl)oxy)-2-methoxybenzyl)piperazin-1-yl)-1-oxoisoindolin-2-yl)piperidine-2,6-dione;

3-(6-(4-(4-(((6aR,8R)-2-(3-chloro-5-fluoro-2-hydroxyphenyl)-5,6,6a, 7,8,9-hexahydropyrrolo[1',2':4,5]pyrazino[2,3-c]pyridazin-8-yl)oxy)benzyl)piperazin-1-yl)-1-oxoisoindolin-2-yl)piperidine-2,6-dione;

3-(6-(4-(4-(((6aR,8R)-2-(2-hydroxy-3-methylphenyl)-5,6,6a,7,8,9-hexahydro-pyrrolo[1',2':4,5]pyrazino[2,3-c]pyridazin-8-yl)oxy)benzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-2-(trifluoromethoxy)benzyl)piperazin-1-yl)-1-oxoisoindolin-2-yl)piperidine-2,6-dione;

(S)-3-(6-(4-(4-(((6aR,8R)-2-(3-chloro-2-hydroxyphenyl)-5,6,6a,7,8,9-hexahydro-pyrrolo[1',2':4,5]pyrazino[2,3-c]pyridazin-8-yl)oxy)benzyl)piperazin-1-yl)-1-oxoisoindolin-2-yl)piperidine-2,6-dione;

3-(6-(4-((2-(((6aR,8R)-2-(3,5-difluoro-2-hydroxyphenyl)-5,6,6a, 7,8,9-hexahydro-pyrrolo[1',2':4,5]pyrazino[2,3-c]pyridazin-8-yl)thio) pyrimidin-5-yl)methyl)piperazin-1-yl)-1-oxoisoindolin-2-yl)piperidine-2,6-dione;

3-(6-(4-((6-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione;

(S)-3-(6-(4-((6-(((6aR,8R)-2-(3,5-difluoro-2-hydroxyphenyl)-5,6,6a,7,8,9-hexahydro-pyrrolo[11,2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione;

(S)-3-(6-(1-((6-(((6aR,8R)-2-(3,5-difluoro-2-hydroxyphenyl)-5,6,6a,7,8,9-hexahydro-pyrrolo[11,2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione;

(S)-3-(6-(4-((6-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-2-methylpyridin-3-yl)methyl)piperazin-1-yl)-1-oxoisoindolin-2-yl)piperidine-2,6-dione;

3-(6-(4-((6-(((6aR,8R)-2-(3,5-difluoro-2-hydroxyphenyl)-5,6,6a, 7,8,9-hexahydro-pyrrolo[1',2':4,5]pyrazino[2,3-c]pyridazin-8-yl)oxy)-5-methylpyridin-3-yl)methyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)thio)benzyl)piperazin-1-yl)-1-oxoisoindolin-2-yl)piperidine-2,6-dione;

3-(6-(4-((6-(((6aR,8R)-2-(3,5-difluoro-2-hydroxyphenyl)-5,6,6a,7,8,9-hexahydro-pyrrolo[11,2':4,5]pyrazino[2,3-c]pyridazin-8-yl)oxy) pyridin-3-yl)methyl)piperazin-1-yl)-1-oxoisoindolin-2-yl)piperidine-2,6-dione;

3-(6-(4-(((3R,5S)-4-((6aR,8R)-2-(3-fluoro-2-hydroxyphenyl)-5,6,6a,7,8,9-hexahydro-pyrrolo[11,2':4,5]pyrazino[2,3-c]pyridazine-8-carbonyl)-3,5-dimethylpiperazin-1-yl)methyl) piperidin-1-yl)-1-oxoisoindolin-2-yl)piperidine-2,6-dione;

3-(6-(4-((6-(((6aR,8R)-2-(3-fluoro-2-hydroxyphenyl)-5,6,6a,7,8,9-hexahydro-pyrrolo[11,2':4,5]pyrazino[2,3-c]pyridazin-8-yl) (methyl) amino) pyridin-3-yl)methyl)piperazin-1-yl)-1-oxoisoindolin-2-yl)piperidine-2,6-dione;

3-(6-(4-(4-(((6aS,8R)-2-(3-fluoro-2-hydroxyphenyl)-5,6,6a,7,8,9-hexahydropyrrolo [1',2':4,5]pyrazino[2,3-c]pyridazin-8-yl)oxy)-2-methylbenzyl)piperazin-1-yl)-1-oxoisoindolin-2-yl)piperidine-2,6-dione;

3-(6-(1-(4-(((6aS,8R)-2-(3-fluoro-2-hydroxyphenyl)-5,6,6a,7,8,9-hexahydropyrrolo [1',2':4,5]pyrazino[2,3-c]pyridazin-8-yl)oxy)-2-methylbenzyl)piperidin-4-yl)-1-oxoisoindolin-2-yl)piperidine-2,6-dione;

(S)-3-(6-(4-((6-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)thio)-4-methylpyridin-3-yl)methyl)piperazin-1-yl)-1-oxoisoindolin-2-yl)piperidine-2,6-dione;

3-(6-(4-((4-(((6aR,8R)-2-(3,5-difluoro-2-hydroxyphenyl)-5,6,6a, 7,8,9-hexahydropyrrolo [1',2':4,5]pyrazino[2,3-c]pyridazin-8-yl)oxy)-1H-pyrazol-1-yl)methyl)piperidin-1-yl)-1-oxoisoindolin-2-yl)piperidine-2,6-dione;

or a pharmaceutically acceptable salt thereof.

In yet further embodiments, the compounds of Formula (I) are:

3-(6-(4-((5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-6-ethylpyrazin-2-yl)methyl)piperazin-1-yl)-1-oxoisoindolin-2-yl)piperidine-2,6-dione;

3-(6-(4-((2-(((6aS,8R)-6a-(Difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-4,6-dimethylpyrimidin-5-yl)methyl)piperazin-1-yl)-1-oxoisoindolin-2-yl)piperidine-2,6-dione;

3-(6-(4-((2-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)pyrimidin-5-yl)methyl)piperazin-1-yl)-1-oxoisoindolin-2-yl)piperidine-2,6-dione;

(S)-3-(6-(4-((6-(((6a R,8R)-6a-(difluoromethyl)-2-(3-fluoro-2-hydroxyphenyl)5,6,6a,7,8,9-hexahydropyrrolo [1',2':4,5]pyridizan)methyl)piperazin-1-yl-oxoisoindolin-2-yl)piperidine-2,6-dione;

(S)-3-(6-(4-((6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-3-methylpyridin-2-yl)methyl)piperazin-1-yl)-1-oxoisoindolin-2-yl)piperidine-2,6-dione;

(S)-3-(6-(4-((5-(((6aR,8R)-6a-(difluoromethyl)-2-(3-fluoro-2-hydroxyphenyl)-5,6,6a,7,8,9-hexahydropyrrolo[2':4,5]pyrazino[2,3-c]pyridazin-8-yl)oxy)-3-fluoro-4-methylpyridin-2-yl)methyl)piperazin-1-yl)-1-oxoisoindolin-2-yl)piperidine-2,6-dione;

(S)-3-(6-(4-((5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-3,4-dimethylpyridin-2-yl)methyl)piperazin-1-yl)-1-oxoisoindolin-2-yl)piperidine-2,6-dione;

(S)-3-(6-(4-((6-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-5-ethylpyridin-3-yl)methyl)piperazin-1-yl)-1-oxoisoindolin-2-yl)piperidine-2,6-dione;

(S)-3-(6-(4-((5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-3,6-dimethylpyrazin-2-yl)methyl)piperazin-1-yl)-1-oxoisoindolin-2-yl)piperidine-2,6-dione;

(S)-3-(6-(4-((5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)pyridin-2-yl)methyl)piperazin-1-yl)-1-oxoisoindolin-2-yl)piperidine-2,6-dione;

3-(6-(4-((2-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-4-isopropylpyrimidin-5-yl)methyl)piperazin-1-yl)-1-oxoisoindolin-2-yl)piperidine-2,6-dione;

3-(6-(4-((5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-3-methylpyrazin-2-yl)methyl)piperazin-1-yl)-1-oxoisoindolin-2-yl)piperidine-2,6-dione;

3-(6-(4-((5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)pyrazin-2-yl)methyl)piperazin-1-yl 1-oxoisoindolin-2-yl)piperidine-2,6-di one;

3-(6-(4-((6-(((6aS,8R)-6a-(difluoromethyl)-2-(3-fluoro-2-hydroxyphenyl)-5,6,6a,7,8,9-hexahydropyrrolo[1',2:4,5]pyrazino[2,3-c]pyridazin-8-yl)oxy)-5-methoxypyridin-3-yl)methyl)piperazin-1-yl)-1-oxoisoindolin-2-yl)piperidine-2,6-dione;

3-(6-(4-((6-(((6aS,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-5-fluoropyridin-3-yl)methyl)piperazin-1-yl)-1-oxoisoindolin-2-yl)piperidine-2,6-dione;

3-(6-(4-((6-(((6aR,8R)-2-(3-fluoro-2-hydroxyphenyl)-6a-methyl-5,6,6a,7,8,9-hexahydropyrrolo[1',2' 74, S]pyrazino[2,3-c]pyridazin-8-yl)oxy)-4-methyl pyridin-3-yl)methyl)piperazin-1-yl)-1-oxoisoindolin-2-yl)piperidine-2,6-dione;

3-(6-(4-((6-(((6aR,8R)-6a-Ethyl-2-(3-fluoro-2-hydroxyphenyl)-5,6,6a,7,8,9-hexahydropyrrolo[1',2:4,5]pyrazino[2,3-c]pyridazin-8-yl)oxy)-4-methylpyridin-3-yl)methyl)piperazin-1-yl)-1-oxoisoindolin-2-yl)piperidine-2,6-dione;

(S)-3-(6-(44(5-(((6aR,8R)-6a-ethyl-2-(3-fluoro-2-hydroxyphenyl)-5,6,6a,7,8,9-hexahydropyrrolo[1',2':4,5]pyrazino [2,3-c]pyridazin-8-yl)oxy)-3-methyl pyrazin-2-yl)methyl)piperazin-1-yl)-1-oxoisoindolin-2-yl)piperidine-2,6-dione;

(S)-3-(6-(4-((6-(((6aR,8R)-2-(3-Fluoro-2-hydroxyphenyl)-6a-(fluoromethyl)-5,6,6a, 7,8,9-hexahydropyrrolo[1',2' 74, S]pyrazino[2,3-c]pyridazin-8-yl)oxy)-4-methyl pyridin-3-yl)methyl)piperazin-1-yl)-1-oxoisoindolin-2-yl)piperidine-2,6-dione;

5-((4-(2-((S)-2,6-dioxopiperidin-3-yl)-3-oxoisoindolin-5-yl)piperazin-1-yl)methyl) 2-(((6aR,8R)-6a-ethyl-2-(3-fluoro-2-hydroxyphenyl)-5,6,6a,7,8,9-hexahydropyrrolo [1',2':4,5]pyrazino[2,3-c]pyridazin-8-yl)oxy)-6-methylnicotinonitrile;

3-(6-(4-((6-(((6aR,8R)-6a-ethyl-2-(3-fluoro-2-hydroxyphenyl)-5,6,6a, 7,8,9-hexahydropyrrolo[1',2':4,5]pyrazino[2,3-c]pyridazin-8-yl)thio)-4-methylpyridin-3-yl)methyl)piperazin-1-yl)-1-oxoisoindolin-2-yl)piperidine-2,6-dione;

3-(6-(4-((6-((f 6aR,8R)-6a-ethyl-2-(3-fluoro-2-hydroxyphenyl)-5,6,6a,7,8,9-hexahydropyrrolo[1',2':4.5]pyrazino[2, 3-c]pyridazin-8-yl)oxy)-5-fluoro-4-methylpyridin-3-yl) methyl)piperazin-1-yl)-1-oxoisoindolin-2-yl)piperidine-2,6-dione;

3-(6-(4-((6-(((6aR,8R)-6a-ethyl-2-(3-fluoro-2-hydroxyphenyl)-5,6,6a, 7,8,9-hexahydropyrrolo[1',2':4,5]pyrazino[2,3-c]pyridazin-8-yl)oxy)-2,4-di methylpyridin-3-yl) methyl)piperazin-1-yl)-1-oxoisoindolin-2-yl)piperidine-2,6-dione;

3-(6-(4-((6-(((6aR,8R)-2-(3,5-difluoro-2-hydroxyphenyl)-6a-ethyl-5,6,6a,7,8,9-hexahydropyrrolo[1',2:4,5]pyrazino[2,3-c]pyridazin-8-yl)oxy)pyridin-3-yl)methyl)piperazin-1-yl)-1-oxoisoindolin-2-yl)piperidine-2,6-dione;

(S)-3-(6-(44(5-(((6aR,8R)-2-(3-fluoro-2-hydroxyphenyl)-6a-(fluoromethyl)-5,6,6a, 7,8,9-hexahydropyrrolo[1',2':4,5]pyrazino[2,3-c]pyridazin-8-yl)axy)-6-methyl pyrazin-2-yl)methyl)piperazin-1-yl)-1-oxoisoindolin-2-yl) piperidine-2,6-dione;

(S)-3-(6-(1-((5-(((6aR,8R)-2-(3-Fluoro-2-hydroxyphenyl)-6a-fluoromethyl)-5,6,6a,7,8,9-hexahydropyrrolo[1',2'74,S]pyrazino[2,3-c]pyridazin-8-yl)oxy)-6-methylpyrazin-2-yl)methyl)piperidin-4-yl)-1-oxoisoindolin-2-yl)piperidine-2,6-dione;

(S)-3-(6-(4-((5-(((6aS,8R)-2-(3-fluoro-2-hydroxyphenyl)-6a-(fluoromethyl)-5,6,6a,7,8,9-hexahydropyrrolo[1',2:4,5]pyrazino[2,3-c]pyridazin-8-yl)oxy)-6-methylpyrazin-2-yl)methyl)piperazin-1-yl)-1-oxoisoindolin-2-yl) piperidine-2,6-dione;

(S)-3-(6-(4-((6-ethyl-5-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)pyrazin-2-yl)methyl)piperazin-1-yl)-1-oxoisoindolin-2-yl) piperidine-2,6-dione;

(S)-3-(6-(1-((6-ethyl-5-((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)pyrazin-2-yl)methyl)piperidin-4-yl)-1-oxoisoindolin-2-yl) piperidine-2,6-dione;

(S)-3-(6-(4-((5-fluoro-6-(((6aS,8K)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-2-methylpyridin-3-yl)methyl)piperazin-1-yl)-1-oxoisoindolin-2-yl)piperidine-2,6-dione;

3-(6-(4-((5-fluoro-6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)pyridin-3-yl) methyl)piperazin-1-yl)-1-oxoisoindolin-2-yl)piperidine-2,6-dione;

(S)-3-(6-(4-((5-fluoro-6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione:

(S)-3-(6-(4-((5-(((6aR,8R)-6a-Ethyl-2-(3-fluoro-2-hydroxyphenyl)-5,6,6a,7,8,9-exahydropyrrolo[1',2':4,5]pyrazino[2,3-c]pyridazin-8-yl)oxy)-3-fluoropyridin-2-yl)methyl) piperazin-1-yl)-1-oxoisoindolin-2-yl)piperidine-2,6-dione;

(S)-3-(5-(4-((5-(116aS,8R)-6a-ethyl-2-(3-fluoro-2-hydroxyphenyl)-5,6,6a,7,8,9-hexahydropyrrolo[1',2:4,5]pyrazino[2,3-c]pyridazin-8-yl)oxy)-3-(trifluoromethyl)pyridin-2-yl)methyl)piperazin-1-yl)-1-oxoisoindolin-2-yl) piperidine-2,6-dione;

(S)-3-(5-(4-((5-(((6aS,8R)-6a-ethyl-2-(3-fluoro-2-hydroxyphenyl)-5,6,6a, 7,8,9-hexahydropyrrolo[1',2':4.5] pyrazino[2,3-c]pyridazin-8-yl)oxy)-3-methyl pyridin-2-yl)methyl)piperazin-1-yl)-1-oxoisoindolin-2-yl) piperidine-2,6-dione:

(S)-3-(6-(4-((2-(((6aR,8R)-2-(3-fluoro-2-hydroxyphenyl)-6a-methyl-5,6,6a,7,8,9-hexahydropyrrolo[1',2'74,S]pyrazino[2,3-c]pyridazin-8-yl)oxy)-4,6-dimethylpyrimidin-5-yl)methyl)piperazin-1-yl)-1-oxoisoindolin-2-yl)piperidine-2,6-dione;

5-((4-(2-((S)-2,6-dioxopiperidin-3-yl)-3-oxoisoindolin-5-yl)piperazin-1-yl)methyl)-2-(((6aS,8R)-2-(3-fluoro-2-hydroxyphenyl)-6a-methyl-5,6,6a,7,8,9-hexahydropyrrolo[1',2':4,5]pyrazino[2,3]-pyridazin-8-yl)oxy) isonicotinonitrile;

(S)-3-(6-(1-((2-(((6aR,8R)-2-(3-fluoro-2-hydroxyphenyl)-6a-methyl-5,6,6a,7,8,9-hexahydropyrrolo[1',2':4.5] pyrazino[2,3-c]pyridazin-8-yl)oxy)-4-methylpyrimidin-5-yl)methyl)piperidin-4-yl)-1-oxoisoindolin-2-yl) piperidine-2,6-dione;

(S)-3-(6-(1-((2-(((6aR,8R)-2-(3-fluoro-2-hydroxyphenyl)-6a-methyl-5,6,6a, 7,8,9-hexahydropyrrolo[1',2':4,5] pyrazino[2,3-c]pyridazin-8-yl)oxy)-4,6-dimethylpyrimidin-5-yl)methyl)piperidin-4-yl)-1-oxoisoindolin-2-yl) piperidine-2,6-dione;

(S)-3-(6-(4-((5-(((6aS,8R)-2-(3-fluoro-2-hydroxyphenyl)-6a-methyl-5,6,6a,7,8,9-hexahydropyrrolo[1',2:4,5] pyrazino[2,3-c]pyridazin-8-yl)oxy)pyrazin-2-yl)methyl) piperazin-1-yl)-1-oxoisoindolin-2-yl)piperidine-2,6-dione;

(S)-3-(6-(4-((5-(((6aS,8R)-2-(3-fluoro-2-hydroxyphenyl)-6a-methyl-5,6,6a, 7,8,9-hexahydropyrrolo[1',2':4.5] pyrazino[2,3-c]pyridazin-8-yl)oxy)-3,6-dimethyl pyridin-2-yl)methyl)piperazin-1-yl)-1-oxoisoindolin-2-yl) piperidine-2,6-dione:

(S)-3-(6-(4-((5-(((6aR,8R)-2-(3-fluoro-2-hydroxyphenyl)-6a-methyl-5,6,6a, 7,8,9-hexahydropyrrolo[1',2':4,5] pyrazino[2,3-c]pyridazin-8-yl)oxy)-3-methylpyridin-2-yl)methyl)piperazin-1-yl)-1-oxoisoindolin-2-yl) piperidine-2,6-dione;

(S)-3-(6-(4-((5-(((6aS,8R)-2-(3-fluoro-2-hydroxyphenyl)-6a-methyl-5,6,6a,7,8,9-hexahydropyrrolo[1',2':4,5] pyrazino[2,3-c]pyridazin-8-yl)oxy)-3-methylpyridin-2-yl)methyl)piperazin-1-yl)-1-oxoisoindolin-2-yl) piperidine 2,6-dione;

(S)-3-(6-(4-((6-((6aS,8R)-2-(3-fluoro-2-hydroxyphenyl)-6a-methyl-5,6,6a,7,8,9-hexahydropyrrolo[1',2:4,5] pyrazino[2,3-c]pyridazin-8-yl)oxy)-5-methylpyridin-3-yl)methyl)piperazin-1-yl)-1-oxoisoindolin-2-yl) piperidine-2,6-dione;

3-(6-(4-((6-(((6aR,8R)-6a-(difluoromethyl)-2-(3-fluoro-2-hydroxy phenyl)-5,6,6a,7,8,9-hexahydropyrrolo[1',2':4,5] pyrazino[2,3-c]pyridazin-8-yl)oxy)-5-fluoropyridin-3-yl) methyl)piperazin-1-yl)-1-oxoisoindolin-2-yl)piperidine-2,6-dione;

3-(6-(4-((5-chloro-6-(((6aR,8R)-6a-(difluoromethyl)-2-(3-fluoro-2-hydroxyphenyl)-5,6,6a,7,8,9-hexahydropyrrolo [1',2':4,5]pyrazino[2,3-c]pyridazin-8-yl)oxy)pyridin-3-yl)methyl)piperazin-1-yl)-1-oxoisoindolin-2-yl) piperidine 2,6-dione;

(S)-3-(6-(4-((6-((16aR,8R)-6a-(di fluoromethyl)-2-(3-fluoro-2-hydroxy phenyl)-5,6,6a,7,8,9-hexahydropyrrolo [1',2:4,5]pyrazino[2,3-c]pyridazin-8-yl)oxy)-4,5-dimethylpyridin-3-yl)methyl)piperazin-1-yl)-1-oxoisoindolin-2-yl)piperidine-2,6-dione;

(S)-3-(6-(4-((6-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-2,5-dimethylpyridin-3-yl)methyl)piperazin-1-yl)-1-oxoisoindolin-2-yl) piperidine-2,6-dione;

3-(6-(1-((6-(((6aR,8R)-6a-(difluoromethyl)-2-(3-fluoro-2-hydroxyphenyl)-5,6,6a,7,8,9-hexahydropyrrolo[1',2'4, S]pyrazino[2,3-c]pyridazin-8-yl)oxy)-5-fluoropyridin-3-yl)methyl)piperidin-4-yl)-1-oxoisoindolin-2-yl)piperidine-2,6-dione;

(S)-3-(6-(1-((6-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazine-8-yl)oxy)-5-fluoro-4-methylpyridin-3-yl)methyl)piperidin-4-yl)-1-oxoisoindolin-2-yl)piperidine-2,6-dione;

(S)-3-(6-(1-((6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)pyridin-3-yl)methyl)piperidin-4-yl)-1-oxoisoindolin-2-yl)piperidine-2,6-dione;

(S)-3-(6-(1-((5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-6-methylpyrazin-2-yl)methyl)piperidin-4-yl)-1-oxoisoindolin-2-yl)piperidine-2,6-dione;

(S)-3-(6-(1-((5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-4-methylpyridin-2-yl)methyl)piperidin-4-yl)-1-oxoisoindolin-2-yl)piperidine-2,6-dione;

(S)-3-(6-(1-((6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione;

(S)-3-(6-(1-((5-(((6aS,8R)-6a-(difluoromethyl)-2-(2-hydroxy-3-methylphenyl)-5,6,6a,7,8,9-hexahydropyrrolo[1',2':4,5]pyrazino[2,3-c]pyridazin-8-yl)oxy)-4-methylpyridin-2-yl)methyl)piperidin-4-yl)-1-oxoisoindolin-2-yl)piperidine-2,6-dione;

(S)-3-(6-(1-((5-(((6aR,8R)-6a-ethyl-2-(2-hydroxy-3-methylphenyl)-5,6,6a,7,8,9-hexahydropyrrolo[1',2':4,5]pyrazino[2,3-c]pyridazin-8-yl)oxy)-3,4-dimethylpyridin-2-yl)methyl)piperidin-4-yl)-1-oxoisoindolin-2-yl)piperidine-2,6-dione;

(S)-3-(6-(1-((2-(((6aS,8R)-6a-ethyl-2-(2-hydroxy-3-methylphenyl)-5,6,6a,7,8,9-hexahydropyrrolo[1',2':4,5]pyrazino[2,3-c]pyridazin-8-yl)oxy)-4,6-dimethylpyrimidin-5-yl)methyl)piperidin-4-yl)-1-oxoisoindolin-2-yl)piperidine-2,6-dione;

(S)-3-(6-(1-((5-(((6aS,8R)-6a-ethyl-2-(2-hydroxy-3-methylphenyl)-5,6,6a,7,8,9-hexahydropyrrolo[1',2':4,5]pyrazino[2,3-c]pyridazin-8-yl)oxy)-3-methylpyridin-2-yl)methyl)piperidin-4-yl)-1-oxoisoindolin-2-yl)piperidine-2,6-dione;

(S)-3-(6-(1-((3-chloro-5-(((6aS,8R)-2-(3-chloro-2-hydroxyphenyl)-6a-ethyl-5,6,6a,7,8,9-hexahydropyrrolo[1',2':4,5]pyrazino[2,3-c]pyridazin-8-yl)oxy)pyridin-2-yl)methyl)piperidin-4-yl)-1-oxoisoindolin-2-yl)piperidine-2,6-dione;

(S)-3-(6-(1-((6-(((6aR,8R)-2-(3-chloro-2-hydroxyphenyl)-6a-ethyl-5,6,6a,7,8,9-hexahydropyrrolo[1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione;

(S)-3-(6-(1-((5-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-3-fluoropyridin-2-yl)methyl)piperidin-4-yl)-1-oxoisoindolin-2-yl)piperidine-2,6-dione;

(S)-3-(6-(1-((2-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-4,6-dimethylpyrimidin-5-yl)methyl)piperidin-4-yl)-1-oxoisoindolin-2-yl)piperidine-2,6-dione;

(S)-3-(6-(1-((5-(((6aS,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)pyrazin-2-yl)methyl)piperidin-4-yl)-1-oxoisoindolin-2-yl)piperidine-2,6-dione;

(S)-3-(6-(1-((5-(((6aS,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-3-methylpyridin-2-yl)methyl)piperidin-4-yl)-1-oxoisoindolin-2-yl)piperidine-2,6-dione;

(S)-3-(6-(1-((2-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-4-methylpyrimidin-5-yl)methyl)piperidin-4-yl)-1-oxoisoindolin-2-yl)piperidine-2,6-dione;

3-(6-(1-((6-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione;

3-(6-(1-((6-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione;

or a pharmaceutically acceptable salt thereof.

It will be apparent that the compounds of Formula I, including all subgenera described herein, may have multiple stereogenic centers. As a result, there exist multiple stereoisomers (enantiomers and diastereomers) of the compounds of Formula I (and subgenera described herein). The present disclosure contemplates and encompasses each stereoisomer of any compound of Formula I (and subgenera described herein), as well as mixtures of said stereoisomers.

Pharmaceutically acceptable salts and solvates of the compounds of Formula I (including all subgenera described herein) are also within the scope of the disclosure.

Isotopic variants of the compounds of Formula I (including all subgenera described herein) are also contemplated by the present disclosure.

Pharmaceutical Compositions and Methods of Administration

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds of the invention is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5,3 g, 3.5,4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (e.g., a compound of the disclosure) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form.

Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period.

For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (e.g., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof, polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-lOoleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%), 100%, or up to about 200%> by weight, based on the combined weight of the drug, and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g., Transdermal) Delivery

In some embodiments, the invention provides a pharmaceutical composition for transdermal delivery containing a compound of the present invention and a pharmaceutical excipient suitable for transdermal delivery.

Compositions of the present invention can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present invention can be affected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. Compounds can also be administered intraadiposally or intrathecally.

In some embodiments, the compounds or pharmaceutical composition of the present invention are administered by intravenous injection.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, a compound of the invention is administered in a single dose.

Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses.

Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

Methods of Use

The method typically comprises administering to a subject a therapeutically effective amount of a compound of the invention. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

In certain embodiment, the present invention provides a pharmaceutical composition comprising a compound of bispecific formula, or pharmaceutically acceptable salt thereof.

In certain embodiment, the present invention provides a pharmaceutical composition comprising a compound of bispecific formula for use in degrading a target protein in a cell.

In certain embodiment, a method of degrading a target protein comprising administering to a cell therapeutically effective amount of a bispecific compound, or pharmaceutically acceptable salt, wherein the compound is effective for degrading the target protein.

In certain embodiment, the present invention provides a pharmaceutical composition comprising a compound of bispecific formula, for use in treating or preventing of a disease or disorder in which SMARCA2 and/or SMARCA4 plays a role.

In certain embodiment, the present invention provides a pharmaceutical composition comprising a compound of bispecific formula, for use in treating or preventing of a disease or disorder in which SWI/SNF mutations plays a role.

In certain embodiment, target proteins are SMARCA2, SMARCA4 and/or PB1.

In certain embodiment, target protein complex is SWI/SNF in a cell.

In certain embodiment, diseases or disorders dependent on SMARCA2 or SMARCA4 include cancers.

In certain embodiment, diseases or disorders dependent on SWI/SNF complex include cancers.

Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas.

In certain embodiments, the cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

In certain further embodiment, the cancer is a SMARCA2 and/or SMARAC4-dependent cancer.

In certain embodiment, the present invention provides a pharmaceutical composition comprising a compound of bispecific formula for use in the diseases or disorders dependent upon SMARCA2 and/or SMARCA4 is cancer.

Compounds of the disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other aspects, compounds of the disclosure, as well as pharmaceutical compositions comprising them, can be administered to treat any of the described diseases, alone or in combination with one or more other agents.

In other methods, the compounds of the disclosure, as well as pharmaceutical compositions comprising them, can be administered in combination with agonists of nuclear receptors agents.

In other methods, the compounds of the disclosure, as well as pharmaceutical compositions comprising them, can be administered in combination with antagonists of nuclear receptors agents.

In other methods, the compounds of the disclosure, as well as pharmaceutical compositions comprising them, can be administered in combination with an anti-proliferative agent.

Combination Therapies

For treating cancer and other proliferative diseases, the compounds of the invention can be used in combination with chemotherapeutic agents, agonists or antagonists of nuclear receptors, or other anti-proliferative agents. The compounds of the invention can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, all-trans retinoic acid, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinstat and zoledronate.

In some embodiments, the compounds of the invention can be used in combination with a therapeutic agent that targets an epigenetic regulator. Examples of epigenetic regulators include bromodomain inhibitors, the histone lysine methyltransferase inhibitors, histone arginine methyl transferase inhibitors, histone demethylase inhibitors, histone deacetylase inhibitors, histone acetylase inhibitors, and DNA methyltransferase inhibitors. Histone deacetylase inhibitors include, e.g., vorinostat. Histone arginine methyl transferase inhibitors include inhibitors of protein arginine methyltransferases (PRMTs) such as PRMT5, PRMT1 and PRMT4. DNA methyltransferase inhibitors include inhibitors of DNMT1 and DNMT3.

For treating cancer and other proliferative diseases, the compounds of the invention can be used in combination with targeted therapies, including JAK kinase inhibitors (e.g. Ruxolitinib), PI3 kinase inhibitors including PI3K-delta selective and broad spectrum PI3K inhibitors, MEK inhibitors, Cyclin Dependent kinase inhibitors, including CDK4/6 inhibitors and CDK9 inhibitors, BRAF inhibitors, mTOR inhibitors, proteasome inhibitors (e.g. Bortezomib, Carfilzomib), HDAC inhibitors (e.g. panobinostat, vorinostat), DNA methyl transferase inhibitors, dexamethasone, bromo and extra terminal family member (BET) inhibitors, BTK inhibitors (e.g. ibrutinib, acalabrutinib), BCL2 inhibitors (e.g. venetoclax), dual BCL2 family inhibitors (e.g. BCL2/BCLxL), PARP inhibitors, FLT3 inhibitors, or LSD1 inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), or PDR001. In some embodiments, the anti-PD-1 monoclonal antibody is nivolumab or pembrolizumab. In some embodiments, the anti-PD1 antibody is pembrolizumab. In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, durvalumab, or BMS-935559. In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Compounds of the invention can be prepared using numerous preparatory reactions known in the literature. The Schemes below provide general guidance in connection with preparing the compounds of the invention. One skilled in the art would understand that the preparations shown in the Schemes can be modified or optimized using general knowledge of organic chemistry to prepare various compounds of the invention. Example synthetic methods for preparing compounds of the invention are provided in the Schemes below.

The following Examples are provided to illustrate some of the concepts described within this disclosure. While the Examples are considered to provide an embodiment, it should not be considered to limit the more general embodiments described herein.

EXAMPLES

General Synthetic Procedures

The compounds described herein may be prepared according to the following synthetic schemes and general synthetic procedures.

Scheme 1

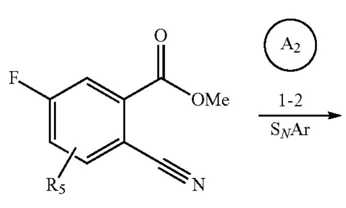

1-1

-continued

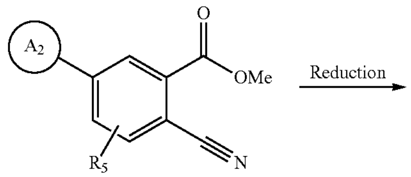

1-3

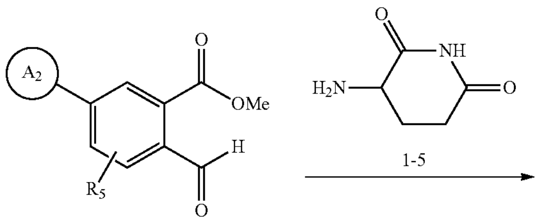

1-4

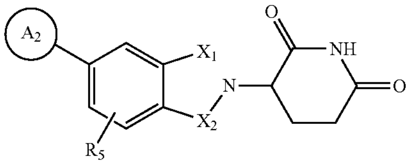

1-6

Intermediates 1-6, where $X_1$=CO and $X_2$=$CH_2$, can be synthesized according to the route described Scheme 1. $S_NAr$ between fluorophenyl 1-1 and amines 1-2 utilizing an appropriate base (e.g., DIPEA, $K_2CO_3$, etc.) and heating in a suitable solvent (DMF, DMSO, THF, etc.) can afford compounds 1-3. Reduction of the nitrile in 1-3 can be achieved under appropriate conditions (e.g., Raney Nickel) to yield 1-4. Reductive amination and cyclization of 1-4 with 1-5 (e.g., DIPEA followed by AcOH and sodium triacetoxyborohydride) provides intermediates 1-6.

Scheme 2

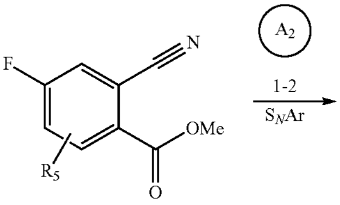

2-1

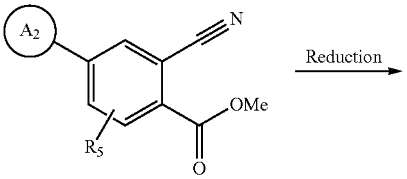

2-2

-continued

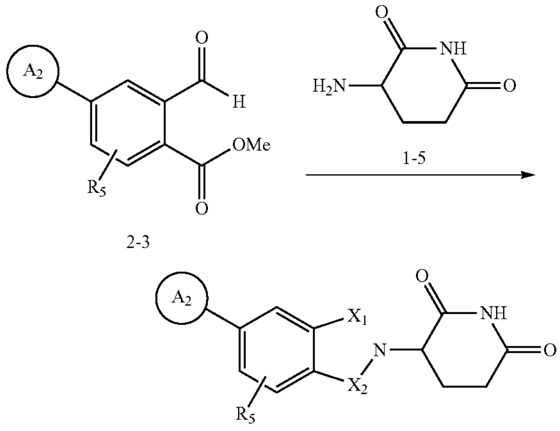

2-3

1-6

Intermediates 1-6, where $X_1$=$CH_2$ and $X_2$=CO, can be synthesized according to the route described Scheme 2. $S_NAr$ between fluorophenyl 2-1 and amines 1-2 utilizing an appropriate base (e.g., DIPEA, $K_2CO_3$, etc.) and heating in a suitable solvent (DMF, DMSO, THF, etc.) can afford compounds 2-2. Reduction of the nitrile in 2-2 can be achieved under appropriate conditions (e.g., Raney Nickel) to yield 2-3. Reductive amination and cyclization of 2-3 with 1-5 (e.g., DIPEA followed by AcOH and sodium triacetoxyborohydride) provides intermediates 1-6.

Scheme 3

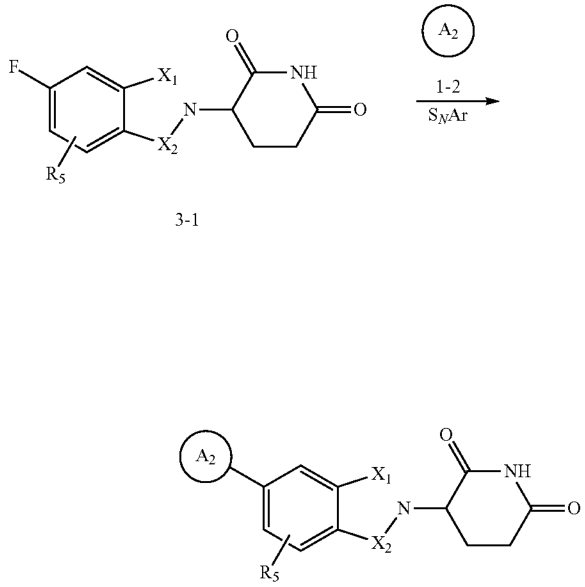

3-1

1-6

Intermediates 1-6, where $X_1$ and $X_2$=CO, can be synthesized according to the route described in Scheme 3. $S_NAr$ between fluorophenyl 3-1 and amines 1-2 utilizing an appropriate base (e.g., DIPEA, $K_2CO_3$, etc.) and heating in a suitable solvent (DMF, DMSO, THF, etc.) can afford compounds 1-6.

Scheme 4

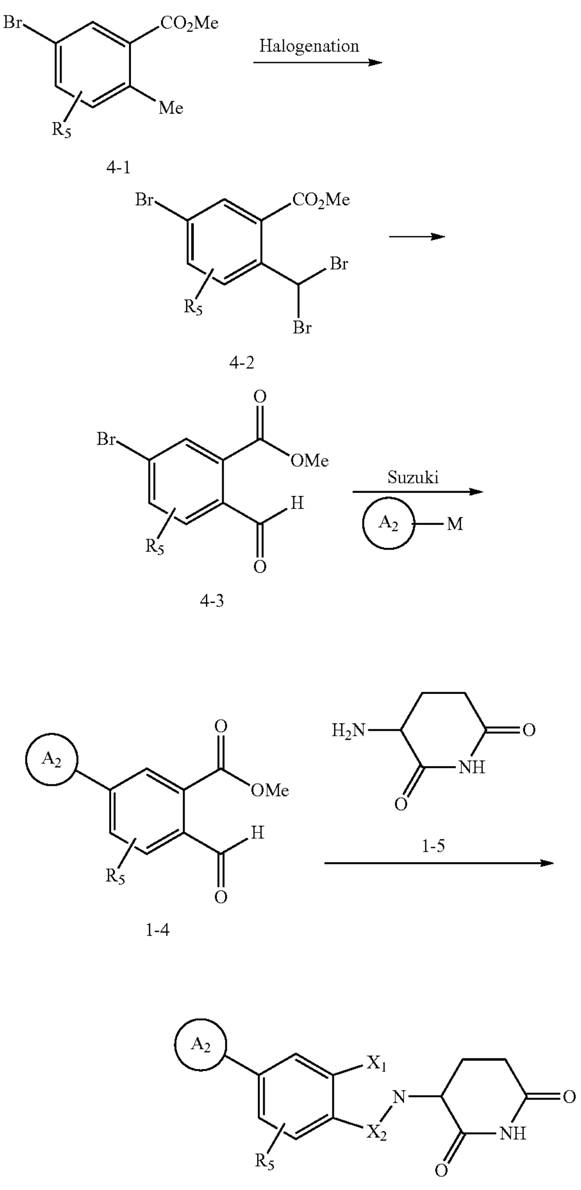

4-1

4-2

4-3

1-4

1-6

Intermediates 1-6, where $X_1$=CO and $X_2$=$CH_2$, can be synthesized according to the route described in Scheme 4. Halogenation of 4-1 (e.g., NBS and peroxide, etc.) in a suitable solvent (DCE, etc.) can afford compounds 4-2, 4-2 can be converted to 4-3 utilizing an appropriate oxidizing agent (e.g., $AgNO_3$ in water and IPA, etc.). Coupling of halides 4-3 with $A_2$ (wherein M=$B(OH)_2$, $B(OR)_2$, or $SnR_3$) under standard cross-coupling conditions (e.g., in the presence of a palladium catalyst such as tetrakis(triphenylphosphine)palladium(0) or [1,1'-bis(diphenyl-phosphino)ferrocene] dichloropalladium (II) and a base e.g. CsF, $Na_2CO_3$, or $Cs_2CO_3$) in a suitable solvent such as dioxane or DMF, with or without water as cosolvent affords intermediates 1-4. The reductive amination and cyclization of 1-4 with 1-5 (e.g., DIPEA followed by AcOH and sodium triacetoxyborohydride) affords compound 1-6.

Scheme 5

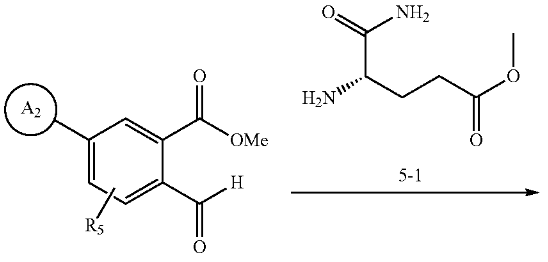

1-4

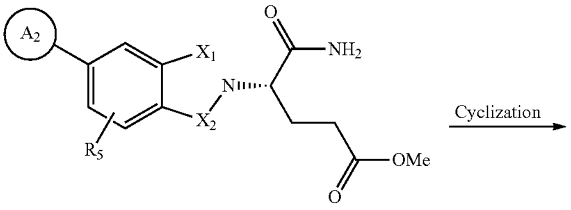

5-2

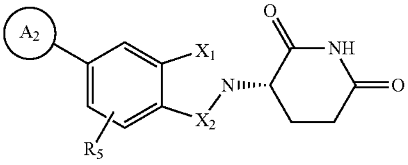

5-3

Enantiomerically pure intermediates 5-3, where $X_1$=CO and $X_2$=$CH_2$, can be synthesized according to the route described in Scheme 5. The reductive amination and cyclization of 1-4 with 5-1 (e.g., DIPEA followed by AcOH and sodium triacetoxyborohydride) affords compound 5-2. Cyclization of 5-2 utilizing an appropriate base such as KOtBu then provides intermediates 5-3.

Scheme 6

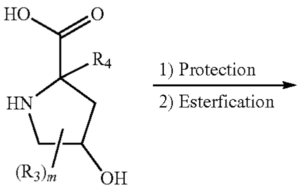

6-1

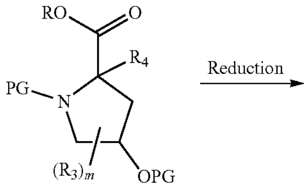

6-2

-continued

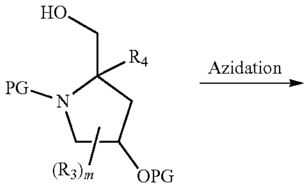

6-3

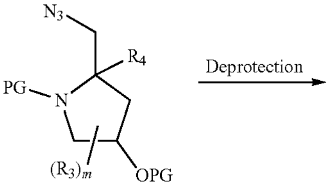

6-4

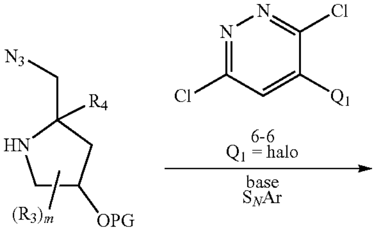

6-5

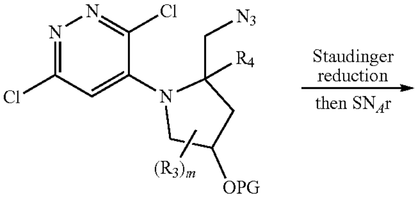

6-7

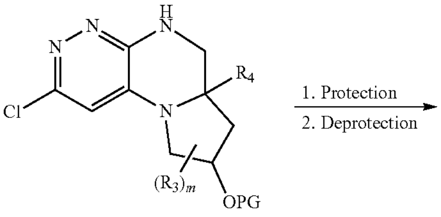

6-8

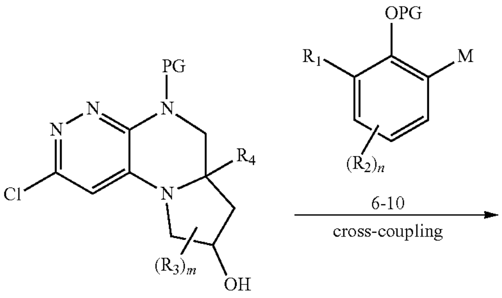

6-9

-continued

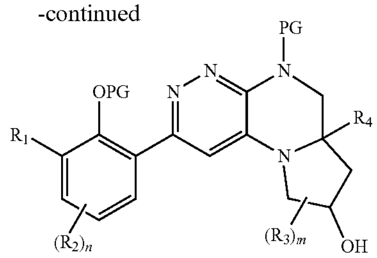

6-11

Tricyclic intermediates 6-11, where $R_4$=H, can be synthesized according to the route described in Scheme 6. Protection of the —NH and —OH groups of commercially available starting materials 6-1 with an appropriate protecting group (e.g., Boc, SEM, Bn, TBDMS, etc.), followed by esterification, affords esters 6-2. Conversion of 6-2 to 6-3 can be achieved with reducing agents (e.g., $LiAlH_4$, DIBAL-H, etc.). Substitution of the hydroxyl group in 6-3 by conversion to a leaving group under appropriate conditions (e.g., $TsCl/Et_3N$, $MsCl/Et_3N$, etc.) followed by substitution (e.g., $NaN_3$) affords azides 6-4. Alternatively, compound 6-3 can be converted to an azide 6-4 under Mitsunobu conditions ($((PhO)_2PON_3$, DEAD in THF). Deprotection of 6-4 (e.g., TFA or HCl for Boc deprotection) gives amines 6-5. $S_NAR$ reaction between amines 6-5 and pyridazines 6-6 in the presence of a base, such as DIPEA, affords intermediates 6-7. Reduction of the azido group in compounds 6-7 via Staudinger reduction or hydrogenation, followed by intramolecular cyclization provides compounds 6-8. Protection of the —NH group and deprotection of the-OPG then gives compounds 6-9. Coupling of halides 6-9 with phenols 6-10 (wherein M=$B(OH)_2$, $B(OR)_2$, or $SnR_3$) under standard cross-coupling conditions (e.g., in the presence of a palladium catalyst such as tetrakis(triphenylphosphine)palladium (0) or [1,1'-bis(diphenylphosphino)-ferrocene]dichloropalladium (II) and a base e.g. CsF, $Na_2CO_3$, or $Cs_2CO_3$) in a suitable solvent such as dioxane or DMF, with or without water as cosolvent affords intermediates 6-11.

Scheme 7

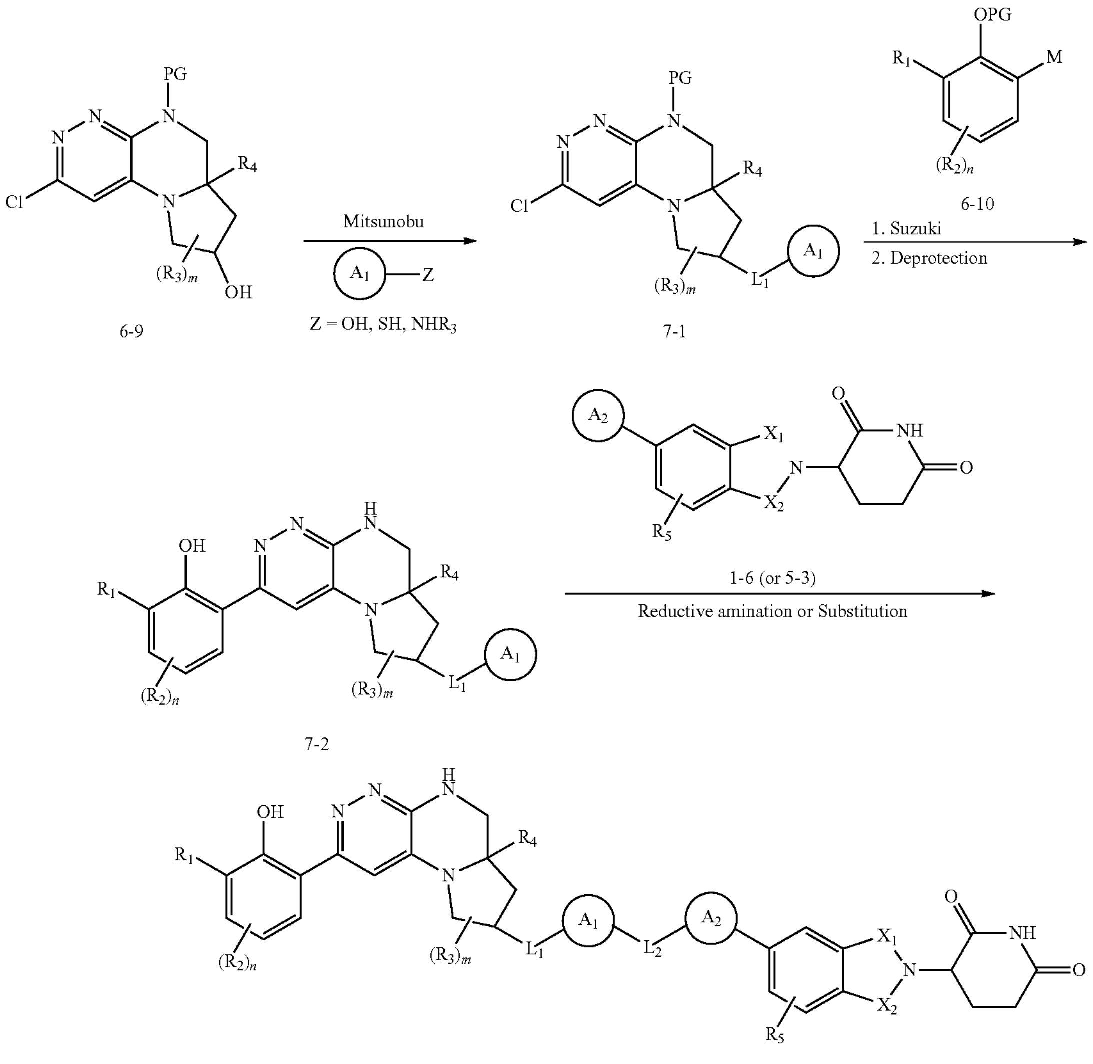

6-9

7-1

6-10

7-2

Formula (I)

The compounds of the Formula (I) can also be synthesized according to the route described in Scheme 7. Mitsunobu reaction of the alcohol in compounds 6-9 with $A_1$, where Z═SH, OH, or $NHR_3$, yields compound 7-1. Cross-coupling of halides 7-1 with phenols 6-10, where the phenol is optionally protected, followed by deprotection, affords intermediates 7-2. Reaction of 7-2 with 1-6 (or 5-3), either through reductive amination or substitution affords compounds of the Formula (I).

Scheme 8

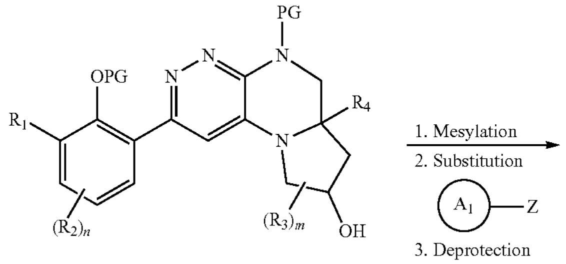

6-11

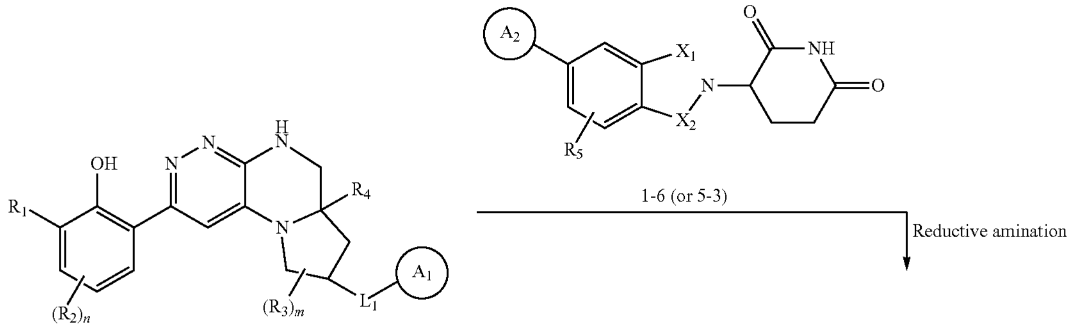

7-2

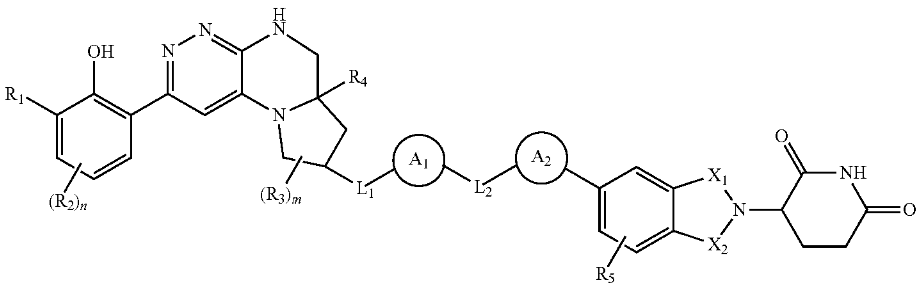

Formula (I)

The compounds of the Formula (I) can also be made according to the route described in Scheme 8. Mesylation of the alcohol in compounds 6-11 followed by substitution with $A_1$ and deprotection yields compound 7-2. Subsequent reductive amination of 7-2 with 1-6 (or 5-3) affords compounds of the Formula (I).

Scheme 9

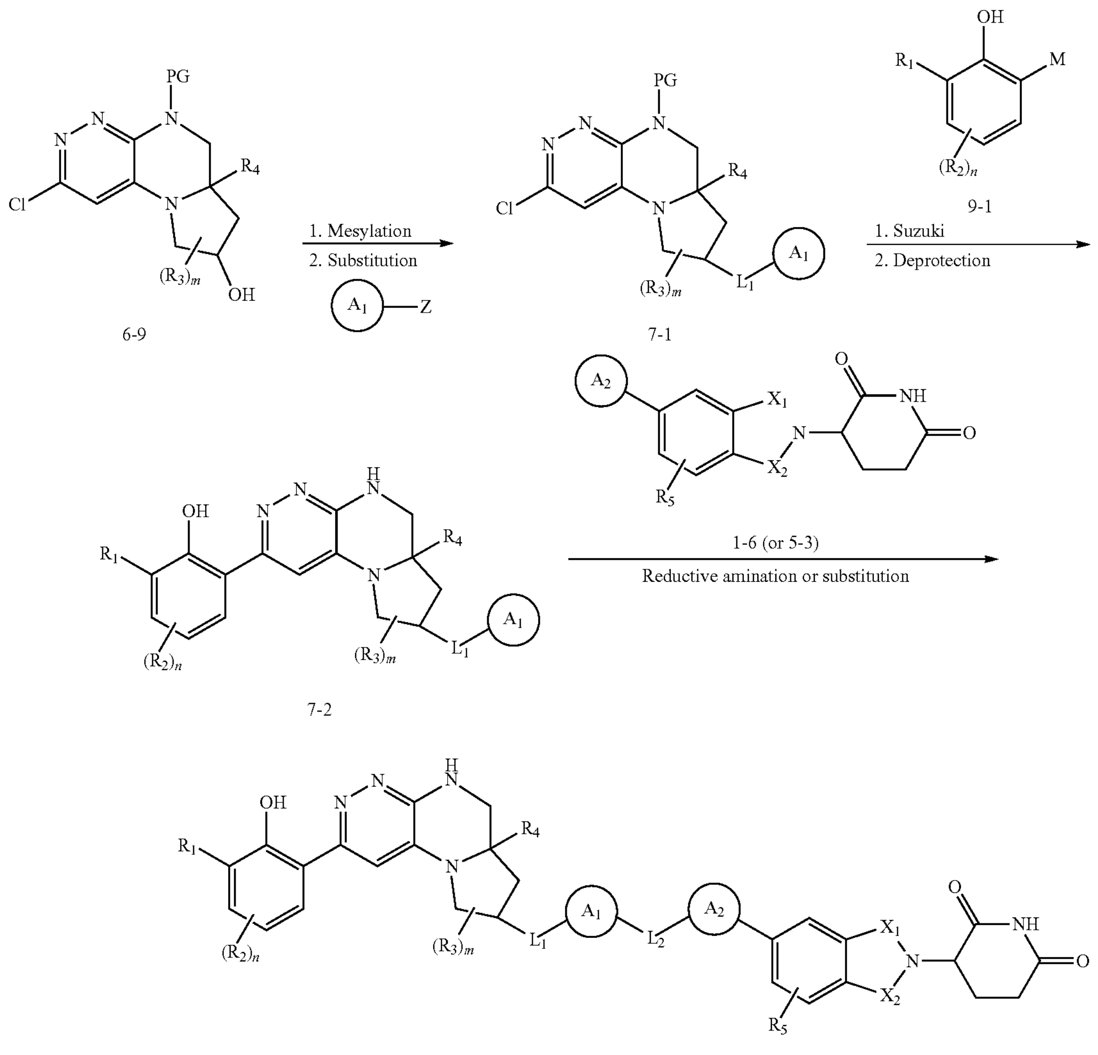

Formula (I)

The compounds of the Formula (I) can also be made according to the route described in Scheme 9. Mesylation of the alcohol in compounds 6-9, followed by substitution with $A_1$, yields compound 7-1. Cross coupling of halides 7-1 with phenols 9-1, followed by deprotection, affords intermediates 7-2. Reaction of intermediates 7-2 with 1-6 (or 5-3), either through reductive amination or substitution affords compounds of the Formula (I).

Scheme 10

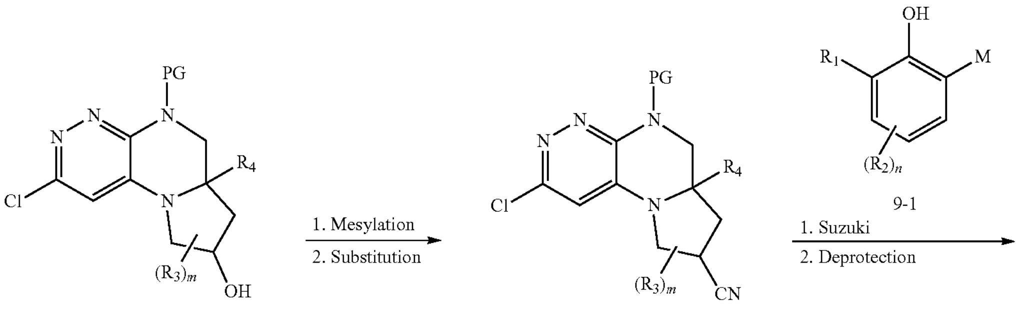

6-9

10-1

-continued

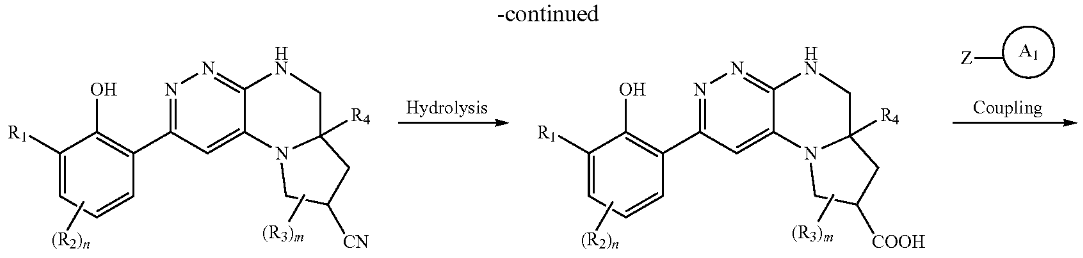

10-2 10-3

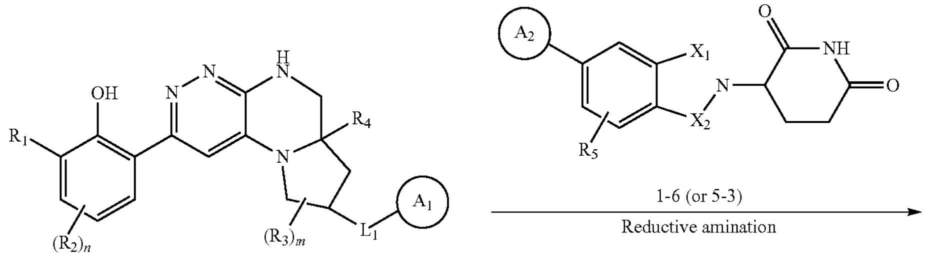

10-4

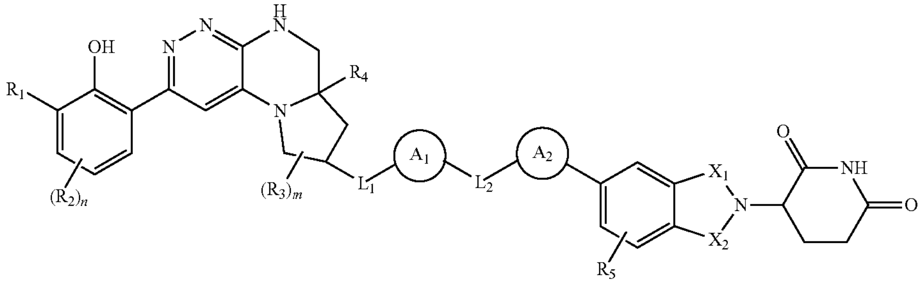

Formula (I)

The compounds of the Formula (I) can also be made according to the route described in Scheme 10. Mesylation of the alcohol in compounds 6-9 followed by substitution with cyanide (e.g., NaCN, KCN) yields nitriles 10-1. Cross-coupling of 10-1 with phenols 9-1, followed by deprotection, affords intermediates 10-2. Hydrolysis of the nitrile in 10-2, followed by amide coupling (e.g., HATU, DIPEA in DMF) provides compounds 10-4 (where $L_1$=CO). Reaction of 10-4 with 1-6 (or 5-3), through reductive amination affords compounds of the Formula (I).

Scheme 11

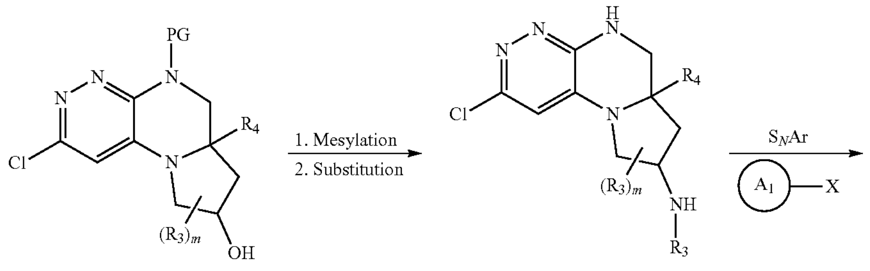

6-9 11-1

-continued

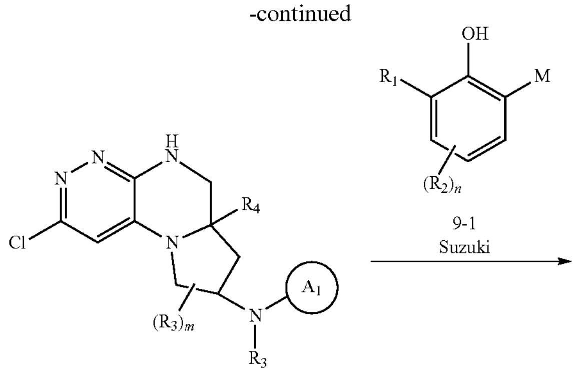

11-2

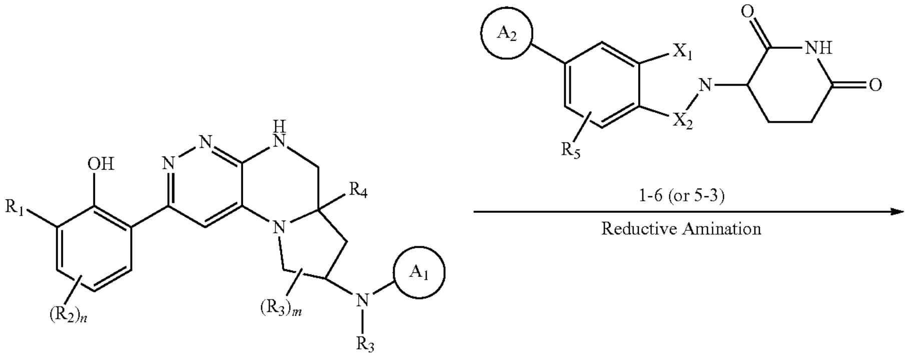

11-3

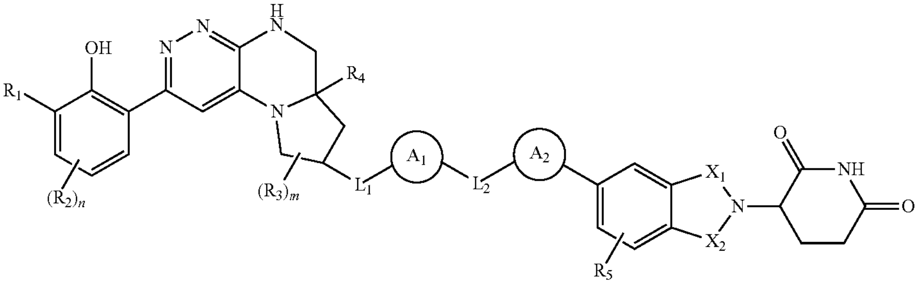

Formula (I)

Compounds of the Formula (I) can also be synthesized according to the route described in Scheme 11. Mesylation of the alcohol in compounds 6-9 followed by substitution with $NH_2R_3$ yields amines 11-1. $S_NAr$ of 11-1 with $A_1$ (where X=halogen) affords compounds 11-2. Cross-coupling of 11-2 with phenols 9-1 then provides intermediates 11-3. Reaction of 11-3 with 1-6 (or 5-3), through reductive amination affords compounds of the Formula (I).

Scheme 12

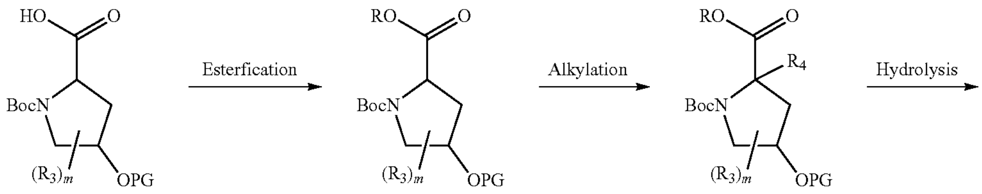

12-1 12-2 12-3

-continued

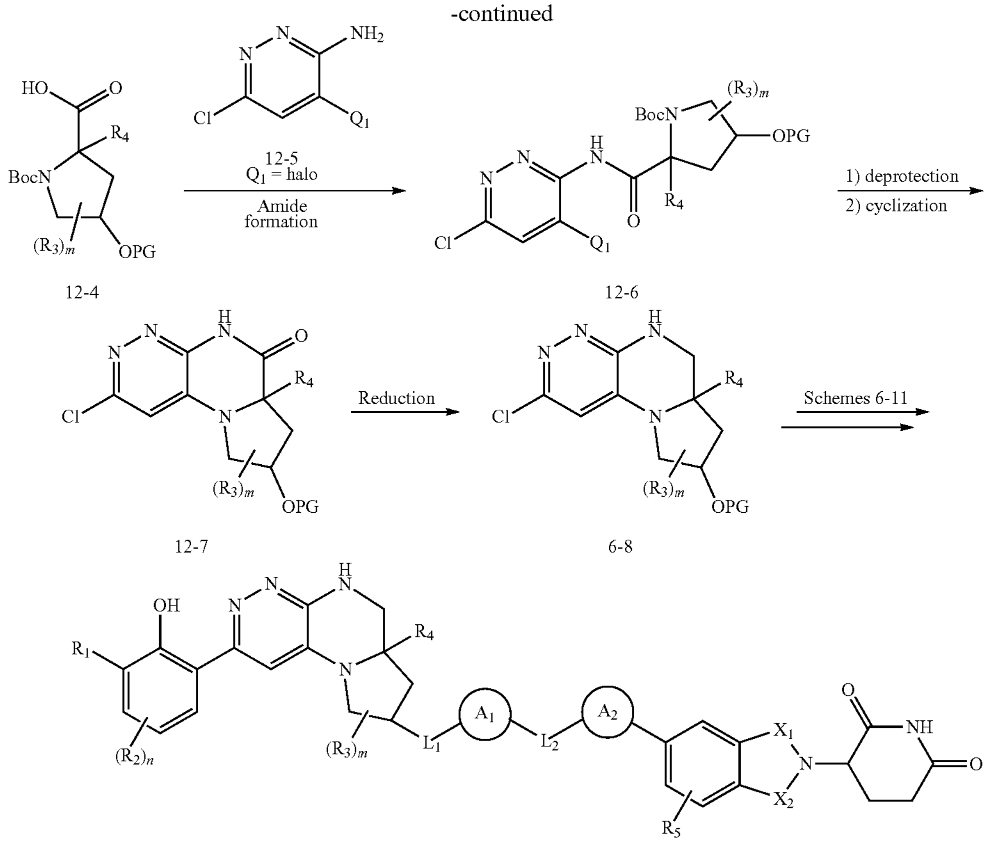

12-4 12-6 12-7 6-8

Formula (I)

Compounds of the Formula (I) wherein $R_4$≠H can be synthesized according to the route outlined in Scheme 12. Esterification of commercially available acids 12-1 followed by alkylation provides compounds 12-3, which can be hydrolyzed to obtain 12-4. Amide formation with 12-5 leads to intermediates 12-6, which can undergo deprotection and cyclization to afford tricycles 12-7. Reduction of the amide gives amines 6-8 (wherein $R_4$≠R), which can subsequently be converted to compounds of the Formula (I) via the steps outlined in Schemes 6-11.

Intermediate 1: tert-butyl (6aR,8S)-2-chloro-8-hydroxy-6a,7,8,9-tetrahydropyrrolo [1',2':4,5]pyrazino [2,3-c]pyridazine-5(6H)-carboxylate

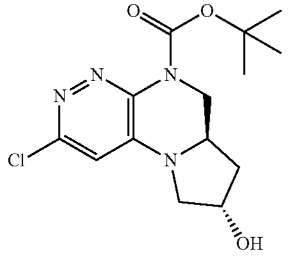 [SMILES: CC(C)(C)OC(=O)N1C[C@H]2C[C@H](O)CN2c2cc(Cl)nnc21]

Step 1: (2R,4S)-1-(tert-butoxycarbonyl)-4-((tert-butyldimethylsilyl)oxy)pyrrolidine-2-carboxylic acid

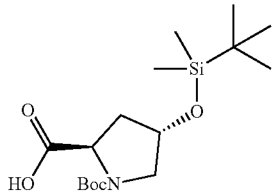 [SMILES: CC(C)(C)OC(=O)N1C[C@@H](O[Si](C)(C)C(C)(C)C)C[C@@H]1C(=O)O]

A round-bottomed flask containing a solution of (2R,4S)-1-(tert-butoxycarbonyl)-4-hydroxypyrrolidine-2-carboxylic acid (1.0 g, 4.3 mmol) and imidazole (1.47 g, 21.6 mmol) in DCM (7 mL) and DMF (1.4 mL) was charged with tert-butyldimethylsilyl chloride (1.43 g, 9.51 mmol). The reaction mixture was stirred at rt for 18 h, then poured into water, extracted with DCM (25 mL), and concentrated under reduced pressure. The residue was dissolved in 20% MTBE/hexanes (v/v) (50 mL), washed with brine and concentrated. The residue was dissolved in MeOH (7 mL) and THF (7 mL). Lithium hydroxide (176 mg) in water (9 mL) was added and the mixture was stirred at rt for three hours. The mixture was poured into water, acidified to pH~2 with 1 N HCl, extracted with 20% MTBE/hexanes (v/v) (3×50 mL), and washed with brine (50 mL). The organic fraction was dried with $MgSO_4$, filtered and concentrated under reduced pressure to give (2R,4S)-1-(tert-butoxycarbonyl)-4-((tert-butyldimethylsilyl)oxy)pyrrolidine-2-carboxylic acid (assumed quantitative yield, 4.3 mmol). LCMS calcd for $C_{11}H_{24}NO_3Si$ (M+2H-Boc)+m/z: 246.2; Found: 246.1.

Step 2: tert-butyl (2R,4S)-4-((tert-butyldimethylsilyl)oxy)-2-(hydroxymethyl)pyrrolidine-1-carboxylate

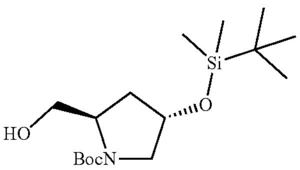 [SMILES: CC(C)(C)OC(=O)N1C[C@@H](O[Si](C)(C)C(C)(C)C)C[C@@H]1CO]

A round-bottomed flask containing a solution of (2R,4S)-1-(tert-butoxycarbonyl)-4-((tert-butyldimethylsilyl)oxy) pyrrolidine-2-carboxylic acid (1.5 g, 4.3 mmol) in THE (16 mL) at 0° C. was charged with $BH_3 \cdot SMe_2$ (0.82 mL, 8.6 mmol) dropwise. The solution was allowed to warm to rt and stir for 24 h. The reaction was quenched with saturated aqueous $NH_4Cl$, extracted with EtOAc (2×25 mL), washed with brine (25 mL), dried with $MgSO_4$, filtered, and concentrated under reduced pressure to give tert-butyl (2R,4S)-4-((tert-butyldimethylsilyl)oxy)-2-(hydroxy-methyl)pyrrolidine-1-carboxylate (assumed quantitative yield, 4.3 mmol). LCMS calcd for $C_{12}H_{26}NO_4Si$ $(M+2H-tBu)^+$m/z: 276.2; Found: 276.0.

Step 3: tert-butyl (2R,4S)-4-((tert-butyldimethylsilyl)oxy)-2-((tosyloxy)methyl)pyrrolidine-1-carboxylate

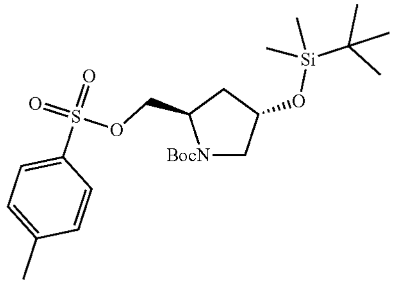 [SMILES: Cc1ccc(S(=O)(=O)OC[C@H]2C[C@H](O[Si](C)(C)C(C)(C)C)CN2C(=O)OC(C)(C)C)cc1]

To a solution of tert-butyl (2R,4S)-4-((tert-butyldimethylsilyl)oxy)-2-(hydroxymethyl) pyrrolidine-1-carboxylate (1.4 g, 4.3 mmol) and 4-methylbenzenesulfonyl chloride (1.0 g, 5.4 mmol) in DCM (8.6 mL) at 0° C. was added pyridine (2.6 mL). The reaction was allowed to warm to rt and stirred for 23 h. The reaction was diluted with DCM, washed with water (2×50 mL), 10 wt % aqueous citric acid solution (2×50 mL), brine (50 mL) and dried with $MgSO_4$. The mixture was filtered and concentrated under reduced pressure. The residue was purified by column chromatography on a silica gel column (0-100% EtOAc/hexanes) to give tert-butyl (2R,4S)-4-((tert-butyldimethylsilyl)oxy)-2-((tosyloxy)methyl) pyrrolidine-1-carboxylate (1.6 g, 3.3 mmol, 76% yield) as a clear oil. LCMS calcd for $C_{18}H_{32}NO_4SSi$ $(M+H-Boc)^+$ m/z: 386.2; Found: 386.1.

Step 4: tert-butyl (2R,4S)-2-(azidomethyl)-4-((tert-butyldimethylsilyl)oxy)pyrrolidine-1-carboxylate

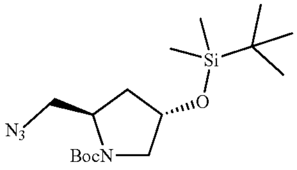 [SMILES: CC(C)(C)OC(=O)N1C[C@@H](O[Si](C)(C)C(C)(C)C)C[C@@H]1CN=[N+]=[N-]]

To a solution of tert-butyl (2R,4S)-4-((tert-butyldimethylsilyl)oxy)-2-((tosyloxy) methyl)pyrrolidine-1-carboxylate (500 mg, 1.0 mmol) in DMSO (5.1 mL) was added sodium azide (170 mg, 2.6 mmol). The reaction mixture was stirred at 65° C. for 22 h. The reaction mixture was allowed to cool to rt, diluted with MTBE, then washed with water (4×50 mL) and brine (50 mL). The organic layer was dried over $MgSO_4$, filtered, and concentrated under reduced pressure to afford tert-butyl(2R,4S)-2-(azidomethyl)-4-((tert-butyldimethylsilyl)oxy)pyrrolidine-1-carboxylate (343 mg, 94% yield) as a clear oil which was taken on without further purification. LCMS calcd for $C_{12}H_{25}N_4O_3Si$ $(M+H-tBu)^+$ m/z: 301.2; Found 301.0.

Step 5: (2R,4S)-2-(azidomethyl)-4-((tert-butyldimethylsilyl)oxy)pyrrolidine

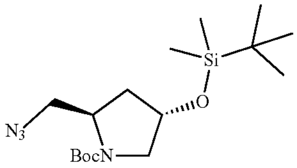 [SMILES: CC(C)(C)OC(=O)N1C[C@@H](O[Si](C)(C)C(C)(C)C)C[C@@H]1CN=[N+]=[N-]]

To a solution of tert-butyl (2R,4S)-2-(azidomethyl)-4-((tert-butyldimethylsilyl)oxy) pyrrolidine-1-carboxylate (343 mg, 0.96 mmol) in DCM (1.5 mL) was added trifluoroacetic acid (1.5 mL, 19 mmol). The reaction mixture was stirred at rt for 1 h and basified to pH~ 12 with aqueous 2 N NaOH. The reaction mixture was extracted with DCM (3×25 mL), washed with brine (25 mL), dried with $MgSO_4$, filtered and concentrated under reduced pressure to afford (2R,4S)-2-(azidomethyl)-4-((tert-butyldimethylsilyl)oxy) pyrrolidine (165 mg, 67% yield) as a clear oil which was taken on without further purification. LCMS calcd for $C_{11}H_{25}N_4OSi$ $(M+H)^+$ m/z: 257.2; Found: 257.1.

Step 6:4-((2R,4S)-2-(azidomethyl)-4-((tert-butyldimethylsilyl)oxy)pyrrolidin-1-yl)-3,6-dichloropyridazine

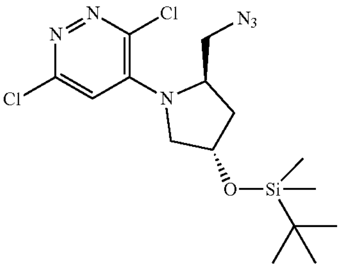 [SMILES: CC(C)(C)[Si](C)(C)O[C@H]1C[C@H](CN=[N+]=[N-])N(c2cc(Cl)nnc2Cl)C1]

To a solution of (2R,4S)-2-(azidomethyl)-4-((tert-butyldimethylsilyl)oxy)pyrrolidine (1.48 g, 5.8 mmol, 1.5 eq) and 3,4,6-trichloropyridazine (124 mg, 0.68 mmol) in DMF (1 mL) was added N, N-diisopropylethylamine (120 μL, 0.71 mmol). The reaction was stirred at 80° C. for 20 h, then poured into water and extracted with EtOAc (2×25 mL). The combined organic layers were washed with water (4×50 mL), then brine (50 mL), then dried with $MgSO_4$ and filtered. The filtrate was concentrated under reduced pressure to afford 4-((2R,4S)-2-(azido-methyl)-4-((tert-butyldimethyl-silyl)oxy) pyrrolidin-1-yl)-3,6-dichloropyridazine (144 mg, 56% yield) which was taken on without further purification. LCMS calcd for $C_{15}H_{25}Cl_2N_6OSi$ $(M+H)^+$ m/z: 403.1/405.1; Found: 403.0/405.0. $^1H$ NMR (400 MHz, DMSO) δ 7.41 (s, 1H), 4.59 (tt, J=7.6, 3.7 Hz, 1H), 4.56-4.51 (m, 1H), 3.93 (dd, J=11.3, 3.4 Hz, 1H), 3.69 (dd, J=13.2, 4.5 Hz, 1H), 3.39-3.28 (m, 5H), 2.08-1.95 (m, 2H), 0.77 (s, 9H), 0.06 (s, 3H).

Step 7: (6aR,8S)-8-((tert-butyldimethylsilyl)oxy)-2-chloro-5,6,6a, 7,8,9-hexahydropyrrolo [1',2':4,5] pyrazino[2,3-c]pyridazine

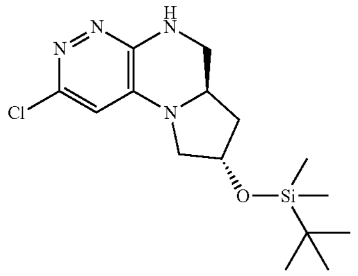 [SMILES: CC(C)(C)[Si](C)(C)O[C@H]1C[C@@H]2CNc3nnc(Cl)cc3N2C1]

To a solution of 4-((2R,4S)-2-(azidomethyl)-4-((tert-butyldimethylsilyl)oxy)pyrrolidin-1-yl)-3,6-dichloropyridazine (144 mg, 0.36 mmol) in THE (4 mL) was added triphenylphosphine (103 mg, 0.39 mmol). The reaction mixture was stirred at 60° C. for 80 min. Water (0.4 mL) and N,N-diisopropylethylamine (190 μL, 1.1 mmol) were added and the reaction mixture was stirred at 60° C. for 24 h. The mixture was allowed to cool to rt and then was extracted with EtOAc (3×25 mL). The combined organic layers were washed with brine (25 mL), dried with $MgSO_4$, filtered and concentrated under reduced pressure to afford tert-butyl (6aR,8S)-8-((tert-butyl-dimethyl-silyl)oxy)-2-chloro-5,6,6a, 7,8,9-hexahydropyrrolo[1',2':4,5]pyrazino[2,3-c]pyridazine (120 mg crude, 0.36 mmol, assumed quant. yield) which was taken on without further purification. LCMS calcd for $C_{15}H_{26}ClN_4OSi$ $(M+H)^+$ m/z: 341.2/343.2; Found 341.0/342.9.

Step 8: tert-butyl (6aR,8S)-8-((tert-butyldimethylsilyl)oxy)-2-chloro-6a,7,8,9-tetrahydro-pyrrolo[1',2':4,5]pyrazino[2,3-c]pyridazine-5(6H)-carboxylate

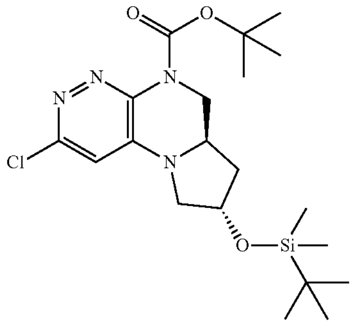 [SMILES: CC(C)(C)OC(=O)N1C[C@H]2C[C@H](O[Si](C)(C)C(C)(C)C)CN2c2cc(Cl)nnc21]

To a mixture of tert-butyl (6aR,8S)-8-((tert-butyldimethylsilyl)oxy)-2-chloro-5,6,6a,7,8,9-hexahydropyrrolo[1',2':4,5]pyrazino[2,3-c]pyridazine (120 mg, 0.36 mmol, 1.0 eq) in DCM (3.6 mL) was added di-tert-butyl dicarbonate (234 mg, 1.1 mmol) and 4-(dimethyl-amino)pyridine (43.6 mg, 0.36 mmol). The mixture was stirred at rt for 1 h then charged with additional di-tert-butyl dicarbonate (156 mg, 0.71 mmol) and 4-(dimethylamino) pyridine (21.8 mg, 0.18 mmol). The mixture was stirred at rt for 20 min then concentrated under reduced pressure and purified via silica gel chromatography (0-100% EtOAc/hexanes) to afford tert-butyl (6aR,8S)-8-((tert-butyl-dimethylsilyl)oxy)-2-chloro-6a,7,8,9-tetrahydropyrrolo[1',2':4,5]pyrazino[2,3-c] pyridazine-5(6H)-carboxylate (97 mg, 0.22 mmol, 62% yield) as a white solid. LCMS calcd for $C_{20}H_{34}ClN_4O_3Si$ $(M+H)^+$ m/z=441.2/443.2; Found: 441.1/443.0.

Step 9: tert-butyl (6aR,8S)-2-chloro-8-hydroxy-6a, 7,8,9-tetrahydropyrrolo[1',2':4,5]-pyrazino[2,3-c] pyridazine-5(6H)-carboxylate To a solution of tert-butyl (6aR,8S)-8-((tert-butyldimethylsilyl)oxy)-2-chloro-6a,7,8,9-tetrahydropyrrolo[1',2':4,5] pyrazino[2,3-c]pyridazine-5(6H)-carboxylate (550 mg, 1.25 mmol) in THE (25 mL) at 0° C. was added tetrabutylammonium fluoride (1 M in THF, 3.1 mL, 3.1 mmol). The mixture was stirred at 0° C. for 5 min then allowed to stir at rt for 19 h. $NH_4Cl$ (sat., aq.) was added to the reaction and the mixture was extracted with DCM (3×25 mL). The combined organic layers were washed with brine (25 mL), dried with $MgSO_4$, filtered and concentrated under reduced pressure. The residue was purified via silica gel chromatography (0-100% EtOAc/hexanes) to afford tert-butyl (6aR,8S)-2-chloro-8-hydroxy-6a,7,8,9-tetrahydropyrrolo-[1',2':4,5]pyrazino[2,3-c]pyridazine-5(6H)-carboxylate (251 mg, 0.77 mmol, 62% yield) as a yellow-orange solid. LCMS calcd for $C_{14}H_{20}ClN_4O_3(M+H)^+$ m/z=327.1/329.1; Found: 327.0/328.9.

Intermediate 2: 3-(1-oxo-6-(piperazin-1-yl)isoindolin-2-yl)piperidine-2,6-dione

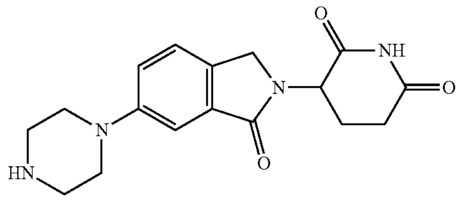 [SMILES: O=C1CCC(N2Cc3ccc(N4CCNCC4)cc3C2=O)C(=O)N1]

Step 1: tert-butyl 4-(4-cyano-3-(methoxycarbonyl) phenyl)piperazine-1-carboxylate

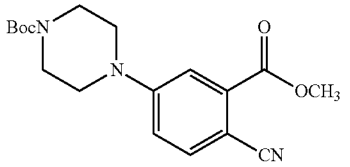 [SMILES: COC(=O)c1cc(N2CCN(C(=O)OC(C)(C)C)CC2)ccc1C#N]

To the solution of methyl 2-cyano-5-fluorobenzoate (5.00 g, 27.9 mmol) and tert-butyl 1-piperazinecarboxylate (15.6 g, 83.7 mmol) in NMP (20.0 mL) was added N,N-diisopropylethylamine (7.29 mL, 41.9 mmol). The solution was heated at 120° C. for 4 h then cooled to −20° C. overnight. The observed solid product was filtered and washed with heptanes to obtain tert-butyl 4-(4-cyano-3-(methoxycarbonyl)phenyl)piperazine-1-carboxylate as a yellow solid. LCMS calcd for $C_{13}H_{16}N_3O_2$ (M-Boc+2H)$^+$ m/z=246.1; Found: 245.9

Step 2: tert-butyl 4-(4-formyl-3-(methoxycarbonyl) phenyl)piperazine-1-carboxylate

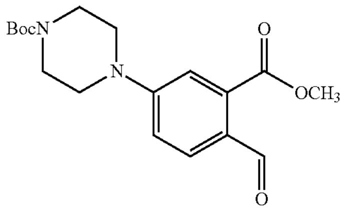 [SMILES: COC(=O)c1cc(N2CCN(C(=O)OC(C)(C)C)CC2)ccc1C=O]

To a solution of tert-butyl 4-(4-cyano-3-(methoxycarbonyl)phenyl)piperazine-1-carboxylate (28.0 g, 81.1 mmol) in pyridine (39.3 mL, 486 mmol) and acetic acid (27.8 mL, 486 mmol) was added sodium; phosphinate; hydrate (17.2 g, 162 mmol) and water (10.0 mL) followed by Raney-nickel (9.52 g, 162.14 mmol). The reaction was heated to 75° C. for 7 h and monitored by HPLC to see only ~50% conversion. An additional 1.0 equiv. of raney-nickel was added and left to heat at 75° C. overnight. HPLC monitoring showed ~94% conversion. The reaction was cooled and diluted with MeOH, filtered through celite, and washed with MeOH. The filtrate was concentrated then diluted in EtOAc and washed with water. The organic phase was dried over $Na_2SO_4$, filtered and concentrated to obtain the crude which was purified by FCC (0% to 60% ethyl acetate/heptanes) to obtain tert-butyl 4-(4-formyl-3-(methoxycarbonyl)phenyl) piperazine-1-carboxylate (13.5 g, 47.8%). $^1$H NMR (300 MHz, DMSO) δ 10.02 (s, 1H), 7.8307.73 (m, 1H), 7.17 (dd, J=12.7, 2.5 Hz, 2H), 3.86 (s, 3H), 3.44 (s, 8H), 3.32 (s, 2H), 1.42 (s, 9H).

Step 3: tert-butyl 4-(2-(2,6-dioxopiperidin-3-yl)-3-oxoisoindolin-5-yl)piperazine-1-carboxylate

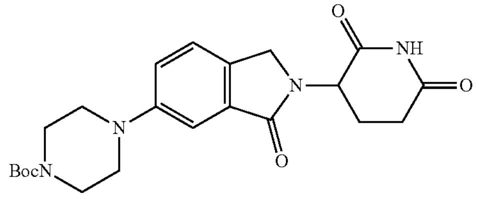 [SMILES: CC(C)(C)OC(=O)N1CCN(c2ccc3c(c2)C(=O)N(C2CCC(=O)NC2=O)C3)CC1]

To a solution of tert-butyl 4-(4-formyl-3-(methoxycarbonyl)phenyl)piperazine-1-carboxylate (3.20 g, 9.19 mmol) in DCM (20.0 mL) and DMF (5.00 mL), was added N,N-diisopropylethylamine (1.92 mL, 11.1 mmol) and pyroglutamine (1.18 g, 9.19 mmol). The reaction was stirred at RT for 1 h and acetic acid (5.25 mL, 91.9 mmol) was added to this solution. The reaction was further stirred for another hour and sodium triacetoxyborohydride (5.84 g, 27.6 mmol) was added. The reaction was stirred overnight to see full conversion, monitored by HPLC. The reaction was stopped and diluted with DCM (50.0 mL) and quenched by sat $NaHCO_3$ solution dropwise until pH of 8-9 was maintained. The organic phase separated dried over $Na_2SO_4$, filtered and concentrated under reduced pressure to obtain the crude material. Purified by FCC (0% to 80% EA/Heptanes) to obtain tert-butyl 4-(2-(2,6-dioxopiperidin-3-yl)-3-oxoisoindolin-5-yl)piperazine-1-carboxylate (3.00 g, 76.3%). LCMS calcd for $C_{22}H_{29}N_4O_5$ (M+H)+m/z=429.2; Found: 428.9.

Step 4: 3-(1-oxo-6-(piperazin-1-yl)isoindolin-2-yl) piperidine-2,6-dione

To a solution of tert-butyl 4-(2-(2,6-dioxopiperidin-3-yl)-3-oxoisoindolin-5-yl)piperazine-1-carboxylate (3.80 g, 8.87 mmol) in DCM (80.0 mL) was added 2,2,2-trifluoroacetic acid; TFA (20.0 mL, 261.36 mmol) dropwise at 0° C. The reaction was stirred for 3 h at RT to observe full conversion by HPLC. DCM and TFA was concentrated and then further diluted with 10 mL of $CHCl_3$:IPA (3:1). To this solution was added 10% $Na_2CO_3$ dropwise at 0° C. to observe the formation of precipitate around pH 8-9. The solid was filtered and dried to obtain desired product 3-(1-oxo-6-(piperazin-1-yl)isoindolin-2-yl)piperidine-2,6-dione (2.60 g, 89.3%). LCMS calcd for $C_{17}H_{21}N_4O_3$ (M+2H-Boc)$^+$ m/z=329.2; Found: 329.1 Intermediate 3: 1-(2-(2,6-dioxopiperidin-3-yl)-3-oxoisoindolin-5-yl)piperidine-4-carbaldehyde

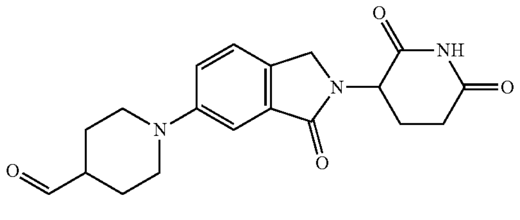 [SMILES: O=CC1CCN(c2ccc3c(c2)C(=O)N(C2CCC(=O)NC2=O)C3)CC1]

Step 1: methyl 5-amino-4-(6-(4-(dimethoxymethyl)piperidin-1-yl)-1-oxoisoindolin-2-yl)-5-oxopentanoate

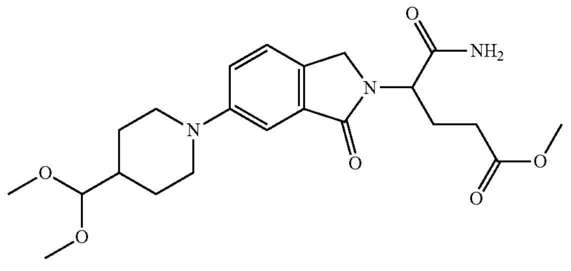

The title compound was prepared using the procedure analogous to those described for Intermediate 2, Steps 1-3 using the appropriate starting materials.

Step 2: 3-(6-(4-(dimethoxymethyl)piperidin-1-yl)-1-oxoisoindolin-2-yl)piperidine-2,6-dione

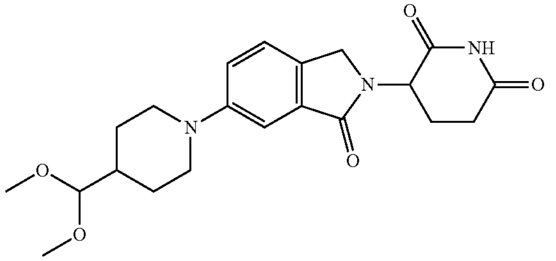 [SMILES: COC(OC)C1CCN(c2ccc3c(c2)C(=O)N(C2CCC(=O)NC2=O)C3)CC1]

A 1.0 M solution of potassium t-butoxide (8.30 mL, 8.30 mmol) in THE was added to a solution of methyl 5-amino-4-(6-(4-(dimethoxymethyl)piperidin-1-yl)-1-oxoisoindolin-2-yl)-5-oxopentanoate (3.00 g, 6.92 mmol) in THE (80.0 mL) at −78° C. and the reaction was stirred for 3 hours. The reaction was warmed to 0° C. and the pH was carefully adjusted to ~3 using a 1N aqueous HCl solution. To this solution, a saturated aqueous $NaHCO_3$ was carefully added dropwise to adjust the pH~6. DCM was added and the phases were separated. The combined organics were washed with water, dried over $MgSO_4$, filtered and concentrated under reduced pressure. The crude material was triturated with DCM (5.00 mL) followed by MTBE (20.0 mL) upon which a white precipitate crashed out. The solids were filtered and dried via vacuum filtration to obtain 3-(6-(4-(dimethoxymethyl)piperidin-1-yl)-1-oxoisoindolin-2-yl)piperidine-2,6-dione (1.89 g, 68% yield). $^1H$ NMR (300 MHz, DMSO) δ 10.97 (s, 1H), 7.41 (d, J=8.4 Hz, 1H), 7.25 (dd, J=8.5, 2.3 Hz, 1H), 7.14 (d, J=2.2 Hz, 1H), 5.10 (dd, J=13.3, 5.1 Hz, 1H), 4.33 (d, J=16.8 Hz, 1H), 4.19 (d, J=16.7 Hz, 1H), 4.08 (d, J=6.6 Hz, 1H), 3.77 (d, J=12.3 Hz, 2H), 3.27 (s, 6H), 2.98-2.82 (m, 1H), 2.65 (dd, J=29.4, 15.4 Hz, 3H), 2.38 (qd, J=13.3, 4.4 Hz, 1H), 2.04-1.92 (m, 1H), 1.72 (d, J=10.8 Hz, 3H), 1.34 (dt, J=21.6, 10.9 Hz, 2H).

Step 3: 1-(2-(2,6-dioxopiperidin-3-yl)-3-oxoisoindolin-5-yl)piperidine-4-carbaldehyde 2,2,2-Trifluoroacetic acid (2.38 mL, 31.1 mmol) was added to a solution of 3-(6-(4-(dimethoxymethyl)piperidin-1-yl)-1-oxoisoindolin-2-yl)piperidine-2,6-dione (500 mg, 1.25 mmol) in a 3 to 1 mixture of DCM (9.34 mL) and acetone (3.11 mL). The reaction was stirred overnight. The reaction mixture was concentrated under reduced pressure to obtain 1-(2-(2,6-dioxopiperidin-3-yl)-3-oxoisoindolin-5-yl)piperidine-4-carbaldehyde (440 mg, quantitative yield) as the TFA salt. LCMS calcd for $C_{19}H_{22}N_3O_4$ $(M+H)^+$ m/z=356.2; Found: 356.2.

Intermediate 4: (1-(2-(2,6-dioxopiperidin-3-yl)-3-oxoisoindolin-5-yl)piperidin-4-yl)methyl 4-methylbenzenesulfonate

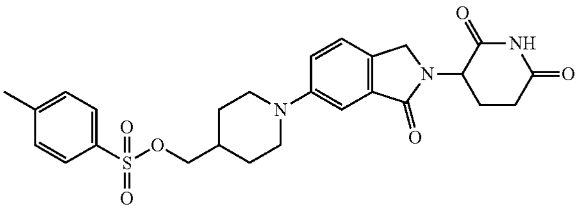 [SMILES: Cc1ccc(S(=O)(=O)OCC2CCN(c3ccc4c(c3)C(=O)N(C3CCC(=O)NC3=O)C4)CC2)cc1]

Step 1: Methyl 2-cyano-5-(4-(hydroxymethyl)piperidin-1-yl)benzoate

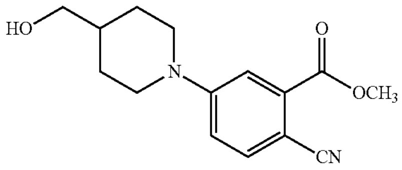 [SMILES: COC(=O)c1cc(N2CCC(CO)CC2)ccc1C#N]

To a solution of methyl 2-cyano-5-fluorobenzoate (2.00 g, 11.2 mmol) and 4-piperidine-methanol (1.67 g, 14.5 mmol) in dimethyl sulfoxide (22.3 mL) was added N,N-diisopropylethylamine (5.83 mL, 33.5 mmol). The reaction mixture was heated to 110° C. and stirred for 1.5 hours. The product mixture was diluted with EtOAc (100 mL) and transferred to a separatory funnel.

The diluted reaction mixture was washed with a saturated aqueous sodium chloride solution (50 mL×2). The organic layer was dried over sodium sulfate, filtered and concentrated under reduced pressure. The crude residue was purified by silica gel flash column chromatography, eluting with a gradient 0-100% EtOAc/hexanes to obtain methyl 2-cyano-5-(4-(hydroxymethyl)piperidin-1-yl)benzoate (3.02 g, 98% yield) as a yellow oil. LCMS calcd for $C_{15}H_{18}N_2O_3$ $[M+H]^+$: m/z=275.1; Found: 275.1.

Step 2: Methyl 2-formyl-S-(4-(hydroxymethyl)piperidin-1-yl)benzoate

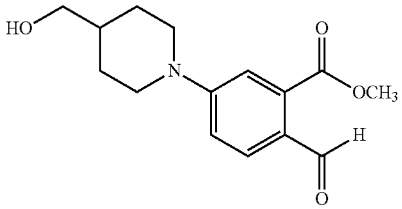 [SMILES: COC(=O)c1cc(N2CCC(CO)CC2)ccc1C=O]

To a solution of methyl 2-cyano-5-(4-(hydroxymethyl) piperidin-1-yl)benzoate (3.00 g, 10.9 mmol), sodium hypophosphite monohydrate (11.7 g, 111 mmol) and acetic acid (12.7 mL, 222 mmol) in pyridine (26.3 mL) was added a slurry of Raney nickel (1.97 g, 33.6 mmol) in water (28.0 mL). The reaction mixture was heated to 70° C. and stirred for 8 hours. The product mixture was filtered through celite and the celite was washed with EtOAc (50 mL×2). The filtrate was transferred to a separatory funnel and washed with water (150 mL). The aqueous layer was extracted with EtOAc (75 mL×2). The combined organic layers were dried over sodium sulfate, filtered, and concentrated under reduced pressure. The crude residue was purified by silica gel flash column chromatography eluting with a gradient of 0-100% EtOAc/hexanes to give methyl 2-formyl-5-(4-(hydroxymethyl)piperidin-1-yl)benzoate (2.31 g, 76.0%) as a yellow oil. LCMS calcd for $C_{15}H_{20}NO_4$ $[M+H]^+$: m/z=278.1; Found: 278.1.

Step 3: 3-(6-(4-(hydroxymethyl)piperidin-1-yl)-1-oxoisoindolin-2-yl)piperidine-2,6-dione

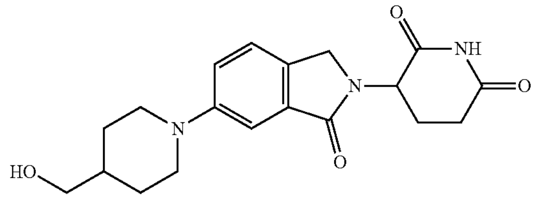 [SMILES: O=C1CCC(N2Cc3ccc(N4CCC(CO)CC4)cc3C2=O)C(=O)N1]

To a stirring solution of methyl 2-formyl-5-(4-(hydroxymethyl)piperidin-1-yl)benzoate (2.40 g, 8.65 mmol) in DCM (48.8 mL) and DMF (48.8 mL) was added 3-aminopiperidine-2,6-dione hydrochloride (1.85 g, 11.3 mmol) followed by N,N-diisopropylethylamine (3.77 mL, 21.6 mmol).

The reaction mixture was stirred at room temperature for 3 hours. The reaction mixture was cooled to 0° C. and acetic acid (5.94 mL, 104 mmol) followed by sodium triacetoxyborohydride (5.50 g, 26.0 mmol) was added. The reaction mixture was allowed to slowly warm to room temperature and stirred for an additional 3 hours. The reaction mixture was diluted with water (10 mL) and the solution was basified with saturated aqueous $NaHCO_3$ solution until no further evolution of gas was observed. The basified product mixture was filtered and the solid was washed with water (10 mL×2). The solid was collected and dried under vacuum to obtain 3-(6-(4-(hydroxymethyl)piperidin-1-yl)-1-oxoisoindolin-2-yl)piperidine-2,6-dione (1.95 g, 63%) as a grey-white solid. LCMS calcd for $C_{19}H_{23}N_3O_4$ $[M+H]^+$: m/z=358.2; Found: 358.1.

Step 4: (1-(2-(2,6-dioxopiperidin-3-yl)-3-oxoisoindolin-5-yl)piperidin-4-yl)methyl 4-methylbenzenesulfonate Tosyl chloride (107 mg, 0.560 mmol) was added to a solution of 3-(6-(4-(hydroxymethyl) piperidin-1-yl)-1-oxoisoindolin-2-yl)piperidine-2,6-dione (100 mg, 0.280 mmol) in pyridine (3.00 mL). The reaction was stirred at room temperature for 1 hour. The reaction mixture was diluted with DCM and the organics were washed with water, dried over $MgSO_4$, filtered and concentrated under reduced pressure. The crude residue was purified by silica gel flash column chromatography eluting with a gradient of 0-100% EtOAc/DCM to obtain (1-(2-(2,6-dioxopiperidin-3-yl)-3-oxoisoindolin-5-yl)piperidin-4-yl)methyl 4-methylbenzenesulfonate (43.7 mg, 31%) as a grey-white solid. LCMS calcd for $C_{19}H_{23}N_3O_4$ $[M+H]^+$: m/z=512.4; Found: 511.7.

Intermediate 5: 3-(1-oxo-6-(piperidin-4-yl)isoindolin-2-yl)piperidine-2,6-dione

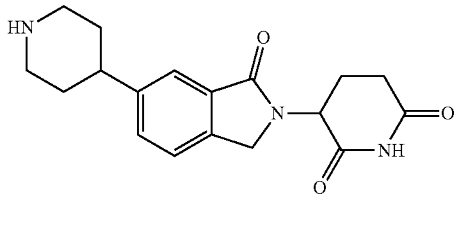 [SMILES: O=C1CCC(N2Cc3ccc(C4CCNCC4)cc3C2=O)C(=O)N1]

Step 1: Methyl 5-bromo-2-(dibromomethyl)benzoate

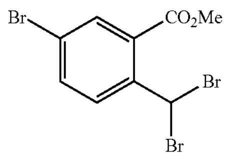 [SMILES: COC(=O)c1cc(Br)ccc1C(Br)Br]

A suspension of methyl 5-bromo-2-methylbenzoate (6.08 g, 26.6 mmol), NBS (14.0 g, 79.7 mmol), and benzoyl peroxide (0.32 g, 1.33 mmol) in DCE (60.0 mL) was stirred at 80° C. for 18 h.

The reaction mixture was cooled to ambient temperature, diluted with DCM (140 mL), washed with 10% $Na_2S_2O_3$ solution (100 mL), saturated $NaHCO_3$ solution (100 mL), water (100 mL), and brine (100 mL), then dried over $Na_2SO_4$, filtered and concentrated. The residue was dried under high vacuum to give the desired product, methyl 5-bromo-2-(dibromomethyl)-benzoate (9.875 g, 96.1%), as light yellow solid. $^1H$ NMR (300 MHz, $CDCl_3$) δ 8.04 (dd, J=5.4, 3.1 Hz, 2H), 7.97 (s, 1H), 7.74 (dd, J=8.6, 2.1 Hz, 1H), 3.96 (s, 3H).

Step 2: Methyl 5-bromo-2-formylbenzoate

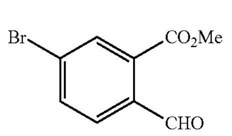 [SMILES: COC(=O)c1cc(Br)ccc1C=O]

Silver nitrate (6.57 g, 38.7 mmol) was dissolved in water (60.0 mL). This solution was added dropwise into the stirred solution of methyl 5-bromo-2-(dibromomethyl)benzoate (5.99 g, 15.5 mmol) in IPA (60.0 mL) at 0° C. The resulting mixture was stirred at ambient temperature in the dark for 4 h, when HPLC indicated the disappearance of the starting material. The precipitated silver salt was filtered off and washed with IPA in small portions. IPA was evaporated under reduced pressure and the remaining aqueous phase was extracted with EtOAc (50.0 mL×3). The combined organic phase was washed with water (50.0 mL), brine (50.0 mL), then dried over $Na_2SO_4$, filtered and concentrated under reduced pressure. The residue was dried under high vacuum to give the desired product, methyl 5-bromo-2-formylbenzoate (3.26 g, 13.4 86.8%), as white solid. LCMS calculated for $C_9H_8BrO_3$ $(M+H)^+$: m/z=242.9; found: 242.8. $^1H$ NMR (300 MHz, $CDCl_3$) δ 10.58 (s, 1H), 8.13 (d, J=1.5 Hz, 1H), 7.85-7.76 (m, 2H), 3.99 (s, 3H).

Step 3: tert-Butyl 4-(4-formyl-3-methoxycarbonylphenyl)-3,6-dihydro-2H-pyridine-1-carboxylate

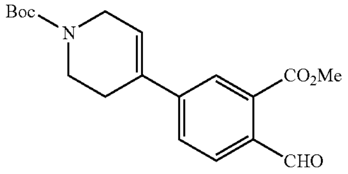 [SMILES: COC(=O)c1cc(C2=CCN(C(=O)OC(C)(C)C)CC2)ccc1C=O]

A suspension of N-Boc-1,2,3,6-tetrahydropyridine-4-boronic acid pinacol ester (5.55 g, 17.9 mmol), methyl 5-bromo-2-formylbenzoate (2.91 g, 12.0 mmol), Pd(dppf) $Cl_2$ (0.44 g, 0.6 mmol), and CsOAc (9.18 g, 47.8 mmol) in 1,4-dioxane (40.0 mL) and water (10.0 mL) was heated at 95° C. under $N_2$ atmosphere for 1.5 h, when HPLC indicated the full conversion of the starting material.

The reaction was cooled to ambient temperature and partitioned between EtOAc and water (100 mL each). The organic layer was separated, and the aqueous layer extracted with EtOAc (50 mL×3).

The combined organic phase was washed with water and brine (100 mL each), dried over $Na_2SO_4$, filtered and concentrated. The residue was purified by flash column chromatography (0~25% EtOAc in heptanes) to give the desired product, tert-butyl 4-(4-formyl-3-methoxycarbonylphenyl)-3,6-dihydro-2H-pyridine-1-carboxylate (3.30 g, 79.9%), as yellow solid. $R_f$=0.4 (25% EtOAc in heptanes). $^1H$ NMR (300 MHz, $CDCl_3$) δ 10.57 (s, 1H), 7.93 (t, J=4.8 Hz, 2H), 7.63 (dd, J=8.1, 1.5 Hz, 1H), 6.25 (s, 1H), 4.12 (d, J=2.8 Hz, 2H), 3.98 (s, 3H), 3.66 (t, J=5.7 Hz, 2H), 2.56 (d, J=1.4 Hz, 2H), 1.49 (s, 9H).

Step 4: tert-Butyl 4-[2-(2,6-dioxopiperidin-3-yl)-3-oxo-1H-isoindol-5-yl]-3,6-dihydro-2H-pyridine-1-carboxylate

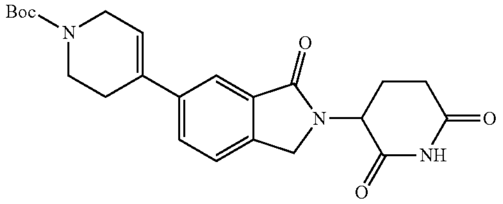 [SMILES: CC(C)(C)OC(=O)N1CC=C(c2ccc3c(c2)C(=O)N(C2CCC(=O)NC2=O)C3)CC1]

To a suspension tert-butyl 4-(4-formyl-3-methoxycarbonylphenyl)-3,6-dihydro-2H-pyridine-1-carboxylate (310 mg, 0.900 mmol) and 3-aminopiperidine-2,6-dione hydrochloride (185 mg, 1.12 mmol) in DCM (4 mL) and DMF (2 mL) was slowly added DIPEA (0.47 mL, 2.69 mmol) and the resulting mixture was stirred at ambient temperature for 30 min. AcOH (0.31 mL, 5.39 mmol) was then added and the mixture was stirred for 1 h. $NaBH(OAc)_3$ (571 mg, 2.69 mmol) was added in portions and the reaction was stirred at ambient temperature for 18 h. The reaction was diluted with DCM (150 mL), washed with saturated $NaHCO_3$ solution, dried over $Na_2SO_4$, filtered and concentrated. The residue was purified by flash column chromatography (0-5% MeOH in DCM) to give the desired product, tert-butyl 4-[2-(2,6-dioxopiperidin-3-yl)-3-oxo-1H-isoindol-5-yl]-3,6-dihydro-2H-pyridine-1-carboxylate (290 mg, 75.9%), as white solid. $R_f$=0.3 (5% MeOH in DCM). LCMS calculated for $C_{23}H_{28}N_3O_5$ $(M+H)^+$: m/z=426.2; found: 426.0. $^1H$ NMR (300 MHz, DMSO) δ 10.99 (s, 1H), 7.77-7.69 (m, 2H), 7.58 (d, J=8.5 Hz, 1H), 6.28 (s, 1H), 5.13 (dd, J=13.2, 5.1 Hz, 1H), 4.39 (dd, J=41.6, 17.4 Hz, 2H), 4.02 (s, 2H), 3.57 (dd, J=10.6, 5.1 Hz, 2H), 3.00-2.84 (m, 1H), 2.71-2.54 (m, 3H), 2.46-2.31 (m, 1H), 2.07-1.95 (m, 1H), 1.43 (s, 9H).

Step 5: tert-Butyl 4-[2-(2,6-dioxopiperidin-3-yl)-3-oxo-1H-isoindol-5-yl]piperidine-1-carboxylate

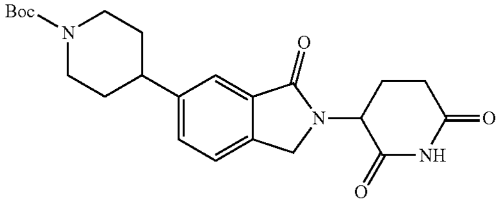 [SMILES: CC(C)(C)OC(=O)N1CCC(c2ccc3c(c2)C(=O)N(C2CCC(=O)NC2=O)C3)CC1]

tert-Butyl 4-[2-(2,6-dioxopiperidin-3-yl)-3-oxo-1H-isoindol-5-yl]-3,6-dihydro-2H-pyridine-1-carboxylate (290 mg, 0.680 mmol) in MeOH (5.00 mL) and THF (5.00 mL) was hydrogenated under 30 psi for 2 h with 10% Pd/C. The solid materials were filtered off and washed with MeOH in small portions. The filtrate was concentrated and the residue was purified by flash column chromatography on silica gel (0~4% MeOH in DCM) to give tert-butyl 4-[2-(2,6-dioxopiperidin-3-yl)-3-oxo-1H-isoindol-5-yl]piperidine-1-carboxylate (265 mg, 90.9%) as white solid. $R_f$=0.25 (5% MeOH in DCM). LCMS calculated for $C_{23}H_{30}N_3O_5$ $(M+H)^+$: m/z=428.2; found: 427.9. $^1H$ NMR (300 MHz, DMSO) δ 10.99 (s, 1H), 7.55 (d, J=11.3 Hz, 3H), 5.11 (dd, J=13.2, 5.0 Hz, 1H), 4.35 (dd, J=41.1, 17.1 Hz, 2H), 4.09 (d, J=12.2 Hz, 2H), 2.98-2.79 (m, 3H), 2.70-2.55 (m, 2H), 2.39 (ddd, J=26.2, 13.3, 4.3 Hz, 1H), 1.98 (dd, J=11.3, 4.6 Hz, 1H), 1.83-1.73 (m, 2H), 1.65-1.49 (m, 2H), 1.40 (d, J=11.4 Hz, 9H).

Step 6: 3-(1-oxo-6-(piperidin-4-yl)isoindolin-2-yl) piperidine-2,6-dione

The title compound was prepared using the procedure analogous to those described for Intermediate 2, Step 4 replacing tert-butyl 4-(2-(2,6-dioxopiperidin-3-yl)-3-oxoisoindolin-5-yl)piperazine-1-carboxylate with tert-butyl 4-[2-(2,6-dioxopiperidin-3-yl)-3-oxo-1H-isoindol-5-yl]piperidine-1-carboxylate, LCMS calcd for $C_{18}H_{22}N_3O_3$ $[M+H]^+$: m/z=328.2; Found: 328.1.

Intermediate 6: (S)-3-(1-oxo-6-(piperidin-4-yl)isoindolin-2-yl)piperidine-2,6-dione

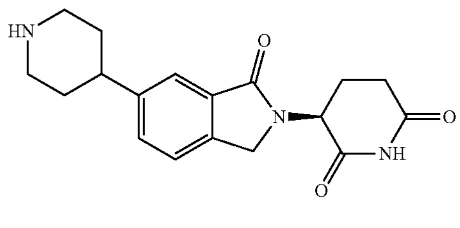 [SMILES: O=C1CC[C@H](N2Cc3ccc(C4CCNCC4)cc3C2=O)C(=O)N1]

Step 1: tert-butyl (S)-4-(2-(1-amino-5-methoxy-1,5-dioxopentan-2-yl)-3-oxoisoindolin-5-yl)-3,6-dihydropyridine-1(2H)-carboxylate

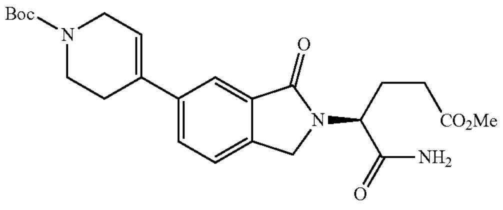 [SMILES: COC(=O)CC[C@@H](C(N)=O)N1Cc2ccc(C3=CCN(C(=O)OC(C)(C)C)CC3)cc2C1=O]

To a suspension tert-butyl 4-(4-formyl-3-methoxycarbonylphenyl)-3,6-dihydro-2H-pyridine-1-carboxylate (Intermediate 5, Step 3) (2.88 g, 8.34 mmol) and H-Glu(OMe)-$NH_2$ hydrochloride (2.05 g, 10.4 mmol) in DCM (40 mL) was slowly added DIPEA (4.36 mL, 25.0 mmol) and the resulting mixture was stirred at ambient temperature for 30 min. AcOH (2.86 mL, 50.0 mol) was then added and the mixture was stirred for 1 h. $NaBH(OAc)_3$ (5.30 g, 25.0 mmol) was added in portions and the reaction was stirred at ambient temperature for 18 h. The reaction was diluted with DCM (150 mL), washed with saturated $NaHCO_3$ solution, dried over $Na_2SO_4$, filtered and concentrated. The residue was purified by flash column chromatography (0-5% MeOH in DCM) to give the desired product, tert-butyl (S)-4-(2-(1-amino-5-methoxy-1,5-dioxopentan-2-yl)-3-oxoisoindolin-5-yl)-3,6-dihydropyridine-1(2H)-carboxylate (3.01 g, 78.9%), as white solid. $R_f$=0.3 (5% MeOH in DCM). LCMS calculated for $C_{24}H_{32}N_3O_6$ $(M+H)^+$: m/z=458.2; found: 458.1. $^1H$ NMR (300 MHz, DMSO) δ 7.75-7.67 (m, 2H), 7.57 (d, J=8.3 Hz, 2H), 7.20 (s, 1H), 6.26 (s, 1H), 4.75 (dd, J=10.2, 4.6 Hz, 1H), 4.52 (dd, J=45.0, 17.7 Hz, 2H), 4.02 (d, J=7.1 Hz, 2H), 3.56 (t, J=5.5 Hz, 2H), 3.50 (s, 3H), 2.58-2.50 (m, 2H), 2.29-1.96 (m, 4H), 1.43 (s, 9H).

Step 2: tert-butyl (S)-4-(2-(2,6-dioxopiperidin-3-yl)-3-oxoisoindolin-5-yl)-3,6-dihydro-pyridine-1(2H)-carboxylate

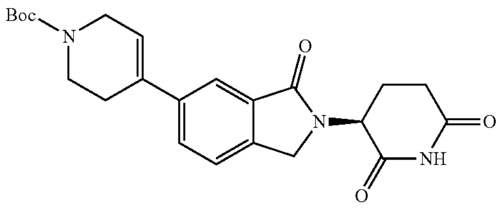 [SMILES: CC(C)(C)OC(=O)N1CC=C(c2ccc3c(c2)C(=O)N([C@H]2CCC(=O)NC2=O)C3)CC1]

tert-butyl (S)-4-(2-(1-amino-5-methoxy-1,5-dioxopentan-2-yl)-3-oxoisoindolin-5-yl)-3,6-dihydropyridine-1(2H)-carboxylate (1.01 g, 2.20 mmol) in THE (15.0 mL) was added t-BuOK (1.0 M in THF, 2.75 mmol, 2.75 mL) dropwise at −78° C. The resulting mixture was stirred at −78° C. for 2 h. The reaction was quenched by the addition of 1 N HCl solution until pH 6 and extracted with DCM (50 mL×3). The combined organic phase was washed with brine (50 mL), dried over $Na_2SO_4$, filtered and concentrated. The residue was suspended in a minimum amount of DCM (2.00 mL) and MTBE (20.0 mL) was added at 0° C. The white precipitate was filtered off and washed with cold MTBE. The filter cake was dried under air flow to give tert-butyl (S)-4-(2-(2,6-dioxopiperidin-3-yl)-3-oxoisoindolin-5-yl)-3,6-dihydropyridine-1(2H)-carboxylate (718 mg, 1.69 mmol, 76.7% yield) as white solid. LCMS calculated for $C_{19}H_{20}N_3O_5$ $(M+2H-^tBu)^+$: m/z=370.14; found: 370.09. $^1H$ NMR (300 MHz, DMSO) δ 10.99 (s, 1H), 7.75-7.71 (m, 2H), 7.58 (d, J=8.5 Hz, 1H), 6.28 (s, 1H), 5.13 (dd, J=13.2, 5.1 Hz, 1H), 4.39 (dd, J=41.6, 17.5 Hz, 2H), 4.02 (s, 2H), 3.56 (t, J=5.6 Hz, 2H), 3.01-2.83 (m, 1H), 2.71-2.51 (m, 3H), 2.40 (qd, J=13.3, 4.5 Hz, 1H), 2.01 (ddd, J=10.2, 5.1, 3.1 Hz, 1H), 1.43 (s, 9H).

Step 3. tert-butyl (S)-4-(2-(2,6-dioxopiperidin-3-yl)-3-oxoisoindolin-5-yl)piperidine-1-carboxylate

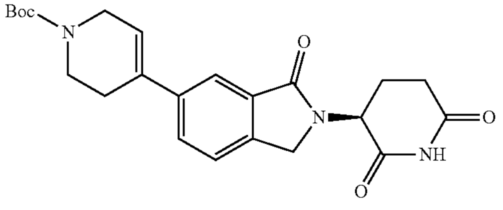 [SMILES: CC(C)(C)OC(=O)N1CC=C(c2ccc3c(c2)C(=O)N([C@H]2CCC(=O)NC2=O)C3)CC1]

tert-butyl (S)-4-(2-(2,6-dioxopiperidin-3-yl)-3-oxoisoindolin-5-yl)-3,6-dihydropyridine-1(2H)-carboxylate (818 mg, 1.92 mmol) in MeOH (5.00 mL) and THF (5.00 mL) was hydrogenated under 30 psi for 2 h with 10% Pd/C. The solid materials were filtered off and washed with MeOH in small portions. The filtrate was concentrated and the residue was purified by flash column chromatography on silica gel (0~4% MeOH in DCM) to give tert-butyl (S)-4-(2-(2,6-dioxopiperidin-3-yl)-3-oxoisoindolin-5-yl)piperidine-1-carboxylate (809 mg, 98.4%) as white solid. $R_f$=0.25 (5% MeOH in DCM). LCMS calculated for $C_{19}H_{22}N_3O_5$ $(M+2H-tBu)^+$: m/z=372.2; found: 372.0. $^1H$ NMR (300 MHz, DMSO) δ 10.99 (s, 1H), 7.55 (d, J=11.0 Hz, 3H), 5.11 (dd, J=13.3, 5.1 Hz, 1H), 4.35 (dd, J=41.3, 17.1 Hz, 2H), 4.08 (d, J=10.3 Hz, 2H), 2.99-2.74 (m, 4H), 2.59 (dd, J=15.4, 2.2 Hz, 1H), 2.39 (qd, J=13.1, 4.3 Hz, 1H), 2.10-1.92 (m, 1H), 1.79 (d, J=12.1 Hz, 2H), 1.66-1.45 (m, 2H), 1.42 (s, 9H).

Step 4: (S)-3-(1-oxo-6-(piperidin-4-yl)isoindolin-2-yl)piperidine-2,6-dione; hydrochloride tert-butyl (S)-4-(2-(2,6-dioxopiperidin-3-yl)-3-oxoisoindolin-5-yl)piperidine-1-carboxylate (809 mg, 1.89 mmol) was suspended in 1,4-dioxane (2.00 mL) and 4 N HCl in 1,4-dioxane (15.0 mL) was added at 0° C. The reaction was stirred at ambient temperature for 18 h. The white precipitate was filtered off and washed with cold 1,4-dioxane in small portions. The filter cake was dried under air flow to give (S)-3-(1-oxo-6-(piperidin-4-yl)isoindolin-2-yl)piperidine-2,6-dione hydrochloride (688 mg, quant.) as white solid. LCMS calculated for $C_{18}H_{22}N_3O_3$ (M+H)$^+$: m/z=328.2; found: 328.1.

Intermediate 7: (S)-3-(1-oxo-6-(piperazin-1-yl)isoindolin-2-yl)piperidine-2,6-dione; hydrochloride

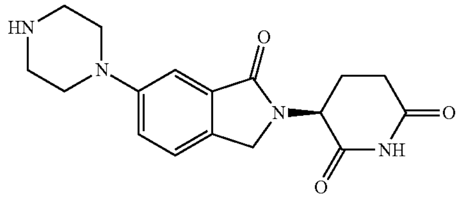 [SMILES: O=C1CC[C@H](N2Cc3ccc(N4CCNCC4)cc3C2=O)C(=O)N1]

Step 1: tert-butyl 4-(4-cyano-3-methoxycarbonylphenyl)piperazine-1-carboxylate

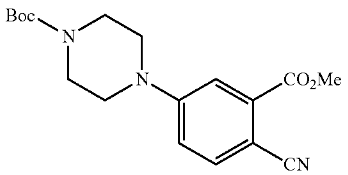 [SMILES: COC(=O)c1cc(N2CCN(C(=O)OC(C)(C)C)CC2)ccc1C#N]

To a solution of methyl 2-cyano-5-fluorobenzoate (20.0 g, 112 mmol) and tert-butyl 1-piperazinecarboxylate (31.2 g, 167 mmol) in NMP (20.0 mL) was added N,N-diisopropylethylamine (0.01 mL, 0.04 mmol) and heated to 120° C. for 4 h. HPLC monitoring after 4 h showed the consumption of starting material. The reaction mixture was cooled to −20° C. overnight and product crashed out. The solid was filtered and washed with heptanes to obtain yellow solid as the desired product tert-butyl 4-(4-cyano-3-(methoxycarbonyl)phenyl)piperazine-1-carboxylate (28.0 g, 72.6%). LCMS calculated for $C_{13}H_{16}N_3O_2$ (M+2H-Boc)$^+$: m/z=246.17; found: 245.99. $^1$H NMR (300 MHz, DMSO) δ 7.73 (d, J=8.8 Hz, 1H), 7.47 (d, J=2.7 Hz, 1H), 7.22 (dd, J=8.8, 2.7 Hz, 1H), 3.89 (s, 3H), 3.51-3.38 (m, 8H), 1.42 (s, 9H).

Step 2: tert-butyl 4-(4-formyl-3-(methoxycarbonyl)phenyl)piperazine-1-carboxylate

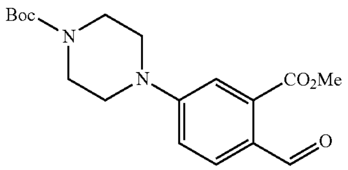 [SMILES: COC(=O)c1cc(N2CCN(C(=O)OC(C)(C)C)CC2)ccc1C=O]

To a solution of tert-butyl 4-(4-cyano-3-methoxycarbonylphenyl)piperazine-1-carboxylate (8.10 g, 23.5 mmol) in pyridine (11.4 mL, 141 mmol) and acetic acid (8.05 mL, 141 mmol) was added sodium phosphinate monohydrate (4.97 g, 46.9 mmol) and water (10.0 mL). To the stirring solution was added Raney Nickel (2.75 g, 46.9 mmol) in multiple portions to avoid the emulsion formation. The reaction was heated to 75° C. for 7 h and monitored by HPLC to see only ~50% conversion. To the solution was added another 1.0 equiv of Raney Nickel and heated at 75° C. overnight. HPLC monitoring showed ~94% conversion. The heating was stopped and the reaction was cooled down, diluted with MeOH and filtered through celite and washed with MeOH to remove Raney Nickel. The filtrate was concentrated to remove pyridine and MeOH. The concentrated solution was then washed with water. The organic phase was dried over $Na_2SO_4$, filtered and concentrated to obtain the crude. Purified by FCC (0% to 60% EA/Heptanes) to obtain yellowish solid as desired product tert-butyl 4-(4-formyl-3-methoxy-carbonylphenyl)piperazine-1-carboxylate (5.00 g, 61.1%). LCMS calculated for $C_{18}H_{25}N_2O_5$ (M+H)$^+$: m/z=349.2; found: 348.9. $^1$H NMR (300 MHz, CDCl3) δ 10.34 (s, 1H), 7.92 (d, J=8.8 Hz, 1H), 7.26 (d, J=1.6 Hz, 1H), 7.00 (dd, J=8.8, 2.6 Hz, 1H), 3.96 (s, 3H), 3.66-3.55 (m, 4H), 3.39 (dd, J=13.4, 8.6 Hz, 4H), 1.48 (s, 9H).

Step 3: tert-butyl (S)-4-(2-(I-amino-5-methoxy-1,5-dioxopentan-2-yl)-3-oxoisoindolin-5-yl)piperazine-1-carboxylate

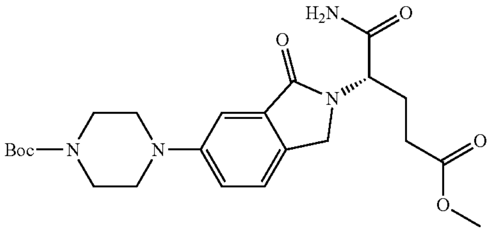 [SMILES: COC(=O)CC[C@@H](C(N)=O)N1Cc2ccc(N3CCN(C(=O)OC(C)(C)C)CC3)cc2C1=O]

To a solution of tert-butyl 4-(4-formyl-3-methoxycarbonylphenyl)piperazine-1-carboxylate (4.20 g, 12.0 mmol) in DCM (50.0 mL) was added N,N-diisopropylethylamine (5.25 mL, 30.1 mmol) and methyl (4S)-4,5-diamino-5-oxopentanoate (2.32 g, 14.5 mmol). The reaction was stirred at RT for 1 h and acetic acid (6.89 mL, 121 mmol) was added to this solution. The reaction was further stirred for another hour and sodium triacetoxyborohydride (7.66 g, 36.2 mmol) was added. The reaction was stirred overnight to see full conversion, monitored by HPLC. The reaction mixture was diluted with DCM (30.0 mL) and quenched with water (30.0 mL). Further extraction was done by DCM (30 mL×2). The organic phase was dried over $Na_2SO_4$, filtered, and concentrated to obtain the crude. Crude was further purified by FCC (0% to 7% MeOH/DCM) to obtain white solid as desired compound tert-butyl (S)-4-(2-(1-amino-5-methoxy-1,5-dioxopentan-2-yl)-3-oxoisoindolin-5-yl)piperazine-1-carboxylate (3.80 g, 68.5%). LCMS calculated for $C_{23}H_{33}N_4O_6$ (M+H)$^+$: m/z=461.2; found: 461.1. $^1$H NMR (300 MHz, CDCl3) δ 7.33 (dd, J=10.8, 5.3 Hz, 2H), 7.16 (dd, J=8.4, 2.4 Hz, 1H), 6.40 (s, 1H), 5.58 (s, 1H), 5.00-4.83 (m, 1H), 4.39 (q, J=16.8 Hz, 2H), 3.63 (s, 3H), 3.62-3.55 (m, 4H), 3.22-3.13 (m, 4H), 2.49-2.28 (m, 3H), 2.20 (tt, J=11.4, 8.2 Hz, 1H), 1.49 (s, 9H).

Step 4: tert-butyl (S)-4-(2-(2,6-dioxopiperidin-3-yl)-3-oxoisoindolin-5-yl)piperazine-1-carboxylate

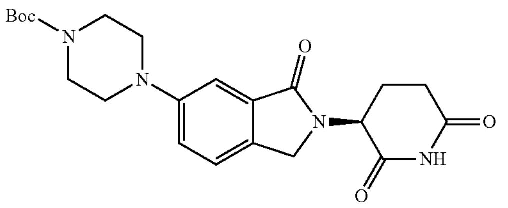 [SMILES: CC(C)(C)OC(=O)N1CCN(c2ccc3c(c2)C(=O)N([C@H]2CCC(=O)NC2=O)C3)CC1]

To a solution of tert-butyl (S)-4-(2-(1-amino-5-methoxy-1,5-dioxopentan-2-yl)-3-oxoisoindolin-5-yl)piperazine-1-carboxylate (3.80 g, 8.25 mmol) in THE (80.0 mL), was added potassium t-butoxide (1.0 M in THF, 9.90 mL, 9.90 mmol) at −78° C. The reaction was stirred at −78° C. for 3 h. The reaction temperature was maintained at 0° C. and quenched by addition of 1N HCl to achieve pH 3. To this solution $NaHCO_3$ (sat. aq.) was added dropwise slowly to achieve pH ~6. The reaction mixture was then diluted further by DCM and washed with water.

Water phase was further extracted by DCM. Organic phase was collected, dried over $Na_2SO_4$, filtered and concentrated to obtain the crude. tert-butyl (S)-4-(2-(2,6-dioxopiperidin-3-yl)-3-oxoisoindolin-5-yl)piperazine-1-carboxylate (2.90 g, 82.0%). The crude was about 96% pure (HPLC) which was taken to the next step without further purification. LCMS calculated for $C_{15}H_{21}N_4O_5$ (M+2H-$^t$Bu)$^+$: m/z=373.2; found: 373.0. 1H NMR (300 MHz, $CDCl_3$) δ 8.06 (s, 1H), 7.37 (dd, J=9.3, 5.3 Hz, 2H), 7.17 (dd, J=8.4, 2.3 Hz, 1H), 5.22 (dd, J=13.1, 5.2 Hz, 1H), 4.35 (dd, J=43.1, 15.6 Hz, 2H), 3.72-3.49 (m, 4H), 3.30-3.13 (m, 4H), 2.96-2.73 (m, 2H), 2.43-2.15 (m, 2H), 1.49 (s, 9H).

Step 5: (S)-3-(I-oxo-6-(piperazin-1-yl)isoindolin-2-yl)piperidine-2,6-dione

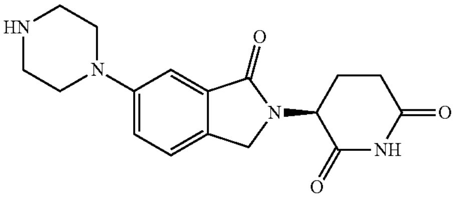 [SMILES: O=C1CC[C@H](N2Cc3ccc(N4CCNCC4)cc3C2=O)C(=O)N1]

To a round bottomed flask containing tert-butyl (S)-4-(2-(2,6-dioxopiperidin-3-yl)-3-oxoisoindolin-5-yl)piperazine-1-carboxylate (4.3 g, 10.0 mmol) was added 4N HCl in dioxane (34.0 mL, 136 mmol) at 0° C. The solution was stirred at 0° C. to RT for 3 h to see full conversion. The precipitate was filtered and dried under air flow to yield (S)-3-(1-oxo-6-(piperazin-1-yl)isoindolin-2-yl)piperidine-2,6-dione; hydrochloride (3.30 g, 90.1%). LCMS calculated for $C_{17}H_{21}N_4O_3$ (M+H)$^+$: m/z=329.2; found: 329.0. $^1$H NMR (300 MHz, DMSO) δ 10.98 (s, 1H), 9.27 (s, 2H), 7.49 (d, J=8.3 Hz, 1H), 7.39-7.19 (m, 2H), 5.10 (dd, J=13.2, 5.1 Hz, 1H), 4.27 (dt, J=27.7, 13.9 Hz, 2H), 3.49-3.40 (m, 4H), 3.22 (s, 4H), 2.98-2.83 (m, 1H), 2.59 (d, J=16.3 Hz, 1H), 2.46-2.27 (m, 1H), 2.09-1.94 (m, 1H).

Intermediate 8a and 8b: (6aR,8R)-8-(Benzyloxy)-2-chloro-6a-ethyl-6a,7,8,9-tetrahydro-pyrrolo[1',2':4,5]pyrazino[2,3-c]pyridazin-6(5H)-one and (6aS,8R)-8-(benzyloxy)-2-chloro-6a-ethyl-6a,7,8,9-tetrahydropyrrolo[1',2':4,5]pyrazino[2,3-c]pyridazin-6(5H)-one

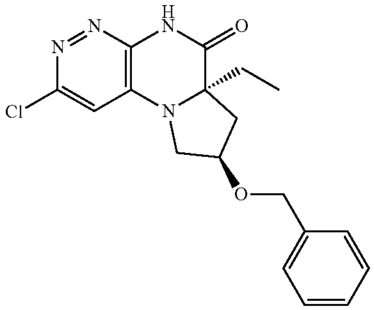

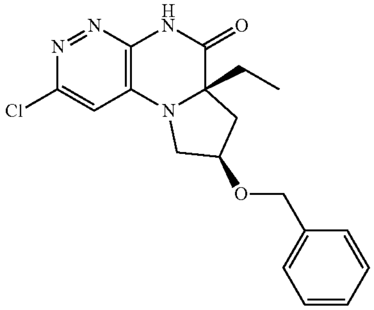

Step 1: 1-(tert-Butyl) 2-methyl (4R)-4-(benzyloxy)-2-ethylpyrrolidine-1,2-dicarboxylate

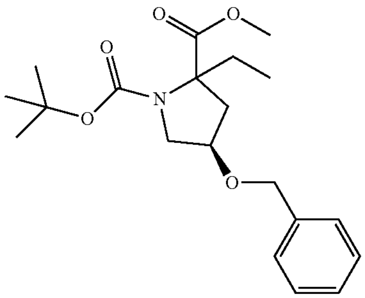 [SMILES: CCC1(C(=O)OC)C[C@@H](OCc2ccccc2)CN1C(=O)OC(C)(C)C]

To 1-(tert-butyl) 2-methyl (2R,4R)-4-(benzyloxy)pyrrolidine-1,2-dicarboxylate (2.00 g, 5.96 mmol) in THE (55 mL) was added LiHMDS (12 mL, 12 mmol) slowly at −78° C. The reaction mixture was stirred at −78° C. for 1 h, after which ethyl iodide (1.9 mL, 23.6 mmol) was added. The reaction was stirred at −78° C. for 5 min then allowed to warm to room temperature with stirring. After 3.5 h, the reaction was quenched with MeOH (55 mL). A solution of NaOH (1.91 g, 47.7 mmol) in water (55 mL) was added and the mixture was stirred at room temperature for 20 min then poured into water. The aqueous layer was extracted with EtOAc (3×). The combined organic layers were washed with brine (1×) then concentrated and purified via $SiO_2$ FCC (0-30% EtOAc in hexanes) to afford 1-(tert-butyl) 2-methyl (4R)-4-(benzyloxy)-2-ethylpyrrolidine-1,2-dicarboxylate (1.11 g, 51%). LCMS calcd for $C_{15}H_{22}NO_3$ [M-Boc+2H]$^+$: m/z=264.2; Found: 264.0.

Step 2: (4R)-4-(Benzyloxy)-1-(tert-butoxycarbonyl)-2-ethylpyrrolidine-2-carboxylic acid

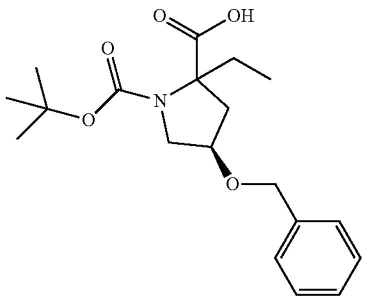 [SMILES: CCC1(C(=O)O)C[C@@H](OCc2ccccc2)CN1C(=O)OC(C)(C)C]

To 1-(tert-butyl) 2-methyl (4R)-4-(benzyloxy)-2-ethylpyrrolidine-1,2-dicarboxylate (2.72 g, 7.48 mmol) in 1:1 THF/MeOH (40 mL) was added a solution of NaOH (2.99 g, 74.8 mmol) in water (20 mL). The reaction was stirred at 75° C. for 2.5 h then allowed to cool to room temperature. The mixture was poured into water then extracted with MTBE (3×). The combined organic layers were washed with water (2×). The combined aqueous layers were extracted once more with MTBE then acidified to pH<2 with 2 N HCl (aq) and subsequently extracted with EtOAc (3×). The combined EtOAc layers were washed with brine, dried with $MgSO_4$, filtered then concentrated to give crude (4R)-4-(benzyloxy)-1-(tert-butoxycarbonyl)-2-ethylpyrrolidine-2-carboxylic acid (assumed quantitative yield) as a yellow oil. LCMS calcd for $C_{14}H_{20}NO_3$ [M-Boc+2H]$^+$: m/z=250.1; Found: 250.0.

Step 3: tert-Butyl (2R,4R)-4-(benzyloxy)-2-((4-bromo-6-chloropyridazin-3-yl)carbamoyl)-2-ethylpyrrolidine-1-carboxylate and tert-butyl (2S,4R)-4-(benzyloxy)-2-((4-bromo-6-chloropyridazin-3-yl)carbamoyl)-2-ethylpyrrolidine-1-carboxylate

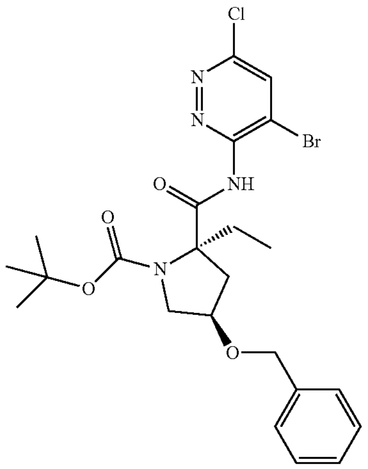

-continued

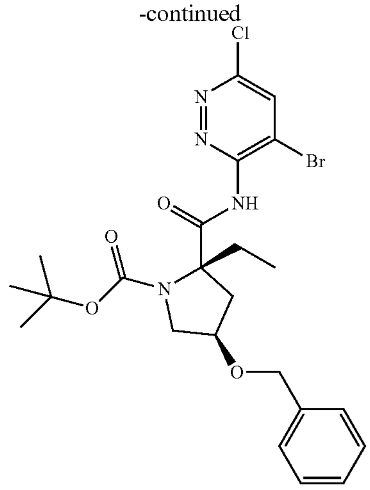

To crude 1-(tert-butyl) 2-methyl (4R)-4-(benzyloxy)-2-ethylpyrrolidine-1,2-dicarboxylate (672 mg, 1.43 mmol) and N,N-diisopropylethylamine (1.21 mL, 6.92 mmol) in MeCN (10 mL) was added HATU (880 mg, 2.31 mmol). The reaction was stirred at room temperature for 20 min then concentrated. The residue was taken up in THE (8 mL) then 4-bromo-6-chloropyridazin-3-amine (802 mg, 3.85 mmol) was added, followed by NaH (60% dispersion in mineral oil; 385 mg, 9.62 mmol). After rinsing the sides of the flask with THE (2 mL), the reaction was stirred at room temperature for 50 min then cooled to 0° C. and quenched with sat. $NH_4Cl$ (aq). The mixture was poured into water then extracted with EtOAc (3×). The combined organic layers were washed with brine (1×) then concentrated. The residue was purified via $SiO_2$ FCC (0-100% EtOAc in hexanes) to afford "diastereomer A" tert-butyl (2R,4R)-4-(benzyloxy)-2-((4-bromo-6-chloropyridazin-3-yl)carbamoyl)-2-ethylpyrrolidine-1-carboxylate (473 mg, 46%) and "diastereomer B" tert-butyl (2S,4R)-4-(benzyloxy)-2-((4-bromo-6-chloropyridazin-3-yl)carbamoyl)-2-ethylpyrrolidine-1-carboxylate (286 mg, 28%). LCMS calcd for $C_{23}H_{29}BrClN_4O_4$ [M+H]$^+$: m/z=539.1; Found: 539.0 (diastereomer A) and 539.0 (diastereomer B).

Step 4: (6aR,8R)-8-(Benzyloxy)-2-chloro-6a-ethyl-6a, 7,8,9-tetrahydropyrrolo[1',2':4,5]pyrazino[2,3-c]pyridazin-6(5H)-one and (6aS,8R)-8-(benzyloxy)-2-chloro-6a-ethyl-6a, 7,8,9-tetrahydropyrrolo[1',2':4,5]pyrazino[2,3-c]pyridazin-6(5H)-one To tert-butyl (2R,4R)-4-(benzyloxy)-2-((4-bromo-6-chloropyridazin-3-yl)carbamoyl)-2-ethylpyrrolidine-1-carboxylate (473 mg, 0.88 mmol) in DCM (17 mL) was added TFA (17 mL, 222 mmol). The reaction was stirred at room temperature for 3 h then concentrated. The residue was dissolved in MeCN (15 mL). N,N-Diisopropylethylamine (0.76 mL, 4.38 mmol) was added and the reaction was stirred at 80° C. for 2 h then allowed to cool to room temperature overnight. The reaction was concentrated to afford crude (6aR,8R)-8-(benzyloxy)-2-chloro-6a-ethyl-6a, 7,8,9-tetrahydropyrrolo[1',2':4,5]pyrazino[2,3-c]pyridazin-6(5H)-one (Intermediate 8; assumed quantitative yield) which was used directly without further purification. The other diastereomer was synthesized using an identical procedure. Note: (6aR,8R)-8-(benzyloxy)-2-chloro-6a-ethyl-6a,7,8,9-tetrahydropyrrolo[1',2':4,5]pyrazino[2,3-c]pyridazin-6(5H)-one may be purified via $SiO_2$ FCC (0:20:80 to 60:20:40

EtOAc/DCM/hexanes). LCMS calcd for $C_{18}H_{20}ClN_4O_2$ $[M+H]^+$: m/z=359.1; Found: 359.1.

Intermediate 9: (6aR,8S)-2-chloro-6a-ethyl-5,6,6a,7,8,9-hexahydropyrrolo[1',2':4,5]pyrazino[2,3-c]pyridazin-8-ol

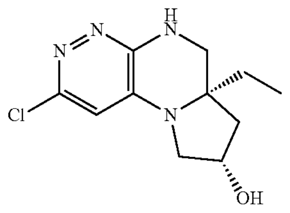 [SMILES: CC[C@@]12CNc3nnc(Cl)cc3N1C[C@@H](O)C2]

Step 1: (6aR,8R)-8-(benzyloxy)-2-chloro-6a-ethyl-5,6,6a, 7,8,9-hexahydropyrrolo [1',2':4,5]pyrazino[2,3-c]pyridazine

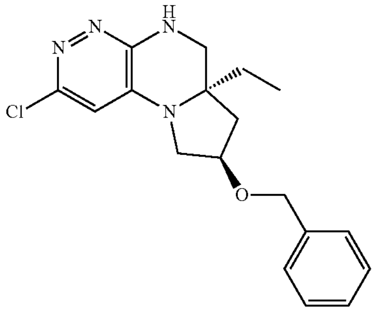 [SMILES: CC[C@@]12CNc3nnc(Cl)cc3N1C[C@H](OCc1ccccc1)C2]

To a solution of (6aR,8R)-8-(benzyloxy)-2-chloro-6a-ethyl-6a,7,8,9-tetrahydropyrrolo[1',2':4,5]pyrazino[2,3-c]pyridazin-6(5H)-one (1.9 g, 5.3 mmol, Intermediate 8a) in THF (25 mL) at 0° C. was added $BH_3 \cdot Me_2S$ (2 M in THF; 5 mL, 10 mmol). The reaction mixture was stirred at 55° C. for ~48 h, after which additional $BH_3 \cdot Me_2S$ (2 M in THF; 2.5 mL, 5 mmol) was added. The reaction was stirred at 55° C. for 3 h then cooled, quenched with MeOH, and concentrated. The residue was dissolved in EtOH (40 mL) then cooled to 0° C. and treated with AcOH (6.3 mL, 105 mmol) then $NaBH_3CN$ (0.8 g, 12.7 mmol) in two portions. The reaction was warmed to room temperature then stirred at 70° C. for 6 h, after which it was cooled to room temperature and concentrated. The residue was diluted with DCM and sat. $NaHCO_3$ (aq) and extracted with DCM (3×). The combined organic layers were dried with $Na_2SO_4$, filtered and concentrated. The crude material was purified via $SiO_2$ FCC (0-20% MeOH in DCM) to give (6aR,8R)-8-(benzyloxy)-2-chloro-6a-ethyl-5,6,6a,7,8,9-hexahydropyrrolo[1',2':4,5]pyrazino[2,3-c]pyridazine (1.22 g, 60%). LCMS calcd for $C_{18}H_{22}ClN_4O$ $[M+H]^+$: m/z=345.1; Found: 345.0.

Step 2: (6aR,8R)-2-chloro-6a-ethyl-5,6,6a, 7,8,9-hexahydropyrrolo[1',2':4,5]pyrazino[2,3-c]pyridazin-8-ol

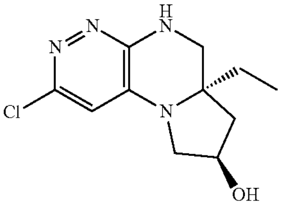 [SMILES: CC[C@@]12CNc3nnc(Cl)cc3N1C[C@H](O)C2]

To (6aR,8R)-8-(benzyloxy)-2-chloro-6a-ethyl-5,6,6a,7,8,9-hexahydropyrrolo[1',2':4,5]pyrazino[2,3-c]pyridazine (1.2 g, 3.5 mmol) in DCM (35 mL) at 0° C. was added $BCl_3$ (1 M in DCM; 10 mL, 10 mmol). The reaction was stirred at 0° C. for 1.5 h then quenched slowly with sat.

$NaHCO_3$ (aq). The mixture was poured into water, neutralized with additional sat. $NaHCO_3$ (aq), then extracted with DCM (3×). The combined organic layers were washed with brine (1×), dried with $MgSO_4$, filtered then concentrated. The residue was taken up in MTBE then sonicated and filtered to give (6aR,8R)-2-chloro-6a-ethyl-5,6,6a,7,8,9-hexahydropyrrolo[1',2':4,5]pyrazino[2,3-c]pyridazin-8-ol (740 mg, 84%) as a white solid. LCMS calcd for $C_{11}H_{16}ClN_4O$ $[M+H]^+$: m/z=255.1; Found: 255.0.

Step 3: (6aR,8S)-2-chloro-6a-ethyl-5,6,6a, 7,8,9-hexahydropyrrolo[1',2':4,5]pyrazino[2,3-c]pyridazin-8-yl 4-nitrobenzoate

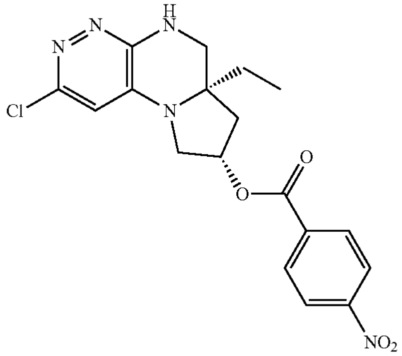 [SMILES: CC[C@@]12CNc3nnc(Cl)cc3N1C[C@@H](OC(=O)c1ccc([N+](=O)[O-])cc1)C2]

To a mixture of (6aR,8R)-2-chloro-6a-ethyl-5,6,6a,7,8,9-hexahydropyrrolo[1',2':4,5]pyrazino[2,3-c]pyridazine-8-ol (200 mg, 0.79 mmol), 4-nitrobenzoic acid (262 mg, 1.57 mmol), and polymer-supported $PPh_3$ (100-200 mesh, ~1.6 mmol/g loading; 735 mg, 1.18 mmol) in THF (10 mL) was added diisopropyl azodicarboxylate (0.23 mL, 1.18 mmol). The reaction was stirred at 65° C. 25 min then allowed to cool to room temperature. The mixture was filtered and the resulting filtrate was purified via $SiO_2$ FCC (0-10% MeOH in DCM) to afford (6aR,8S)-2-chloro-6a-ethyl-5,6,6a,7,8,9-hexahydropyrrolo[1',2':4,5]pyrazino[2,3-c]pyridazin-8-yl 4-nitrobenzoate (assumed quantitative yield) as a yellow solid. LCMS calcd for $C_{18}H_{19}ClN_5O_4[M+H]^+$: m/z=404.1; Found: 404.0.

Step 4: (6aR,8S)-2-chloro-6a-ethyl-5,6,6a, 7,8,9-hexahydropyrrolo[1',2':4,5]pyrazino[2,3-c]pyridazin-8-ol To (6aR,8S)-2-chloro-6a-ethyl-5,6,6a,7,8,9-hexahydropyrrolo[1',2':4,5]pyrazino[2,3-c]pyridazin-8-yl 4-nitrobenzoate (1.16 g, 2.86 mmol) in MeOH (8 mL) and THE (16 mL) was added NaOH (802 mg, 1.18 mmol) in water (9 mL). The reaction was stirred at room temperature for 15 min then diluted with a small amount of water and subsequently bulk-extracted with DCM (3×). The combined organic layers were washed with brine (1×) then dried with $MgSO_4$, filtered and concentrated. The residue was taken up in MTBE and the resulting mixture was filtered through a 0.45 μm PTFE fritted filter. The collected solids were washed with MTBE and dried to give the title compound (Intermediate 9; 548 mg, 75%) as a white solid. LCMS calcd for $C_{11}H_{16}ClN_4O$ $[M+H]^+$: m/z=255.1; Found: 255.0.

Intermediate 10: (6aR,8S)-6a-ethyl-2-(3-fluoro-2-methoxyphenyl)-5,6,6a,7,8,9-hexahydropyrrolo[1',2':4,5]pyrazino[2,3-c]pyridazin-8-ol

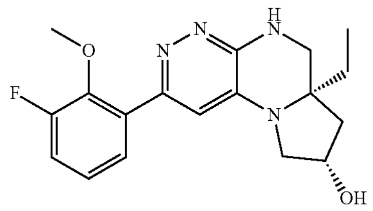 [SMILES: CC[C@@]12CNc3nnc(-c4cccc(F)c4OC)cc3N1C[C@@H](O)C2]

Step 1. (6aR,8R)-8-(benzyloxy)-6a-ethyl-2-(3-fluoro-2-methoxyphenyl)-6a, 7,8,9-tetrahydropyrrolo[1',2':4,5]pyrazino[2,3-c]pyridazin-6(5H)-one

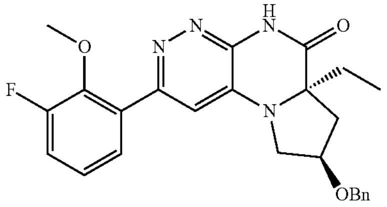 [SMILES: CC[C@]12C[C@@H](OCc3ccccc3)CN1c1cc(-c3cccc(F)c3OC)nnc1NC2=O]

A mixture of (6aR,8R)-8-(benzyloxy)-2-chloro-6a-ethyl-6a,7,8,9-tetrahydropyrrolo[1',2':4,5]pyrazino[2,3-c]pyridazin-6(5H)-one (1.1 g, 3.0 mmol, Intermediate 8a), 3-fluoro-2-methoxyphenylboronic acid (1.3 g, 7.6 mmol), dichloro-1,1'-bisdiphenylphosphino) ferrocene palladium (II) dichloromethane (744 mg, 0.9 mmol) and potassium carbonate (2.1 g, 15.2 mmol) in dioxane (25.0 mL) and water (7.0 mL) was sparged for ~5 min with $N_2$. Reaction stirred at 100° C. and monitored by LCMS. After 3 hours, the reaction was resubjected with equal amounts of all reagents, sparged for 5 min with $N_2$ then resumed heating at 100° C. for an additional hour. Reaction was then cooled to room temperature and poured into water. Extracted with EtOAc (3×) then dried with $MgSO_4$, filtered and concentrated. Crude was purified via $SiO_2$ FCC: 0-100% EtOAc/hexanes to yield the title compound (1.11 g, 82% yield) as an orange foam. LCMS calcd for $C_{25}H_{26}FN_4O_3[M+H]^+$: m/z=449.2; Found: 449.1.

Step 2. (6aR,8R)-8-(benzyloxy)-6a-ethyl-2-(3-fluoro-2-methoxyphenyl)-5,6,6a, 7,8,9-hexahydro-pyrrolo[1',2':4,5]pyrazino[2,3-c]pyridazine

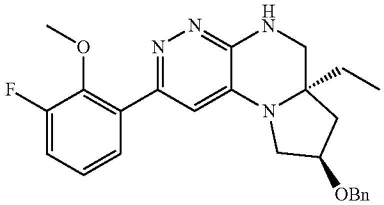 [SMILES: CC[C@@]12CNc3nnc(-c4cccc(F)c4OC)cc3N1C[C@H](OCc1ccccc1)C2]

To (6aR,8R)-8-(benzyloxy)-6a-ethyl-2-(3-fluoro-2-methoxyphenyl)-6a,7,8,9-tetrahydro-pyrrolo[1',2':4,5]pyrazino[2,3-c]pyridazin-6(5H)-one (393 mg, 0.88 mmol) in THE (5.00 mL) was added lithium aluminum hydride (1M in THF, 5.3 mL, 5.3 mmol) dropwise at 0° C. The reaction was left to warm to ambient temperature. After 2 hours, additional lithium aluminum hydride (1.50 mL, 1.50 mmol) was added. After 1 hour, the reaction was cooled to 0° C. then methanol (8.0 mL) was added dropwise, followed by acetic acid (1.5 mL, 26.3 mmol). The reaction was left to warm to ambient temperature, then sodium cyanoborohydride (551 mg, 8.8 mmol) was added and stirred at 80° C. overnight. Reaction was then neutralized with sat. $NaHCO_3$ (aq) then poured into water and extracted with EtOAc (3×). The combined organic layers were washed with brine (1×), dried with $MgSO_4$, filtered then concentrated. Purified via $SiO_2$ FCC: 0-10% MeOH/DCM to yield the title compound (347 mg, 91% yield) as a beige solid. LCMS calcd for $C_{25}H_{28}FN_4O_2[M+H]^+$: m/z=435.2; Found: 435.1.

Step 3. (6aR,8R)-6a-ethyl-2-(3-fluoro-2-methoxyphenyl)-5,6,6a, 7,8,9-hexahydropyrrolo-[1',2':4,5]pyrazino[2,3-c]pyridazin-8-ol

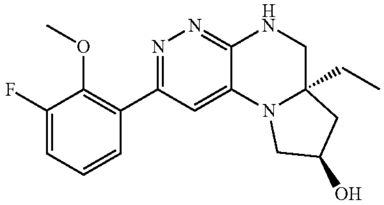 [SMILES: CC[C@@]12CNc3nnc(-c4cccc(F)c4OC)cc3N1C[C@H](O)C2]

To (6aR,8R)-8-(benzyloxy)-6a-ethyl-2-(3-fluoro-2-methoxyphenyl)-5,6,6a,7,8,9-hexahydropyrrolo[1',2':4,5]pyrazino[2,3-c]pyridazine (961 mg, 2.21 mmol) in DCM (25.0 mL) was added trichloroborane (6.63 mL, 6.63 mmol) slowly (down side of flask) at −78° C. After complete addition, the reaction stirred for ~2 min then warmed to 0° C. (ice-water bath). After 20 min, the reaction was quenched with dropwise addition of water at 0° C. and neutralized with sat. $NaHCO_3$ (aq) then extracted with DCM (3×). The DCM layers were combined, dried with $MgSO_4$, filtered then concentrated. Crude was purified via $SiO_2$ FCC: 0-20% MeOH/DCM to yield the title compound (551 mg, 72%). LCMS calcd for $C_{18}H_{22}FN_4O_2[M+H]^+$: m/z=345.2; Found: 345.1.

Step 4. (6aR,8S)-6a-ethyl-2-(3-fluoro-2-methoxyphenyl)-5,6,6a, 7,8,9-hexahydropyrrolo [1',2':4,5] pyrazino[2,3-c]pyridazin-8-ol To a briefly sonicated mixture of 4-nitrobenzoic acid (485 mg, 2.90 mmol), (6aR,8R)-6a-ethyl-2-(3-fluoro-2-methoxyphenyl)-5,6,6a,7,8,9-hexahydropyrrolo[1',2':4,5]pyrazino[2,3-c]pyridazin-8-ol (500.0 mg, 1.45 mmol) and triphenylphosphine (2.72 g, 4.36 mmol, 1.6 mmol/g polymer-bound) in THE (20.0 mL) was added diisopropyl azodicarboxylate (858 uL, 4.36 mmol). Stirred at 65° C. and monitored by LC-MS. After 1.5 hours, the reaction was cooled and filtered to remove the triphenylphosphine, rinsed with THE (20 mL) then methanol (40 mL). To the filtrate was added potassium carbonate (815 mg, 5.90 mmol), and the suspension was allowed to stir for 2 hours. Reaction was diluted with DCM and sat. sodium bicarbonate (aq). The organic layer was separated, and the water layer was extracted 1× with DCM then 1× with EtOAc. The organic layers were combined, dried with sodium sulfate, filtered, and condensed. Crude was purified via $SiO_2$ (0-20% MeOH/DCM) to yield the desired product as a white solid (330 mg, 66% yield). LCMS calcd for $C_{18}H_{22}FN_4O_2[M+H]^+$: m/z=345.2; Found: 345.0.

Intermediate 11: (6aS,8S)-6a-ethyl-2-(3-fluoro-2-methoxyphenyl)-5,6,6a,7,8,9-hexahydropyrrolo[1',2':4,5]pyrazino[2,3-c]pyridazin-8-ol

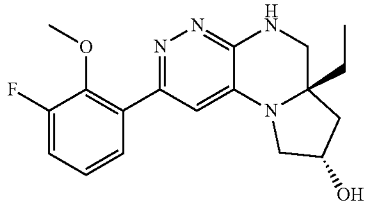 [SMILES: CC[C@]12CNc3nnc(-c4cccc(F)c4OC)cc3N1C[C@@H](O)C2]

The title compound was prepared according to the procedure used for Intermediate 10, starting from Intermediate 8b. LCMS calcd for $C_{18}H_{22}FN_4O_2[M+H]^+$: m/z=345.2; Found: 345.0.

Intermediate 12: (6aR,8S)-2-chloro-6a-methyl-5,6,6a,7,8,9-hexahydropyrrolo[1',2':4,5]pyrazino[2,3-c]pyridazin-8-ol

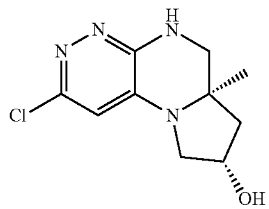 [SMILES: C[C@@]12CNc3nnc(Cl)cc3N1C[C@@H](O)C2]

Step 1. (2R,4S)-4-(benzyloxy)-N-(4-bromo-6-chloropyridazin-3-yl)-2-methylpyrrolidine-2-carboxamide

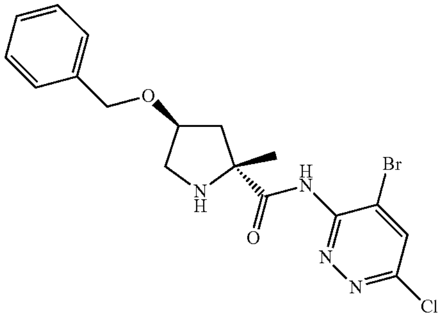 [SMILES: C[C@]1(C(=O)Nc2nnc(Cl)cc2Br)C[C@H](OCc2ccccc2)CN1]

To a cold solution of (6S,7aR)-6-(benzyloxy)-7a-methyltetrahydro-1H,3H-pyrrolo[1,2-c]oxazole-1,3-dione (12.0 g, 45.9 mmol, prepared by an analogous procedure to that described in Example 55) and 4-bromo-6-chloropyridazin-3-amine (8.6 g, 41.3 mmol) in THE (60.0 mL), was added NaH (60% in mineral oil, 2.76 g, 68.9 mmol) in portions. The reaction was left to stir until no more starting material was consumed. After that, another portion of 60% NaH (0.5 eq) was added and the HPLC showed a significant improvement of conversion. The reaction mixture was quenched with 10% citric acid solution (100 mL) and extracted with a mixture of chloroform and IPA (3:1; 75 mL×5), the combined organic layers were dried over $Na_2SO_4$, filtered, and evaporated to dryness to give the title compound (19.5 g), which was used for next reaction without further purification. LCMS calcd for $C_{17}H_{19}BrClN_4O_2[M+H]^+$: m/z=427.03; Found: 427.2.

Step 2. (6aR,8S)-8-(benzyloxy)-2-chloro-6a-methyl-6a, 7,8,9-tetrahydropyrrolo[1',2':4,5]pyrazino[2,3-c]pyridazin-6(5H)-one

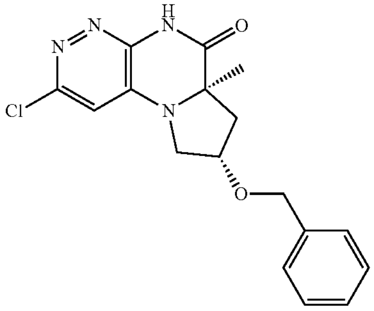 [SMILES: C[C@]12C[C@H](OCc3ccccc3)CN1c1cc(Cl)nnc1NC2=O]

To a solution of (2R,4S)-4-(benzyloxy)-N-(4-bromo-6-chloropyridazin-3-yl)-2-methyl-pyrrolidine-2-carboxamide (19.5 g, 45.9 mmol) in THE (100 mL) was added $Na_2CO_3$ (19.5 g, 184 mmol) and stirred at ambient temperature for 12 h. The reaction mixture was condensed and diluted with 100 mL of heptane. The solid was filtered and washed with water to give a white solid. The solid was taken up in DCM and sat. $Na_2CO_3$ (aq) then separated. The water layer was re-extracted with DCM (3×). The organic layers were combined, filtered through a layer of silica gel and condensed to yield the title compound (8.5 g, 54% yield). The crude was taken to the next step without further purification. LCMS calcd for $C_{17}H_{18}ClN_4O_2[M+H]^+$: m/z=345.1; Found: 345.5.

Step 3. (6aR,8S)-8-(benzyloxy)-2-chloro-6a-methyl-5,6,6a, 7,8,9-hexahydropyrrolo [1',2':4,5]pyrazino[2,3-c]pyridazine

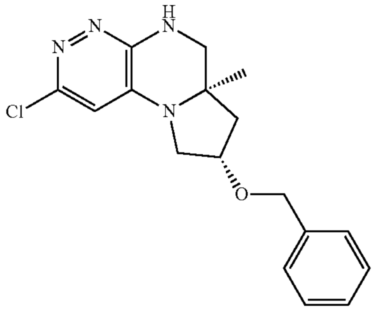 [SMILES: C[C@@]12CNc3nnc(Cl)cc3N1C[C@@H](OCc1ccccc1)C2]

To a solution of (6aR,8S)-8-(benzyloxy)-2-chloro-6a-methyl-6a,7,8,9-tetrahydropyrrolo [1',2':4,5]pyrazino[2,3-c] pyridazin-6(5H)-one (8.20 g, 23.0 mmol) in dry THE (60.0 mL) was added $BH_3$·DMS (18.1 mL, 191 mmol) at 0° C. The reaction was warmed to room temperature and stirred at 50° C. for 90 min. Once complete by LCMS, the reaction was cooled to 0° C. and quenched by adding methanol dropwise. The reaction was condensed, then taken up in EtOH (60 mL). To this solution was added $NaBH_3CN$ (11.9 g, 191 mmol) and acetic acid (21.8 mL, 381 mmol) at 0° C. The reaction was slowly heated to 80° C. and stirred overnight. The reaction was cooled to room temperature, poured into sat. $NaHCO_3$ (aq) and extracted with DCM (3×). The combined organic phase was dried over $Na_2SO_4$ and filtered. The residue was purified by SiO2 FCC 10-60% DCM/(EtOAc with 1% MeOH) to give the title compound (5.3 g, 6% yield) as a colorless solid. LCMS calcd for $C_{17}H_{20}ClN_4O$ $[M+H]^+$: m/z=331.1; Found: 331.5.

Step 4. (6aR,8S)-2-chloro-6a-methyl-5,6,6a, 7,8,9-hexahydropyrrolo[1',2':4,5]pyrazino[2,3-c]pyridazin-8-ol Trichloroborane (1M in DCM, 3.05 mL, 3.05 mmol) was added dropwise to a solution of (6aR,8S)-8-(benzyloxy)-2-chloro-6a-methyl-5,6,6a,7,8,9-hexahydropyrrolo[1',2':4,5] pyrazino[2,3-c]pyridazine (202 mg, 0.61 mmol) in DCM (3.00 mL) at −78° C. The resulting mixture was stirred at −78° C. for 30 min and quenched with MeOH (10 mL). The volatiles were evaporated, and the residue was basified by addition of 10% $Na_2CO_3$ solution, then extracted with $CHCl_3$/IPA (3:1, 10 mL×6). The combined organic phase was dried over $Na_2SO_4$, filtered and concentrated. The residue was dried under high vacuum to give the title compound (140 mg, 95% yield) as a white solid. The crude was taken to the next step without further purification. LCMS calcd for $C_{10}H_{14}ClN_4O$ $[M+H]^+$: m/z=241.1; Found: 241.3.

Intermediate 13: (6aS,8S)-2-chloro-6a-methyl-5,6,6a,7,8,9-hexahydropyrrolo[1',2':4,5]pyrazino[2,3-c] pyridazin-8-ol

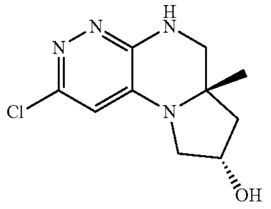 [SMILES: C[C@]12CNc3nnc(Cl)cc3N1C[C@@H](O)C2]

Step 1. (6aS,8S)-2-chloro-6a-methyl-5,6,6a, 7,8,9-hexahydropyrrolo[1',2':4,5]pyrazino[2,3-c]pyridazin-8-ol The title compound was synthesized according to the procedure described for Intermediate 12. LCMS calcd for $C_{10}H_{14}ClN_4O$ $[M+H]^+$: m/z=241.1; Found: 241.2.

Intermediate 14: (6aS,8R)-2-chloro-6a-methyl-5,6,6a,7,8,9-hexahydropyrrolo[1',2':4,5]pyrazino[2,3-c] pyridazin-8-ol

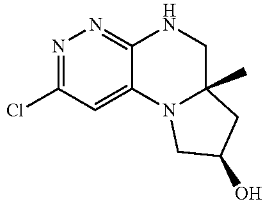 [SMILES: C[C@]12CNc3nnc(Cl)cc3N1C[C@H](O)C2]

The title compound was synthesized according to the procedure described for Intermediate 12 using "diastereomer B" from Example 55, Step 5. LCMS calcd for $C_{10}H_{14}ClN_4O$ $[M+H]^+$: m/z=241.1; Found: 241.2.

Intermediate 15: (6aS,8R)-2-(3-fluoro-2-hydroxyphenyl)-6a-methyl-5,6,6a,7,8,9-hexahydropyrrolo[1',2':4,5]pyrazino[2,3-c]pyridazin-8-ol

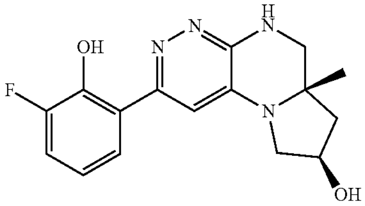 [SMILES: C[C@]12CNc3nnc(-c4cccc(F)c4O)cc3N1C[C@H](O)C2]

A mixture of (6aS,8R)-2-chloro-6a-methyl-5,6,6a,7,8,9-hexahydropyrrolo[1',2':4,5]pyrazino[2,3-c]pyridazin-8-ol (Intermediate 14) (200 mg, 0.83 mmol), 3-fluoro-2-hydroxy-phenyl-boronic acid (518 mg, 3.32 mmol), $K_3PO_4$ (1.06 g, 4.99 mmol) and XPhos Pd G2 (65 mg, 0.08 mmol) in 1,4-dioxane (6.00 mL) and water (0.30 mL) was purged with $N_2$ for 2 mins. The reaction was stirred at 100° C. overnight. The reaction was poured into saturated $NaHCO_3$ (aq) solution and was extracted by $CHCl_3$/IPA (3:1, 5×). The combined organic phase was dried over $Na_2SO_4$. After removal of solvent, the residue was purified by $SiO_2$ FCC 0-10% MeOH in DCM to give the title compound (160 mg, 61% yield) as a yellow solid. LCMS calc. for $C_{16}H_{18}FN_4O_2$ $[M+H]^+$: m/z=317.1; Found: 317.5.

Intermediate 16: 5-(Trifluoromethyl)-6-vinylpyridin-3-ol

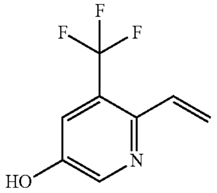

To a vial was added 6-chloro-5-(trifluoromethyl)-3-pyridinol (500 mg, 2.53 mmol), cesium carbonate (1.51 g, 4.56 mmol), potassium vinyltrifluoroborate (610 mg, 4.56 mmol), followed by 1,4-dioxane (7.23 mL) and water (1.21 mL). The mixture was sparged with $N_2$ for 5 minutes then SPhos Pd G2 (220 mg, 0.31 mmol) was added, reaction was sealed with a septacap, purged with $N_2$ for another 5 min then stirred at 95° C. After 5 h, the reaction was cooled to room temperature, filtered through celite, condensed, then purified using $SiO_2$ FCC 0-20% MeOH in DCM to yield the title compound (280 mg, 59% yield). LCMS calcd for $C_8H_7F_3NO$ $[M+H]^+$: m/z=190.1; Found: 190.0.

Intermediate 17: 6-Fluoro-4-iodonicotinic acid

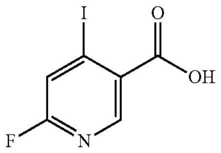

To a solution of 6-fluoronicotinic acid (1.0 g, 7.09 mmol) in THE (14.0 mL) was added LDA (8.9 mL, 17.7 mmol) dropwise at −78° C. The reaction was stirred at −78° C. for 10 min then stirred at −50° C. for 90 min. The reaction was brought back to −78° C. and iodine (1.80 g, 7.09 mmol) in 4.0 mL of THE was added dropwise and the reaction was stirred at −50° C. for 1 h, then quenched by the addition of acetic acid (2.84 mL, 49.6 mmol) in 3.0 mL of THF at −78° C. The resulting mixture was poured into a 10% citric acid solution and was extracted by EtOAc (3×). The combined organic phase was dried over $Na_2SO_4$, filtered, and condensed. Crude was purified by prep-HPLC on a $C_{18}$ column (30×250 mm, 10 μM) using mobile phase 8-55% MeCN/$H_2O$ (w/0.1% TFA) (tR=18 min).

The desired fractions were collected and extracted with EtOAc (3×). The organic phase was dried with $Na_2SO_4$, filtered, and concentrated to yield the title compound (505 mg, 27% yield). LCMS calcd for $C_6H_4FINO_2$ $[M+H]^+$: m/z=267.9; Found: 268.2.

Intermediate 18: 5-Fluoro-6-vinylpyridin-3-ol

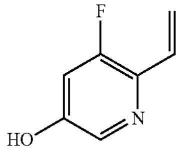

A mixture of 4,4,5,5-tetramethyl-2-vinyl-1,3,2-dioxaborolane (500 uL, 2.95 mmol), potassium carbonate (1.42 g, 10.3 mmol), 6-chloro-5-fluoropyridin-3-ol (300 mg, 2.03 mmol) and XPhos Pd G2 (80.0 mg, 0.10 mmol) in 1,4-dioxane (15.8 mL) and water (3.20 mL) was sparged with $N_2$ for ~10 min then stirred at 80° C. overnight. The reaction was left to cool to room temperature then filtered through celite and rinsed with MeOH. Filtrate was concentrated, dissolved in DCM then purified via $SiO_2$ FCC: 0-100% EtOAC/Hexane to yield the title compound (300 mg, quant. yield) as a yellow oil. LCMS calcd for $C_7H_7FNO$ $[M+H]^+$: m/z=140.1; Found: 139.9.

Intermediate 19: 5-Hydroxy-3,6-dimethylpicolinonitrile

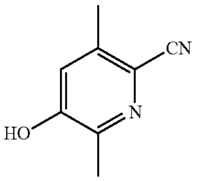

Step 1. 6-Bromo-2,5-dimethylpyridin-3-ol

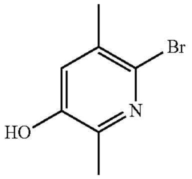

6-bromo-2,5-dimethylpyridin-3-amine (1.0 g, 4.97 mmol) was dissolved in water (9.0 mL) and sulfuric acid (2.5 mL, 4.97 mmol). The solution was cooled to 0° C. and sodium nitrite (686 mg, 9.95 mmol) was added portion wise over 10 min. The solution was stirred at room temperature for 5 min and then stirred at 90° C. for 1-2 h or until LCMS confirmed complete consumption of starting material. The reaction mixture was cooled to room temperature and carefully neutralized to pH ~7-8 with saturated $NaHCO_3$ (aq). The aqueous layer was washed with brine and extracted with EtOAc (4×). The combined organic layers were dried with $Na_2SO_4$ and concentrated to dryness to yield the title compound (850 mg, 72% yield). The crude was taken to the next step without further purification. LCMS calcd for $C_7H_9BrNO$ $[M+H]^+$: m/z=202.0 Found: 202.1.

Step 2. 5-Hydroxy-3,6-dimethylpicolinonitrile

6-Bromo-2,5-dimethylpyridin-3-ol (720 mg, 3.56 mmol) and copper (I) cyanide (638 mg, 7.13 mmol) were dissolved in DMF (11.8 mL) and the resulting mixture was degassed by sparging nitrogen. The mixture was heated at 130° C. for 3 h. After cooling to room temperature, the reaction mixture was diluted with EtOAc and washed with brine. The aqueous layer was re-extracted 2× with EtOAc and the combined organic layers were dried with $Na_2SO_4$ and concentrated to dryness. The crude mixture was dissolved in DMSO and centrifuged to remove any undissolved solids. The crude mixture was then purified by reverse phase prep-HPLC 10-30% ACN/water (w/0.1% TFA) to give the title compound (407 mg, 77% yield). LCMS calcd for $C_8H_9N_2O$ $[M+H]^+$: m/z=149.1; Found: 149.2.

Example 1: 3-(6-(4-(4-(((6aR,8R)-2-(3,5-difluoro-2-hydroxyphenyl)-5,6,6a,7,8,9-hexa-hydropyrrolo[1',2':4,5]pyrazino[2,3-c]pyridazin-8-yl)oxy)benzyl)piperazin-1-yl)-1-oxoisoindolin-2-yl)piperidine-2,6-dione Step 2: tert-butyl (6aR,8R)-2-(3,5-difluoro-2-hydroxyphenyl)-8-(4-formylphenoxy)-6a, 7,8,9-tetrahydropyrrolo[1',2':4,5]pyrazino[2,3-c]pyridazine-5(6H)-carboxylate

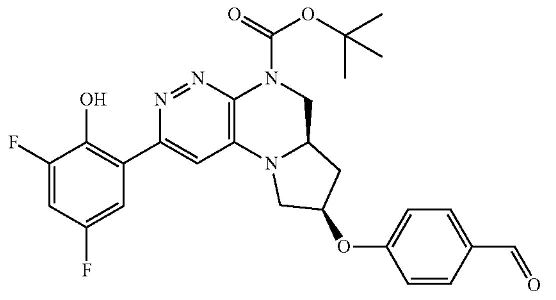

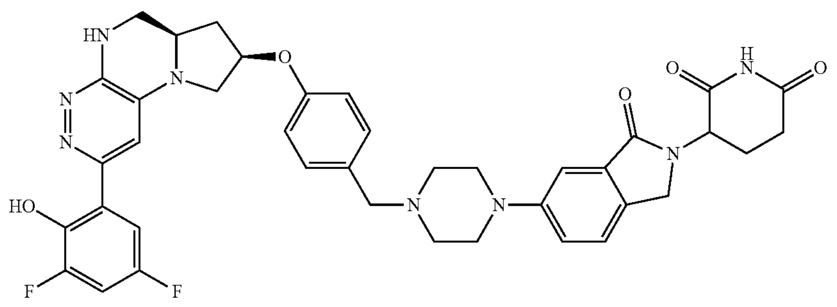 [SMILES: O=C1CCC(N2Cc3ccc(N4CCN(Cc5ccc(O[C@@H]6C[C@@H]7CNc8nnc(-c9cc(F)cc(F)c9O)cc8N7C6)cc5)CC4)cc3C2=O)C(=O)N1]

Step 1: tert-butyl (6aR,8R)-2-chloro-8-(4-formylphenoxy)-6a, 7,8,9-tetrahydropyrrolo [1',2':4,5]pyrazino[2,3-c]pyridazine-5(6H)-carboxylate

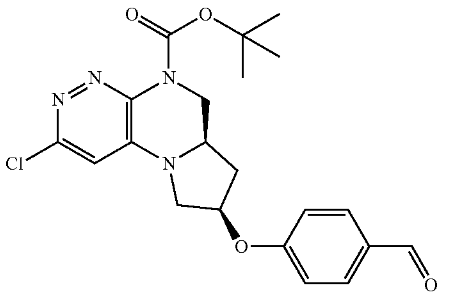 [SMILES: CC(C)(C)OC(=O)N1C[C@H]2C[C@@H](Oc3ccc(C=O)cc3)CN2c2cc(Cl)nnc21]

To tert-butyl (6aR,8S)-2-chloro-8-hydroxy-6a,7,8,9-tetrahydropyrrolo[1',2':4,5]pyrazino[2,3-c]pyridazine-5(6H)-carboxylate (200 mg, 0.610 mmol, Intermediate 1), polymer-supported triphenylphosphine (0.760 g, 1.22 mmol, 100-200 mesh with 1.6 mmol $PPh_3$/g loading) and 4-hydroxybenzaldehyde (299 mg, 2.45 mmol) in THF (7.00 mL) was added diisopropyl azodicarboxylate (181 uL, 0.920 mmol). The solution was stirred at 80° C. for 0.5 h then cooled to RT, filtered and concentrated under reduced pressure. The crude material was purified via $SiO_2$ FCC: 0-100% EtOAc/hexane to obtain tert-butyl (6aR,8R)-2-chloro-8-(4-formylphenoxy)-6a,7,8,9 tetrahydropyrrolo[1',2':4,5]pyrazino[2,3-c]pyridazine-5(6H)-carboxylate (172 mg, 65%) as an off-white foam. LCMS calcd for $C_{21}H_{24}ClN_4O_4$ $[M+H]^+$: m/z=431.2; Found: 431.1.

To crude tert-butyl (6aR,8R)-2-chloro-8-(4-formylphenoxy)-6a,7,8,9 tetrahydropyrrolo-[1',2':4,5]pyrazino[2,3-c]pyridazine-5(6H)-carboxylate (19.8 mg, 50.0 μmol) in THE (1.00 mL) and water (200 μL) was added dichloro-1,1'-bisdiphenylphosphino)ferrocene palladium (II) dichloromethane (11.3 mg, 10.0 μmol), (3,5-difluoro-2-hydroxyphenyl)boronic acid (24.0 mg, 140 μmol) and potassium carbonate (31.8 mg, 230 μmol). The solution was sparged with $N_2$ for ~2 min then stirred at 100° C. After 1 h, reaction was cooled to RT, concentrated under reduced pressure and purified via $SiO_2$ FCC: 0-100% EtOAc/hexanes to obtain tert-butyl (6aR,8R)-2-(3,5-difluoro-2-hydroxyphenyl)-8-(4-formylphenoxy)-6a,7,8,9-tetrahydropyrrolo[1',2':4,5]pyrazino-[2,3-c]pyridazine-5(6H)-carboxylate (10.0 mg, 41%) as a yellow film. LCMS calcd for $C_{27}H_{27}F_2N_4O_5$ $[M+H]^+$: m/z=525.2; Found: 525.0.

Step 3:4-(((6aR,8R)-2-(3,5-difluoro-2-hydroxyphenyl)-5,6,6a, 7,8,9-hexahydropyrrolo [1',2':4,5]pyrazino[2,3-c]pyridazin-8-yl)oxy)benzaldehyde

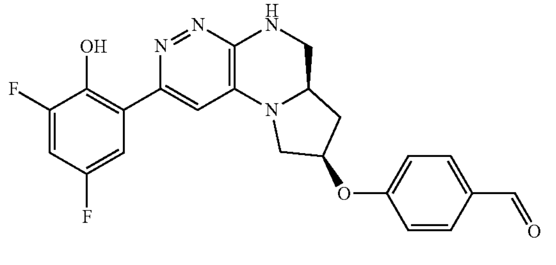 [SMILES: O=Cc1ccc(O[C@@H]2C[C@@H]3CNc4nnc(-c5cc(F)cc(F)c5O)cc4N3C2)cc1]

To tert-butyl (6aR,8R)-2-(3,5-difluoro-2-hydroxyphenyl)-8-(4-formylphenoxy)-6a,7,8,9-tetrahydropyrrolo[1',2':4,5]pyrazino[2,3-c]pyridazine-5(6H)-carboxylate (10.0 mg, 20.0 μmol) in DCM (2.00 mL) was added 2,2,2-trifluoroacetic acid (150 μL, 1.96 mmol). The solution was stirred at room temperature for 1.5 h and concentrated under reduced pressure to yield 4-(((6aR,8R)-2-(3,5-difluoro-2-hydroxyphenyl)-5,6,6a,7,8,9-hexahydropyrrolo[1',2':4,5]pyrazino-[2,3-c]pyridazin-8-yl)oxy)benzaldehyde (10.3 mg, quant.) as the TFA salt. LCMS calcd for $C_{22}H_{19}F_2N_4O_3[M+H]^+$: m/z=425.1; Found: 425.2.

Step 4: 3-(6-(4-(4-(((6aR,8R)-2-(3,5-difluoro-2-hydroxyphenyl)-5,6,6a, 7,8,9-hexahydro-pyrrolo[1',2':4,5]pyrazino[2,3-c]pyridazin-8-yl)oxy)benzyl)piperazin-1-yl)-1-oxoisoindolin-2-yl)piperidine-2,6-dione To 4-(((6aR,8R)-2-(3,5-difluoro-2-hydroxyphenyl)-5,6,6a,7,8,9-hexahydropyrrolo [1',2':4,5]pyrazino[2,3-c]pyridazin-8-yl)oxy)benzaldehyde trifluoroacetate (10.3 mg, 20.0 μmol) and 3-(3-oxo-5-piperazin-1-yl-1H-isoindol-2-yl)piperidine-2,6-dione (12.4 mg, 30.0 μmol, Intermediate 2) in NMP (1.00 mL) was added acetic acid (5.50 μL, 100 μmol). The reaction was sonicated, stirred for 1 h at 50° C. and then sodium triacetoxyborohydride (13.0 mg, 60.0 μmol) was added. The solution was stirred at 50° C. for 20 min., then 70° C. for 1.5 h. The reaction was cooled to room temperature, filtered and directly purified via prep-LCMS (7.8-25.8% $CH_3CN$ in $H_2O$ with 0.1% TFA) to yield 3-(6-(4-(4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)benzyl)piperazin-1-yl)-1-oxoisoindolin-2-yl)piperidine-2,6-di one (0.50 mg, 2.700 yield) as a white TFA salt. LCMS calcd for $C_{39}H_{39}F_2N_8O_5[M+H]+$: m/z=737.3; Found: 737.2.

Examples 2-25

Examples 2-25 shown below in Table 1 were prepared as TFA salts by the method used in preparing Example 1, utilizing the appropriate starting materials and intermediates.

TABLE 1

Examples 2-25

| Example | Structure/Name | Calcd. (M + H)+ m/z | Found (M + H)+ m/z |
|---|---|---|---|
| 2 | 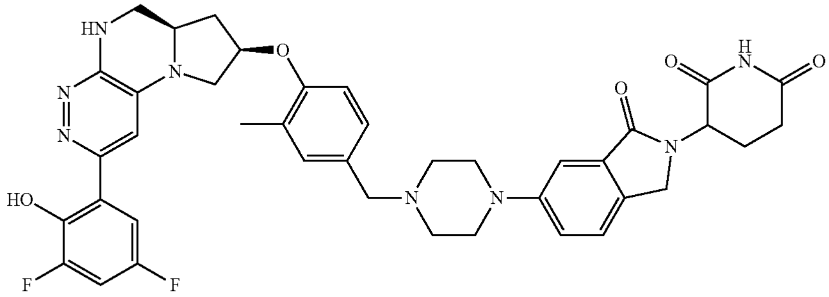 3-(6-(4-(4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-3-methylbenzyl)piperazin-1-yl)-1-oxoisoindolin-2-yl) piperidine-2,6-dione | 751.3 | 751.2 |
| 3 | 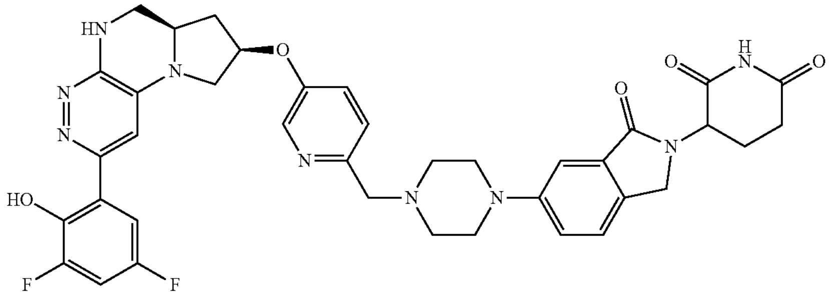 3-(6-(4-((5-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)pyridin-2-yl)methyl)piperazin-1-yl)-1-oxoisoindolin-2-yl) piperidine-2,6-dione | 738.3 | 738.2 |

TABLE 1-continued

| Examples 2-25 | | | |
|---|---|---|---|
| Example | Structure/Name | Calcd. (M + H)+ m/z | Found (M + H)+ m/z |
| 4 | 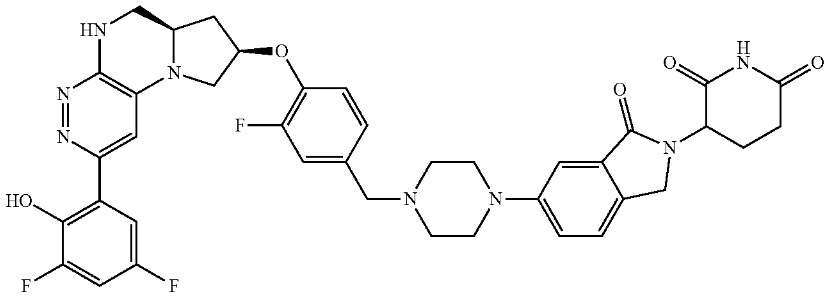 3-(6-(4-(4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-3-fluorobenzyl)piperazin-1-yl)-1-oxoisoindolin-2-yl) piperidine-2,6-dione | 755.3 | 755.2 |
| 5 | 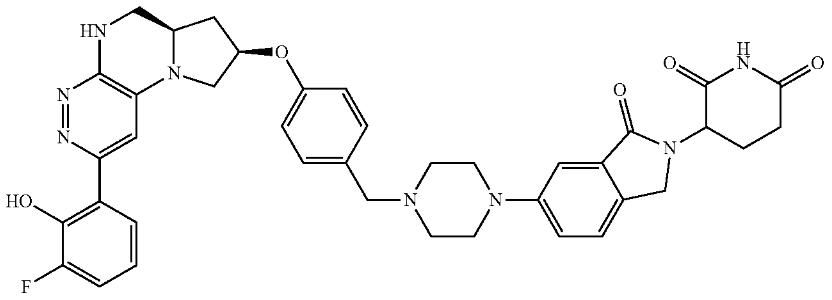 [SMILES: O=C1CCC(N2Cc3ccc(N4CCN(Cc5ccc(O[C@@H]6C[C@@H]7CNc8nnc(-c9cccc(F)c9O)cc8N7C6)cc5)CC4)cc3C2=O)C(=O)N1] 3-(6-(4-(4-(((6aR,8R)-2-(3-fluoro-2-hydroxyphenyl)-5,6,6a,7,8,9-hexahydropyrrolo[1',2':4,5]pyrazino[2,3-c]pyridazin-8-yl)oxy) benzyl)piperazin-1-yl)-1-oxoisoindolin-2-yl)piperidine-2,6-dione | 719.3 | 719.2 |
| 6 | 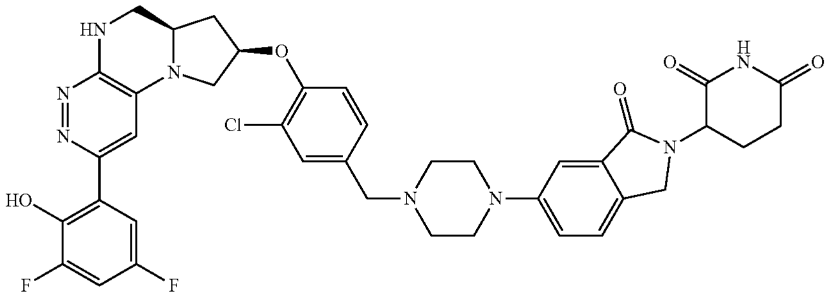 [SMILES: O=C1CCC(N2Cc3ccc(N4CCN(Cc5ccc(O[C@@H]6C[C@@H]7CNc8nnc(-c9cc(F)cc(F)c9O)cc8N7C6)c(Cl)c5)CC4)cc3C2=O)C(=O)N1] 3-(6-(4-(3-chloro-4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)benzyl)piperazin-1-yl)-1-oxoisoindolin-2-yl)piperidine-2,6-dione | 771.3 | 771.2 |

TABLE 1-continued

| Example | Structure/Name (Examples 2-25) | Calcd. (M + H)+ m/z | Found (M + H)+ m/z |
|---|---|---|---|
| 7 | 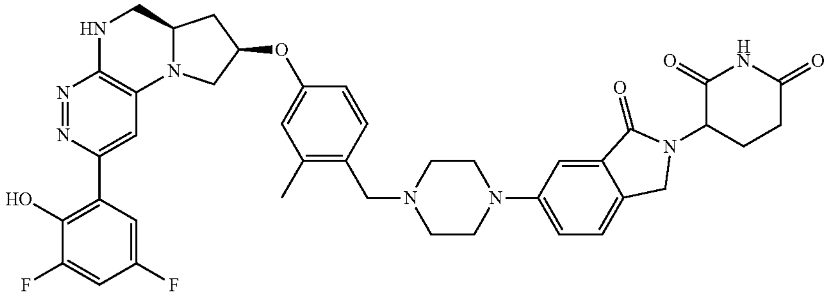 [SMILES: Cc1cc(O[C@@H]2C[C@@H]3CNc4nnc(-c5cc(F)cc(F)c5O)cc4N3C2)ccc1CN1CCN(c2ccc3c(c2)C(=O)N(C2CCC(=O)NC2=O)C3)CC1] 3-(6-(4-(4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-2-methylbenzyl)piperazin-1-yl)-1-oxoisoindolin-2-yl)piperidine-2,6-dione | 751.3 | 751.2 |
| 8 | 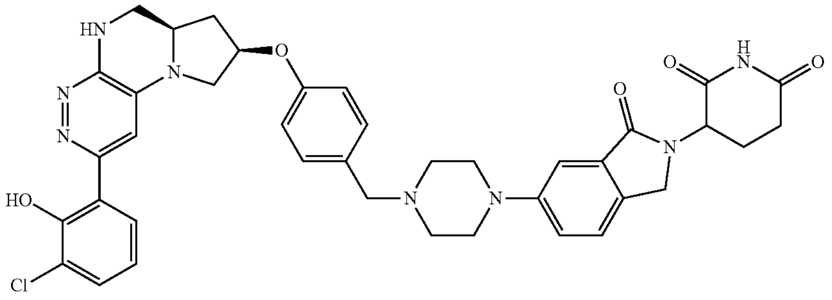 [SMILES: O=C1CCC(N2Cc3ccc(N4CCN(Cc5ccc(O[C@@H]6C[C@@H]7CNc8nnc(-c9cccc(Cl)c9O)cc8N7C6)cc5)CC4)cc3C2=O)C(=O)N1] 3-(6-(4-(4-(((6aR,8R)-2-(3-chloro-2-hydroxyphenyl)-5,6,6a,7,8,9-hexahydropyrrolo[1',2':4,5]pyrazino[2,3-c]pyridazin-8-yl)oxy)benzyl)piperazin-1-yl)-1-oxoisoindolin-2-yl)piperidine-2,6-dione $^1$H NMR (400 MHz, MeOD) δ 7.58 - 7.48 (m, 4H), 7.42 (dd, J = 7.8, 1.6 Hz, 1H), 7.39 - 7.32 (m, 2H), 7.13 (d, J = 8.7 Hz, 2H), 7.04 (t, J = 7.9 Hz, 1H), 6.84 (s, 1H), 5.41 - 5.33 (m, 1H), 5.14 (dd, J = 13.3, 5.2 Hz, 1H), 4.49 - 4.35 (m, 4H), 4.10 (dd, J = 12.7, 6.4 Hz, 1H), 4.03 - 3.80 (m, 4H), 3.62 - 3.35 (m, 2H), 3.23 (dd, J = 11.6, 9.5 Hz, 2H), 2.96 - 2.74 (m, 3H), 2.49 (qd, J = 13.0, 4.6 Hz, 1H), 2.21 - 2.12 (m, 1H), 2.04 - 1.93 (m, 1H). | 735.3 | 735.2 |
| 9 | 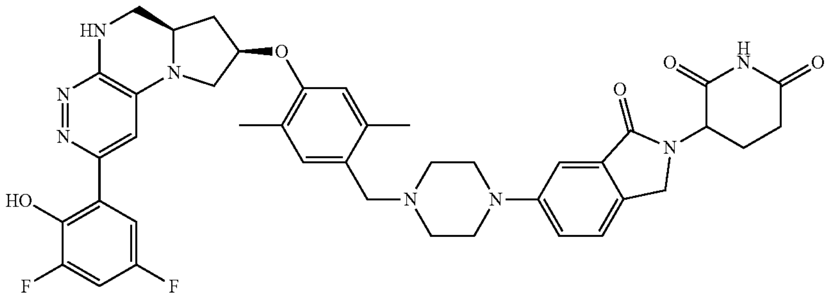 [SMILES: Cc1cc(O[C@@H]2C[C@@H]3CNc4nnc(-c5cc(F)cc(F)c5O)cc4N3C2)c(C)cc1CN1CCN(c2ccc3c(c2)C(=O)N(C2CCC(=O)NC2=O)C3)CC1] 3-(6-(4-(4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-2,5-dimethylbenzyl)piperazin-1-yl)-1-oxoisoindolin-2-yl)piperidine-2,6-dione | 765.3 | 765.2 |

TABLE 1-continued

| Example | Structure/Name | Calcd. (M + H)+ m/z | Found (M + H)+ m/z |
|---|---|---|---|
| | Examples 2-25 | | |
| 10 | 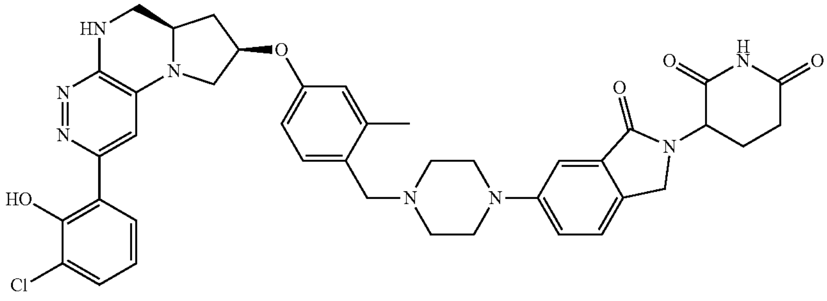 3-(6-(4-(4-(((6aR,8R)-2-(3-chloro-2-hydroxyphenyl)-5,6,6a,7,8,9-hexahydropyrrolo[1',2':4,5]pyrazino[2,3-c]pyridazin-8-yl)oxy)-2-methylbenzyl)piperazin-1-yl)-1-oxoisoindolin-2-yl)piperidine-2,6-dione | 749.3 | 749.2 |
| 11 | 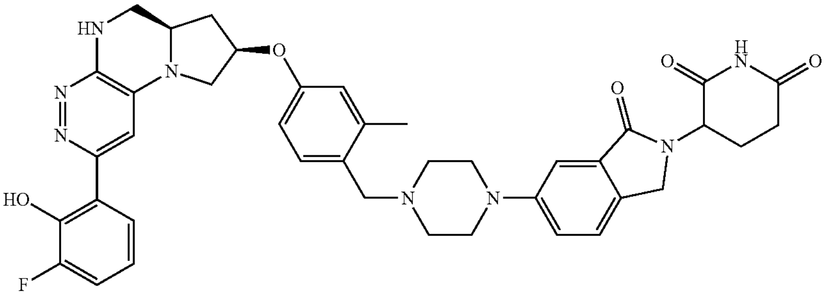 [SMILES: Cc1cc(O[C@@H]2C[C@@H]3CNc4nnc(-c5cccc(F)c5O)cc4N3C2)ccc1CN1CCN(c2ccc3c(c2)C(=O)N(C2CCC(=O)NC2=O)C3)CC1] 3-(6-(4-(4-(((6aR,8R)-2-(3-fluoro-2-hydroxyphenyl)-5,6,6a,7,8,9-hexahydropyrrolo[1',2':4,5]pyrazino[2,3-c]pyridazin-8-yl)oxy)-2-methylbenzyl)piperazin-1-yl)-1-oxoisoindolin-2-yl)piperidine-2,6-dione | 733.3 | 733.2 |
| 12 | 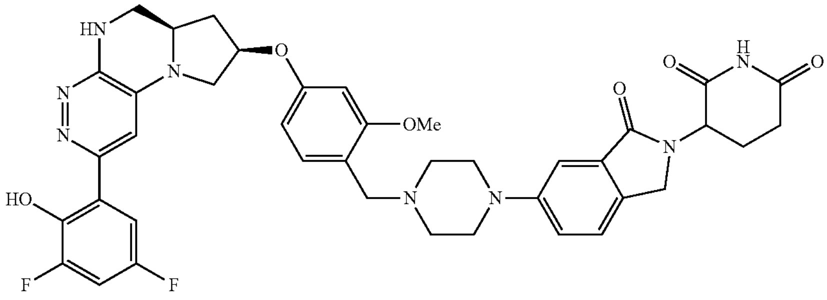 3-(6-(4-(4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-2-methoxybenzyl)piperazin-1-yl)-1-oxoisoindolin-2-yl)piperidine-2,6-dione | 767.3 | 767.2 |

TABLE 1-continued

| Examples 2-25 | | | |
|---|---|---|---|
| Example | Structure/Name | Calcd. (M + H)+ m/z | Found (M + H)+ m/z |
| 13 | 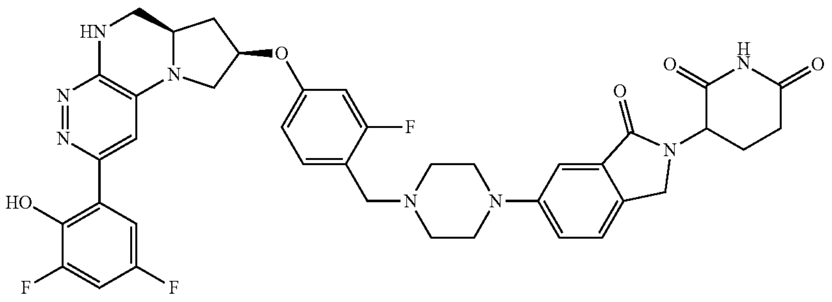<br>3-(6-(4-(4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-2-fluorobenzyl)piperazin-1-yl)-1-oxoisoindolin-2-yl) piperidine-2,6-dione | 755.3 | 755.2 |
| 14 | 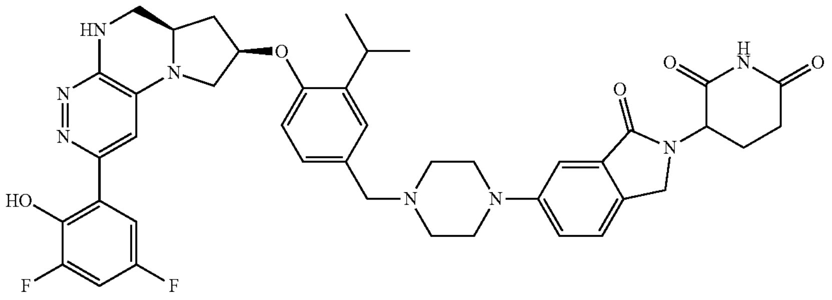 [SMILES: CC(C)c1cc(CN2CCN(c3ccc4c(c3)C(=O)N(C3CCC(=O)NC3=O)C4)CC2)ccc1O[C@@H]1C[C@@H]2CNc3nnc(-c4cc(F)cc(F)c4O)cc3N2C1]<br>3-(6-(4-(4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-3-isopropylbenzyl)piperazin-1-yl)-1-oxoisoindolin-2-yl) piperidine-2,6-dione | 779.3 | 779.3 |
| 15 | 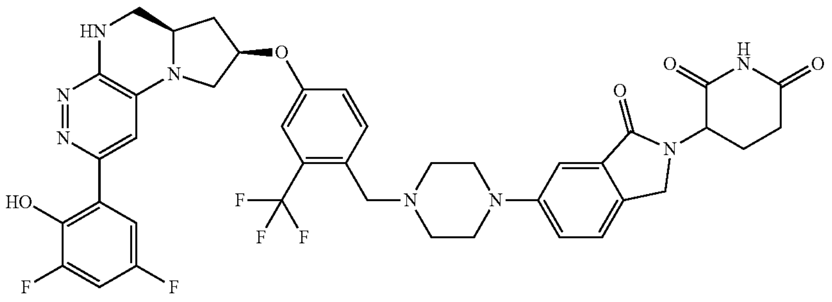 [SMILES: O=C1CCC(N2Cc3ccc(N4CCN(Cc5ccc(O[C@@H]6C[C@@H]7CNc8nnc(-c9cc(F)cc(F)c9O)cc8N7C6)cc5C(F)(F)F)CC4)cc3C2=O)C(=O)N1]<br>3-(6-(4-(4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-2-(trifluoromethyl)benzyl)piperazin-1-yl)-1-oxoisoindolin-2-yl)piperidine-2,6-dione | 805.3 | 805.2 |

TABLE 1-continued

| Examples 2-25 | | | |
|---|---|---|---|
| Example | Structure/Name | Calcd. (M + H)+ m/z | Found (M + H)+ m/z |
| 16 | 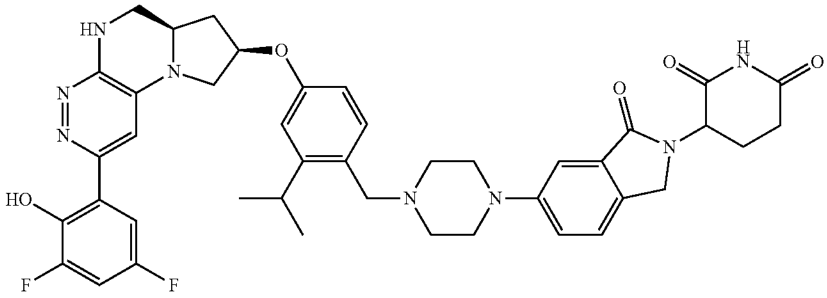 3-(6-(4-(4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-2-isopropylbenzyl)piperazin-1-yl)-1-oxoisoindolin-2-yl) piperidine-2,6-dione | 779.3 | 779.3 |
| 17 | 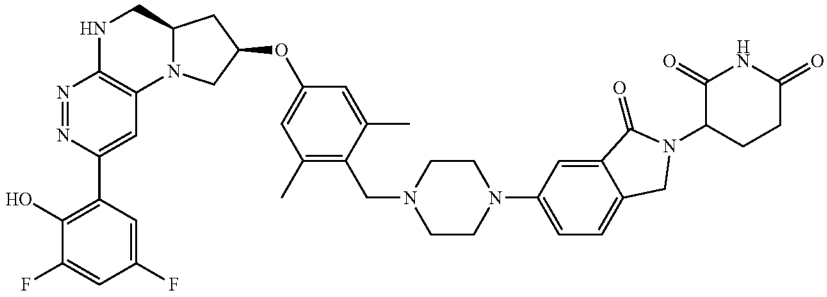 3-(6-(4-(4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-2,6-dimethylbenzyl)piperazin-1-yl)-1-oxoisoindolin-2-yl) piperidine-2,6-dione | 765.3 | 765.3 |
| 18 | 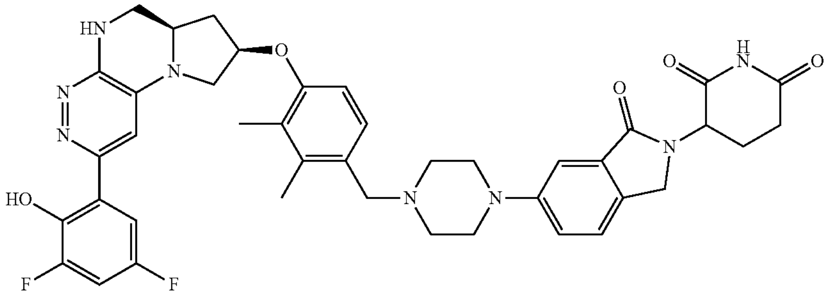 3-(6-(4-(4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-2,3-dimethylbenzyl)piperazin-1-yl)-1-oxoisoindolin-2-yl) piperidine-2,6-dione | 765.3 | 765.3 |

TABLE 1-continued

| Examples 2-25 | | | |
|---|---|---|---|
| Example | Structure/Name | Calcd. $(M+H)^+$ m/z | Found $(M+H)^+$ m/z |
| 19 | 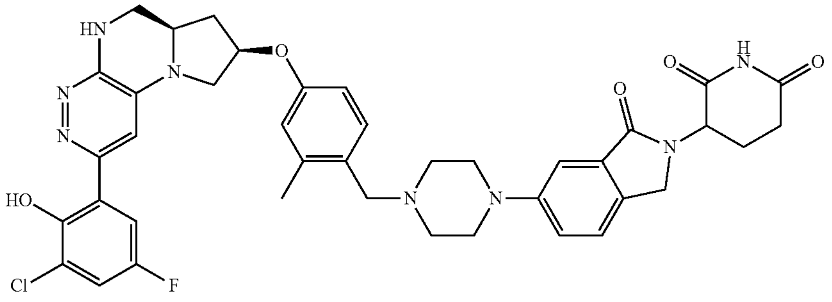 3-(6-(4-(4-(((6aR,8R)-2-(3-chloro-5-fluoro-2-hydroxyphenyl)-5,6,6a,7,8,9-hexahydropyrrolo[1',2':4,5]pyrazino[2,3-c]pyridazin-8-yl)oxy)-2-methylbenzyl)piperazin-1-yl)-1-oxoisoindolin-2-yl)piperidine-2,6-dione | 767.3 | 767.2 |
| 20 | 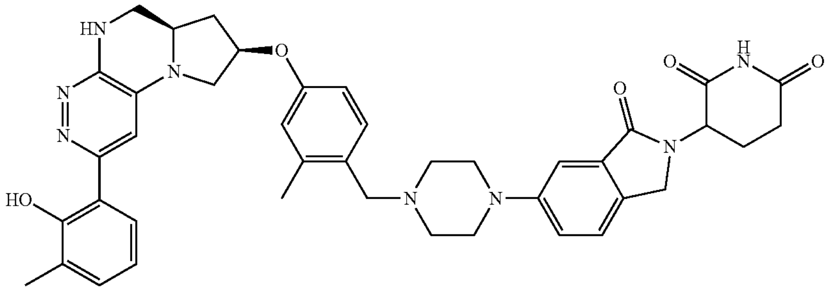 [SMILES: Cc1cc(O[C@@H]2C[C@@H]3CNc4nnc(-c5cccc(C)c5O)cc4N3C2)ccc1CN1CCN(c2ccc3c(c2)C(=O)N(C2CCC(=O)NC2=O)C3)CC1] 3-(6-(4-(4-(((6aR,8R)-2-(2-hydroxy-3-methylphenyl)-5,6,6a,7,8,9-hexahydropyrrolo[1',2':4,5]pyrazino[2,3-c]pyridazin-8-yl)oxy)-2-methylbenzyl)piperazin-1-yl)-1-oxoisoindolin-2-yl)piperidine-2,6-dione | 729.4 | 729.3 |
| 21 | 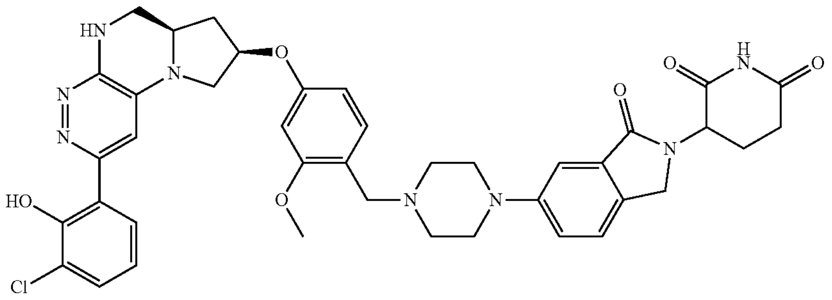 [SMILES: COc1cc(O[C@@H]2C[C@@H]3CNc4nnc(-c5cccc(Cl)c5O)cc4N3C2)ccc1CN1CCN(c2ccc3c(c2)C(=O)N(C2CCC(=O)NC2=O)C3)CC1] 3-(6-(4-(4-(((6aR,8R)-2-(3-chloro-2-hydroxyphenyl)-5,6,6a,7,8,9-hexahydropyrrolo[1',2':4,5]pyrazino[2,3-c]pyridazin-8-yl)oxy)-2-methoxybenzyl)piperazin-1-yl)-1-oxoisoindolin-2-yl)piperidine-2,6-dione | 765.3 | 765.2 |

TABLE 1-continued

| Examples 2-25 | | | |
|---|---|---|---|
| Example | Structure/Name | Calcd. (M + H)+ m/z | Found (M + H)+ m/z |
| 22 | 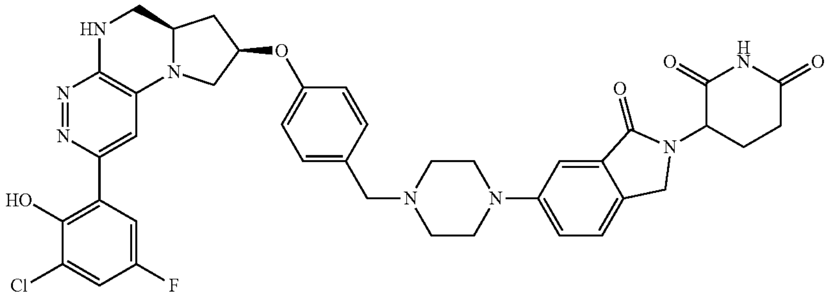<br>3-(6-(4-(4-(((6aR,8R)-2-(3-chloro-5-fluoro-2-hydroxyphenyl)-5,6,6a,7,8,9-hexahydropyrrolo[1',2':4,5]pyrazino[2,3-c]pyridazin-8-yl)oxy)benzyl)piperazin-1-yl)-1-oxoisoindolin-2-yl)piperidine-2,6-dione | 753.3 | 753.2 |
| 23 | 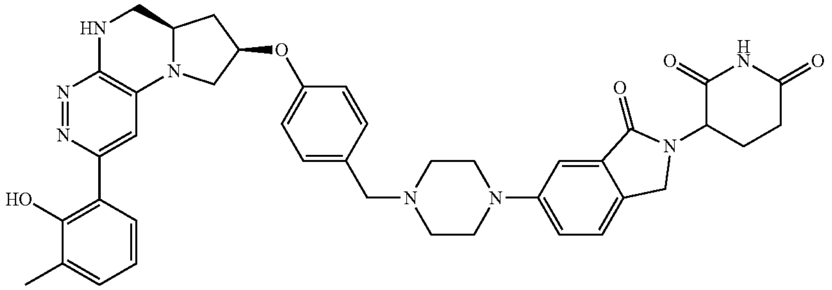 [SMILES: Cc1cccc(-c2cc3c(nn2)NC[C@H]2C[C@@H](Oc4ccc(CN5CCN(c6ccc7c(c6)C(=O)N(C6CCC(=O)NC6=O)C7)CC5)cc4)CN32)c1O]<br>3-(6-(4-(4-(((6aR,8R)-2-(2-hydroxy-3-methylphenyl)-5,6,6a,7,8,9-hexahydropyrrolo[1',2':4,5]pyrazino[2,3-c]pyridazin-8-yl)oxy)benzyl)piperazin-1-yl)-1-oxoisoindolin-2-yl)piperidine-2,6-dione | 715.3 | 715.2 |
| 24 | 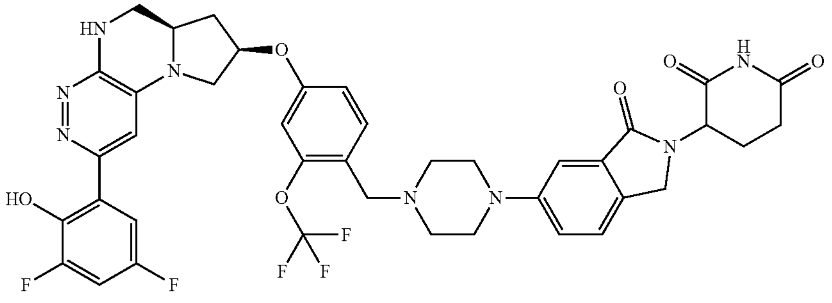 [SMILES: O=C1CCC(N2Cc3ccc(N4CCN(Cc5ccc(O[C@@H]6C[C@@H]7CNc8nnc(-c9cc(F)cc(F)c9O)cc8N7C6)cc5OC(F)(F)F)CC4)cc3C2=O)C(=O)N1]<br>3-(6-(4-(4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-2-(trifluoromethoxy)benzyl)piperazin-1-yl)-1-oxoisoindolin-2-yl)piperidine-2,6-dione | 821.3 | 821.3 |

TABLE 1-continued

| Example | Structure/Name | Calcd. (M + H)+ m/z | Found (M + H)+ m/z |
|---|---|---|---|
| Examples 2-25 | | | |
| 25 | 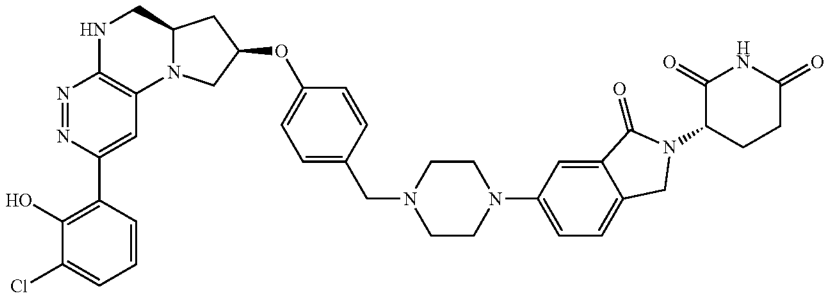 [SMILES: O=C1CC[C@H](N2Cc3ccc(N4CCN(Cc5ccc(O[C@@H]6C[C@@H]7CNc8nnc(-c9cccc(Cl)c9O)cc8N7C6)cc5)CC4)cc3C2=O)C(=O)N1] (S)-3-(6-(4-(4-(((6aR,8R)-2-(3-chloro-2-hydroxyphenyl)-5,6,6a,7,8,9-hexahydropyrrolo[1',2':4,5]pyrazino[2,3-c]pyridazin-8-yl)oxy)benzyl)piperazin-1-yl)-1-oxoisoindolin-2-yl)piperidine-2,6-dione $^{1}$H NMR (300 MHz, MeOD) δ 7.56 - 7.48 (m, 4H), 7.42 (dd, J = 7.8, 1.5 Hz, 1H), 7.37 - 7.30 (m, 2H), 7.13 - 6.99 (m, 3H), 6.83 (s, 1H), 5.40 - 5.32 (m, 1H), 5.12 (dd, J = 13.2, 5.1 Hz, 1H), 4.51 - 4.30 (m, 4H), 4.10 (dd, J = 12.6, 6.3 Hz, 1H), 4.05 - 3.71 (m, 3H), 3.68 - 3.31 (m, 7H), 3.23 (dd, J = 11.3, 9.5 Hz, 2H), 2.97 - 2.65 (m, 3H), 2.48 (qd, J = 13.1, 4.8 Hz, 1H), 2.22 - 1.90 (m, 2H). | 734.3 | 735.6 |

Example 26: 3-(6-(4-((2-(((6aR,8R)-2-(3,5-difluoro-2-hydroxyphenyl)-5,6,6a,7,8,9-hexa-hydropyrrolo[1',2':4,5]pyrazino[2,3-c]pyridazin-8-yl)thio)pyrimidin-5-yl)methyl)piperazin-1-yl)-1-oxoisoindolin-2-yl)piperidine-2,6-dione

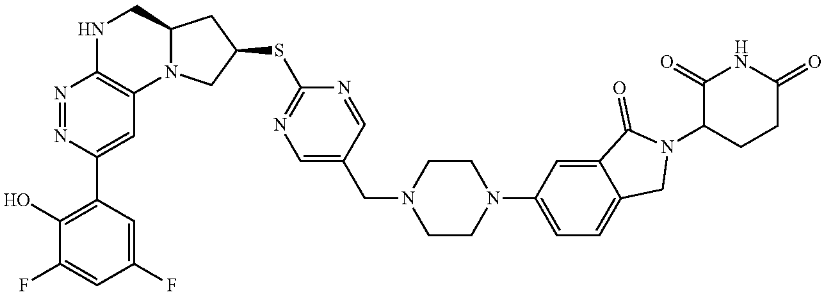 [SMILES: O=C1CCC(N2Cc3ccc(N4CCN(Cc5cnc(S[C@@H]6C[C@@H]7CNc8nnc(-c9cc(F)cc(F)c9O)cc8N7C6)nc5)CC4)cc3C2=O)C(=O)N1]

Step 1: tert-butyl (6aR,8S)-2-(3,5-difluoro-2-methoxyphenyl)-8-hydroxy-6a,7,8,9-tetrahydropyrrolo[1',2':4,5]pyrazino[2,3-c]pyridazine-5(6H)-carboxylate

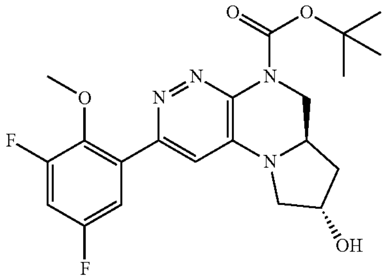 [SMILES: COc1c(F)cc(F)cc1-c1cc2c(nn1)N(C(=O)OC(C)(C)C)C[C@H]1C[C@H](O)CN21]

The title compound was prepared using the procedure analogous to those described for Example 1, Step 2, using Intermediate 1 instead of tert-butyl (6aR,8R)-2-chloro-8-(4-formyl-phenoxy)-6a,7,8,9 tetrahydropyrrolo[1',2':4,5]pyrazino[2,3-c]pyridazine-5(6H)-carboxylate and (3,5-difluoro-2-methoxyphenyl)boronic acid instead of (3,5-difluoro-2-hydroxyphenyl)boronic acid. LCMS calcd for $C_{21}H_{25}F_2N_4O_4[M+H]^+$: m/z=435.2; Found: 435.1.

Step 2: tert-butyl (6aR,8S)-2-(3,5-difluoro-2-methoxyphenyl)-8-((methylsulfonyl)oxy)-6a, 7,8,9-tetrahydropyrrolo[1',2':4,5]pyrazino[2,3-c]pyridazine-5(6H)-carboxylate

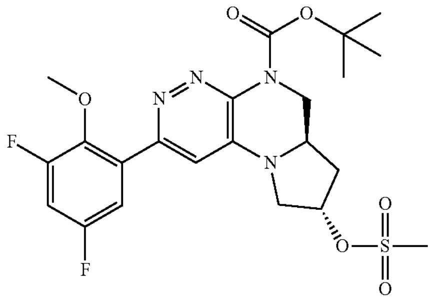 [SMILES: COc1c(F)cc(F)cc1-c1cc2c(nn1)N(C(=O)OC(C)(C)C)C[C@H]1C[C@H](OS(C)(=O)=O)CN21]

To a mixture of tert-butyl (6aR,8S)-2-(3,5-difluoro-2-methoxyphenyl)-8-hydroxy-6a,7,8,9-tetrahydropyrrolo[1',2':4,5]pyrazino[2,3-c]pyridazine-5(6H)-carboxylate (93.3 mg, 215 μmol) and triethylamine (89.8 μL, 644 μmol) in THE (4.00 mL) was added methanesulfonyl chloride (24.9 uL, 32.2 μmol). The reaction mixture was stirred overnight. LCMS analysis showed an incomplete reaction and additional triethylamine (479 μL, 3.44 mmol) and methanesulfonyl chloride (249 uL, 3.22 mmol) were added. The reaction was concentrated under reduced pressure and purified via $SiO_2$ FCC: 0-100% EtOAc/hexanes to obtain tert-butyl (6aR,8S)-2-(3,5-difluoro-2-methoxyphenyl)-8-((methylsulfonyl)oxy)-6a,7,8,9-tetrahydropyrrolo[1',2':4,5]pyrazino[2,3-c]pyridazine-5(6H)-carboxylate (110 mg, quantitative yield) as a white solid. LCMS calcd for $C_{22}H_{27}F_2N_4O_6S$ $[M+H]^+$: m/z=513.2; Found: 513.1.

Step 3: tert-butyl (6aR,8R)-2-(3,5-difluoro-2-methoxyphenyl)-8-((5-formylpyrimidin-2-yl)thio)-6a, 7,8,9-tetrahydropyrrolo[1',2':4,5]pyrazino[2,3-c]pyridazine-5(6H)-carboxylate

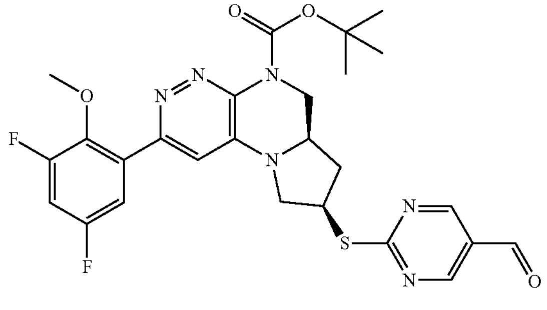 [SMILES: COc1c(F)cc(F)cc1-c1cc2c(nn1)N(C(=O)OC(C)(C)C)C[C@H]1C[C@@H](Sc3ncc(C=O)cn3)CN21]

To a mixture of tert-butyl (6aR,8S)-2-(3,5-difluoro-2-methoxyphenyl)-8-((methyl-sulfonyl)oxy)-6a,7,8,9-tetrahydropyrrolo[1',2':4,5]pyrazino[2,3-c]pyridazine-5(6H)-carboxylate (44.0 mg, 85.8 μmol), 2-sulfanylpyrimidine-5-carbaldehyde (24.1 mg, 172 μmol) and potassium carbonate (23.7 mg, 172 μmol) in MeCN (1.00 mL) was stirred at 90° C. for 24 hours. The reaction was cooled to room temperature, diluted with EtOAc, filtered and concentrated under reduced pressure. The crude material was purified via $SiO_2$ FCC: 0-100% EtOAc/hexanes to obtain tert-butyl (6aR,8R)-2-(3,5-difluoro-2-methoxyphenyl)-8-((5-formylpyrimidin-2-yl)thio)-6a,7,8,9-tetrahydropyrrolo[1',2':4,5]pyrazino[2,3-c]pyridazine-5(6H)-carboxylate (21.8 mg, 46% yield) as a white film. LCMS calcd for $C_{26}H_{27}F_2N_6O_4S$ $[M+H]^+$: m/z=557.2; Found: 557.1.

Step 4: 2-(((6aR,8R)-2-(3,5-difluoro-2-hydroxyphenyl)-5,6,6a, 7,8,9-hexahydropyrrolo [1',2':4,5]pyrazino[2,3-c]pyridazin-8-yl)thio)pyrimidine-5-carbaldehyde

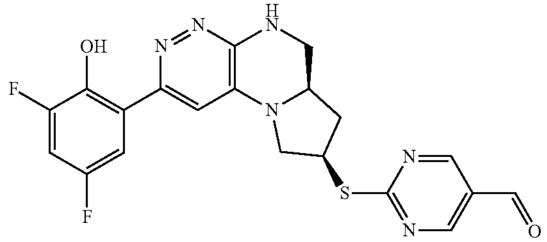 [SMILES: O=Cc1cnc(S[C@@H]2C[C@@H]3CNc4nnc(-c5cc(F)cc(F)c5O)cc4N3C2)nc1]

Boron tribromide (1.18 mL, 1.18 mmol) was added to a solution of tert-butyl (6aR,8R)-2-(3,5-difluoro-2-methoxyphenyl)-8-((5-formylpyrimidin-2-yl)thio)-6a,7,8,9-tetrahydropyrrolo [1',2':4,5]pyrazino[2,3-c]pyridazine-5(6H)-carboxylate (21.8 mg, 39.2 μmol) in DCM (2.00 mL).

The reaction was stirred at room temperature for 48 hours. The reaction mixture was carefully poured into a saturated aqueous solution of $NaHCO_3$ and the aqueous phase was extracted with DCM. The combined organics were washed with a saturated brine solution, dried over $MgSO_4$, filtered and concentrated under reduced pressure to obtain the title compound (10.6 mg, 61% yield) as a pale-yellow solid. LCMS calcd for $C_{20}H_{17}F_2N_6O_2S$ $[M+H]^+$: m/z=443.1; Found: 442.9.

Step 5: 3-(6-(4-((2-(((6aR,8R)-2-(3,5-difluoro-2-hydroxyphenyl)-5,6,6a, 7,8,9-hexahydro-pyrrolo[1',2':4,5]pyrazino[2,3-c]pyridazin-8-yl)thio)pyrimidin-5-yl)methyl)piperazin-1-yl)-1-oxoisoindolin-2-yl)piperidine-2,6-dione Sodium cyanoborohydride (4.52 mg, 71.9 μmol) was added to a solution of 2-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)thio)pyrimidine-5-carbaldehyde (10.6 mg, 24.0 μmol), 3-(3-oxo-5-piperazin-1-yl-1H-isoindol-2-yl)piperidine-2,6-dione (15.7 mg, 47.9 μmol, Intermediate 2) and acetic acid (6.90 μL, 121 μmol) in MeOH (1.00 mL). The reaction was stirred at 80° C. for 4 hours. The reaction mixture was cooled to room temperature, diluted with MeOH and filtered. The filtrate was directly purified via prep-HPLC (Waters CSH-C18, 5 uM, 30×100 mm, 6.5-24.5% MeCN/water (containing 0.1% TFA) over 5 min) to give the TFA salt of the title compound (1.2 mg, 5.1% yield) as a white solid. LCMS calcd for $C_{37}H_{37}F_2N_{10}O_4S$ $[M+H]^+$: m/z=755.3; Found: 755.2.

Example 27: 3-(6-(4-((6-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione

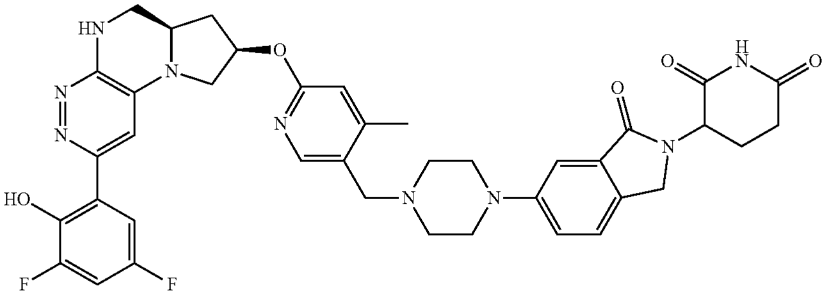 [SMILES: Cc1cc(O[C@@H]2C[C@@H]3CNc4nnc(-c5cc(F)cc(F)c5O)cc4N3C2)ncc1CN1CCN(c2ccc3c(c2)C(=O)N(C2CCC(=O)NC2=O)C3)CC1]

Step 1:4-methyl-5-vinylpyridin-2-ol

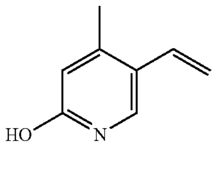

A solution 5-bromo-4-methylpyridin-2-ol (150 mg, 798 μmol), 4,4,5,5-tetramethyl-2-vinyl-1,3,2-dioxaborolane (338 μL, 1.99 mmol), potassium carbonate (441 mg, 3.19 mmol) and dichloro 1,1'-bisdiphenylphosphino)ferrocene palladium (II) dichloromethane (196 mg, 239 μmol) in a mixture of 1,4-dioxane (4.00 mL) and water (1.00 mL) was sparged with nitrogen for 5 minutes. The reaction was heated at 100° C. for 1 hour. The reaction was cooled to room temperature, quenched with a saturated aqueous solution of $NH_4Cl$ (1.00 mL), filtered and concentrated under reduced pressure. The crude material was purified via $SiO_2$ FCC: 0-5% MeOH/DCM to obtain 4-methyl-5-vinylpyridin-2-ol (108 mg, quantitative yield). LCMS calcd for $C_8H_{10}NO$ $[M+H]^+$: m/z=136.1; Found: 136.0.

Step 2: tert-butyl (6aR,8R)-2-chloro-8-((4-methyl-5-vinylpyridin-2-yl)oxy)-6a, 7,8,9-tetrahydropyrrolo[1',2':4,5]pyrazino[2,3-c]pyridazine-5(6H)-carboxylate

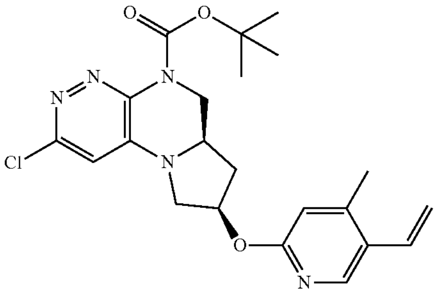 [SMILES: C=Cc1cnc(O[C@@H]2C[C@@H]3CN(C(=O)OC(C)(C)C)c4nnc(Cl)cc4N3C2)cc1C]

Diisopropyl azodicarboxylate (169 μL, 857 μmol) was added to a solution of tert-butyl (6aR,8S)-2-chloro-8-hydroxy-6a,7,8,9-tetrahydropyrrolo[1',2':4,5]pyrazino[2,3-c]pyridazine-5(6H)-carboxylate (70.0 mg, 214 μmol, Intermediate 1), 4-methyl-5-vinylpyridin-2-ol (107 mg, 793 μL) and triphenylphosphine (225 mg, 857 μL) in THE (2.00 mL), and the reaction mixture was heated at 60° C. for 30 minutes. The reaction was cooled to room temperature and directly purified via $SiO_2$ FCC: 0-100% EtOAC/hexanes to obtain tert-butyl (6aR,8R)-2-chloro-8-((4-methyl-5-vinylpyridin-2-yl)oxy)-6a,7,8,9-tetrahydropyrrolo[1',2':4,5]pyrazino[2,3-c]pyridazine-5(6H)-carboxylate (95.1 mg, quantitative yield). LCMS calcd for $C_{22}H_{27}ClN_5O_3$ $[M+H]^+$: m/z=444.2/446.2; Found: 444.1/446.2.

Step 3: tert-butyl (6aR,8R)-2-chloro-8-((5-formyl-4-methylpyridin-2-yl)oxy)-6a,7,8,9-tetrahydropyrrolo[1',2':4,5]pyrazino[2,3-c]pyridazine-5(6H)-carboxylate

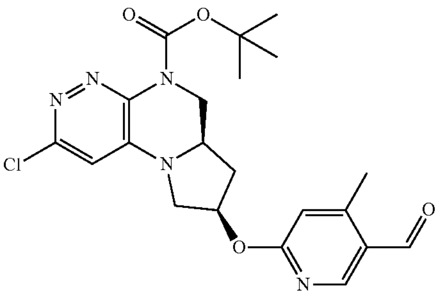

Osmium tetroxide (49.0 μL, 153 μmol) was added to a solution of tert-butyl (6aR,8R)-2-chloro-8-((4-methyl-5-vinylpyridin-2-yl)oxy)-6a,7,8,9-tetrahydropyrrolo[1',2':4,5]pyrazino[2,3-c]pyridazine-5(6H)-carboxylate (68.0 mg, 153 μmol) and sodium periodate (98.3 mg, 460 μmol) in a mixture of THE (4.00 mL) and water (1.00 mL). The reaction was stirred at room temperature overnight. The reaction was poured into water and extracted with DCM. The combined organics layers were washed with a saturated brine solution, dried over $MgSO_4$, filtered and concentrated under reduced pressure to obtain crude tert-butyl (6aR,8R)-2-chloro-8-((5-formyl-4-methylpyridin-2-yl)oxy)-6a,7,8,9-tetrahydropyrrolo[1',2':4,5]pyrazino[2,3-c]pyridazine-5(6H)-carboxylate (68 mg, quantitative yield). The material was used in the following step without additional purification. LCMS calcd for $C_{21}H_{25}ClN_5O_4[M+H]^+$: m/z=446.2; Found: 446.1.

Step 4: tert-butyl (6aR,8R)-2-(3,5-difluoro-2-methoxyphenyl)-8-((5-formyl-4-methylpyridin-2-yl)oxy)-6a, 7,8,9-tetrahydropyrrolo[1',2':4,5]pyrazino[2,3-c]pyridazine-5(6H)-carboxylate

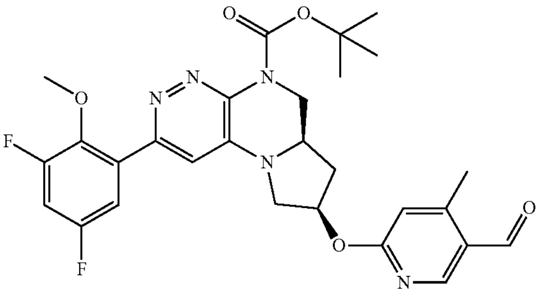 [SMILES: COc1c(F)cc(F)cc1-c1cc2c(nn1)N(C(=O)OC(C)(C)C)C[C@H]1C[C@@H](Oc3cc(C)c(C=O)cn3)CN21]

The title compound was prepared using the procedure analogous to that described for Example 1, Step 2, using tert-butyl (6aR,8R)-2-chloro-8-((5-formyl-4-methylpyridin-2-yl)oxy)-6a,7,8,9-tetrahydropyrrolo[1',2':4,5]pyrazino[2,3-c]pyridazine-5(6H)-carboxylate instead of tert-butyl (6aR,8R)-2-chloro-8-(4-formylphenoxy)-6a,7,8,9 tetrahydropyrrolo[1',2':4,5]pyrazino[2,3-c]pyridazine-5(6H)-carboxylate and (3,5-difluoro-2-methoxyphenyl)boronic acid instead of (3,5-difluoro-2-hydroxyphenyl)boronic acid. LCMS calcd for $C_{28}H_{30}F_2N_5O_5[M+H]^+$: m/z=554.2; Found: 554.2.

Step 5: tert-butyl (6aR,8R)-2-(3,5-difluoro-2-methoxyphenyl)-8-((5-(hydroxymethyl)-4-methylpyridin-2-yl)oxy)-6a, 7,8,9-tetrahydropyrrolo[1',2':4,5]pyrazino[2,3-c]pyridazine-5(6H)-carboxylate

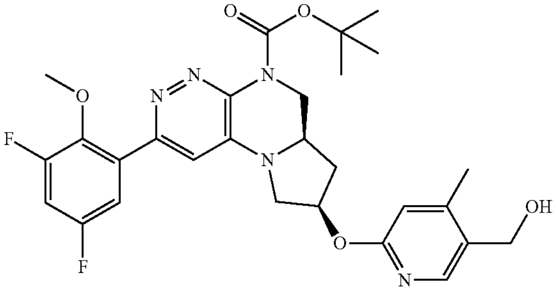 [SMILES: COc1c(F)cc(F)cc1-c1cc2c(nn1)N(C(=O)OC(C)(C)C)C[C@H]1C[C@@H](Oc3cc(C)c(CO)cn3)CN21]

Sodium borohydride (21.0 mg, 555 μL) was added to a solution of tert-butyl (6aR,8R)-2-(3,5-difluoro-2-methoxyphenyl)-8-((5-formyl-4-methylpyridin-2-yl)oxy)-6a,7,8,9-tetrahydro-pyrrolo[1',2':4,5]pyrazino[2,3-c]pyridazine-5(6H)-carboxylate (119 mg, 214 μL) in a mixture of MeOH (1.00 mL) and THE (1.00 mL). The reaction was stirred at room temperature for 30 minutes. The reaction was quenched with a saturated aqueous solution of $NH_4Cl$ and extracted with DCM. The combined organics were washed with a saturated brine solution, dried over $MgSO_4$, filtered and concentrated under reduced pressure to obtain crude tert-butyl (6aR,8R)-2-(3,5-difluoro-2-methoxyphenyl)-8-((5-(hydroxymethyl)-4-methylpyridin-2-yl)oxy)-6a,7,8,9-tetrahydropyrrolo[1',2':4,5]pyrazino[2,3-c]pyridazine-5(6H)-carboxylate (119 mg, quantitative yield). The material was used in the following step without additional purification. LCMS calcd for $C_{28}H_{32}F_2N_5O_5[M+H]^+$: m/z=556.2; Found: 556.2.

Step 6: tert-butyl (6aR,8R)-8-((5-(chloromethyl)-4-methylpyridin-2-yl)oxy)-2-(3,5-difluoro-2-methoxyphenyl)-6a, 7,8,9-tetrahydropyrrolo[1',2':4,5]pyrazino[2,3-c]pyridazine-5(6H)-carboxylate

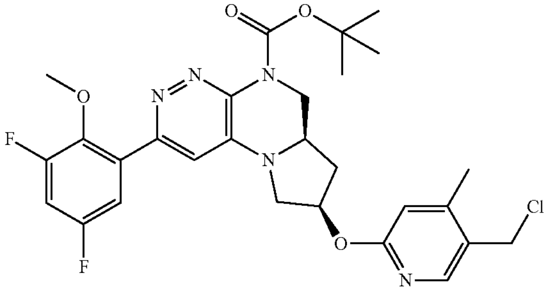 [SMILES: COc1c(F)cc(F)cc1-c1cc2c(nn1)N(C(=O)OC(C)(C)C)C[C@H]1C[C@@H](Oc3cc(C)c(CCl)cn3)CN21]

The title compound was prepared using a procedure analogous to that described for Example 26, Step 2, using crude tert-butyl (6aR,8R)-2-(3,5-difluoro-2-methoxyphenyl)-8-((5-(hydroxymethyl)-4-methylpyridin-2-yl)oxy)-6a,7,8,9-tetrahydropyrrolo[1',2':4,5]pyrazino[2,3-c]pyridazine-5(6H)-carboxylate instead of tert-butyl (6aR,8S)-2-(3,5-difluoro-2-methoxyphenyl)-8-hydroxy-6a,7,8,9-tetrahydropyrrolo[1',2':4,5]pyrazino[2,3-c]pyridazine-5(6H)-carboxylate. LCMS calcd for $C_{28}H_{31}C_1F_2N_5O_4[M+H]^+$: m/z=574.2/576.2; Found: 574.2/576.1.

Step 7: tert-butyl (6aR,8R)-2-(3,5-difluoro-2-methoxyphenyl)-8-((5-((4-(2-(2,6-dioxo-piperidin-3-yl)-3-oxoisoindolin-5-yl)piperazin-1-yl)methyl)-4-methylpyridin-2-yl)oxy)-6a, 7,8,9-tetrahydropyrrolo [1',2':4,5]pyrazino[2,3-c]pyridazine-5(6H)-carboxylate

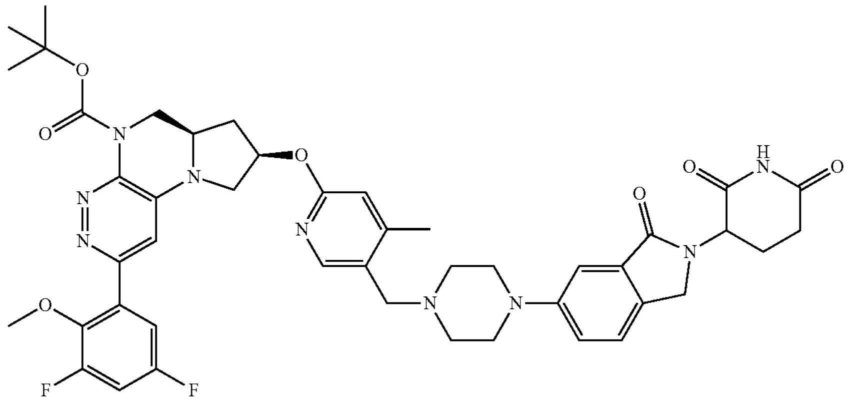 [SMILES: COc1c(F)cc(F)cc1-c1cc2c(nn1)N(C(=O)OC(C)(C)C)C[C@H]1C[C@@H](Oc3cc(C)c(CN4CCN(c5ccc6c(c5)C(=O)N(C5CCC(=O)NC5=O)C6)CC4)cn3)CN21]

A solution of tert-butyl (6aR,8R)-8-((5-(chloromethyl)-4-methylpyridin-2-yl)oxy)-2-(3,5-difluoro-2-methoxyphenyl)-6a,7,8,9-tetrahydropyrrolo[1',2':4,5]pyrazino[2,3-c] pyridazine-5(6H)-carboxylate (11.9 mg, 20.7 μmol) and 3-(3-oxo-5-piperazin-1-yl-1H-isoindol-2-yl)piperidine-2,6-dione (7.90 mg, 24.1 μmol, Intermediate 2) in THE (1.00 mL) was sonicated until an even suspension occurred. N,N-Diisopropylethylamine (7.94 μL, 45.6 μmol) and MeCN (1.00 mL) were added and the reaction was stirred at 120° C. for 2 hours. The reaction was cooled to room temperature and concentrated under reduced pressure to obtain crude tert-butyl (6aR,8R)-2-(3,5-difluoro-2-methoxyphenyl)-8-((5-((4-(2-(2,6-dioxopiperidin-3-yl)-3-oxoisoindolin-5-yl)piperazin-1-yl)methyl)-4-methylpyridin-2-yl)oxy)-6a,7,8,9-tetrahydropyrrolo[1',2':4,5]pyrazino [2,3-c]pyridazine-5(6H)-carboxylate. LCMS calcd for $C_{45}H_{50}F_2N_9O_7$ $[M+H]^+$: m/z=866.4; Found: 866.4.

Step 8: 3-(6-(4-((6-(((6aR,8R)-2-(3,5-difluoro-2-hydroxyphenyl)-5,6,6a, 7,8,9-hexahydro-pyrrolo[1', 2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione The title compound was prepared using a procedure analogous to that described for Example 26, Step 4, using tert-butyl (6aR,8R)-2-(3,5-difluoro-2-methoxyphenyl)-8-((5-((4-(2-(2,6-dioxopiperidin-3-yl)-3-oxoisoindolin-5-yl) piperazin-1-yl)methyl)-4-methylpyridin-2-yl)oxy)-6a,7,8,9-tetrahydropyrrolo[1',2':4,5]pyrazino[2,3-c]pyridazine-5 (6H)-carboxylate instead of tert-butyl (6aR,8R)-2-(3,5-difluoro-2-methoxyphenyl)-8-((5-formylpyrimidin-2-yl) thio)-6a,7,8,9-tetrahydropyrrolo[1',2':4,5]pyrazino[2,3-c] pyridazine-5 (6H)-carb oxylate. LCMS calcd for $C_{39}H_{40}F_2N_9C_5$ $[M+H]^+$: m/z=752.3; Found: 752.3.

Examples 28-31

Examples 28-31 shown below in Table 2 were prepared as TFA salts by the methods used in preparing Example 27, utilizing the appropriate starting materials and intermediates.

TABLE 2

| Example | Structure/Name | Calcd. (M + H)+ m/z | Found (M + H)+ m/z |
|---|---|---|---|
| | Examples 28-31 | | |
| 28 | 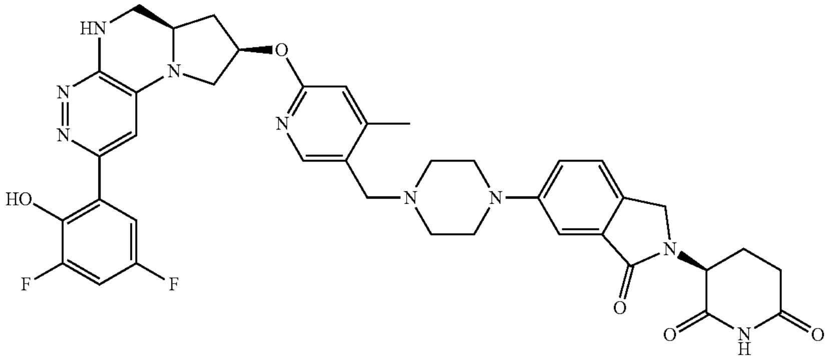 (S)-3-(6-(4-((6-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione $^1$H NMR (400 MHz, MeOD) δ 8.30 (s, 1H), 7.51 (d, J = 8.2 Hz, 1H), 7.40 - 7.33 (m, 2H), 7.25 (ddd, J = 11.0, 8.3, 3.0 Hz, 1H), 7.18 (ddd, J = 8.7, 3.0, 1.9 Hz, 1H), 6.82 (d, J = 9.3 Hz, 2H), 5.85 - 5.76 (m, 1H), 5.14 (dd, J = 13.4, 5.1 Hz, 1H), 4.51 - 4.36 (m, 4H), 4.19 (dd, J = 13.0, 6.8 Hz, 1H), 4.02 - 3.87 (m, 2H), 3.78 (dd, J = 12.8, 4.6 Hz, 1H), 3.65 - 3.44 (m, 4H), 3.24 (dd, J = 11.5, 9.3 Hz, 1H), 2.96 - 2.74 (m, 3H), 2.56 - 2.42 (m, 4H), 2.21 - 2.12 (m, 1H), 2.05 - 1.94 (m, 1H). | 752.3 | 752.1 |
| 29 | 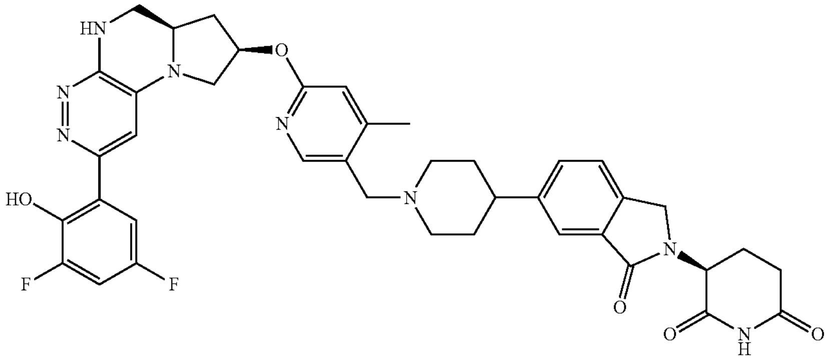 (S)-3-(6-(1-((6-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione $^1$H NMR (400 MHz, MeOD) δ 8.30 (s, 1H), 7.70 (s, 1H), 7.57 (s, 2H), 7.23 (ddd, J = 11.0, 8.3, 3.0 Hz, 1H), 7.20 - 7.15 (m, 1H), 6.84 - 6.79 (m, 2H), 5.86 - 5.76 (m, 1H), 5.15 (dd, J = 13.3, 5.2 Hz, 1H), 4.56 - 4.37 (m, 4H), 4.18 (dd, J = 12.8, 6.8 Hz, 1H), 4.02 - 3.87 (m, 2H), 3.78 (dd, J = 12.8, 4.6 Hz, 1H), 3.74 - 3.62 (m, 2H), 3.24 (dd, J = 11.4, 9.3 Hz, 1H), 3.13 - 3.02 (m, 1H), 2.97 - 2.82 (m, 2H), 2.82 - 2.74 (m, 1H), 2.57 - 2.43 (m, 4H), 2.23 - 2.12 (m, 3H), 2.12 - 1.94 (m, 3H). | 751.3 | 751.3 |

TABLE 2-continued

| Example | Structure/Name | Calcd. (M + H)+ m/z | Found (M + H)+ m/z |
|---|---|---|---|
| Examples 28-31 | | | |
| 30 | 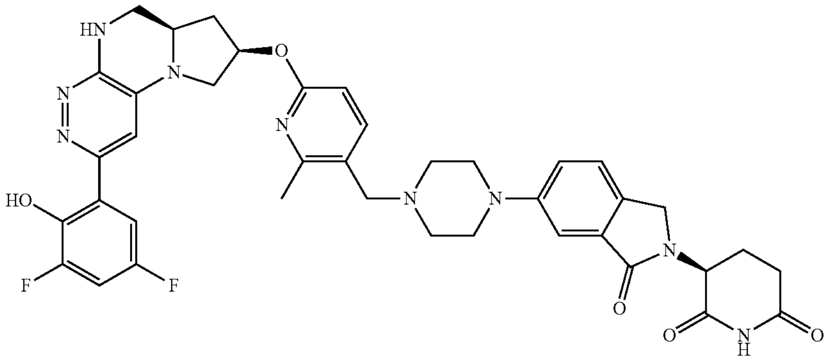 [SMILES: Cc1nc(O[C@@H]2C[C@@H]3CNc4nnc(-c5cc(F)cc(F)c5O)cc4N3C2)ccc1CN1CCN(c2ccc3c(c2)C(=O)N([C@H]2CCC(=O)NC2=O)C3)CC1] (S)-3-(6-(4-((6-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-2-methylpyridin-3-yl)methyl)piperazin-1-yl)-1-oxoisoindolin-2-yl)piperidine-2,6-dione $^{1}$H NMR (400 MHz, MeOD) δ 7.81 (d, J = 8.5 Hz, 1H), 7.50 (d, J = 8.2 Hz, 1H), 7.41 - 7.31 (m, 2H), 7.24 (ddd, J = 10.9, 8.2, 3.0 Hz, 1H), 7.18 (dt, J = 8.6, 2.4 Hz, 1H), 6.82 (s, 1H), 6.77 (d, J = 8.4 Hz, 1H), 5.89 - 5.78 (m, 1H), 5.13 (dd, J = 13.3, 5.1 Hz, 1H), 4.50 - 4.35 (m, 4H), 4.21 (dd, J = 12.8, 6.9 Hz, 1H), 4.02 - 3.95 (m, 1H), 3.92 (dd, J = 11.5, 4.1 Hz, 1H), 3.81 - 3.71 (m, 1H), 3.70 - 3.35 (m, 6H), 3.25 (dd, J = 11.5, 9.3 Hz, 1H), 2.96 - 2.83 (m, 2H), 2.83 - 2.74 (m, 1H), 2.64 (s, 3H), 2.49 (qd, J = 13.1, 4.6 Hz, 1H), 2.22 - 2.11 (m, 1H), 2.05 - 1.93 (m, 1H). | 752.3 | 752.3 |
| 31 | 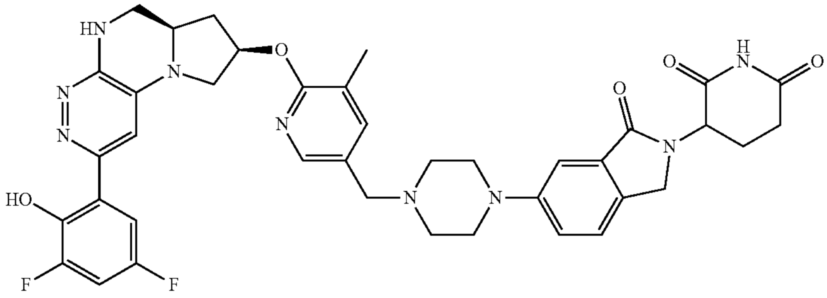 3-(6-(4-((6-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-5-methylpyridin-3-yl)methyl)piperazin-1-yl)-1-oxoisoindolin-2-yl)piperidine-2,6-dione | 752.3 | 752.3 |

Example 32:3 3-(6-(4-(4-(((6aR,8R)-2-(3,5-difluoro-2-hydroxyphenyl)-5,6,6a,7,8,9-hexahydropyrrolo[1' 2':4,5]pyrazino[2,3-c]pyridazin-8-yl)thio)benzyl) piperazin-1-yl)-1-oxoisoindolin-2-yl)piperidine-2,6-dione

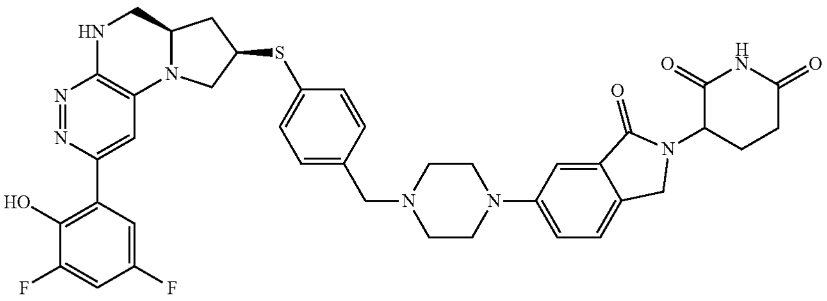

The title compound was prepared using a procedure analogous to those described in Example 26, Steps 2-3 and Example 1, Step 2-4 using the appropriate starting materials and intermediates. LCMS calcd for $C_{39}H_{39}F_2N_8O_4S$ $[M+H]^+$: m/z=753.3; Found: 753.2.

Example 33: 3-(6-(4-((6-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)pyridin-3-yl)methyl)piperazin-1-yl)-1-oxoisoindolin-2-yl) piperidine-2,6-dione

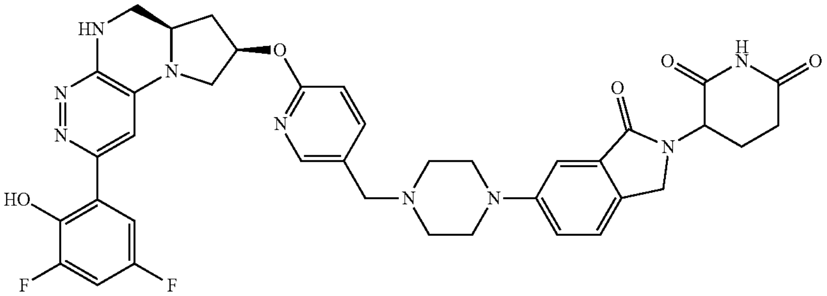 [SMILES: O=C1CCC(N2Cc3ccc(N4CCN(Cc5ccc(O[C@@H]6C[C@@H]7CNc8nnc(-c9cc(F)cc(F)c9O)cc8N7C6)nc5)CC4)cc3C2=O)C(=O)N1]

The title compound was prepared using the procedure analogous to those described for Example 27, Step 2-3 and Example 1, Steps 2-4, using the appropriate starting materials and intermediates. LCMS calcd for $C_{38}H_{38}F_2N_9O_5[M+H]^+$: m/z=738.3; Found: 738.2.

Example 34: 3-(6-(4-(((3R,5S)-4-((6aR,8R)-2-(3-fluoro-2-hydroxyphenyl)-5,6,6a,7,8,9-hexahydropyrrolo[1',2':4,5]pyrazino[2,3-c]pyridazine-8-carbonyl)-3,5-dimethylpiperazin-1-yl)methyl)piperidin-1-yl)-1-oxoisoindolin-2-yl)piperidine-2,6-dione

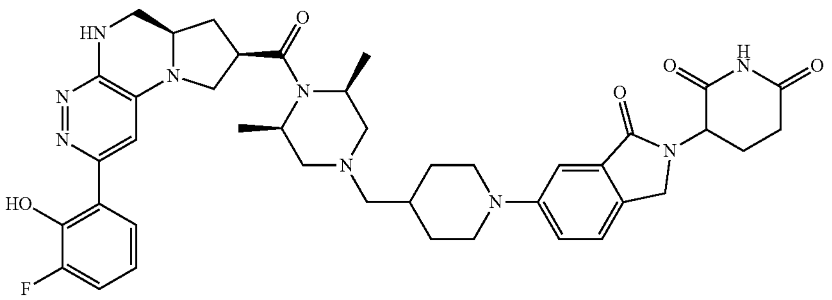 [SMILES: C[C@@H]1CN(CC2CCN(c3ccc4c(c3)C(=O)N(C3CCC(=O)NC3=O)C4)CC2)C[C@H](C)N1C(=O)[C@@H]1C[C@@H]2CNc3nnc(-c4cccc(F)c4O)cc3N2C1]

Step 1: tert-butyl (6aR,8S)-2-chloro-8-((methylsulfonyl)oxy)-6a, 7,8,9-tetrahydropyrrolo [1',2':4,5] pyrazino[2,3-c]pyridazine-5(6H)-carboxylate

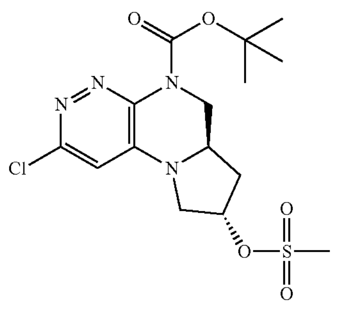 [SMILES: CC(C)(C)OC(=O)N1C[C@H]2C[C@H](OS(C)(=O)=O)CN2c2cc(Cl)nnc21]

The title compound was prepared using the procedure analogous to those described for Example 26, Step 2, using tert-butyl (6aR,8S)-2-chloro-8-hydroxy-6a,7,8,9-tetrahydropyrrolo-[1',2':4,5]pyrazino[2,3-c]pyridazine-5(6H)-carboxylate (Intermediate 1) instead of tert-butyl (6aR,8S)-2-(3,5-difluoro-2-methoxyphenyl)-8-hydroxy-6a,7,8,9-tetrahydropyrrolo-[1',2':4,5]pyrazino[2,3-c]pyridazine-5(6H)-carboxylate. LCMS calcd for $C_{15}H_{22}ClN_4O_5S$ $[M+H]^+$: m/z=405.1; Found: 405.0.

Step 2: tert-butyl (6aR,8R)-2-chloro-8-cyano-6a, 7,8,9-tetrahydropyrrolo[1',2':4,5]pyrazino[2,3-c] pyridazine-5(6H)-carboxylate

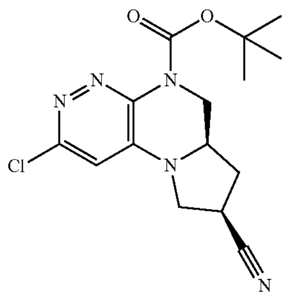 [SMILES: CC(C)(C)OC(=O)N1C[C@H]2C[C@@H](C#N)CN2c2cc(Cl)nnc21]

A mixture of tert-butyl (6aR,8S)-2-chloro-8-((methylsulfonyl)oxy)-6a,7,8,9-tetrahydro-pyrrolo[1',2':4,5]pyrazino[2,3-c]pyridazine-5(6H)-carboxylate (265 mg, 655 μL) and sodium cyanide (96.2 mg, 1.96 mmol) in DMSO (500 μL) was stirred at 80° C. overnight. The mixture was cooled to room temperature and diluted with DCM and washed with water. The organics were dried over $MgSO_4$, filtered, and concentrated under reduced pressure. The crude material was purified via $SiO_2$ FCC: 0-100% EtOAC/hexanes to obtain tert-butyl (6aR,8R)-2-chloro-8-cyano-6a,7,8,9-tetrahydropyrrolo[1',2':4,5]pyrazino[2,3-c]pyridazine-5(6H)-carboxylate (150 mg, 72% yield). LCMS calcd for $C_{15}H_{19}ClN_5O_2[M+H]^+$: m/z=336.1; Found: 336.1.

Step 3: tert-butyl (6aR,8R)-8-cyano-2-(3-fluoro-2-hydroxyphenyl)-6a,7,8,9-tetrahydro-pyrrolo[1',2':4,5]pyrazino[2,3-c]pyridazine-5(6H)-carboxylate

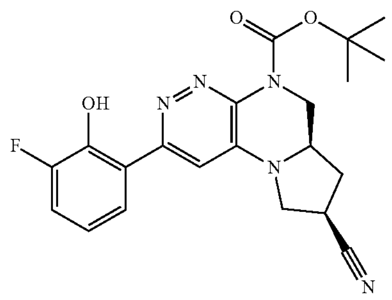 [SMILES: CC(C)(C)OC(=O)N1C[C@H]2C[C@@H](C#N)CN2c2cc(-c3cccc(F)c3O)nnc21]

The title compound was prepared using a procedure analogous to that described for Example 1, Step 2, using tert-butyl (6aR,8R)-2-chloro-8-cyano-6a,7,8,9-tetrahydropyrrolo-[1',2':4,5]pyrazino[2,3-c]pyridazine-5(6H)-carboxylate instead of tert-butyl (6aR,8R)-2-chloro-8-(4-formylphenoxy)-6a,7,8,9 tetrahydropyrrolo[1',2':4,5]pyrazino[2,3-c]pyridazine-5(6H)-carboxylate and 5-fluoro-2-hydroxyphenylboronic acid instead of (3,5-difluoro-2-hydroxy-phenyl)boronic acid. LCMS calcd for $C_{21}H_{23}FN_5O_3[M+H]^+$: m/z=412.2; Found: 412.1.

Step 4: (6aR,8R)-2-(3-fluoro-2-hydroxyphenyl)-5,6, 6a, 7,8,9-hexahydropyrrolo [1',2':4,5]pyrazino[2,3-c]pyridazine-8-carboxylic acid

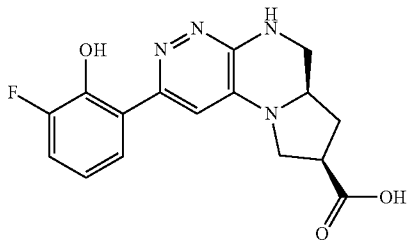 [SMILES: O=C(O)[C@@H]1C[C@@H]2CNc3nnc(-c4cccc(F)c4O)cc3N2C1]

A solution of tert-butyl (6aR,8R)-8-cyano-2-(3-fluoro-2-hydroxyphenyl)-6a,7,8,9-tetrahydropyrrolo[1',2':4,5]pyrazino[2,3-c]pyridazine-5(6H)-carboxylate (60.0 mg, 146 μmol) in NMP (1.00 mL) was treated with a 11.6 M HCl aqueous solution (1.00 mL, 11.6 mmol). The reaction was stirred at 100° C. for 2 hours. The reaction was cooled to room temperature, filtered, diluted with MeOH and the filtrate directly purified via prep-HPLC (Waters CSH-C18, 5 uM, 30×100 mm, 8.1-28.1% MeCN/water (containing 0.1% TFA) over 5 min) to give the TFA salt of the title compound (6aR,8R)-2-(3-fluoro-2-hydroxyphenyl)-5,6,6a,7,8,9-hexahydropyrrolo-[1',2':4,5]pyrazino[2,3-c]pyridazine-8-carboxylic acid (30.0 mg, 62% yield). LCMS calcd for $C_{16}H_{16}FN_4O_3[M+H]^+$: m/z=331.1; Found: 330.9.

Step 5: tert-butyl (3R,5S)-4-((6aR,8R)-2-(3-fluoro-2-hydroxyphenyl)-5,6,6a, 7,8,9-hexahydropyrrolo[1',2':4,5]pyrazino[2,3-c]pyridazine-8-carbonyl)-3,5-dimethylpiperazine-1-carboxylate

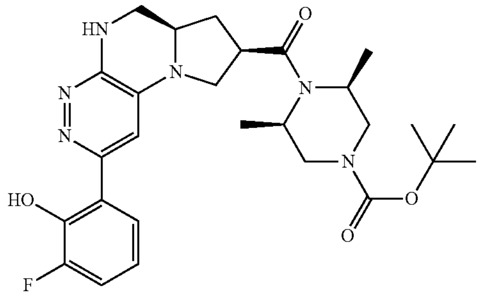 [SMILES: C[C@@H]1CN(C(=O)OC(C)(C)C)C[C@H](C)N1C(=O)[C@@H]1C[C@@H]2CNc3nnc(-c4cccc(F)c4O)cc3N2C1]

A mixture of (6aR,8R)-2-(3-fluoro-2-hydroxyphenyl)-5,6,6a,7,8,9-hexahydropyrrolo-[1',2':4,5]pyrazino[2,3-c]pyridazine-8-carboxylic acid (16.0 mg, 48.4 μmol), tert-butyl (3R,5S)-3,5-dimethylpiperazine-1-carboxylate (15.6 mg, 72.7 μmol), HATU (36.8 mg, 96.9 μmol) and N,N-diisopropylethylamine (33.7 μL, 194 μmol) in DMF (1.00 mL) was stirred at room temperature for 2 hours. treated with a 11.6 M HCl aqueous solution (1.00 mL, 11.6 mmol). The reaction was filtered, diluted with MeOH and the filtrate directly purified via prep-HPLC (Waters CSH-C18, 5 uM, 30×100 mm, 24.9-44.9% MeCN/water (containing 0.1% TFA) over 5 min) to give the TFA salt of the title compound tert-butyl (3R,5S)-4-((6aR,8R)-2-(3-fluoro-2-hydroxyphenyl)-5,6,6a,7,8,9-hexahydropyrrolo[1',2':4,5]pyrazino[2,3-c]pyridazine-8-carbonyl)-3,5-dimethylpiperazine-1-carboxylate (1.60 mg, 6.3% yield). LCMS calcd for $C_{27}H_{36}FN_6O_4$ $[M+H]^+$: m/z=527.3; Found: 527.2.

Step 6: ((2R,6S)-2,6-dimethylpiperazin-1-yl)((6aR,8R)-2-(3-fluoro-2-hydroxyphenyl)-5,6,6a, 7,8,9-hexahydropyrrolo[1',2':4,5]pyrazino[2,3-c]pyridazin-8-yl)methanone

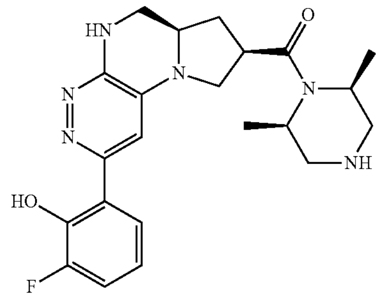 [SMILES: C[C@@H]1CNC[C@H](C)N1C(=O)[C@@H]1C[C@@H]2CNc3nnc(-c4cccc(F)c4O)cc3N2C1]

A 4N HCl solution in 1,4-dioxane (320 μL, 10.3 mmol) was added to a solution of tert-butyl (3R,5S)-4-((6aR,8R)-2-(3-fluoro-2-hydroxyphenyl)-5,6,6a,7,8,9-hexahydropyrrolo-[1',2':4,5]pyrazino[2,3-c]pyridazine-8-carbonyl)-3,5-dimethylpiperazine-1-carboxylate (11.6 mg, 3.04 μmol) in DCM (1.00 mL). The reaction was stirred at room temperature for 1 hour and then concentrated under reduced pressure to give the HCl salt of ((2R,6S)-2,6-dimethylpiperazin-1-yl)((6aR,8R)-2-(3-fluoro-2-hydroxyphenyl)-5,6,6a,7,8,9-hexahydropyrrolo[1',2':4,5]pyrazino-[2,3-c]pyridazin-8-yl)methanone (36.8 mg, 96.9 μmol). LCMS calcd for $C_{22}H_{28}FN_6O_2[M+H]^+$: m/z=427.2; Found: 427.2.

Step 7: 3-(6-(4-(((3R,5S)-4-((6aR,8R)-2-(3-fluoro-2-hydroxyphenyl)-5,6,6a, 7,8,9-hexahydropyrrolo[1',2':4,5]pyrazino[2,3-c]pyridazine-8-carbonyl)-3,5-dimethylpiperazin-1-yl)methyl)piperidin-1-yl)-1-oxoisoindolin-2-yl)piperidine-2,6-dione The title compound was prepared using the procedure analogous to those described for Example 26, Step 5, utilizing ((2R,6S)-2,6-dimethylpiperazin-1-yl)((6aR,8R)-2-(3-fluoro-2-hydroxyphenyl)-5,6,6a,7,8,9-hexahydropyrrolo[1',2':4,5]pyrazino[2,3-c]pyridazin-8-yl)methanone; dihydrochloride instead of 2-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)thio)pyrimidine-5-carbaldehyde and 1-(2-(2,6-dioxopiperidin-3-yl)-3-oxoisoindolin-5-yl)piperidine-4-carbaldehyde (Intermediate 3) instead of 3-(3-oxo-5-piperazin-1-yl-1H-isoindol-2-yl)piperidine-2,6-dione (Intermediate 2). LCMS calcd for $C_{41}H_{49}FN_9O_5[M+H]^+$: m/z=766.4; Found: 766.2.

Example 35: 3-(6-(4-((6-(((6aR,8R)-2-(3-fluoro-2-hydroxyphenyl)-5,6,6a,7,8,9-hexahydro-pyrrolo[1',2':4,5]pyrazino[2,3-c]pyridazin-8-yl)(methyl)amino)pyridin-3-yl)methyl)piperazin-1-yl)-1-oxoisoindolin-2-yl)piperidine-2,6-dione

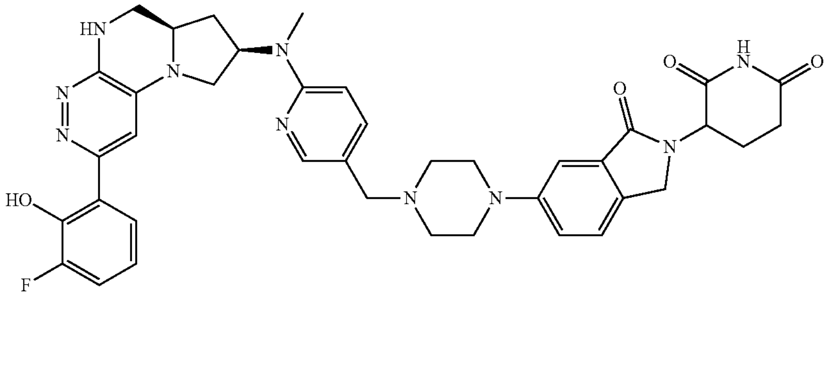 [SMILES: CN(c1ccc(CN2CCN(c3ccc4c(c3)C(=O)N(C3CCC(=O)NC3=O)C4)CC2)cn1)[C@@H]1C[C@@H]2CNc3nnc(-c4cccc(F)c4O)cc3N2C1]

Step 1: (6aR,8R)-2-chloro-N-methyl-5,6,6a, 7,8,9-hexahydropyrrolo[1',2':4,5]pyrazino[2,3-c]pyridazin-8-amine

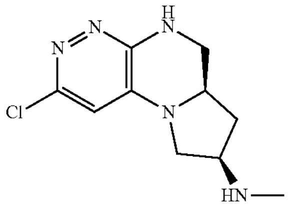 [SMILES: CN[C@@H]1C[C@@H]2CNc3nnc(Cl)cc3N2C1]

A 40% solution of methylamine in water (1.00 mL, 24.3 mmol) was added to a solution of tert-butyl (6aR,8S)-2-chloro-8-((methylsulfonyl)oxy)-6a,7,8,9-tetrahydropyrrolo[1',2':4,5]-pyrazino[2,3-c]pyridazine-5(6H)-carboxylate (25.0 mg, 61.7 μmol, Intermediate from Example 34, Step 1) in ethanol (500 μL). The reaction was stirred at 100° C. overnight. The reaction was cooled to room temperature and concentrated under reduced pressure to obtain (6aR,8R)-2-chloro-N-methyl-5,6,6a,7,8,9-hexahydropyrrolo[1',2':4,5]pyrazino[2,3-c]pyridazin-8-amine (14.0 mg, 95% yield). LCMS calcd for $C_{10}H_{15}ClN_5$ $[M+H]^+$: m/z=240.1; Found: 240.1.

Step 2: 6-(((6aR,8R)-2-chloro-5,6,6a, 7,8,9-hexahydropyrrolo[1',2':4,5]pyrazino[2,3-c]pyridazin-8-yl)(methyl)amino)nicotinaldehyde

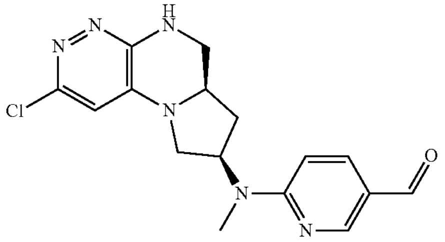 [SMILES: CN(c1ccc(C=O)cn1)[C@@H]1C[C@@H]2CNc3nnc(Cl)cc3N2C1]

A mixture of (6aR,8R)-2-chloro-N-methyl-5,6,6a,7,8,9-hexahydropyrrolo[1',2':4,5]-pyrazino[2,3-c]pyridazin-8-amine (14.0 mg, 58.4 μmol), 2-fluoropyridine-5-carbaldehyde (7.31 mg, 58.4 μmol) and N,N-diisopropylethylamine (20.3 μL, 117 μmol) in DMSO (1.00 mL) was stirred at 110° C. for 2 hours. The reaction was cooled to room temperature, diluted in MeOH, filtered and purified via prep-HPLC (Waters CSH-C18, 5 uM, 30×100 mm, 6.4-26.4% MeCN/water (containing 0.1% TFA) over 5 min) to give the TFA salt of the title compound 6-(((6aR,8R)-2-chloro-5,6,6a,7,8,9-hexahydropyrrolo[1',2':4,5]pyrazino[2,3-c]pyridazin-8-yl)(methyl)amino)nicotinaldehyde (15.0 mg, 75% yield). LCMS calcd for $C_{16}H_{18}ClN_6O$ $[M+H]^+$: m/z=345.1; Found: 345.1.

Step 3: 3-(6-(4-((6-(((6aR,8R)-2-(3-fluoro-2-hydroxyphenyl)-5,6,6a, 7,8,9-hexahydro-pyrrolo[1',2':4,5]pyrazino[2,3-c]pyridazin-8-yl)(methyl)amino)pyridin-3-yl)methyl)piperazin-1-yl)-1-oxoisoindolin-2-yl)piperidine-2,6-dione The title compound was prepared using the procedures analogous to those described for Example 1, Step 2 and Step 4, using the appropriate starting materials and intermediates. LCMS calcd for $C_{39}H_{42}FN_{10}O_4$ $[M+H]^+$: m/z=733.3; Found: 733.3.

Example 36: 3-(6-(4-(4-(((6aS,8R)-2-(3-fluoro-2-hydroxyphenyl)-5,6,6a,7,8,9-hexahydro-pyrrolo[1',2':4,5]pyrazino[2,3-c]pyridazin-8-yl)oxy)-2-methylbenzyl)piperazin-1-yl)-1-oxoisoindolin-2-yl)piperidine-2,6-dione

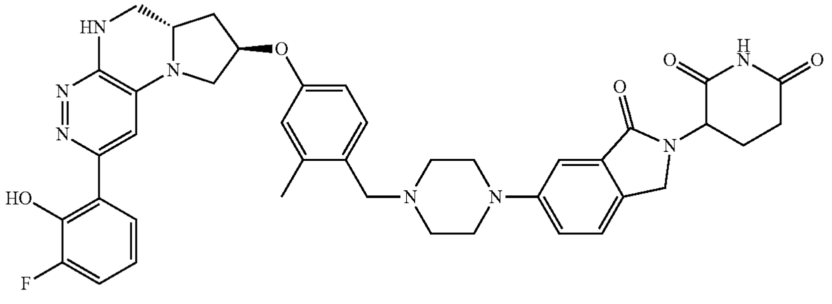 [SMILES: Cc1cc(O[C@@H]2C[C@H]3CNc4nnc(-c5cccc(F)c5O)cc4N3C2)ccc1CN1CCN(c2ccc3c(c2)C(=O)N(C2CCC(=O)NC2=O)C3)CC1]

Step 1: (2S,4R)-2-(azidomethyl)-4-((tert-butyldimethylsilyl)oxy)pyrrolidine

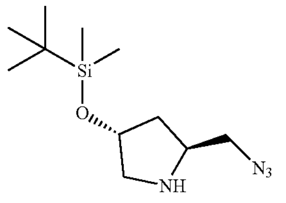 [SMILES: CC(C)(C)[Si](C)(C)O[C@H]1CN[C@H](CN=[N+]=[N-])C1]

2,2,2-Trifluoroacetic acid (5.00 mL, 65.3 mmol) was added to a solution of tert-butyl (2S,4R)-2-(azidomethyl)-4-((tert-butyldimethylsilyl)oxy)pyrrolidine-1-carboxylate (1.40 g, 3.93 mmol, prepared as described for Intermediate 1, Step 4) in DCM (6.00 mL). The reaction was stirred at room temperature for 1 hour. The reaction was basified to a pH of ~12 using a 2 N aqueous NaOH solution. The layers were separated, and the aqueous phase was extracted with DCM (3×25.0 mL). The combined organics were washed with a saturated brine solution, dried over $MgSO_4$, filtered and concentrated under reduced pressure to obtain (2S,4R)-2-(azidomethyl)-4-((tert-butyldimethylsilyl)oxy)pyrrolidine (900 mg, 89% yield). The material was used in the following step without additional purification. LCMS calcd for $C_{11}H_{25}N_4OSi$ $[M+H]^+$: m/z=257.2; Found: 257.1.

Step 2: tert-butyl (6aS,8R)-2-chloro-8-hydroxy-6a,7,8,9-tetrahydropyrrolo[1',2':4,5]pyrazino[2,3-c]pyridazine-5(6H)-carboxylate

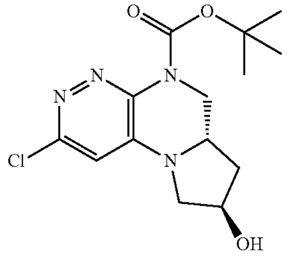 [SMILES: CC(C)(C)OC(=O)N1C[C@@H]2C[C@@H](O)CN2c2cc(Cl)nnc21]

The title compound was prepared using the procedures analogous to those described for Intermediate 1, Steps 6 through 9. LCMS calcd for $C_{14}H_{20}ClN_4O_3[M+H]^+$: m/z=327.1/329.1; Found: 327.8/328.9.

Step 3: tert-butyl (6aS,8S)-2-chloro-8-((4-nitrobenzoyl)oxy)-6a,7,8,9-tetrahydropyrrolo [1',2':4,5]pyrazino[2,3-c]pyridazine-5(6H)-carboxylate

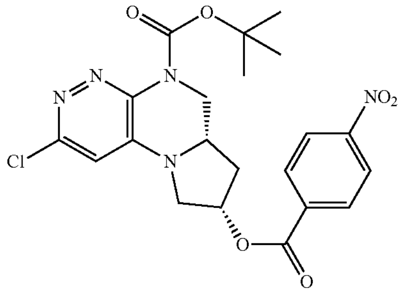 [SMILES: CC(C)(C)OC(=O)N1C[C@@H]2C[C@H](OC(=O)c3ccc([N+](=O)[O-])cc3)CN2c2cc(Cl)nnc21]

Diisopropyl azodicarboxylate (84.0 μL, 427 μmol) was added dropwise to a solution of tert-butyl (6aS,8R)-2-chloro-8-hydroxy-6a,7,8,9-tetrahydropyrrolo[1',2':4,5]pyrazino[2,3-c]pyridazine-5(6H)-carboxylate (70.0 mg, 214 μmol), 4-nitrobenzoic acid (71.6 mg, 428 μmol) and triphenylphosphine (112 mg, 428 μmol) in THE at 0° C. The reaction was heated to 60° C. and stirred for 1 hour. The mixture was cooled to room temperature and quenched with water. The mixture was directly purified via $SiO_2$ FCC: 0-100% EtOAC/Hexanes to obtain tert-butyl (6aS,8S)-2-chloro-8-((4-nitrobenzoyl)oxy)-6a,7,8,9-tetrahydropyrrolo[1',2':4,5]pyrazino[2,3-c]pyridazine-5(6H)-carboxylate (100 mg, quantitative yield). LCMS calcd for $C_{21}H_{23}ClN_5O_6[M+H]^+$: m/z=476.1; Found: 476.1.

Step 4: tert-butyl (6aS,8S)-2-chloro-8-hydroxy-6a,7,8,9-tetrahydropyrrolo[1',2':4,5]pyrazino[2,3-c]pyridazine-5(6H)-carboxylate

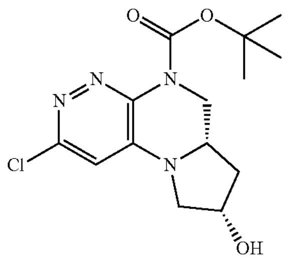 [SMILES: CC(C)(C)OC(=O)N1C[C@@H]2C[C@H](O)CN2c2cc(Cl)nnc21]

Lithium hydroxide (35.0 mg, 1.46 mmol) was added to a solution of tert-butyl (6aS,8S)-2-chloro-8-((4-nitrobenzoyl)oxy)-6a,7,8,9-tetrahydropyrrolo[1',2':4,5]pyrazino[2,3-c]pyridazine-5(6H)-carboxylate (100 mg, 210 μmol) in a mixture of MeOH (1.00 mL), THE (1.00 mL) and water (1.00 mL). The reaction was stirred at room temperature for 1 hour. The mixture was diluted with water and then extracted with ethyl acetate. The organics were dried over $MgSO_4$, filtered, and concentrated under reduced pressure. The crude material was purified via $SiO_2$ FCC: 0-10% MeOH/DCM to obtain tert-butyl (6aS,8S)-2-chloro-8-hydroxy-6a,7,8,9-tetrahydropyrrolo [1',2':4,5]pyrazino[2,3-c]pyridazine-5(6H)-carboxylate (45.0 mg, 65% yield). LCMS calcd for $C_{14}H_{20}ClN_4O_3[M+H]^+$: m/z=327.1; Found: 327.1.

Step 5: 3-(6-(4-(4-(((6aS,8R)-2-(3-fluoro-2-hydroxyphenyl)-5,6,6a, 7,8,9-hexahydro-pyrrolo[1',2':4,5]pyrazino[2,3-c]pyridazin-8-yl)oxy)-2-methylbenzyl)piperazin-1-yl)-1-oxoisoindolin-2-yl)piperidine-2,6-dione The title compound was prepared using the procedures analogous to those described for Example 1, Steps 1 through 4, using the appropriate starting materials and intermediates. LCMS calcd for $C_{40}H_{42}FN_8O_5[M+H]^+$: m/z=733.3; Found: 733.2.

Example 37

Example 37 shown below in Table 3 was prepared as the TFA salt by the methods used in preparing Example 36, utilizing the appropriate starting materials and intermediates.

TABLE 3

| Example | Structure/Name | Calcd. (M + H)+ m/z | Found (M + H)+ m/z |
|---|---|---|---|
| | Example 37 | | |
| 37 | 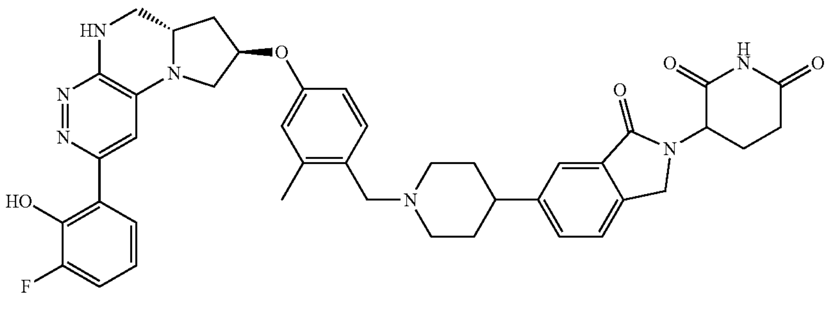 [SMILES: Cc1cc(O[C@@H]2C[C@H]3CNc4nnc(-c5cccc(F)c5O)cc4N3C2)ccc1CN1CCC(c2ccc3c(c2)C(=O)N(C2CCC(=O)NC2=O)C3)CC1] 3-(6-(1-(4-(((6aS,8R)-2-(3-fluoro-2-hydroxyphenyl)-5,6,6a,7,8,9-hexahydropyrrolo[1',2':4,5]pyrazino[2,3-c]pyridazin-8-yl)oxy)-2-methylbenzyl)piperidin-4-yl)-1-oxoisoindolin-2-yl)piperidine-2,6-dione | 732.3 | 732.2 |

Example 38: (S)-3-(6-(4-((6-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)thio)-4-methylpyridin-3-yl)methyl)piperazin-1-yl)-1-oxoisoindolin-2-yl)piperidine-2,6-dione

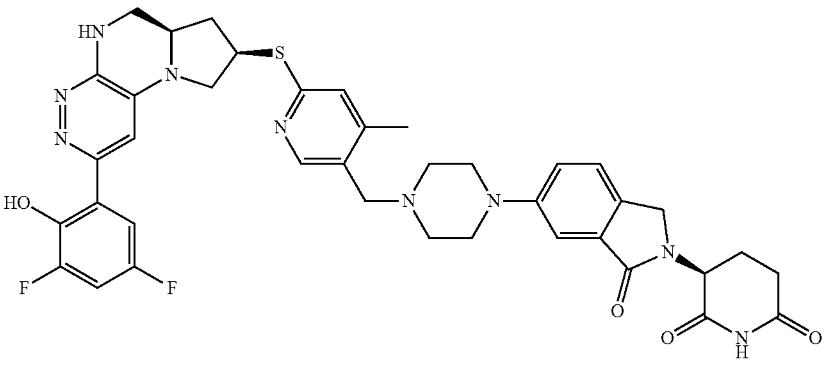 [SMILES: Cc1cc(S[C@@H]2C[C@@H]3CNc4nnc(-c5cc(F)cc(F)c5O)cc4N3C2)ncc1CN1CCN(c2ccc3c(c2)C(=O)N([C@H]2CCC(=O)NC2=O)C3)CC1]

Step 1: tert-butyl (6aR,8R)-2-chloro-8-((5-formyl-4-methylpyridin-2-yl)thio)-6a, 7,8,9-tetrahydropyrrolo[1',2':4,5]pyrazino[2,3-c]pyridazine-5(6H)-carboxylate

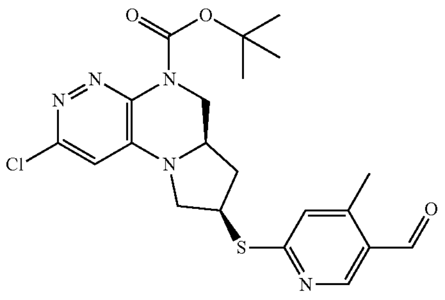 [SMILES: Cc1cc(S[C@@H]2C[C@@H]3CN(C(=O)OC(C)(C)C)c4nnc(Cl)cc4N3C2)ncc1C=O]

The title compound was prepared using the procedure analogous to those described for Example 26, Step 2-3 using the appropriate intermediates and starting materials. LCMS calcd for $C_{21}H_{25}ClN_5O_3S$ $[M+H]^+$: m/z=462.1/464.1; Found: 462.1/464/1.

Step 2: (S)-3-(6-(4-((6-(((6aR,8R)-2-(3,5-difluoro-2-hydroxyphenyl)-5,6,6a, 7,8,9-hexahydropyrrolo[1', 2':4,5]pyrazino[2,3-c]pyridazin-8-yl)thio)-4-methylpyridin-3-yl)methyl) piperazin-1-yl)-1-oxoisoindolin-2-yl)piperidine-2,6-dione The title compound was prepared using the procedure analogous to those described for Example 27, Steps 4-7 and Example 26, Step 4 using the appropriate intermediates and starting materials. LCMS calcd for $C_{39}H_{40}F_2N_9O_4S$ $[M+H]^+$: m/z=768.3; Found: 768.2.

Example 39: 3-(6-(4-((4-(((6aR,8R)-2-(3,5-difluoro-2-hydroxyphenyl)-5,6,6a,7,8,9-hexahydropyrrolo[1',2':4,5]pyrazino[2,3-c]pyridazin-8-yl)oxy)-1H-pyrazol-1-yl)methyl) piperidin-1-yl)-1-oxoisoindolin-2-yl)piperidine-2,6-dione

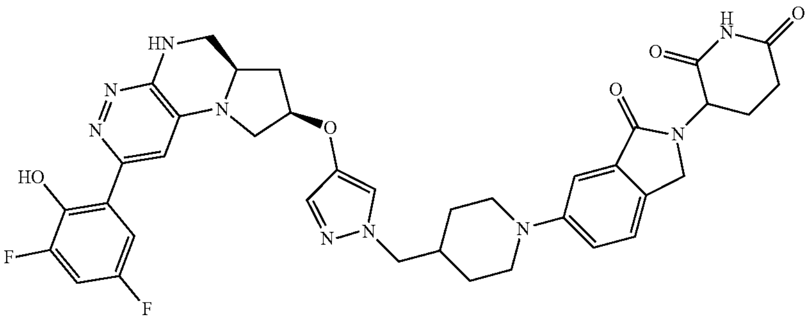 [SMILES: O=C1CCC(N2Cc3ccc(N4CCC(Cn5cc(O[C@@H]6C[C@@H]7CNc8nnc(-c9cc(F)cc(F)c9O)cc8N7C6)cn5)CC4)cc3C2=O)C(=O)N1]

Step 1: tert-butyl (6aR,8R)-8-((1-(tert-butoxycarbonyl)-1H-pyrazol-4-yl)oxy)-2-chloro-6a, 7,8,9-tetrahydropyrrolo[1',2':4,5]pyrazino[2,3-c]pyridazine-5(6H)-carboxylate

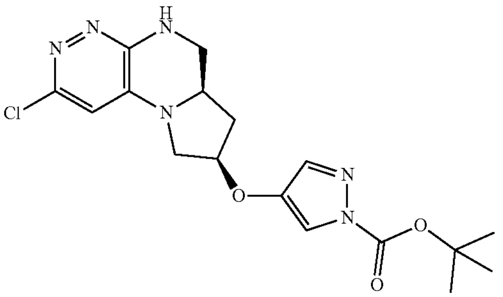

+

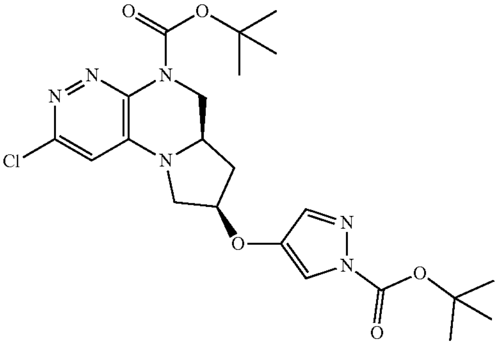

A mixture of tert-butyl (6aR,8S)-2-chloro-8-((methylsulfonyl)oxy)-6a,7,8,9-tetra-hydropyrrolo[1',2':4,5]pyrazino[2,3-c]pyridazine-5(6H)-carboxylate (100 mg, 0.247 mmol, intermediate from Example 34, Step 1), tert-butyl 4-hydroxypyrazole-1-carboxylate (182 mg, 0.988 mmol) and potassium carbonate (172 mg, 1.24 mmol) in NMP (2.00 mL) was stirred overnight at 100° C. The reaction was cooled to room temperature, diluted with water and the aqueous phase was extracted with DCM. The combined organics were dried over $MgSO_4$, filtered and concentrated under reduced pressure to give a crude mixture of tert-butyl (6aR,8R)-8-((1-(tert-butoxycarbonyl)-1H-pyrazol-4-yl)oxy)-2-chloro-6a,7,8,9-tetrahydropyrrolo[1',2':4,5]pyrazino[2,3-c]pyridazine-5(6H)-carboxylate and tert-butyl 4-(((6aR,8R)-2-chloro-5,6,6a,7,8,9-hexa-hydropyrrolo[1',2':4,5]pyrazino[2,3-c]pyridazin-8-yl)oxy)-1H-pyrazole-1-carboxylate (122 mg). LCMS calcd for $C_{22}H_{30}ClN_6O_5[M+H]^+$: m/z=493.2/495.2; Found: 493.1/495.1.

Step 2: tert-butyl (6aR,8R)-8-((1-(tert-butoxycarbonyl)-1H-pyrazol-4-yl)oxy)-2-chloro-6a, 7,8,9-tetrahydropyrrolo[1',2':4,5]pyrazino[2,3-c]pyridazine-5(6H)-carboxylate

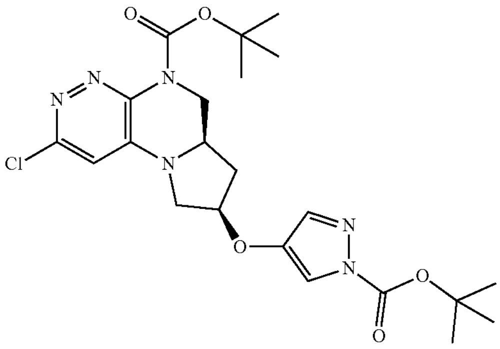 [SMILES: CC(C)(C)OC(=O)N1C[C@H]2C[C@@H](Oc3cnn(C(=O)OC(C)(C)C)c3)CN2c2cc(Cl)nnc21]

To a mixture of tert-butyl (6aR,8R)-8-((1-(tert-butoxycarbonyl)-1H-pyrazol-4-yl)oxy)-2-chloro-6a,7,8,9-tetrahydropyrrolo[1',2':4,5]pyrazino[2,3-c]pyridazine-5(6H)-carboxylate and tert-butyl 4-(((6aR,8R)-2-chloro-5,6,6a,7,8,9-hexahydropyrrolo[1',2':4,5]pyrazino[2,3-c]pyrid-azin-8-yl)oxy)-1H-pyrazole-1-carboxylate (122 mg, 0.247 mmol) was added 4-(dimethylamino) pyridine (30.2 mg, 0.247 mmol) and di-tert butyl dicarbonate (270 mg, 1.24 mmol) in NMP (2.00 mL). The reaction was stirred at room temperature for 1 hour. The crude reaction mixture was purified directly via $SiO_2$ FCC: 0-100% EtOAC/hexanes to obtain tert-butyl (6aR,8R)-8-((1-(tert-butoxycarbonyl)-1H-pyrazol-4-yl)oxy)-2-chloro-6a,7,8,9-tetrahydro-pyrrolo[1',2':4,5]pyrazino[2,3-c]pyridazine-5(6H)-carboxylate (122 mg, quantitative yield), LCMS calcd for $C_{22}H_{30}ClN_6O_5[M+H]^+$: m/z=493.2/495.2; Found: 493.1/495.1.

Step 3: tert-butyl (6aR,8R)-8-((1-(tert-butoxycarbonyl)-1H-pyrazol-4-yl)oxy)-2-(3,5-difluoro-2-methoxyphenyl)-6a, 7,8,9-tetrahydropyrrolo[1',2':4,5]pyrazino[2,3-c]pyridazine-5(6H)-carboxylate

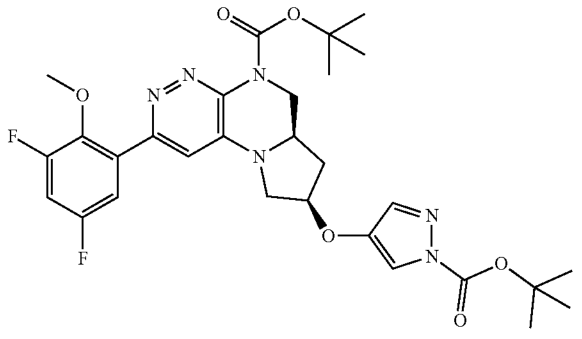 [SMILES: COc1c(F)cc(F)cc1-c1cc2c(nn1)N(C(=O)OC(C)(C)C)C[C@H]1C[C@@H](Oc3cnn(C(=O)OC(C)(C)C)c3)CN21]

The title compound was prepared using the procedure analogous to those described for Example 1, Step 2, utilizing tert-butyl (6aR,8R)-8-((1-(tert-butoxycarbonyl)-1H-pyrazol-4-yl)oxy)-2-chloro-6a,7,8,9-tetrahydropyrrolo[1',2':4,5]pyrazino[2,3-c]pyridazine-5(6H)-carboxylate instead of tert-butyl (6aR,8R)-2-chloro-8-(4-formylphenoxy)-6a,7,8,9 tetrahydro-pyrrolo[1',2':4,5]pyrazino[2,3-c]pyridazine-5 (6H)-carboxylate and (3,5-difluoro-2-methoxyphenyl) boronic acid instead of (3,5-difluoro-2-hydroxyphenyl)boronic acid. LCMS calcd for $C_{29}H_{35}F_2N_6O_6[M+H]^+$: m/z=601.3; Found: 601.2.

Step 4: (6aR,8R)-8-((1H-pyrazol-4-yl)oxy)-2-(3,5-difluoro-2-methoxyphenyl)-5,6,6a,7,8,9-hexahydropyrrolo[1',2':4,5]pyrazino[2,3-c]pyridazine

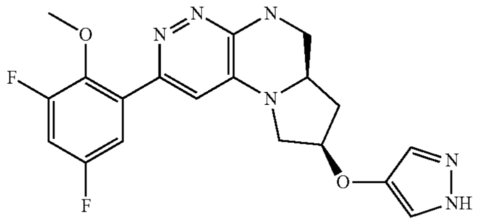 [SMILES: COc1c(F)cc(F)cc1-c1cc2c(nn1)NC[C@H]1C[C@@H](Oc3cn[nH]c3)CN21]

2,2,2-Trifluoroacetic acid (0.835 mL, 10.9 mmol) was added to a solution of tert-butyl (6aR,8R)-8-((1-(tert-butoxycarbonyl)-1H-pyrazol-4-yl)oxy)-2-(3,5-difluoro-2-methoxyphenyl)-6a,7,8,9-tetrahydropyrrolo[1',2':4,5]pyrazino[2,3-c]pyridazine-5(6H)-carboxylate (65.5 mg, 0.109 mmol) in DCM (2.00 mL). The reaction was stirred at room temperature for 3 hours. The reaction was neutralized with a saturated aqueous solution of $NaHCO_3$ and extracted with DCM. The combined organics were washed with a saturated aqueous brine solution, dried over $MgSO_4$, filtered and concentrated under reduced pressure to obtain (6aR,8R)-8-((1H-pyrazol-4-yl)oxy)-2-(3,5-difluoro-2-methoxyphenyl)-5,6,6a,7,8,9-hexahydropyrrolo[1',2':4,5]pyrazino[2,3-c]pyridazine (43.7 mg, quantitative yield). The material was used without additional purification. LCMS calcd for $C_{19}H_{19}F_2N_6O_2[M+H]^+$: m/z=401.2; Found: 401.1.

Step 5: 3-(6-(4-((4-(((6aR,8R)-2-(3,5-difluoro-2-methoxyphenyl)-5,6,6a, 7,8,9-hexahydropyrrolo[1',2':4,5]pyrazino[2,3-c]pyridazin-8-yl)oxy)-1H-pyrazol-1-yl)methyl)piperidin-1-yl)-1-oxoisoindolin-2-yl)piperidine-2,6-dione

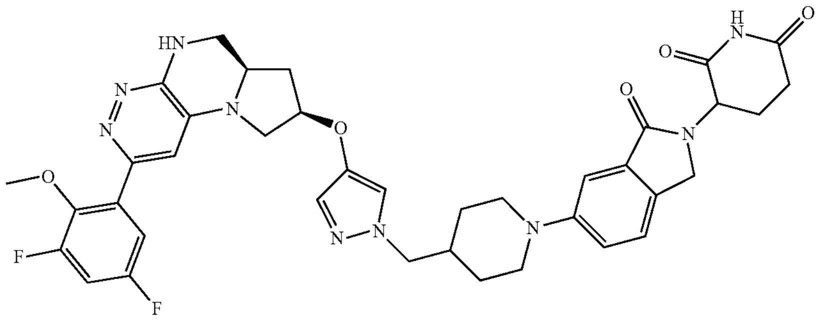 [SMILES: COc1c(F)cc(F)cc1-c1cc2c(nn1)NC[C@H]1C[C@@H](Oc3cnn(CC4CCN(c5ccc6c(c5)C(=O)N(C5CCC(=O)NC5=O)C6)CC4)c3)CN21]

The title compound was prepared using the procedure analogous to those described for Example 27, Step 7, utilizing (6aR,8R)-8-((1H-pyrazol-4-yl)oxy)-2-(3,5-difluoro-2-methoxy-phenyl)-5,6,6a,7,8,9-hexahydropyrrolo[1',2':4,5]pyrazino[2,3-c]pyridazine instead of tert-butyl (6aR,8R)-8-((5-(chloromethyl)-4-methylpyridin-2-yl)oxy)-2-(3,5-difluoro-2-methoxy-phenyl)-6a,7,8,9-tetrahydropyrrolo[1',2':4,5]pyrazino[2,3-c]pyridazine-5(6H)-carboxylate and (1-(2-(2,6-dioxopiperidin-3-yl)-3-oxoisoindolin-5-yl)piperidin-4-yl)methyl 4-methylbenzene-sulfonate (Intermediate 4) instead of 3-(3-oxo-5-piperazin-1-yl-1H-isoindol-2-yl)piperidine-2,6-dione (Intermediate 2). LCMS calcd for $C_{38}H_{40}F_2N_9O_5[M+H]+$: m/z=740.3; Found: 740.4.

Step 6. 3-(6-(4-((4-(((6aR,8R)-2-(3,5-difluoro-2-hydroxyphenyl)-5,6,6a, 7,8,9-hexahydropyrrolo[1',2':4,5]pyrazino[2,3-c]pyridazin-8-yl)oxy)-1H-pyrazol-1-yl)methyl)piperidin-1-yl)-1-oxoisoindolin-2-yl)piperidine-2,6-dione The title compound was prepared using the procedure analogous to those described for Example 26, Step 4, utilizing 3-(6-(4-((4-(((6aR,8R)-2-(3,5-difluoro-2-methoxy-phenyl)-5,6,6a,7,8,9-hexahydropyrrolo[1',2':4,5]pyrazino[2,3-c]pyridazin-8-yl)oxy)-1H-pyrazol-1-yl)methyl)piperidin-1-yl)-1-oxoisoindolin-2-yl)piperidine-2,6-dione instead of tert-butyl (6aR,8R)-2-(3,5-difluoro-2-methoxyphenyl)-8-((5-formylpyrimidin-2-yl)thio)-6a,7,8,9-tetrahydropyrrolo[1',2':4,5]pyrazino[2,3-c]pyridazine-5(6H)-carboxylate. LCMS calcd for $C_{37}H_{38}F_2N_9O_5[M+H]+$: m/z=726.3; Found: 726.3.

Example 40: 3-6-(4(((6aS8R$_Y$)-6-(difluoromethyl)-2-(3-fluoro-2-hydroxyphenyl)-5,6,6a,7,8,9-hexahydropyrrolo[1,2°:4,5]pyrazino[2,3-c]pyridazin-8-yl)oxy)-6-methylpyrazin-2-yl)methyl)piperazin-1-yl)-1-oxoisoindolin-2-yl)piperidine-2,6-dione

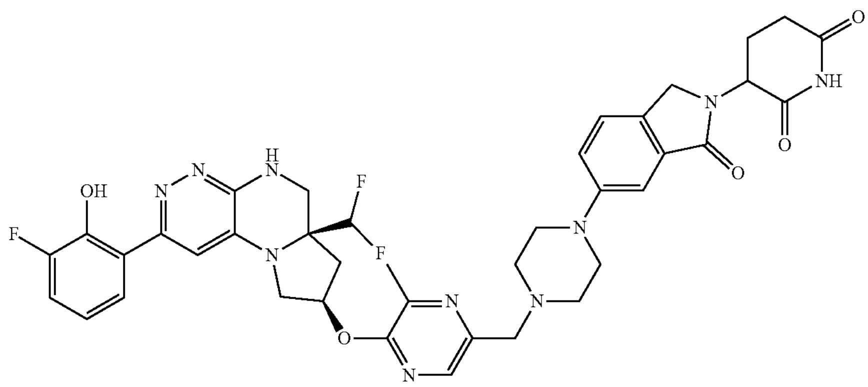 [SMILES: Cc1nc(CN2CCN(c3ccc4c(c3)C(=O)N(C3CCC(=O)NC3=O)C4)CC2)cnc1O[C@H]1CN2c3cc(-c4cccc(F)c4O)nnc3NC[C@]2(C(F)F)C1]

Step 1. 1-(tert-Butyl) 2-methyl (2S,4R)-4-(benzyloxy)pyrrolidine-1,2-dicarboxylate

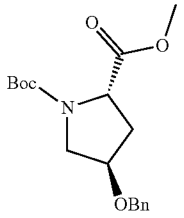 [SMILES: COC(=O)[C@@H]1C[C@@H](OCc2ccccc2)CN1C(=O)OC(C)(C)C]

Iodomethane (3.0 mL, 48.2 mmol) was added to a stirring solution of (2S,4R)-4-(benzyloxy)-1-(tert-butoxycarbonyl) pyrrolidine-2-carboxylic acid (6.2 g, 19.3 mmol) and potassium carbonate (3.32 g, 24 mmol) in DMF (46.4 mL). The reaction was stirred at room temperature for 2 hours. The product mixture was diluted with EtOAc (200 mL). The diluted product mixture was washed with water (200 mL) and a saturated sodium chloride aqueous solution (2×200 mL). The organic layer was dried over $Na_2SO_4$, filtered, and concentrated under reduced pressure. The residue obtained was used without further purification. 1-(tert-butyl) 2-methyl (2S,4R)-4-(benzyloxy)pyrrolidine-1,2-dicarboxylate was obtained as a yellow oil (6.46 g, 99%). LCMS calcd for $C_{13}H_{18}NO_3$ [M+H-$C_5H_9O_2$]+: m/z=236.1; Found: 236.1.

Step 2. 1-(tert-Butyl) 2-methyl (4R)-4-(benzyloxy)-2-(difluoromethyl)pyrrolidine-1,2-dicarboxylate

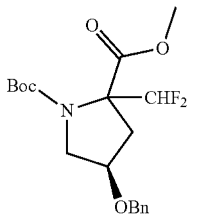 [SMILES: COC(=O)C1(C(F)F)C[C@@H](OCc2ccccc2)CN1C(=O)OC(C)(C)C]

Lithium bis(trimethylsilyl)amide (1 M in THF, 30 mL, 30 mmol) was added to a stirring solution of 1-(tert-butyl) 2-methyl (2S,4R)-4-(benzyloxy)pyrrolidine-1,2-dicarboxylate (6.7 g, 20 mmol) in THE (100 mL) at −78° C. For 45 minutes, the reaction mixture was slowly warmed until reaching room temperature. Then the reaction mixture cooled to −78° C. Difluoromethyl trifluoromethanesulfonate (5.06 mL, 39.9 mmol) was added dropwise to the reaction mixture at −78° C. The reaction mixture was allowed to slowly warm to room temperature and stirred overnight.

The product mixture was diluted with a saturated ammonium chloride aqueous solution (200 mL) and stirred for 10 minutes. The diluted product mixture was transferred to a separatory funnel and extracted with EtOAc (200 mL). The organic layer was washed with a saturated sodium chloride aqueous solution (2×200 mL). The organic layer was dried over $Na_2SO_4$, filtered, and concentrated under reduced pressure. The residue obtained was purified by silica gel flash column chromatography with a gradient of 0-50% EtOAc/hexanes to obtain 1-(tert-butyl) 2-methyl (4R)-4-(benzyloxy)-2-(difluoromethyl)pyrrolidine-1,2-dicarboxylate as an inseparable mixture of diastereomers (5.6 g, 73%). LCMS calcd for $C_{14}H_{18}F_2NO_3$ [M+H-$C_5H_9O_2$]+: m/z=286.1; Found: 286.0.

Step 3. (4R)-4-(Benzyloxy)-1-(tert-butoxycarbonyl)-2-(difluoromethyl)pyrrolidine-2-carboxylic acid

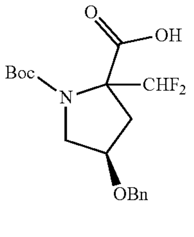 [SMILES: CC(C)(C)OC(=O)N1C[C@H](OCc2ccccc2)CC1(C(=O)O)C(F)F]

An aqueous solution of sodium hydroxide (2.5 M, 58.4 mL, 146 mmol) was added to a stirring solution of 1-(tert-butyl) 2-methyl (4R)-4-(benzyloxy)-2-(difluoromethyl)pyrrolidine-1,2-dicarboxylate (5.6 g, 14.5 mmol) in THE (27 mL) and MeOH (27 mL) at room temperature. The reaction mixture was heated to 65° C. and stirred for 2 hours. The product mixture was cooled to room temperature and acidified with an aqueous solution of hydrochloric acid (1 M, 160 mL, 160 mmol). The acidified product mixture was transferred to a separatory funnel and extracted with EtOAc (2×200 mL). The combined organic layers were dried over $Na_2SO_4$, filtered, and concentrated under reduced pressure. The residue obtained was used without further purification. (4R)-4-(benzyloxy)-1-(tert-butoxycarbonyl)-2-(difluoromethyl)pyrrolidine-2-carboxylic acid was obtained as an orange oil (5.4 g, 100%). LCMS calcd for $C_{13}H_{16}F_2NO_3$ $[M+H-C_5H_9O_2]+$: m/z=272.1; Found: 271.9

Step 4 tert-Butyl (4R)-4-(benzyloxy)-2-((4-bromo-6-chloropyridazin-3-yl)carbamoyl)-2-(difluoromethyl)pyrrolidine-1-carboxylate

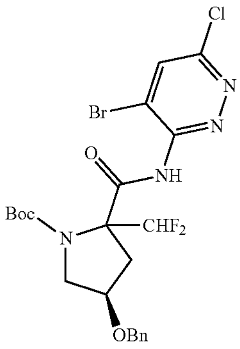 [SMILES: CC(C)(C)OC(=O)N1C[C@H](OCc2ccccc2)CC1(C(=O)Nc1nnc(Cl)cc1Br)C(F)F]

1-[Bis(dimethylamino)-methylene]-1H-1,2,3-triazolo[4,5-b]pyridinium 3-oxid hexafluorophosphate (6.55 g, 17.2 mmol) was added to a stirring solution of (4R)-4-(benzyloxy)-1-(tert-butoxycarbonyl)-2-(difluoromethyl)pyrrolidine-2-carboxylic acid (5.77 g, 15.5 mmol) and N,N-diisopropylethylamine (9.72 mL, 55.8 mmol) in acetonitrile (75 mL). The reaction mixture was stirred 40 minutes at room temperature. The product mixture was concentrated under reduced pressure. The resulting residue was dissolved in THE (62.4 mL). 4-Bromo-6-chloro-pyridazin-3-amine (4.2 g, 20.2 mmol) was added to the solution and the resulting solution was stirred. Sodium hydride (2.2 g, 55.2 mmol, 60% dispersion in mineral oil) was added portion-wise to the stirring reaction mixture at room temperature. After 1 hour, the product mixture was cooled to 0° C. and quenched with a saturated ammonium chloride aqueous solution (100 mL). The quenched product mixture was transferred to a separatory funnel and was diluted with water (100 mL). The diluted product mixture was extracted with EtOAc (2×200 mL). The combined organic layers were dried over $Na_2SO_4$, filtered, and concentrated under reduced pressure. The residue obtained was purified by silica gel flash column chromatography with a gradient of 0-50% EtOAc/hexanes to obtain tert-butyl (4R)-4-(benzyloxy)-2-((4-bromo-6-chloropyridazin-3-yl)carbamoyl)-2-(difluoromethyl)pyrrolidine-1-carboxylate (5.4 g, 62%). LCMS calcd for $C_{22}H_{25}BrClF_2N_4O_4$ $[M+H]^+$: m/z=561.1; Found: 561.9.

Step 5. (6aS,8R)-8-(Benzyloxy)-2-chloro-6a-(difluoromethyl)-6a,7,8,9-tetrahydropyrrolo [1',2':4,5]pyrazino[2,3-c]pyridazin-6(5H)-one and (6aR,8R)-8-(benzyloxy)-2-choro-6a-(difluoromethyl)6a,7,8,9-tetrahydropyrrolo[1',2':4,5]pyrazino[2,3-c]pyridazin-6(5H)-one

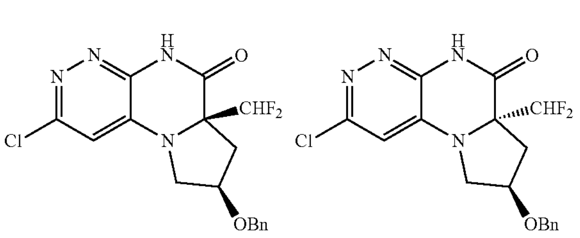 [SMILES: O=C1Nc2nnc(Cl)cc2N2C[C@H](OCc3ccccc3)C[C@@]12C(F)F ; O=C1Nc2nnc(Cl)cc2N2C[C@H](OCc3ccccc3)C[C@]12C(F)F]

Trifluoroacetic acid (7.36 mL, 96.1 mmol) was added to a stirring solution of tert-butyl (4R)-4-(benzyloxy)-2-((4-bromo-6-chloropyridazin-3-yl)carbamoyl)-2-(difluoromethyl)-pyrrolidine-1-carboxylate (5.4 g, 9.61 mmol) at room temperature. The reaction mixture was stirred for 5 hours. The product mixture was concentrated under reduced pressure. The residue obtained was dissolved in acetonitrile (15 mL). N,N-Diisopropylethylamine (8.37 mL, 48.1 mmol) was added to the stirring reaction mixture. The reaction mixture was heated to 80° C. and stirred for 16 hours. The product mixture was concentrated under reduced pressure. The residue obtained was purified by silica gel flash column chromatography with a gradient of 0-100% EtOAc/hexanes to obtain (6aS,8R)-8-(benzyloxy)-2-chloro-6a-(difluoromethyl)-6a,7,8,9-tetrahydropyrrolo[1',2':4,5]pyrazino[2,3-c]pyridazin-6(5H)-one (562 mg, 15%) and (6aR,8R)-8-(benzyloxy)-2-chloro-6a-(difluoromethyl)-6a,7,8,9-tetrahydropyrrolo[1',2':4,5]pyrazino[2,3-c]pyridazin-6(5H)-one (1.87 g, 51%). LCMS calcd for $C_{17}H_{16}ClF_2N_4O_2$ $[M+H]+$: m/z=381.1; Found: 381.0.

Step 6. (6aS,8R)-8-(Benzyloxy)-6a-(difluoromethyl)-2-(3 fluoro-2-methoxyphenyl)-6a, 7,8,9-tetrahydropyrrolo[1',2':4,5]pyrazino[2,3-c]pyridazin-6(5H)-one

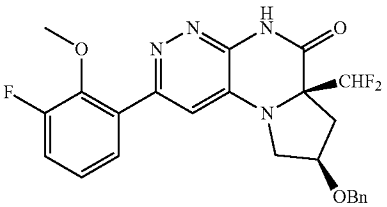 [SMILES: COc1c(F)cccc1-c1cc2c(nn1)NC(=O)[C@]1(C(F)F)C[C@@H](OCc3ccccc3)CN21]

A 20 mL scintillation vial was charged with (6aS,8R)-8-(benzyloxy)-2-chloro-6a-(difluoromethyl)-6a,7,8,9-tetrahydropyrrolo[1',2':4,5]pyrazino[2,3-c]pyridazin-6(5H)-one (400 mg, 1.05 mmol), cesium carbonate (1.37 g, 4.2 mmol), 3-fluoro-2-methoxyphenylboronic acid (357 mg, 2.1 mmol), and [1,1'-bis(diphenylphosphino)ferrocene]dichloropalladium(II), complex with dichloromethane (129 mg, 0.16 mmol). The solid mixture was dissolved in 1,4-dioxane (8 mL) and water (0.8 mL). The reaction mixture was sparged with $N_2$ gas for 5 minutes, sealed, and heated to 100° C. The reaction mixture was stirred for 1 hour at 100° C. The product mixture was diluted with EtOAc (50 mL). The diluted product mixture was washed with a saturated sodium bicarbonate aqueous solution (50 mL). The aqueous layer was extracted with EtOAc (2×50 mL).

The combined organic layers were dried over $Na_2SO_4$, filtered, and concentrated under reduced pressure. The residue obtained was purified by silica gel flash column chromatography with a gradient of 0-100% EtOAc/hexanes to obtain (6aS,8R)-8-(benzyloxy)-6a-(difluoromethyl)-2-(3-fluoro-2-methoxyphenyl)-6a,7,8,9-tetrahydropyrrolo[1',2':4,5]pyrazino[2,3-c]pyridazin-6(5H)-one (318 mg, 64%). LCMS calcd for $C_{24}H_{22}F_3N_4O_3[M+H]^+$: m/z=471.2; Found: 471.0.

Step 7. (6aS,8R)-8-(Benzyloxy)-6a-(difluoromethyl)-2-(3-fluoro-2-methoxyphenyl)-5,6,6a,7,8,9-hexahydropyrrolo[1,2':4,5]pyrazino[2,3-c]pyridazine

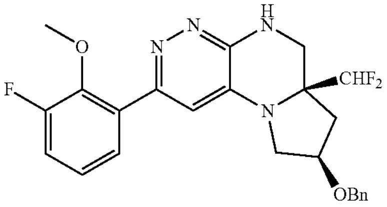

Lithium aluminum hydride (1.0 M in THF, 2.03 mL, 2.03 mmol) was added to a stirring solution of (6aS,8R)-8-(benzyloxy)-6a-(difluoromethyl)-2-(3-fluoro-2-methoxyphenyl)-6a,7,8,9-tetrahydropyrrolo[1',2':4,5]pyrazino[2,3-c]pyridazin-6(5H)-one (318 mg, 0.68 mmol) in THF (6 mL) at 0° C. The reaction mixture was warmed to room temperature and stirred for 1.5 hours. The reaction mixture was cooled to 0° C. and quenched by a slow addition of methanol (7.7 mL). The reaction mixture was warmed to room temperature. Acetic acid (770 μL, 13.5 mmol) and sodium cyanoborohydride (428 mg, 6.81 mmol) were added in sequence to the reaction mixture at room temperature. The reaction mixture was heated to 80° C. and stirred for 14 hours. The product mixture was cooled to room temperature and transferred to a separatory funnel with a saturated potassium carbonate solution (100 mL). The diluted product mixture was extracted with EtOAc (4×100 mL). The combined organic layers were dried over $Na_2SO_4$, filtered, and concentrated under reduced pressure. The residue obtained was purified by silica gel flash column chromatography with a gradient of 0-15% MeOH/DCM to obtain (6aS,8R)-8-(benzyloxy)-6a-(difluoromethyl)-2-(3-fluoro-2-methoxyphenyl)-5,6,6a,7,8,9-hexahydropyrrolo[1',2',4,5]pyrazino[2,3-c]pyridazine (290 mg, 94° as a white foamy solid. LCMS calcd for $C_{24}H_{24}F_3N_4O_2$ $[M+H]^+$: m/z=457.2; Found: 457.1.

Step 8. (6aS,8R)-6a-(Difluoromethyl)-2-(3-fluoro-2-methoxyphenyl)-5,6,6a,7,8,9-hexahydropyrrolo[1',2':4,5]pyrazino[2,3-c]pyridazin-8-ol and (6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-ol

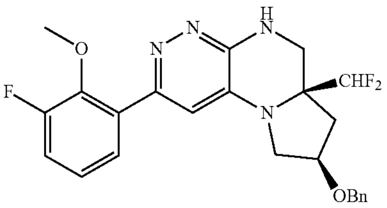 [SMILES: COc1c(F)cccc1-c1cc2c(nn1)NC[C@]1(C(F)F)C[C@@H](OCc3ccccc3)CN21]

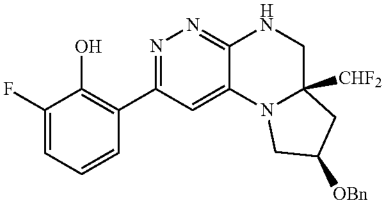

Boron trichloride (1.0 M in DCM, 3.29 mL, 3.29 mmol) was added dropwise to a stirring solution of (6aS,8R)-8-(benzyloxy)-6a-(difluoromethyl)-2-(3-fluoro-2-methoxyphenyl)-5,6,6a7,8,7,9-hexahydropyrrolo[1',2':4,5]pyrazino[2,3-c]pyridazine (500 mg, 1.1 mmol) in DCM (11.5 mL) at −78° C. The reaction mixture was warmed to 0° C. and stirred for 30 minutes. The product mixture was quenched with water (5 mL) and transferred to a separatory funnel with a saturated sodium carbonate aqueous solution (100 mL). The quenched product mixture was extracted with a 3:1 chloroform:isopropanol solution (4×100 mL). The combined organic layers were dried over $MgSO_4$, filtered, and concentrated under reduced pressure. The residue obtained was purified by silica gel flash column chromatography with a gradient of 0-20% MeOH/DCM to obtain (6aS,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-ol (221 mg, 55%) and (6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-ol (83 mg, 21%). LCMS calcd for $C_{17}H_{18}F_3N_4O_2$ [M+H]+: m/z=367.1; Found: 367.0. LCMS calcd for $C_{16}H_{16}F_3N_4O_2$ $[M+H]^+$: m/z=353.1. Found: 353.0.

Step 9. Methyl 5-(((6aS,8R)-6a-(difluoromethyl)-2-(3-fluoro-2 methoxyphenyl)-5,6,6a,7,8,9-hexahydropyrrolo[1',2':4,5]pyrazino[2,3-c]pyridazin-8 yl)oxy)-6-methylpyrazine-2-carboxylate

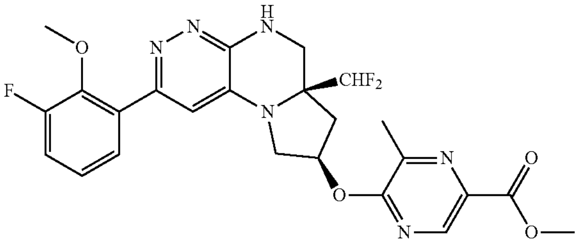 [SMILES: COC(=O)c1cnc(O[C@H]2CN3c4cc(-c5cccc(F)c5OC)nnc4NC[C@]3(C(F)F)C2)c(C)n1]

Sodium hydride (55 mg, 1.38 mmol, 60% dispersion in mineral oil) was added to a stirring solution of methyl-5-chloro-6-methylpyrazine-2-carboxylate (171.2 mg, 0.92 mmol) and (6aS,8R)-6a-(difluoromethyl)-2-(3-fluoro-2-methoxyphenyl)-5,6,6a,7,8,9-hexahydropyrrolo [1',2':4,5] pyrazino[2,3-c]pyridazin-8-ol (84 mg, 0.23 mmol) in THE (2.5 mL) at 0° C. The reaction mixture was warmed to 35° C. and stirred for 1.5 hours. The product mixture was cooled to 0° C. and quenched with a saturated ammonium chloride aqueous solution (30 mL). The quenched product mixture was transferred to a separatory funnel and extracted with a 3:1 chloroform:isopropanol solution (3×30 mL). The combined organic layers were dried over $MgSO_4$, filtered, and concentrated under reduced pressure. The residue obtained was purified by silica gel flash column chromatography with a gradient of 0-15% MeOH/DCM to obtain methyl 5-(((6aS,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-yl)oxy)-6-methylpyrazine-2-carboxylate (104 mg, 88%). LCMS calcd for $C_{24}H_{24}F_3N_6O_4$ $[M+H]^+$: m/z=517.2; Found: 517.0.

Step 10. (5-(((6aS,8R)-6a-(Difluoromethyl)-2-(3 fluoro-2-methoxyphenyl)-5,6,6a,7,8,9-hexahydropyrrolo[1',2':4,5]pyrazino[2,3-c]pyridazin-8 yl)oxy)-6-methylpyrazin-2 yl)methanol

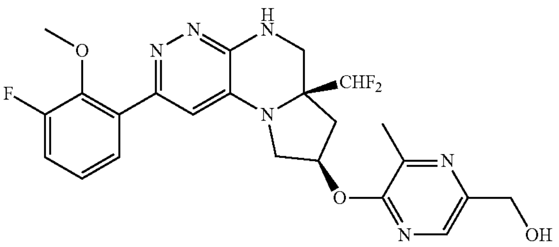 [SMILES: COc1c(F)cccc1-c1cc2c(nn1)NC[C@]1(C(F)F)C[C@@H](Oc3ncc(CO)nc3C)CN21]

Diisobutylaluminium hydride (1.0 M in toluene, 0.81 mL, 0.81 mL) was added to a stirring solution of methyl 5-(((6aS,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-yl)oxy)-6-methylpyrazine-2-carboxylate (104 mg, 0.20 mmol) in THE (4 mL) at −78° C. The reaction mixture was warmed to 0° C. and stirred for 1 hour. The reaction mixture was quenched with a saturated potassium sodium tartrate aqueous solution (30 mL) and stirred at room temperature for 30 minutes. The quenched reaction mixture was transferred to a separatory funnel and extracted with a 3:1 chloroform:isopropanol solution (3×30 mL.). The combined organic layers were dried over $MgSO_4$, filtered, and concentrated under reduced pressure. The residue obtained was dissolved in methanol (3 mL) and cooled to 0° C. Sodium borohydride (22.8 mg, 0.6 mmol) was added to the reaction mixture at 0° C. and stirred for 30 minutes. The product mixture was transferred to a separatory funnel containing a saturated ammonium chloride aqueous solution (30 mL) and extracted with a 3:1 chloroform:isopropanol solution (3×30 mL.). The combined organic layers were dried over $MgSO_4$, filtered, and concentrated under reduced pressure. The residue obtained was purified by silica gel flash column chromatography with a gradient of 0-20% MeOH/DCM to obtain (5-(((6aS,8R)-6a-(difluoromethyl)-2-(3-fluoro-2-methoxyphenyl)-5,6,6a, 7,8,9-hexahydropyrrolo[1',2':4,5]pyrazino[2,3-c]pyridazin-8-yl)oxy)-6-methylpyrazin-2-yl)methanol (88 mg, 89%). LCMS calcd for $C_{23}H_{24}F_3N_6O_3$ $[M+H]^+$: m/z=489.2. Found: 489.0.

Step 11. 2-((6aS,8R)-8-((5-(Chloromethyl)-3-methylpyrazin-2-yl)oxy)-6a-(difluoromethyl)-5.6.6a, 7,8, 9-hexahydropyrrolo[1',2':4,5]pyrazino[2,3-c]pyridazin-2-yl)-6(fluorophenol

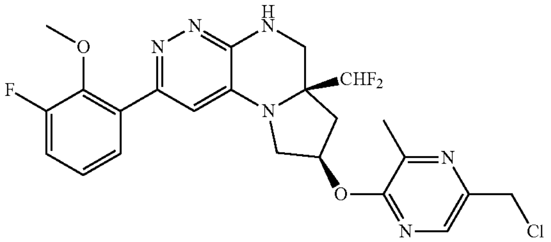 [SMILES: COc1c(F)cccc1-c1cc2c(nn1)NC[C@]1(C(F)F)C[C@@H](Oc3ncc(CCl)nc3C)CN21]

Boron trichloride (1.0 M in DCM, 2.7 mL, 2.7 mmol) was added to a stirring solution of (5-(((6aS,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-yl)oxy)-6-methylpyrazin-2-yl)methanol (88 mg, 0.18 mmol) in DCM (1 mL) at 0° C. The reaction mixture was warmed to room temperature and stirred for 16 hours. The product mixture was cooled to 0° C. and quenched with slow addition of water (2 mL). The quenched product mixture was transferred to a separatory funnel with a saturated potassium carbonate aqueous solution (30 mL) and extracted with a 3:1 chloroform:isopropanol solution (4×30 mL). The combined organic layers were dried over $MgSO_4$, filtered, and concentrated under reduced pressure. The residue obtained was dissolved in THE (1 mL). The reaction mixture was cooled to 0° C. Thionyl chloride (39.3 μL, 0.54 mmol) was added to the reaction mixture at 0° C. The reaction mixture was warmed to room temperature and stirred for 30 minutes. The product mixture was diluted with water (10 mL) and transferred to a separatory funnel with a saturated potassium carbonate aqueous solution (30 mL) and extracted with a 3:1 chlaraform:isopropanol solution (4×30 mL) The combined organic layers were dried over $MgSO_4$, filtered, and concentrated under reduced pressure to obtain 2-((6aS,8R)-8-((5-(chloromethyl)-3-methyl pyrazin-2-yl)oxy)-6a-(difluoromethyl)-5,6,6a,7,8,9-hexahydropyrrolo[1',2:4,5]pyrazino [2,3-c]pyridazin-2-yl)-6-fluorophenol (88 mg, 99%). The residue was used directly in the next step without further purification. LCMS calcd for $C_{22}H_{21}ClF_3N_6O_2$ $[M+H]^+$: m/z=493.1; Found: 493.0.

Step 12. 3-(6-(4-((5-((6aS,8R)-6a-(difluoromethyl)-2-(3 fluoro-2-hydroxyphenyl)-5,6,6a,7,8,9-hexahydropyrrolo[1',2':4,5]pyrazino[2,3-c]pyridazin-8 yl)oxy)-6-(methylpyrazin-2-yl)methyl)piperazin-1-yl)-1-oxoisoindolin-2-yl)piperidine-2,6-dione (Example 40)

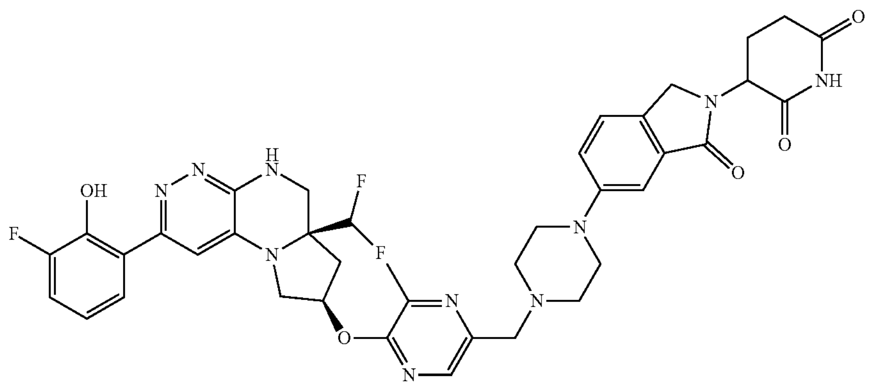 [SMILES: Cc1nc(CN2CCN(c3ccc4c(c3)C(=O)N(C3CCC(=O)NC3=O)C4)CC2)cnc1O[C@H]1CN2c3cc(-c4cccc(F)c4O)nnc3NC[C@]2(C(F)F)C1]

N,N-Diisopropylethylamine (156 μL, 0.89 mmol) was added to a stirring solution of 2-((6aS,8R)-8-((5-(chloromethyl)-3-methyl pyrazin-2-yl)oxy)-6a-(difluoromethyl)-5,6,6a,7,8,9-hexahydropyrrolo[1',2':4,5]pyrazino[2,3-c] pyridazin-2-yl)-6-fluorophenol (88 mg, 0.181 mmol) and (S)-3-(1-oxo-6-(piperazin-1-yl)isoindolin-2-yl)piperidine-2,6-dione; hydrochloride (97.7 mg, 0.27 mmol) in acetonitrile (5 mL) at room temperature. The reaction mixture was heated to 120° C. and stirred for 1.5 hours. The product mixture was cooled to room temperature, diluted with DMSO, and filtered through celite. The diluted product mixture was purified directly by prep-HPLC (Waters CSH-Flouro-Phenyl, 5 μM, 30×100 mm, 10.1-30.1% MeCN/water (containing 0.1% TFA) over 5 min) to give 3-(6-(4-((5-(((6aS,8R)-6a-(difluoromethyl)-2-(3-fluoro-2-hydroxyphenyl)-5,6,6a,7,8,9-hexahydropyrrolo[1',2':4,5] pyrazino[2,3-c]pyridazin-8-yl)oxy)-6-methyl pyrazin-2-yl) methyl)piperazin-1-yl)-1-oxoisoindolin-2-yl)piperidine-2,6-dione (50.4 mg, 25%) as its TFA Salt.

$^1$H NMR (400 MHz, MeOD) δ 8.19 (s, 1H), 7.51 (d, J=8.2 Hz, 1H), 7.40-7.29 (m, 4H), 7.08 (s, 1H), 7.02 (td, J=8.1, 4.8 Hz, 1H), 6.27 (t, J=55.6 Hz, 1H), 5.87 (t, J=7.6 Hz, 1H), 5.13 (dd, J=13.3, 5.2 Hz, 1H), 4.53-4.34 (m, 4H), 4.08 (d, J=12.6 Hz, 1H), 4.00 (dd, J=13.2, 3.0 Hz, 1H), 3.26 (d, J=3.9 Hz, 1H), 2.98-2.84 (m, 1H), 2.81-2.76 (m, 1H), 2.74 (d, J=14.8 Hz, 1H), 2.56 (s, 3H), 2.54-2.40 (m, 2H), 2.17 (dtd, J=12.9, 5.3, 2.5 Hz, 1H). LCMS calcd for $C_{39}H_{40}F_3N_{10}O_5$ $[M+H]^+$: m/z=785.3: Found. 785.1.

Example 41: 3-(6-(4-((2-(((6aS,8R)-6a-(Difluoromethyl)-2-(3-fluoro-2-hydroxy-phenyl)-5,6,6a,7,8,9-hexahydropyrrolo[1',2':4,5]pyrazino[2,3-c]pyridazin-8-yl)oxy)-4,6-dimethylpyrimidin-5-yl)methyl) piperazin-1-yl)-1-oxoisoindolin-2-yl)piperidine-2,6-dione

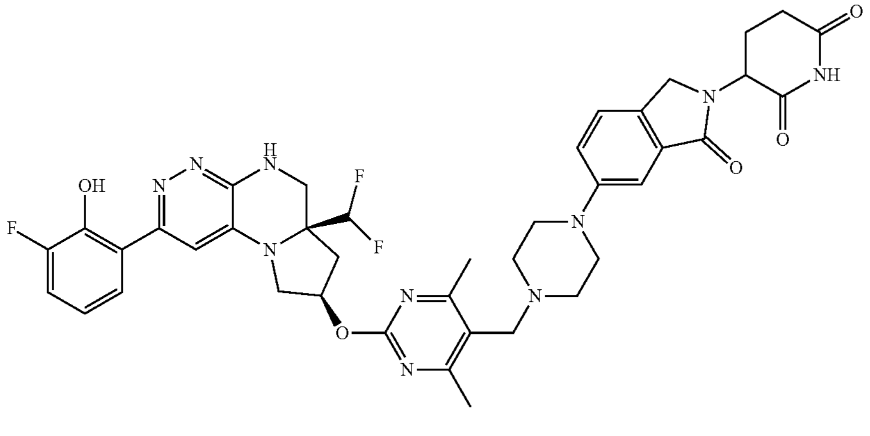 [SMILES: Cc1nc(O[C@H]2CN3c4cc(-c5cccc(F)c5O)nnc4NC[C@]3(C(F)F)C2)nc(C)c1CN1CCN(c2ccc3c(c2)C(=O)N(C2CCC(=O)NC2=O)C3)CC1]

Step 1. 5-(((tert Butyldimethylsilyl)oxy)methyl)-2-chloro-4,6-dimethylpyrimidin

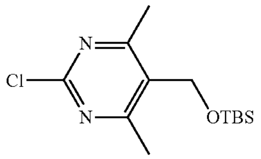 [SMILES: Cc1nc(Cl)nc(C)c1CO[Si](C)(C)C(C)(C)C]

Diisobutylaluminium hydride (1.0 M in toluene, 5.59 mL, 5.59 mmol) was added dropwise to a stirring solution of ethyl 2-chloro-4,6-dimethylpyrimidine-5-carboxylate (480.0 mg, 2.24 mmol) in THE (12.8 mL) at −78° C. The reaction mixture was allowed to slowly warm to room temperature over 3 hours. The reaction mixture was stirred for 1 hour at room temperature. The product mixture was quenched with a saturated potassium sodium tartrate aqueous solution (15 mL) and stirred for 30 minutes. The quenched product mixture was transferred to a separatory funnel with a saturated potassium sodium tartrate aqueous solution (70 mL) and was extracted with EtOAc (3×80 mL). The combined organic layers were dried over $Na_2SO_4$, filtered, and concentrated under reduced pressure. The resulting residue was dissolved in DCM (13 mL). Imidazole (305 mg, 4.47 mmol) and tert-butyl dimethylchlorosilane (506 mg, 3.35 mmol) were added in sequence to the stirring reaction mixture. The reaction mixture was stirred for 30 minutes. The product mixture was filtered through celite and concentrated under reduced pressure. The residue obtained was purified by silica gel flash column chromatography with a gradient of 0-50% EtOAc/Hexanes to obtain 5-(((tert-butyldimethylsilyl)oxy)methyl)-2-chloro-4,6-dimethylpyrimidine (213 mg, 33%). LCMS calcd for $C_{13}H_{24}ClN_2OSi$ $[M+H]^+$: m/z=287.1, Found. 287.0.

Step 2. (6aS,8R)-8-((5-(((tert-Butyldimethylsilyl)oxy)methyl)-4,6-dimethylpyrimidin-2-yl)oxy)-6a-(difluoromethyl)-2-(3 fluoro-2-methoxyphenyl)-5,6,6a,7,8,9-hexahydropyrrolo[1',2':4,5]pyrazino[2,3-c]pyridazine

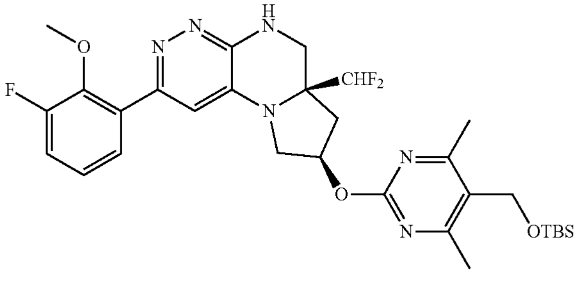 [SMILES: COc1c(F)cccc1-c1cc2c(nn1)NC[C@]1(C(F)F)C[C@@H](Oc3nc(C)c(CO[Si](C)(C)C(C)(C)C)c(C)n3)CN21]

Sodium hydride (11 mg, 0.27 mmol, 60% dispersion in mineral oil) was added to a stirring solution of 5-(((tert-butyldimethylsilyl)oxy)methyl)-2-chloro-4,6-dimethyl-pyrimidine (39 mg, 0.14 mmol) and (6aS,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-ol (20 mg, 0.05 mmol) in THF (2 mL) at 0° C. The reaction mixture was warmed to room temperature and stirred for 1 hour. The product mixture was cooled to 0° C. and quenched with a slow addition of methanol (1 mL). The quenched product mixture was transferred to a separatory funnel with a saturated ammonium chloride aqueous solution (35 mL) and extracted with ethyl acetate (3×35 mL). The combined organic layers were dried over $Na_2SO_4$, filtered, and concentrated under reduced pressure. The residue obtained was purified by silica gel flash column chromatography with a gradient of 0-10% MeOH/DCM to obtain (6aS,8R)-8-((5-(((tert-butyldimethylsilyl)oxy)methyl)-4,6-dimethylpyrimidin-2-yl)oxy)-6a-(difluoromethyl)-2-(3-fluoro-2-methoxyphenyl)-5,6,6a,7,8,9-hexahydropyrrolo[1',2':4,5]pyrazino[2,3-c]pyridazine (23 mg, 68%). LCMS calcd for $C_{30}H_{40}F_3N_6O_3Si$ $[M+H]^+$: m/z=617.3; Found: 617.1.

Step 3. 2-((6aS,8R)-8-((5-(Chloromethyl)-4,6-dimethylpyrimidin-2 yl)oxy)-6a-(difluoromethyl)-5,6,6a,7,8,9-hexahydropyrrolo[1',2':4,5]pyrazino[2,3-c]pyridazin-2-yl-6-fluorophenol

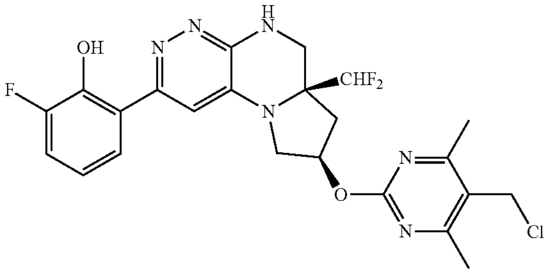 [SMILES: Cc1nc(O[C@H]2CN3c4cc(-c5cccc(F)c5O)nnc4NC[C@]3(C(F)F)C2)nc(C)c1CCl]

Boron trichloride (1.0 M in DCM, 1.19 mL, 1.19 mmol) was added to a stirring solution of (6aS,8R)-8-((5-(((tert-butyldimethyl silyl)oxy)methyl)-4,6-dimethylpyrimidin-2-yl)oxy)-6a-(difluoromethyl)-2-(3-fluoro-2-methoxyphenyl)-5,6,6a, 7,8,9-hexahydropyrrolo[1',2':4,5]pyrazino[2,3-c]pyridazine (23 mg, 0.037 mmol) in DCM (1 mL) at 0° C. The reaction mixture was warmed to room temperature and stirred for 24 hours. An additional portion of boron trichloride (1.0 M in DCM, 1.19 mL, 1.19 mmol) was added to the reaction mixture and stirred for an additional 48 hours. The product mixture was cooled to 0° C. The product mixture was quenched with water (2 mL). The quenched product mixture was transferred to a separatory funnel containing a saturated potassium carbonate aqueous solution (30 mL). The diluted product mixture was extracted with a 3:1 chloroform:isopropanal solution (4×30 mL). The combined organic layers were dried over $MgSO_4$, filtered, and concentrated under reduced pressure to obtain 2-((6aS,8R)-8-((5-(chloromethyl)-4,6-dimethylpyrimidin-2-yl)oxy)-6a-(difluoromethyl)-5,6,6a,7,8,9-hexahydropyrrolo[1',2':4,5]pyrazino[2,3-c]pyridazin-2-yl)-6-fluorophenol. The residue was used directly in the next step without further purification. LCMS calcd for $C_{23}H_{23}ClF_3N_6O_2$ $[M+H]^+$: m/z=507.2; Found. 507.1.

Step 4. 3-(6-(4-((2-(((6aS,8R)-6a-(Difluoromethyl)-2-(3 fluoro-2-hydroxyphenyl)-5,6,6a,7,8,9-hexahydropyrrolo[1',2':4,5]pyrazino[2,3-c]pyridazin-8 yl)oxy)-4,6-dimethylpyrimidin-5 yl)methyl)piperazin-1 yl)-1-oxoisoindolin-2 yl)piperidine-2,6-dione Example 41

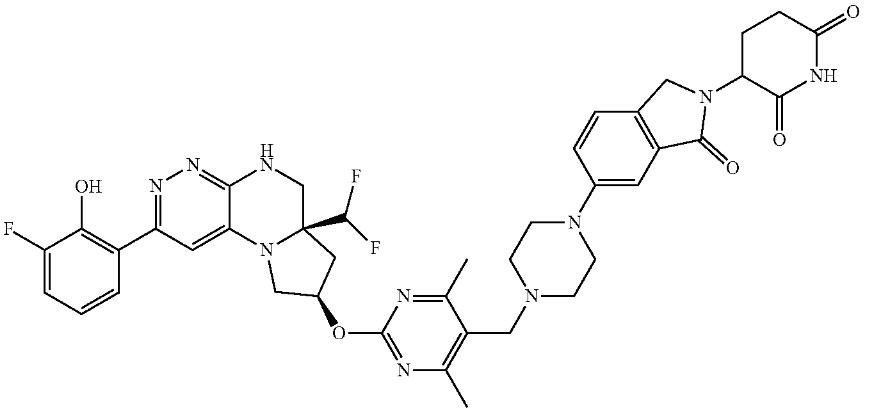 [SMILES: Cc1nc(O[C@H]2CN3c4cc(-c5cccc(F)c5O)nnc4NC[C@]3(C(F)F)C2)nc(C)c1CN1CCN(c2ccc3c(c2)C(=O)N(C2CCC(=O)NC2=O)C3)CC1]

N,N-Diisopropylethylamine (18.9 μL, 0.11 mmol) was added to a stirring solution of 2-((6aS,8R)-8-((5-(chloromethyl)-4,6-dimethylpyrimidin-2-yl)oxy)-6a-(difluoromethyl)-5,6,6a,7,8,9-hexahydropyrrolo[1',2':4,5]pyrazino[2,3-c]pyridazin-2-yl)-6-fluorophenol (11 mg, 0.022 mmol) and (S)-3-(1-oxo-6-(piperazin-1-yl)isoindolin-2-yl)piperidine-2,6-dione; hydrochloride (11.9 mg, 0.33 mmol) in acetonitrile (1 mL) at room temperature. The reaction mixture was heated to 120° C. and stirred for 1.5 hours. The product mixture was cooled to room temperature, diluted with DMSO, and filtered through celite. The diluted product mixture was purified directly by prep-HPLC (Waters CSH-C18, 5 μM, 30×100 mm, 10.1-30.1% MeCN/water (containing 0.1% TFA) over 5 min) to give 3-(6-(4-((2-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-4,6-dimethylpyrimidin-5-yl)methyl)piperazin-1-yl)-1-oxoisoindolin-2-yl)piperidine-2,6-dione (8.7 mg, 35%) as its TFA salt.

$^1$H NMR (400 MHz, MeOD) δ 7.50 (d, J=8.3 Hz, 1H), 7.40-7.30 (m, 4H), 7.09 (s, 1H), 7.02 (td, J=8.1, 4.8 Hz, 1H), 6.32 (t, J=55.5 Hz, 1H), 5.87 (t, J=7.1 Hz, 1H), 5.13 (dd, J=13.3, 5.2 Hz, 1H), 4.53-4.33 (m, 5H), 4.13 (d, J=12.7 Hz, 1H), 4.02 (dd, J=13.2, 2.8 Hz, 1H), 3.25 (d, J=3.5 Hz, 1H), 2.96-2.84 (m, 1H), 2.82-2.73 (m, 1H), 2.69 (d, J=12.0 Hz, 1H), 2.66 (s, 6H), 2.56-2.41 (m, 2H), 2.23-2.12 (m, 1H). LCMS calcd for $C_{40}H_{42}F_3N_{10}O_5$ $[M+H]^+$: m/z=799.3. Found. 799.2.

Example 42: 3-(6-(4-((2-(((6aS,8R)-6a-(difluoromethyl)-2-(3-fluoro-2-hydroxyphenyl)-5,6,6a,7,8,9-hexahydropyrrolo[1%2':4,5]pyrazino[2,3-c]pyridazin-8-yl)oxy)pyrimidin-5-yl)methyl)piperazin-1-yl)-1-oxoisoindolin-2-yl)piperidine-2,6-dione

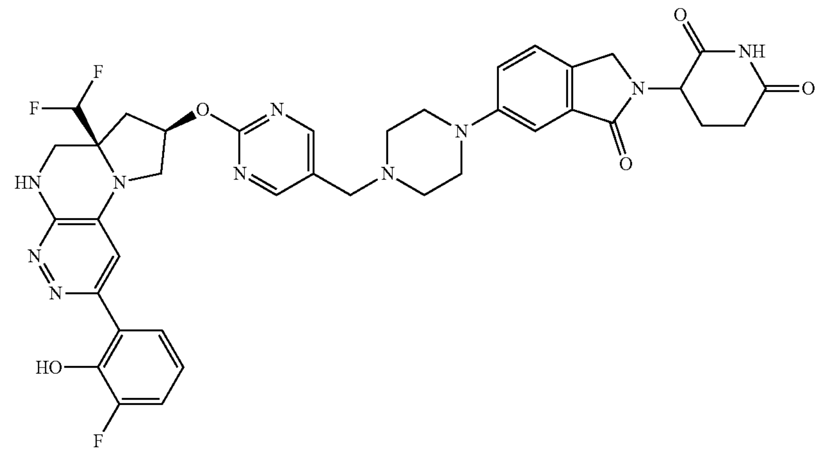 [SMILES: O=C1CCC(N2Cc3ccc(N4CCN(Cc5cnc(O[C@H]6CN7c8cc(-c9cccc(F)c9O)nnc8NC[C@]7(C(F)F)C6)nc5)CC4)cc3C2=O)C(=O)N1]

Step 1. 5-(((tert-butyldimethylsilyl)oxy)methyl)-2-chloropyrimidine

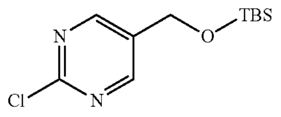

Diisobutylaluminium hydride (1.0 M in toluene, 3.19 mL, 3.19 mmol) was added to a stirring solution of methyl 2-chloropyrimidine-5-carboxylate (220 mg, 1.27 mmol) in THE (6 mL) at −78° C.

The reaction mixture was allowed to slowly warm to room temperature. The product mixture was quenched with a saturated potassium sodium tartrate aqueous solution (20 mL) and stirred at room temperature for 30 minutes. The quenched product mixture was diluted with EtOAc (50 mL) and transferred to a separatory funnel containing a saturated potassium sodium tartrate aqueous solution (30 mL). The diluted product mixture was extracted with EtOAc (2×50 mL). The combined organic layers were dried over $Na_2SO_4$, filtered, and concentrated under reduced pressure. The residue obtained was dissolved in DCM (6 mL). Imidazole (278 mg, 4.09 mmol) and tert-butyldimethylsilyl chloride (308 mg, 2.04 mmol) were added in sequence to the reaction mixture. The reaction mixture was stirred for 30 minutes. The product mixture was filtered through celite and concentrated under reduced pressure. The residue obtained was purified by silica gel flash column chromatography with a gradient of 0-50% EtOAc/Hexanes to obtain 5-(((tert-butyldimethylsilyl)oxy)methyl)-2-chloropyrimidine (210 mg, 64%). LCMS calcd for $C_{11}H_{20}ClN_2OSi$ $[M+H]^+$: m/z=259.1. Found: 259.0.

Step 2. 3-(6-(4-((2-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)pyrimidin-5-yl)methylpiperazin-1-yl)-1-oxoisoindolin-2-yl)piperidine-2,6-dione (Example 42)

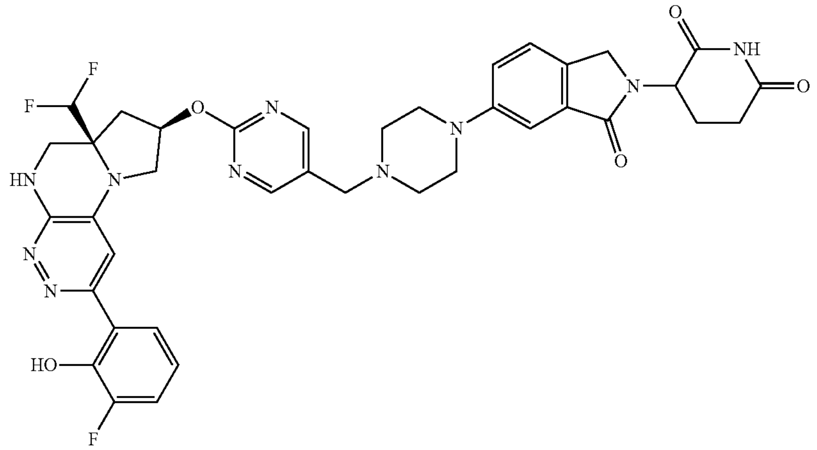

This example was synthesized by procedures analogous to that described in Example 41, using 5-(((tert-butyldimethylsilyl)oxy)methyl)-2-chloropyrimidine instead of 5-(((tert-butyldimethylsilyl)oxy)methyl)-2-chloro-4,6-dimethylpyrimidine.

$^1$H NMR (400 MHz, MeOD) δ 8.80 (s, 2H), 7.50 (d, J=8.3 Hz, 1H), 7.39-7.28 (m, 4H), 7.09 (s, 1H), 7.02 (td, J=8.0, 4.8 Hz, 1H), 6.30 (t, J=55.5 Hz, 1H), 5.89 (t, J=7.2 Hz, 1H), 5.13 (dd, J=13.3, 5.1 Hz, 1H), 4.51-4.31 (m, 5H), 4.12 (d, J=12.6 Hz, 1H), 4.05 (dd, J=13.1, 2.9 Hz, 1H), 3.48 (br, 7H) 3.30-3.24 (m, 1H), 2.96-2.84 (m, 1H), 2.80 (dd, J=4.8, 2.5 Hz, 1H), 2.78-2.68 (m, 2H), 2.57-2.42 (m, 2H), 2.23-2.11 (m, 1H). LCMS calcd for $C_{38}H_{38}F_3N_{10}O_5$ $[M+H]^+$: m/z=771.3, Found: 771.2.

Example 43: (S)-3-(6-(4-((6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)pyridin-3-yl)methyl)piperazin-1-yl)-1-oxoisoindolin-2-yl)piperidine-2,6-dione

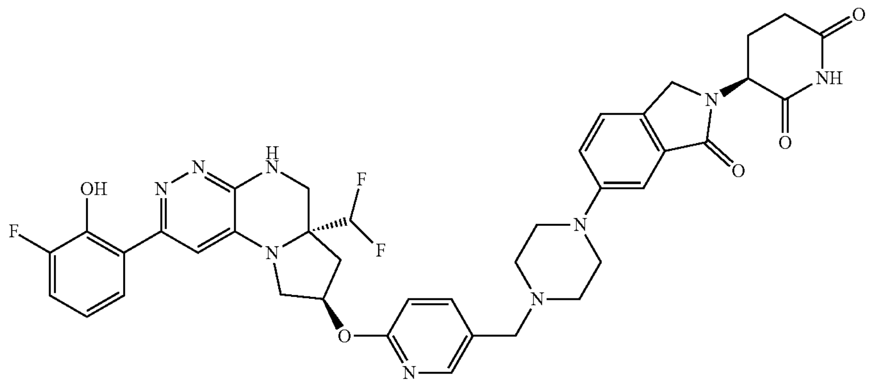 [SMILES: O=C1CC[C@H](N2Cc3ccc(N4CCN(Cc5ccc(O[C@H]6CN7c8cc(-c9cccc(F)c9O)nnc8NC[C@@]7(C(F)F)C6)nc5)CC4)cc3C2=O)C(=O)N1]

Step 1. 5-(1,3-dioxolan-2 yl)-2 fluoropyridine

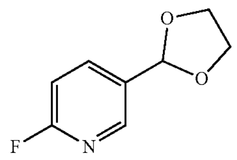 [SMILES: Fc1ccc(C2OCCO2)cn1]

p-Toluenesulfonic acid (3.4 g, 20 mmol) was added to a stirring solution of 6-fluoronicotinaldehyde (25 g, 0.20 mol) and ethylene glycol (25 g, 0.40 mol) in toluene (250 mL). The reaction mixture was heated to 110° C. and stirred for 1 hour. The product mixture was cooled to room temperature and quenched with a saturated sodium bicarbonate aqueous solution. The quenched product mixture was extracted twice with EtOAc. The combined organic layers were washed with a saturated sodium chloride solution and then were dried over $Na_2SO_4$, filtered, and concentrated under reduced pressure. The residue was purified by flash chromatography on a silica gel column with a gradient of 0-10% EtOAc/hexane to obtain 5-(1,3-dioxolan-2-yl)-2-fluoropyridine (22.6, 67%). LCMS calcd for $C_8H_9FNO_2$ $[M+H]^+$: m/z=170.1; Found: 170.3.

Step 2. (6aR,8R)-8-(benzyloxy)-2-chloro-6a-(difluoromethyl)-5,6,6a,7,8,9-hexahydropyrrolo[1',2':4,5]pyrazino[2,3-c]pyridazine

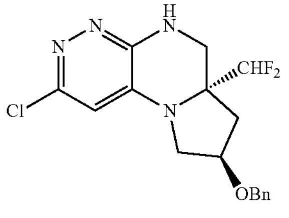 [SMILES: FC(F)[C@@]12CNc3nnc(Cl)cc3N1C[C@H](OCc1ccccc1)C2]

Sodium borohydride (1.49 g, 39.4 mmol) was added to a stirring solution of (6aR,8R)-8-(benzyloxy)-2-chloro-6a-(difluoromethyl)-6a,7,8,9-tetrahydropyrrolo[1',2':4,5]pyrazino[2,3-c]pyridazin-6(5H)-one (5.0 g, 13.1 mmol) in THE (50 mL), then $BF_3{\cdot}Et_2O$ (7.45 g, 52.5 mmol) drop-wise at 15-25° C. was added. the mixture was stirred at 25° C. for 16 hours. The mixture was cooled to 0° C. and quenched with MeOH (5 mL) and stirred for 30 minutes. The mixture was concentrated in vacuo to give crude product (4.82 g) used in next step without any further purification. Acetic acid (7.56 g, 125.9 mol) and sodium cyanoborohydride (3.96 g, 62.9 mmol) were added in sequence to a stirring solution of crude product (4.82 g) in EtOH (50 mL) and heated to reflux for 2 hours. The mixture was cooled to 25° C. and water (50 mL) was added to quench the mixture. The product solution was concentrated under reduced pressure to remove EtOH. The mixture was basified with saturated sodium bicarbonate aqueous solution to pH 7-8 and extracted with EtOAc (30 mL×2). the combined organic phase was washed with a saturated sodium chloride aqueous solution (50 mL), dried over $Na_2SO_4$, filtered and concentrated in vacuo to give a residue, which was purified by silica gel flash column chromatography with a gradient of 50-100% MTBE/hexanes to obtain (6aR,8R)-8-(benzyloxy)-2-chloro-6a-(difluoromethyl)-5,6,6a,7,8,9-hexahydropyrrolo[1',2':4,5]pyrazino[2,3-c]pyridazine (4.78 g, 99%) as white solid. LCMS calcd for $C_{17}H_{18}ClF_2N_4O$ $[M+H]^+$: m/z=367.1; Found: 367.0.

Step 3. (6aR,8R)-2-chloro-6a-(Difluoromethyl)-5,6,6a,7,8,9-hexahydropyrrolo[1',2':4,5]pyrazino[2,3-c]pyridazin-8-ol

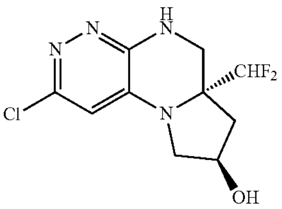 [SMILES: O[C@H]1CN2c3cc(Cl)nnc3NC[C@@]2(C(F)F)C1]

(6aR,8R)-8-(Benzyloxy)-2-chloro-6a-(difluoromethyl)-5,6,6a,7,8,9-hexahydropyrrolo [1',2':4,5]pyrazino[2,3-c]pyridazine (35 g) was dissolved in DCM (700 mL) in a 3-necked 2000 mL flask. The solution was cooled down to −5° C., boron trichloride (1M, 280 mL, 280 mmol) was added to the mixture while the temperature was maintained below −5° C. The mixture was stirred below −5° C. for 1 hour. MeOH (175 mL) was added to the mixture with temperature rising to no more than 10° C. The reaction mixture was concentrated under reduced pressure. The residue was purified by flash chromatography on a silica gel column with a gradient of 0-10% DCM/MeOH to obtain (6aR,8R)-2-chloro-6a-(difluoromethyl)-5,6,6a,7,8,9-hexahydropyrrolo[1',2':4,5]pyrazino[2,3-c]pyridazin-8-ol (25.1 g, 95%). LCMS calcd for $C_{10}H_{12}ClF_2N_4O$ $[M+H]^+$: m/z=277.1; Found: 277.3.

Step 4. (6aR,8R)-8-((5-(1,3 Dioxolan-2 yl)pyridin-2 yl)oxy)-2-chloro-6a-(difluoromethyl)-5,6,6a, 7,8,9 hexahydropyrrolo[1',2':4,5]pyrazino[2,3-c] pyridazine

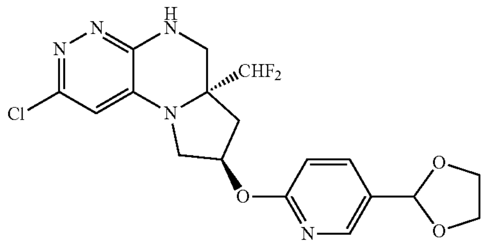 [SMILES: FC(F)[C@@]12CNc3nnc(Cl)cc3N1C[C@H](Oc1ccc(C3OCCO3)cn1)C2]

Sodium hydride (105 mg, 2.6 mmol, 60% dispersion in mineral oil) was added to a stirring solution of (6aR,8R)-2-chloro-6a-(difluoromethyl)-5,6,6a,7,8,9-hexahydropyrrolo[1',2':4,5]pyrazino[2,3-c]pyridazin-8-ol (243 mg, 0.87 mmol) in dimethylacetamide (2.4 mL) at room temperature. The reaction mixture was heated to 80° C. and 5-(1,3-dioxolan-2-yl)-2-fluoropyridine (156 mg, 0.92 mmol) was added to the reaction mixture. The reaction mixture was stirred at 80° C. until consumption of the starting material was observed. The product mixture was cooled to room temperature and quenched with saturated ammonium chloride aqueous solution (3 mL). The quenched product mixture was transferred to a separatory funnel and extracted with DCM (2×3 mL). The combined organic layers were dried over $Na_2SO_4$, filtered, and concentrated under reduced pressure. The residue obtained was dissolved in EtOAc (3 mL) and washed with a saturated sodium chloride aqueous solution (3×2 mL). The organic layer was dried over $Na_2SO_4$, filtered, and concentrated under reduced pressure. The residue was purified by flash chromatography on a silica gel column with a gradient of 0-66% EtOAc/DCM to obtain the title compound (250 mg, 67%). LCMS calcd for $C_{18}H_{19}ClF_2N_5O_3$ $[M+H]^+$: m/z=426.1; Found: 426.2.

Step 5. 2-((6aR,8R)-8-((5-(1,3-Dioxolan-2-yl)pyridin-2 yl)oxy)-6a-(difluoromethyl)-5,6,6a, 7,8,9-hexahydropyrrolo[1;2':4,5]pyrazino[2,3-c]pyridazin-2-yl)-6 fluorophenol

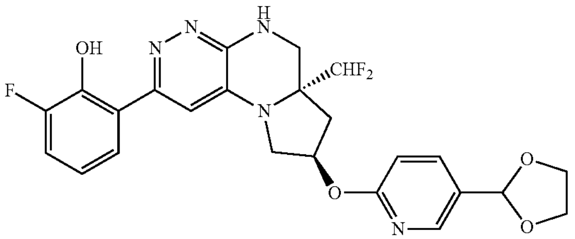 [SMILES: Oc1c(F)cccc1-c1cc2c(nn1)NC[C@@]1(C(F)F)C[C@@H](Oc3ccc(C4OCCO4)cn3)CN21]

(6aR,8R)-8-((5-(1,3-dioxolan-2-yl)pyridin-2-yl)oxy)-2-chloro-6a-(difluoromethyl)-5,6,6a,7,8,9-hexahydropyrrolo[1',2':4,5]pyrazino[2,3-c]pyridazine (220 mg, 0.56 mmol), (3-fluoro-2-hydroxyphenyl)boronic acid (121 mg, 0.78 mmol), tribasic potassium phosphate (415 mg, 1.96 mmol), and Xphos Pd G2 (44 mg, 0.056 mmol) were added to a degassed solution of 1,4-dioxane (2.2 mL) and water (0.22 mL). The reaction mixture was heated to 100° C. for 1.5 hours. The product mixture was diluted with water (2.5 mL) and DCM (3 mL). The aqueous layer was extracted with DCM (3 mL). The combined organic layers were dried over $Na_2SO_4$, filtered, and concentrated under reduced pressure. The residue was purified by flash chromatography on a silica gel column with a gradient of 0–50% EtOAc/DCM to obtain the title compound (124 mg, 48%) LCMS calcd for $C_{24}H_{23}F_3N_5O_4$ $[M+H]^+$: m/z=502.2; Found. 502.3.

Step 6. 6-(((6aR,8R)-6a-(Difluoromethyl)-2-(3 fluoro-2-hydroxyphenyl)-5,6,6a,7,8,9-hexahydropyrrolo[1,2':4,5]pyrazino[2,3-c]pyridazin-8 yl)oxy)nicotinaldehyde

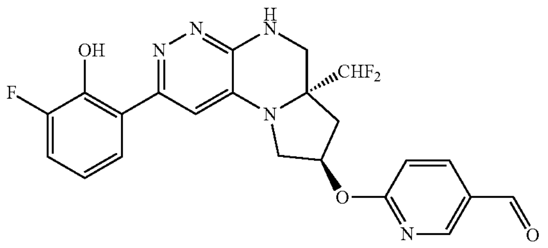 [SMILES: O=Cc1ccc(O[C@H]2CN3c4cc(-c5cccc(F)c5O)nnc4NC[C@@]3(C(F)F)C2)nc1]

Trifluoroacetic acid (0.83 mL, 1.08 mol) was added dropwise to 2-((6aR,8R)-8-((5-(1,3-dioxolan-2-yl)pyridin-2-yl)oxy)-6a-(difluoromethyl)-5,6,6a, 7,8,9-hexahydropyrrolo[1',2:4,5]pyrazino[2,3-c]pyridazin-2-yl)-6-fluorophenol (166 mg, 0.33 mmol). The reaction mixture was heated to 55° C. and stirred overnight. The product mixture was quenched with saturated sodium bicarbonate aqueous solution and extracted twice with DCM. The combined organic layers were dried over $Na_2SO_4$, filtered, and concentrated under reduced pressure to obtain the title compound (151 mg, 100%), which was used without further purification. LCMS calcd for $C_{22}H_{19}F_3N_5O_3$ $[M+H]^+$: m/z=458.1; Found: 458.3.

Step 7. (S)-3-(6-(4-((6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)pyridin-3-yl)methyl)piperazin-1-yl)-1-oxoisoindolin-2 yl)piperidine-2,6-dione (Example 43)

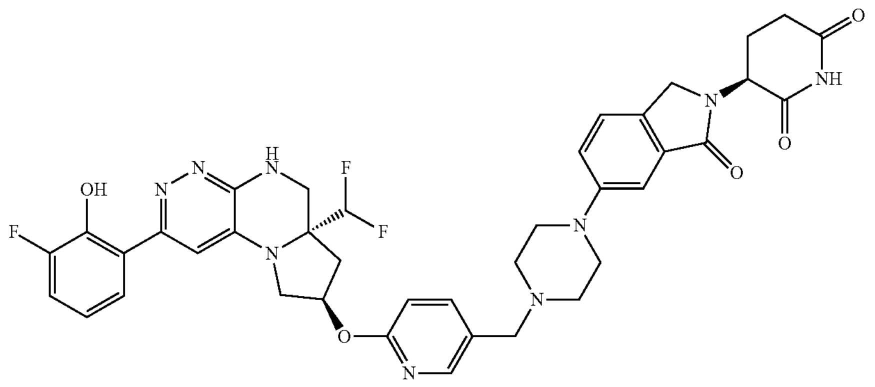 [SMILES: O=C1CC[C@H](N2Cc3ccc(N4CCN(Cc5ccc(O[C@H]6CN7c8cc(-c9cccc(F)c9O)nnc8NC[C@@]7(C(F)F)C6)nc5)CC4)cc3C2=O)C(=O)N1]

N,N-Diisopropylethylamine (213 mg, 1.65 mmol) was added to a stirring solution of 6-(((6aR,8R)-6a-(difluoromethyl)-2-(3-fluoro-2-hydroxyphenyl)-5,6,6a, 7,8,9-hexahydropyrrolo [1',2':4,5]pyrazino[2,3-c]pyridazin-8-yl)oxy) nicotinaldehyde (151 mg, 0.33 mmol) and (S)-3-(1-oxo-6-(piperazin-1-yl)isoindolin-2-yl)piperidine-2,6-dione; hydrochloride (240 mg, 0.66 mmol) in a solution of DMSO (1.5 mL). The reaction mixture was heated to 45° C. and stirred for 2 hours. The reaction mixture was cooled to room temperature. Sodium triacetoxyborohydride (210 mg, 0.99 mmol) was added to the reaction mixture at room temperature. The reaction mixture was heated to 35° C. and stirred for 16 hours. The product mixture was quenched with water and extracted twice with DCM. The combined organic layers were dried over $Na_2SO_4$, filtered, and concentrated under reduced pressure. The residue was purified by prep-HPLC to obtain (S)-3-(6-(4-((6-(((6aR,8R)-6a-(difluoromethyl)-2-(3-fluoro-2-hydroxyphenyl)-5,6,6a,7,8,9-hexahydro-pyrrolo[1',2':4,5]pyrazino[2,3-c]pyridazin-8-yl)oxy) pyridin-3-yl)methyl)piperazin-1-yl)-1-oxoisoindolin-2-yl) piperidine-2,6-dione (114 mg, 45%).

$^1H$ NMR (400 MHz, $CD_3OD$) δ 8.46 (d, J=2.3 Hz, 1H), 8.08 (dd, J=8.7, 2.4 Hz, 1H), 7.49 (d, J=8.8 Hz, 1H), 7.38-7.29 (m, 4H), 7.10 (s, 1H), 7.06-6.96 (m, 2H), 6.20 (t, J=55.7 Hz, 1H), 5.90 (s, 1H), 5.11 (dd, J=13.3, 5.1 Hz, 1H), 4.47 (s, 2H), 4.44-4.34 (m, 2H), 4.29 (dd, J=12.9, 6.1 Hz, 1H), 4.11-3.97 (m, 2H), 3.89 (s, 2H), 3.61 (s, 2H), 3.45-3.33 (m, 3H), 3.25 (s, 2H), 3.08 (dd, J=14.5, 6.9 Hz, 1H), 2.95-2.83 (m, 1H), 2.77 (ddd, J=17.5, 4.5, 2.3 Hz, 1H), 2.48 (qd, J=13.2, 4.7 Hz, 1H), 2.31-2.11 (m, 2H). LCMS calcd for $C_{39}H_{39}F_3N_9O_5$ $[M+H]^+$: m/z=770.3; Found. 770.8.

Example 44: (S)-3-(6-(4-((6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-5-ethylpyridin-3-yl)methyl)piperazin-1-yl)-1-oxoisoindolin-2-yl)piperidine-2,6-dione

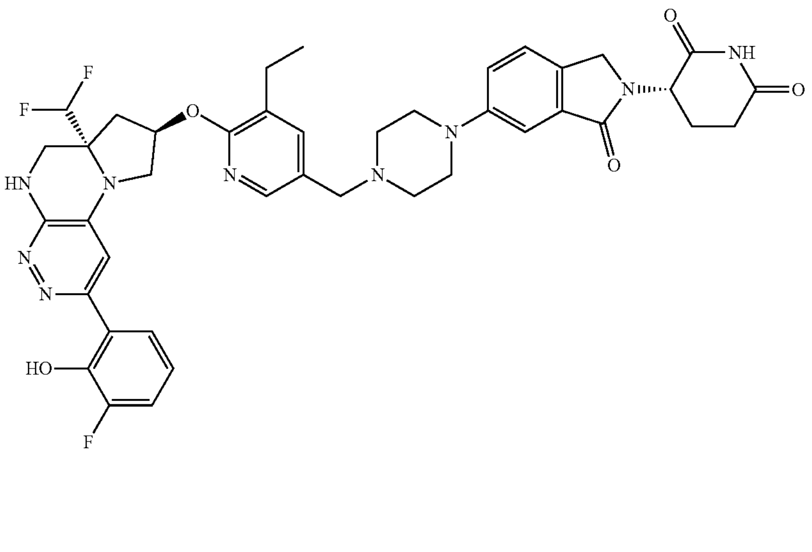 [SMILES: CCc1cc(CN2CCN(c3ccc4c(c3)C(=O)N([C@H]3CCC(=O)NC3=O)C4)CC2)cnc1O[C@H]1CN2c3cc(-c4cccc(F)c4O)nnc3NC[C@@]2(C(F)F)C1]

Step 1. 5-bromo-3-ethylpyridin-2-amine

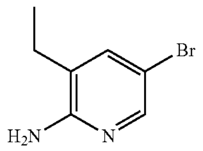

N-Bromosuccinimide (1460 mg, 8.19 mmol) was added to a stirring solution of 3-ethylpyridin-2-amine (1.0 g, 8.19 mmol) in MeCN (30 mL) at 0° C. The reaction mixture was stirred for 1 hour at 0° C. then warmed to room temperature and concentrated under reduced pressure. The residue obtained was purified by silica gel flash column chromatography with a gradient of 0-10% MeOH/DCM to obtain 5-bromo-3-ethylpyridin-2-alpine (1.52 g, 92%). LCMS calcd for $C_7H_{10}BrN_2$ $[M+H]^+$: m/z=201.0; Found: 201.0.

Step 2. 5-bromo-3-ethylpyridin-2-ol

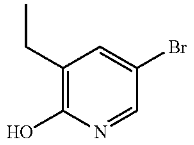

Sodium nitrite (2.57 g, 37.3 mmol) dissolved in water (15) mL was added over 15 minutes to a stirring solution of 5-bromo-3-ethylpyridin-2-amine (600 mg, 2.98 mmol) and sulfuric acid (18.4 M, 19.2 mL 360.2 mmol) in water (65 ml.) at 0° C. The rection mixture was stirred at 0° C. for 2 hours. The product mixture was diluted with water (50 mL) and extracted with a 3:1 chloroform:isopropanol solution (4×100 mL). The combined organic layers were dried over $MgSO_4$, filtered, and concentrated under reduced pressure to obtain 5-bromo-3-ethylpyridin-2-ol (603 mg, 100%) which was used without further purification. LCMS calcd for $C_7H_9BrNO$ $[M+H]^+$: m/z=202.0; Found: 202.0.

Step 3. 3-ethyl-5-vinylpyridin-2-ol

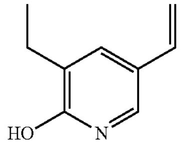

A 40 mL scintillation vial was charged with vinylboronic acid pinacol ester (1.82 mL, 10.7 mmol), 5-bromo-3-ethylpyridin-2-ol (542 mg, 2.68 mmol), XPhos Pd G2 (105 mg, 0.134 mmol) and potassium carbonate (1.85 g, 13.4 mmol). The mixture was dissolved in 1,4-dioxane (10 mL) and water (3 mL). The reaction mixture was sparged with $N_2$ gas for 5 minutes, sealed, and heated to 100° C. The reaction mixture was stirred for 1 hour at 100° C. The product mixture was diluted with MeOH (10 mL), filtered, and concentrated under reduced pressure. The residue obtained was purified by silica gel flash column chromatography with a gradient of 0-20% MeOH/DCM to obtain 3-ethyl-5-vinylpyridin-2-ol (385 mg, 96%). LCMS calcd for $C_9H_{12}NO$ $[M+H]^+$: m/z=150.1; Found: 150.0.

Step 4. 1-(tert-butyl) 2-methyl (2R,4S)-4-(benzyloxy)pyrrolidine-1,2-dicarboxylate

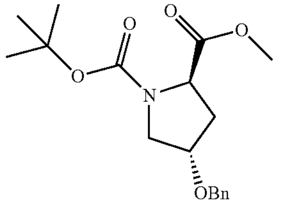 [SMILES: COC(=O)[C@H]1C[C@H](OCc2ccccc2)CN1C(=O)OC(C)(C)C]

Sodium hydride (2.45 g, 61.2 mmol, 60% dispersion in mineral oil) was added to a stirring solution of 1-(tert-butyl) 2-methyl (2R,4S)-4-hydroxypyrrolidine-1,2-dicarboxylate (10.0 g, 40.8 mmol) in THE (100 mL) at 0° C. The reaction mixture was stirred for 30 minutes. Benzyl bromide (7.27 mL, 61.2 mmol) was added to the stirring reaction mixture at 0° C. The reaction mixture was warmed to room temperature and stirred for 3 hours. The product mixture was poured into a saturated ammonium chloride aqueous solution (200 mL) and extracted with DCM (3×150 mL). The combined organic layers were dried over $Na_2SO_4$, filtered, and concentrated under reduced pressure. The residue obtained was purified by silica gel flash column chromatography with a gradient of 0-50% EtOAc/hexanes to obtain 1-(tert-butyl) 2-methyl (2R,4S)-4-(benzyloxy)pyrrolidine-1,2-dicarboxylate (10.7 g, 78%). LCMS calcd for $C_{13}H_{18}NO_3$ $[M+H-C_5H_9O_2]^+$: m/z=236.1; Found: 236.0.

Step 5. (6aR,8S)-8-(benzyloxy)-2-chloro-6a-(difluoromethyl)-6a,7,8,9-tetrahydropyrrolo[1',2':4,5]pyrazino[2,3-c]pyridazin-6(5H)-one

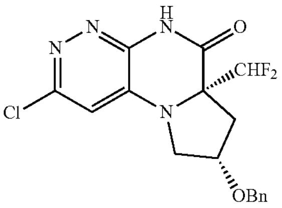 [SMILES: O=C1Nc2nnc(Cl)cc2N2C[C@@H](OCc3ccccc3)C[C@]12C(F)F]

This intermediate was synthesized by procedures analogous to that described in Example 40, using 1-(tert-butyl) 2-methyl (2R,4S)-4-(benzyloxy)pyrrolidine-1,2-dicarboxylate instead of 1-(tert-butyl) 2-methyl (2S,4R)-4-(benzyloxy)pyrrolidine-1,2-dicarboxylate in Example 40, Step 2. LCMS calcd for $C_{17}H_{16}ClF_2N_4O_2$ $[M+H]^+$: m/z=381.1; Found: 380.9.

Step 6. (6aR,8S)-, Y-(benzyloxy)-2-chloro-6a-(difluoromethyl)-5,6,6a, 7,8,9-hexahydropyrrolo[1',2':4, 5]pyrazino[2,3-c]pyridazine

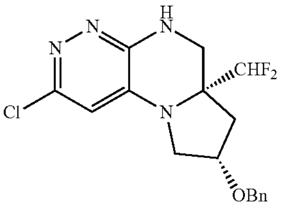 [SMILES: FC(F)[C@@]12CNc3nnc(Cl)cc3N1C[C@@H](OCc1ccccc1)C2]

Borane dimethyl sulfide complex (2.0 M in THF, 3.28 mL, 6.57 mmol) was added to a stirring solution of (6aR, 8S)-8-(benzyloxy)-2-chloro-6a-(difluoromethyl)-6a,7,8,9-tetrahydropyrrolo[1',2':4,5]pyrazino[2,3-c]pyridazin-6(5H)-one (1.00 g, 2.63 mmol) in THF (13.4 mL) at room temperature. The reaction mixture was heated to 55° C. and stirred for 2 hours. The reaction mixture was cooled to room temperature and a second portion of borane dimethyl sulfide complex (2.0 M, 1.00 mL, 2.00 mmol) was added. The reaction mixture was heated to 55° C. and stirred another 2 hours. The reaction mixture was cooled to 0° C. and quenched by slow addition of MeOH (10 mL). The quenched reaction mixture was concentrated under reduced pressure. The residue obtained was dissolved in EtOH (21.4 mL). Acetic acid (2.98 mL, 52.03 mmol) and sodium cyanoborohydride (397 mg, 6.31 mmol) were added in sequence to the reaction mixture. The reaction mixture was heated to 70° C. and stirred for 30 hours. The product mixture was cooled to 0° C. and quenched with a saturated sodium bicarbonate aqueous solution (150 mL). The diluted product mixture was extracted with DCM (3×200 mL). The combined organic layers were dried over $Na_2SO_4$, filtered, and concentrated under reduced pressure. The residue obtained was purified by silica gel flash column chromatography with a gradient of 0-10% MeOH/DCM to obtain (6aR,8S)-8-(benzyloxy)-2-chloro-6a-(difluoromethyl)-5,6,6a,7,8,9-hexahydropyrrolo[1',2':4,5]pyrazino[2,3-c]pyridazine (573 mg, 60%). LCMS calcd for $C_{17}H_{18}ClF_2N_4O$ $[M+H]^+$: m/z=367.1; Found. 367.0.

Step 7. (6aR,8S)-2-chloro-6a-(difluoromethyl)-5,6,6a,7,8,9-hexahydropyrrolo[1',2':4,5]pyrazino[2,3-c]pyridazin-8-ol

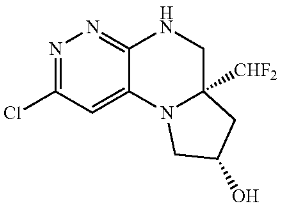 [SMILES: O[C@@H]1CN2c3cc(Cl)nnc3NC[C@@]2(C(F)F)C1]

Boron trichloride (1.0 M in DCM, 4.69 mL, 4.69 mmol) was added to a stirring solution of (6aR,8)-8-(benzyloxy)-2-chloro-6a-(difluoromethyl)-5,6,6a,7,8,9-hexahydropyrrolo[1',2':4,5]pyrazino[2,3-c]pyridazine (573 mg, 1.56 mmol) in DCM (15.6 mL) at 0° C. The reaction mixture was stirred at 0° C. for 30 minutes. The product mixture was quenched by slow addition of a saturated sodium bicarbonate aqueous solution (60 mL). The diluted product mixture was extracted with a 3:1 chloroform:isopropanol solution (4×100 mL). The combined organic layers were dried over $MgSO_4$, filtered, and concentrated under reduced pressure to obtain (6aR,8S)-2-chloro-6a-(difluoromethyl)-5,6,6a,7,8,9-hexahydropyrrolo[1',2':4,5]pyrazino[2,3-c]pyridazin-8-ol as a white solid (420 mg, 97%). LCMS calcd for $C_{10}H_{12}ClF_2N_4O$ $[M+H]^+$: m/z=277.1; Found: 276.9.

Step 8. (6aR,8R)-2-chloro-6a-(difluoromethyl)-8-((3-ethyl-5-vinylpyridin-2 yl)oxy)-5,6,6a, 7,8,9 hexahydropyrrolo[1',2':4,5]pyrazino[2,3-c]pyridazine

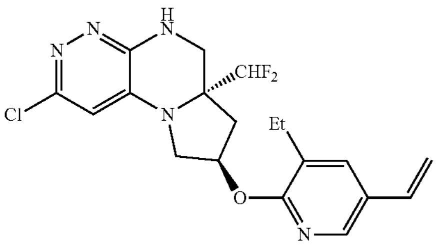 [SMILES: C=Cc1cnc(O[C@H]2CN3c4cc(Cl)nnc4NC[C@@]3(C(F)F)C2)c(CC)c1]

Diisopropyl azodicarboxylate (64.0 μL, 0.33 mmol) was added to a stirring solution of polymer bound triphenylphosphine (~1.6 mmol/g, 203 mg, 0.33 mmol), 3-ethyl-5-vinylpyridin-2-ol (97.1 mg, 0.65 mmol) and (6aR,8S)-2-chloro-6a-(difluoromethyl)-5,6,6a,7,8,9-hexahydropyrrolo[1',2':4,5]pyrazino[2,3-c]pyridazin-8-ol (60 mg, 0.217 mmol) in THE (3 mL). The reaction mixture was heated to 60° C. and stirred for 1 hour. The product mixture was filtered and solid was washed with MeOH (20 mL). The filtrate was concentrated under reduced pressure and the residue obtained was purified by silica gel flash column chromatography with a gradient of 0-10% MeOH/DCM to obtain (6aR,8R)-2-chloro-6a-(difluoromethyl)-8-((3-ethyl-5-vinylpyridin-2-yl)oxy)-5,6,6a,7,8,9-hexahydropyrrolo[1',2':4,5]pyrazino[2,3-c]pyridazine (43 mg, 49%). LCMS calcd for $C_{19}H_{21}ClF_2N_5O$ $[M+H]^+$: m/z=408.1, Found. 408.1.

Step 9. 2-((6aR,8R)-6a-(difluoromethyl)-8-((3-ethyl-5-vinylpyridin-2 yl)oxy)-5,6,6a,7,8,9-hexahydropyrrolo[1',2':4,5]pyrazino[2,3-c]pyridazin-2 yl)-6-fluorophenol

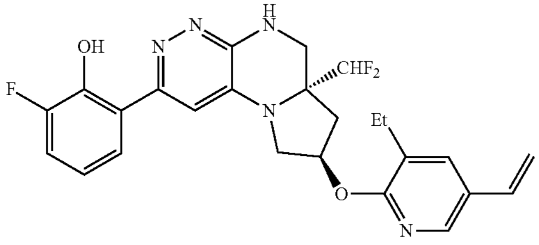 [SMILES: C=Cc1cnc(O[C@H]2CN3c4cc(-c5cccc(F)c5O)nnc4NC[C@@]3(C(F)F)C2)c(CC)c1]

A 20 mL scintillation vial was charged with 3-fluoro-2-hydroxyphenylboronic acid (91.8 mg, 0.588 mmol), (6aR, 8R)-2-chloro-6a-(difluoromethyl)-8-((3-ethyl-5-vinylpyridin-2-yl)oxy)-5,6,6a,7,8,9-hexahydropyrrolo[1',2':4,5]pyrazino[2,3-c]pyridazine (80 mg, 0.196 mmol), XPhos Pd G2 (15.4 mg, 0.020 mmol) and potassium carbonate (136 mg, 0.98 mmol). The mixture was dissolved in 1,4-dioxane (1.5 mL) and water (400 μL). The reaction mixture was sparged with $N_2$ gas for 5 minutes, sealed, and heated to 80° C. The reaction mixture was stirred for 1 hour at 80° C. The product mixture was transferred to a separatory funnel containing a saturated sodium bicarbonate solution (40 mL) and was extracted with a 3:1 chloroform:isopropanol solution (3×30 mL). The combined organic layers were dried over $MgSO_4$, filtered, and concentrated under reduced pressure. The residue obtained was purified by silica gel flash column chromatography with a gradient of 0-10% MeOH/DCM to obtain the title compound (90 mg, 95%). LCMS calcd for $C_{25}H_{25}F_3N_5O_2$ $[M+H]^+$: m/z=484.2; Found. 484.0.

Step 10. 6-(((6aR,8R)-6a-(difluoromethyl)-2-(3 fluoro-2-hydroxyphenyl)-5,6,6a,7,8,9-hexahydropyrrolo[1',2':4,5]pyrazino[2,3-c]pyridazin-8 yl)oxy)-5-ethylnicotinaldehyde

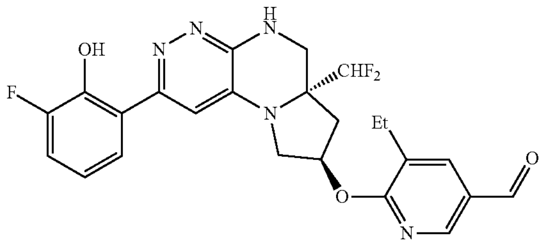 [SMILES: CCc1cc(C=O)cnc1O[C@H]1CN2c3cc(-c4cccc(F)c4O)nnc3NC[C@@]2(C(F)F)C1]

Osmium tetroxide (4% in water, 118 μL, 0.0186 mmol) was added to a stirring solution of 2-((6aR,8R)-6a-(difluoromethyl)-8-((3-ethyl-5-vinylpyridin-2-yl)oxy)-5,6,6a, 7,8, 9-hexahydropyrrolo[1',2':4,5]pyrazino[2,3-c]pyridazin-2-yl)-6-fluorophenol (90 mg, 0.186 mmol) and 4-methylmorpholine N-oxide (110 mg, 0.931 mmol) in THE (780 μL), water (250 μL) and tert-butanol (200 μL). The reaction mixture was stirred for 3 hours at room temperature. The product mixture was quenched with a saturated sodium sulfite aqueous solution (10 mL). The quenched product mixture was transferred to a separatory funnel and diluted with water (10 mL) and a saturated sodium chloride aqueous solution (10 mL). The diluted product mixture was extracted with a 31 chloroform:isopropanol solution (3×30 mL) The combined organic layers were dried over $MgSO_4$, filtered, and concentrated under reduced pressure. The residue obtained was dissolved in MeCN (1 mL) and water (1 mL). Sodium periodate (159 mg, 0.74 mmol) was added to the reaction mixture and stirred for 30 minutes at room temperature. The product mixture was transferred to a separatory funnel with a saturated sodium bicarbonate aqueous solution (30 mL). The diluted product mixture was extracted with a 3:1 chloroform:isopropanol solution (3×30 mL). The combined organic layers were dried over $MgSO_4$, filtered, and concentrated under reduced pressure to obtain the title compound (70 mg, 78%). The residue obtained was used directly in the next step. LCMS calcd for $C_{24}H_{23}F_3N_5O_3$ $[M+H]^+$: m/z=486.2; Found: 486.0.

Step 11. (S)-3-(6-(4-((6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-5-ethylpyridin-3-yl)methyl)piperazin-1-yl)-1-oxoisoindolin-2-yl)piperidine-2,6-dione (Example 44)

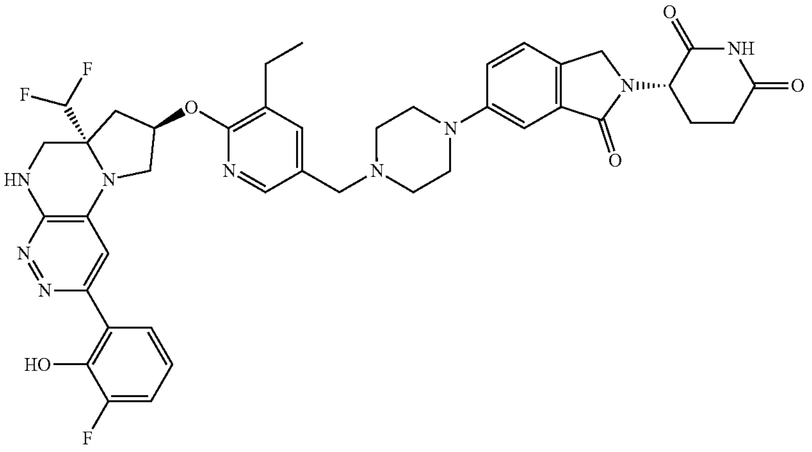 [SMILES: CCc1cc(CN2CCN(c3ccc4c(c3)C(=O)N([C@H]3CCC(=O)NC3=O)C4)CC2)cnc1O[C@H]1CN2c3cc(-c4cccc(F)c4O)nnc3NC[C@@]2(C(F)F)C1]

N,N-Diisopropylethylamine (37.7 μL, 0.216 mmol) was added to a stirring solution of 6-(((6aR,8R)-6a-(difluoromethyl)-2-(3-fluoro-2-hydroxyphenyl)-5,6,6a, 7,8,9-hexahydropyrrolo [1',2':4,5]pyrazino[2,3-c]pyridazin-8-yl)oxy)-5-ethylnicotinaldehyde (70 mg, 0.072 mmol) and (S)-3-(1-oxo-6-(piperazin-1-yl)isoindolin-2-yl)piperidine-2,6-dione; hydrochloride (52.6 mg, 0.144 mmol) in DMSO (566 μL). The reaction mixture was stirred at room temperature for 1 hour. Sodium triacetoxyborohydride (45.8 mg, 0.216 mmol) was added to the reaction mixture. The reaction mixture was heated to 35° C. and stirred for 18 hours. The product mixture was diluted with DMSO and purified directly by prep-HPLC (Waters CSH-Phenyl-Hexyl, 5 μM, 30×100 mm, 7.2-25.2% MeCN/water (containing 0.1% TFA) over 12 min) to give the title compound (19.7 mg, 27%) as its TFA salt.

$^1H$ NMR (600 MHz, DMSO) δ 10.90 (s, 1H), 9.90 (s, 1H), 8.10 (s, 1H), 7.66 (s, 1H), 7.43 (d, J=8.4 Hz, 2H), 7.32-7.23 (m, 2H), 7.20 (d, J=2.4 Hz, 1H), 7.13 (s, 1H), 6.89-6.83 (m, 1H), 6.27 (t, J=55.4 Hz, 1H), 5.76 (p, J=5.8 Hz, 1H), 5.03 (dd, J=13.3, 5.1 Hz, 1H), 4.34-4.26 (m, 3H), 4.17 (d, J=16.9 Hz, 1H), 4.09 (dd, J=12.8, 6.2 Hz, 1H), 3.94-3.76 (m, 4H), 3.26-3.19 (m, 2H), 3.11 (s, 2H), 2.98 (s, 2H), 2.84 (ddt, J=13.8, 9.4, 5.5 Hz, 2H), 2.58-2.50 (m, 1H), 2.46 (d, J=8.7 Hz, 1H), 2.38-2.27 (m, 1H), 2.07 (dd, J=14.2, 5.1 Hz, 1H), 1.92 (dtd, J=12.9, 5.5, 2.4 Hz, 1H), 1.05 (t, J=7.5 Hz, 3H). LCMS calcd for $C_{41}H_{43}F_3N_9O_5$ $[M+H]^+$: m/z=798.3; Found: 798.0.

Example 45: (S)-3-(6-(4-((5-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-3-fluoro-4-methylpyridin-2-yl)methyl)piperazin-t-yl)-1-oxoisoindolin-2-yl)piperidine-2,6-dione

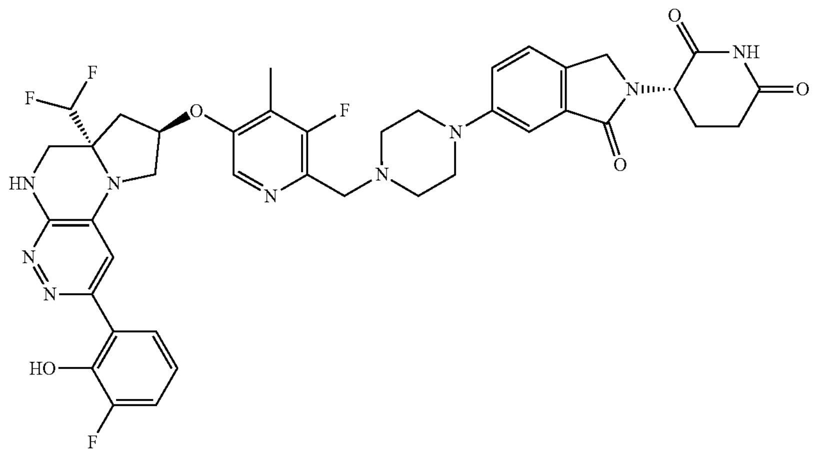 [SMILES: Cc1c(O[C@H]2CN3c4cc(-c5cccc(F)c5O)nnc4NC[C@@]3(C(F)F)C2)cnc(CN2CCN(c3ccc4c(c3)C(=O)N([C@H]3CCC(=O)NC3=O)C4)CC2)c1F]

Step 1. 5-bromo-3-fluoro-4-methylpyridin-2-amine

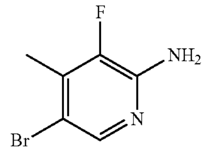

N-Bromosuccinimide (776 mg, 4.36 mmol) was added to a stirring solution of 3-fluoro-4-methylpyridin-2-amine (500 mg, 3.96 mmol) in MeCN (20 mL). The reaction mixture was heated to 50° C. and stirred for 30 minutes. The product mixture was concentrated and purified directly by silica gel flash column chromatography with a gradient of 0–50% EtOAc/Hexanes to obtain 5-bromo-3-fluoro-4-methylpyridin-2-amine (538 mg, 66%). LCMS calcd for $C_6H_7BrFN_2$ $[M+H]^+$: m/z=205.0, Found. 204.9.

Step 2. 5-bromo-3 fluoro-iodo-4-methylpyridine

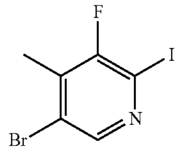

Isoamyl nitrite (528 µL, 3.94 mmol) was added to a stirring solution of 5-bromo-3-fluoro-4-methylpyridin-2-amine (538 mg, 2.62 mmol) in diiodomethane (2.0 mL, 24.8 mmol) at 0° C. The reaction mixture was warmed to room temperature and stirred for 10 minutes. Copper (I) iodide (250 mg, 1.31 mmol) and iodine (799 mg, 3.15 mmol) were added in sequence to the reaction mixture. The reaction mixture was stirred for 48 hours. The product mixture was quenched with a saturated sodium thiosulfate aqueous solution (30 mL). The quenched product mixture was extracted with DCM (3×30 mL). The combined organic layers were washed with a saturated sodium chloride aqueous solution (50 mL). The combined organic layers were dried over $MgSO_4$, filtered, and concentrated under reduced pressure. The residue obtained was purified by silica gel flash column chromatography with a gradient of 0-25% EtOAc/Hexanes to obtain 5-bromo-3-fluoro-2-iodo-4-methylpyridine (377 mg, 45%). LCMS calcd for $C_6H_5BrFIN$ $[M+H]^+$: m/z=315.9; Found: 315.7.

Step 3. 5-bromo-3. fluoro-4-methyl-2-vinylpyridine

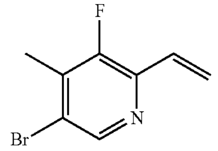

A 20 mL scintillation vial was charged with 5-bromo-3-fluoro-2-iodo-4-methylpyridine (377 mg, 1.19 mmol), vinylboronic acid pinacol ester (306 µL, 1.79 mmol), potassium carbonate (330 mg, 2.39 mmol), and [1,1'-Bis(diphenylphosphino)ferrocene]dichloropalladium(II), complex with dichloromethane (195 mg, 0.24 mmol). The mixture was dissolved in 1,4-dioxane (8 mL) and water (1.5 mL) and sparged with $N_2$ for 2 minutes. The reaction mixture was sealed and heated to 80° C. The reaction mixture was stirred at 80° C. for 14 hours. The product mixture was concentrated and purified directly by silica gel flash column chromatography with a gradient of 0–50% EtOAc/Hexanes to obtain 5-bromo-3-fluoro-4-methyl-2-vinylpyridine (181 mg, 70%). LCMS calcd for $C_8H_8BrFN$ $[M+H]^+$: m/z=216.0, Found: 215.9.

Step 4. 5-fluoro-4-methyl-6-vinylpyridin-3-ol

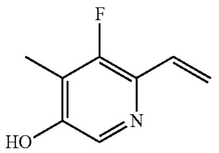

A 20 mL scintillation vial was charged with 5-bromo-3-fluoro-4-methyl-2-vinylpyridine (181 mg, 0.84 mmol), tris (dibenzylideneacetone)dipalladium (0) (38 mg, 0.042 mmol), 2-di-tert-butylphosphino-2',4',6'-triisopropylbiphenyl (35.6 mg, 0.084 mmol) and potassium hydroxide (245 mg, 4.37 mmol). The mixture was dissolved in water (5 mL) and sparged with $N_2$ for 5 minutes. The reaction mixture was heated to 85° C. and stirred for 1.5 hours. The product mixture was adjusted to a pH of 8 by the addition of a saturated sodium bicarbonate aqueous solution. The diluted product mixture was extracted with DCM (3×40 mL) then with a 3:1 chloroform:isopropanol solution (2×30 mL). The combined organic layers were dried over $MgSO_4$, filtered, and concentrated under reduced pressure. The residue obtained was purified by silica gel flash column chromatography with a gradient of 0–5% MeOH/DCM to obtain 5-fluoro-4-methyl-6-vinylpyridin-3-ol (84 mg, 65%). LCMS calcd for $C_8H_9FNO$ [M+H]$^+$: m/z=154.1; Found: 154.0.

Step 5. (S)-3-(h-(4-((5-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-3 fluoro-4-methylpyridin-2 yl)methyl) piperazin-1-yl)-1-oxoisoindolin-2-yl)piperidine-2,6-dione (Example 45)

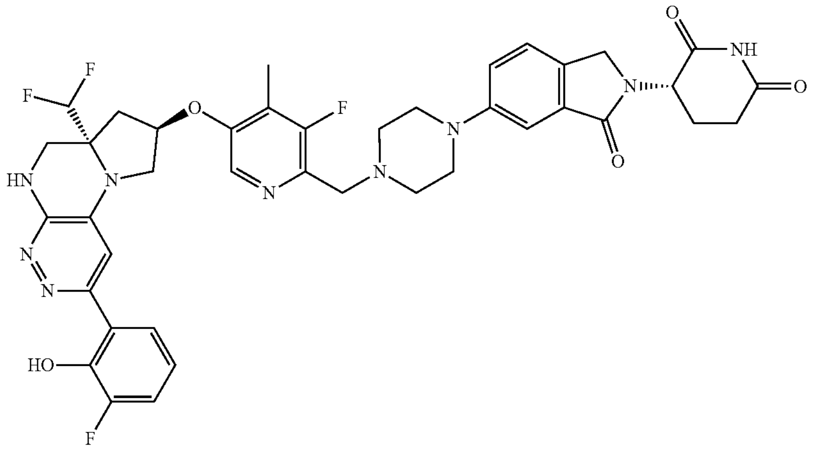 [SMILES: Cc1c(O[C@H]2CN3c4cc(-c5cccc(F)c5O)nnc4NC[C@@]3(C(F)F)C2)cnc(CN2CCN(c3ccc4c(c3)C(=O)N([C@H]3CCC(=O)NC3=O)C4)CC2)c1F]

This example was synthesized by procedures analogous to that described in Example 44, using 5-fluoro-4-methyl-6-vinylpyridin-3-ol instead of 3-ethyl-5-vinylpyridin-2-ol. LCMS calcd for $C_{40}H_{40}F_4N_9O_5$ [M+H]$^+$: m/z=802.3; Found: 802.2.

Example 46: (S)-3-(6-(4-((5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c] pyridazin-8-yl)oxy)-3,4-dimethylpyridin-2-yl) methyl)piperazin-1-yl)-1-oxoisoindolin-2-yl) piperidine-2,6-dione

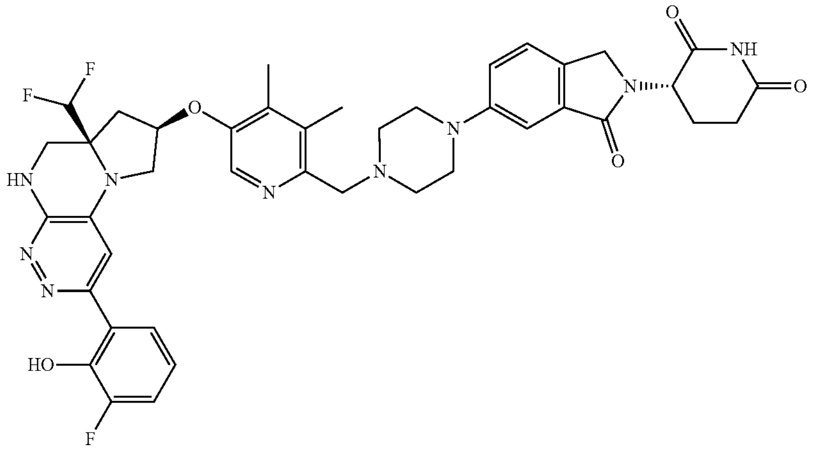 [SMILES: Cc1c(O[C@H]2CN3c4cc(-c5cccc(F)c5O)nnc4NC[C@]3(C(F)F)C2)cnc(CN2CCN(c3ccc4c(c3)C(=O)N([C@H]3CCC(=O)NC3=O)C4)CC2)c1C]

Step 1. (6aS,8S)-6a-(difluoromethyl)-2-(3 fluoro-2-methoxyphenyl)-5,6,6a,7,8,9-hexahydropyrrolo[1',2':4,5]pyrazino[2,3-c]pyridazin-8-ol

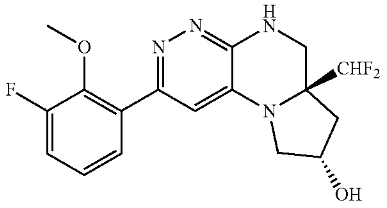 [SMILES: COc1c(F)cccc1-c1cc2c(nn1)NC[C@]1(C(F)F)C[C@H](O)CN21]

This intermediate was synthesized by procedures analogous to that described in Example 40, using 1-(tert-butyl) 2-methyl (2R,4S)-4-(benzyloxy)pyrrolidine-1,2-dicarboxylate instead of 1-(tert-butyl) 2-methyl (2S,4R)-4-(benzyloxy)pyrrolidine-1,2-dicarboxylate in Step 2. LCMS calcd for $C_{17}H_{18}F_3N_4O_2$ $[M+H]^+$: m/z=367.1; Found. 367.0.

Step 2. (6aS,8R)-6a-(difluoromethyl)-8-((4,5-dimethyl-6-vinylpyridin-3 yl)oxy)-2-(3 fluoro-2-methoxyphenyl)-5,6,6a,7,8,9-hexahydropyrrolo[1',2':4,5]pyrazino[2,3-c]pyridazine

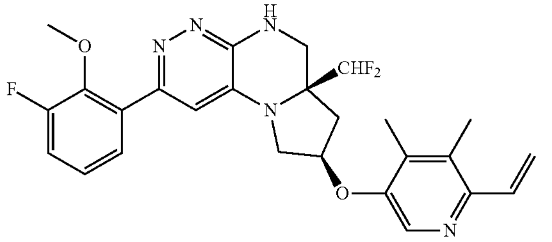 [SMILES: C=Cc1ncc(O[C@H]2CN3c4cc(-c5cccc(F)c5OC)nnc4NC[C@]3(C(F)F)C2)c(C)c1C]

Diisopropyl azodicarboxylate (26.9 μL, 0.136 mmol) was added to a stirring solution of triphenylphosphine (37.6 mg, 0.143 mmol), 4,5-dimethyl-6-vinylpyridin-3-ol (20.4 mg, 0.136 mmol) and (6aR,8S)-2-chloro-6a-(difluoromethyl)-5,6,6a,7,8,9-hexahydropyrrolo[1',2':4,5]pyrazino[2,3-c]pyridazin-8-ol (25 mg, 0.068 mmol) in THE (1 mL). The reaction mixture was heated to 60° C. and stirred for 1 hour. The product mixture was purified directly by silica gel flash column chromatography with a gradient of 0-10% MeOH/DCM to obtain the title compound (31 mg, 91%). LCMS calcd for $C_{26}H_{27}F_3N_5O_2$ $[M+H]^+$: m/z=498.2; Found: 498.0.

Step 3. 2-((6aS,8R)-6a-(difluoromethyl)-8-((4,5-dimethyl-6-vinylpyridin-3 yl)oxy)-5,6,6a,7,8,9-hexahydropyrrolo[1',2':4,5]pyrazino[2,3-c]pyridazin-2 yl)-6-fluorophenol

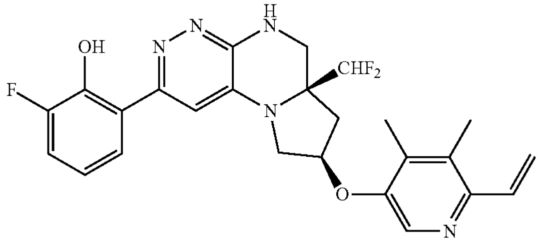 [SMILES: C=Cc1ncc(O[C@H]2CN3c4cc(-c5cccc(F)c5O)nnc4NC[C@]3(C(F)F)C2)c(C)c1C]

Boron trichloride (1.0 M in DCM, 1.00 mL, 1.00 mmol) was added to a stirring solution of (6aS,8R)-6a-(difluoromethyl)-8-((4,5-dimethyl-6-vinylpyridin-3-yl)oxy)-2-(3-fluoro-2-methoxyphenyl)-5,6,6a,7,8,9-hexahydropyrrolo[1',2':4,5]pyrazino[2,3-c]pyridazine (31.0 mg, 0.062 mmol) in DCM (500 μL) at 0° C. The reaction mixture warmed to room temperature and was stirred for 16 hours at room temperature. The product mixture cooled to 0° C. and diluted with MeOH (3 mL). The diluted product mixture was transferred to a separatory funnel containing a saturated sodium carbonate aqueous solution (30 mL). The diluted product mixture was extracted with a 3:1 chloroform:isopropanol solution (3×30 mL). The combined organic layers were dried over $MgSO_4$, filtered, and concentrated under reduced pressure to obtain the title compound (29 mg, 96%). The residue obtained was used directly in the next step. LCMS calcd for $C_{25}H_{25}F_3N_5O_2$ $[M+H]^+$: m/z=484.2; Found: 484.0.

Step 4. 5-(((6aS,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazino-8-yl)oxy)-3,4-dimethylpicolinaldehyde

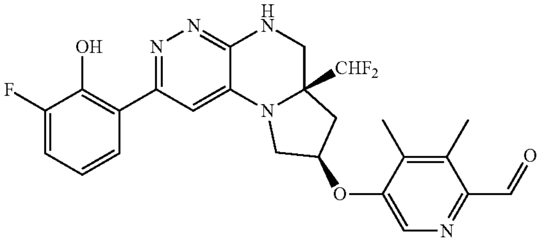 [SMILES: Cc1c(O[C@H]2CN3c4cc(-c5cccc(F)c5O)nnc4NC[C@]3(C(F)F)C2)cnc(C=O)c1C]

Osmium tetroxide (4% in water, 38.1 μL, 0.006 mmol) was added to a stirring solution of 2-((6aS,8R)-6a-(difluoromethyl)-8-((4,5-dimethyl-6-vinylpyridin-3-yl)oxy)-5,6,6a,7,8,9-hexahydropyrrolo[1',2':4,5]pyrazino[2,3-c]pyridazin-2-yl)-6-fluorophenol (29 mg, 0.06 mmol) and 4-methylmorpholine N-oxide (35.4 mg, 0.30 mmol) in THE (1.1 mL), water (360 μL) and tert-butanol (270 μL). The reaction mixture was stirred for 3 hours at room temperature. The product mixture was quenched with a saturated sodium sulfite aqueous solution (10 mL). The quenched product mixture was transferred to a separatory funnel and diluted with water (10 mL) and a saturated sodium chloride aqueous solution (10 mL). The diluted product mixture was extracted with a 3:1 chloroform:isopropanol solution (3×30 mL). The combined organic layers were dried over $MgSO_4$, filtered, and concentrated under reduced pressure. The residue obtained was dissolved in MeCN (1 mL) and water (1 mL). Sodium periodate (51.3 mg, 0.24 mmol) was added to the reaction mixture and stirred for 30 minutes at room temperature. The product mixture was transferred to a separatory funnel with a saturated sodium bicarbonate aqueous solution (30 mL). The diluted product mixture was extracted with a 3:1 chloroform:isopropanol solution (3×30 mL). The combined organic layers were dried over $MgSO_4$, filtered, and concentrated under reduced pressure to obtain the title compound (20 mg, 69%). The residue obtained was used directly in the next step. LCMS calcd for $C_{24}H_{23}F_3N_5O_3$ $[M+H]^+$: m/z=486.2; Found: 486.0.

Step 5. 3-(6-(4-((5-(((6aS,8R)-6a-(difluoromethyl)-2-(3 fluoro-2-hydroxyphenyl)-5,6,6a,7,8,9-hexahydropyrrolo[1',2':4,5]pyrazino[2,3-c]pyridazin-8 yl)oxy)-3,4-dimethylpyridin-2-yl)methyl)piperazin-1 yl)-1-oxoisoindolin-2 yl)piperidine-2,6-dione (Example 46)

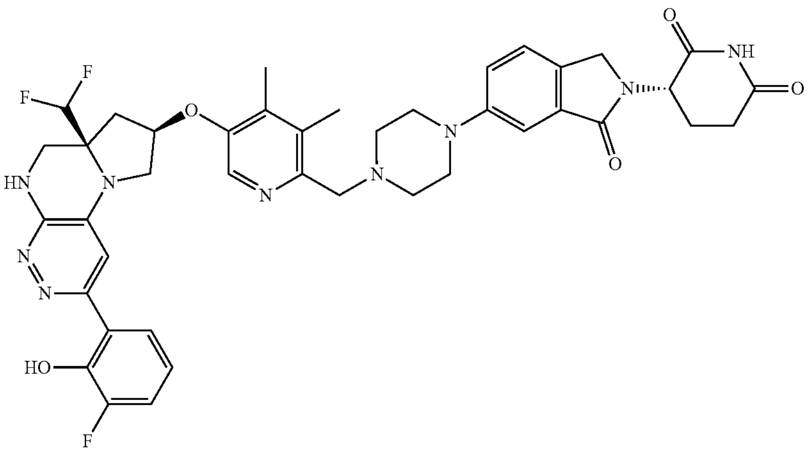 [SMILES: Cc1c(O[C@H]2CN3c4cc(-c5cccc(F)c5O)nnc4NC[C@]3(C(F)F)C2)cnc(CN2CCN(c3ccc4c(c3)C(=O)N([C@H]3CCC(=O)NC3=O)C4)CC2)c1C]

N,N-Diisopropylethylamine (21.5 μL, 0.124 mmol) was added to a stirring solution of 5-(((6aS,8R)-6a-(difluoromethyl)-2-(3-fluoro-2-hydroxyphenyl)-5,6,6a,7,8,9-hexahydropyrrolo [1',2':4,5]pyrazino[2,3-c]pyridazin-8-yl)oxy)-3,4-dimethylpicolinaldehyde (20 mg, 0.041 mmol) and (S)-3-(1-oxo-6-(piperazin-1-yl)isoindolin-2-yl)piperidine-2,6-dione; hydrochloride (30 mg, 0.082 mmol) in DMSO (300 μL). The reaction mixture was stirred at room temperature for 1 hour. Sodium triacetoxyborohydride (26.2 mg, 0.124 mmol) was added to the reaction mixture. The reaction mixture was heated to 35° C. and stirred for 18 hours. The product mixture was diluted with DMSO and purified directly by prep-HPLC (Waters CSH-Fluoro-Phenyl, 5 μM, 30×100 mm, 19.1-35.1% MeCN/water (containing 0.1% TFA) over 5 min) to give the title compound (10.8 mg, 26%) as its TFA salt. LCMS calcd for $C_{41}H_{43}F_3N_9O_5$ $[M+H]^+$: m/z=798.3, Found. 798.2.

Example 47: (S)-3-(6-(4-((6-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-5-ethyl pyridin-3-yl)methyl)piperazin-1-yl)-1-oxoisoindolin-2-yl)piperidine-2,6-dione

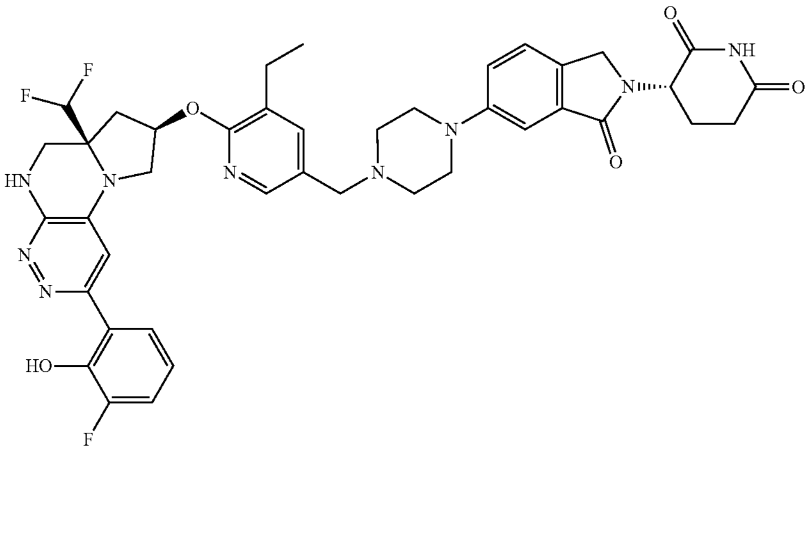 [SMILES: CCc1cc(CN2CCN(c3ccc4c(c3)C(=O)N([C@H]3CCC(=O)NC3=O)C4)CC2)cnc1O[C@H]1CN2c3cc(-c4cccc(F)c4O)nnc3NC[C@]2(C(F)F)C1]

Step 1. (S)-3-(6-(4-((6-(((6aS,8R)-6a-(d fluoromethyl)-2-(3 fluoro-2 hydroxyphenyl)-5,6,6a,7,8,9-hexahydropyrrolo[1',2':4,5]pyrazino[2,3-c] pyridazin-8 yl)oxy)-5-ethylpyridin-3-yl)methyl) piperazin-1 yl)-1-oxoisoindolin-2 yl)piperidine-2,6-dione (Example 47)

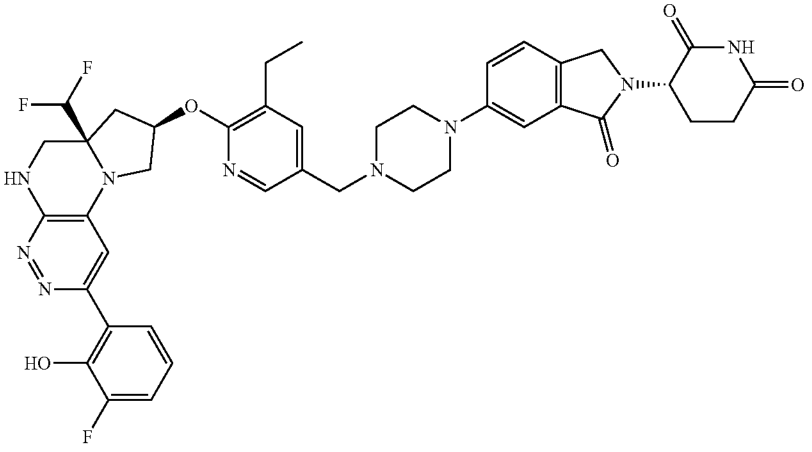 [SMILES: CCc1cc(CN2CCN(c3ccc4c(c3)C(=O)N([C@H]3CCC(=O)NC3=O)C4)CC2)cnc1O[C@H]1CN2c3cc(-c4cccc(F)c4O)nnc3NC[C@]2(C(F)F)C1]

This example was synthesized by procedures analogous to that described in Example 46, using 3-ethyl-5-vinylpyridin-2-ol instead of 4,5-dimethyl-6-vinylpyridin-3-ol in Step 2. LCMS calcd for $C_{41}H_{43}F_3N_9O_5$ $[M+H]^+$: m/z=798.3. Found: 798.2.

Example 48: (S)-3-(6-(4-((5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c] pyridazin-8-yl)oxy)-3,6-dimethylpyrazin-2-yl) methyl)piperazin-1-yl)-1-oxoisoindolin-2-yl) piperidine-2,6-dione

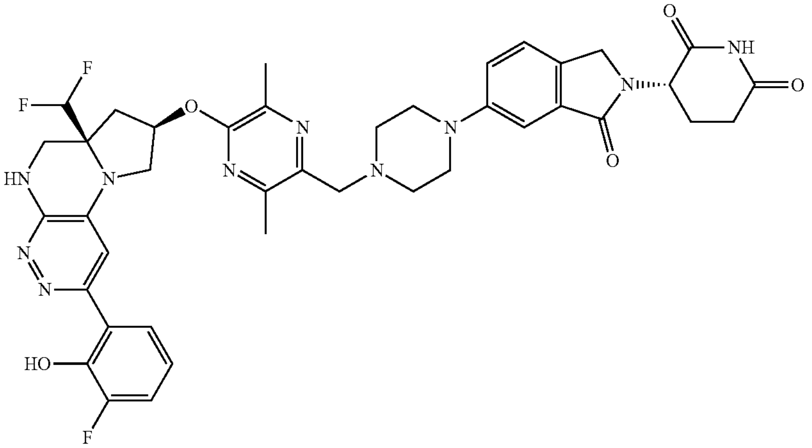 [SMILES: Cc1nc(O[C@H]2CN3c4cc(-c5cccc(F)c5O)nnc4NC[C@]3(C(F)F)C2)c(C)nc1CN1CCN(c2ccc3c(c2)C(=O)N([C@H]2CCC(=O)NC2=O)C3)CC1]

Step 1. 3,6-dimethylpyrazin-2-01

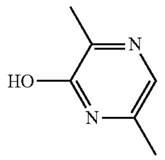

3-chloro-2,5-Dimethylpyrazine (720, 5.05 mmol) was dissolved in an aqueous solution of HCl (15%, 15 mL, 66.5 mmol). The reaction mixture was refluxed for 18 hours. The product mixture was cooled to 0° C. and quenched by slow addition of a saturated potassium carbonate aqueous solution to reach a pH of 6. The quenched product mixture was transferred to a separatory funnel with saturated sodium bicarbonate (150 mL). The diluted product mixture was extracted with a 3:1 chloroform:isopropanol solution (3×100 mL). The combined organic layers were dried over $MgSO_4$, filtered, and concentrated under reduced pressure to obtain 3,6-dimethylpyrazin-2-ol (609 mg, 97%) which was used without purification. LCMS calcd for $C_6H_9N_{20}$ $[M+H]^+$: m/z=125.1; Found: 124.9.

Step 2. 5-bromo-3,6-dimethylpyrazin-2-ol

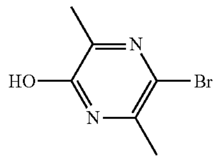

N-Bromosuccinimide was added to a stirring solution of 3,6-dimethylpyrazin-2-ol (609 mg, 4.91 mmol) in DMF (12 mL) at 0° C. The reaction mixture was stirred for 1 hour at 0° C. The product mixture cooled to −30° C. and allowed for the product to precipitate out of solution. The precipitated product was filtered to obtain 5-bromo-3,6-dimethylpyrazin-2-ol (350 mg, 35%) as a white solid. The filtrate was concentrated and purified by silica gel flash column chromatography with a gradient of 0-10% MeOH/DCM to obtain 5-bromo-3,6-dimethylpyrazin-2-ol (600 mg, 60%). LCMS calcd for $C_6H_8BrN_2O$ $[M+H]^+$: m/z=203.0; Found: 202.9.

Step 3. 3,6-dimethyl-5-vinylpyrazin-2-ol

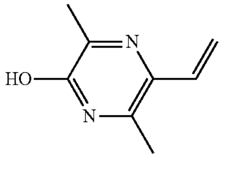

A 40 mL scintillation vial was charged with vinylboronic acid pinacol ester (0.75 mL, 4.43 mmol), 5-bromo-3,6-dimethylpyrazin-2-ol (300 mg, 1.48 mmol), XPhos Pd G2 (81.4 mg, 0.103 mmol) and potassium carbonate (1.03 g, 7.45 mmol). The mixture was dissolved in 1,4-dioxane (8.2 mL) and water (1.6 mL). The reaction mixture was sparged with $N_2$ gas for 5 minutes, sealed, and heated to 100° C. The reaction mixture was stirred for 1 hour at 100° C. The product mixture was diluted with MeOH (10 mL), filtered, and concentrated under reduced pressure. The residue obtained was purified by silica gel flash column chromatography with a gradient of 0-20% MeOH/DCM to obtain 3,6-dimethyl-5-vinylpyrazin-2-ol (220, 99%). LCMS calcd for Cali $[M+H]^+$: m/z=151.1; Found: 150.9.

Step 4. (6aS,8R)-6a-(d fluoromethyl)-8-((3,6-dimethyl-5-vinylpyrazin-2 yl)oxy)-2-(3 fluoro-2-methoxyphenyl)-5,6,6a, 7,8,9 hexahydropyrrolo[1',2':4,5]pyrazino[2,3-c]pyridazine

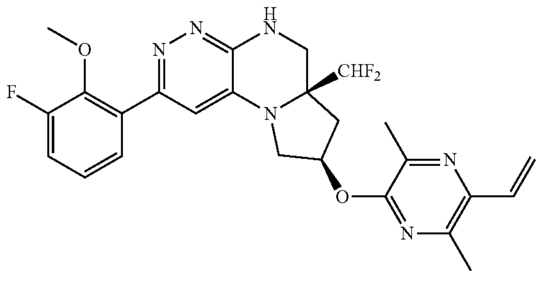 [SMILES: C=Cc1nc(C)c(O[C@H]2CN3c4cc(-c5cccc(F)c5OC)nnc4NC[C@]3(C(F)F)C2)nc1C]

Diisopropyl azodicarboxylate (32.2 μL, 0.164 mmol) was added to a stirring solution of triphenylphosphine (43.0 mg, 0.16 mmol), 3,6-dimethyl-5-vinylpyrazin-2-ol (28.2 mg, 0.19 mmol) and (6aS,8S)-6a-(difluoromethyl)-2-(3-fluoro-2-methoxyphenyl)-5,6,6a,7,8,9-hexahydropyrrolo[1',2':4,5]pyrazino[2,3-c]pyridazin-8-ol (20 mg, 0.055 mmol) in THE (1 mL). The reaction mixture was heated to 60° C. and stirred for 1 hour. The product mixture was purified directly by silica gel flash column chromatography with a gradient of 0-15% MeOH/DCM to obtain the title compound (16 mg, 59%). LCMS calcd for $C_{25}H_{26}F_3N_6O_2$ $[M+H]^+$: m/z=499.2; Found: 499.1.

Step 5. 5-(((6aS,8R)-6a-(difluoromethyl)-2-(3 fluoro-2 methoxyphenyl)-5,6,6a,7,8,9-hexahydropyrrolo[1',2':4,5]pyrazino[2,3-c]pyridazin-8 yl)oxy)-3, 6-dimethylpyrazine-2-carbaldehyde

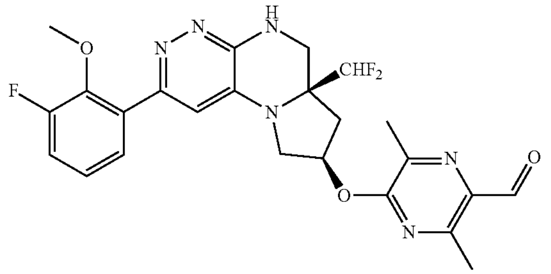 [SMILES: COc1c(F)cccc1-c1cc2c(nn1)NC[C@]1(C(F)F)C[C@@H](Oc3nc(C)c(C=O)nc3C)CN21]

Osmium tetroxide (4% in water, 20.4 μL, 0.003 mmol) was added to a stirring solution of (6aS,8R)-6a-(difluoromethyl)-8-((3,6-dimethyl-5-vinylpyrazin-2-yl)oxy)-2-(3-fluoro-2-methoxyphenyl)-5,6,6a,7,8,9-hexahydropyrrolo[1',2':4,5]pyrazino[2,3-c]pyridazine (16 mg, 0.032 mmol) and 4-methylmorpholine N-oxide (19 mg, 0.16 mmol) in THE (600 μL), water (200 μL) and tert-butanol (150 μL). The reaction mixture was stirred for 3 hours at room temperature. The product mixture was quenched with a saturated sodium sulfite aqueous solution (10 mL). The quenched product mixture was transferred to a separatory funnel and diluted with water (10 mL) and a saturated sodium chloride aqueous solution (10 mL). The diluted product mixture was extracted with a 3:1 chloroform:isopropanol solution (3×30 mL). The combined organic layers were dried over $MgSO_4$, filtered, and concentrated under reduced pressure. The residue obtained was dissolved in MeCN (1 mL) and water (1 mL). Sodium periodate (27.5 mg, 0.128 mmol) was added to the reaction mixture and stirred for 30 minutes at room temperature. The product mixture was transferred to a separatory funnel with a saturated sodium bicarbonate aqueous solution (30 mL). The diluted product mixture was extracted with a 3:1 chloroform:isopropanol solution (3×30 mL). The combined organic layers were dried over $MgSO_4$, filtered, and concentrated under reduced pressure. The residue obtained was purified by silica gel flash column chromatography with a gradient of 0-15% MeOH/DCM to obtain the title compound (8 mg, 50%). LCMS calcd for $C_{24}H_{24}F_3N_6O_3$ $[M+H]^+$: m/z=501.2; Found: 501.0.

Step 6. 5-(((6aS,8R)-6a-(difluoromethyl)-2-(3 fluoro-2 hydroxyphenyl)-5,6,6a,7,8,9-hexahydropyrrolo[1',2':4, 5]pyrazino[2, 3-c]pyridazin-8 yl)oxy)-3, 6-dimethylpyrazine-2-carbaldehyde

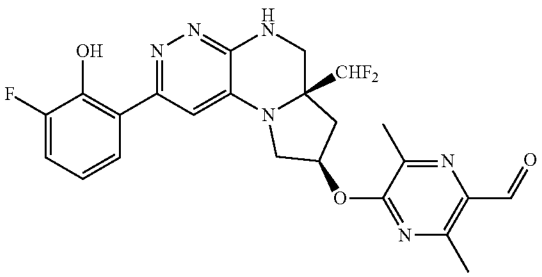 [SMILES: Cc1nc(O[C@H]2CN3c4cc(-c5cccc(F)c5O)nnc4NC[C@]3(C(F)F)C2)c(C)nc1C=O]

Boron trichloride (1.0 M in DCM, 558 μL, 0.558 mmol) was added to a stirring solution of 5-(((6aS,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-yl)oxy)-3,6-dimethylpyrazine-2-carbaldehyde (8 mg, 0.016 mmol) in DCM (500 μL) at 0° C. The reaction mixture was warmed to room temperature and stirred for 18 hours. The product mixture was cooled to 0° C. and quenched with a saturated potassium carbonate solution (1 mL). The quenched product mixture was transferred to a separatory funnel containing a saturated potassium carbonate solution (30 mL) and was extracted with a 3:1 chloroform:isopropanol solution (3×30 mL). The combined organic layers were dried over $MgSO_4$, filtered, and concentrated under reduced pressure to obtain the title compound (4 mg, 52%) which was used without further purification. LCMS calcd for $C_{23}H_{22}F_3N_6O_3$ $[M+H]^+$: m/z=487.2, Found: 486.9.0.

Step 7. (S)-3-(6-(4-((5-(((6aS,8R)-6a-(difluoromethyl)-2-(3 fluoro-2 hydroxyphenyl)-5,6,6a,7,8,9-hexahydropyrrolo[1',2':4,5]pyrazino[2,3-c]pyridazin-8 yl)oxy)-3,6-dimethylpyrazin-2-yl)methyl)piperazin-1 yl)-1-oxoisoindolin-2 yl)piperidine-2,6-dione (Example 48)

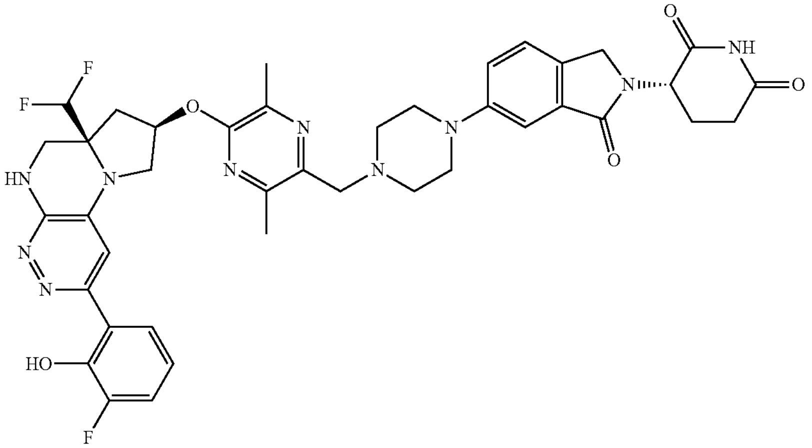 [SMILES: Cc1nc(O[C@H]2CN3c4cc(-c5cccc(F)c5O)nnc4NC[C@]3(C(F)F)C2)c(C)nc1CN1CCN(c2ccc3c(c2)C(=O)N([C@H]2CCC(=O)NC2=O)C3)CC1]

N,N-Diisopropylethylamine (4.3 μL, 0.025 mmol) was added to a stirring solution of 5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-3,6-dimethylpyrazine-2-carbaldehyde (4.0 mg, 0.0082 mmol) and (S)-3-(1-oxo-6-(piperazin-1-yl)isoindolin-2-yl)piperidine-2,6-dione; hydrochloride (6.0 mg, 0.016 mmol) in DMSO (200 μL). The reaction mixture was stirred at room temperature for 1 hour. Sodium triacetoxyborohydride (5.2 mg, 0.025 mmol) was added to the reaction mixture. The reaction mixture was heated to 35° C. and stirred for 18 hours. The product mixture was diluted with DMSO and purified directly by prep-HPLC (Waters CSH-C18, 5 μM, 30×100 mm, 12.9-32.9% MeCN/water (containing 0.1% TFA) over 5 min) to give the title compound (2.6 mg, 31%) as its TFA salt. LCMS calcd for $C_{40}H_{42}F_3N_{10}O_5$ $[M+H]^+$: m/z=799.3: Found. 799.2.

Example 49: (S)-3-(6-(4-((5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)pyridin-2-yl)methyl)piperazin-1-yl)-1-oxoisoindolin-2-yl)piperidine-2,6-dione

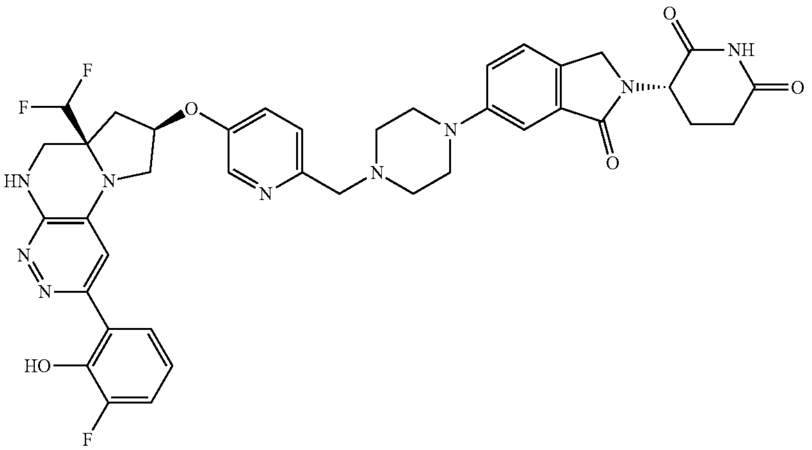 [SMILES: O=C1CC[C@H](N2Cc3ccc(N4CCN(Cc5ccc(O[C@H]6CN7c8cc(-c9cccc(F)c9O)nnc8NC[C@]7(C(F)F)C6)cn5)CC4)cc3C2=O)C(=O)N1]

Step 1. (S)-3-(6-(4-((5-(((6aS,8R)-6a-(d fluoromethyl)-2-(3 fluoro-2 hydroxyphenyl)-5,6,6a,7,8,9-hexahydropyrrolo[1',2':4,5]pyrazino[2,3-c]pyridazin-8 yl)oxy)pyridin-2-yl)methyl)piperazin-1 yl)-1-oxoisoindolin-2 yl)piperidine-2,6-dione (Example 49)

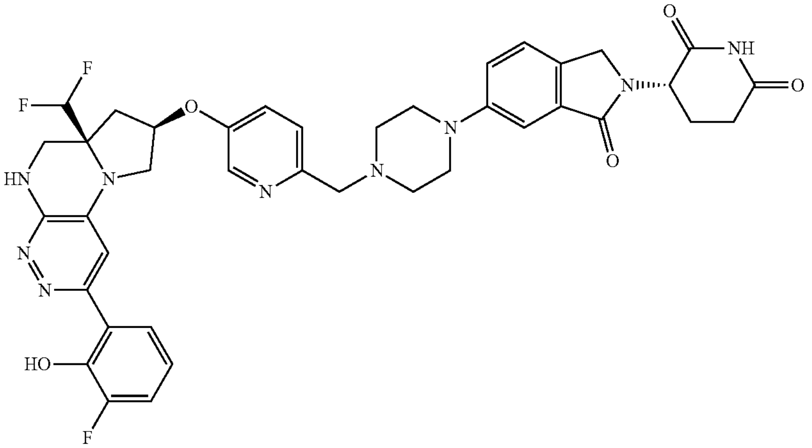 [SMILES: O=C1CC[C@H](N2Cc3ccc(N4CCN(Cc5ccc(O[C@H]6CN7c8cc(-c9cccc(F)c9O)nnc8NC[C@]7(C(F)F)C6)cn5)CC4)cc3C2=O)C(=O)N1]

This example was synthesized by procedures analogous to that described in Example 48, using 6-bromopyridin-3-ol instead of 5-bromo-3,6-dimethylpyrazin-2-ol in Step 3 and 6-vinylpyridin-3-ol instead of 4,5-dimethyl-6-vinylpyridin-3-ol in Step 4. LCMS calcd for $C_{39}H_{39}F_3N_9O_5$ $[M+H]^+$: m/z=770.3; Found. 770.0.

Example 50: 3-(6-(4-((2-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-4-isopropylpyrimidin-5-yl)methyl)piperazin-1-yl)-1-oxoisoindolin-2-yl)piperidine-2,6-dione

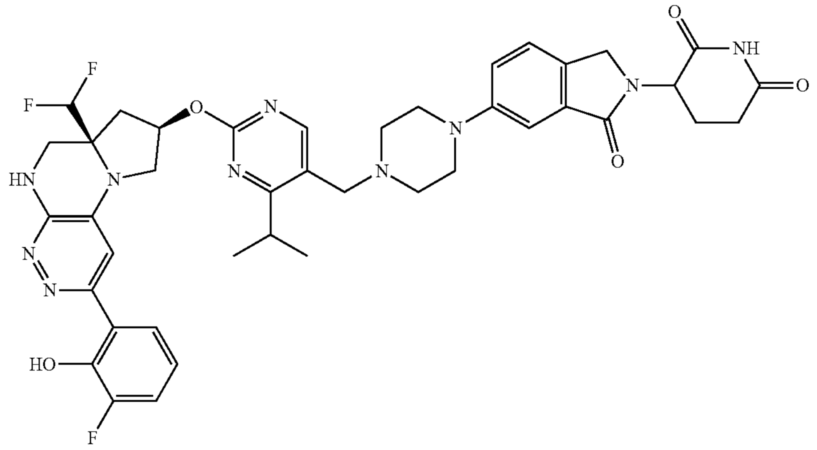 [SMILES: CC(C)c1nc(O[C@H]2CN3c4cc(-c5cccc(F)c5O)nnc4NC[C@]3(C(F)F)C2)ncc1CN1CCN(c2ccc3c(c2)C(=O)N(C2CCC(=O)NC2=O)C3)CC1]

Step 1. methyl 4-isopropyl-2-oxo-1,2-dihydropyrimidine-5-carboxylate

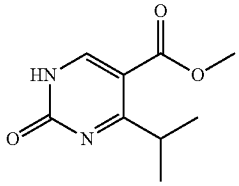

A 40 mL scintillation vial was charged with trimethyl orthoformate (1.61 g, 15.2 mmol), methyl 4-methyl-3-oxopentanoate (2.14 mL, 15 mmol), and urea (907 mg, 15.1 mmol). The mixture was dissolved in MeOH (4 mL). The reaction mixture was heated to 80° C. and stirred for 16 hours. The reaction mixture was cooled to room temperature, and sodium methoxide (3.86 g, 15 mmol) was added to the reaction mixture at room temperature. The reaction mixture was stirred overnight. Acetic acid (858 μL, 15 mmol) was added to the product mixture. The reaction mixture was concentrated under reduced pressure. 5% MeOH/DCM was added to the residue obtained. The mixture was sonicated then filtered and washed with 5% MeOH/DCM. The filtrate was concentrated under reduced pressure. The residue obtained was purified by silica gel flash column chromatography with a gradient of 0-20% MeOH/DCM to obtain methyl 4-isopropyl-2-oxo-1,2-dihydropyrimidine-5-carboxylate (540 mg, 18%). LCMS calcd for $C_9H_{13}N_2O_3$ $[M+H]^+$: m/z=197.1; Found: 197.0.

Step 2. methyl 2-chloro-4-isopropylpyrimidine-5-carboxylate

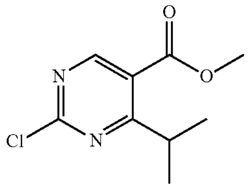

Methyl 4-isopropyl-2-oxo-1,2-dihydropyrimidine-5-carboxylate (540 mg, 2.75 mmol) was dissolved in phosphorus (V) oxychloride (3.5 mL, 37.6 mmol). The reaction was heated to reflux and stirred for 16 hours. The product mixture was concentrated under reduced pressure and purified directly by silica gel flash column chromatography with a gradient of 0-100% EtOAc/Hexanes to obtain methyl 2-chloro-4-isopropylpyrimidine-5-carboxylate (235 mg, 40%) LCMS calcd for $C_9H_{12}ClN_2O_2$ $[M+H]^+$: m/z=215.1; Found: 215.0.

Step 3,5-(((tert-butyldimethylsilyl)oxy)methyl)-2-chloro-4-isopropylpyrimidine

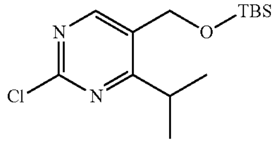

Diisobutylaluminium hydride (1.0 M in toluene, 3.28 mL, 3.28 mmol) was added dropwise to a stirring solution of methyl 2-chloro-4-isopropylpyrimidine-5-carboxylate (235 mg, 1.09 mmol) in THE (5.5 mL) at 0° C. The reaction mixture was stirred for 2 hours at 0° C. The product mixture was quenched with a saturated potassium sodium tartrate aqueous solution (15 mL) and stirred for 30 minutes. The quenched product mixture was transferred to a separatory funnel with a saturated potassium sodium tartrate aqueous solution (70 mL) and was extracted with EtOAc (3×80 mL). The combined organic layers were dried over $Na_2SO_4$, filtered, and concentrated under reduced pressure. The resulting residue was dissolved in DCM (5.5 mL). Imidazole (149 mg, 2.19 mmol) and tert-butyl dimethylchlorosilane (247 mg, 1.64 mmol) were added in sequence to the stirring reaction mixture. The reaction mixture was stirred for 30 minutes. The product mixture was filtered through celite and concentrated under reduced pressure. The residue obtained was purified by silica gel flash column chromatography with a gradient of 0-50% EtOAc/Hexanes to obtain 5-(((tert-butyldimethylsilyl)oxy)methyl)-2-chloro-4-isopropylpyrimidine (182 mg, 55%). LCMS calcd for $C_{14}H_{26}ClN_2OSi$ $[M+H]^+$: m/z=301.1, Found: 301.0.

Step 4. 2-((6aS,8R)-8-((5-(((tert-butyldimethylsilyl)oxy)methyl)-4-isopropylpyrimidin-2-yl)oxy)-6a-(difluoromethyl)-5,6,6a,7,8,9-hexahydropyrrolo[1',2':4,5]pyrazino[2,3-c]pyridazin-2 yl)-6-fluorophenol

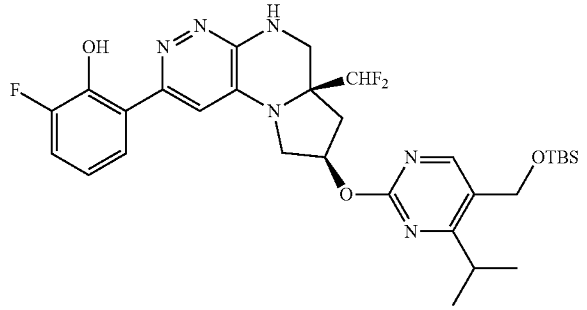 [SMILES: CC(C)c1nc(O[C@H]2CN3c4cc(-c5cccc(F)c5O)nnc4NC[C@]3(C(F)F)C2)ncc1CO[Si](C)(C)C(C)(C)C]

Sodium hydride (11.3 mg, 0.28 mmol, 60% dispersion in mineral oil) was added to a stirring solution of (6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-ol (20 mg, 0.057 mmol) and 5-(((tert-butyldimethylsilyl)oxy)methyl)-2-chloro-4-isopropylpyrimidine (34.2 mg, 0.114 mmol) in THF (1 mL) at 0° C. The reaction mixture was heated to 35° C. and stirred for 6 hours. The product mixture was cooled to 0° C. and quenched with MeOH (2 mL). The quenched product mixture was diluted with EtOAc (40 mL) and washed with a saturated ammonium chloride aqueous solution. The organic layer was dried over $Na_2SO_4$, filtered, and concentrated under reduced pressure. The residue obtained was purified by silica gel flash column chromatography with a gradient of 0-10% MeOH/DCM to obtain the title compound (15 mg, 43%). LCMS calcd for $C_{30}H_{40}F_3N_6O_3Si$ $[M+H]^+$: m/z=617.3; Found: 617.1.

Step 5. 2-((6aS,8R)-8-((5-(chloromethyl)-4-isopropylpyrimidin-2 yl)oxy)-6a-(difluoromethyl)-5,6,6a,7,8,9-hexahydropyrrolo[1',2':4,5]pyrazino[2,3-c]pyridazin-2-yl)-6-fluorophenol

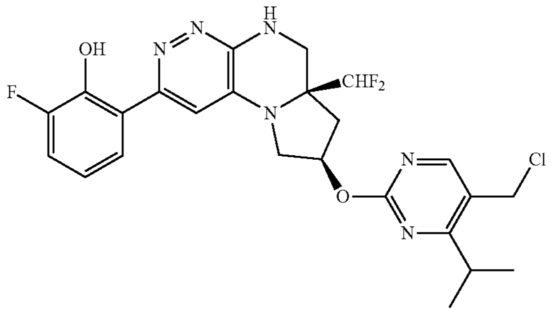 [SMILES: CC(C)c1nc(O[C@H]2CN3c4cc(-c5cccc(F)c5O)nnc4NC[C@]3(C(F)F)C2)ncc1CCl]

Hydrochloric acid (4 M in dioxane, 300 μL, 1.2 mmol) was added to a stirring solution of 2-((6aS,8R)-8-((5-(((tert-butyldimethyl silyl)oxy)methyl)-4-isopropylpyrimidin-2-yl)oxy)-6a-(difluoromethyl)-5,6,6a,7,8,9-hexahydropyrrolo[1',2':4,5]pyrazino[2,3-c]pyridazin-2-yl)-6-fluorophenol (15.4 mg, 0.13 mmol) in DCM (1 mL). The reaction mixture was stirred for 1 hour. The reaction mixture was concentrated under reduced pressure. The residue obtained was dissolved in THF (2 mL). Thionyl chloride (9.4 μL, 0.13 mmol) was added to the reaction mixture at room temperature. The reaction mixture was stirred for 30 minutes. The product mixture was transferred to a separatory funnel with a saturated potassium carbonate aqueous solution (30 mL). The diluted product mixture was extracted with a 3:1 chloroform:isopropanol solution (3×30 mL). The combined organic layers were dried over $MgSO_4$, filtered, and concentrated under reduced pressure to obtain the title compound (12 mg, 89%). The residue obtained was used without further purification. LCMS calcd for $C_{24}H_{25}ClF_3N_6O_2$ $[M+H]^+$: m/z=521.2; Found: 521.0.

Step 6. 3-(6-(4-((2-(((6aS,8R)-6a-(difluoromethyl)-2-(3-fluoro-2-hydroxyphenyl)-5,6,6a,7,8, 9-hexahydropyrrolo[1',2':4,5]pyrazino[2,3-c]pyridazin-8-yl)oxy)-4-isopropylpyrimidin-5-yl)methyl)piperazin-1-yl)-1-oxoisoindolin-2-yl)piperidine-2,6-dione (Example 50)

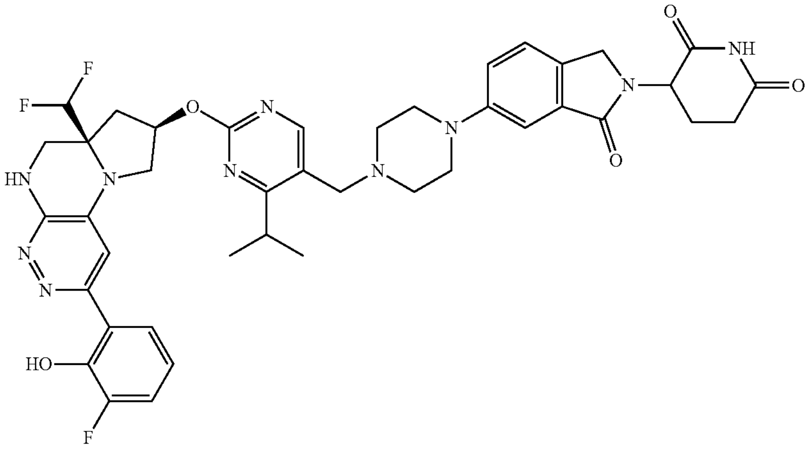 [SMILES: CC(C)c1nc(O[C@H]2CN3c4cc(-c5cccc(F)c5O)nnc4NC[C@]3(C(F)F)C2)ncc1CN1CCN(c2ccc3c(c2)C(=O)N(C2CCC(=O)NC2=O)C3)CC1]

N,N-Diisopropylethylamine (20.1 μL, 0.115 mmol) was added to a stirring solution of 2-((6aS,8R)-8-((5-(chloromethyl)-4-isopropylpyrimidin-2-yl)oxy)-6a-(difluoromethyl)-5,6,6a, 7,8,9-hexahydropyrrolo[1',2':4,5]pyrazino[2,3-c]pyridazin-2-yl)-6-fluorophenol (12 mg, 0.023 mmol) and (S)-3-(1-oxo-6-(piperazin-1-yl)isoindolin-2-yl)piperidine-2,6-dione; hydrochloride (12.6 mg, 0.035 mmol) in MeCN (1 mL). The reaction mixture was heated to 120° C. and stirred for 1.5 hours. The product mixture was cooled to room temperature. The product mixture was diluted with DMSO, filtered and purified directly by prep-HPLC (Waters CSH-C18, 5 μM, 30×100 mm, 17-25% MeCN/water (containing 0.1% TFA) over 5 min) to give the title compound (2.4 mg, 9%) as its TFA salt. LCMS calcd for $C_{41}H_{44}F_3N_{10}O_5$ $[M+H]^+$: m/z=813.3; Found: 813.2.

Example 51: 3-(6-(4-((5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-3-methylpyrazin-2-yl)methyl)piperazin-1-yl)-1-oxoisoindolin-2-yl)piperidine-2,6-dione

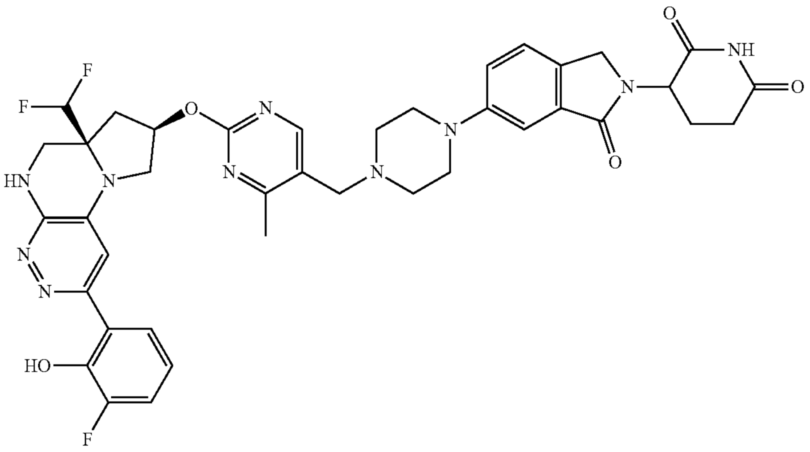 [SMILES: Cc1nc(O[C@H]2CN3c4cc(-c5cccc(F)c5O)nnc4NC[C@]3(C(F)F)C2)ncc1CN1CCN(c2ccc3c(c2)C(=O)N(C2CCC(=O)NC2=O)C3)CC1]

Step 1. 3-(b-(4-((5-(((6aS,8R)-6a-(difluoromethyl)-2-(3 fluoro-2 hydroxyphenyl)-5,6,6a, 7,8,9 hexahydropyrrolo[1,2':4,5]pyrazino[2,3-c]pyridazin-8 yl)oxy)-3-methylpyrazin-2-yl)methyl)piperazin-1 yl)-1-oxoisoindolin-211)piperidine-2,6-dione (Example 51)

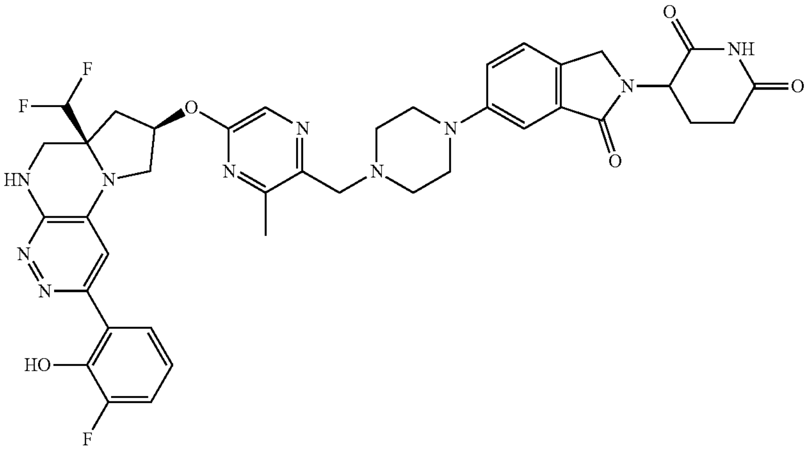 [SMILES: Cc1nc(O[C@H]2CN3c4cc(-c5cccc(F)c5O)nnc4NC[C@]3(C(F)F)C2)cnc1CN1CCN(c2ccc3c(c2)C(=O)N(C2CCC(=O)NC2=O)C3)CC1]

This example was synthesized by procedures analogous to that described in Example 40, using methyl-5-chloro-3-methylpyrazine-2-carboxylate instead of methyl-5-chloro-6-methylpyrazine-2-carboxylate in Step 9. LCMS calcd for $C_{39}H_{40}F_3N_{10}O_5$ $[M+H]^+$: m/z=785.3; Found; 785.1.

Example 52: 3-(6-(4-((5-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)pyrazin-2-yl)methyl)piperazin-1-yl)1-oxoisoindolin-2-yl)piperidine-2,6-dione

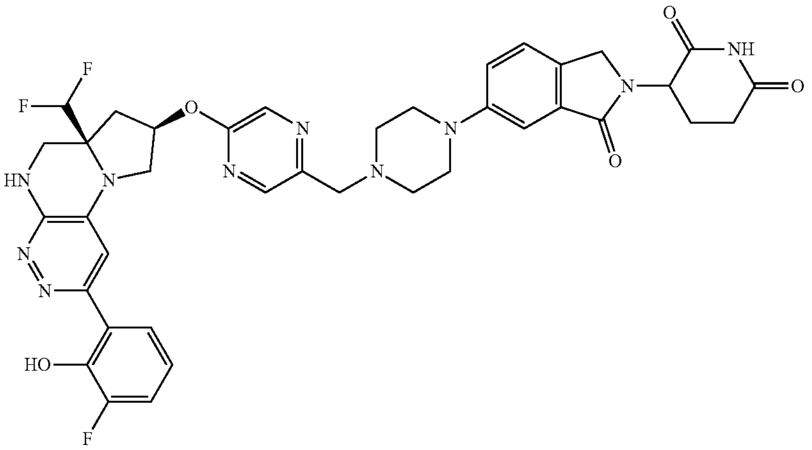 [SMILES: O=C1CCC(N2Cc3ccc(N4CCN(Cc5cnc(O[C@H]6CN7c8cc(-c9cccc(F)c9O)nnc8NC[C@]7(C(F)F)C6)cn5)CC4)cc3C2=O)C(=O)N1]

Step 1. 2-(((tert-butyldimethylsilyl)oxy)methyl)-5-chloropyrazine

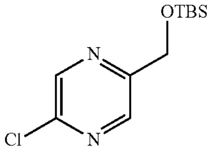 [SMILES: CC(C)(C)[Si](C)(C)OCc1cnc(Cl)cn1]

Diisobutylaluminium hydride (1.0 M in toluene, 3.19 mL, 3.19 mmol) was added to a stirring solution of methyl 5-chloropyrazine-2-carboxylate (220 mg, 1.27 mmol) in THE (6 mL) at −78° C. The reaction mixture was allowed to slowly warm to room temperature. The product mixture was quenched with a saturated potassium sodium tartrate aqueous solution (20 mL) and stirred at room temperature for 30 minutes. The quenched product mixture was diluted with EtOAc (50 mL) and transferred to a separatory funnel containing a saturated potassium sodium tartrate aqueous solution (30 mL). The diluted product mixture was extracted with EtOAc (2×50 mL). The combined organic layers were dried over $Na_2SO_4$, filtered, and concentrated under reduced pressure. The residue obtained was dissolved in DCM (6 mL). Imidazole (278 mg, 4.09 mmol) and tert-butyldimethylsilyl chloride (308 mg, 2.04 mmol) were added in sequence to the reaction mixture. The reaction mixture was stirred for 30 minutes. The product mixture was filtered through celite and concentrated under reduced pressure. The residue obtained was purified by silica gel flash column chromatography with a gradient of 0–50% EtOAc/Hexanes to obtain 2-(((tert-butyldimethylsilyl)oxy)methyl)-5-chloropyrazine (232 mg, 71%). LCMS calcd for $C_{11}H_{20}ClN_2OSi$ $[M+H]^+$: m/z=259.1; Found: 259.0.

Step 2. (6aS,8R)-8-((5-(((tert-butyldimethylsilyl)oxy)methyl)pyrazin-2 yl)oxy)-6a-(difluoromethyl)-2-(3-fluoro-2-methoxyphenyl)-5,6,6a,7,8,9-hexahydropyrrolo[1',2:4,5]pyrazino[2,3-c]pyridazine

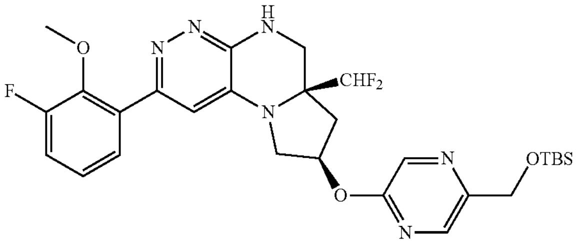 [SMILES: COc1c(F)cccc1-c1cc2c(nn1)NC[C@]1(C(F)F)C[C@@H](Oc3cnc(CO[Si](C)(C)C(C)(C)C)cn3)CN21]

Sodium hydride (11.5 mg, 0.29 mmol, 60% dispersion in mineral oil) was added to a stirring solution of 2-(((tert-butyldimethylsilyl)oxy)methyl)-5-chloropyrazine (22.3 mg, 0.086 mmol) and (6aS,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-ol (21 mg, 0.057 mmol) in THE (1 mL) at 0° C. The reaction mixture was heated to 40° C. and stirred for 1 hour. Another portion of 2-(((tert-butyldimethylsilyl)oxy)methyl)-5-chloropyrazine (22.3 mg, 0.086 mmol) was added and the reaction mixture was heated to 50° C. and stirred another 1 hour. The product mixture was cooled to 0° C. and quenched with a saturated ammonium chloride aqueous solution (30 mL). The quenched product mixture was extracted with EtOAc (3×30 mL). The combined organic layers were dried over $Na_2SO_4$, filtered, and concentrated under reduced pressure. The residue obtained was purified by silica gel flash column chromatography with a gradient of 0-10% MeOH/DCM to obtain the title compound (21 mg, 62%) LCMS calcd for $C_{28}H_{36}F_3N_6O_3Si$ $[M+H]^+$: m/z=589.3; Found. 589.1.

Step 3. 2-((6aS,8R)-8-((5-(chloromethyl)pyrazin-2-yl)oxy)-6a-(difluoromethyl)-5,6,6a, 7,8,9-hexahydropyrrolo[1',2':4,5]pyrazino[2,3-c]pyridazin-2-yl)-6-fluorophenol

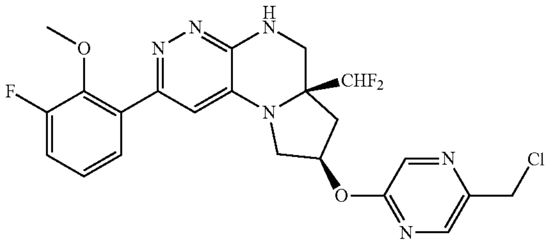 [SMILES: COc1c(F)cccc1-c1cc2c(nn1)NC[C@]1(C(F)F)C[C@@H](Oc3cnc(CCl)cn3)CN21]

Boron trichloride (1.0 M in DCM, 1.5 mL, 1.5 mmol) was added to a stirring solution of (6aS,8R)-8-((5-(((tert-butyldimethyl silyl)oxy)methyl)pyrazin-2-yl)oxy)-6a-(difluoromethyl)-2-(3-fluoro-2-methoxyphenyl)-5,6,6a,7,8,9-hexahydropyrrolo[1',2':4,5]pyrazino[2,3-c]pyridazine (26 mg, 0.044 mmol) at 0° C. The reaction mixture was warmed to room temperature and stirred overnight. The product mixture was cooled to 0° C. and quenched by slow addition of water (2 mL). The quenched product mixture was transferred to a separatory funnel containing a saturated sodium carbonate aqueous solution (30 mL). The diluted product mixture was extracted with a 3:1 chloroform:isopropanol solution (3×30 mL). The combined organic layers were dried over $MgSO_4$, filtered, and concentrated under reduced pressure. The residue obtained was dissolved in THE (1 mL) and cooled to 0° C. Thionyl chloride (16 μL, 0.22 mmol) was added to the reaction mixture.

The reaction mixture was warmed to room temperature and stirred for 30 minutes. The product mixture was transferred to a separatory funnel containing a saturated sodium carbonate aqueous solution (30 mL). The diluted product mixture was extracted with a 3:1 chloroform:isopropanol solution (3×30 mL). The combined organic layers were dried over $MgSO_4$, filtered, and concentrated under reduced pressure to obtain the title compound (18 mg, 85%) which was used in the following step without further purification. LCMS calcd for $C_{21}H_{19}ClF_3N_6O_2$ $[M+H]^+$: m/z=479.1; Found: 478.9.

Step 4. 3-(6-(4-((5-(((6aS,8R)-6a-(difluoromethyl)-2-(3 fluoro-2-hydroxyphenyl)-5,6,6a,7,8,9-hexahydropyrrolo[1, 2':4,5]pyrazino[2,3-c]pyridazin-8-yl) oxy)pyrazin-2-yl)methyl)piperazin-1-yl)-1-oxoisoindolin-2-yl)piperidine-2,6-dione (Example 52)

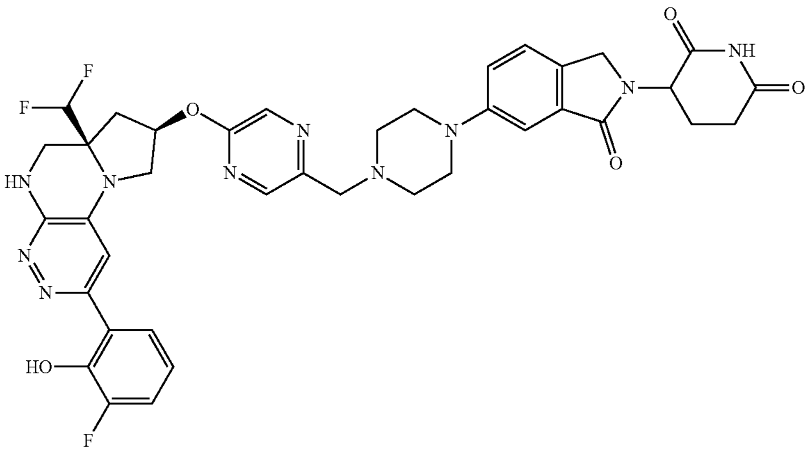 [SMILES: O=C1CCC(N2Cc3ccc(N4CCN(Cc5cnc(O[C@H]6CN7c8cc(-c9cccc(F)c9O)nnc8NC[C@]7(C(F)F)C6)cn5)CC4)cc3C2=O)C(=O)N1]

N,N-Diisopropylethylamine (41.5 μL, 0.24 mmol) was added to a stirring solution of 2-((6aS,8R)-8-((5-(chloromethyl)pyrazin-2-yl)oxy)-6a-(difluoromethyl)-5,6,6a,7,8,9-hexahydropyrrolo[1',2':4,5]pyrazino[2,3-c]pyridazin-2-yl)-6-fluorophenol (21.7 mg, 0.060 mmol) and (S)-3-(1-oxo-6-(piperazin-1-yl)isoindolin-2-yl)piperidine-2,6-dione; hydrochloride (19 mg, 0.040 mmol) in MeCN (1 mL). The reaction mixture was heated to 120° C. and stirred for 1.5 hours. The product mixture was cooled to room temperature. The product mixture was diluted with DMSO, filtered and purified directly by prep-HPLC (Waters CSH-C18, 5 μM, 30×100 mm, 10.6-30.6% MeCN/water (containing 0.1% TFA) over 5 min) to give the title compound (2.4 mg, 5%) as its TFA salt. LCMS calcd for $C_{38}H_{38}F_3N_{10}O_5$ $[M+H]^+$: m/z=771.3, Found: 771.3.

Example 53: 3-(6-(4-((6-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-5-methoxypyridin-3-yl)methyl)piperazin-1-yl)-1-oxoisoindolin-2-yl)piperidine-2,6-dione

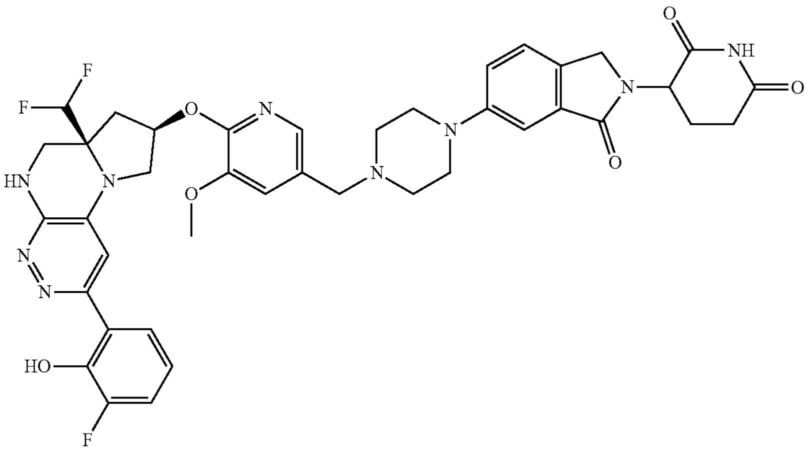

Step 1. (6-(((6aS,8R)-6a-(difluoromethyl)-2-(3 fluoro-2-methoxyphenyl)-5,6, 6a,7,8,9-hexahydro-pyrrolo[1',2':4,5]pyrazino[2,3-c]pyridazin-8 yl)oxy)-5-methoxypyridin-3 yl)methanol

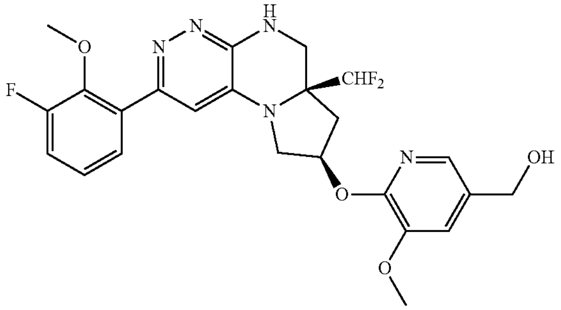 [SMILES: COc1cc(CO)cnc1O[C@H]1CN2c3cc(-c4cccc(F)c4OC)nnc3NC[C@]2(C(F)F)C1]

Sodium hydride (13.8 mg, 0.34 mmol, 60% dispersion in mineral oil) was added to a stirring solution of (6aS,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-ol (21 mg, 0.057 mmol) and methyl 6-chloro-5-methoxynicotinate (46.3 mg, 0.23 mmol) in THE (1 mL) at 0° C. The reaction mixture was stirred at room temperature for 4 hours. The product mixture was cooled to 0° C. and quenched by addition of MeOH (1 mL) and hydrochloric acid (4.0 M in dioxane, 144 μL, 0.57 mmol). The quenched product mixture was concentrated then dissolved in THE (2 mL). The reaction mixture was cooled to 0° C. and lithium aluminium hydride (1.0 M in THF, 344 μL, 0.344 mmol) was added to the reaction mixture. The reaction mixture was stirred for 30 minutes at 0° C. The product mixture was quenched with the addition of a saturated ammonium chloride aqueous solution (30 mL). The diluted product mixture was extracted with a 3:1 chloroform:isopropanol solution (3×30 mL). The combined organic layers were dried over $MgSO_4$, filtered, and concentrated under reduced pressure. The residue obtained was purified by silica gel flash column chromatography with a gradient of 0-15% MeOH/DCM to obtain the title compound (20.5 mg, 71%). LCMS calcd for $C_{24}H_{25}F_3N_5O_4$ $[M+H]^+$: m/z=504.2, Found: 504.0.

Step 2. 2-((6aS,8R)-8-((5-(chloromethyl)-3-methoxypyridin-2 yl)oxy)-6a-(difluoromethyl)-5,6,6a,7,8,9-hexahydropyrrolo[1',2':4,5]pyrazino[2,3-c] pyridazin-2 yl)-6-fluorophenol

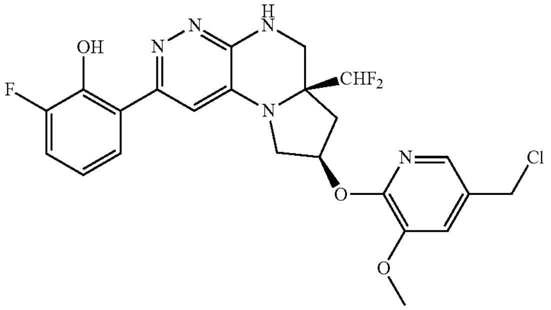 [SMILES: COc1cc(CCl)cnc1O[C@H]1CN2c3cc(-c4cccc(F)c4O)nnc3NC[C@]2(C(F)F)C1]

Boron trichloride (1.0 M in DCM, 1.38 mL, 1.38 mmol) was added to a stirring solution of (6-(((6aS,8R)-6a-(di fluoromethyl)-2-(3-fluoro-2-methoxyphenyl)-5,6,6a, 7,8,9-hexahydro-pyrrolo[1',2':4,5]pyrazino[2,3-c]pyridazin-8-yl) oxy)-5-methoxypyridin-3-yl)methanol (20.5 mg, 0.041 mmol) in DCM (500 μL) at 0° C. The reaction mixture was warmed to room temperature and stirred for 24 hours. Another portion of boron trichloride (1.0 M in DCM, 1.38 mL, 1.38 mmol) was added to the reaction mixture and it was stirred an additional 16 hours. The product mixture was quenched by slow addition of water (3 mL). The quenched product mixture was transferred to a separatory funnel containing a saturated sodium carbonate aqueous solution (30 mL). The diluted product mixture was extracted with a 3:1 chloroform:isopropanal solution (3×30 mL.) The combined organic layers were dried over $MgSO_4$, filtered, and concentrated under reduced pressure to obtain the title compound (17 mg, 85%) which was used without further purification. LCMS calcd for $C_{23}H_{22}ClF_3N_5O_3$ $[M+H]^+$: m/z=508.1; Found: 508.0.

Step 3. 3-(6-(4-((6-(((6aS,8R)-6a-(difluoromethyl)-2-(3-fluoro-2-hydroxyphenyl)-5,6,6a, 7,8,9-hexahydropyrrolo[1, 2':4,5]pyrazino[2,3-c]pyridazin-8-yl)oxy)-5-methoxypyridin-3-yl)methyl)piperazin-1-yl-1-oxoisoindolin-2-yl)piperidine-2,6-dione (Example 53)

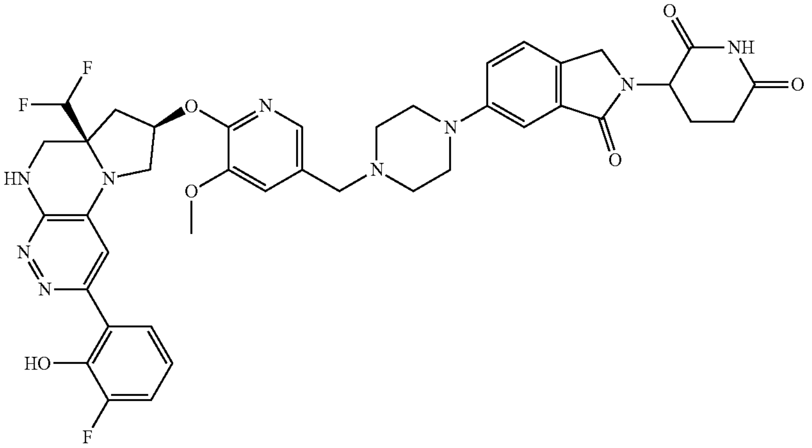 [SMILES: COc1cc(CN2CCN(c3ccc4c(c3)C(=O)N(C3CCC(=O)NC3=O)C4)CC2)cnc1O[C@H]1CN2c3cc(-c4cccc(F)c4O)nnc3NC[C@]2(C(F)F)C1]

N,N-Diisopropylethylamine (35 μL, 0.20 mmol) was added to a stirring solution of 2-((6aS,8R)-8-((5-(chloromethyl)-3-methoxypyridin-2-yl)oxy)-6a-(difluoromethyl)-5,6,6a,7,8,9-hexahydropyrrolo[1',2':4,5]pyrazino[2,3-c]pyridazin-2-yl)-6-fluorophenol (17 mg, 0.034 mmol) and (S)-3-(1-oxo-6-(piperazin-1-yl)isoindolin-2-yl)piperidine-2,6-dione; hydrochloride (18.3 mg, 0.050 mmol) in MeCN (1 mL). The reaction mixture was heated to 120° C. and stirred for 1.5 hours. The product mixture was cooled to room temperature. The product mixture was diluted with DMSO, filtered and purified directly by prep-HPLC (Waters CSH-Fluoro-Phenyl, 5 μM, 30×100 mm, 6.4-24.4% MeCN/water (containing 0.1% TFA) over 12 min) to give the title compound (4.6 mg, 12%) as its TFA salt. LCMS calcd for $C_{40}H_{41}F_3N_9O_6[M+H]^+$: m/z=800.3: Found: 800.2.

Example 54: 3-(6-(4-((6-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-5-fluoropyridin-3-yl)methyl)piperazin-1-yl)-1-oxoisoindolin-2-yl)piperidine-2,6-dione

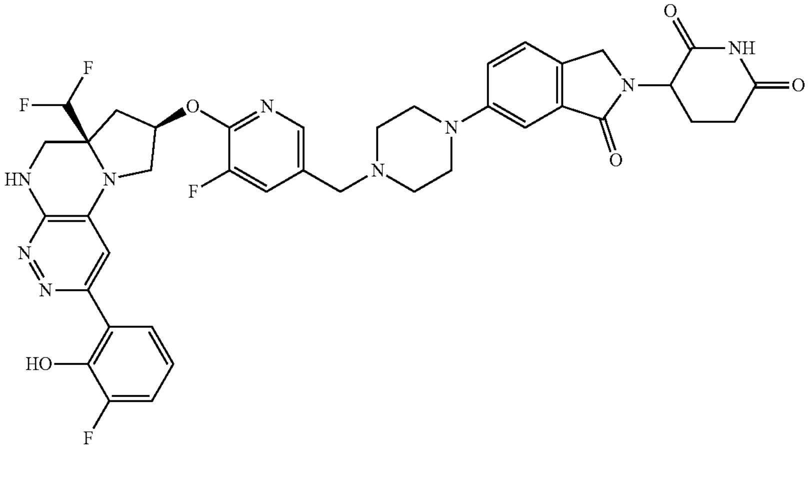 [SMILES: O=C1CCC(N2Cc3ccc(N4CCN(Cc5cnc(O[C@H]6CN7c8cc(-c9cccc(F)c9O)nnc8NC[C@]7(C(F)F)C6)c(F)c5)CC4)cc3C2=O)C(=O)N1]

Step 1. 3-(6-(4-((6-(((6aS,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-5-fluoropyridin-3-yl)methyl)piperazin-1-yl)-1-oxoisoindolin-2-yl)piperidine-2,6-dione

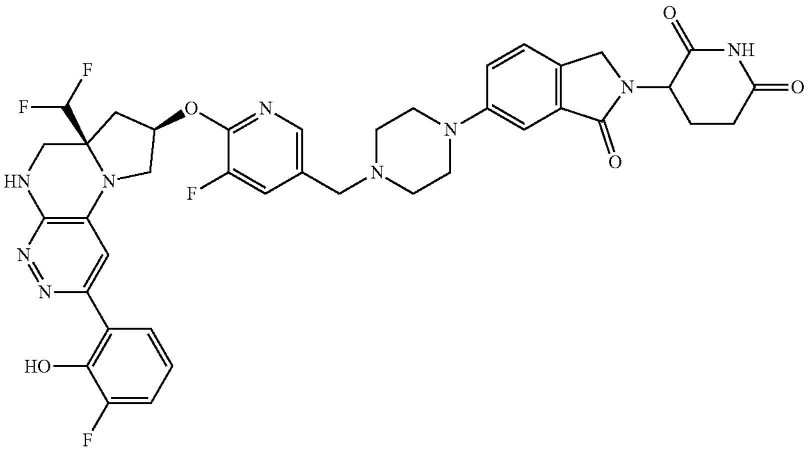 [SMILES: O=C1CCC(N2Cc3ccc(N4CCN(Cc5cnc(O[C@H]6CN7c8cc(-c9cccc(F)c9O)nnc8NC[C@]7(C(F)F)C6)c(F)c5)CC4)cc3C2=O)C(=O)N1]

This example was synthesized by procedures analogous to that described in Example 53, using methyl 6-chloro-5-fluoronicotinate instead of methyl 6-chloro-5-methoxynicotinate in Step 1. LCMS calcd for $C_{39}H_{38}F_4N_9O_5[M+H]^+$: m/z=788.3; Found: 788. 1.

Example 55: 3-(6-(4-((6-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione

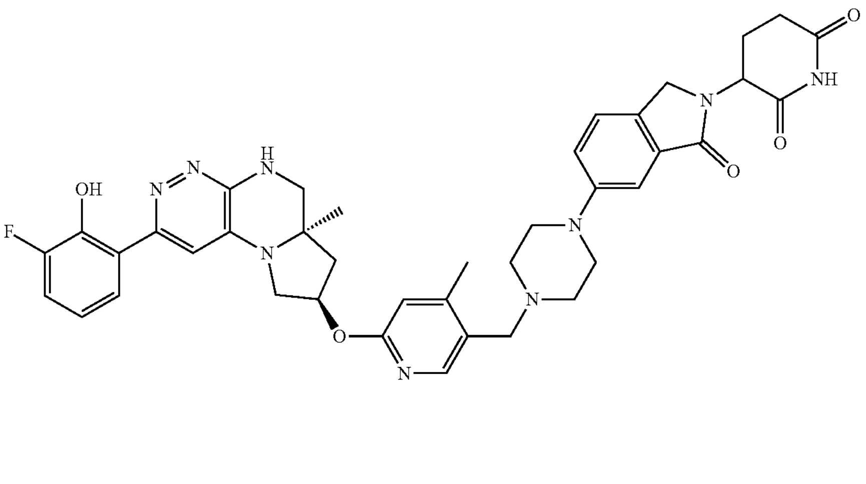 [SMILES: Cc1cc(O[C@H]2CN3c4cc(-c5cccc(F)c5O)nnc4NC[C@@]3(C)C2)ncc1CN1CCN(c2ccc3c(c2)C(=O)N(C2CCC(=O)NC2=O)C3)CC1]

Step 1: 2-benzyl 1-(tert-butyl) (2S,4R)-4-hydroxypyrrolidine-1,2-dicarboxylate

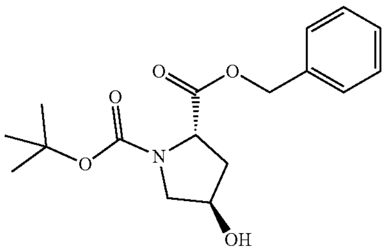 [SMILES: CC(C)(C)OC(=O)N1C[C@H](O)C[C@H]1C(=O)OCc1ccccc1]

To a mixture of (2S,4R)-1-(tert-butoxycarbonyl)-4-hydroxypyrrolidine-2-carboxylic acid (25.0 g, 108 mmol) and $K_2CO_3$ (44.8 g, 324 mmol) in DMF (250 mL) was added benzyl bromide (26.7 mL, 216 mmol). The reaction was stirred at room temperature for 2 h then diluted with MTBE (500 mL) and filtered through a pad of Celite©. The filtrate was dried over $Na_2SO_4$, filtered then concentrated to give crude give 2-benzyl 1-(tert-butyl) (2S,4R)-4-hydroxypyrrolidine-1,2-dicarboxylate (assumed quantitative yield) which was used without further purification. LCMS calcd for $C_{17}H_{24}NO_5$ $[M+H]^+$: m/z=322.2; Found: 322.5.

Step 2: 2-benzyl 1-(tert-butyl) (2S,4R)-4-(benzyloxy)pyrrolidine-1,2-dicarboxylate

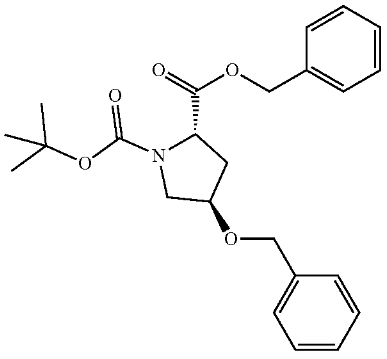 [SMILES: CC(C)(C)OC(=O)N1C[C@H](OCc2ccccc2)C[C@H]1C(=O)OCc1ccccc1]

To crude 2-benzyl 1-(tert-butyl) (2S,4R)-4-hydroxypyrrolidine-1,2-dicarboxylate (34.7 g, 108 mmol) in DMF (300 mL) was added benzyl bromide (19.2 mL, 162 mmol) then KOH (18.2 g, 324 mmol). The reaction was stirred at room temperature for 3 h then diluted with MTBE (500 mL) and filtered through a pad of Celite©. The filtrate was washed with 1 N HCl (aq; 500 mL), sat. $NaHCO_3$ (aq; 500 mL), then brine (500 mL). The organic layer was dried over $Na_2SO_4$, filtered and concentrated. The residue was purified via $SiO_2$ FCC (0-40% MTBE in heptanes) to give 2-benzyl 1-(tert-butyl) (2S,4R)-4-(benzyloxy)pyrrolidine-1,2-dicarboxylate (26.0 g, 59%) as a colorless oil. LCMS calcd for $C_{24}H_{30}NO_5$ $[M+H]^+$: m/z=412.2; Found: 412.5.

Step 3: 2-benzyl 1-(tert-butyl) (4R)-4-(benzyloxy)-2-methylpyrrolidine-1,2-dicarboxylate

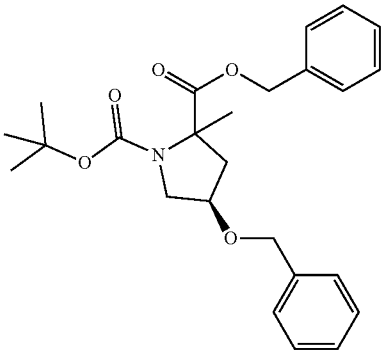 [SMILES: CC(C)(C)OC(=O)N1C[C@H](OCc2ccccc2)CC1(C)C(=O)OCc1ccccc1]

To 2-benzyl 1-(tert-butyl) (2S,4R)-4-(benzyloxy)pyrrolidine-1,2-dicarboxylate (34.7 g, 84.3 mmol) in THE (8 mL) at 0° C. was added methyl iodide (6.3 mL, 101 mmol) portion-wise. The reaction was stirred for 30 min, after which LiHMDS (16.9 g, 101 mmol) was added. The reaction was allowed to warm to room temperature, stirred for 12 h, then quenched with sat. $NH_4Cl$ (aq; 200 mL) and extracted with MTBE (3×200 mL). The combined organic phase was dried over $Na_2SO_4$, filtered and concentrated. The residue was purified via $SiO_2$ FCC (0-20% MTBE in heptanes) to give 2-benzyl 1-(tert-butyl) (4R)-4-(benzyloxy)-2-methylpyrrolidine-1,2-dicarboxylate (33.2 g, 93%) as a colorless, viscous oil. LCMS calcd for $C_{25}H_{32}NO_5$ $[M+H]^+$: m/z=426.2; Found: 426.1.

Step 4: (4R)-4-(benzyloxy)-1-(tert-butoxycarbonyl)-2-methylpyrrolidine-2-carboxylic acid

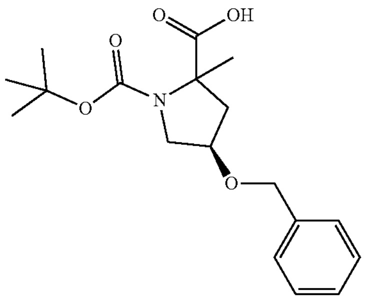 [SMILES: CC(C)(C)OC(=O)N1C[C@H](OCc2ccccc2)CC1(C)C(=O)O]

To 2-benzyl 1-(tert-butyl) (4R)-4-(benzyloxy)-2-methylpyrrolidine-1,2-dicarboxylate (33.2 g, 78.0 mmol) in MeOH (150 mL) at 0° C. was added NaOH (12.5 g, 312 mmol) in water (150 mL) dropwise. The reaction was stirred at 75° C. for 12 h, after which MeOH was removed via rotary evaporation. The resultant aqueous phase was diluted with water (150 mL), washed with 2:1 heptanes/MTBE (3×150 mL), then acidified to pH~2 with 4 N HCl (aq) and extracted with MTBE (3×150 mL). The combined organic phase from the latter three MTBE extractions was dried over $Na_2SO_4$, filtered and concentrated to afford (4R)-4-(benzyloxy)-1-(tert-butoxycarbonyl)-2-methylpyrrolidine-2-carboxylic acid (27.0 g, quant) which was used without further purification. LCMS calcd for $C_{18}H_{26}NO_5$ $[M+H]^+$: m/z=336.2; Found: 336.3.

Step 5: (6R,7aR)-6-(benzyloxy)-7a-methyltetrahydro-1H,3H-pyrrolo[1,2-c]oxazole-1,3-dione and (6R,7aS)-6-(benzyloxy)-7a-methyltetrahydro-1H,3H-pyrrolo[1,2-c]oxazole-1,3-dione

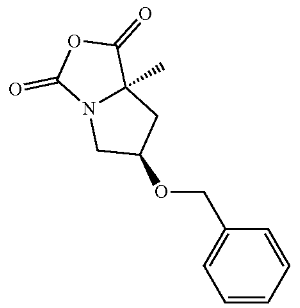

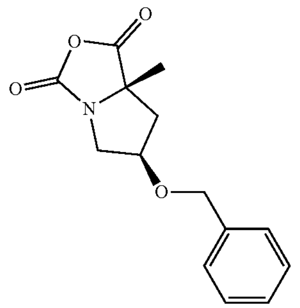

To a solution of DMF (4.5 mL, 58 mmol) in DCM (20 mL) at 0° C. was added oxalyl chloride (4.32 mL, 50.4 mmol) dropwise. The reaction was stirred at 0° C. for 30 min, after which a solution of (4R)-4-(benzyloxy)-1-(tert-butoxycarbonyl)-2-methylpyrrolidine-2-carboxylic acid (13.0 g, 38.8 mmol) and pyridine (3.12 mL, 38.8 mmol) in DCM (100 mL) was added, dropwise. After an additional 30 min of stirring at 0° C., the reaction was washed with cold water (100 mL), then dried over $Na_2SO_4$, filtered and concentrated. The residue was purified via SiO2 FCC (0-100% EtOAc in heptanes) to give "diastereomer A" (6R,7aR)-6-(benzyloxy)-7a-methyltetra-hydro-1H,3H-pyrrolo[1,2-c]oxazole-1,3-dione (3.46 g, 34%) and "diastereomer B" (6R,7aS)-6-(benzyloxy)-7a-methyltetrahydro-1H,3H-pyrrolo[1,2-c]oxazole-1,3-dione (820 mg, 8%) as colorless, viscous oils.

Step 6: (2R,4R)-4-(benzyloxy)-N-(4-bromo-6-chloropyridazin-3-yl)-2-methylpyrrolidine-2-carboxamide

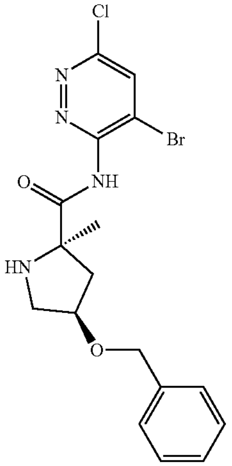 [SMILES: C[C@]1(C(=O)Nc2nnc(Cl)cc2Br)C[C@@H](OCc2ccccc2)CN1]

To (6R,7aR)-6-(benzyloxy)-7a-methyltetrahydro-1H,3H-pyrrolo[1,2-c]oxazole-1,3-dione (3.46 g, 13.2 mmol) and 4-bromo-6-chloropyridazin-3-amine (2.48 g, 11.9 mmol) in THE (40 mL) at 0° C. was added NaH (60% dispersion in mineral oil; 0.48 g, 19.9 mmol) portion-wise. When HPLC analysis indicated the reaction had stalled, additional NaH (60% dispersion in mineral oil; 0.16 g, 6.62 mmol) was added. HPLC analysis indicated improved conversion. The reaction mixture was quenched with a 10% citric acid solution (aq; 100 mL) then extracted with 3:1 $CHCl_3$/IPA (5×75 mL). The combined organic phase was dried over $Na_2SO_4$, filtered and concentrated to provide crude (2R,4R)-4-(benzyloxy)-N-(4-bromo-6-chloropyridazin-3-yl)-2-methylpyrrolidine-2-carboxamide (assumed quantitative yield) which was used without further purification. LCMS calcd for $C_{17}H_{19}BrClN_4O_2[M+H]^+$: m/z=425.0; Found: 425.3.

Step 7: (6aR,8R)-8-(benzyloxy)-2-chloro-6a-methyl-6a, 7,8,9-tetrahydropyrrolo [1',2':4,5] pyrazino[2,3-c]-172-yridazine-6(5H)-one

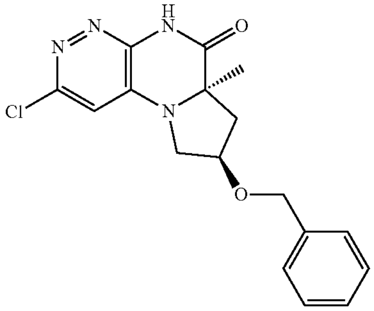 [SMILES: C[C@]12C[C@@H](OCc3ccccc3)CN1c1cc(Cl)nnc1NC2=O]

To crude (2R,4R)-4-(benzyloxy)-N-(4-bromo-6-chloropyridazin-3-yl)-2-methylpyrrolidine-2-carboxamide (5.07 g, 11.9 mmol) in THE (20 mL) was added N-methylmorpholine (1.58 g, 15.6 mmol) slowly. The reaction was stirred overnight at room temperature then concentrated. The residue was taken up in water (50 mL) and DCM (50 mL) and the organic layer was separated. The aqueous layer was extracted with DCM (3×50 mL) and the combined organic phase was dried over $Na_2SO_4$, filtered and concentrated. The residue was purified via $SiO_2$ FCC (30-50% EtOAc in heptanes) to afford (6aR,8R)-8-(benzyloxy)-2-chloro-6a-methyl-6a,7,8,9-tetrahydropyrrolo[1',2':4,5]pyrazino[2,3-c]-173-yridazine-6(5H)-one (2.86 g, 64%) as a white solid. LCMS calcd for $C_{17}H_{18}ClN_4O_2[M+H]^+$: m/z=345.1; Found: 345.4.

Step 8: (6aR,8R)-8-(benzyloxy)-2-chloro-6a-methyl-5,6,6a, 7,8,9-hexahydropyrrolo [1',2':4,5] pyrazino[2,3-c]pyridazine

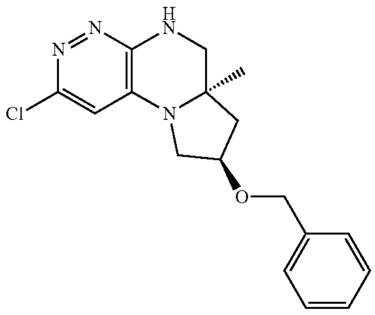 [SMILES: C[C@@]12CNc3nnc(Cl)cc3N1C[C@H](OCc1ccccc1)C2]

To (6aR,8R)-8-(benzyloxy)-2-chloro-6a-methyl-6a,7,8,9-tetrahydropyrrolo [1',2':4,5]pyrazino[2,3-c]-173-yridazine-6 (5H)-one (550 mg, 1.6 mmol) in THE (16 mL) was added $BH_3 \cdot Me_2S$ (605 μL, 6.38 mmol). The reaction was stirred at 60° C. for 2 h, after which additional $BH_3 \cdot Me_2S$ (150 μL, 1.6 mmol) was added. After stirring at 60° C. for an additional 1 h, the reaction was allowed to cool to room temperature then quenched slowly with MeOH and concentrated. The residue was taken up in EtOAc and washed with sat. $NaHCO_3$ (aq). The organic layer was dried with $Na_2SO_4$ then concentrated to give a crude mixture that was then dissolved in MeOH (4 mL) and THE (8 mL). AcOH (2.74 mL, 48 mmol) was added, followed by portion-wise addition of sodium cyanoborohydride (1.0 g, 16 mmol). The mixture was stirred at 80° C. for 4 h then allowed to cool to room temperature. Additional sodium cyanoborohydride (1.0 g, 16 mmol) was added and the reaction was stirred for an additional 2 h. The reaction was diluted with EtOAc and washed with sat. $NaHCO_3$ (aq). The organic layer was dried with $Na_2SO_4$ then concentrated. The residue was purified via $SiO_2$ FCC (0-4% MeOH in DCM) to give (6aR,8R)-8-(benzyloxy)-2-chloro-6a-methyl-5,6,6a,7,8,9-hexahydropyrrolo[1',2':4,5]pyrazino[2,3-c]pyridazine (410 mg, 76%) as a viscous, colorless oil. LCMS calcd for $C_{17}H_{20}ClN_4O$ $[M+H]^+$: m/z=331.1; Found: 331.2.

Step 9: tert-butyl (6aR,8R)-8-(benzyloxy)-2-chloro-6a-methyl-6a, 7,8,9-tetrahydro-pyrrolo[1',2':4,5] pyrazino[2,3-c]pyridazine-5(6H)-carboxylate

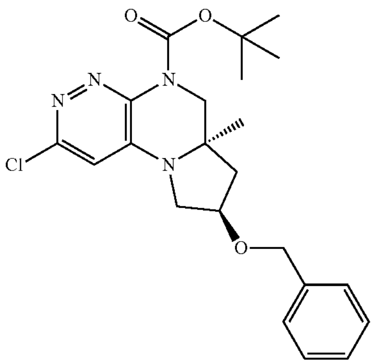 [SMILES: CC(C)(C)OC(=O)N1C[C@@]2(C)C[C@@H](OCc3ccccc3)CN2c2cc(Cl)nnc21]

To (6aR,8R)-8-(benzyloxy)-2-chloro-6a-methyl-5,6,6a,7,8,9-hexahydropyrrolo[1',2':4,5]pyrazino[2,3-c]pyridazine (410 mg, 1.24 mmol), DMAP (15 mg, 0.12 mmol) and N,N-diisopropylethylamine (866 μL, 5.0 mmol) in THE (4.1 mL) was added a solution of $Boc_2O$ (1.62 g, 7.44 mmol) in THE (2.1 mL), dropwise. The resulting mixture was stirred at 35° C. for 4 h then cooled to room temperature. The reaction was diluted with EtOAc and washed with sat. $NH_4Cl$ (aq) then brine. The organic layer was dried with $Na_2SO_4$, concentrated, then purified via $SiO_2$ FCC (20-50% EtOAc in hexanes) to give tert-butyl (6aR,8R)-8-(benzyloxy)-2-chloro-6a-methyl-6a,7,8,9-tetrahydropyrrolo[1',2':4,5]pyrazino[2,3-c]pyridazine-5(6H)-carboxylate (460 mg, 85%). LCMS calcd for $C_{22}H_{28}ClN_4O_3[M+H]^+$: m/z=431.2; Found: 431.1.

Step 10: tert-butyl (6aR,8R)-8-(benzyloxy)-2-(3-fluoro-2-methoxyphenyl)-6a-methyl-6a, 7,8,9-tetrahydropyrrolo[1',2':4,5]pyrazino[2,3-c]pyridazine-5 (6H)-carboxylate

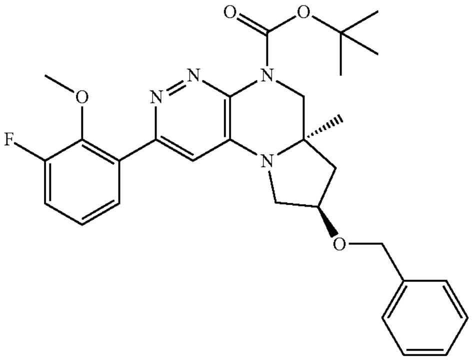 [SMILES: COc1c(F)cccc1-c1cc2c(nn1)N(C(=O)OC(C)(C)C)C[C@@]1(C)C[C@@H](OCc3ccccc3)CN21]

A mixture of tert-butyl (6aR,8R)-8-(benzyloxy)-2-chloro-6a-methyl-6a,7,8,9-tetrahydropyrrolo[1',2':4,5]pyrazino[2,3-c]pyridazine-5(6H)-carboxylate (445 mg, 1.03 mmol), 3-fluoro-2-methoxyphenylboronic acid (526 mg, 3.1 mmol), XPhos Pd G2 (40.6 mg, 0.05 mmol) and $K_3PO_4$ (877 mg, 4.13 mmol) in 1,4-dioxane (5.2 mL) and water (0.18 mL) was sparged with $N_2$ then stirred at 90° C. for 2-3 h. The reaction was cooled to room temperature then diluted with EtOAc and brine. The layers were separated and the aqueous was extracted with EtOAc (1×). The combined organic layers were dried with $Na_2SO_4$, concentrated, then purified via $SiO_2$ FCC (20-50% EtOAc in hexanes then 0-3% MeOH in DCM) to give a brown oil. Trituration via the addition of water and subsequent filtration afforded tert-butyl (6aR,8R)-8-(benzyloxy)-2-(3-fluoro-2-methoxyphenyl)-6a-methyl-6a,7,8,9-tetrahydropyrrolo[1',2':4,5]pyrazino[2,3-c]pyridazine-5(6H)-carboxylate (475 mg, 86%) as a tan solid. LCMS calcd for $C_{29}H_{34}FN_4O_4[M+H]^+$: m/z=521.3; Found: 521.2.

Step 11: (6aR,8R)-2-(3-fluoro-2-methoxyphenyl)-6a-methyl-5,6,6a, 7,8,9-hexahydropyrrolo[1',2':4,5]pyrazino[2,3-c]pyridazin-8-ol

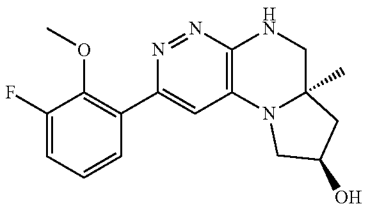 [SMILES: COc1c(F)cccc1-c1cc2c(nn1)NC[C@@]1(C)C[C@@H](O)CN21]

To tert-butyl (6aR,8R)-8-(benzyloxy)-2-(3-fluoro-2-methoxyphenyl)-6a-methyl-6a,7,8,9-tetrahydropyrrolo[1',2':4,5]pyrazino[2,3-c]pyridazine-5(6H)-carboxylate (146 mg, 0.28 mmol) in DCM (5.6 mL) was added $BCl_3$ (1 M in DCM; 1.4 mL, 1.4 mmol) at −78° C. The reaction was allowed to warm slowly to 0° C. over 1 h then quenched with MeOH. The reaction was concentrated then purified via reverse phase prep-HPLC (10-50% MeCN/water (containing 0.1% TFA)) to give (6aR,8R)-2-(3-fluoro-2-methoxyphenyl)-6a-methyl-5,6,6a,7,8,9-hexahydropyrrolo[1',2':4,5]pyrazino[2,3-c]pyridazin-8-ol (76 mg, 82%). LCMS calcd for $C_{17}H_{20}FN_4O_2[M+H]^+$: m/z=331.2; Found: 331.0.

Step 12: 6-(((6aR,8R)-2-(3-fluoro-2-methoxyphenyl)-6a-methyl-5,6,6a, 7,8,9-hexahydropyrrolo[1',2':4,5]pyrazino[2,3-c]pyridazin-8-yl)oxy)-4-methylnicotinic acid

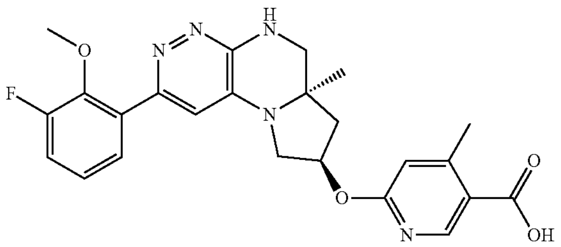 [SMILES: COc1c(F)cccc1-c1cc2c(nn1)NC[C@@]1(C)C[C@@H](Oc3cc(C)c(C(=O)O)cn3)CN21]

To NaH (60% dispersion in mineral oil; 7.4 mg, 0.31 mmol) was added a solution of (6aR,8R)-2-(3-fluoro-2-methoxyphenyl)-6a-methyl-5,6,6a,7,8,9-hexahydropyrrolo[1',2':4,5]pyrazino[2,3-c]pyridazin-8-ol (34 mg, 0.10 mmol) in DMA (0.3 mL) under an inert atmosphere. The resulting suspension was stirred at room temperature for 10 min. A solution of 6-fluoro-4-methylnicotinic acid (32 mg, 0.21 mmol) in DMA (0.2 mL) was added dropwise at room temperature and the reaction was stirred at 80° C. for 2 h. The mixture was cooled to 0° C. then quenched via slow addition of water and purified via reverse phase prep-HPLC (10-60% MeCN/water (containing 0.1% TFA)). The MeCN was removed from the fractions containing product (via rotary evaporation) and the resulting aqueous layer was neutralized with sat. $NaHCO_3$ (aq) then diluted with brine. Extraction of the aqueous layer with 3:1 $CHCl_3$/IPA (3×), followed by concentration of the combined organic layers gave 6-(((6aR,8R)-2-(3-fluoro-2-methoxyphenyl)-6a-methyl-5,6,6a,7,8,9-hexahydropyrrolo[1',2':4,5]pyrazino[2,3-c]pyridazin-8-yl)oxy)-4-methylnicotinic acid (40 mg, 82%). LCMS calcd for $C_{24}H_{25}FN_5O_4[M+H]^+$: m/z=466.2; Found: 466.1.

Step 13: 6-(((6aR,8R)-2-(3-fluoro-2-hydroxyphenyl)-6a-methyl-5,6,6a, 7,8,9-hexahydropyrrolo[1',2':4,5]pyrazino[2,3-c]pyridazin-8-yl)oxy)-4-methylnicotinic acid

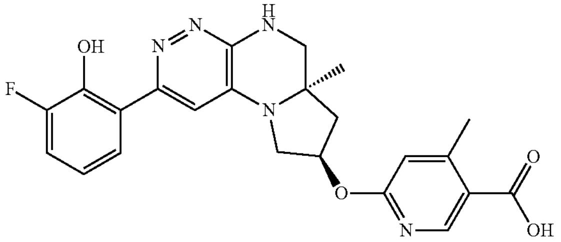 [SMILES: Cc1cc(O[C@H]2CN3c4cc(-c5cccc(F)c5O)nnc4NC[C@@]3(C)C2)ncc1C(=O)O]

To a vigorously stirred suspension of 6-(((6aR,8R)-2-(3-fluoro-2-methoxyphenyl)-6a-methyl-5,6,6a,7,8,9-hexahydropyrrolo[1',2':4,5]pyrazino[2,3-c]pyridazin-8-yl)oxy)-4-methylnicotinic acid (21 mg, 0.05 mmol) in anhydrous DCM (0.2 mL) was added $BBr_3$ (1 M in DCM; 1.14 mL, 1.14 mmol) dropwise at 0° C. under an inert atmosphere. The mixture was warmed to room temperature and vigorously stirred overnight. The DCM was evaporated and the reaction was cooled to 0° C. then quenched via dropwise addition of sat. $NaHCO_3$ (aq). After bubbling had ceased, the reaction was directly purified via reverse phase prep-HPLC (10-60% MeCN/water (containing 0.1% TFA) to afford 6-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4-methylnicotinic acid (17 mg, 82%). LCMS calcd for $C_{23}H_{23}FN_5O_4[M+H]^+$: m/z=452.2; Found: 452.1.

Step 14: 2-fluoro-6-((6aR,8R)-8-((5-(hydroxymethyl)-4-methylpyridin-2-yl)oxy)-6a-methyl-5,6,6a, 7,8,9-hexahydropyrrolo[1',2':4,5]pyrazino[2,3-c]pyridazin-2-yl)phenol

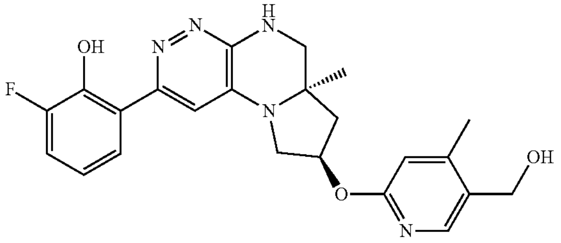 [SMILES: Cc1cc(O[C@H]2CN3c4cc(-c5cccc(F)c5O)nnc4NC[C@@]3(C)C2)ncc1CO]

To a solution of 6-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4-methylnicotinic acid (17 mg, 0.04 mmol) in THE (0.4 mL) was added $BH_3 \cdot Me_2S$ (15 μL, 0.15 mmol). The reaction was heated to 50° C. for 1 h then cooled to 0° C. and quenched with MeOH. The crude mixture was concentrated, dissolve in DMSO, then purified via reverse phase prep-HPLC (10-40% MeCN/water (containing 0.1% TFA) to give 2-fluoro-6-((6aR,8R)-8-((5-(hydroxymethyl)-4-methylpyridin-2-yl)oxy)-6a-methyl-5,6,6a,7,8,9-hexahydropyrrolo[1',2':4,5]pyrazino[2,3-c]pyridazin-2-yl)phenol (3.2 mg, 18%). LCMS calcd for $C_{23}H_{25}FN_5O_3[M+H]^+$: m/z=438.2; Found: 438.5.

Step 15: 6-(((6aR,8R)-2-(3-fluoro-2-hydroxyphenyl)-6a-methyl-5,6,6a, 7,8,9-hexahydropyrrolo[1',2':4,5]pyrazino[2,3-c]pyridazin-8-yl)oxy)-4-methylnicotinaldehyde

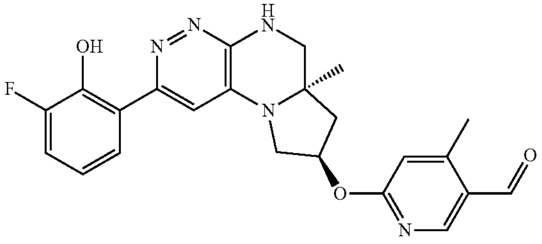

To 2-fluoro-6-((6aR,8R)-8-((5-(hydroxymethyl)-4-methylpyridin-2-yl)oxy)-6a-methyl-5,6,6a,7,8,9-hexahydropyrrolo[1',2':4,5]pyrazino[2,3-c]pyridazin-2-yl)phenol (3.2 mg, 7.3 μmol) in anhydrous $CHCl_3$ (75 μL) was added $MnO_2$ (13 mg, 0.15 mmol). The reaction was stirred at 60° C. 1 h then centrifuged to remove the solids which were subsequently washed with $CHCl_3$ (2×). The combined $CHCl_3$ layers were concentrated to afford crude 6-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4-methylnicotinaldehyde (assumed quantitative yield) which was used directly without further purification. LCMS calcd for $C_{23}H_{23}FN_5O_3[M+H]^+$: m/z=436.2; Found: 436.6.

Step 16: (S)-3-(6-(4-((6-(((6aR,8R)-2-(3-fluoro-2-hydroxyphenyl)-6a-methyl-5,6,6a, 7,8,9-hexahydropyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione To 6-(((6aR,8R)-2-(3-fluoro-2-hydroxyphenyl)-6a-methyl-5,6,6a,7,8,9-hexahydropyrrolo [1',2':4,5]pyrazino[2,3-c]pyridazin-8-yl)oxy)-4-methylnicotinaldehyde (3.0 mg, 6.9 μmol) in DMSO (92 μL) was added (S)-3-(1-oxo-6-(piperazin-1-yl)isoindolin-2-yl)piperidine-2,6-dione (HCl salt; 3.0 mg, 8.3 μmol) then N,N-diisopropylethylamine (1.4 μL, 8.3 μmol). After stirring for 10 min, sodium triacetoxyborohydride (4.4 mg, 0.02 mmol) was added portion-wise over 2 min. The reaction was stirred at room temperature 2 h then diluted with DMSO and purified by reverse phase prep-HPLC (10-40% MeCN/water (containing 0.1% TFA)) to give the TFA salt of the title compound (1.1 mg, 20%). LCMS calcd for $C_{40}H_{43}FN_9O_5[M+H]^+$: m/z=748.3; Found: 748.7.

Example 56: 3-(6-(4-((6-(((6aR,8R)-6a-Ethyl-2-(3-fluoro-2-hydroxyphenyl)-5,6,6a,7,8,9-hexahydropyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione

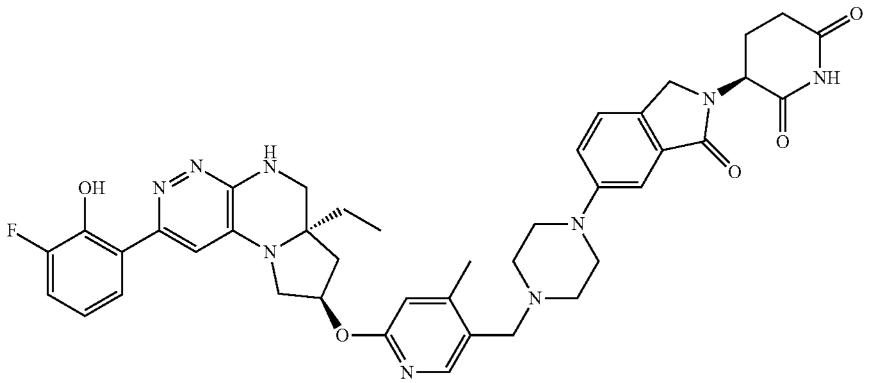

Step 1: (6aR,8R)-8-(Benzyloxy)-6a-ethyl-2-(3-fluoro-2-methoxyphenyl)-6a, 7,8,9-tetrahydropyrrolo[1',2':4,5]pyrazino[2,3-c]pyridazin-6(5H)-one

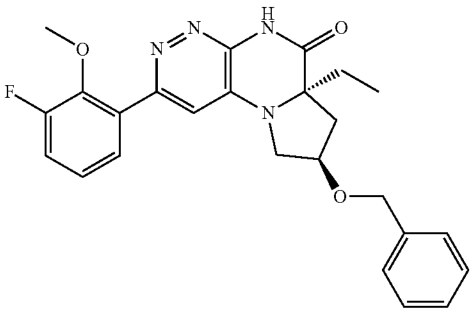 [SMILES: CC[C@]12C[C@@H](OCc3ccccc3)CN1c1cc(-c3cccc(F)c3OC)nnc1NC2=O]

A mixture of (6aR,8R)-8-(benzyloxy)-2-chloro-6a-ethyl-6a,7,8,9-tetrahydropyrrolo[1',2':4,5]pyrazino[2,3-c]pyridazin-6(5H)-one (314 mg, 0.88 mmol, Intermediate 8a), 3-fluoro-2-methoxyphenylboronic acid (447 mg, 2.63 mmol), dichloro-1,1'-bisdiphenylphosphino)ferrocene palladium (II) dichloromethane (215 mg, 0.26 mmol) and $K_2CO_3$ (605 mg, 4.38 mmol) in 1,4-dioxane (8 mL) and water (2 mL) was sparged with $N_2$ for 5 min then stirred at 100° C. for 2 h. The reaction was allowed to cool to room temperature and subsequently filtered through a 0.45 μm PTFE fritted filter which was then washed with EtOAc. The filtrate was concentrated and the resulting residue was purified via $SiO_2$ FCC (0-10% MeOH in DCM) to give (6aR,8R)-8-(benzyloxy)-6a-ethyl-2-(3-fluoro-2-methoxyphenyl)-6a,7,8,9-tetrahydropyrrolo[1',2':4,5]pyrazino[2,3-c]pyridazin-6(5H)-one as an orange solid (468 mg, 119%). LCMS calcd for $C_{25}H_{26}FN_4O_3[M+H]^+$: m/z=449.2; Found: 449.1.

Step 2: (6aR,8R)-8-(Benzyloxy)-6a-ethyl-2-(3-fluoro-2-methoxyphenyl)-5,6,6a, 7,8,9-hexahydropyrrolo[1',2':4,5]pyrazino[2,3-c]pyridazine

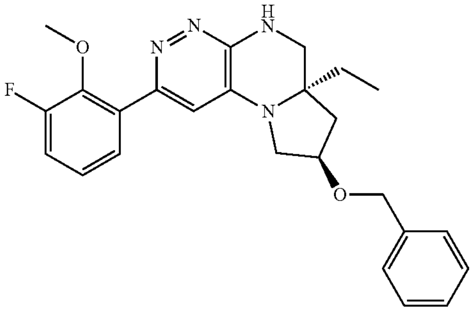 [SMILES: CC[C@@]12CNc3nnc(-c4cccc(F)c4OC)cc3N1C[C@H](OCc1ccccc1)C2]

To (6aR,8R)-8-(benzyloxy)-6a-ethyl-2-(3-fluoro-2-methoxyphenyl)-6a,7,8,9-tetrahydropyrrolo[1',2':4,5]pyrazino[2,3-c]pyridazin-6(5H)-one (393 mg, 0.88 mmol) in THF (5 mL) was added $LiAlH_4$ (1M in THF; 1.5 mL, 1.5 mmol) slowly at 0° C. The reaction was allowed to warm to room temperature. After 100 min, additional $LiAlH_4$ (1 M in THF; 1.5 mL, 1.5 mmol) was added. The reaction was stirred for 1 h then cooled to 0° C. MeOH (8 mL) was added slowly, followed by AcOH (1.5 mL, 26 mmol). The reaction was allowed to warm to room temperature. Sodium cyanoborohydride (551 mg, 8.76 mmol) was added and the reaction was stirred at 80° C. for 17 h. After cooling to 0° C., the mixture was neutralized with sat. $NaHCO_3$ (aq) then poured into water and extracted with EtOAc (3×). The combined organic layers were washed with brine, dried with $MgSO_4$, filtered then concentrated. The crude residue was purified via $SiO_2$ FCC (0-10% MeOH in DCM) to afford (6aR,8R)-8-(benzyloxy)-6a-ethyl-2-(3-fluoro-2-methoxyphenyl)-5,6,6a,7,8,9-hexahydropyrrolo[1',2':4,5]pyrazino[2,3-c]pyridazine as a beige solid (347 mg, 91%). LCMS calcd for $C_{25}H_{28}FN_4O_2[M+H]^+$: m/z=435.2; Found: 435.1.

Step 3: tert-Butyl (6aR,8R)-8-(benzyloxy)-6a-ethyl-2-(3-fluoro-2-methoxyphenyl)-6a, 7,8,9-tetrahydropyrrolo[1',2':4,5]pyrazino[2,3-c]pyridazine-5(6H)-carboxylate

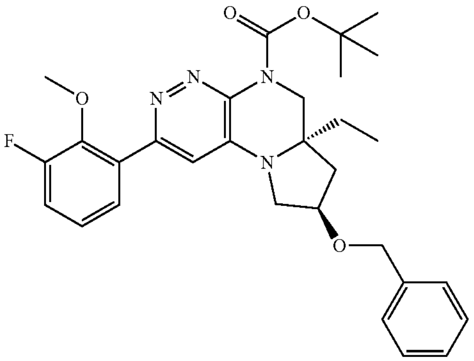 [SMILES: CC[C@]12C[C@@H](OCc3ccccc3)CN1c1cc(-c3cccc(F)c3OC)nnc1N(C(=O)OC(C)(C)C)C2]

To (6aR,8R)-8-(benzyloxy)-6a-ethyl-2-(3-fluoro-2-methoxyphenyl)-5,6,6a,7,8,9-hexahydropyrrolo[1',2':4,5]pyrazino[2,3-c]pyridazine (347 mg, 0.80 mmol) in THF (5 mL) was added DMAP (98 mg, 0.8 mmol), followed by $Boc_2O$ (261 mg, 1.2 mmol). The reaction was stirred at room temperature overnight. Additional $Boc_2O$ (88 mg, 0.40 mmol) was added, and the reaction was stirred at room temperature overnight. Purification via $SiO_2$ FCC (0-100% EtOAc in hexanes) gave tert-butyl (6aR,8R)-8-(benzyloxy)-6a-ethyl-2-(3-fluoro-2-methoxyphenyl)-6a,7,8,9-tetrahydropyrrolo[1',2':4,5]pyrazino[2,3-c]pyridazine-5(6H)-carboxylate (300 mg, 70%). LCMS calcd for $C_{30}H_{36}FN_4O_4[M+H]^+$: m/z=535.3; Found: 535.2.

Step 4: tert-Butyl (6aR,8R)-6a-ethyl-2-(3-fluoro-2-methoxyphenyl)-8-hydroxy-6a,7,8,9-tetrahydropyrrolo[1',2':4,5]pyrazino[2,3-c]pyridazine-5(6H)-carboxylate

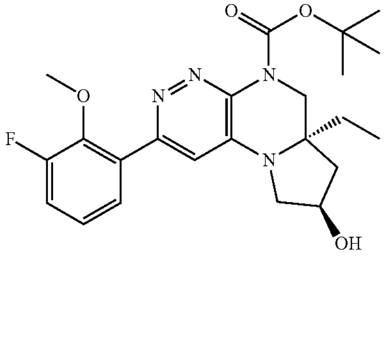 [SMILES: CC[C@]12C[C@@H](O)CN1c1cc(-c3cccc(F)c3OC)nnc1N(C(=O)OC(C)(C)C)C2]

A mixture of tert-butyl (6aR,8R)-8-(benzyloxy)-6a-ethyl-2-(3-fluoro-2-methoxyphenyl)-6a,7,8,9-tetrahydropyrrolo [1',2':4,5]pyrazino[2,3-c]pyridazine-5(6H)-carboxylate (300 mg, 0.56 mmol) and 10% Pd/C (180 mg, 0.17 mmol) in MeOH (6 mL) was degassed and equipped with a $H_2$ balloon. The reaction was stirred at 50° C. overnight then filtered and purified via $SiO_2$ FCC (0-10% MeOH in DCM) to give tert-butyl (6aR,8R)-6a-ethyl-2-(3-fluoro-2-methoxyphenyl)-8-hydroxy-6a,7,8,9-tetrahydropyrrolo[1',2':4,5] pyrazino[2,3-c]pyridazine-5(6H)-carboxylate (167 mg, 67%). LCMS calcd for $C_{23}H_{30}FN_4O_4[M+H]^+$: m/z=445.2; Found: 445.2.

Step 5: Methyl 6-(((6aR,8R)-6a-ethyl-2-(3-fluoro-2-methoxyphenyl)-5,6,6a, 7,8,9-hexahydropyrrolo[1',2':4,5]pyrazino[2,3-c]pyridazin-8-yl)oxy)-4-methylnicotinate

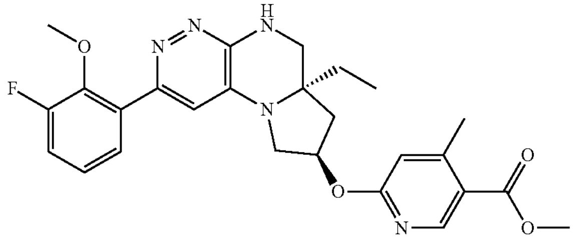 [SMILES: CC[C@@]12CNc3nnc(-c4cccc(F)c4OC)cc3N1C[C@H](Oc1cc(C)c(C(=O)OC)cn1)C2]

To tert-butyl (6aR,8R)-6a-ethyl-2-(3-fluoro-2-methoxyphenyl)-8-hydroxy-6a,7,8,9-tetrahydropyrrolo[1',2':4,5] pyrazino[2,3-c]pyridazine-5(6H)-carboxylate (150 mg, 0.11 mmol) and methyl 6-fluoro-4-methylnicotinate (124 mg, 0.73 mmol) in THE (2 mL) was added NaH (60% dispersion in mineral oil; 42 mg, 1.05 mmol). The mixture was stirred at room temperature for 3 h then quenched with TFA (0.16 mL, 2.09 mmol) and concentrated. The residue was taken up in DCM (2 mL) then treated with anhydrous HCl (4N in 1,4-dioxane, 1.0 mL, 4.0 mmol). The reaction was stirred at room temperature for 2 h then concentrated. The residue was purified via $SiO_2$ FCC (0-10% MeOH in DCM) to give methyl 6-(((6aR,8R)-6a-ethyl-2-(3-fluoro-2-methoxyphenyl)-5,6,6a,7,8,9-hexahydropyrrolo[1',2':4,5]pyrazino[2,3-c]pyridazin-8-yl)oxy)-4-methylnicotinate (160 mg, quant. yield assumed). LCMS calcd for $C_{26}H_{29}FN_5O_4$ $[M+H]^+$: m/z=494.2; Found: 494.2.

Step 6: (6-(((6aR,8R)-6a-Ethyl-2-(3-fluoro-2-methoxyphenyl)-5,6,6a, 7,8,9-hexahydropyrrolo[1',2':4,5]pyrazino[2,3-c]pyridazin-8-yl)oxy)-4-methylpyridin-3-yl)methanol

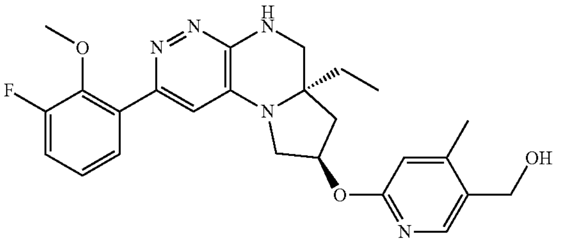 [SMILES: CC[C@@]12CNc3nnc(-c4cccc(F)c4OC)cc3N1C[C@H](Oc1cc(C)c(CO)cn1)C2]

To methyl 6-(((6aR,8R)-6a-ethyl-2-(3-fluoro-2-methoxyphenyl)-5,6,6a,7,8,9-hexahydropyrrolo[1',2':4,5]pyrazino[2,3-c]pyridazin-8-yl)oxy)-4-methylnicotinate (160 mg, 0.32 mmol) in THE (3 mL) was added $LiAlH_4$ (1 M in THF; 0.65 mL, 0.65 mmol) dropwise at 0° C. The mixture was stirred vigorously at 0° C. for 30 min then quenched slowly with sat. potassium sodium tartrate (aq). The mixture was diluted with water then extracted with EtOAc (2×). The combine organic layers were washed with brine, concentrated, then purified via $SiO_2$ FCC (0-10% MeOH in DCM) to give (6-(((6aR,8R)-6a-ethyl-2-(3-fluoro-2-methoxyphenyl)-5,6,6a,7,8,9-hexahydropyrrolo[1',2':4,5]pyrazino[2,3-c] pyridazin-8-yl)oxy)-4-methylpyridin-3-yl)methanol (130 mg, 86%). LCMS calcd for $C_{25}H_{29}FN_5O_3[M+H]^+$: m/z=466.2; Found: 466.2.

Step 7: 2-((6aR,8R)-8-((5-(Chloromethyl)-4-methylpyridin-2-yl)oxy)-6a-ethyl-5,6,6a, 7,8,9-hexahydropyrrolo[1',2':4,5]pyrazino[2,3-c]pyridazin-2-yl)-6-fluorophenol

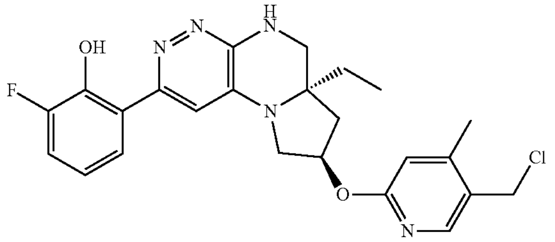 [SMILES: CC[C@@]12CNc3nnc(-c4cccc(F)c4O)cc3N1C[C@H](Oc1cc(C)c(CCl)cn1)C2]

To (6-(((6aR,8R)-6a-ethyl-2-(3-fluoro-2-methoxyphenyl)-5,6,6a,7,8,9-hexahydropyrrolo [1',2':4,5]pyrazino[2,3-c]pyridazin-8-yl)oxy)-4-methylpyridin-3-yl)methanol (110 mg, 0.24 mmol) in DCM (2 mL) at 0° C. was added $BCl_3$ (1M in DCM; 8.0 mL, 8.0 mmol). The mixture was allowed to warm to room temperature and stirred overnight. The reaction was quenched by slow addition of water, poured into sat. $NaHCO_3$ (aq), then extracted with 3:1 $CHCl_3$:IPA (3×). The combined organic layers were dried with $MgSO_4$, filtered, then concentrated to give crude 2-((6aR,8R)-8-((5-(chloromethyl)-4-methylpyridin-2-yl)oxy)-6a-ethyl-5,6,6a, 7,8,9-hexahydro-pyrrolo[1',2':4,5]pyrazino[2,3-c]pyridazin-2-yl)-6-fluorophenol (100 mg, 90%) which was used directly without further purification. LCMS calcd for $C_{24}H_{26}ClFN_5O_2[M+H]^+$: m/z=470.2; Found: 470.2.

Step 8: 3-(6-(4-((6-(((6aR,8R)-6a-ethyl-2-(3-fluoro-2-hydroxyphenyl)-5,6,6a, 7,8,9-hexahydropyrrolo [1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione To crude 2-((6aR,8R)-8-((5-(chloromethyl)-4-methylpyridin-2-yl)oxy)-6a-ethyl-5,6,6a,7,8,9-hexahydropyrrolo [1',2':4,5]pyrazino[2,3-c]pyridazin-2-yl)-6-fluorophenol (54 mg, 0.37 mmol) and (S)-3-(1-oxo-6-(piperazin-1-yl)isoindolin-2-yl)piperidine-2,6-dione (HCl salt; 45 mg, 0.14 mmol) in MeCN (2 mL) was added N,N-diisopropylethylamine (60 μL, 0.35 mmol). The reaction was stirred at 120° C. for 1 hour then allowed to cool to room temperature. The reaction was purified via prep-HPLCMS (Waters CSH Phenyl-Hexyl, 5 μm, 30×100 mm, 11.8-31.8% MeCN/water (containing 0.1% TFA) over 5 min) to afford the TFA salt of the title compound (28 mg, 32% yield). LCMS calcd for $C_{41}H_{45}FN_9O_5[M+H]^+$: m/z=762.4; Found: 762.1.

$^1H$ NMR (400 MHz, DMSO) δ 10.97 (s, 1H), 9.65-9.41 (m, 1H), 8.35-8.22 (m, 1H), 8.22-8.08 (m, 1H), 7.55-7.44 (m, 1H), 7.44-7.18 (m, 4H), 7.03-6.94 (m, 1H), 6.92 (s, 1H), 6.86-6.77 (m, 1H), 5.77 (s, 1H), 5.14-5.05 (m, 1H), 4.48-4.31 (m, 3H), 4.23 (d, J=18.1 Hz, 1H), 4.19-4.11 (m, 1H), 4.03-3.88 (m, 2H), 3.79 (d, J=12.5 Hz, 1H), 3.70 (d, J=11.9 Hz, 1H), 3.13-3.01 (m, 3H), 2.97-2.85 (m, 1H), 2.75-2.56 (m, 3H), 2.44-2.31 (m, 5H), 2.04-1.89 (m, 2H), 1.69-1.52 (m, 2H), 0.90 (t, J=8.2 Hz, 3H).

Example 57: (S)-3-(6-(4-((5-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-3-methylpyrazin-2-yl)methyl)piperazin-1-yl)-1-oxoisoindolin-2-yl)piperidine-2,6-dione

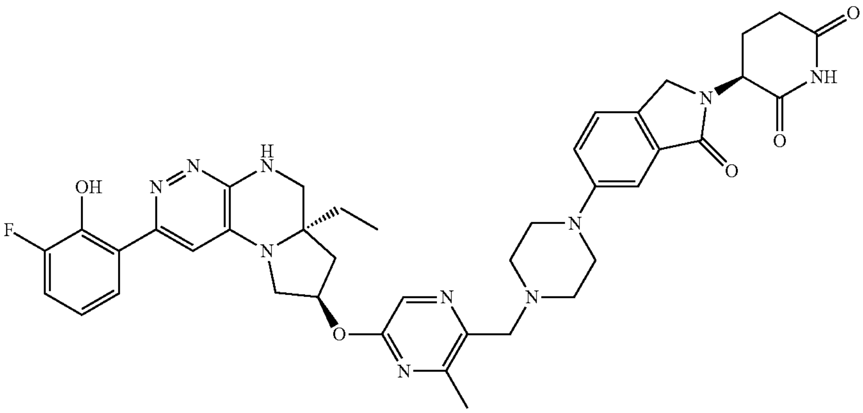 [SMILES: CC[C@@]12CNc3nnc(-c4cccc(F)c4O)cc3N1C[C@H](Oc1cnc(CN3CCN(c4ccc5c(c4)C(=O)N([C@H]4CCC(=O)NC4=O)C5)CC3)c(C)n1)C2]

Step 1: 5-bromo-6-methylpyrazine-2-ol

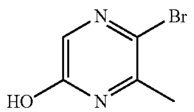

A mixture of 5-bromo-6-methylpyrazin-2-amine (150 mg, 0.8 mmol) in conc. $H_2SO_4$ (1.0 mL) and a separate mixture of $NaNO_2$ (83 mg, 1.2 mmol) in conc. $H_2SO_4$ (1.0 mL) were stirred at room temperature for 5-10 min (or until all $NaNO_2$ had solubilized). The solution of activated $NaNO_2$ was slowly added to the vial containing 5-bromo-6-methylpyrazin-2-amine in $H_2SO_4$. The reaction was stirred at 50° C. overnight then cooled to 0° C. and poured slowly into 10 N NaOH (5.0 mL, 50 mmol) with stirring. Water (5 mL) was added and the reaction was stirred for an additional 5 min before warming to room temperature. After 2 h, the reaction was further diluted with water, acidified to pH<2 with 6 N HCl (aq), then extracted with DCM (3×). The combined organic layers were dried with $MgSO_4$, filtered, then concentrated to afford 5-bromo-6-methylpyrazin-2-ol (133 mg, 88%). LCMS calcd for $C_5H_5BrN_2O$ $[M+H]^+$: m/z=189.0; Found: 188.9.

Step 2: 6-methyl-5-vinylpyrazin-2-ol

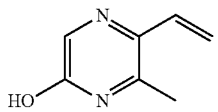

A mixture of 5-bromo-6-methylpyrazin-2-ol (133 mg, 0.70 mmol), 4,4,5,5-tetramethyl-2-vinyl-1,3,2-dioxaborolane (0.36 mL, 2.11 mmol), XPhos Pd G2 (83 mg, 0.11 mmol) and $K_2CO_3$ (510 mg, 3.7 mmol) in 1,4-dioxane (4 mL) and water (1 mL) was sparged with $N_2$ for 5 min. The reaction was stirred at 100° C. for 1 h then allowed to cool to room temperature and subsequently purified via $SiO_2$ FCC (0-100% EtOAc in hexanes then 0-15% MeOH in DCM) to give 6-methyl-5-vinylpyrazin-2-ol (147 mg, 153%) as a sticky, yellow solid. LCMS calcd for $C_7H_9N_2O$ $[M+H]^+$: m/z=137.1; Found: 136.9.

Step 3: (6aR,8R)-2-chloro-6a-ethyl-8-((6-methyl-5-vinylpyrazin-2-yl)oxy)-5,6,6a, 7,8,9-hexahydropyrrolo[1',2':4,5]pyrazino[2,3-c]pyridazine

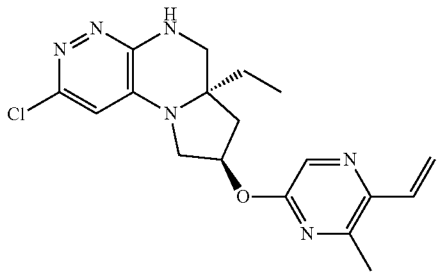 [SMILES: C=Cc1ncc(O[C@H]2CN3c4cc(Cl)nnc4NC[C@@]3(CC)C2)nc1C]

To a suspension of (6aR,8S)-2-chloro-6a-ethyl-5,6,6a,7,8,9-hexahydropyrrolo[1',2':4,5]pyrazino[2,3-c]pyridazin-8-ol (Intermediate 9; 20 mg, 79 μmol), 6-methyl-5-vinylpyrazin-2-ol (13 mg, 98 μmol) and polymer-supported $PPh_3$ (100-200 mesh, ~1.6 mmol/g loading; 83 mg, 133 μmol) in THF (1.5 mL) was added diisopropyl azodicarboxylate (26 μL, 133 μmol) at room temperature. The mixture was stirred at 65° C. for 25 min then allowed to cool to room temperature. The reaction was quenched with a small amount of water then filtered through a 0.45 um PTFE fritted filter. The filtrate was purified directly via $SiO_2$ FCC (0-15% MeOH in DCM) to afford (6aR,8R)-2-chloro-6a-ethyl-8-((6-methyl-5-vinylpyrazin-2-yl)oxy)-5,6,6a,7,8,9-hexahydropyrrolo[1',2':4,5]pyrazino[2,3-c]pyridazine as a white solid (assumed quantitative yield). LCMS calcd for $C_{18}H_{22}ClN_6O$ $[M+H]^+$: m/z=373.2; Found: 373.1.

Step 4: 2-((6aR,8R)-6a-Ethyl-8-((6-methyl-5-vinylpyrazin-2-yl)oxy)-5,6,6a, 7,8,9-hexahydropyrrolo[1',2':4,5]pyrazino[2,3-c]pyridazin-2-yl)-6-fluorophenol

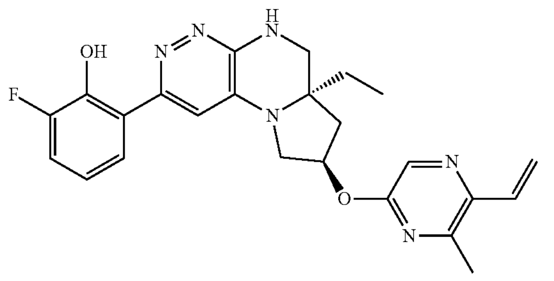 [SMILES: C=Cc1ncc(O[C@H]2CN3c4cc(-c5cccc(F)c5O)nnc4NC[C@@]3(CC)C2)nc1C]

A mixture of (6aR,8R)-2-chloro-6a-ethyl-8-((6-methyl-5-vinylpyrazin-2-yl)oxy)-5,6,6a,7,8,9-hexahydropyrrolo[1',2':4,5]pyrazino[2,3-c]pyridazine (29 mg, 79 μmol), 3-fluoro-2-hydroxyphenylboronic acid (37 mg, 236 μmol), XPhos Pd G2 (12 mg, 16 μmol) and $K_2CO_3$ (54 mg, 393 μmol) in 1,4-dioxane (1 mL) and water (0.2 mL) was sparged with $N_2$ for 2 min. The reaction was stirred at 100° C. for 75 min then allowed to cool to room temperature. After allowing the reaction to cool briefly, additional 3-fluoro-2-hydroxyphenylboronic acid (37 mg, 236 μmol), XPhos Pd G2 (12 mg, 16 μmol) and $K_2CO_3$ (54 mg, 393 μmol) was added. The mixture was sparged with $N_2$ for 1 min, stirred at 100° C. for 45 min, allowed to cool to room temperature, then purified directly via $SiO_2$ FCC (0-10% MeOH in DCM). The product was further purified via prep-HPLCMS (Waters CSH-C18, 5 μm, 30×100 mm, 26.1-46.1% MeCN/water (containing 0.1% TFA) over 5 min) to give the TFA salt of the title compound which was further purified via prep-HPLCMS (Waters CSH-C18, 5 μm, 30×100 mm, 27.5-47.5% MeCN/water (containing 0.1% TFA) over 5 min).

Fractions containing the title compound were combined then neutralized with sat. $NaHCO_3$ (aq). The aqueous layer was extracted with DCM (3×). The combined organic layers were dried with $MgSO_4$, filtered then concentrated to afford 2-((6aR,8R)-6a-ethyl-8-((6-methyl-5-vinylpyrazin-2-yl)oxy)-5,6,6a,7,8,9-hexahydropyrrolo[1',2':4,5]pyrazino[2,3-c]pyridazin-2-yl)-6-fluorophenol (4.4 mg, 13%) as a yellow film. LCMS calcd for $C_{24}H_{26}FN_6O_2[M+H]^+$: m/z=449.2; Found: 449.1.

Step 5: 5-(((6aR,8R)-6a-Ethyl-2-(3-fluoro-2-hydroxyphenyl)-5,6,6a, 7,8,9-hexahydro-pyrrolo[1',2':4,5]pyrazino[2,3-c]pyridazin-8-yl)oxy)-3-methylpyrazine-2-carbaldehyde

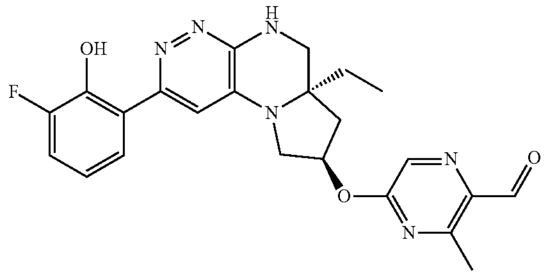 [SMILES: CC[C@@]12CNc3nnc(-c4cccc(F)c4O)cc3N1C[C@H](Oc1cnc(C=O)c(C)n1)C2]

To 2-((6aR,8R)-6a-ethyl-8-((6-methyl-5-vinylpyrazin-2-yl)oxy)-5,6,6a,7,8,9-hexahydro-pyrrolo[1',2':4,5]pyrazino[2,3-c]pyridazin-2-yl)-6-fluorophenol (4.4 mg, 9.8 μmol) and $NaIO_4$ (6.3 mg, 29 μmol) in THE (1 mL) and water (0.5 mL) was added $OsO_4$ (4% in water; 6.2 μL, 1.0 μmol). The reaction was stirred at room temperature for 3 h then poured into ~1:1 brine/water. The aqueous layer was extracted with DCM (3×). The combine organic layers were washed with brine (1×), dried with $MgSO_4$, filtered then concentrated to give 5-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-3-methylpyrazine-2-carbaldehyde (assumed quantitative yield) which was used directly without further purification. LCMS calcd for $C_{23}H_{24}FN_6O_3[M+H]^+$: m/z=451.2; Found: 451.1.

Step 6: (S)-3-(6-(4-((5-(((6aR,8R)-6a-Ethyl-2-(3-fluoro-2-hydroxyphenyl)-5,6,6a, 7,8,9-hexahydropyrrolo[1',2':4,5]pyrazino[2,3-c]pyridazin-8-yl)oxy)-3-methylpyrazin-2-yl)methyl)piperazin-1-yl)-1-oxoisoindolin-2-yl)piperidine-2,6-dione A mixture of 5-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-3-methylpyrazine-2-carbaldehyde (4.4 mg, 0.010 mmol), (S)-3-(1-oxo-6-(piperazin-1-yl)isoindolin-2-yl)piperidine-2,6-dione (HCl salt; 10 mg, 0.027 mmol) and N,N-diisopropylethylamine (5.1 μL, 0.029 mmol) was stirred at room temperature for 1 h. Sodium triacetoxyborohydride (10 mg, 0.049 mmol) was added and the reaction was stirred at 35° C. for an additional 18 h then allowed to cool to room temperature. Dilution with DMSO and a small amount of TFA, followed by purification by prep-HPLCMS (Waters CSH-Fluoro-Phenyl, 5 μm, 30×100 mm, 6.4-24.4% MeCN/water (containing 0.1% TFA) over 12 min) gave the TFA salt of the title compound (3.1 mg, 32% yield) as a white solid. LCMS calcd for $C_{40}H_{44}FN_{10}O_5$ $[M+H]^+$: m/z=763.3; Found: 763.3.

Example 58: (S)-3-(6-(4-((6-(((6aR,8R)-2-(3-Fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione

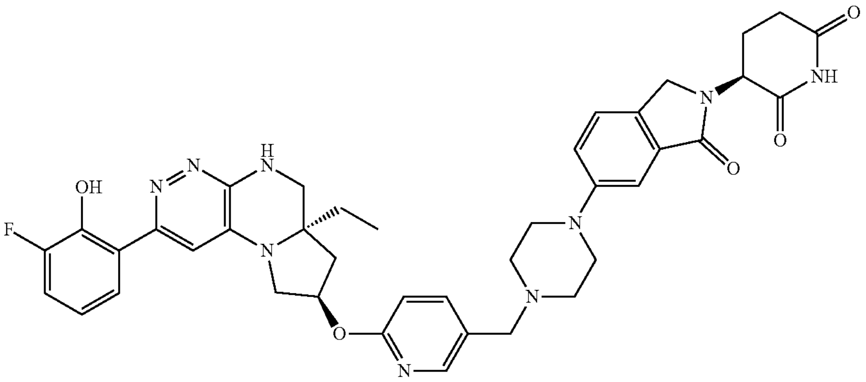 [SMILES: CC[C@@]12CNc3nnc(-c4cccc(F)c4O)cc3N1C[C@H](Oc1ccc(CN3CCN(c4ccc5c(c4)C(=O)N([C@H]4CCC(=O)NC4=O)C5)CC3)cn1)C2]

Step 1: (6aR,8R)-2-chloro-6a-(fluoromethyl)-5,6,6a,7,8,9-hexahydropyrrolo[1',2':4,5]pyrazino[2,3-c]pyridazin-8-ol

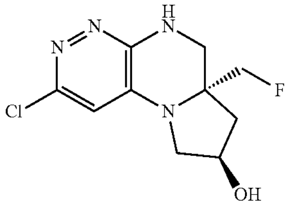 [SMILES: O[C@H]1CN2c3cc(Cl)nnc3NC[C@@]2(CF)C1]

This intermediate was synthesized by procedures analogous to that described in Examples 40 and 43, using fluoroiodomethane instead of difluoromethyl trifluoromethanesulfonate in Example 40, Step 2. LCMS calcd for $C_{10}H_{13}ClFN_4O$ $[M+H]^+$: m/z=259.1; Found: 259.2.

Step 2: Methyl 6-(((6aR,8R)-2-chloro-6a-(fluoromethyl)-5,6,6a,7,8,9-hexahydropyrrolo[1',2':4,5]pyrazino[2,3-c]pyridazin-8-yl)oxy)-4-methylnicotinate

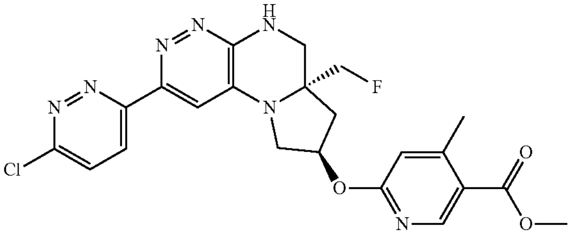 [SMILES: COC(=O)c1cnc(O[C@H]2CN3c4cc(-c5ccc(Cl)nn5)nnc4NC[C@@]3(CF)C2)cc1C]

To (6aR,8R)-2-chloro-6a-(fluoromethyl)-5,6,6a,7,8,9-hexahydropyrrolo[1',2':4,5]pyrazino[2,3-c]pyridazin-8-ol (HCl salt) (250 mg, 0.85 mmol) and methyl 6-fluoro-4-methylnicotinate (430 mg, 2.54 mmol) in THE (10 mL) and DMF (1 mL) was added sodium hydride (60% dispersion in mineral oil; 169 mg, 4.24 mmol) at room temperature. The mixture was stirred at 40° C. for 2 h then allowed to cool to room temperature. The reaction was quenched with a small amount of sat. $NH_4Cl$ (aq) then extracted with DCM (3×). The combined organic layers were washed with brine (1×) then dried with $MgSO_4$, filtered and concentrated. The residue was purified via $SiO_2$ FCC (0-40% EtOAc in hexanes to 100% DCM) to afford methyl 6-(((6aR,8R)-2-chloro-6a-(fluoromethyl)-5,6,6a,7,8,9-hexahydropyrrolo[1',2':4,5]pyrazino[2,3-c]pyridazin-8-yl)oxy)-4-methylnicotinate (quantitative yield assumed) as a yellow-orange oil. LCMS calcd for $C_{18}H_{20}ClFN_5O_3[M+H]^+$: m/z=408.1; Found: 408.0.

Step 3: Methyl 6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methylnicotinate

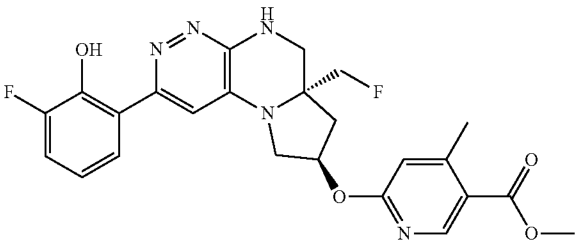 [SMILES: COC(=O)c1cnc(O[C@H]2CN3c4cc(-c5cccc(F)c5O)nnc4NC[C@@]3(CF)C2)cc1C]

A mixture of methyl 6-(((6aR,8R)-2-chloro-6a-(fluoromethyl)-5,6,6a,7,8,9-hexahydro-pyrrolo[1',2':4,5]pyrazino[2,3-c]pyridazin-8-yl)oxy)-4-methylnicotinate (346 mg, 0.85 mmol), 3-fluoro-2-hydroxyphenylboronic acid (396 mg, 2.54 mmol), XPhos Pd G2 (133 mg, 0.17 mmol) and $K_2CO_3$ (585 mg, 4.24 mmol) in 1,4-dioxane (10 mL) and water (2 mL) was sparged with $N_2$ for 2 min. The reaction was stirred at 100° C. for 45 min then allowed to cool to room temperature. The reaction was concentrated to ~½ volume then purified via $SiO_2$ FCC (0-5% MeOH in DCM) to afford methyl 6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methylnicotinate (assumed quantitative yield). LCMS calcd for $C_{24}H_{24}F_2N_5O_4$ $[M+H]^+$: m/z=484.2; Found: 484.0.

Step 4: 2-fluoro-6-((6aR,8R)-6a-(fluoromethyl)-8-((5-(hydroxymethyl)-4-methylpyridin-2-yl)oxy)-5,6,6a, 7,8,9-hexahydropyrrolo[1',2':4,5]pyrazino[2,3-c]pyridazin-2-yl)phenol

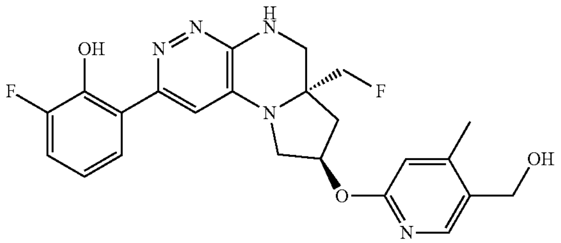 [SMILES: Cc1cc(O[C@H]2CN3c4cc(-c5cccc(F)c5O)nnc4NC[C@@]3(CF)C2)ncc1CO]

To methyl 6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methylnicotinate (410 mg, 0.85 mmol) in THF (20 mL) at 0° C. was added lithium aluminum hydride (1 M in THF; 2.54 mL) slowly. After full conversion was observed by LC-MS, the reaction was quenched with sat. $NH_4Cl$ (aq) then poured into water. The aqueous layer was extracted with 3:1 $CHCl_3$/IPA. The organic layer was washed with brine then dried with $MgSO_4$, filtered and concentrated to afford crude 2-fluoro-6-((6aR,8R)-6a-(fluoromethyl)-8-((5-(hydroxymethyl)-4-methylpyridin-2-yl)oxy)-5,6,6a,7,8,9-hexahydropyrrolo[1',2':4,5]pyrazino[2,3-c]pyridazin-2-yl)phenol (270 mg, 70%) as a brown solid which was used directly without further purification. LCMS calcd for $C_{23}H_{24}F_2N_5O_3[M+H]^+$: m/z=456.2; Found: 456.1.

Step 5: 6-(((6aR,8R)-2-(3-Fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy)-4-methylnicotinaldehyde

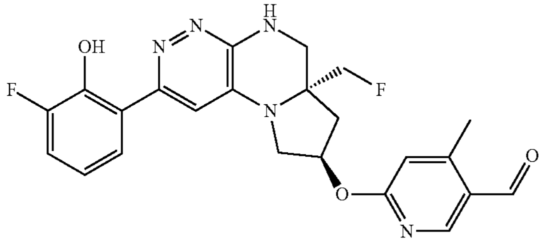 [SMILES: Cc1cc(O[C@H]2CN3c4cc(-c5cccc(F)c5O)nnc4NC[C@@]3(CF)C2)ncc1C=O]

To 2-fluoro-6-((6aR,8R)-6a-(fluoromethyl)-8-((5-(hydroxymethyl)-4-methylpyridin-2-yl)oxy)-5,6,6a,7,8,9-hexahydropyrrolo[1',2':4,5]pyrazino[2,3-c]pyridazin-2-yl)phenol (265 mg, 0.58 mmol) and $Et_3N$ (973 μL, 6.98 mmol) in DMSO (6 mL) was added sulfur trioxide pyridine complex (741 mg, 4.65 mmol). The reaction was stirred at room temperature then poured into 1:1 sat.

$NaHCO_3$ (aq)/water. The aqueous layer was extracted with DCM (3×). The combined organic layers were washed with brine, then dried with $MgSO_4$, filtered and concentrated. The residue was purified via $SiO_2$ FCC (0-10% MeOH in DCM) to afford 6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methylnicotinaldehyde (66 mg, 25%) as a beige solid. LCMS calcd for $C_{23}H_{22}F_2N_5O_3[M+H]^+$: m/z=454.2; Found: 454.1.

Step 6: (S)-3-(6-(4-((6-(((6aR,8R)-2-(3-Fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione A mixture of 6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methylnicotinaldehyde (66 mg, 0.15 mmol), (S)-3-(1-oxo-6-(piperazin-1-yl)isoindolin-2-yl)piperidine-2,6-dione (HCl salt; 133 mg, 0.37 mmol) and N,N-diisopropylethylamine (76 μL, 0.44 mmol) was stirred at 35° C. for 1 hour. Sodium triacetoxyborohydride (155 mg, 0.73 mmol) was added and the reaction was stirred at 35° C. for an additional 1 h then allowed to cool to room temperature. Dilution with DMSO and a small amount of a water/MeCN/TFA mixture, followed by filtration through a 0.2 μm PTFE syringe filter and subsequent purification by prep-HPLCMS (Waters CSH-C18, 5 μm, 30×100 mm, 16.0-23.0% MeCN/water (containing 0.1% TFA) over 5 min) gave the TFA salt of the title compound (18.2 mg, 12.5% yield) as a white solid. LCMS calcd for $C_{40}H_{42}F_2N_9O_5[M+H]^+$: m/z=766.3; Found: 765.9. $^1H$ NMR (400 MHz, MeOD) δ 8.35-8.27 (m, 1H), 7.51 (d, J=8.2 Hz, 1H), 7.44-7.28 (m, 4H), 7.00 (td, J=8.0, 4.8 Hz, 1H), 6.95 (s, 1H), 6.82 (s, 1H), 5.97-5.84 (m, 1H), 5.14 (dd, J=13.4, 5.2 Hz, 1H), 4.68-4.25 (m, 7H), 3.96-3.81 (m, 2H), 3.58-3.49 (m, 3H), 3.01-2.84 (m, 2H), 2.84-2.74 (m, 1H), 2.56-2.41 (m, 4H), 2.25-2.10 (m, 2H). Note: some protons hidden due to overlap with water or NMR solvent peaks.

Example 59: 5-((4-(2-((S)-2,6-dioxopiperidin-3-yl)-3-oxoisoindolin-5-yl)piperazin-1-yl)methyl)-2-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-6-methylnicotinonitrile

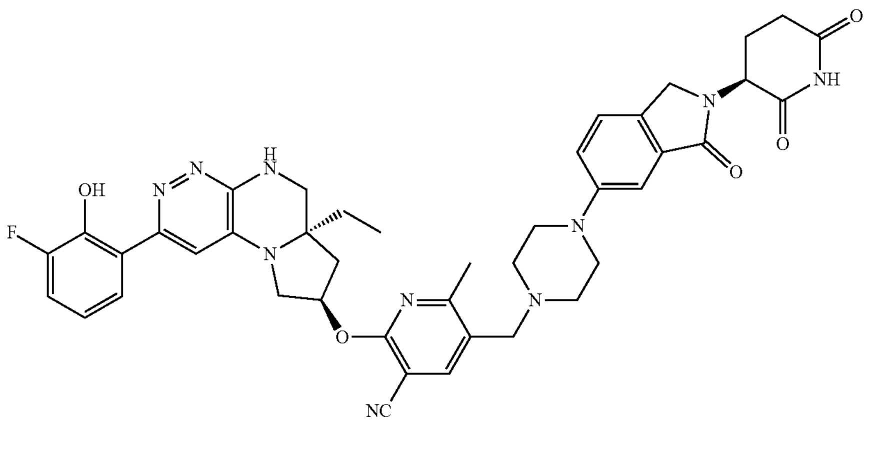 [SMILES: CC[C@@]12CNc3nnc(-c4cccc(F)c4O)cc3N1C[C@H](Oc1nc(C)c(CN3CCN(c4ccc5c(c4)C(=O)N([C@H]4CCC(=O)NC4=O)C5)CC3)cc1C#N)C2]

Step 1: 6-methyl-2-oxo-5-vinyl-1,2-dihydropyridine-3-carbonitrile

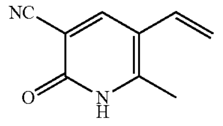

A mixture of 5-bromo-6-methyl-2-oxo-1,2-dihydropyridine-3-carbonitrile (100 mg, 0.469 mmol), 4,4,5,5-tetramethyl-2-vinyl-1,3,2-dioxaborolane (0.24 mL, 1.41 mmol), XPhos Pd G2 (74 mg, 0.094 mmol) and $K_2CO_3$ (327 mg, 2.37 mmol) in 1,4-dioxane (4 mL) and water (1 mL) was sparged with $N_2$ for 2 min then stirred at 100° C. for 1 h. The reaction was allowed to cool to room temperature then purified directly via $SiO_2$ FCC (0-100% EtOAc/hexanes) to give 6-methyl-2-oxo-5-vinyl-1,2-dihydropyridine-3-carbonitrile (83 mg, 110%) as a yellow solid. LCMS calcd for $C_9H_9N_2O$ $[M+H]^+$: m/z=161.1; Found: 160.9.

Step 2: 2-(((6aR,8R)-2-chloro-6a-ethyl-5,6,6a, 7,8, 9-hexahydropyrrolo[1',2':4,5]pyrazino[2,3-c] pyridazin-8-yl)oxy)-6-methyl-5-vinylnicotinonitrile

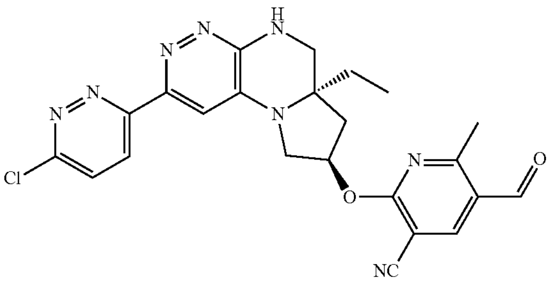 [SMILES: CC[C@@]12CNc3nnc(-c4ccc(Cl)nn4)cc3N1C[C@H](Oc1nc(C)c(C=O)cc1C#N)C2]

To a mixture of (6aR,8S)-2-chloro-6a-ethyl-5,6,6a,7,8,9-hexahydropyrrolo[1',2':4,5]pyrazino[2,3-c]pyridazin-8-ol (20 mg, 0.079 mmol), 5-bromo-6-methyl-2-oxo-1,2-dihydropyridine-3-carbonitrile (19 mg, 0.12 mmol) and $PPh_3$ (100-200 mesh, ~1.6 mmol/g loading; 76 mg, 0.12 mmol) in THE (1.5 mL) was added diisopropyl azodicarboxylate (23 uL, 0.12 mmol). The reaction was stirred at 60° C. for 30 min then allowed to cool to room temperature, at which point a small amount of water was added. The mixture was filtered through a 0.45 um PTFE fritted filter. The filtrate was purified via $SiO_2$ FCC (0-15% MeOH in DCM) to give 2-(((6aR,8R)-2-chloro-6a-ethyl-5,6,6a,7,8,9-hexahydropyrrolo[1',2':4,5]pyrazino[2,3-c]pyridazin-8-yl)oxy)-6-methyl-5-vinylnicotinonitrile (35 mg, 113%) as a clear oil. LCMS calcd for $C_{20}H_{22}ClN_6O$ $[M+H]^+$: m/z=397.2; Found: 397.1.

Step 3: 2-(((6aR,8R)-6a-ethyl-2-(3-fluoro-2-hydroxyphenyl)-5,6,6a, 7,8,9-hexahydropyrrolo[1',2':4,5]pyrazino[2,3-c]pyridazin-8-yl)oxy)-6-methyl-5-vinylnicotinonitrile

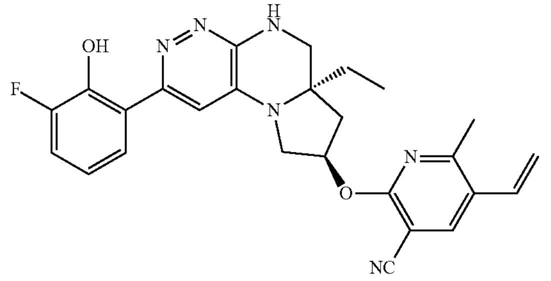 [SMILES: C=Cc1cc(C#N)c(O[C@H]2CN3c4cc(-c5cccc(F)c5O)nnc4NC[C@@]3(CC)C2)nc1C]

A mixture of 2-(((6aR,8R)-2-chloro-6a-ethyl-5,6,6a,7,8,9-hexahydropyrrolo[1',2':4,5]pyrazino[2,3-c]pyridazin-8-yl)oxy)-6-methyl-5-vinylnicotinonitrile (35 mg, 0.089 mmol), (2-hydroxy-3-methylphenyl)boronic acid (42 mg, 0.27 mmol), XPhos Pd G2 (14 mg, 0.018 mmol) and $K_2CO_3$ (62 mg, 0.45 mmol) in 1,4-dioxane (1.2 mL) and water (0.3 mL) was sparged with $N_2$ for 2 min. The reaction was stirred at 100° C. for 15 min then cooled to room temperature and purified via $SiO_2$ FCC (0-10%0 MeOH in DCM) to give 2-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-6-methyl-5-vinylnicotinonitrile (~70%0 purity; 39 mg, 920%) as an orange oil. LCMS calcd for $C_{26}H_{26}FN_6O_2$ $[M+H]^+$: m/z=473.2; Found: 473.1.

Step 4: 2-(((6aR,8R)-6a-ethyl-2-(3-fluoro-2-hydroxyphenyl)-5,6,6a, 7,8,9-hexahydropyrrolo[1',2':4,5]pyrazino[2,3-c]pyridazin-8-yl)oxy)-5-formyl-6-methylnicotinonitrile

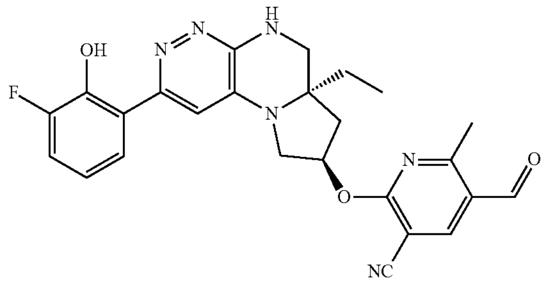 [SMILES: CC[C@@]12CNc3nnc(-c4cccc(F)c4O)cc3N1C[C@H](Oc1nc(C)c(C=O)cc1C#N)C2]

To 2-(((6aR,8R)-6a-ethyl-2-(3-fluoro-2-hydroxyphenyl)-5,6,6a,7,8,9-hexahydro-pyrrolo[1',2':4,5]pyrazino[2,3-c]pyridazin-8-yl)oxy)-6-methyl-5-vinylnicotinonitrile (~70% purity; 39 mg, 0.057 mmol) and $NaIO_4$ (34 mg, 0.16 mmol) in THE (1.5 mL) and water (0.5 mL) was added $OsO_4$ (4% in water; 36 μL, 0.057 mmol). The reaction was stirred at room temperature overnight then poured into ~1:1 brine/water. The aqueous layer was extracted with DCM (3×). The combine organic layers were washed with brine (1×), dried with $MgSO_4$, filtered then concentrated to give 2-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-5-formyl-6-methylnicotinonitrile (assumed quantitative yield) which was used directly without further purification. LCMS calcd for $C_{25}H_{24}FN_6O_3[M+H]^+$: m/z=475.2; Found: 475.1.

Step 5: 5-((4-(2-((S)-2,6-dioxopiperidin-3-yl)-3-oxoisoindolin-5-yl)piperazin-1-yl)methyl)-2-(((6aR,8R)-6a-ethyl-2-(3-fluoro-2-hydroxyphenyl)-5,6,6a,7,8,9-hexahydropyrrolo [1',2':4,5]pyrazino[2,3-c]pyridazin-8-yl)oxy)-6-methylnicotinonitrile To 2-(((6aR,8R)-6a-ethyl-2-(3-fluoro-2-hydroxyphenyl)-5,6,6a,7,8,9-hexahydropyrrolo [1',2':4,5]pyrazino[2,3-c]pyridazin-8-yl)oxy)-5-formyl-6-methylnicotinonitrile (27 mg, 0.057 mmol) and (S)-3-(1-oxo-6-(piperazin-1-yl)isoindolin-2-yl)piperidine-2,6-dione (HCl salt; 28 mg, 0.077 mmol) in DMSO (1 mL) was added N,N-diisopropylethylamine (30 uL, 0.17 mmol). The reaction was sonicated briefly, stirred at room temperature for 1 h, then treated with $NaBH(OAc)_3$ (36 mg, 0.17 mmol). The reaction was stirred at 35° C. for 4 h, after which additional $NaBH(OAc)_3$ (24 mg, 0.11 mmol) was added. After stirring overnight at 35° C., the reaction was allowed to cool to room temperature, diluted with DMSO then purified via prep-HPLCMS (Waters CSH Fluoro-Phenyl, 5 μm, 30×100 mm, 10.1-30.1% MeCN/water (containing 0.1% TFA) over 5 min) to give the TFA salt of the title compound (4 mg, 7%) as a white solid. LCMS calcd for $C_{42}H_{44}FN_{10}O_5[M+H]^+$: m/z=787.3; Found: 787.3.

Example 60: 3-(6-(4-((6-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)thio)-4-methylpyridin-3-yl)methyl)piperazin-1-yl)-1-oxoisoindolin-2-yl)piperidine-2,6-dione

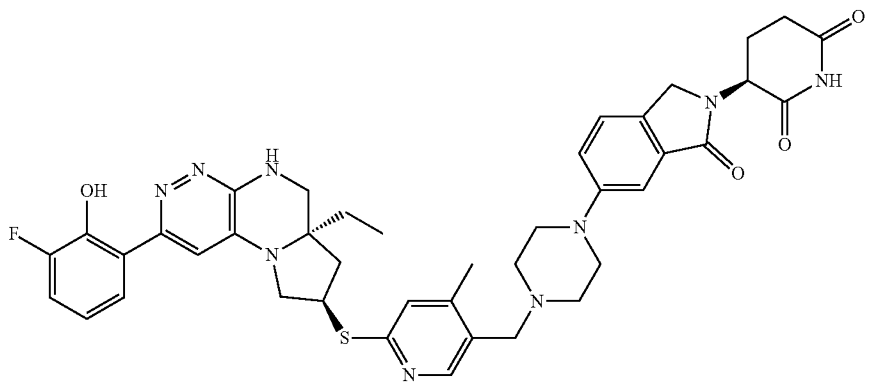

Step 1: methyl 4-methyl-6-thioxo-1,6-dihydropyridine-3-carboxylate

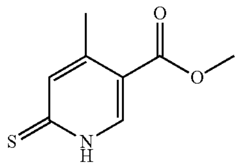

A mixture of methyl 4-methyl-6-oxo-1,6-dihydropyridine-3-carboxylate (100 mg, 0.60 mmol) and 2,4-bis(4-methoxyphenyl)-1,3,2,4-dithiadiphosphetane 2,4-disulfide (145 mg, 0.359 mmol) in toluene (3 mL) was stirred at 100° C. for 19 h. The reaction was allowed to cool to room temperature and directly purified via $SiO_2$ FCC (0-100% EtOAc in hexanes then 0-15% MeOH in DCM) to afford methyl 4-methyl-6-thioxo-1,6-dihydropyridine-3-carboxylate (52 mg, 47%). LCMS calcd for $C_8H_{10}NO_2S$ $[M+H]^+$: m/z=184.0; Found: 183.9.

Step 2: methyl 6-(((6aR,8R)-2-chloro-6a-ethyl-5,6,6a, 7,8,9-hexahydropyrrolo[1',2':4,5]pyrazino[2,3-c]pyridazin-8-yl)thio)-4-methylnicotinate

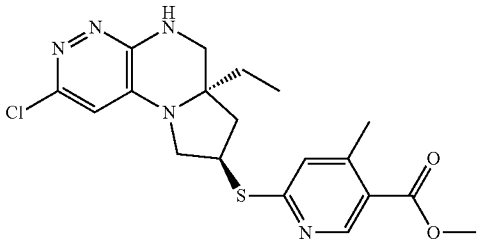 [SMILES: CC[C@@]12CNc3nnc(Cl)cc3N1C[C@H](Sc1cc(C)c(C(=O)OC)cn1)C2]

To a mixture of (6aR,8S)-2-chloro-6a-ethyl-5,6,6a,7,8,9-hexahydropyrrolo[1',2':4,5]pyrazino[2,3-c]pyridazin-8-ol (20 mg, 0.079 mmol), methyl 4-methyl-6-thioxo-1,6-dihydropyridine-3-carboxylate (22 mg, 0.12 mmol) and $PPh_3$ (100-200 mesh, ~1.6 mmol/g loading; 83 mg, 0.13 mmol) in THE (1.5 mL) was added diisopropyl azodicarboxylate (26 μL, 0.13 mmol). The reaction was stirred at 65° C. for 75 min, after which additional $PPh_3$ (100-200 mesh, ~1.6 mmol/g loading; 25 mg, 0.039 mmol) then diisopropyl azodicarboxylate (7.7 μL, 0.039 mmol) were added. The mixture was stirred for an additional 20 min then allowed to cool to room temperature. The reaction was quenched with a small amount of water, filtered through a 0.45 μm PTFE fritted filter, then purified via $SiO_2$ FCC (0-15% MeOH in DCM) to give methyl 6-(((6aR,8R)-2-chloro-6a-ethyl-5,6,6a,7,8,9-hexahydropyrrolo[1',2':4,5]pyrazino[2,3-c]pyridazin-8-yl)thio)-4-methylnicotinate (42 mg, 126%) as a clear oil. LCMS calcd for $C_{19}H_{23}ClN_5O_2S$ $[M+H]^+$: m/z=420.1; Found: 420.1.

Step 3: methyl 6-(((6aR,8R)-6a-ethyl-2-(3-fluoro-2-hydroxyphenyl)-5,6,6a, 7,8,9-hexahydropyrrolo[1', 2':4,5]pyrazino[2,3-c]pyridazin-8-yl)thio)-4-methylnicotinate

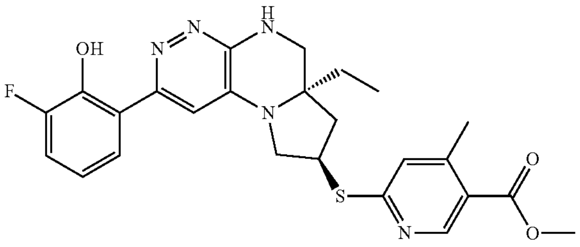

A mixture of methyl 6-(((6aR,8R)-2-chloro-6a-ethyl-5,6,6a,7,8,9-hexahydropyrrolo [1',2':4,5]pyrazino[2,3-c]pyridazin-8-yl)thio)-4-methylnicotinate (33 mg, 0.079 mmol), (2-hydroxy-3-methylphenyl)boronic acid (40 mg, 0.26 mmol), XPhos Pd G2 (13 mg, 0.017 mmol) and $K_2CO_3$ (64 mg, 0.46 mmol) in 1,4-dioxane (1.2 mL) and water (0.3 mL) was sparged with $N_2$ for 2 min. The reaction was stirred at 100° C. for 2 h then allowed to cool to room temperature, at which point additional (2-hydroxy-3-methylphenyl)boronic acid (40 mg, 0.26 mmol), XPhos Pd G2 (13 mg, 0.017 mmol), $K_2CO_3$ (60 mg, 0.43 mmol) and 1,4-dioxane (1 mL) were added. The reaction was sparged with $N_2$ for 1 min then stirred at 100° C. for 45 min. The reaction mixture was allowed to cool to room temperature and subsequently purified via $SiO_2$ FCC (0-10% MeOH in DCM) to give methyl 6-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)thio)-4-methylnicotinate (assumed quantitative yield). LCMS calcd for $C_{25}H_{27}FN_5O_3S$ $[M+H]^+$: m/z=496.2; Found: 496.1.

Step 4: 2-((6aR,8R)-6a-ethyl-8-((5-(hydroxymethyl)-4-methylpyridin-2-yl)thio)-5,6,6a,7,8,9-hexahydropyrrolo[1',2':4,5]pyrazino[2,3-c]pyridazin-2-yl)-6-fluorophenol

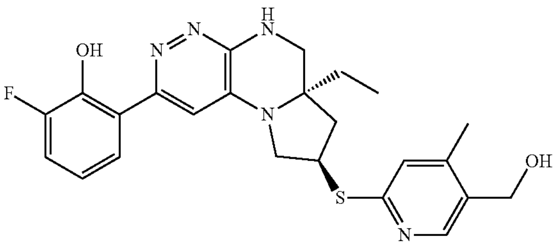 [SMILES: CC[C@@]12CNc3nnc(-c4cccc(F)c4O)cc3N1C[C@H](Sc1cc(C)c(CO)cn1)C2]

To methyl 6-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)thio)-4-methylnicotinate (39 mg, 0.079 mmol) in THF (2 mL) at 0° C. was added $LiAlH_4$ (1 M in THF; 235 uL, 0.235 mmol) dropwise. The reaction was stirred at 0° C. for 15 min then slowly quenched with sat. $NH_4Cl$ (aq) and poured into water. The aqueous layer was extracted with DCM (3×) and the combined organic layers were dried with $MgSO_4$, filtered then concentrated to give 2-((6aR,8R)-6a-ethyl-8-((5-(hydroxymethyl)-4-methylpyridin-2-yl)thio)-5,6,6a,7,8,9-hexahydropyrrolo[1',2':4,5]pyrazino[2,3-c]pyridazin-2-yl)-6-fluorophenol (assumed quantitative yield) which was used directly without further purification. LCMS calcd for $C_{24}H_{27}FN_5O_2S$ $[M+H]^+$: m/z=468.2; Found: 468.1.

Step 5: 2-((6aR,8R)-8-((5-(chloromethyl)-4-methylpyridin-2-yl)thio)-6a-ethyl-5,6,6a, 7,8,9-hexahydropyrrolo[1',2':4,5]pyrazino[2,3-c]pyridazin-2-yl)-6-fluorophenol

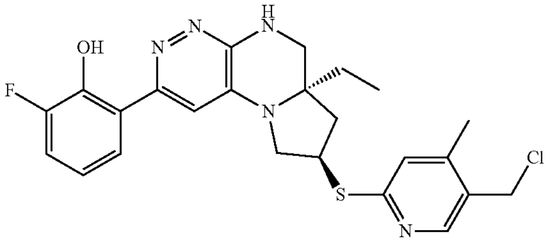

To 2-((6aR,8R)-6a-ethyl-8-((5-(hydroxymethyl)-4-methylpyridin-2-yl)thio)-5,6,6a,7,8,9-hexahydropyrrolo[1',2':4,5]pyrazino[2,3-c]pyridazin-2-yl)-6-fluorophenol (37 mg, 0.079 mmol) in THF (2 mL) was added $SOCl_2$ (29 μL, 0.39 mmol). The reaction was stirred at room temperature until full conversion observed by LC-MS (<1 h). The reaction was quenched with sat. $NaHCO_3$ (aq) then poured into water. The aqueous phase was extracted with DCM (3×), dried with $MgSO_4$, filtered then concentrated to give 2-((6aR,8R)-8-((5-(chloromethyl)-4-methylpyridin-2-yl)thio)-6a-ethyl-5,6,6a,7,8,9-hexahydropyrrolo[1',2':4,5]pyrazino[2,3-c]pyridazin-2-yl)-6-fluorophenol (assumed quantitative yield) which was used directly without further purification. LCMS calcd for $C_{24}H_{26}ClFN_5OS$ $[M+H]^+$: m/z=486.2; Found: 486.1.

Step 6: 3-(6-(4-((6-(((6aR,8R)-6a-ethyl-2-(3-fluoro-2-hydroxyphenyl)-5,6,6a, 7,8,9-hexahydropyrrolo[1',2':4,5]pyrazino[2,3-c]pyridazin-8-yl)thio)-4-methylpyridin-3-yl)methyl)piperazin-1-yl)-1-oxoisoindolin-2-yl)piperidine-2,6-dione To a vial containing 2-((6aR,8R)-8-((5-(chloromethyl)-4-methylpyridin-2-yl)thio)-6a-ethyl-5,6,6a,7,8,9-hexahydropyrrolo[1',2':4,5]pyrazino[2,3-c]pyridazin-2-yl)-6-fluorophenol (38 mg, 0.079 mmol) was added MeCN (2 mL), (S)-3-(1-oxo-6-(piperazin-1-yl)isoindolin-2-yl)piperidine-2,6-dione (HCl salt; 28 mg, 0.077 mmol) and N,N-diisopropylethylamine (68 μL, 0.39 mmol). The reaction was stirred at 120° C. for 40 min then allowed to cool to room temperature and subsequently diluted with DMSO and a minimal amount of TFA. Purification via prep-HPLCMS (Waters CSH Phenyl-Hexyl, 5 μm, 30×100 mm, 10.9-30.9% MeCN/water (containing 0.1% TFA) over 5 min then Waters CSH Fluoro-Phenyl, 5 μm, 30×100 mm, 11.8-31.8% MeCN/water (containing 0.1% TFA) over 5 min) afforded the TFA salt of the title compound (1.6 mg, 2%) as a white solid. LCMS calcd for $C_{41}H_{45}FN_9O_4S$ $[M+H]^+$: m/z=778.3; Found: 778.2.

Example 61: 3-(6-(4-((6-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-5-fluoro-4-methylpyridin-3-yl)methyl)piperazin-1-yl)-1-oxoisoindolin-2-yl)piperidine-2,6-dione

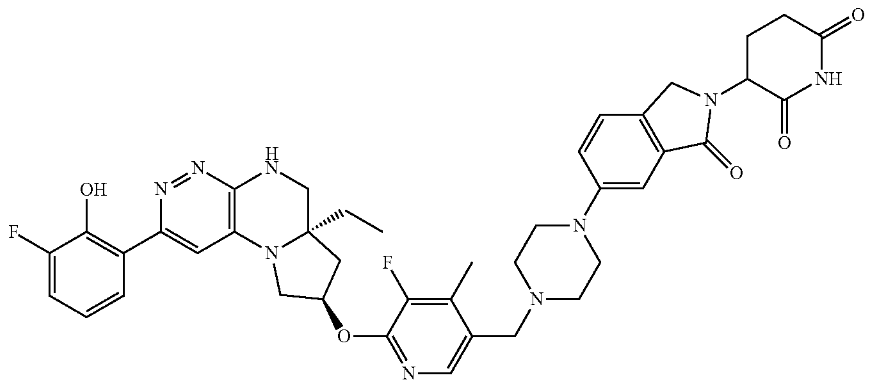 [SMILES: CC[C@@]12CNc3nnc(-c4cccc(F)c4O)cc3N1C[C@H](Oc1ncc(CN3CCN(c4ccc5c(c4)C(=O)N(C4CCC(=O)NC4=O)C5)CC3)c(C)c1F)C2]

Step 1: methyl 6-(((6aR,8R)-2-chloro-6a-ethyl-5,6,6a, 7,8,9-hexahydropyrrolo[1',2':4,5]pyrazino[2,3-c]pyridazin-8-yl)oxy)-5-fluoro-4-methylnicotinate

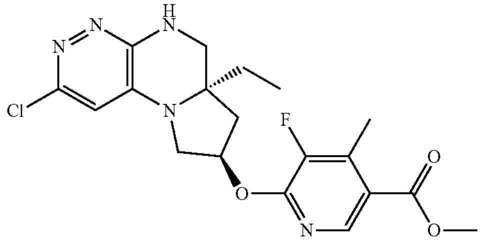

To a mixture of (6aR,8S)-2-chloro-6a-ethyl-5,6,6a,7,8,9-hexahydropyrrolo[1',2':4,5]pyrazino[2,3-c]pyridazin-8-ol (15 mg, 0.057 mmol), methyl 5-fluoro-4-methyl-6-oxo-1,6-dihydropyridine-3-carboxylate (17 mg, 0.090 mmol) and $PPh_3$ (100-200 mesh, ~1.6 mmol/g loading; 53 mg, 0.085 mmol) in THE (2 mL) was added diisopropyl azodicarboxylate (17 μL, 0.085 mmol). The reaction was stirred at 65° C. for 35 min, after which additional $PPh_3$ (100-200 mesh, ~1.6 mmol/g loading; 53 mg, 0.085 mmol) then diisopropyl azodicarboxylate (17 μL, 0.085 mmol) were added. The mixture was stirred for an additional 15 min at 65° C. then allowed to cool to room temperature. The reaction was quenched with a small amount of water, filtered, then purified via $SiO_2$ FCC (0-10% MeOH in DCM) to give methyl 6-(((6aR,8R)-2-chloro-6a-ethyl-5,6,6a,7,8,9-hexahydropyrrolo[1',2':4,5]pyrazino[2,3-c]pyridazin-8-yl)oxy)-5-fluoro-4-methylnicotinate (28 mg, 117%). LCMS calcd for $C_{19}H_{22}ClFN_5O_3[M+H]^+$: m/z=422.1; Found: 422.1.

Step 2: methyl 6-(((6aR,8R)-6a-ethyl-2-(3-fluoro-2-methoxyphenyl)-5,6,6a, 7,8,9-hexahydropyrrolo[1',2':4,5]pyrazino[2,3-c]pyridazin-8-yl)oxy)-5-fluoro-4-methylnicotinate

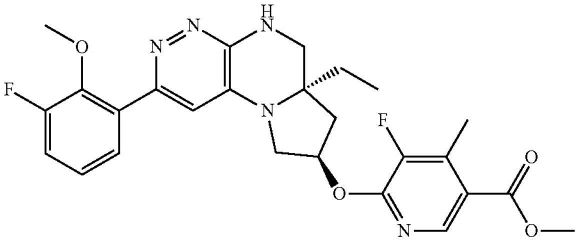

A mixture of methyl 6-(((6aR,8R)-2-chloro-6a-ethyl-5,6,6a,7,8,9-hexahydropyrrolo [1',2':4,5]pyrazino[2,3-c]pyridazin-8-yl)oxy)-5-fluoro-4-methylnicotinate (24 mg, 0.057 mmol), (3-fluoro-2-methoxyphenyl)boronic acid (29 mg, 0.17 mmol), dichloro-1,1'-bisdiphenyl-phosphino)ferrocene palladium (II) dichloromethane (14 mg, 0.017 mmol) and $K_2CO_3$ (39 mg, 0.28 mmol) in 1,4-dioxane (1 mL) and water (0.25 mL) was sparged with $N_2$ for 5 min. The reaction was stirred at 100° C. for 30 min then allowed to cool to room temperature and purified via $SiO_2$ FCC (0-10% MeOH in DCM) to give methyl 6-(((6aR,8R)-6a-ethyl-2-(3-fluoro-2-methoxyphenyl)-5,6,6a,7,8,9-hexahydropyrrolo[1',2':4,5]pyrazino[2,3-c]pyridazin-8-yl)oxy)-5-fluoro-4-methylnicotinate (7.9 mg, 27%). LCMS calcd for $C_{26}H_{28}F_2N_5O_4[M+H]^+$: m/z=512.2; Found: 512.1.

Step 3: (6-(((6aR,8R)-6a-ethyl-2-(3-fluoro-2-methoxyphenyl)-5,6,6a, 7,8,9-hexahydropyrrolo[1',2':4,5]pyrazino[2,3-c]pyridazin-8-yl)oxy)-5-fluoro-4-methylpyridin-3-yl)methanol

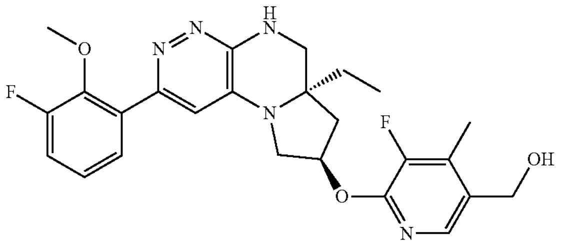 [SMILES: CC[C@@]12CNc3nnc(-c4cccc(F)c4OC)cc3N1C[C@H](Oc1ncc(CO)c(C)c1F)C2]

To methyl 6-(((6aR,8R)-6a-ethyl-2-(3-fluoro-2-methoxyphenyl)-5,6,6a,7,8,9-hexahydropyrrolo[1',2':4,5]pyrazino[2,3-c]pyridazin-8-yl)oxy)-5-fluoro-4-methylnicotinate (7.9 mg, 0.015 mmol) in THE (1 mL) at 0° C. was added $LiAlH_4$ (1 M in THF; 40 uL, 0.040 mmol) dropwise. The reaction was stirred at 0° C. for 20 min, at which point additional $LiAlH_4$ (1 M in THF; 20 uL, 0.020 mmol) was added. After stirring for an additional 5 min, the reaction was quenched with sat. $NH_4Cl$ (aq) then poured into water and extracted with DCM (3×). The combined organic layers were washed with brine (1×) then dried with $MgSO_4$, filtered, and concentrated to afford (6-(((6aR,8R)-6a-ethyl-2-(3-fluoro-2-methoxyphenyl)-5,6,6a,7,8,9-hexahydropyrrolo[1',2':4,5]pyrazino[2,3-c]pyridazin-8-yl)oxy)-5-fluoro-4-methylpyridin-3-yl)methanol (assumed quantitative yield) which was used directly without further purification. LCMS calcd for $C_{25}H_{28}F_2N_5O_3$[M+H]$^+$: m/z=484.2; Found: 484.1.

Step 4: 2-((6aR,8R)-8-((5-(chloromethyl)-3-fluoro-4-methylpyridin-2-yl)oxy)-6a-ethyl-5,6,6a, 7,8,9-hexahydropyrrolo[1',2':4,5]pyrazino[2,3-c]pyridazin-2-yl)-6-fluorophenol

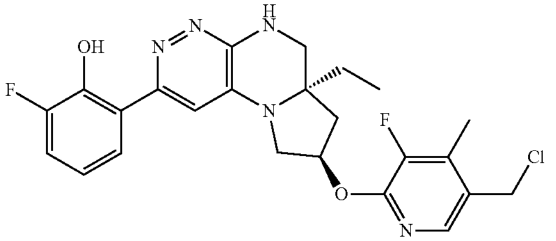 [SMILES: CC[C@@]12CNc3nnc(-c4cccc(F)c4O)cc3N1C[C@H](Oc1ncc(CCl)c(C)c1F)C2]

To (6-(((6aR,8R)-6a-ethyl-2-(3-fluoro-2-methoxyphenyl)-5,6,6a,7,8,9-hexahydropyrrolo [1',2':4,5]pyrazino[2,3-c]pyridazin-8-yl)oxy)-5-fluoro-4-methylpyridin-3-yl) methanol (7.5 mg, 0.015 mmol) in DCM (2 mL) was added $BCl_3$ (1 M in DCM; 1.4 mL, 1.4 mmol). The reaction was stirred at room temperature for 19 h then cooled to 0° C. and quenched with water. The mixture was neutralized with sat. $NaHCO_3$ (aq) then extracted with DCM (3×). The combined DCM layers were washed with brine (1×), dried with $MgSO_4$, filtered then concentrated to give a residue which was taken up in THE (2 mL) then treated with $SOCl_2$ (3.5 µL, 0.048 mmol). The reaction was stirred at room temperature for 20 min then neutralized with sat. $NaHCO_3$ (aq) and extracted with DCM (3×).

The combined DCM layers were washed with brine (1×), dried with $MgSO_4$, filtered then concentrated to give 2-((6aR,8R)-8-((5-(chloromethyl)-3-fluoro-4-methylpyridin-2-yl)oxy)-6a-ethyl-5,6,6a,7,8,9-hexahydropyrrolo[1',2':4,5]pyrazino[2,3-c]pyridazin-2-yl)-6-fluorophenol (assumed quantitative yield) which was used directly without further purification. LCMS calcd for $C_{24}H_{25}ClF_2N_5O_2$ [M+H]$^+$: m/z=488.2; Found: 488.1.

Step 6: 3-(6-(4-((6-(((6aR,8R)-6a-ethyl-2-(3-fluoro-2-hydroxyphenyl)-5,6,6a, 7,8,9-hexahydropyrrolo [1',2':4,5]pyrazino[2,3-c]pyridazin-8-yl)oxy)-5-fluoro-4-methylpyridin-3-yl)methyl)piperazin-1-yl)-1-oxoisoindolin-2-yl)piperidine-2,6-dione To 2-((6aR,8R)-8-((5-(chloromethyl)-3-fluoro-4-methylpyridin-2-yl)oxy)-6a-ethyl-5,6,6a,7,8,9-hexahydropyrrolo [1',2':4,5]pyrazino[2,3-c]pyridazin-2-yl)-6-fluorophenol (6.3 mg, 0.013 mmol) and (S)-3-(1-oxo-6-(piperazin-1-yl) isoindolin-2-yl)piperidine-2,6-dione (HCl salt; 14 mg, 0.039 mmol) in MeCN (1 mL) was added N,N-diisopropylethylamine (18 µL, 0.10 mmol). The reaction was stirred at 120° C. for 30 min then allowed to cool to room temperature, subsequently diluted with DMSO and purified via prep-HPLCMS (Waters CSH-C18, 5 µm, 30×100 mm, 13.2-33.2% MeCN/water (containing 0.1% TFA) over 5 min) to give the TFA salt of the title compound (1.6 mg, 12%). LCMS calcd for $C_{41}H_{44}F_2N_9O_5$[M+H]$^+$: m/z=780.3; Found: 780.3.

Example 62: 3-(6-(4-((6-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-2,4-dimethylpyridin-3-yl)methyl)piperazin-1-yl)-1-oxoisoindolin-2-yl)piperidine-2,6-dione

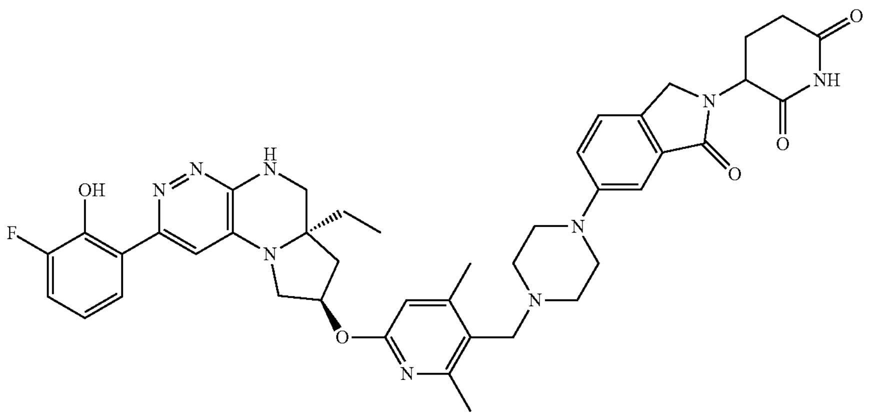 [SMILES: CC[C@@]12CNc3nnc(-c4cccc(F)c4O)cc3N1C[C@H](Oc1cc(C)c(CN3CCN(c4ccc5c(c4)C(=O)N(C4CCC(=O)NC4=O)C5)CC3)c(C)n1)C2]

Step 1: ethyl 6-fluoro-2,4-dimethylnicotinate

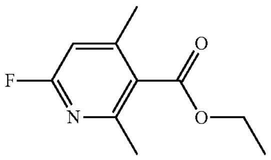

To CsF (355 mg, 2.34 mmol) in DMSO (2 mL) was added ethyl 6-chloro-2,4-dimethylnicotinate (100 mg, 0.083 mmol). The reaction was stirred at 120° C. for 25 min then at 150° C. for 1.5 h. The reaction was allowed to cool to room temperature then directly purified via $SiO_2$ FCC (0-50% EtOAc in hexanes) to give ethyl 6-fluoro-2,4-dimethylnicotinate (contaminated with starting material; 68 mg, 74%) as a clear oil. LCMS calcd for $C_{10}H_{13}FNO_2$ $[M+H]^+$: m/z=198.1; Found: 198.0.

Step 2: ethyl 6-(((6aR,8R)-6a-ethyl-2-(3-fluoro-2-methoxyphenyl)-5,6,6a, 7,8,9-hexahydropyrrolo[1', 2':4,5]pyrazino[2,3-c]pyridazin-8-yl)oxy)-2,4-dimethylnicotinate

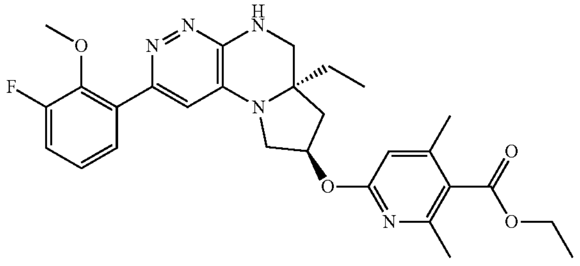 [SMILES: CCOC(=O)c1c(C)cc(O[C@H]2CN3c4cc(-c5cccc(F)c5OC)nnc4NC[C@@]3(CC)C2)nc1C]

To (6aR,8R)-6a-ethyl-2-(3-fluoro-2-methoxyphenyl)-5,6,6a,7,8,9-hexahydropyrrolo [1',2':4,5]pyrazino[2,3-c]pyridazin-8-ol (20 mg, 0.058 mmol) and methyl 5-fluoro-4-methyl-6-oxo-1,6-dihydropyridine-3-carboxylate (25 mg, 0.13 mmol) in DMF (1 mL) was added NaH (60% dispersion in mineral oil; 12 mg, 0.29 mmol). The reaction was stirred at 60° C. for 30 min, after which additional DMF (1 mL) was added. The reaction was stirred for an additional 30 min at 60° C., after which additional DMF (1 mL) was added. The reaction was stirred for 10 min at 60° C., allowed to cool briefly, then treated with additional NaH (60% dispersion in mineral oil; 12 mg, 0.29 mmol). The reaction was stirred for 1 h at 60° C., allowed to cool to room temperature, then quenched with sat. $NH_4Cl$ (aq) and purified via $SiO_2$ FCC (0-15% MeOH in DCM) to give ethyl 6-(((6aR,8R)-6a-ethyl-2-(3-fluoro-2-methoxyphenyl)-5,6,6a,7,8,9-hexahydropyrrolo[1',2':4,5]pyrazino[2,3-c]pyridazin-8-yl)oxy)-2,4-dimethylnicotinate (assumed quantitative yield) as a clear film. LCMS calcd for $C_{28}H_{33}FN_5O_4$ $[M+H]^+$: m/z=522.3; Found: 522.2.

Step 3: (6-(((6aR,8R)-6a-ethyl-2-(3-fluoro-2-methoxyphenyl)-5,6,6a, 7,8,9-hexahydro-pyrrolo[1', 2':4,5]pyrazino[2,3-c]pyridazin-8-yl)oxy)-2,4-dimethylpyridin-3-yl)methanol

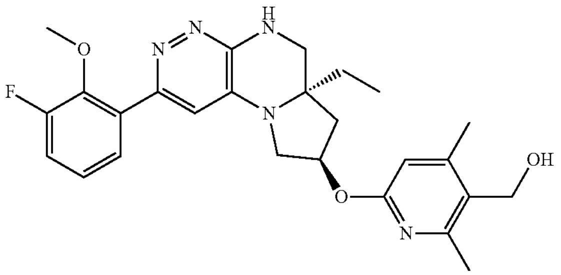 [SMILES: CC[C@@]12CNc3nnc(-c4cccc(F)c4OC)cc3N1C[C@H](Oc1cc(C)c(CO)c(C)n1)C2]

To ethyl 6-(((6aR,8R)-6a-ethyl-2-(3-fluoro-2-methoxyphenyl)-5,6,6a,7,8,9-hexahydropyrrolo[1',2':4,5]pyrazino[2,3-c]pyridazin-8-yl)oxy)-2,4-dimethylnicotinate (30 mg, 0.058 mmol) in THE (1 mL) at 0° C. was added $LiAlH_4$ (1 M in THF; 0.17 mL, 0.17 mmol) dropwise. The reaction was stirred at 0° C. for 75 min then quenched with sat. $NH_4Cl$ (aq), poured into water then extracted with DCM (3×). The combined organic layers were washed with brine (1×), dried with $MgSO_4$, filtered then concentrated. The residue was purified via $SiO_2$ FCC (0-15% MeOH in DCM) to afford (6-(((6aR,8R)-6a-ethyl-2-(3-fluoro-2-methoxyphenyl)-5,6,6a,7,8,9-hexahydropyrrolo[1',2':4,5]pyrazino[2,3-c]pyridazin-8-yl)oxy)-2,4-dimethylpyridin-3-yl)methanol (16 mg, 58%). LCMS calcd for $C_{26}H_{31}FN_5O_3$$[M+H]^+$: m/z=480.2; Found: 480.2.

Step 4: 2-((6aR,8R)-8-((5-(chloromethyl)-4,6-dimethylpyridin-2-yl)oxy)-6a-ethyl-5,6,6a, 7,8,9-hexahydropyrrolo[1',2':4,5]pyrazino[2,3-c]pyridazin-2-yl)-6-fluorophenol

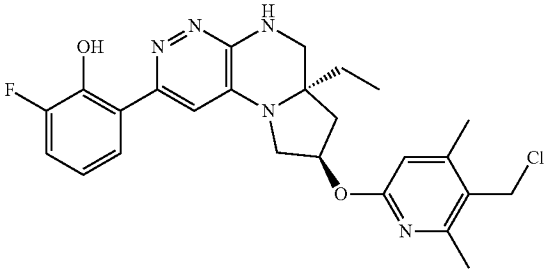 [SMILES: CC[C@@]12CNc3nnc(-c4cccc(F)c4O)cc3N1C[C@H](Oc1cc(C)c(CCl)c(C)n1)C2]

To (6-(((6aR,8R)-6a-ethyl-2-(3-fluoro-2-methoxyphenyl)-5,6,6a,7,8,9-hexahydro-pyrrolo[1',2':4,5]pyrazino[2,3-c]pyridazin-8-yl)oxy)-2,4-dimethylpyridin-3-yl)methanol (16 mg, 0.034 mmol) in DCM (3 mL) was added $BCl_3$ (1 M in DCM; 3.0 mL, 3.0 mmol). The reaction was stirred at room temperature for 45 h then cooled to 0° C. and quenched with water. The mixture was neutralized with sat. $NaHCO_3$ (aq) then extracted with DCM (3×). The combined organic layers were washed with brine (1×), dried with $MgSO_4$, filtered then concentrated to give 2-((6aR,8R)-8-((5-(chloromethyl)-4,6-dimethylpyridin-2-yl)oxy)-6a-ethyl-5,6,6a,7,8,9-hexahydropyrrolo[1',2':4,5]pyrazino[2,3-c]pyridazin-2-yl)-6-fluorophenol (16 mg, 58%). LCMS calcd for $C_{25}H_{28}ClFN_5O_2$$[M+H]^+$: m/z=484.2; Found: 484.1.

Step 5: 3-(6-(4-((6-(((6aR,8R)-6a-ethyl-2-(3-fluoro-2-hydroxyphenyl)-5,6,6a, 7,8,9-hexahydropyrrolo[1',2':4,5]pyrazino[2,3-c]pyridazin-8-yl)oxy)-2,4-dimethylpyridin-3-yl)methyl)piperazin-1-yl)-1-oxoisoindolin-2-yl)piperidine-2,6-dione To 2-((6aR,8R)-8-((5-(chloromethyl)-4,6-dimethylpyridin-2-yl)oxy)-6a-ethyl-5,6,6a,7,8,9-hexahydropyrrolo[1',2':4,5]pyrazino[2,3-c]pyridazin-2-yl)-6-fluorophenol (16 mg, 0.034 mmol) and (S)-3-(1-oxo-6-(piperazin-1-yl)isoindolin-2-yl)piperidine-2,6-dione (HCl salt; 37 mg, 0.10 mmol) in MeCN (2 mL) was added N,N-diisopropylethylamine (47 µL, 0.27 mmol). The reaction was stirred at 120° C. for 30 min then allowed to cool to room temperature, subsequently diluted with DMSO, filtered through a 0.2 µm PTFE syringe filter, and purified via prep-HPLCMS (Waters CSH-C18, 5 µm, 30×100 mm, 13.8-33.8% MeCN/water (containing 0.1% TFA) over 5 min) to give the TFA salt of the title compound (7.4 mg, 22%). LCMS calcd for $C_{42}H_{47}FN_9O_5$ $[M+H]^+$: m/z=776.4; Found: 776.3.

Example 63: 3-(6-(4-((6-(((6aR,8R)-2-(3,5-difluoro-2-hydroxyphenyl)-6a-ethyl-5,6,6a,7,8,9-hexahydropyrrolo[1',2':4,5]pyrazino[2,3-c]pyridazin-8-yl)oxy)pyridin-3-yl)methyl)piperazin-1-yl)-1-oxoisoindolin-2-yl)piperidine-2,6-dione

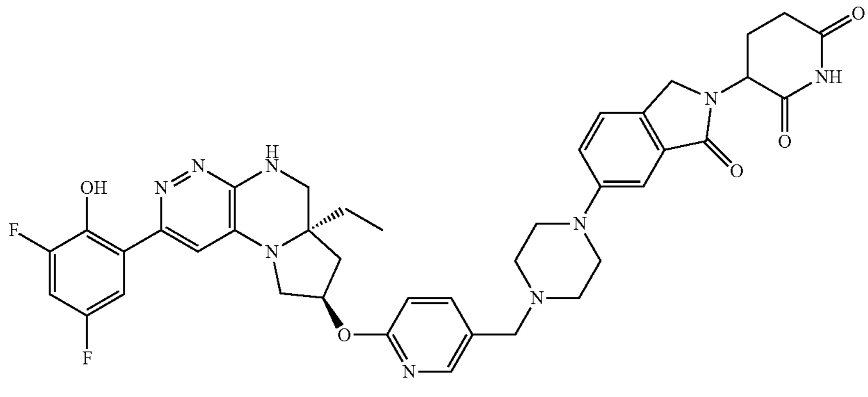 [SMILES: CC[C@@]12CNc3nnc(-c4cc(F)cc(F)c4O)cc3N1C[C@H](Oc1ccc(CN3CCN(c4ccc5c(c4)C(=O)N(C4CCC(=O)NC4=O)C5)CC3)cn1)C2]

Step 1: (8R)-8-(benzyloxy)-2-(3,5-difluoro-2-methoxyphenyl)-6a-ethyl-5,6,6a, 7,8,9-hexahydropyrrolo[1',2':4,5]pyrazino[2,3-c]pyridazine

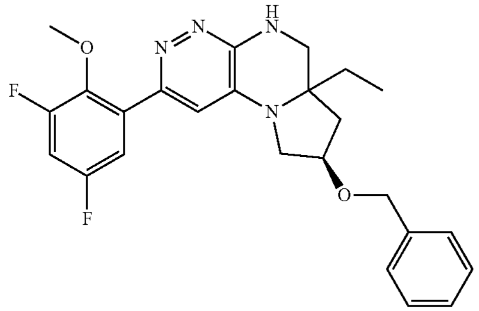 [SMILES: CCC12CNc3nnc(-c4cc(F)cc(F)c4OC)cc3N1C[C@H](OCc1ccccc1)C2]

This compound was synthesized using procedures analogous to those described in the synthesis of Intermediate 10, Step 3. LCMS calcd for $C_{25}H_{27}F_2N_4O_2$ $[M+H]^+$: m/z=453.2; Found: 453.1.

Step 2: tert-butyl (6aR,8R)-8-(benzyloxy)-2-(3,5-difluoro-2-methoxyphenyl)-6a-ethyl-6a, 7,8,9-tetrahydropyrrolo[1',2':4,5]pyrazino[2,3-c]pyridazine-5(6H)-carboxylate and tert-butyl (6aS,8R)-8-(benzyloxy)-2-(3,5-difluoro-2-methoxyphenyl)-6a-ethyl-6a, 7,8,9-tetrahydropyrrolo[1',2':4,5]pyrazino[2,3-c]pyridazine-5(6H)-carboxylate

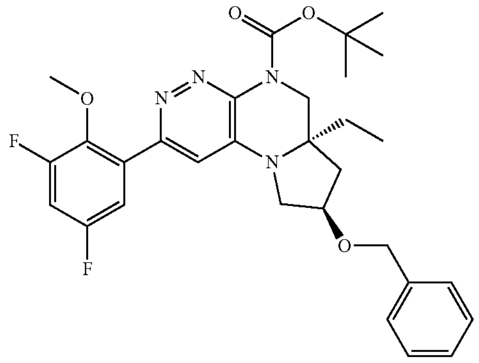

-continued

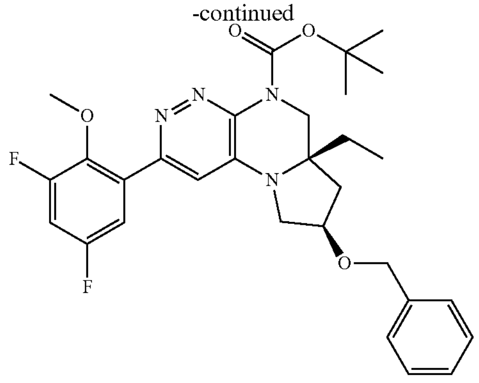

To (8R)-8-(benzyloxy)-2-(3,5-difluoro-2-methoxyphenyl)-6a-ethyl-5,6,6a,7,8,9-hexahydropyrrolo[1',2':4,5]pyrazino[2,3-c]pyridazine (192 mg, 0.43 mmol) and DMAP (10 mg, 0.085 mmol) in THF (2 mL) was added $Boc_2O$ (185 mg, 0.85 mmol). The reaction was stirred at room temperature for 29 h then purified via $SiO_2$ FCC (0-100% EtOAc in hexanes) to afford "diastereomer A" tert-butyl (6aR,8R)-8-

(benzyloxy)-2-(3,5-difluoro-2-methoxyphenyl)-6a-ethyl-6a,7,8,9-tetrahydropyrrolo[1',2':4,5]pyrazino[2,3-c]pyridazine-5(6H)-carboxylate (79 mg, 34%) as a clear oil and "diastereomer B" tert-butyl (6aS,8R)-8-(benzyloxy)-2-(3,5-difluoro-2-methoxyphenyl)-6a-ethyl-6a,7,8,9-tetrahydropyrrolo[1',2':4,5]pyrazino[2,3-c]pyridazine-5(6H)-carboxylate (80 mg, 34%) as a yellow oil. LCMS calcd for $C_{30}H_{35}F_2N_4O_4[M+H]^+$: m/z=553.3; Found: 553.1 (diastereomer A) and 553.1 (diastereomer B).

Step 3: tert-butyl (6aR,8R)-2-(3,5-difluoro-2-methoxyphenyl)-6a-ethyl-8-hydroxy-6a, 7,8,9-tetrahydropyrrolo[1',2':4,5]pyrazino[2,3-c]pyridazine-5(6H)-carboxylate

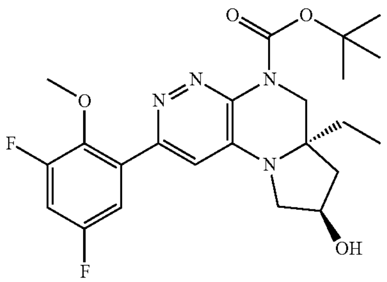 [SMILES: CC[C@]12C[C@@H](O)CN1c1cc(-c3cc(F)cc(F)c3OC)nnc1N(C(=O)OC(C)(C)C)C2]

A vial containing a mixture of tert-butyl (6aR,8R)-8-(benzyloxy)-2-(3,5-difluoro-2-methoxyphenyl)-6a-ethyl-6a,7,8,9-tetrahydropyrrolo[1',2':4,5]pyrazino[2,3-c]pyridazine-5(6H)-carboxylate (79 mg, 0.14 mmol) and 10% Pd/C (121 mg, 0.11 mmol) was purged with $N_2$ for 30 sec. A solution of ammonium formate (177 mg, 2.85 mmol) in MeOH (2 mL) was added slowly and the resulting mixture was sparged with $N_2$ for 1 min. The reaction was stirred at 80° C. for 1 h then allowed to cool to room temperature. The mixture was filtered through a celite pad and the filter cake was washed with MeOH. The filtrate was concentrated then purified via $SiO_2$ FCC (0-100% EtOAc in hexanes) to afford tert-butyl (6aR,8R)-2-(3,5-difluoro-2-methoxyphenyl)-6a-ethyl-8-hydroxy-6a,7,8,9-tetrahydropyrrolo[1',2':4,5]pyrazino[2,3-c]pyridazine-5(6H)-carboxylate (39.5 mg, 60%) as a white solid. LCMS calcd for $C_{23}H_{29}F_2N_4O_4[M+H]^+$: m/z=463.2; Found: 463.2.

Step 4: tert-butyl (6aR,8R)-2-(3,5-difluoro-2-methoxyphenyl)-6a-ethyl-8-((5-(methoxycarbonyl)pyridin-2-yl)oxy)-6a, 7,8,9-tetrahydropyrrolo[1',2':4,5]pyrazino[2,3-c]pyridazine-5(6H)-carboxylate

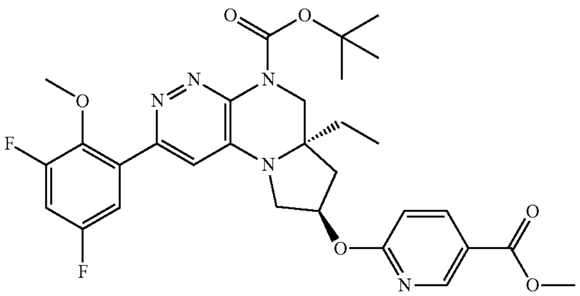 [SMILES: CC[C@]12C[C@@H](Oc3ccc(C(=O)OC)cn3)CN1c1cc(-c3cc(F)cc(F)c3OC)nnc1N(C(=O)OC(C)(C)C)C2]

To tert-butyl (6aR,8R)-2-(3,5-difluoro-2-methoxyphenyl)-6a-ethyl-8-hydroxy-6a,7,8,9-tetrahydropyrrolo[1',2':4,5]pyrazino[2,3-c]pyridazine-5(6H)-carboxylate (39.5 mg, 0.085 mmol) and methyl 6-fluoronicotinate (106 mg, 0.683 mmol) in THE (1.5 mL) was added NaH (60% dispersion in mineral oil; 35.5 mg, 0.888 mmol) at room temperature. The reaction was stirred at room temperature for 3 h then quenched with sat. $NH_4Cl$ (aq) and filtered. The filtrate was purified via $SiO_2$ FCC (0-100% EtOAc in hexanes) to give tert-butyl (6aR,8R)-2-(3,5-difluoro-2-methoxyphenyl)-6a-ethyl-8-((5-(methoxycarbonyl)pyridin-2-yl)oxy)-6a,7,8,9-tetrahydropyrrolo [1',2':4,5]pyrazino[2,3-c]pyridazine-5(6H)-carboxylate (46 mg, 90%) as a clear oil. LCMS calcd for $C_{30}H_{34}F_2N_5O_6[M+H]^+$: m/z=598.2; Found: 598.1.

Step 5: methyl 6-(((6aR,8R)-2-(3,5-difluoro-2-methoxyphenyl)-6a-ethyl-5,6,6a, 7,8,9-hexahydropyrrolo[1',2':4,5]pyrazino[2,3-c]pyridazin-8-yl)oxy) nicotinate

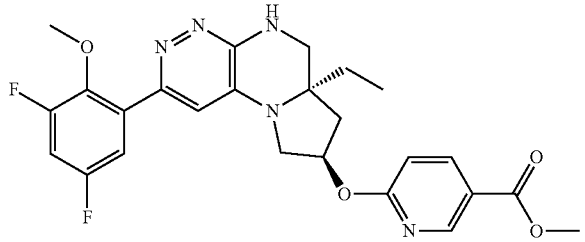

To tert-butyl (6aR,8R)-2-(3,5-difluoro-2-methoxyphenyl)-6a-ethyl-8-((5-(methoxy-carbonyl)pyridin-2-yl)oxy)-6a,7,8,9-tetrahydropyrrolo[1',2':4,5]pyrazino[2,3-c]pyridazine-5(6H)-carboxylate (46 mg, 0.077 mmol) in DCM (1 mL) was added TFA (0.59 mL, 7.7 mmol). The reaction was stirred at room temperature for 1 h then quenched with sat. $NaHCO_3$ (aq) and extracted with DCM (3×). The combined DCM layers were washed with brine (1×), dried with $MgSO_4$, filtered then concentrated to give methyl 6-(((6aR,8R)-2-(3,5-difluoro-2-methoxy-phenyl)-6a-ethyl-5,6,6a,7,8,9-hexahydropyrrolo[1',2':4,5]pyrazino[2,3-c]pyridazin-8-yl)oxy) nicotinate (assumed quantitative yield) which was used directly without further purification. LCMS calcd for $C_{25}H_{26}F_2N_5O_4[M+H]^+$: m/z=498.2; Found: 498.0.

Step 6: (6-(((6aR,8R)-2-(3,5-difluoro-2-methoxyphenyl)-6a-ethyl-5,6,6a, 7,8,9-hexahydropyrrolo[1',2':4,5]pyrazino[2,3-c]pyridazin-8-yl)oxy)pyridin-3-yl)methanol

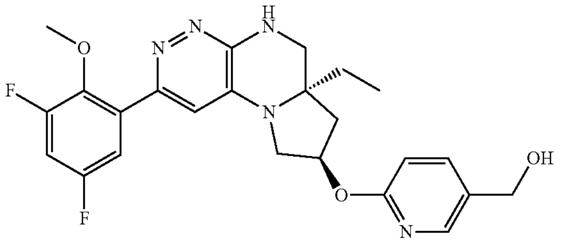 [SMILES: CC[C@@]12CNc3nnc(-c4cc(F)cc(F)c4OC)cc3N1C[C@H](Oc1ccc(CO)cn1)C2]

To methyl 6-(((6aR,8R)-2-(3,5-difluoro-2-methoxyphenyl)-6a-ethyl-5,6,6a,7,8,9-hexahydropyrrolo[1',2':4,5]

pyrazino[2,3-c]pyridazin-8-yl)oxy)nicotinate (38 mg, 0.077 mmol) in THE (1 mL) at 0° C. was added $LiAlH_4$ (1 M in THF; 0.15 mL, 0.15 mmol) dropwise. The reaction was stirred at 0° C. for 20 min then quenched with sat. $NH_4Cl$ (aq), poured into water then extracted with DCM (3×). The combined organic layers were washed with brine (1×), dried with $MgSO_4$, filtered then concentrated to afford (6-(((6aR, 8R)-2-(3,5-difluoro-2-methoxy-phenyl)-6a-ethyl-5,6,6a,7,8, 9-hexahydropyrrolo[1',2':4,5]pyrazino[2,3-c]pyridazin-8-yl)oxy) pyridin-3-yl)methanol (assumed quantitative yield) which was used directly without further purification. LCMS calcd for $C_{24}H_{26}F_2N_5O_3[M+H]^+$: m/z=470.2; Found: 470.1.

Step 7: (6aR,8R)-8-((5-(chloromethyl)pyridin-2-yl) oxy)-2-(3,5-difluoro-2-methoxy-phenyl)-6a-ethyl-5, 6,6a, 7,8,9-hexahydropyrrolo[1',2':4,5]pyrazino[2,3-c]pyridazine

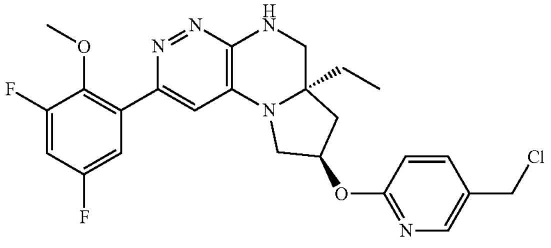 [SMILES: CC[C@@]12CNc3nnc(-c4cc(F)cc(F)c4OC)cc3N1C[C@H](Oc1ccc(CCl)cn1)C2]

To (6-(((6aR,8R)-2-(3,5-difluoro-2-methoxyphenyl)-6a-ethyl-5,6,6a,7,8,9-hexahydro-pyrrolo[1',2':4,5]pyrazino[2, 3-c]pyridazin-8-yl)oxy)pyridin-3-yl)methanol (36 mg, 0.077 mmol) in THE (1 mL) at 0° C. was added $SOCl_2$ (17 μL, 0.23 mmol). The reaction was stirred at room temperature for 40 min then quenched with sat. $NaHCO_3$ (aq) and extracted with DCM (3×). The combined DCM layers were washed with brine (1×), dried with $MgSO_4$, filtered then concentrated to give (6aR,8R)-8-((5-(chloromethyl)pyridin-2-yl)oxy)-2-(3,5-difluoro-2-methoxy-phenyl)-6a-ethyl-5,6, 6a,7,8,9-hexahydropyrrolo[1',2':4,5]pyrazino[2,3-c] pyridazine (assumed quantitative yield) which was used directly without further purification. LCMS calcd for $C_{24}H_{25}F_2N_5O_2[M+H]^+$: m/z=488.2; Found: 488.0.

Step 8: 3-(6-(4-((6-(((6aR,8R)-2-(3,5-difluoro-2-hydroxyphenyl)-6a-ethyl-5,6,6a, 7,8,9-hexahydropyrrolo[1',2':4,5]pyrazino[2,3-c]pyridazin-8-yl)oxy) pyridin-3-yl)methyl)piperazin-1-yl)-1-oxoisoindolin-2-yl)piperidine-2,6-dione To (6aR,8R)-8-((5-(chloromethyl)pyridin-2-yl)oxy)-2-(3, 5-difluoro-2-methoxyphenyl)-6a-ethyl-5,6,6a,7,8,9-hexahydropyrrolo[1',2':4,5]pyrazino[2,3-c]pyridazine (37 mg, 0.076 mmol) in MeCN (5 mL) was added (S)-3-(1-oxo-6-(piperazin-1-yl)isoindolin-2-yl)piperidine-2,6-dione (HCl salt; 84 mg, 0.23 mmol) then N,N-diisopropylethylamine (107 μL, 0.612 mmol). The reaction was sonicated briefly then stirred at 120° C. for 1 h. The reaction was allowed to cool to room temperature then concentrated. The residue was taken up in DCM and sonicated briefly to form a suspension then treated with $BBr_3$ (0.59 mL, 6.1 mmol). The reaction was stirred overnight at room temperature then quenched by slow addition to cold water. The mixture was diluted with DMSO and the volatiles were subsequently evaporated. Additional DMSO was added to the reaction vial and the mixture was filtered through a 0.45 μm PTFE syringe filter then purified via prep-HPLCMS (Waters CSH Phenyl-Hexyl, 5 μm, 30×100 mm, 12.2-32.2% MeCN/water (containing 0.1% TFA) over 5 min) to give the TFA salt of the title compound (4.2 mg, 6%). LCMS calcd for $C_{40}H_{42}F_2N_9O_5[M+H]^+$: m/z=766.3; Found: 766.3.

Example 64: (S)-3-(6-(4-((5-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-6-methylpyrazin-2-yl)methyl)piperazin-1-yl)-1-oxoisoindolin-2-yl)piperidine-2,6-dione

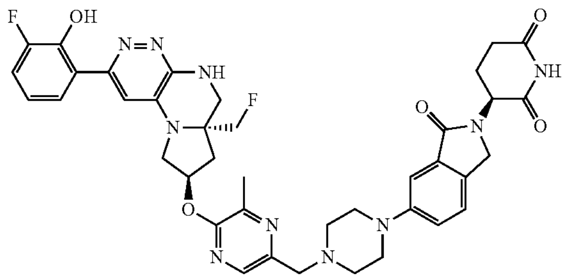 [SMILES: Cc1nc(CN2CCN(c3ccc4c(c3)C(=O)N([C@H]3CCC(=O)NC3=O)C4)CC2)cnc1O[C@H]1CN2c3cc(-c4cccc(F)c4O)nnc3NC[C@@]2(CF)C1]

Step 1: 5-Bromo-3-methylpyrazin-2-ol

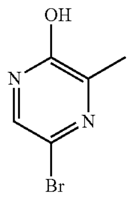

To a solution of 3-methylpyrazin-2-ol (1.0 g, 8.06 mmol) in DMF (10 mL) was added N-bromosuccinimide (1.72 g, 9.67 mmol) at 0° C. The reaction mixture was slowly warmed to room temperature and stirred overnight. The resulting mixture was poured into water, and extracted with EA, concentrated and purified by column chromatography (0-10% MeOH/DCM) to give 5-bromo-3-methylpyrazin-2-ol (1.13 g, 5.57 mmol, 69% yield). LCMS calcd for $C_5H_6BrN_2O$ [M+H]$^+$: m/z=189.0; Found: 189.1.

Step 2: 3-Methyl-5-vinylpyrazin-2-ol

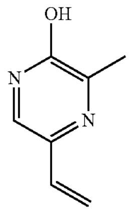

A mixture of 5-bromo-3-methylpyrazin-2-ol (1.13 g, 5.57 mmol), 4,4,5,5-tetramethyl-2-vinyl-1,3,2-dioxaborolane (2.57 g, 16.7 mmol), potassium carbonate (1.54 g, 11.1 mmol) and dichloro 1,1'-bisdiphenylphosphino)ferrocene palladium (II) dichloromethane (456 mg, 0.56 mmol) in 1,4-dioxane (10 mL) and water (1 mL) was stirred at 100° C. overnight. The reaction was purified on FCC (0-100% EA/Hex) to give 3-methyl-5-vinylpyrazin-2-ol (800 mg, 5.33 mmol, 96% yield). LCMS calcd for $C_7H_9N_2O$ $[M+H]^+$: m/z=137.1; Found: 137.1.

Step 3: (6aR,8R)-2-Chloro-6a-(fluoromethyl)-5,6,6a,7,8,9-hexahydropyrrolo[1',2':4,5]pyrazino[2,3-c]pyridazin-8-ol

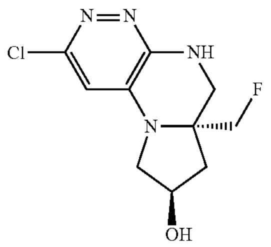 [SMILES: O[C@H]1CN2c3cc(Cl)nnc3NC[C@@]2(CF)C1]

This intermediate was synthesized by procedures analogous to that described in Examples 40 and 43, using fluoroiodomethane instead of difluoromethyl trifluoromethanesulfonate in Example 40, Step 2. LCMS calcd for $C_{10}H_{13}ClFN_4O$ $[M+H]^+$: m/z=259.1; Found: 259.2.

Step 4: (6aR,8S)-2-Chloro-6a-(fluoromethyl)-5,6,6a,7,8,9-hexahydropyrrolo[1',2':4,5]pyrazino[2,3-c]pyridazin-8-ol

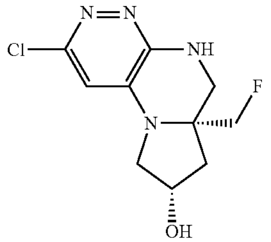 [SMILES: O[C@@H]1CN2c3cc(Cl)nnc3NC[C@@]2(CF)C1]

To a solution of triphenylphosphine (2.17 g, 3.48 mmol, polymer based) in THE (30 mL) was added diisopropyl azodicarboxylate (0.69 mL, 3.48 mmol) dropwise. The mixture was stirred at rt for 10 min, to which was added 4-nitrobenzoic acid (504 mg, 3.02 mmol). The mixture was stirred for 10 min, to which was added (6aR,8R)-2-chloro-6a-(fluoromethyl)-5,6,6a,7,8,9-hexahydropyrrolo[1',2':4,5]pyrazino[2,3-c]pyridazin-8-ol (600.0 mg, 2.32 mmol). The mixture was stirred at rt for 1 h, then filtered and concentrated to give the intermediate as crude. To the intermediate was added methanol (20 mL) and potassium carbonate (1.6 g, 11.6 mmol). The reaction mixture was stirred at rt for 30 min, then poured into water (10 ml) and DCM (10 ml). The solid was collected by filtration, washed with DCM and dried to give the title compound (500 mg, 1.93 mmol, 83% yield). LCMS calcd for $C_{10}H_{13}ClFN_4O$ $[M+H]^+$: m/z=259.1; Found: 259.2.

Step 5: (6aR,8R)-2-Chloro-6a-(fluoromethyl)-8-((3-methyl-5-vinylpyrazin-2-yl)oxy)-5,6,6a, 7,8,9-hexahydropyrrolo[1',2':4,5]pyrazino[2,3-c]pyridazine

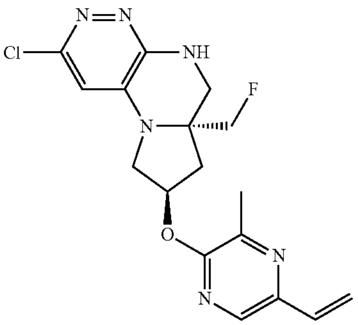 [SMILES: C=Cc1cnc(O[C@H]2CN3c4cc(Cl)nnc4NC[C@@]3(CF)C2)c(C)n1]

To a mixture of (6aR,8S)-2-chloro-6a-(fluoromethyl)-5,6,6a,7,8,9-hexahydropyrrolo [1',2':4,5]pyrazino[2,3-c]pyridazin-8-ol (153 mg, 0.59 mmol), triphenylphosphine (591 mg, 0.95 mmol) and 3-methyl-5-vinylpyrazin-2-ol (96.6 mg, 0.71 mmol) in THE (1 mL) was added diisopropyl azodicarboxylate (175 uL, 0.89 mmol) dropwise at rt. The mixture was then stirred at 65° C. for 2 h. The mixture was diluted with EA, washed with water, concentrated and purified on FCC (0-100% EA/Hex followed by 0-10% MeOH/DCM) to give the title compound (200 mg, 0.53 mmol, 89% yield). LCMS calcd for $C_{17}H_{19}ClFN_6O$ $[M+H]^+$: m/z=377.2; Found: 377.1.

Step 6: 2-Fluoro-6-((6aR,8R)-6a-(fluoromethyl)-8-((3-methyl-5-vinylpyrazin-2-yl)oxy)-5,6,6a, 7,8,9-hexahydropyrrolo[1',2':4,5]pyrazino[2,3-c]pyridazin-2-yl)phenol

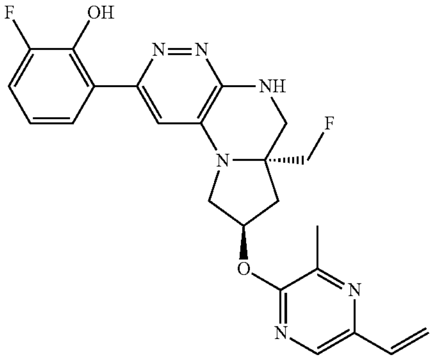 [SMILES: C=Cc1cnc(O[C@H]2CN3c4cc(-c5cccc(F)c5O)nnc4NC[C@@]3(CF)C2)c(C)n1]

A mixture of (6aR,8R)-2-chloro-6a-(fluoromethyl)-8-((3-methyl-5-vinylpyrazin-2-yl)oxy)-5,6,6a,7,8,9-hexahydropyrrolo[1',2':4,5]pyrazino[2,3-c]pyridazine (200 mg, 0.53 mmol), 3-fluoro-2-hydroxyphenylboronic acid (248 mg, 1.59 mmol), potassium carbonate (293 mg, 2.12 mmol) and XPhos Pd G2 (83.5 mg, 0.11 mmol) in 1,4-dioxane (1 mL) and water (0.2 mL) was sparged for ~2 min with $N_2$ and stirred at 90° C. For 1 h. The mixture was purified via $SiO_2$ FCC (0-100% EA/Hex) to give the title compound (130 mg, 0.29 mmol, 54% yield). LCMS calcd for $C_{23}H_{23}F_2N_6O_2$ $[M+H]^+$: m/z=453.2; Found: 453.0.

Step 7: 5-(((6aR,8R)-2-(3-Fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy)-6-methylpyrazine-2-carbaldehyde

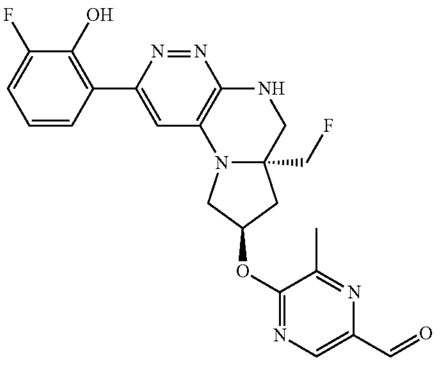 [SMILES: Cc1nc(C=O)cnc1O[C@H]1CN2c3cc(-c4cccc(F)c4O)nnc3NC[C@@]2(CF)C1]

To a mixture of 2-fluoro-6-((6aR,8R)-6a-(fluoromethyl)-8-((3-methyl-5-vinylpyrazin-2-yl)oxy)-5,6,6a,7,8,9-hexahydropyrrolo[1',2':4,5]pyrazino[2,3-c]pyridazin-2-yl)phenol (130.0 mg, 0.29 mmol) and sodium periodate (184 mg, 0.86 mmol) in THE (2 mL) and water (0.5 mL) was added osmium tetroxide (183 uL, 0.03 mmol). The mixture was stirred at room temperature for 2 h.

The mixture was diluted with EA, washed with water, concentrated and purified on FCC (0-10% MeOH/DCM) to give the title compound (82 mg, 0.18 mmol, 63% yield). LCMS calcd for $C_{22}H_{21}F_2N_6O_3$[M+H]$^+$: m/z=455.2 Found: 455.2.

Step 8: (S)-3-(6-(4-((5-(((6aR,8R)-2-(3-Fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy)-6-methylpyrazin-2-yl)methyl)piperazin-1-yl)-1-oxoisoindolin-2-yl)piperidine-2,6-dione

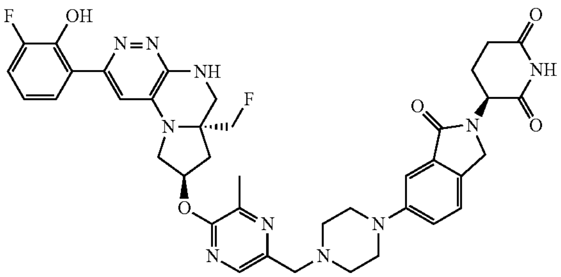 [SMILES: Cc1nc(CN2CCN(c3ccc4c(c3)C(=O)N([C@H]3CCC(=O)NC3=O)C4)CC2)cnc1O[C@H]1CN2c3cc(-c4cccc(F)c4O)nnc3NC[C@@]2(CF)C1]

To a mixture of (S)-3-(1-oxo-6-(piperazin-1-yl)isoindolin-2-yl)piperidine-2,6-dione hydrochloride (85.6 mg, 0.23 mmol) and 5-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-6-methylpyrazine-2-carbaldehyde (82.0 mg, 0.18 mmol) in DMSO (0.5 mL) was added N,N-diisopropylethylamine (94 uL, 0.54 mmol). The mixture was stirred at rt for 30 min., then sodium triacetoxyborohydride (115 mg, 0.54 mmol) was added. The mixture was stirred at 35° C. for 4 h. The mixture was purified with Prep-LCMS (Waters CSH-C18, 5 uM, 30×100 mm, 9.6-29.6% MeCN/water (containing 0.1% TFA) over 5 min) to give the title compound (49 mg, 0.06 mmol, 34% yield) as a white TFA salt. LCMS calcd for $C_{39}H_{41}F_2N_{10}O_5$ [M+H]$^+$: m/z=767.4; Found: 767.2. $^1$H NMR (400 MHz, $CD_3OD$) δ 8.18 (s, 1H), 7.50 (d, J=8.2 Hz, 1H), 7.39-7.27 (m, 3H), 7.00 (dt, J=8.1, 4.0 Hz, 2H), 6.96 (s, 1H), 5.95 (s, 1H), 5.12 (dd, J=13.3, 5.1 Hz, 1H), 4.55 (d, J=9.4 Hz, 1H), 4.51-4.30 (m, 5H), 3.92 (t, J=13.4 Hz, 2H), 3.53 (s, 2H), 3.02 (dd, J=13.6, 6.9 Hz, 1H), 2.96-2.83 (m, 1H), 2.77 (d, J=17.0 Hz, 1H), 2.50 (s, 2H), 2.26 (dd, J=13.9, 5.9 Hz, 1H), 2.20-2.12 (m, 1H).

Example 65: (S)-3-(6-(1-((5-(((6aR,8R)-2-(3-Fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy)-6-methylpyrazin-2-yl)methyl)piperidin-4-yl)-1-oxoisoindolin-2-yl)piperidine-2,6-dione

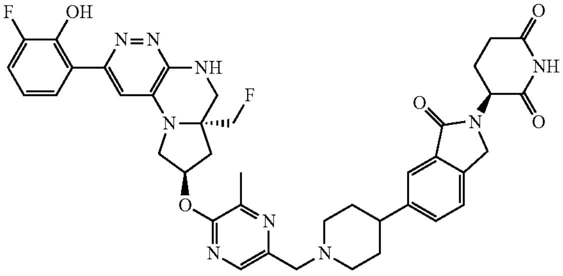 [SMILES: Cc1nc(CN2CCC(c3ccc4c(c3)C(=O)N([C@H]3CCC(=O)NC3=O)C4)CC2)cnc1O[C@H]1CN2c3cc(-c4cccc(F)c4O)nnc3NC[C@@]2(CF)C1]

Step 1: (S)-3-(6-(1-((5-(((6aR,8R)-2-(3-Fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy)-6-methylpyrazin-2-yl)methyl)piperidin-4-yl)-1-oxoisoindolin-2-yl)piperidine-2,6-dione

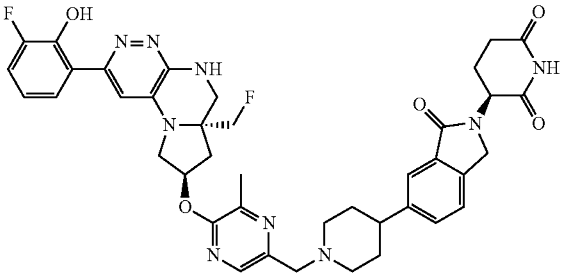 [SMILES: Cc1nc(CN2CCC(c3ccc4c(c3)C(=O)N([C@H]3CCC(=O)NC3=O)C4)CC2)cnc1O[C@H]1CN2c3cc(-c4cccc(F)c4O)nnc3NC[C@@]2(CF)C1]

To a mixture of (S)-3-(1-oxo-6-(piperidin-4-yl)isoindolin-2-yl)piperidine-2,6-dione; hydrochloride (73 mg, 0.2 mmol) and 5-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-6-methylpyrazine-2-carbaldehyde (76.0 mg, 0.17 mmol) in DMSO (0.5 mL) was added N,N-diisopropylethylamine (87 uL, 0.5 mmol). The mixture was stirred at rt for 30 min., then sodium triacetoxyborohydride (106 mg, 0.5 mmol) was added. The mixture was stirred at 35° C. for 4 h. The mixture was purified with Prep-LCMS (Waters CSH-C18, 5 uM, 30×100 mm, 5.3-0% B MeCN/water (containing 0.1% TFA) over 5 min) to give the title compound (39 mg, 0.05 mmol, 30% yield) as a white TFA salt. LCMS calcd for $C_{40}H_{42}F_2N_9O_5$[M+H]$^+$:

m/z=766.4; Found: 766.2. $^1$H NMR (400 MHz, $CD_3OD$) δ 8.18 (s, 1H), 7.70 (s, 1H), 7.57 (s, 1H), 7.31 (t, J=9.1 Hz, 2H), 7.00 (dd, J=8.1, 4.8 Hz, 1H), 6.96 (s, 1H), 5.94 (s, 1H), 5.14 (dd, J=13.3, 5.2 Hz, 1H), 4.67 (d, J=9.4 Hz, 1H), 4.59-4.51 (m, 1H), 4.46 (dd, J=13.9, 7.5 Hz, 3H), 4.34 (dd, J=12.9, 6.6 Hz, 1H), 3.92 (t, J=13.2 Hz, 2H), 3.68 (s, 1H), 3.02 (dd, J=13.7, 7.4 Hz, 2H), 2.88 (dd, J=13.1, 5.2 Hz, 1H), 2.78 (d, J=17.6 Hz, 1H), 2.50 (s, 2H), 2.26 (dd, J=13.9, 5.8 Hz, 1H), 2.16 (d, J=13.2 Hz, 2H), 2.04 (d, J=11.1 Hz, 1H).

Example 66: (S)-3-(6-(4-((5-(((6aS,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-6-methylpyrazin-2-yl)methyl)piperazin-1-yl)-1-oxoisoindolin-2-yl)piperidine-2,6-dione

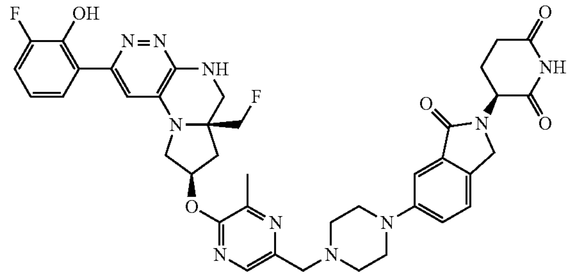 [SMILES: Cc1nc(CN2CCN(c3ccc4c(c3)C(=O)N([C@H]3CCC(=O)NC3=O)C4)CC2)cnc1O[C@H]1CN2c3cc(-c4cccc(F)c4O)nnc3NC[C@]2(CF)C1]

Step 1: (6aS,8R)-2-chloro-6a-(fluoromethyl)-5,6,6a,7,8,9-hexahydropyrrolo[1',2':4,5]pyrazino[2,3-c]pyridazin-8-ol

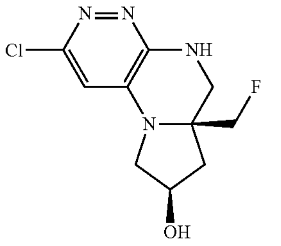 [SMILES: O[C@H]1CN2c3cc(Cl)nnc3NC[C@]2(CF)C1]

This intermediate was synthesized by procedures analogous to that described in Examples 40 and 43, using fluoroiodomethane instead of difluoromethyl trifluoromethanesulfonate in Example 40, Step 2. LCMS calcd for $C_{10}H_{13}ClFN_4O$ [M+H]$^+$: m/z=259.1; Found: 259.2.

Step 2: (6aS,8S)-2-chloro-6a-(fluoromethyl)-5,6,6a,7,8,9-hexahydropyrrolo[1',2':4,5]pyrazino[2,3-c]pyridazin-8-ol

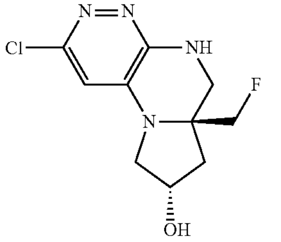 [SMILES: O[C@@H]1CN2c3cc(Cl)nnc3NC[C@]2(CF)C1]

This intermediate was synthesized by procedures analogous to that described in Example 64, using (6aS,8R)-2-chloro-6a-(fluoromethyl)-5,6,6a,7,8,9-hexahydropyrrolo[1',2':4,5]pyrazino[2,3-c]pyridazin-8-ol instead of (6aR,8R)-2-chloro-6a-(fluoromethyl)-5,6,6a,7,8,9-hexahydropyrrolo[1',2':4,5]pyrazino[2,3-c]pyridazin-8-ol in Example 64, Step 4. LCMS calcd for $C_{10}H_{13}ClFN_4O$ [M+H]$^+$: m/z=259.1; Found: 259.2.

Step 3: (S)-3-(6-(4-((5-(((6aS,8R)-2-(3-fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy)-6-methylpyrazin-2-yl)methyl)piperazin-1-yl)-1-oxoisoindolin-2-yl)piperidine-2,6-dione

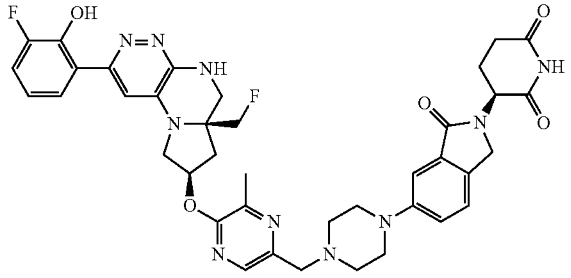 [SMILES: Cc1nc(CN2CCN(c3ccc4c(c3)C(=O)N([C@H]3CCC(=O)NC3=O)C4)CC2)cnc1O[C@H]1CN2c3cc(-c4cccc(F)c4O)nnc3NC[C@]2(CF)C1]

This compound was synthesized by procedures analogous to that described in Example 64 using (6aS,8S)-2-chloro-6a-(fluoromethyl)-5,6,6a,7,8,9-hexahydropyrrolo[1',2':4,5]pyrazino[2,3-c]pyridazin-8-ol instead of (6aR,8S)-2-chloro-6a-(fluoromethyl)-5,6,6a,7,8,9-hexahydropyrrolo [1',2':4,5]pyrazino[2,3-c]pyridazin-8-ol in Step 5. LCMS calcd for $C_{39}H_{41}F_2N_{10}O_5$ [M+H]$^+$: m/z=767.4; Found: 767.2.

Example 67: (S)-3-(6-(4-((6-ethyl-5-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)pyrazin-2-yl)methyl)piperazin-1-yl)-1-oxoisoindolin-2-yl)piperidine-2,6-dione

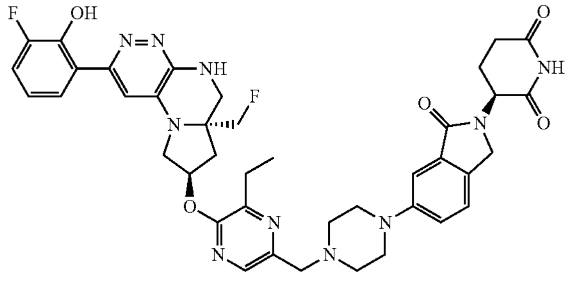 [SMILES: CCc1nc(CN2CCN(c3ccc4c(c3)C(=O)N([C@H]3CCC(=O)NC3=O)C4)CC2)cnc1O[C@H]1CN2c3cc(-c4cccc(F)c4O)nnc3NC[C@@]2(CF)C1]

Step 1: 3-ethyl-5-vinylpyrazin-2-ol

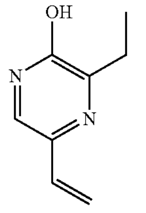

This intermediate was synthesized by procedures analogous to that described in Example 64, using 3-ethylpyrazin-2-ol instead of 3-methylpyrazin-2-ol in Step 1. LCMS calcd for $C_8H_{11}N_2O$ $[M+H]^+$: m/z=151.1; Found: 151.2.

Step 2: (S)-3-(6-(4-((6-ethyl-5-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)pyrazin-2-yl)methyl)piperazin-1-yl)-1-oxoisoindolin-2-yl)piperidine-2,6-dione

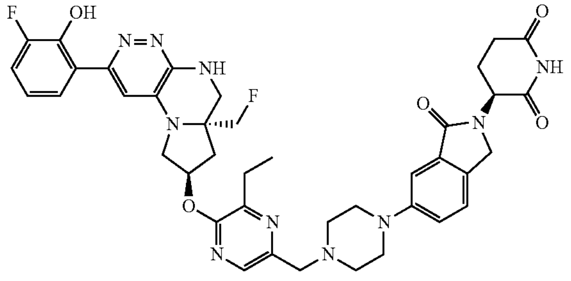 [SMILES: CCc1nc(CN2CCN(c3ccc4c(c3)C(=O)N([C@H]3CCC(=O)NC3=O)C4)CC2)cnc1O[C@H]1CN2c3cc(-c4cccc(F)c4O)nnc3NC[C@@]2(CF)C1]

The title compound was synthesized by procedures analogous to that described in Example 64, using 3-ethyl-5-vinylpyrazin-2-ol instead of 3-methyl-5-vinylpyrazin-2-ol in Step 5. LCMS calcd for $C_{40}H_{43}F_2N_{10}O_5[M+H]^+$: m/z=781.3; Found: 781.4.

Example 68: (S)-3-(6-(1-((6-ethyl-5-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)pyrazin-2-yl)methyl)piperidin-4-yl)-1-oxoisoindolin-2-yl)piperidine-2,6-dione

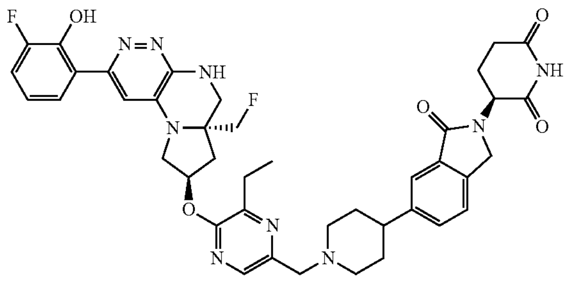 [SMILES: CCc1nc(CN2CCC(c3ccc4c(c3)C(=O)N([C@H]3CCC(=O)NC3=O)C4)CC2)cnc1O[C@H]1CN2c3cc(-c4cccc(F)c4O)nnc3NC[C@@]2(CF)C1]

To a mixture of (S)-3-(1-oxo-6-(piperidin-4-yl)isoindolin-2-yl)piperidine-2,6-dione hydrochloride (84.8 mg, 0.23 mmol) and 6-ethyl-5-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)pyrazine-2-carbaldehyde (91.0 mg, 0.19 mmol) in DMSO (0.5 mL) was added N,N-diisopropylethylamine (101.5 uL, 0.58 mmol). The mixture was stirred at rt for 30 min., then sodium triacetoxyborohydride (123.5 mg, 0.58 mmol) was added. The mixture was stirred at 35° C. overnight. The mixture was purified with Prep-LCMS (Waters CSH Flouro-Phenyl, 5 uM, 30×100 mm, 12.8-32.8% B MeCN/water (containing 0.1% TFA) over 5 min) to give the title compound (18 mg, 0.022 mmol, 11% yield) as a white TFA salt. LCMS calcd for $C_{41}H_{44}F_2N_9O_5[M+H]^+$: m/z=780.4; Found: 780.3. $^1$H NMR (400 MHz, MeOD) δ 8.10 (s, 2H), 7.62 (s, 2H), 7.48 (s, 3H), 7.21 (t, J=9.0 Hz, 4H), 6.94-6.88 (m, 3H), 5.86 (s, 2H), 5.05 (dd, J=13.3, 5.2 Hz, 4H), 4.58 (d, J=9.5 Hz, 4H), 4.46 (d, J=9.5 Hz, 4H), 4.36 (dd, J=17.6, 9.2 Hz, 8H), 4.24 (dd, J=12.8, 6.3 Hz, 4H), 3.83 (t, J=12.5 Hz, 5H), 3.61 (s, 2H), 3.00-2.88 (m, 7H), 2.83-2.69 (m, 9H), 2.66 (s, 2H), 2.40 (dd, J=13.1, 4.4 Hz, 3H), 2.21-2.04 (m, 9H), 1.94 (s, 2H), 1.18 (t, J=7.5 Hz, 6H).

Example 69: (S)-3-(6-(4-((5-fluoro-6-(((6aS,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-2-methylpyridin-3-yl)methyl)piperazin-1-yl)-1-oxoisoindolin-2-yl)piperidine-2,6-dione

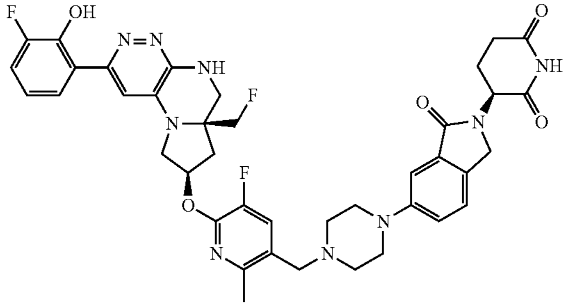 [SMILES: Cc1nc(O[C@H]2CN3c4cc(-c5cccc(F)c5O)nnc4NC[C@]3(CF)C2)c(F)cc1CN1CCN(c2ccc3c(c2)C(=O)N([C@H]2CCC(=O)NC2=O)C3)CC1]

Step 1: 3-fluoro-6-methyl-5-vinylpyridin-2-ol

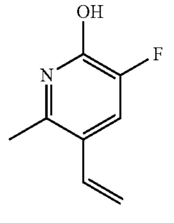

A mixture of 4,4,5,5-tetramethyl-2-vinyl-1,3,2-dioxaborolane (0.52 mL, 3.06 mmol), potassium carbonate (563.5 mg, 4.08 mmol), 5-bromo-3-fluoro-6-methylpyridin-2-ol (210.0 mg, 1.02 mmol) and XPhos Pd G2 (120.3 mg, 0.15 mmol) in 1,4-dioxane (3 mL) and water (1 mL) was sparged with $N_2$ for 10 min then stirred at 100° C. for 2 h. The mixture was filtered through 0.45 um fritted filter, concentrated and purified via $SiO_2$ FCC: 0-100% EA/Hex to give 3-fluoro-6-methyl-5-vinylpyridin-2-ol (150 mg, 0.98 mmol, 96% yield). LCMS calcd for $C_8H_9FNO$ $[M+H]^+$: m/z=154.1; Found: 154.1.

Step 2: (S)-3-(6-(4-((5-fluoro-6-(((6aS,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-2-methylpyridin-3-yl)methyl)piperazin-1-yl)-1-oxoisoindolin-2-yl)piperidine-2,6-dione

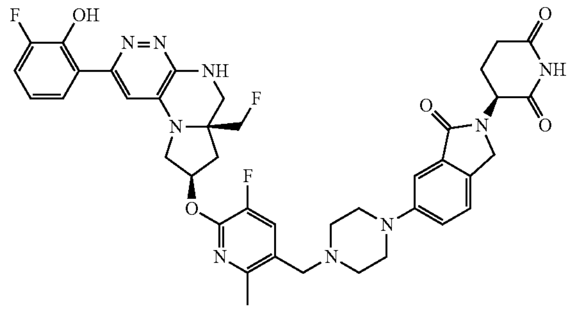 [SMILES: Cc1nc(O[C@H]2CN3c4cc(-c5cccc(F)c5O)nnc4NC[C@]3(CF)C2)c(F)cc1CN1CCN(c2ccc3c(c2)C(=O)N([C@H]2CCC(=O)NC2=O)C3)CC1]

The title compound was synthesized by procedures analogous to that described for Example 64. LCMS calcd for $C_{40}H_{41}F_3N_9O_5[M+H]^+$: m/z=784.3; Found: 784.4.

Example 70: 3-(6-(4-((5-fluoro-6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)pyridin-3-yl)methyl)piperazin-1-yl)-1-oxoisoindolin-2-yl)piperidine-2,6-dione

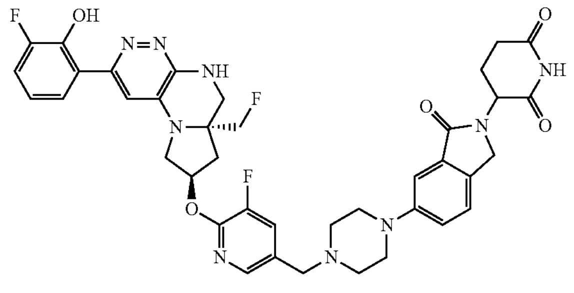 [SMILES: O=C1CCC(N2Cc3ccc(N4CCN(Cc5cnc(O[C@H]6CN7c8cc(-c9cccc(F)c9O)nnc8NC[C@@]7(CF)C6)c(F)c5)CC4)cc3C2=O)C(=O)N1]

Step 1: (8R)-8-(benzyloxy)-2-(3-fluoro-2-methoxyphenyl)-6a-(fluoromethyl)-5,6,6a, 7,8,9-hexahydropyrrolo[1',2':4,5]pyrazino[2,3-c]pyridazine

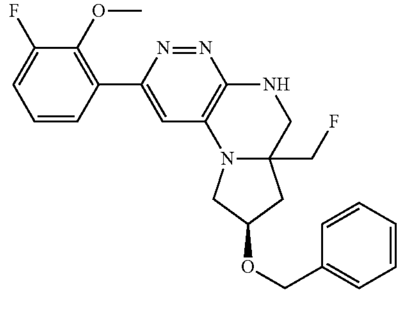 [SMILES: COc1c(F)cccc1-c1cc2c(nn1)NCC1(CF)C[C@@H](OCc3ccccc3)CN21]

This intermediate was synthesized by procedures analogous to that described in Example 40, using fluoroiodomethane instead of difluoromethyl trifluoromethanesulfonate in Step 2. LCMS calcd for $C_{24}H_{25}F_2N_4O_2[M+H]^+$: m/z=259.1; Found: 259.2.

Step 2: tert-butyl (6aR,8R)-8-(benzyloxy)-2-(3-fluoro-2-methoxyphenyl)-6a-(fluoromethyl)-6a, 7,8,9-tetrahydropyrrolo[1',2':4,5]pyrazino[2,3-c]pyridazine-5(6H)-carboxylate and tert-butyl (6aS,8R)-8-(benzyloxy)-2-(3-fluoro-2-methoxyphenyl)-6a-(fluoromethyl)-6a,7,8,9-tetrahydropyrrolo[1',2':4,5]pyrazino[2,3-c]pyridazine-5(6H)-carboxylate

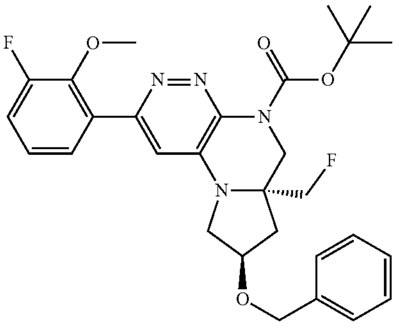

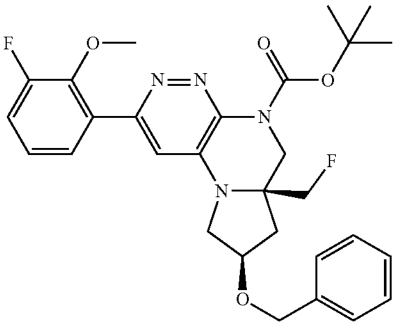

To (8R)-8-(benzyloxy)-2-(3-fluoro-2-methoxyphenyl)-6a-(fluoromethyl)-5,6,6a,7,8,9-hexahydropyrrolo[1',2':4,5]pyrazino[2,3-c]pyridazine (1.0 g, 2.28 mmol) in THE (15 mL) was added 4-(dimethylamino)pyridine (278.6 mg, 2.28 mmol) followed by di-tert butyl dicarbonate (2.49 g, 3.42 mmol). The mixture was stirred at room temperature for 3 h. The mixture was concentrated and purified via FCC (0-80% EtOAc/hexanes) to give tert-butyl (6aR,8R)-8-(benzyloxy)-2-(3-fluoro-2-methoxyphenyl)-6a-(fluoromethyl)-6a,7,8,9-tetrahydropyrrolo[1',2':4,5]pyrazino[2,3-c]pyridazine-5(6H)-carboxylate (490 mg, 0.91 mmol, 40% yield) and tert-butyl (6aS,8R)-8-(benzyloxy)-2-(3-fluoro-2-methoxyphenyl)-6a-(fluoromethyl)-6a,7,8,9-tetrahydropyrrolo[1',2':4,5]pyrazino[2,3-c]pyridazine-5(6H)-carboxylate (240 mg, 0.45 mmol, 20% yield). LCMS calcd for $C_{29}H_{33}F_2N_4O_4$ $[M+H]^+$: m/z=539.2; Found: 539.1.

Step 3: tert-butyl (6aR,8R)-2-(3-fluoro-2-methoxyphenyl)-6a-(fluoromethyl)-8-hydroxy-6a, 7,8,9-tetrahydropyrrolo[1',2':4,5]pyrazino[2,3-c]pyridazine-5(6H)-carboxylate

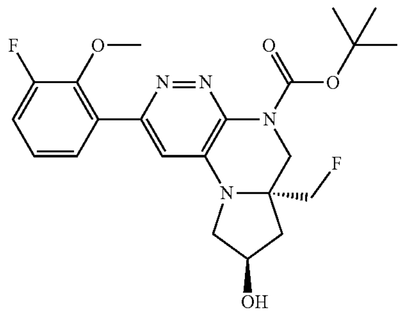 [SMILES: COc1c(F)cccc1-c1cc2c(nn1)N(C(=O)OC(C)(C)C)C[C@@]1(CF)C[C@@H](O)CN21]

A mixture of tert-butyl (6aR,8R)-8-(benzyloxy)-2-(3-fluoro-2-methoxyphenyl)-6a-(fluoromethyl)-6a,7,8,9-tetrahydropyrrolo[1',2':4,5]pyrazino[2,3-c]pyridazine-5(6H)-carboxylate (490.0 mg, 0.91 mmol) and 10% palladium on carbon (290.5 mg, 0.27 mmol) in methanol (10 mL) was degassed and subjected to balloon pressure of hydrogen gas at 50° C. overnight. The mixture was filtered and purified on silica gel column (0-100% EA/Hex followed by 0-10% MeOH/DCM) to give tert-butyl (6aR,8R)-2-(3-fluoro-2-methoxyphenyl)-6a-(fluoromethyl)-8-hydroxy-6a,7,8,9-tetrahydropyrrolo[1',2':4,5]pyrazino[2,3-c]pyridazine-5(6H)-carboxylate (150 mg, 0.33 mmol, 37% yield). LCMS calcd for $C_{22}H_{27}F_2N_4O_4$ $[M+H]^+$: m/z=449.2; Found: 449.1.

Step 4: methyl 5-fluoro-6-(((6aR,8R)-2-(3-fluoro-2-methoxyphenyl)-6a-(fluoromethyl)-5,6,6a, 7,8,9-hexahydropyrrolo[1',2':4,5]pyrazino[2,3-c]pyridazin-8-yl)oxy)nicotinate

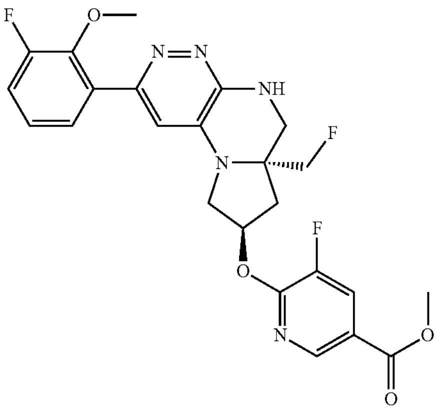 [SMILES: COC(=O)c1cnc(O[C@H]2CN3c4cc(-c5cccc(F)c5OC)nnc4NC[C@@]3(CF)C2)c(F)c1]

To tert-butyl (6aR,8R)-2-(3-fluoro-2-methoxyphenyl)-6a-(fluoromethyl)-8-hydroxy-6a,7,8,9-tetrahydropyrrolo[1',2':4,5]pyrazino[2,3-c]pyridazine-5(6H)-carboxylate (24.0 mg, 0.05 mmol) and methyl 6-chloro-5-fluoropyridine-3-carboxylate (30.4 mg, 0.16 mmol) in THE (2 mL) was added sodium hydride (12.8 mg, 0.32 mmol) at 0° C. The mixture was stirred at rt overnight. The reaction was quenched with MeOH, diluted with EA, washed with water, concentrated and purified via $SiO_2$ FCC: 0-100% EA/Hex followed with 0-10% MeOH/DCM to give methyl 5-fluoro-6-(((6aR,8R)-2-(3-fluoro-2-methoxyphenyl)-6a-(fluoromethyl)-5,6,6a,7,8,9-hexahydropyrrolo[1',2':4,5]pyrazino[2,3-c]pyridazin-8-yl)oxy)nicotinate (12 mg, 0.02 mmol, 45% yield). LCMS calcd for $C_{24}H_{23}F_3N_5O_4[M+H]^+$: m/z=502.2; Found: 502.1.

Step 5: (5-fluoro-6-(((6aR,8R)-2-(3-fluoro-2-methoxyphenyl)-6a-(fluoromethyl)-5,6,6a, 7,8,9-hexahydropyrrolo[1',2':4,5]pyrazino[2,3-c]pyridazin-8-yl)oxy)pyridin-3-yl)methanol

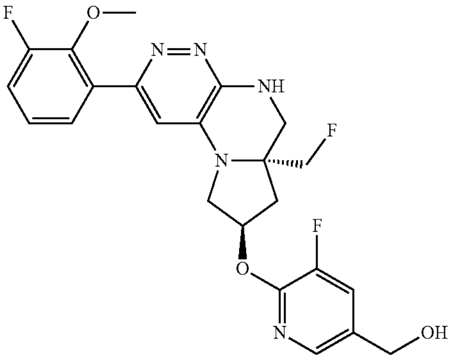 [SMILES: COc1c(F)cccc1-c1cc2c(nn1)NC[C@@]1(CF)C[C@@H](Oc3ncc(CO)cc3F)CN21]

To methyl 5-fluoro-6-(((6aR,8R)-2-(3-fluoro-2-methoxyphenyl)-6a-(fluoromethyl)-5,6,6a,7,8,9-hexahydropyrrolo[1',2':4,5]pyrazino[2,3-c]pyridazin-8-yl)oxy)nicotinate (13.0 mg, 0.03 mmol) in THE (1 mL) was added lithium aluminum hydride (0.03 mL, 0.05 mmol) dropwise at 0° C. The mixture was stirred vigorously at 0° C. for 30 min and then quenched slowly with sat. aq. potassium sodium tartrate solution. The mixture was diluted with water, extracted with EtOAc, washed with brine, concentrated and purified on FCC (0-10% MeOH/DCM) to give (5-fluoro-6-(((6aR,8R)-2-(3-fluoro-2-methoxyphenyl)-6a-(fluoromethyl)-5,6,6a,7,8,9-hexahydropyrrolo[1',2':4,5]pyrazino[2,3-c]pyridazin-8-yl)oxy)pyridin-3-yl)methanol (7 mg, 0.015 mmol, 57% yield). LCMS calcd for $C_{23}H_{23}F_3N_5O_3[M+H]^+$: m/z=474.2; Found: 474.1.

Step 6: 2-((6aR,8R)-8-((5-(chloromethyl)-3-fluoropyridin-2-yl)oxy)-6a-(fluoromethyl)-5,6,6a, 7,8,9-hexahydropyrrolo[1',2':4,5]pyrazino[2,3-c]pyridazin-2-yl)-6-fluorophenol

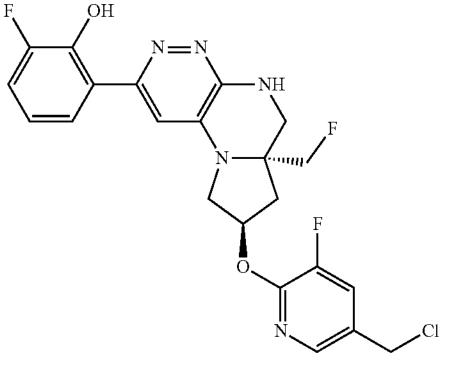 [SMILES: Oc1c(F)cccc1-c1cc2c(nn1)NC[C@@]1(CF)C[C@@H](Oc3ncc(CCl)cc3F)CN21]

To a solution of (5-fluoro-6-(((6aR,8R)-2-(3-fluoro-2-methoxyphenyl)-6a-(fluoromethyl)-5,6,6a,7,8,9-hexahydro-pyrrolo[1',2':4,5]pyrazino[2,3-c]pyridazin-8-yl)oxy)pyridin-3-yl)methanol (9.0 mg, 0.02 mmol) in DCM (1 mL) cooled in an ice bath was added trichloroborane (0.76 mL, 0.76 mmol). The mixture was stirred at rt overnight. The reaction was quenched slowly with water, neutralized with aq. sat. $NaHCO_3$ solution, extracted with 3:1 DCM:iPrOH, dried over $MgSO_4$ and condensed to give 2-((6aR,8R)-8-((5-(chloromethyl)-3-fluoropyridin-2-yl)oxy)-6a-(fluoromethyl)-5,6,6a,7,8,9-hexahydropyrrolo[1',2':4,5]pyrazino[2,3-c]pyridazin-2-yl)-6-fluorophenol (9 mg, 0.019 mmol, 99% yield). LCMS calcd for $C_{22}H_{20}ClF_3N_5O_2$ $[M+H]^+$: m/z=478.1; Found: 478.2.

Step 7: 3-(6-(4-((5-fluoro-6-(((6aR,8R)-2-(3-fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy)pyridin-3-yl)methyl) piperazin-1-yl)-1-oxoisoindolin-2-yl)piperidine-2,6-dione

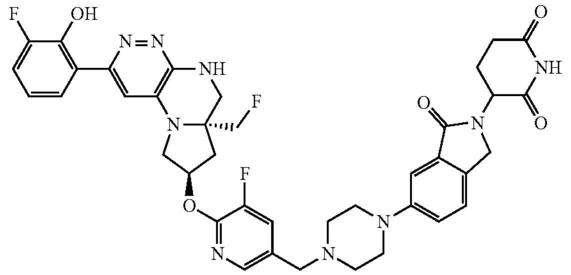 [SMILES: O=C1CCC(N2Cc3ccc(N4CCN(Cc5cnc(O[C@H]6CN7c8cc(-c9cccc(F)c9O)nnc8NC[C@@]7(CF)C6)c(F)c5)CC4)cc3C2=O)C(=O)N1]

A mixture of 2-((6aR,8R)-8-((5-(chloromethyl)-3-fluoropyridin-2-yl)oxy)-6a-(fluoromethyl)-5,6,6a,7,8,9-hexahydropyrrolo[1',2':4,5]pyrazino[2,3-c]pyridazin-2-yl)-6-fluorophenol (9.0 mg, 0.02 mmol), (S)-3-(1-oxo-6-(piperazin-1-yl)isoindolin-2-yl)piperidine-2,6-dione (7.42 mg, 0.02 mmol) and N,N-diisopropylethylamine (16.4 uL, 0.09 mmol) in MeCN (1 mL) was stirred at 120° C. for 1 h. The mixture was purified via prep-LCMS (Waters CSH Phenyl-Hexyl, 5 uM, 30×100 mm, 5.9-23.9% MeCN/water (containing 0.1% TFA) over 5 min) to give the title compound (1 mg, 0.001 mmol, 6.9% yield) as a white TFA salt. LCMS calcd for $C_{39}H_{39}F_3N_9O_5$ $[M+H]^+$: m/z=770.3; Found: 770.4.

Example 71: (S)-3-(6-(4-((5-fluoro-6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methylpyridin-3-yl)methyl) piperazin-1-yl)-1-oxoisoindolin-2-yl)piperidine-2,6-dione

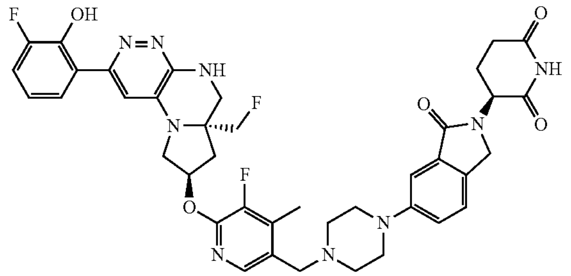 [SMILES: Cc1c(CN2CCN(c3ccc4c(c3)C(=O)N([C@H]3CCC(=O)NC3=O)C4)CC2)cnc(O[C@H]2CN3c4cc(-c5cccc(F)c5O)nnc4NC[C@@]3(CF)C2)c1F]

Step 1: 5-bromo-2,3-difluoro-4-methylpyridine

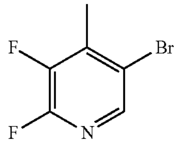

A solution of 5-bromo-2,3-difluoropyridine (5.0 g, 25.8 mmol) in THF (80 mL) was added LDA (15.5 mL, 30.9 mmol) dropwise at −78° C. under $N_2$. The reaction was stirred at −78° C. for 30 mins and was added iodomethane (2.41 mL, 38.7 mmol) in 3 mL of THF dropwise. The reaction was stirred at −78° C. for 40 mins and turned into a yellow suspension.

The HPLC showed full consumption of starting material. The cold reaction mixture was poured into cold saturated $NH_4Cl$ solution and was extracted by MTBE twice. The combined organic phase was dried over $Na_2SO_4$. After removal of solvent, the residue was purified by silica gel column (dry load, hexanes/DCM=0-100%) to give 4.6 g of a mixture of 5-bromo-2,3-difluoro-4-methylpyridine (3.5 g, 16.8 mmol, 65% yield) and 5-bromo-4-ethyl-2,3-difluoropyridine (1.1 g, 4.9 mmol, 19% yield). This product has no ES+ signal. $^1H$ NMR (300 MHz, CDCl3) δ 8.09 (s, 1H), 2.44 (d, J=2.4 Hz, 3H). $^{19}F$ NMR (283 MHz, CDCl3) δ-90.33 (d, J=24.4 Hz, 1F), −138.16-−140.12 (m, 1F).

Step 2: 5-bromo-3-fluoro-4-methylpyridin-2-ol

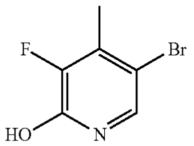

A mixture of 5-bromo-2,3-difluoro-4-methylpyridine (3.5 g, 16.8 mmol) and 5-bromo-4-ethyl-2,3-difluoropyridine (1.1 g, 4.95 mmol) was added sodium hydroxide (4.37 g, 109.37 mmol) aqueous solution in water (30 mL). The reaction mixture was stirred at 100° C. in a sealed tube for 16 hours. The LC-MS and HPLC showed the conversion rate>95%. The reaction was cooled to 0° C. and was acidified by 1 N HCl solution to pH-3. The mixture was extracted by chloroform/IPA (v/v=3/1) three times. The combined organic phase was dried over $Na_2SO_4$. After removal of solvent, the residue was purified by prep-HPLC on C18 column (30×250 mm, 10 m) using mobile phase 10% to 55% MeCN/H2O (w/0.1% TFA) (tR=18 min). The desired fractions were collected, concentrated to dryness to give 5-bromo-3-fluoro-4-methylpyridin-2-ol (2.3 g, 11.2 mmol, 66% yield) as pale yellow solids. LCMS calcd for $C_6H_6BrFNO$ $[M+H]^+$: m/z=206.0; Found: 206.2.

Step 3: 5-fluoro-6-hydroxy-4-methylnicotinonitrile

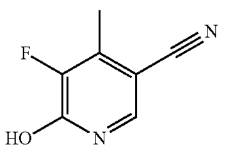

A mixture of 5-bromo-3-fluoro-4-methylpyridin-2-ol (1.75 g, 8.49 mmol), copper(I) cyanide (3.04 g, 33.98 mmol), DPPF (2.35 g, 4.25 mmol) and $Pd_2(dba)_3$ (1.17 g, 1.27 mmol) in 1,4-dioxane (20 mL) was purged with $N_2$ for 1 min. The reaction was stirred at 105° C. overnight. The reaction mixture was filtered through celite. The solvent of the filtrate was removed. The residue was purified by silica gel column chromatography eluted by MeOH/DCM 0~10%. The desired fractions were collected. After removal of solvent, 5-fluoro-6-hydroxy-4-methylpyridine-3-carbonitrile (0.74 g, 4.9 mmol, 57% yield) was obtained as pale green solids. LCMS calcd for $C_7H_6FN_2O$ $[M+H]^+$: m/z=153.0; Found: 153.3.

Step 4: 6-(((6aR,8R)-2-chloro-6a-(fluoromethyl)-5,6,6a, 7,8,9-hexahydropyrrolo[1',2':4,5]pyrazino[2,3-c]pyridazin-8-yl)oxy)-5-fluoro-4-methylnicotinonitrile

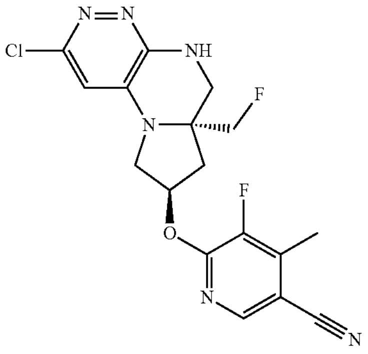 [SMILES: Cc1c(C#N)cnc(O[C@H]2CN3c4cc(Cl)nnc4NC[C@@]3(CF)C2)c1F]

To a mixture of (6aR,8S)-2-chloro-6a-(fluoromethyl)-5,6,6a,7,8,9-hexahydropyrrolo[1',2':4,5]pyrazino[2,3-c]pyridazin-8-ol (185.0 mg, 0.72 mmol), triphenylphosphine (281.4 mg, 1.07 mmol) and 5-fluoro-6-hydroxy-4-methylpyridine-3-carbonitrile (163.2 mg, 1.07 mmol) in THE (6 mL) was added diisopropyl azodicarboxylate (211 uL, 1.07 mmol) dropwise at rt. The mixture was then stirred at 65° C. for 1 h. The mixture was concentrated and purified on FCC (0-5% MeOH/DCM) to give 6-(((6aR,8R)-2-chloro-6a-(fluoromethyl)-5,6,6a,7,8,9-hexahydro-pyrrolo[1',2':4,5]pyrazino[2,3-c]pyridazin-8-yl)oxy)-5-fluoro-4-methylnicotinonitrile (250 mg, 0.64 mmol, 89% yield). LCMS calcd for $C_{17}H_{16}ClF_2N_{60}$ $[M+H]^+$: m/z=393.1; Found: 393.1.

Step 5: 5-fluoro-6-(((6aR,8R)-2-(3-fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy)-4-methylnicotinonitrile

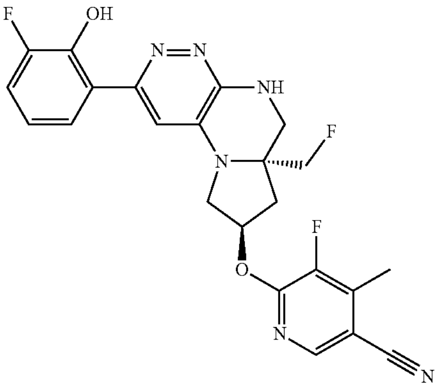 [SMILES: Cc1c(C#N)cnc(O[C@H]2CN3c4cc(-c5cccc(F)c5O)nnc4NC[C@@]3(CF)C2)c1F]

A mixture of 6-(((6aR,8R)-2-chloro-6a-(fluoromethyl)-5,6,6a,7,8,9-hexahydropyrrolo [1',2':4,5]pyrazino[2,3-c]pyridazin-8-yl)oxy)-5-fluoro-4-methylnicotinonitrile (250.0 mg, 0.64 mmol), 3-fluoro-2-hydroxyphenylboronic acid (297.7 mg, 1.91 mmol), potassium carbonate (263.9 mg, 1.91 mmol) and XPhos Pd G2 (100.2 mg, 0.13 mmol) in 1,4-dioxane (2 mL) and water (0.2 mL) was sparged for ~2 min with $N_2$ and stirred at 100° C. for 1 h. The mixture was purified via $SiO_2$ FCC (0-5% MeOH/DCM) to give 5-fluoro-6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methylnicotinonitrile (260 mg, 0.56 mmol, 87% yield). LCMS calcd for $C_{23}H_{20}F_3N_6O_2$ $[M+H]^+$: m/z=469.2; Found: 469.1.

Step 6: 5-fluoro-6-(((6aR,8R)-2-(3-fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy)-4-methylnicotinaldehyde

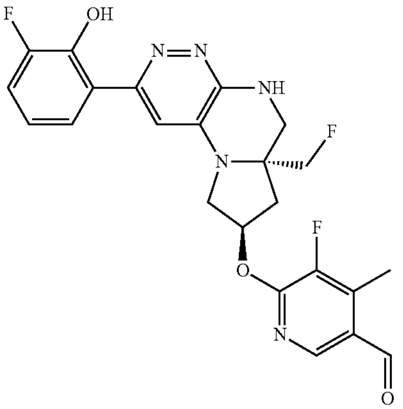 [SMILES: Cc1c(C=O)cnc(O[C@H]2CN3c4cc(-c5cccc(F)c5O)nnc4NC[C@@]3(CF)C2)c1F]

To a solution of 5-fluoro-6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methyl-nicotinonitrile (260.0 mg, 0.56 mmol) in DCM (10 mL) at 0° C. was added DIBAL (3.33 mL, 3.33 mmol) dropwise. The mixture was stirred at 0° C. for 1 h. The mixture was quenched with aq. sat. sodium potassium tartrate solution, extracted with DCM, concentrated and purified on FCC (0-5% MeOH/DCM) to give 5-fluoro-6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methylnicotinaldehyde (64 mg, 0.14 mmol, 24% yield). LCMS calcd for $C_{23}H_{21}F_3N_5O_3$ $[M+H]^+$: m/z=472.2; Found: 472.1.

Step 7: (S)-3-(6-(4-((5-fluoro-6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione

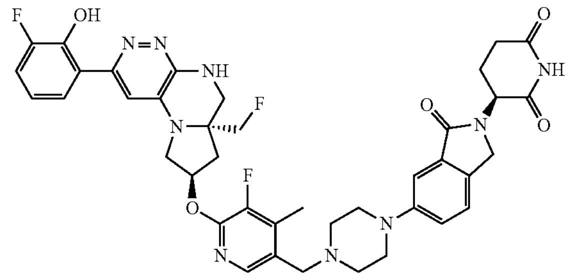 [SMILES: Cc1c(CN2CCN(c3ccc4c(c3)C(=O)N([C@H]3CCC(=O)NC3=O)C4)CC2)cnc(O[C@H]2CN3c4cc(-c5cccc(F)c5O)nnc4NC[C@@]3(CF)C2)c1F]

To a mixture of (S)-3-(1-oxo-6-(piperazin-1-yl)isoindolin-2-yl)piperidine-2,6-dione hydrochloride (54.48 mg, 0.15 mmol) and 5-fluoro-6-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-4-methylnicotinaldehyde (64.0 mg, 0.14 mmol) in DMSO (0.5 mL) was added N,N-diisopropylethylamine (70.9 uL, 0.41 mmol). The mixture was stirred at rt for 30 min., then sodium triacetoxyborohydride (86.3 mg, 0.41 mmol) was added. The mixture was stirred at 35° C. overnight. The mixture was purified with Prep-LCMS (Waters CSH Fluoro-Phenyl, 5 uM, 30×100 mm, 13.3-33.3% MeCN/water (containing 0.1% TFA) over 5 min) to give the title compound (20 mg, 0.025 mmol, 18% yield) as a white TFA salt. LCMS calcd for $C_{40}H_{41}F_3N_9O_5[M+H]^+$: m/z=784.3; Found: 784.4. $^1$H NMR (400 MHz, MeOD) δ 8.04 (s, 1H), 7.41 (d, J=8.2 Hz, 1H), 7.30-7.18 (m, 5H), 6.92 (dd, J=8.1, 4.9 Hz, 1H), 6.87 (s, 1H), 5.89 (s, 1H), 5.04 (dd, J=13.3, 5.2 Hz, 2H), 4.57 (d, J=9.4 Hz, 1H), 4.46 (d, J=9.5 Hz, 2H), 4.41-4.30 (m, 5H), 4.30-4.19 (m, 2H), 3.90-3.76 (m, 3H), 3.41 (s, 3H), 2.91 (dd, J=13.8, 6.9 Hz, 2H), 2.81 (ddd, J=18.4, 13.4, 5.3 Hz, 2H), 2.73-2.64 (m, 2H), 2.41 (td, J=13.2, 4.7 Hz, 2H), 2.33 (d, J=2.3 Hz, 3H), 2.16 (dd, J=13.9, 5.8 Hz, 2H), 2.09 (s, 1H).

Example 72: (S)-3-(6-(4-((5-(((6aR,8R)-6a-Ethyl-2-(3-fluoro-2-hydroxyphenyl)-5,6,6a, 7,8,9-hexahydropyrrolo[1',2':4,5]pyrazino[2,3-c]pyridazin-8-yl)oxy)-3-fluoropyridin-2-yl)methyl)piperazin-1-yl)-1-oxoisoindolin-2-yl)piperidine-2,6-dione

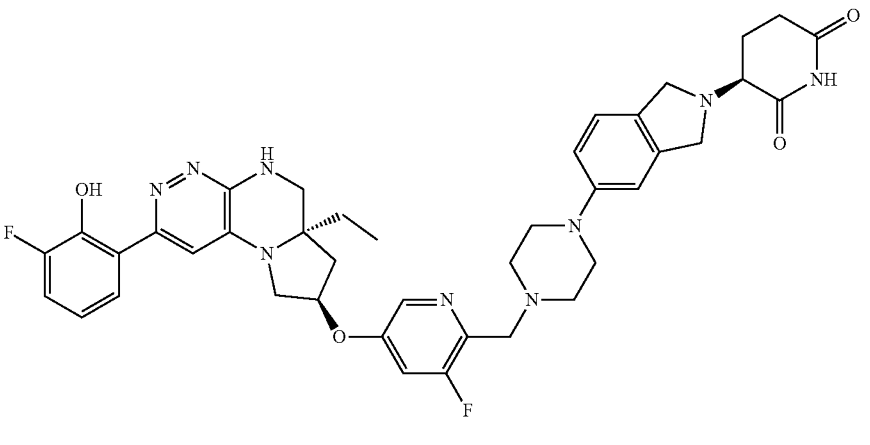 [SMILES: CC[C@@]12CNc3nnc(-c4cccc(F)c4O)cc3N1C[C@H](Oc1cnc(CN3CCN(c4ccc5c(c4)CN([C@H]4CCC(=O)NC4=O)C5)CC3)c(F)c1)C2]

Step 1. (6aR,8R)-6a-Ethyl-2-(3-fluoro-2-methoxyphenyl)-8-((5-fluoro-6-vinylpyridin-3-yl)oxy)-5,6,6a, 7,8,9-hexahydropyrrolo[1',2':4,5]pyrazino[2,3-c]pyridazine

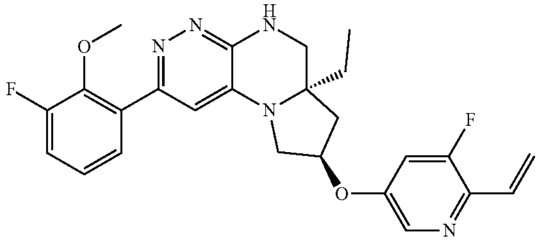 [SMILES: C=Cc1ncc(O[C@H]2CN3c4cc(-c5cccc(F)c5OC)nnc4NC[C@@]3(CC)C2)cc1F]

To (6aR,8S)-6a-ethyl-2-(3-fluoro-2-methoxyphenyl)-5,6,6a,7,8,9-hexahydropyrrolo [1',2':4,5]pyrazino[2,3-c]pyridazin-8-ol (Intermediate 10) (60.0 mg, 0.17 mmol), 5-fluoro-6-vinylpyridin-3-ol (Intermediate 18) (40.0 mg, 0.29 mmol) and triphenylphosphine (1.6 mmol/g polymer bound, 366 mg, 0.59 mmol) in THE (6.00 mL) was added diisopropyl azodicarboxylate (111 μL, 0.56 mmol) at room temperature. Stirred at 55° C. and monitored by LCMS. After 1 hour, the reaction was left to cool to ambient temperature, filtered and purified $SiO_2$ FCC 0-100% EtOAc/Hexane then 0-20% DCM/MeOH to obtain the title compound (25 mg, 29% yield) as a white solid. LCMS calcd for $C_{25}H_{26}F_2N_5O_2[M+H]^+$: m/z=466.2; Found: 465.9.

Step 2. 2-((6aR,8R)-6a-Ethyl-8-((5-fluoro-6-vinylpyridin-3-yl)oxy)-5,6,6a, 7,8,9-hexahydropyrrolo[1',2':4,5]pyrazino[2,3-c]pyridazin-2-yl)-6-fluorophenol

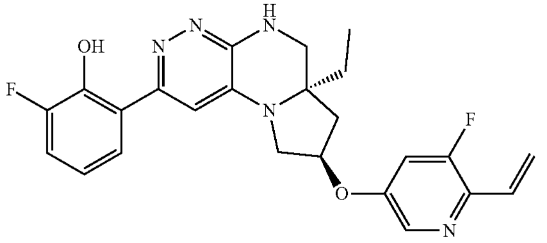 [SMILES: C=Cc1ncc(O[C@H]2CN3c4cc(-c5cccc(F)c5O)nnc4NC[C@@]3(CC)C2)cc1F]

To (6aR,8R)-6a-ethyl-2-(3-fluoro-2-methoxyphenyl)-8-((5-fluoro-6-vinylpyridin-3-yl)oxy)-5,6,6a,7,8,9-hexahydropyrrolo[1',2':4,5]pyrazino[2,3-c]pyridazine (25.0 mg, 0.05 mmol) in DCM (1.10 mL) was added trichloroborane (80.0 μL, 0.80 mmol) at 0° C. Reaction left to warm to ambient temperature overnight. Reaction was quenched with MeOH, diluted in DCM and sat. sodium bicarbonate. The organic layer was separated, and the water layer was re-extracted with DCM (2×) then the combined organic layer was dried over sodium sulfate, filtered and condensed to yield title compound (25 mg, quant.). The crude was taken to the next step without further purification. LCMS calcd for $C_{24}H_{24}F_2N_5O_2$[M+H]$^+$: m/z=452.2; Found: 452.0.

Step 3. 5-(((6aR,8R)-6a-Ethyl-2-(3-fluoro-2-hydroxyphenyl)-5,6,6a, 7,8,9-hexahydropyrrolo[1',2':4,5]pyrazino[2,3-c]pyridazin-8-yl)oxy)-3-fluoropicolinaldehyde

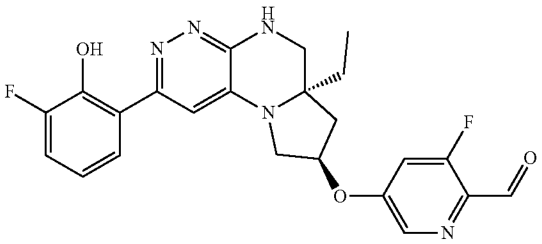 [SMILES: CC[C@@]12CNc3nnc(-c4cccc(F)c4O)cc3N1C[C@H](Oc1cnc(C=O)c(F)c1)C2]

To 2-((6aR,8R)-6a-ethyl-8-((5-fluoro-6-vinylpyridin-3-yl)oxy)-5,6,6a,7,8,9-hexahydropyrrolo[1',2':4,5]pyrazino[2,3-c]pyridazin-2-yl)-6-fluorophenol (25.0 mg, 0.03 mmol) and sodium periodate (13.8 mg, 0.06 mmol) in THE (600 μL) and water (300 μL) was added osmium tetroxide (ReagentPlus, 4% wt in water) (13.8 μL, 0.02 mmol). After stirring at room temperature overnight, the reaction was quenched with sat. sodium sulfite then extracted with DCM (3×). The organic layers were combined, dried with sodium sulfate, filtered, and condensed to yield the title compound (15 mg, 40% yield). The crude was taken to the next step without further purification. LCMS calcd for $C_{23}H_{22}F_2N_5O_3$ [M+H]$^+$: m/z=454.2; Found: 454.0.

Step 4. (S)-3-(6-(4-((5-(((6aR,8R)-6a-ethyl-2-(3-fluoro-2-hydroxyphenyl)-5,6,6a, 7,8,9-hexahydropyrrolo[1',2':4,5]pyrazino[2,3-c]pyridazin-8-yl)oxy)-3-fluoropyridin-2-yl)methyl)piperazin-1-yl)-1-oxoisoindolin-2-yl)piperidine-2,6-dione To 5-(((6aR,8R)-6a-Ethyl-2-(3-fluoro-2-hydroxyphenyl)-5,6,6a,7,8,9-hexahydropyrrolo [1',2':4,5]pyrazino[2,3-c]pyridazin-8-yl)oxy)-3-fluoropicolinaldehyde (15.0 mg, 0.01 mmol) and (S)-3-(1-oxo-6-(piperazin-1-yl)isoindolin-2-yl)piperidine-2,6-dione hydrochloride (Intermediate 7) (10.0 mg, 0.03 mmol) in DMSO (300 μL) was added DIPEA (9 uL, 0.05 mmol). Reaction stirred at 40° C. for 1 hour. Sodium triacetoxyborohydride (16.0 mg, 0.08 mmol) was added after 50 min. Stirred at 35° C. overnight. Reaction was diluted in 1:1 MeOH:DMSO and purified by prep-HPLC (Waters CSH-C18, 11.5-31.5% o ACN in water (containing 0.1% TFA)). Product fractions were lyophilized to yield the TFA salt of the title compound (6 mg, 3700 yield) as a white solid. LCMS calcd for $C_{40}H_{42}F_2N_9O_5$[M+H]$^+$: m/z=766.3; Found: 766.3. $^1$H NMR (400 MHz, DMSO) δ 10.98 (s, 1H), 8.34 (s, 1H), 8.20 (s, 1H), 7.76 (d, J=11.9 Hz, 1H), 7.50 (d, J=8.2 Hz, 1H), 7.42-7.24 (m, 4H), 6.93 (s, 2H), 5.51 (s, 1H), 5.10 (dd, J=12.8, 4.9 Hz, 1H), 4.53 (s, 2H), 4.37 (d, J=17.4 Hz, 1H), 4.27-4.12 (m, 2H), 3.90 (d, J=14.8 Hz, 2H), 3.11 (d, J=12.2 Hz, 2H), 2.99-2.85 (m, 1H), 2.82-2.71 (m, 1H), 2.63 (t, J=18.2 Hz, 1H), 2.45-2.29 (m, 2H), 1.99 (dd, J=13.0, 4.5 Hz, 2H), 1.74-1.50 (m, 2H), 0.91 (t, J=7.5 Hz, 3H). $^{19}$F NMR (376 MHz, DMSO) δ-73.76, −120.88, −136.69.

Examples 73-74

Examples 73-74 shown below in Table 4 were prepared as TFA salts by the method used in preparing Example 72 using the appropriate starting materials and intermediates.

TABLE 4

Examples 73 and 74

| Ex. | Structure/Name | Calcd. (M + H)$^+$ m/z | Found (M + H)$^+$ m/z |
|---|---|---|---|
| 73 | 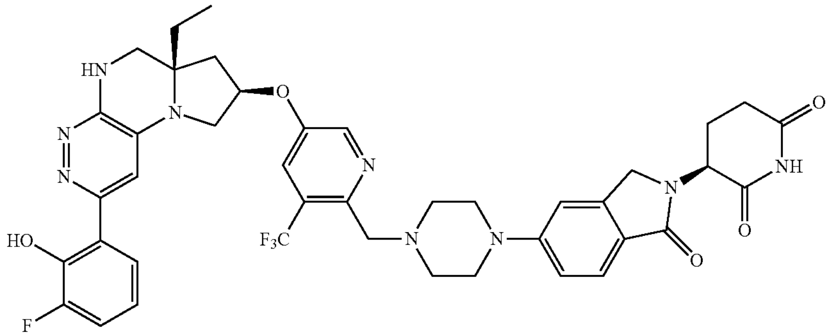 [SMILES: CC[C@]12CNc3nnc(-c4cccc(F)c4O)cc3N1C[C@H](Oc1cnc(CN3CCN(c4ccc5c(c4)CN([C@H]4CCC(=O)NC4=O)C5=O)CC3)c(C(F)(F)F)c1)C2] (S)-3-(5-(4-((5-(((6aS,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-3-(trifluoromethyl)pyridin-2-yl)methyl)piperazin-1-yl)-1-oxoisoindolin-2-yl)piperidine-2,6-dione | 816.3 | 816.2 |

TABLE 4-continued

| Examples 73 and 74 | | | |
|---|---|---|---|
| Ex. | Structure/Name | Calcd. (M + H)+ m/z | Found (M + H)+ m/z |
| 74 | 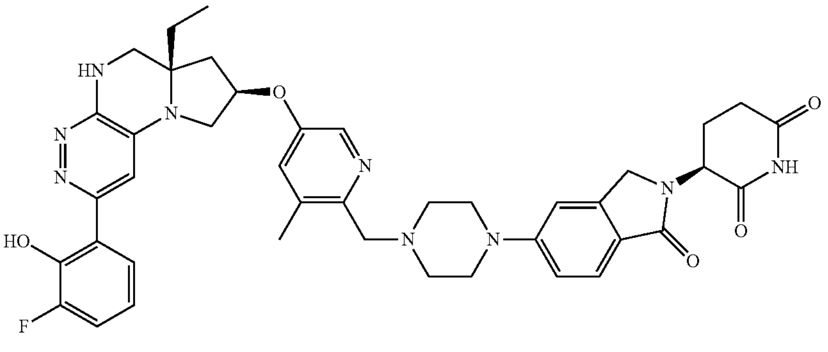 [SMILES: CC[C@]12CNc3nnc(-c4cccc(F)c4O)cc3N1C[C@H](Oc1cnc(CN3CCN(c4ccc5c(c4)CN([C@H]4CCC(=O)NC4=O)C5=O)CC3)c(C)c1)C2] (S)-3-(5-(4-((5-(((6aS,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-3-methylpyridin-2-yl)methyl)piperazin-1-yl)-1-oxoisoindolin-2-yl)piperidine-2,6-dione | 762.3 | 762.2 |

Example 75: (S)-3-(6-(4-((2-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4,6-dimethylpyrimidin-5-yl)methyl)piperazin-1-yl)-1-oxoisoindolin-2-yl)piperidine-2,6-dione

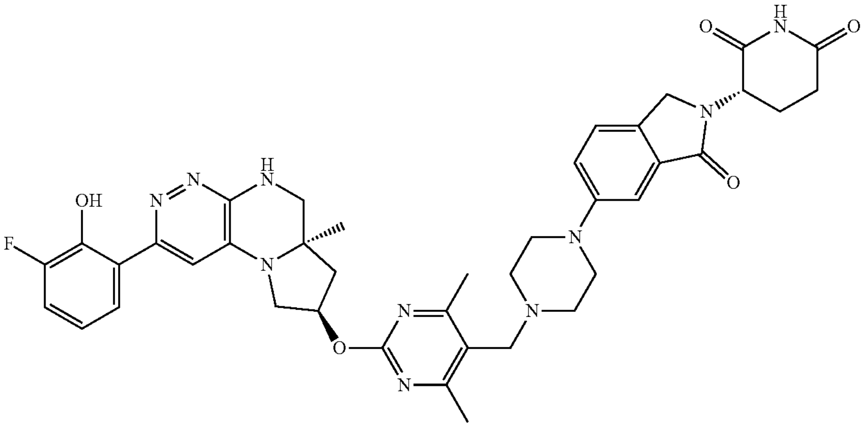 [SMILES: Cc1nc(O[C@H]2CN3c4cc(-c5cccc(F)c5O)nnc4NC[C@@]3(C)C2)nc(C)c1CN1CCN(c2ccc3c(c2)C(=O)N([C@H]2CCC(=O)NC2=O)C3)CC1]

Step 1. Ethyl 2-(((6aR,8R)-2-Chloro-6a-methyl-5,6,6a, 7,8,9-hexahydropyrrolo[1',2':4,5]pyrazino[2,3-c]pyridazin-8-yl)oxy)-4,6-dimethylpyrimidine-5-carboxylate

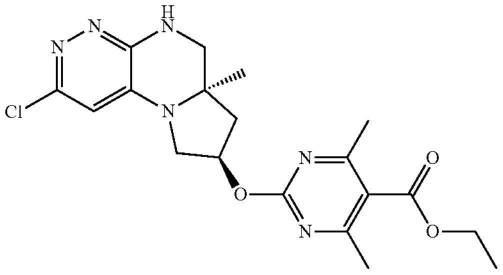 [SMILES: CCOC(=O)c1c(C)nc(O[C@H]2CN3c4cc(Cl)nnc4NC[C@@]3(C)C2)nc1C]

To a mixture of ethyl 2-hydroxy-4,6-dimethylpyrimidine-5-carboxylate (78.5 mg, 0.40 mmol), (6aR,8S)-2-chloro-6a-methyl-5,6,6a,7,8,9-hexahydropyrrolo[1',2':4,5]pyrazino[2,3-c]pyridazin-8-ol (Intermediate 12) (106 mg, 0.44 mmol) and triphenylphosphine (158 mg, 0.6 mmol) in THF (2.00 mL) was added diisopropyl azodicarboxylate (0.12 mL, 0.6 mmol) at 0° C. The reaction mixture was heated to 50° C. and stirred for 2 hours. The reaction was then cooled to rt and partitioned between EtOAc (30 mL) and water (30 mL). The organic phase was separated, and the aqueous phase was re-extracted with EtOAc (15 mL×3). The combined organic phase was dried over sodium sulfate, filtered, concentrated under reduced pressure then purified by prep-HPLC to give the title compound (73.2 mg, 49% yield) as a white solid. LCMS calcd for $C_{19}H_{24}ClN_6O_3$ $[M+H]^+$: m/z=419.2; Found: 419.44.

Step 2. Ethyl 2-(((6aR,8R)-2-(3-fluoro-2-hydroxyphenyl)-6a-methyl-5,6,6a, 7,8,9-hexahydropyrrolo[1',2':4,5]pyrazino[2,3-c]pyridazin-8-yl)oxy)-4,6-dimethylpyrimidine-5-carboxylate

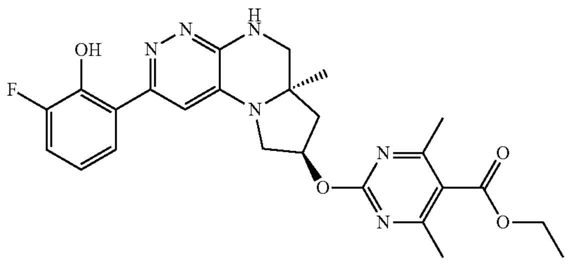 [SMILES: CCOC(=O)c1c(C)nc(O[C@H]2CN3c4cc(-c5cccc(F)c5O)nnc4NC[C@@]3(C)C2)nc1C]

The mixture of cesium acetate (93.7 mg, 0.488 mmol), ethyl 2-(((6aR,8R)-2-chloro-6a-methyl-5,6,6a,7,8,9-hexahydropyrrolo[1',2':4,5]pyrazino[2,3-c]pyridazin-8-yl)oxy)-4,6-dimethylpyrimidine-5-carboxylate (51.1 mg, 0.12 mmol), XPhos Pd G2 (4.8 mg, 0.01 mmol), and 3-fluoro-2-hydroxyphenylboronic acid (57.06 mg, 0.37 mmol) in 1,4-dioxane (1.90 mL) and water (100 μL) was heated to 95° C. under $N_2$ atmosphere for 8 h. The reaction mixture was cooled to ambient temperature and partitioned between EtOAc (30 mL) and water (20 mL). The organic phase was separated, and the aqueous phase was re-extracted with EtOAc (10 mL×3) and $CHCl_3$/IPA (3:1, 10 mL×1). The combined organic phase was concentrated and purified by prep-HPLC (15-60% MeCN in water (containing 0.1% TFA)) to give the title compound (34.3 mg, 57% yield) as a pale-yellow solid. LCMS calcd for $C_{25}H_{28}FN_6O_4[M+H]^+$: m/z=495.2; Found: 495.3.

Step 3. 2-(((6aR,8R)-2-(3-fluoro-2-hydroxyphenyl)-6a-methyl-5,6,6a, 7,8,9-hexahydropyrrolo[1',2':4,5]pyrazino[2,3-c]pyridazin-8-yl)oxy)-4,6-dimethylpyrimidine-5-carbaldehyde

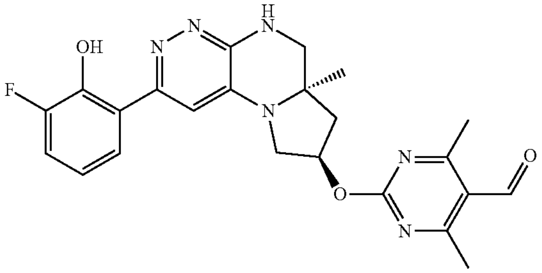 [SMILES: Cc1nc(O[C@H]2CN3c4cc(-c5cccc(F)c5O)nnc4NC[C@@]3(C)C2)nc(C)c1C=O]

A solution of ethyl 2-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4,6-dimethylpyrimidine-5-carboxylate (155 mg, 0.31 mmol) in THE (10 mL) was added lithium diisobutyl-tert-butylaluminum hydride (4.2 mL, 1.05 mmol) at 0° C. under $N_2$ in one portion. The reaction was stirred at 0° C. for 40 min. The reaction was quenched by adding methanol dropwise at 0° C. and was stirred with 10% $Na_2CO_3$ solution at 0° C. for 20 mins. Then it was poured into $NaHCO_3$ solution and was extracted by DCM (3×). The combined organic phase was dried over $Na_2SO_4$. After removal of solvent, the residue was purified by prep-HPLC (15-45% MeCN/$H_2O$ (w/0.1% TFA)). The desired fractions were collected, concentrated, poured into $NaHCO_3$ (aq) and extracted by DCM (3×). The combined organic phase was dried over $Na_2SO_4$, filtered, and condensed to yield the title compound (90.0 mg, 64% yield). LCMS calcd for $C_{23}H_{24}FN_6O_3[M+H]^+$: m/z=451.2; Found: 451.7.

Step 4. (S)-3-(6-(4-((2-(((6aR,8R)-2-(3-fluoro-2-hydroxyphenyl)-6a-methyl-5,6,6a, 7,8,9-hexahydropyrrolo[1',2':4,5]pyrazino[2,3-c]pyridazin-8-yl)oxy)-4,6-dimethylpyrimidin-5-yl)methyl)piperazin-1-yl)-1-oxoisoindolin-2-yl)piperidine-2,6-dione To a solution of 2-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4,6-dimethylpyrimidine-5-carbaldehyde (70.0 mg, 0.16 mmol) and (S)-3-(1-oxo-6-(piperazin-1-yl)isoindolin-2-yl)piperidine-2,6-dione hydrochloride (Intermediate 7) (102 mg, 0.28 mmol) in DMSO (3 mL) was added DIPEA (0.14 mL, 0.78 mmol) and stirred at 38° C. for 30 mins, followed by addition of STAB (98.8 mg, 0.47 mmol). The reaction was stirred at 38° C. overnight. The reaction was purified by prep-HPLC (8-40% MeCN/$H_2O$ (containing 0.1% TFA)) to yield the TFA salt of the title compound (59.0 mg, 50% yield) as a white solid. LCMS calcd for $C_{40}H_{44}FN_{10}O_5[M+H]^+$: m/z=763.3; Found: 763.5.

Example 76: 5-((4-(2-((S)-2,6-dioxopiperidin-3-yl)-3-oxoisoindolin-5-yl)piperazin-1-yl)methyl)-2-(((6aS,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)isonicotinonitrile

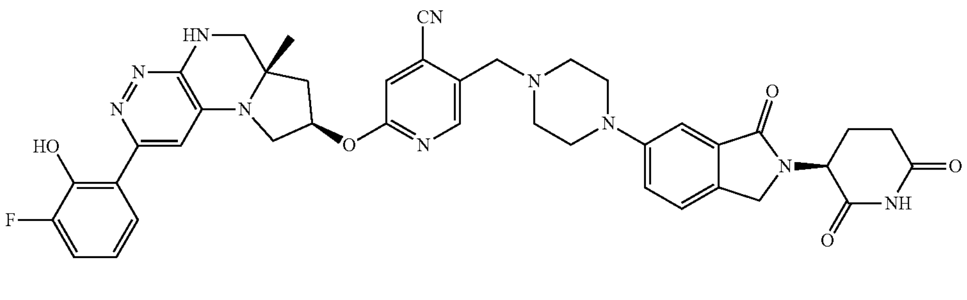 [SMILES: C[C@]12CNc3nnc(-c4cccc(F)c4O)cc3N1C[C@H](Oc1cc(C#N)c(CN3CCN(c4ccc5c(c4)C(=O)N([C@H]4CCC(=O)NC4=O)C5)CC3)cn1)C2]

Step 1. 6-(((6aS,8R)-2-(3-fluoro-2-hydroxyphenyl)-6a-methyl-5,6,6a, 7,8,9-hexahydropyrrolo[1',2':4,5]pyrazino[2,3-c]pyridazin-8-yl)oxy)-4-iodonicotinic acid

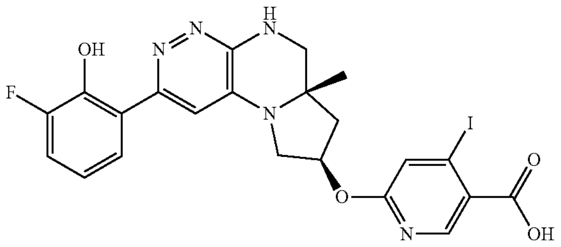 [SMILES: C[C@]12CNc3nnc(-c4cccc(F)c4O)cc3N1C[C@H](Oc1cc(I)c(C(=O)O)cn1)C2]

A mixture of (6aS,8R)-2-(3-fluoro-2-hydroxyphenyl)-6a-methyl-5,6,6a,7,8,9-hexahydropyrrolo[1',2':4,5]pyrazino[2,3-c]pyridazin-8-ol (Intermediate 15) (160 mg, 0.33 mmol) in DMF (3 mL) at 0° C. was added sodium hydride (145 mg, 3.62 mmol) portion wise. The reaction mixture was stirred at rt for 20 min then 6-fluoro-4-iodonicotinic acid (Intermediate 17) (176 mg, 0.66 mmol) was added. The reaction was stirred at 55° C. for 3 h then cooled to rt, poured into $NH_4Cl$ solution and extracted by DCM/MeOH (v/v=10/1) (3×). The combined organic phases were dried over $Na_2SO_4$, filtered and condensed. Residue was purified by prep-HPLC on $C_{18}$ column (30×250 mm, 10 μM) using mobile phase 8-45% $MeCN/H_2O$ (w/0.1% TFA) (tR=18 min). The desired fractions were collected, concentrated, neutralized to pH~6, and was extracted by DCM/MeOH (v/v=10/1) (3×). The combined organic phase was dried over $Na_2SO_4$, filtered and condensed to yield the title compound (122 mg, 66% yield). $^1H$ NMR (300 MHz, DMSO) δ 8.74 (d, J=1.9 Hz, 1H), 8.60 (d, J=1.8 Hz, 1H), 7.76 (d, J=8.3 Hz, 1H), 7.51 (d, J=3.8 Hz, 1H), 7.15 (dd, J=10.4, 8.3 Hz, 1H), 7.02 (s, 1H), 6.77 (td, J=8.0, 5.1 Hz, 1H), 5.89 (t, J=5.4 Hz, 1H), 4.02 (dd, J=13.7, 6.3 Hz, 1H), 3.79 (d, J=13.2 Hz, 1H), 3.54 (dd, J=11.0, 4.2 Hz, 1H), 2.99 (d, J=11.3 Hz, 1H), 2.32 (d, J=14.0 Hz, 1H), 2.20 (dd, J=13.9, 6.0 Hz, 1H), 1.51 (s, 3H). $^{19}F$ NMR (283 MHz, DMSO) δ-137.80 (dd, J=11.1, 5.0 Hz).

Step 2. 2-Fluoro-6-((6aS,8R)-8-((5-(hydroxymethyl)-4-iodopyridin-2-yl)oxy)-6a-methyl-5,6,6a, 7,8,9-hexahydropyrrolo[1',2':4,5]pyrazino[2,3-c]pyridazin-2-yl)phenol

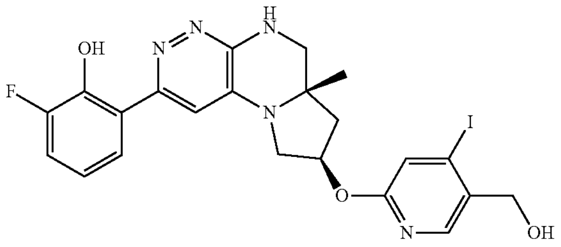 [SMILES: C[C@]12CNc3nnc(-c4cccc(F)c4O)cc3N1C[C@H](Oc1cc(I)c(CO)cn1)C2]

To a solution of 6-(((6aS,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4-iodonicotinic acid (160 mg, 0.28 mmol) in THE (3 mL) was added borane dimethyl sulfide complex (1.08 g, 14.2 mmol) at 0° C. The reaction was stirred at 50° C. and was monitored by HPLC.

The reaction was stopped when the percentage of desired product did not increase, even though ~26% starting material remained. The reaction was quenched by adding methanol dropwise at 0° C. carefully. The solvent was removed, and the residue was redissolved in methanol with 5% TFA and was stirred for 30 mins at rt. The solvent was removed, and the residue was purified by prep-HPLC (C18 column, 8-55% $MeCN/H_2O$ (containing 0.1% formic acid)). The desired fractions were collected, concentrated, poured into saturated $NaHCO_3$ (aq) solution, and was extracted by $CHCl_3$/IPA (3:1, 3×). The combined organic phase was dried over $Na_2SO_4$, filtered and condensed to yield the title compound (40.0 mg, 26% yield) as a yellow solid. LCMS calcd for $C_{22}H_{22}FIN_5O_3[M+H]^+$: m/z=550.1; Found: 550.3.

Step 3. 2-(((6aS,8R)-2-(3-fluoro-2-hydroxyphenyl)-6a-methyl-5,6,6a, 7,8,9-hexahydropyrrolo[1',2':4,5]pyrazino[2,3-c]pyridazin-8-yl)oxy)-5-(hydroxymethyl) isonicotinonitrile

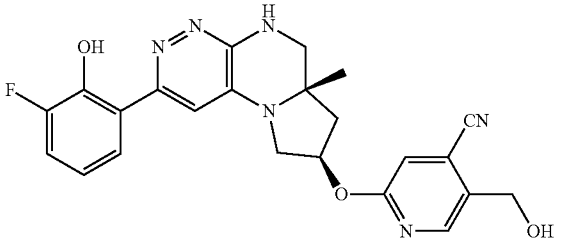 [SMILES: C[C@]12CNc3nnc(-c4cccc(F)c4O)cc3N1C[C@H](Oc1cc(C#N)c(CO)cn1)C2]

A mixture of 2-fluoro-6-((6aS,8R)-8-((5-(hydroxymethyl)-4-iodopyridin-2-yl)oxy)-6a-methyl-5,6,6a,7,8,9-hexahydropyrrolo[1',2':4,5]pyrazino[2,3-c]pyridazin-2-yl)phenol (39.0 mg, 0.07 mmol), copper(I)cyanide (31.8 mg, 0.35 mmol), DPPF (19.7 mg, 0.04 mmol), and $Pd_2(dba)_3$ (13.0 mg, 0.01 mmol) in 1,4-dioxane (0.80 mL) was purged with $N_2$ for 1 min. The reaction was stirred at 100° C. for 1 h. The reaction mixture was filtered through celite, then the filtrate was poured into sat. $NaHCO_3$ (aq) solution and was extracted by $CHCl_3$/IPA (3:1, 3×). The combined organic phase was dried over $Na_2SO_4$, condensed, and purified by prep-HPLC on $C_{18}$ column using mobile phase 20-50% $MeCN/H_2O$ (w/0.1% TFA) (tR=18 min). The desired fractions were collected, concentrated, poured into $NaHCO_3$ solution, and was extracted by chloroform/IPA (3:1, 3×). The combined organic phase was dried over $Na_2SO_4$ and condensed to yield title compound (31.0 mg, 97% yield) as a white solid. LCMS calcd for $C_{23}H_{22}FN_6O_3[M+H]^+$: m/z=449.2; Found: 449.0.

Step 4. 2-(((6aS,8R)-2-(3-fluoro-2-hydroxyphenyl)-6a-methyl-5,6,6a, 7,8,9-hexahydropyrrolo[1',2':4,5]pyrazino[2,3-c]pyridazin-8-yl)oxy)-5-formylisonicotinonitrile

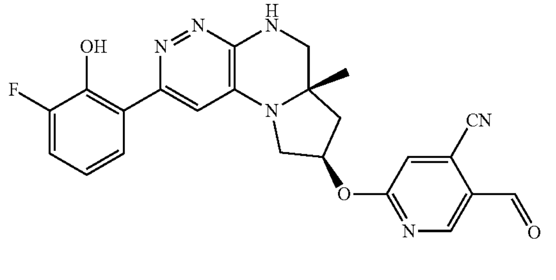 [SMILES: C[C@]12CNc3nnc(-c4cccc(F)c4O)cc3N1C[C@H](Oc1cc(C#N)c(C=O)cn1)C2]

To 2-(((6aS,8R)-2-(3-fluoro-2-hydroxyphenyl)-6a-methyl-5,6,6a,7,8,9-hexahydropyrrolo [1',2':4,5]pyrazino[2,3-c]pyridazin-8-yl)oxy)-5-(hydroxymethyl)isonicotinonitrile (26.0 mg, 0.06 mmol) in chloroform (2 mL) was added manganese (IV) oxide (50.4 mg, 0.58 mmol). The reaction was stirred at 45° C. for 12 h. The reaction was centrifuged, and the supernatant was collected (repeated 3×). After removal of solvent, the residue was purified by $SiO_2$ FCC 0-5% MeOH/DCM to give the title compound (12.0 mg, 46% yield). LCMS calcd for $C_{23}H_{20}FN_6O_3[M+H]^+$: m/z=447.2; Found: 447.3.

Step 5. 5-((4-(2-((S)-2,6-dioxopiperidin-3-yl)-3-oxoisoindolin-5-yl)piperazin-1-yl)methyl)-2-(((6aS,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)isonicotinonitrile To a mixture of 2-(((6aS,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-5-formylisonicotinonitrile (13.0 mg, 0.03 mmol) in DMSO (2 mL) was added (S)-3-(1-oxo-6-(piperazin-1-yl)isoindolin-2-yl)piperidine-2,6-dione hydrochloride (Intermediate 7) (21.3 mg, 0.06 mmol) followed by DIPEA (0.02 mL, 0.12 mmol). The reaction was stirred at 35° C. for 15 min, then STAB (18.5 mg, 0.09 mmol) was added and reaction was stirred at 45° C. for 2 h. The reaction mixture was quenched, then purified by prep-HPLC on C18 column (30×250 mm, 10 m) using mobile phase 8-28% MeCN/$H_2O$ (w/0.1% formic acid) (tR=18 min). The desired fractions were collected, concentrated, redispersed in water with 0.1% TFA and freeze-dried to afford the TFA salt of the title compound (6.20 mg, 28% yield). LCMS calcd for $C_{40}H_{40}FN_{10}O_5[M+H]^+$: m/z=759.3; Found: 759.1. $^1H$ NMR (300 MHz, MeOD-$d_4$)$_{\delta}$ $_{8.61}$ (d, J=2.3 Hz, 1H), 8.35 (d, J=2.3 Hz, 1H), 7.53 (s, 1H), 7.43-7.24 (m, 4H), 7.00 (td, J=8.1, 4.8 Hz, 1H), 6.81 (s, 1H), 6.07 (t, J=5.8 Hz, 1H), 5.14 (dd, J=13.3, 5.2 Hz, 1H), 4.59-4.34 (m, 4H), 4.26 (dd, J=14.3, 6.2 Hz, 1H), 4.02 (d, J=14.3 Hz, 1H), 3.73 (d, J=11.6 Hz, 1H), 3.67-3.37 (m, 7H), 3.35-3.27 (m, 1H), 3.18 (d, J=11.7 Hz, 1H), 2.91 (ddd, J=18.5, 13.3, 5.4 Hz, 1H), 2.78 (ddd, J=7.1, 4.3, 2.2 Hz, 1H), 2.61-2.41 (m, 2H), 2.35 (dd, J=14.4, 6.2 Hz, 1H), 2.24-2.10 (m, 1H), 1.65 (s, 3H).

Example 77: (S)-3-(6-(1-((2-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4-methylpyrimidin-5-yl)methyl)piperidin-4-yl)-1-oxoisoindolin-2-yl)piperidine-2,6-dione

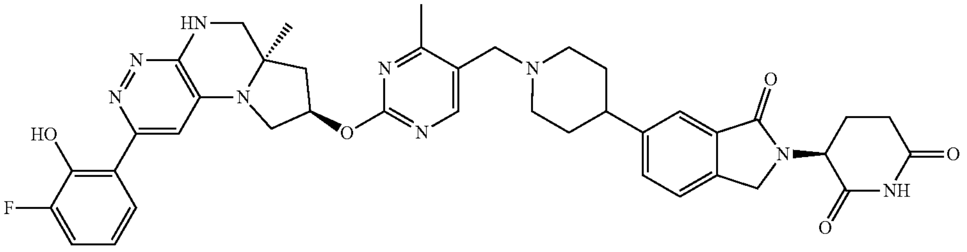 [SMILES: Cc1nc(O[C@H]2CN3c4cc(-c5cccc(F)c5O)nnc4NC[C@@]3(C)C2)ncc1CN1CCC(c2ccc3c(c2)C(=O)N([C@H]2CCC(=O)NC2=O)C3)CC1]

Step 1. Ethyl 2-(((6aR,8R)-2-chloro-6a-methyl-5,6,6a, 7,8,9-hexahydropyrrolo [1',2':4,5]pyrazino[2,3-c]pyridazin-8-yl)oxy)-4-methylpyrimidine-5-carboxylate

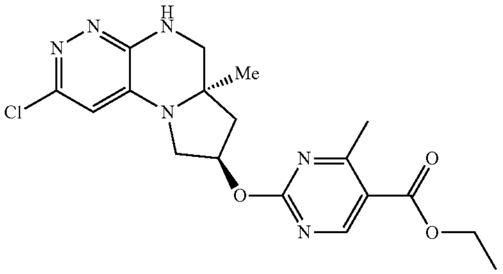 [SMILES: CCOC(=O)c1cnc(O[C@H]2CN3c4cc(Cl)nnc4NC[C@@]3(C)C2)nc1C]

Disopropyl azodicarboxylate (0.16 mL, 0.84 mmol) was added dropwise to a stirred solution of ethyl 2-hydroxy-4-methylpyrimidine-5-carboxylate (153 mg, 0.84 mmol), (6aR,8S)-2-chloro-6a-methyl-5,6,6a,7,8,9-hexahydropyrrolo[1',2':4,5]pyrazino[2,3-c]pyridazin-8-ol (Intermediate 12) (67.2 mg, 0.28 mmol) and triphenylphosphine (219 mg, 0.84 mmol) in THE (2.0 mL) at 0° C. The resulting mixture was warmed to ambient temperature and stirred for another 18 h. The mixture was quenched with ice water (20 mL) and extracted with EtOAc (15 mL×3). The combined organic phase was dried over $Na_2SO_4$, filtered, and concentrated in vacuo. The residue was diluted with DMSO (4 mL) and purified by prep-HPLC (13-55% MeCN in water, 0.1% TFA), concentrated in vacuo, basified by saturated $NaHCO_3$ solution, extracted with DCM (10 mL×3) and a mixture of $CHCl_3$/IPA (3:1, 10 mL×1). The combined organic phase was dried over $Na_2SO_4$, filtered, and evaporated under reduced pressure to afford the title compound (60.7 mg, 54% yield), as light-yellow solid. LCMS calcd for $C_{18}H_{22}ClN_6O_3[M+H]^+$: m/z=405.1; Found: 405.5.

Step 2. Ethyl 2-(((6aR,8R)-2-(3-fluoro-2-hydroxyphenyl)-6a-methyl-5,6,6a, 7,8,9-hexahydropyrrolo[1',2':4,5]pyrazino[2,3-c]pyridazin-8-yl)oxy)-4-methylpyrimidine-5-carboxylate

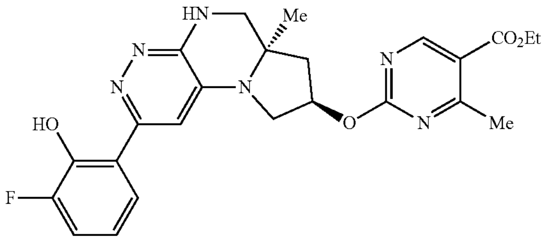 [SMILES: CCOC(=O)c1cnc(O[C@H]2CN3c4cc(-c5cccc(F)c5O)nnc4NC[C@@]3(C)C2)nc1C]

To a mixture of 3-fluoro-2-hydroxyphenylboronic acid (93.5 mg, 0.60 mmol), ethyl 2-(((6aR,8R)-2-chloro-6a-methyl-5,6,6a,7,8,9-hexahydropyrrolo[1',2':4,5]pyrazino[2,3-c]pyridazin-8-yl)oxy)-4-methylpyrimidine-5-carboxylate (60.7 mg, 0.15 mmol), XPhos Pd G2 (11.8 mg, 0.01 mmol) in 1,4-dioxane (0.95 mL) and water (0.05 mL) was added cesium acetate (144 mg, 0.75 mmol). The reaction stirred at 95° C. Once complete the reaction was cooled to rt then partitioned between EtOAc (30 mL) and water (20 mL). The organic phase was separated, and the aqueous phase extracted with EtOAc (10 mL×3) and $CHCl_3$/IPA (10 mL×1). The combined organic phase was concentrated under reduced pressure and the residue was dissolved in DMSO (5 mL) and purified by prep-HPLC (15-60% MeCN in water with 0.1% TFA) to give the title compound (53.6 mg, 74% yield) as a light-yellow solid. LCMS calcd for $C_{24}H_2FN_6O_4[M+H]^+$: m/z=481.2; Found: 481.4.

Step 3. 2-(((6aR,8R)-2-(3-fluoro-2-hydroxyphenyl)-6a-methyl-5,6,6a, 7,8,9-hexahydropyrrolo[1',2':4,5]pyrazino[2,3-c]pyridazin-8-yl)oxy)-4-methylpyrimidine-5-carbaldehyde

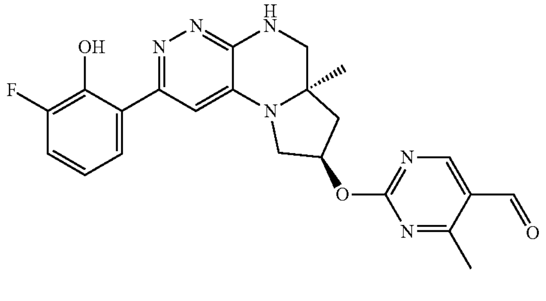 [SMILES: Cc1nc(O[C@H]2CN3c4cc(-c5cccc(F)c5O)nnc4NC[C@@]3(C)C2)ncc1C=O]

Ethyl 2-(((6aR,8R)-2-(3-fluoro-2-hydroxyphenyl)-6a-methyl-5,6,6a,7,8,9-hexahydro-pyrrolo[1',2':4,5]pyrazino[2,3-c]pyridazin-8-yl)oxy)-4-methylpyrimidine-5-carboxylate (47.0 mg, 0.10 mmol) was dissolved in THE (3.00 mL), flushed with nitrogen and cooled in an ice-bath.

Lithium diisobutyl-tert-butylaluminum hydride solution (1.25 mL, 0.31 mmol, 0.25 M) was then added. After 30 min at 0° C., an additional equivalent of the reductant was added. After 30 min, the starting material was mostly consumed and the reaction was quenched with methanol, basified with sodium carbonate, extracted with $CHCl_3$/IPA (3:1), and condensed. Crude was then purified by prep-HPLC to yield the title compound (11.3 mg, 27% yield). LCMS calcd for $C_{22}H_{22}FN_6O_3[M+H]^+$: m/z=437.2; Found: 437.5.

Step 4. (S)-3-(6-(1-((2-(((6aR,8R)-2-(3-fluoro-2-hydroxyphenyl)-6a-methyl-5,6,6a, 7,8,9-hexahydro-pyrrolo[1',2':4,5]pyrazino[2,3-c]pyridazin-8-yl)oxy)-4-methylpyrimidin-5-yl)methyl)piperidin-4-yl)-1-oxoisoindolin-2-yl)piperidine-2,6-dione To 2-(((6aR,8R)-2-(3-fluoro-2-hydroxyphenyl)-6a-methyl-5,6,6a,7,8,9-hexahydropyrrolo [1',2':4,5]pyrazino[2,3-c]pyridazin-8-yl)oxy)-4-methylpyrimidine-5-carbaldehyde (13.0 mg, 0.03 mmol) and (S)-3-(1-oxo-6-(piperidin-4-yl)isoindolin-2-yl)piperidine-2,6-dione; hydrochloride (Intermediate 6) (16.3 mg, 0.04 mmol) was added DMSO (1.00 mL) and N,N-diisopropylethyl-amine (0.03 mL, 0.15 mmol). After 15 min stirring, sodium triacetoxyborohydride (18.9 mg, 0.09 mmol) was added. After stirring at 37° C. overnight, the reaction was purified via prep-HPLC (Acn/$H_2O$). The fractions were evaporated and then 80 mL of 0.1% TFA in water was added and lyophilized to afford the title compound (10.8 mg, 46% yield) as the TFA salt. LCMS calcd for $C_{40}H_{43}FN_9O_5[M+H]^+$: m/z=748.3; Found: 748.6.

Examples 78-79

Examples 78-79 shown below in Table 5 were prepared as TFA salts by the method used in preparing Example 77 using the appropriate starting materials and intermediates.

TABLE 5

| Examples 78 and 79 | | | |
|---|---|---|---|
| Ex. | Structure/Name | Calcd. (M + H)+ m/z | Found (M + H)+ m/z |
| 78 | 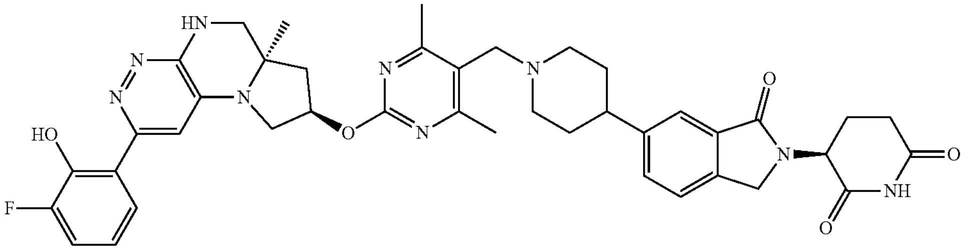 [SMILES: Cc1nc(O[C@H]2CN3c4cc(-c5cccc(F)c5O)nnc4NC[C@@]3(C)C2)nc(C)c1CN1CCC(c2ccc3c(c2)C(=O)N([C@H]2CCC(=O)NC2=O)C3)CC1] (S)-3-(6-(1-((2-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4,6-dimethylpyrimidin-5-yl)methyl)piperidin-4-yl)-1-oxoisoindolin-2-yl)piperidine-2,6-dione | 762.3 | 762.6 |
| 79 | 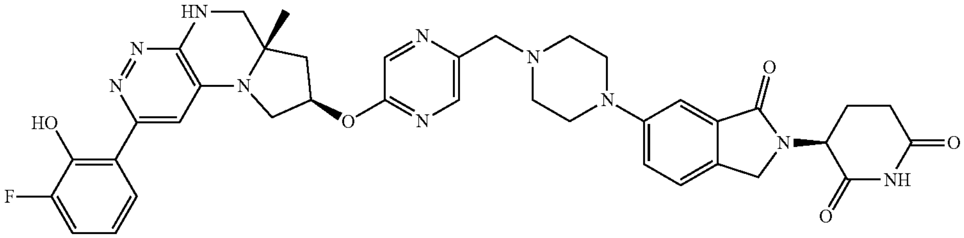 [SMILES: C[C@]12CNc3nnc(-c4cccc(F)c4O)cc3N1C[C@H](Oc1cnc(CN3CCN(c4ccc5c(c4)C(=O)N([C@H]4CCC(=O)NC4=O)C5)CC3)cn1)C2] (S)-3-(6-(4-((5-(((6aS,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)pyrazin-2-yl)methyl)piperazin-1-yl)-1-oxoisoindolin-2-yl)piperidine-2,6-dione | 735.3 | 735.4 |

Example 80: (S)-3-(6-(4-((5-(((6aS,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-3,6-dimethylpyridin-2-yl)methyl)piperazin-1-yl)-1-oxoisoindolin-2-yl)piperidine-2,6-dione

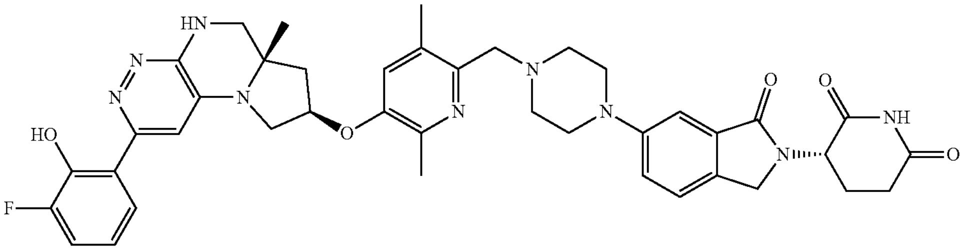 [SMILES: Cc1cc(O[C@H]2CN3c4cc(-c5cccc(F)c5O)nnc4NC[C@]3(C)C2)c(C)nc1CN1CCN(c2ccc3c(c2)C(=O)N([C@H]2CCC(=O)NC2=O)C3)CC1]

Step 1. 5-(((6aS,8R)-2-chloro-6a-methyl-5,6, 6a,7,8, 9-hexahydropyrrolo[1',2':4,5]pyrazino[2,3-c] pyridazin-8-yl)oxy)-3,6-dimethylpicolinonitrile

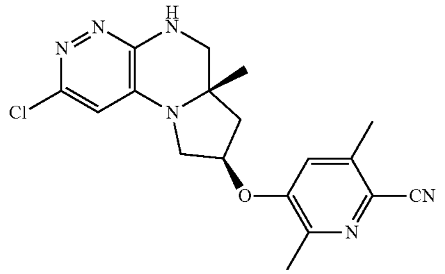 [SMILES: Cc1cc(O[C@H]2CN3c4cc(Cl)nnc4NC[C@]3(C)C2)c(C)nc1C#N]

Triphenylphosphine (188 mg, 0.72 mmol) and diisopropylazo dicarboxylate (0.14 mL, 0.72 mmol) were stirred together in THE (4.75 mL) at rt for 20 min. Then (6aS,8S)-2-chloro-6a-methyl-5,6,6a,7,8,9-hexahydropyrrolo[1',2':4,5]pyrazino[2,3-c]pyridazin-8-ol (Intermediate 13) (115 mg, 0.48 mmol) and 5-hydroxy-3,6-dimethylpyridine-2-carbonitrile (Intermediate 19) (84.9 mg, 0.57 mmol) were added to the solution together as solids and the resulting reaction mixture was stirred at 50° C. for 45 min. The crude mixture was diluted with EtOAc and washed with water. The water layer was extracted once with EtOAc and the combined organic layers were dried with $Na_2SO_4$ and concentrated to dryness to yield a crude oil. The product was purified by prep-HPLC (15-40% ACN/water w/0.1% TFA) to give the title compound (140 mg, 77.7% yield) as a TFA salt. LCMS calcd for $C_{18}H_{20}ClN_6O$ $[M+H]^+$: m/z=371.1; Found: 371.2.

Step 2. 5-(((6aS,8R)-2-(3-fluoro-2-hydroxyphenyl)-6a-methyl-5,6,6a, 7,8,9-hexahydro-pyrrolo[1',2':4,5] pyrazino[2,3-c]pyridazin-8-yl)oxy)-3,6-dimethylpicolinonitrile

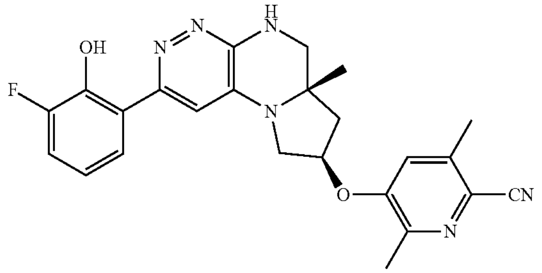 [SMILES: Cc1cc(O[C@H]2CN3c4cc(-c5cccc(F)c5O)nnc4NC[C@]3(C)C2)c(C)nc1C#N]

5-(((6aS,8R)-2-chloro-6a-methyl-5,6,6a,7,8,9-hexahydropyrrolo[1',2':4,5]pyrazino[2,3-c]pyridazin-8-yl)oxy)-3,6-dimethylpicolinonitrile (134 mg, 0.36 mmol), 3-fluoro-2-hydroxy-phenylboronic acid (225 mg, 1.45 mmol), XPhos Pd G2 (42.7 mg, 0.05 mmol), potassium phosphate (384 mg, 1.81 mmol), 1,4-dioxane (3.4 mL), and water (180 µL) were all added to a tube which was then sealed. The solution was degassed by sparging nitrogen, and the reaction mixture was stirred at 90° C. for 2 h. After cooling to ambient temperature, the reaction mixture was diluted with EtOAc and brine. The aqueous layer was reextracted twice with EtOAc. The combined organic layers were dried with $Na_2SO_4$ and concentrated to dryness. The crude mixture was purified by prep-HPLC (20-60% ACN/water w/0.1% TFA) to give the title compound (110 mg, 63% yield) as a TFA salt. LCMS calcd for $C_{24}H_{24}FN_6O_2[M+H]^+$: m/z=447.2; Found: 447.3.

Step 3. 5-(((6aS,8R)-2-(3-fluoro-2-hydroxyphenyl)-6a-methyl-5,6,6a, 7,8,9-hexahydro-pyrrolo[1',2':4,5] pyrazino[2,3-c]pyridazin-8-yl)oxy)-3,6-dimethylpicolinaldehyde

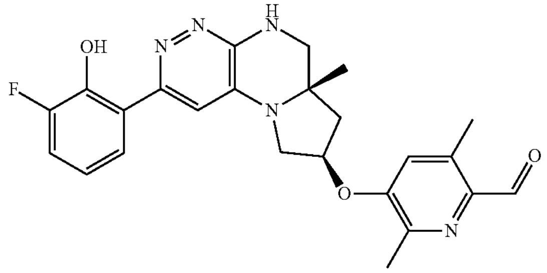 [SMILES: Cc1cc(O[C@H]2CN3c4cc(-c5cccc(F)c5O)nnc4NC[C@]3(C)C2)c(C)nc1C=O]

5-(((6aS,8R)-2-(3-fluoro-2-hydroxyphenyl)-6a-methyl-5,6,6a,7,8,9-hexahydropyrrolo [1',2':4,5]pyrazino[2,3-c]pyridazin-8-yl)oxy)-3,6-dimethylpicolinonitrile (60.0 mg, 0.13 mmol) was dissolved in anhydrous THE (1.10 mL) and DIBAL/morpholine complex solution (~0.4M, 1.35 mL) was added dropwise at rt. The solution was stirred at rt for 10 minutes. An additional portion of DIBAL/morpholine complex solution (~0.4M, 0.67 mL, 2 eq) was added. The reaction was quenched by addition of 1M HCl (aq) and the aqueous layer was basified to ~pH 12 with 15 wt % NaOH (aq). The aqueous layer was saturated with NaCl and extracted with EtOAc (x3). The organic layer was dried with $Na_2SO_4$, condensed, and purified by prep-HPLC (20-30% ACN/water w/0.1% formic acid) to yield the title compound (5 mg, 8% yield). LCMS calcd for $C_{24}H_{25}FN_5O_3[M+H]^+$: m/z=450.2; Found: 450.8.

Step 4. (S)-3-(6-(4-((5-(((6aS,8R)-2-(3-fluoro-2-hydroxyphenyl)-6a-methyl-5,6,6a, 7,8,9-hexahydro-pyrrolo[1',2':4,5]pyrazino[2,3-c]pyridazin-8-yl)oxy)-3,6-dimethylpyridin-2-yl)methyl) piperazin-1-yl)-1-oxoisoindolin-2-yl)piperidine-2,6-dione 5-(((6aS,8R)-2-(3-fluoro-2-hydroxyphenyl)-6a-methyl-5,6,6a,7,8,9-hexahydropyrrolo [1',2':4,5]pyrazino[2,3-c]pyridazin-8-yl)oxy)-3,6-dimethylpicolinaldehyde (4.40 mg, 0.01 mmol), (S)-3-(1-oxo-6-(piperazin-1-yl)isoindolin-2-yl) piperidine-2,6-dione hydrochloride (Intermediate 7) (7.14 mg, 0.02 mmol), and diisopropylethylamine (8.55 uL, 0.05 mmol) were stirred in DMSO (100 uL) at rt for 10-15 minutes. Then, sodium triacetoxyborohydride (6.2 mg, 0.03 mmol) was added and the reaction mixture was stirred at 30° C. overnight. The mixture was diluted with DMSO and purified directly by prep-HPLC (10-30% ACN/water w/0.1% formic acid). The clean fractions were concentrated to dryness and 6 mL of 0.1% TFA (aq) was added and stirred until the solid dissolved. The aqueous solution was lyophilized to afford the title compound (6 mg, 79% yield) as a TFA salt. LCMS calcd for $C_{41}H_{45}FN_9O_5[M+H]^+$: m/z=762.3; Found: 762.6.

Examples 81-82

Examples 81 and 82 shown below in Table 6 were prepared as TFA salts by the method used in preparing Example 80 using the appropriate starting materials and intermediates.

TABLE 6

| Examples 81 - 82 | | | |
|---|---|---|---|
| Example | Structure/Name | Calcd. (M + H)+ m/z | Found (M + H)+ m/z |
| 81 | 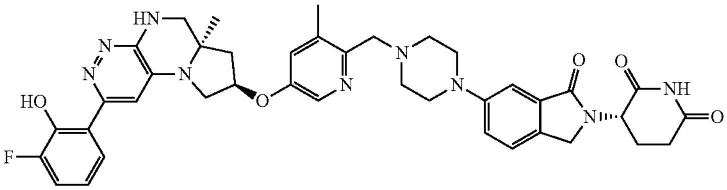 [SMILES: Cc1cc(O[C@H]2CN3c4cc(-c5cccc(F)c5O)nnc4NC[C@@]3(C)C2)cnc1CN1CCN(c2ccc3c(c2)C(=O)N([C@H]2CCC(=O)NC2=O)C3)CC1] (S)-3-(6-(4-((5-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-3-methylpyridin-2-yl)methyl)piperazin-1-yl)-1-oxoisoindolin-2-yl)piperidine-2,6-dione | 748.3 | 748.4 |
| 82 | 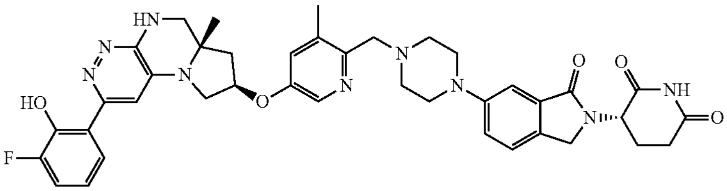 [SMILES: Cc1cc(O[C@H]2CN3c4cc(-c5cccc(F)c5O)nnc4NC[C@]3(C)C2)cnc1CN1CCN(c2ccc3c(c2)C(=O)N([C@H]2CCC(=O)NC2=O)C3)CC1] (S)-3-(6-(4-((5-(((6aS,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-3-methylpyridin-2-yl)methyl)piperazin-1-yl)-1-oxoisoindolin-2-yl)piperidine-2,6-dione | 748.3 | 748.3 |

Example 83: (S)-3-(6-(4-((6-(((6aS,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-5-methylpyridin-3-yl)methyl)piperazin-1-yl)-1-oxoisoindolin-2-yl)piperidine-2,6-dione

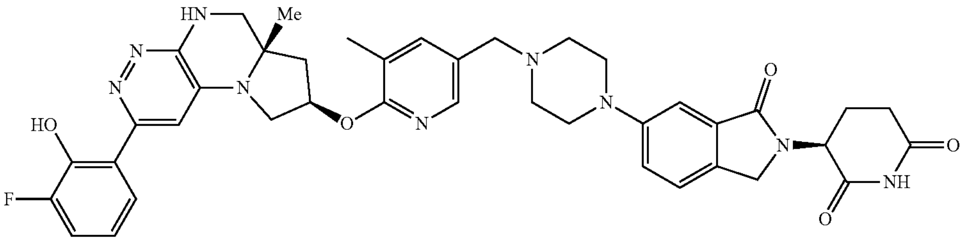 [SMILES: Cc1cc(CN2CCN(c3ccc4c(c3)C(=O)N([C@H]3CCC(=O)NC3=O)C4)CC2)cnc1O[C@H]1CN2c3cc(-c4cccc(F)c4O)nnc3NC[C@]2(C)C1]

Step 1. 6-(((6aS,8R)-2-chloro-6a-methyl-5,6, 6a,7,8,9-hexahydropyrrolo [1',2':4,5]pyrazino[2,3-c]pyridazin-8-yl) oxy)-5-methylnicotinic acid

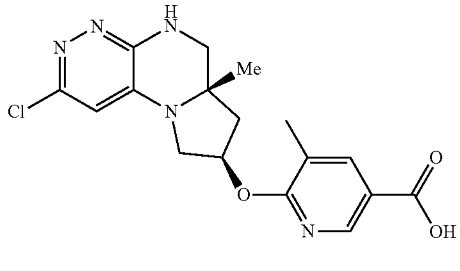 [SMILES: Cc1cc(C(=O)O)cnc1O[C@H]1CN2c3cc(Cl)nnc3NC[C@]2(C)C1]

Sodium hydride (60% in mineral oil, 14.9 mg, 0.62 mmol) was added to the stirring solution of (6aS,8R)-2-chloro-6a-methyl-5,6,6a,7,8,9-hexahydropyrrolo[1',2':4,5]pyrazino[2,3-c]pyridazin-8-ol (Intermediate 14) (50.0 mg, 0.21 mmol) in DMF (0.50 mL) and this mixture was stirred for 30 min at 40° C. Methyl 6-fluoro-5-methylpyridine-3-carboxylate (42.2 mg, 0.25 mmol) was added into the mixture and the reaction was stirred at 40° C. for 18 h. The reaction was quenched with a 10% citric acid solution and extracted with DCM, dried over $Na_2SO_4$, filtered, concentrated, and purified by prep-HPLC (10-50% MeCN in water, 0.1% TFA) to afford the title compound (32.2 mg, 41% yield) as a yellow solid. LCMS calcd for $C_{17}H_{19}ClN_5O_3[M+H]^+$: m/z=376.1; Found: 376.2.

Step 2. (6-(((6aS,8R)-2-chloro-6a-methyl-5,6,6a, 7,8,9-hexahydropyrrolo[1',2':4,5]pyrazino[2,3-c] pyridazin-8-yl)oxy)-5-methylpyridin-3-yl)methanol

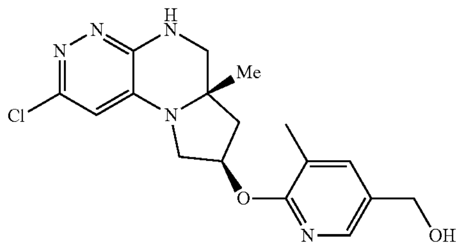 [SMILES: Cc1cc(CO)cnc1O[C@H]1CN2c3cc(Cl)nnc3NC[C@]2(C)C1]

Borane dimethyl sulfide complex (50.4 mg, 0.66 mmol) was added dropwise into the stirred solution of 6-(((6aS, 8R)-2-chloro-6a-methyl-5,6,6a,7,8,9-hexahydropyrrolo[1', 2':4,5]pyrazino[2,3-c]pyridazin-8-yl)oxy)-5-methylnicotinic acid (49.9 mg, 0.13 mmol) in THE (1 mL) at 0° C. The mixture was stirred at 40° C. for 2 h and quenched with MeOH (5 mL) at 0° C. The volatiles were evaporated and the residue was purified by prep-HPLC (10-45% MeCN in water, 0.1% TFA) to yield the title compound (41.1 mg, 86% yield) as yellow solid. LCMS calcd for $C_{17}H_{21}ClN_5O_2$ $[M+H]^+$: m/z=362.1; Found: 362.2.

Step 3. 6-(((6aS,8R)-2-chloro-6a-methyl-5,6,6a, 7,8,9-hexahydropyrrolo[1',2':4,5]pyrazino[2,3-c] pyridazin-8-yl)oxy)-5-methylnicotinaldehyde

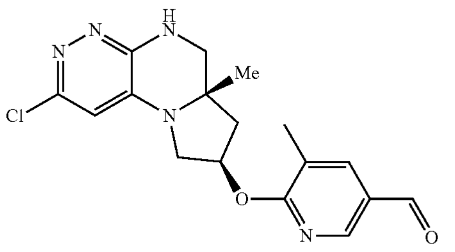 [SMILES: Cc1cc(C=O)cnc1O[C@H]1CN2c3cc(Cl)nnc3NC[C@]2(C)C1]

The mixture of (6-(((6aS,8R)-2-chloro-6a-methyl-5,6,6a, 7,8,9-hexahydropyrrolo[1',2':4,5]pyrazino[2,3-c]pyridazin-8-yl)oxy)-5-methylpyridin-3-yl)methanol (41.1 mg, 0.11 mmol) and manganese (IV) oxide (198 mg, 2.27 mmol) in ethyl acetate (1 mL) was stirred at 40° C. for 18 h (overnight). The reaction mixture was cooled to ambient temperature and the solid materials were filtered off. The filtrate was concentrated under reduced pressure and the residue was purified by prep-HPLC (15-55% MeCN in water, 0.1% TFA) to give the title compound (25.3 mg, 62% yield), as white solid. LCMS calcd for $C_{17}H_{19}ClN_5O_2[M+H]^+$: m/z=360.1; Found: 360.3.

Step 4. 6-(((6aS,8R)-2-(3-fluoro-2-hydroxyphenyl)-6a-methyl-5,6,6a, 7,8,9-hexahydropyrrolo[1',2':4,5] pyrazino[2,3-c]pyridazin-8-yl)oxy)-5-methylnicotinaldehyde

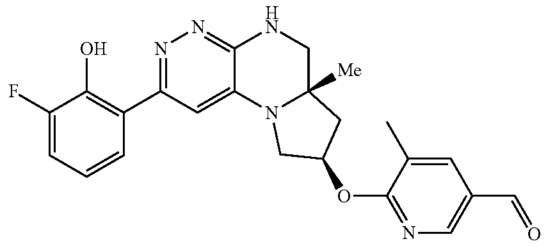 [SMILES: Cc1cc(C=O)cnc1O[C@H]1CN2c3cc(-c4cccc(F)c4O)nnc3NC[C@]2(C)C1]

The mixture of 6-(((6aS,8R)-2-chloro-6a-methyl-5,6,6a, 7,8,9-hexahydropyrrolo[1',2':4,5]pyrazino[2,3-c]pyridazin-8-yl)oxy)-5-methylnicotinaldehyde (25.3 mg, 0.07 mmol), 3-fluoro-2-hydroxyphenylboronic acid (43.9 mg, 0.28 mmol), XPhos Pd G2 (2.77 mg, 0.004 mmol), and potassium phosphate tribasic (59.7 mg, 0.28 mmol) in 1,4-dioxane (1.9 ml) and water (0.1 ml) was heated at 95° C. under $N_2$ atmosphere for 4 h. The mixture was cooled to ambient temperature and diluted with water (25 ml) and extracted with DCM (15 ml×3) and a mixture of $CHCl_3$/IPA (3:1; 15 ml×1). The combined organic phase was dried over $Na_2SO_4$, filtered and concentrated. The residue was purified by prep-hplc (15-55% mecn in water, 0.1% TFA). The fractions containing the desired product were collected and concentrated, basified with $Na_2CO_3$ (10% aq) to pH 9-10, and extracted with DCM (15 ml×3) and a mixture of $CHCl_3$/IPA (3:1; 15 ml×1). The combined organic phase was dried over $Na_2SO_4$, filtered, and evaporated to dryness to the titled compound (70.5 mg, 87% yield) as yellow solid in its free base. LCMS calcd for $C_{23}H_{22}FN_5O_3[M+H]^+$: m/z=360.1; Found: 437.1.

Step 5. (S)-3-(6-(4-((6-(((6aS,8R)-2-(3-fluoro-2-hydroxyphenyl)-6a-methyl-5,6,6a, 7,8,9-hexahydropyrrolo[1',2':4,5]pyrazino[2,3-c]pyridazin-8-yl)oxy)-5-methylpyridin-3-yl)methyl) piperazin-1-yl)-1-oxoisoindolin-2-yl)piperidine-2,6-dione DIPEA (0.02 mL, 0.10 mmol) was added into the stirring solution of 6-(((6aS,8R)-2-(3-fluoro-2-hydroxyphenyl)-6a-methyl-5,6,6a,7,8,9-hexahydropyrrolo[1',2':4,5]pyrazino[2, 3-c]pyridazin-8-yl)oxy)-5-methylnicotinaldehyde (13.9 mg, 0.03 mmol) and (S)-3-(1-oxo-6-(piperazin-1-yl)isoindolin-2-yl)piperidine-2,6-dione hydrochloride (Intermediate 7) (14.5 mg, 0.04 mmol) in DMSO (200 uL) at rt. The mixture was stirred for 30 min and sodium triacetoxyborohydride (20.3 mg, 0.10 mmol) was added in one portion. The reaction was heated at 35° C. for 18 h and purified by prep-HPLC (10-45% MeCN in water, 0.1% formic acid). The fractions were collected and concentrated. The residue was lyophilized with water (0.1% TFA) to afford the title compound (17 mg, 71% yield) as white solid TFA salt. LCMS calcd for $C_{40}H_{43}FN_9O_5$ $[M+H]^+$: m/z=748.3; Found: 748.5.

Example 84: 3-(6-(4-((6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-5-fluoropyridin-3-yl)methyl)piperazin-1-yl)-1-oxoisoindolin-2-yl)piperidine-2,6-dione (PRT7768)

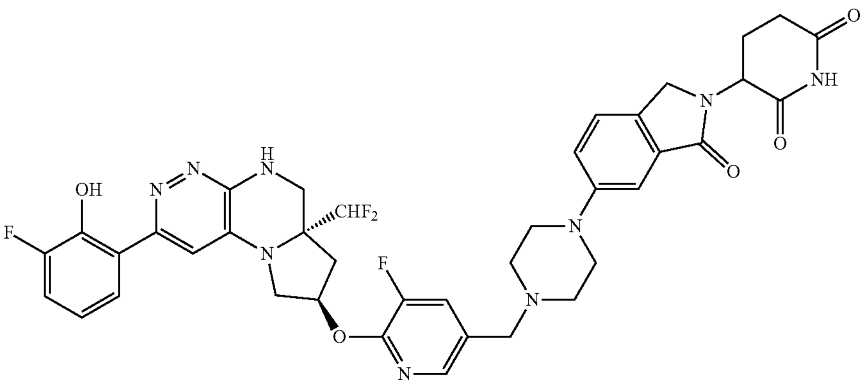 [SMILES: O=C1CCC(N2Cc3ccc(N4CCN(Cc5cnc(O[C@H]6CN7c8cc(-c9cccc(F)c9O)nnc8NC[C@@]7(C(F)F)C6)c(F)c5)CC4)cc3C2=O)C(=O)N1]

Step 1: (6aR,8R)-8-(Benzyloxy)-6a-(difluoromethyl)-2-(3-fluoro-2-methoxyphenyl)-6a, 7,8,9-tetrahydropyrrolo[1',2':4,5]pyrazino[2,3-c]pyridazin-6 (5H)-one

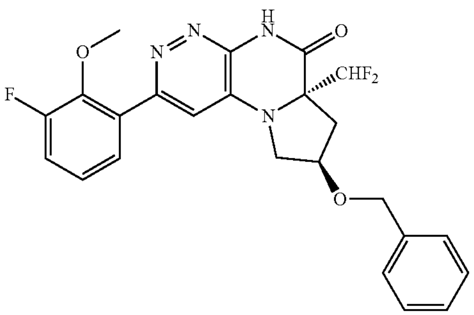 [SMILES: COc1c(F)cccc1-c1cc2c(nn1)NC(=O)[C@@]1(C(F)F)C[C@@H](OCc3ccccc3)CN21]

A suspension of (6aR,8R)-8-(benzyloxy)-2-chloro-6a-(difluoromethyl)-6a,7,8,9-tetrahydropyrrolo[1',2':4,5]pyrazino [2,3-c]pyridazin-6(5H)-one (2.2 g, 5.78 mmol, Example 40, Step 5), 3-fluoro-2-methoxyphenylboronic acid (1.97 g, 11.6 mmol), cesium carbonate (9.47 g, 29.1 mmol, and dichloro 1,1'bis(diphenylphosphino)ferrocene palladium (II) dichloromethane (1.41 g, 1.72 mmol) in 1,4-dioxane (50 mL) and water (5 mL) was sparged with nitrogen for 15 minutes, then heated to 100° C. After 90 minutes, the reaction mixture was cooled to ambient temperature, filtered through celite, and adhered to silica gel. Purified by FCC 0-100% EA/hexanes followed by 0-15% MeOH/DCM to afford the title compound (1.28 g, 47% yield). LCMS calcd for $C_{24}H_{22}F_3N_4O_3$ $[M+H]^+$: m/z=471.2; Found 471.0.

Step 2: (6aR,8R)-8-(Benzyloxy)-6a-(difluoromethyl)-2-(3-fluoro-2-methoxyphenyl)-5,6,6a, 7,8,9-hexahydropyrrolo[1',2':4,5]pyrazino[2,3-c] pyridazine

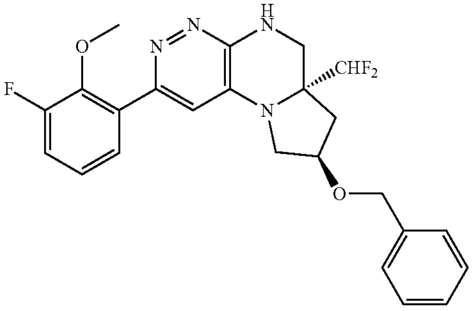 [SMILES: COc1c(F)cccc1-c1cc2c(nn1)NC[C@@]1(C(F)F)C[C@@H](OCc3ccccc3)CN21]

$LiAlH_4$ (1.0 M in THF, 8.15 mL, 8.15 mmol) was added dropwise to a stirring solution of (6aR,8R)-8-(benzyloxy)-6a-(difluoromethyl)-2-(3-fluoro-2-methoxyphenyl)-6a,7,8,9-tetrahydropyrrolo[1',2':4,5]pyrazino[2,3-c]pyridazin-6 (5H)-one (1.28 g, 2.72 mmol) in THE (17 mL) at 0° C., and the reaction was subsequently allowed to warm to ambient temperature. After 90 minutes, the reaction was cooled to 0° C. and quenched with dropwise addition of MeOH (25 mL).

Added AcOH (3.11 mL, 54.3 mmol) and allowed reaction to warm to ambient temperature before adding sodium cyanoborohydride (1.71 g, 27.3 mmol) portionwise to the reaction mixture. The reaction was then fitted with an air reflux condenser and heated to 80° C. overnight. LCMS showed incomplete conversion after 14 hours, so reaction was allowed to cool to ambient temperature and another portion of sodium cyanoborohydride (854 mg, 13.6 mmol) was added. The reaction was stirred at 90° C. for 6 hours, then allowed to cool to ambient temperature and quenched with dropwise addition of sat. $K_2CO_3$ (aq) until no more gas evolution was observed. Reaction mixture was extracted with EtOAc (4×75 mL) and combined extracts were washed with brine, dried, condensed, and purified by $SiO_2FCC$ 0-100% EA/hexanes followed by 0-15% MeOH/DCM to afford the title compound (1.24 g, quant. yield). LCMS calcd for $C_{24}H_{24}F_3N_4O_2[M+H]^+$: m/z=457.2; Found 457.1.

Step 3: (6aR,8R)-6a-(Difluoromethyl)-2-(3-fluoro-2-methoxyphenyl)-5,6,6a, 7,8,9-hexahydropyrrolo [1',2':4,5]pyrazino[2,3-c]pyridazin-8-ol

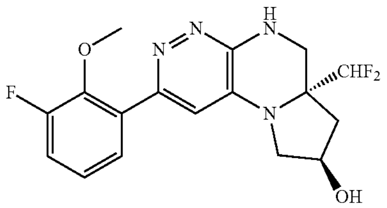 [SMILES: COc1c(F)cccc1-c1cc2c(nn1)NC[C@@]1(C(F)F)C[C@@H](O)CN21]

Trichloroborane (1.0M in DCM, 4.27 mL, 4.27 mmol) was added dropwise to an ice cold, stirring solution of (6aR,8R)-8-(benzyloxy)-6a-(difluoromethyl)-2-(3-fluoro-2-methoxyphenyl)-5,6,6a,7,8,9-hexahydropyrrolo[1',2':4,5] pyrazino[2,3-c]pyridazine (650 mg, 1.42 mmol) in DCM (15 mL). The reaction was stirred at 0° C. for 3 hours, then quenched with dropwise addition of water.

Reaction mixture was poured into sat. $NaHCO_3$ (aq) and extracted with 3:1 isopropanol/chloroform (4×10 mL). Combined extracts were washed with brine, dried, condensed, and purified by $SiO_2$ FCC 0-15% MeOH/DCM to afford the title compound (102 mg, 20% yield). LCMS calcd for $C_{17}H_{18}F_3N_4O_2$[M+H]$^+$: m/z=367.1; Found 367.1.

Step 4: Methyl 6-(((6aR,8R)-6a-(difluoromethyl)-2-(3-fluoro-2-methoxyphenyl)-5,6,6a, 7,8,9-hexahydropyrrolo[1',2':4,5]pyrazino[2,3-c]pyridazin-8-yl) oxy)-5-fluoronicotinate

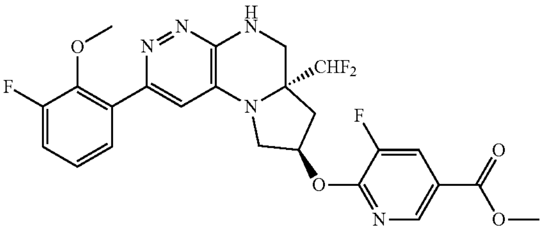 [SMILES: COC(=O)c1cnc(O[C@H]2CN3c4cc(-c5cccc(F)c5OC)nnc4NC[C@@]3(C(F)F)C2)c(F)c1]

To a stirring solution of (6aR,8R)-6a-(difluoromethyl)-2-(3-fluoro-2-methoxyphenyl)-5,6,6a,7,8,9-hexahydropyrrolo [1',2':4,5]pyrazino[2,3-c]pyridazin-8-ol (102 mg, 0.28 mmol) and methyl 6-chloro-5-fluoropyridine-3-carboxylate (59.2 mg, 0.31 mmol) in THF (4.5 mL) at 0° C. was added sodium hydride (60% in mineral oil, 74 mg, 1.85 mmol) portionwise. The reaction was then allowed to warm to ambient temperature and stirred 2.5 hours before adding another portion of methyl 6-chloro-5-fluoropyridine-3-carboxylate (31 mg, 0.16 mmol). After 45 minutes, the reaction was quenched with dropwise addition of sat. $NH_4Cl$ (aq), poured into sat. $K_2CO_3$ (aq), and extracted with DCM (4×5 mL). Combined organics dried, condensed, and purified by $SiO_2$ FCC 0-5% MeOH/DCM to obtain the title compound (95 mg, 66% yield). LCMS calcd for $C_{24}H_{22}F_4N_5O_4$ [M+H]$^+$: m/z=520.2; Found 519.9.

Step 5: 2-((6aR,8R)-6a-(Difluoromethyl)-8-((3-fluoro-5-(hydroxymethyl)pyridin-2-yl)oxy)-5,6,6a, 7,8,9-hexahydropyrrolo[1',2':4,5]pyrazino[2,3-c] pyridazin-2-yl)-6-fluorophenol

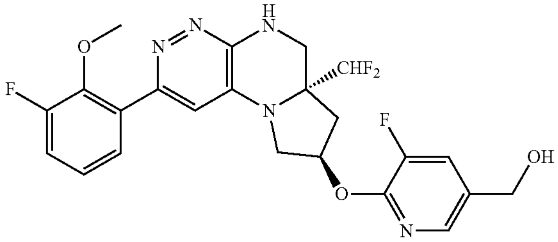 [SMILES: COc1c(F)cccc1-c1cc2c(nn1)NC[C@@]1(C(F)F)C[C@@H](Oc3ncc(CO)cc3F)CN21]

To a stirring solution of methyl 6-(((6aR,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-yl) oxy)-5-fluoronicotinate (95.1 mg, 0.18 mmol) in THE (1.8 mL) at 0° C. was added $LiAlH_4$ (1.0M in THF, 0.55 mL, 0.55 mmol) dropwise. The reaction was stirred for 2 hours, then quenched with dropwise addition of sat. $NH_4Cl$ (aq). Reaction mixture was then poured into sat. sodium potassium tartrate (aq) and extracted with DCM (4×5 mL). Combined organics washed with brine, dried, and condensed to yield the title compound (78 mg, 87% yield). The crude was taken to the next step without further purification. LCMS calcd for $C_{23}H_{22}F_4N_5O_3$[M+H]$^+$: m/z=492.2; Found 491.9.

Step 6: 2-((6aR,8R)-8-((5-(Chloromethyl)-3-fluoro-pyridin-2-yl)oxy)-6a-(difluoromethyl)-5,6,6a, 7,8,9-hexahydropyrrolo[1',2':4,5]pyrazino[2,3-c]pyridazin-2-yl)-6-fluorophenol

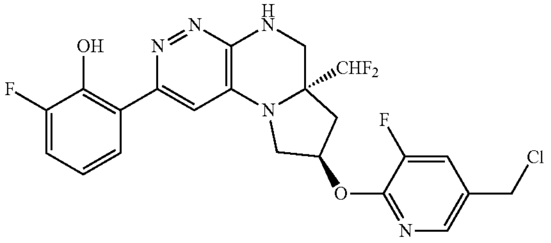 [SMILES: Oc1c(F)cccc1-c1cc2c(nn1)NC[C@@]1(C(F)F)C[C@@H](Oc3ncc(CCl)cc3F)CN21]

Trichloroborane (1.0M in DCM, 3.05 mL, 3.05 mmol) was added dropwise to an ice cold, stirring solution of 2-((6aR,8R)-6a-(difluoromethyl)-8-((3-fluoro-5-(hydroxymethyl)pyridin-2-yl)oxy)-5,6,6a,7,8,9-hexahydropyrrolo[1',2':4,5]pyrazino[2,3-c]pyridazin-2-yl)-6-fluorophenol (78 mg, 0.16 mmol) in DCM (3.1 mL). The reaction was then allowed to warm slowly to ambient temperature and stirred for 4 hours. A second portion of trichloroborane (1.0 M in DCM, 1.5 mL, 1.5 mmol) was added and the reaction stirred for another 16 hours. The reaction mixture was quenched with dropwise addition of water (2 mL), poured into a saturated aqueous $NaHCO_3$ solution (20 mL), and extracted with DCM (4×10 mL). The combined organic layers were washed with brine, dried, and condensed to obtain the title compound (76.9 mg, 98% yield). The crude was taken to the next step without further purification. LCMS calcd for $C_{22}H_{19}ClF_4N_5O_2$ [M+H]$^+$: m/z=496.1; Found 495.9.

Step 7: 3-(6-(4-((6-(((6aR,8R)-6a-(Difluoromethyl)-2-(3-fluoro-2-hydroxyphenyl)-5,6,6a, 7,8,9-hexahydropyrrolo[1',2':4,5]pyrazino[2,3-c]pyridazin-8-yl) oxy)-5-fluoropyridin-3-yl)methyl)piperazin-1-yl)-1-oxoisoindolin-2-yl)piperidine-2,6-dione To a stirring solution of 3-(1-oxo-6-(piperazin-1-yl)isoindolin-2-yl)piperidine-2,6-dione (101 mg, 0.31 mmol, Intermediate 2) and 2-((6aR,8R)-8-((5-(chloromethyl)-3-fluoropyridin-2-yl)oxy)-6a-(difluoromethyl)-5,6,6a,7,8,9-hexahydropyrrolo[1',2':4,5]pyrazino[2,3-c]pyridazin-2-yl)-6-fluorophenol (76 mg, 0.15 mmol) in MeCN (1.5 mL) was added DIPEA (0.16 mL, 0.92 mmol). The reaction was stirred at 120° C. for 90 minutes, then cooled to ambient temperature. The reaction mixture was diluted in DMSO, filtered, and purified via prep-HPLC (Waters CSH-C18, 5 μm, 30×100 mm, 17.6-24.6% MeCN/water (containing 0.1% TFA) over 5 min) to give the TFA salt of the title compound (71.2 mg, 46% yield). LCMS calcd for $C_{39}H_{38}F_4N_9O_5[M+H]^+$: m/z=788.3; Found 788.0. $^1H$ NMR (400 MHz, DMSO) δ 10.91 (s, 1H), 8.10 (s, 1H), 7.83-7.79 (m, 1H), 7.44 (d, J=8.3 Hz, 2H), 7.32-7.20 (m, 3H), 7.14 (s, 1H), 6.88 (t, J=6.7 Hz, 1H), 6.28 (t, J=55.3 Hz, 2H), 5.81 (s, 1H), 5.04 (dd, J=13.3, 5.1 Hz, 1H), 4.31 (d, J=16.8 Hz, 3H), 4.17 (d, J=16.9 Hz, 1H), 4.12 (d, J=6.4 Hz, 1H), 3.85 (dd, J=40.9, 12.1 Hz, 4H), 2.92-2.80 (m, 3H), 2.63-2.48 (m, 2H), 2.39-2.25 (m, 2H), 2.13 (dd, J=14.2, 5.5 Hz, 1H), 1.97-1.89 (m, 1H).

Example 85

Example 85 shown below in Table 7 was prepared as TFA salts by the method used in preparing Example 84, utilizing the appropriate starting materials and intermediates.

TABLE 7

Example 85

| Ex. | Structure/Name | Calcd. (M + H)+ m/z | Found (M + H)+ m/z |
|---|---|---|---|
| 85 | 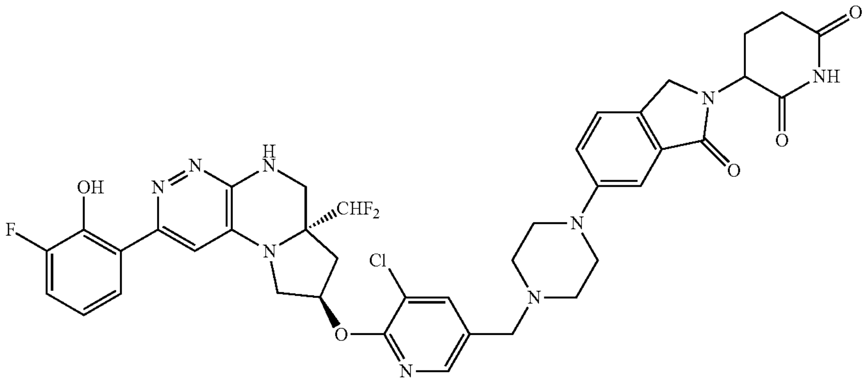 [SMILES: O=C1CCC(N2Cc3ccc(N4CCN(Cc5cnc(O[C@H]6CN7c8cc(-c9cccc(F)c9O)nnc8NC[C@@]7(C(F)F)C6)c(Cl)c5)CC4)cc3C2=O)C(=O)N1] 3-(6-(4-((5-chloro-6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)pyridin-3-yl)methyl)piperazin-1-yl)-1-oxoisoindolin-2-yl)piperidine-2,6-dione | 804.3 | 804.1 |

Example 86: (S)-3-(6-(4-((6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-4,5-dimethylpyridin-3-yl)methyl)piperazin-1-yl)-1-oxoisoindolin-2-yl)piperidine-2,6-dione

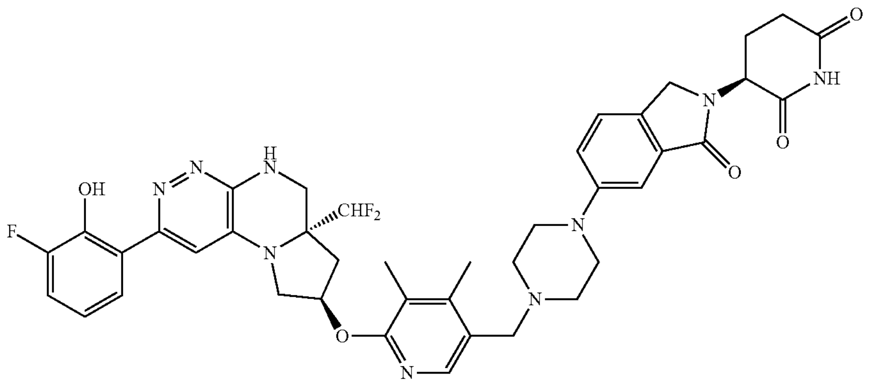 [SMILES: Cc1c(CN2CCN(c3ccc4c(c3)C(=O)N([C@H]3CCC(=O)NC3=O)C4)CC2)cnc(O[C@H]2CN3c4cc(-c5cccc(F)c5O)nnc4NC[C@@]3(C(F)F)C2)c1C]

Step 1: 6-amino-4,5-dimethylnicotinonitrile

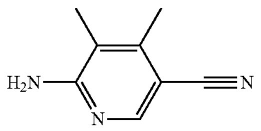

A solution of 5-bromo-3,4-dimethylpyridin-2-amine (500 mg, 2.5 mmol) and CuCN (775 mg, 8.7 mmol) in DMF (2.5 mL) was degassed with $N_2$ for 10 minutes, then sealed and stirred at 145° C. for 8 hours. Reaction was then allowed to cool to ambient temperature, diluted with water (50 mL) and EtOAc (50 mL), and filtered. Solids were treated with conc. $NH_4OH$ (100 mL) and extracted with 3:1 chloroform/IPA (6×50 mL). Combined organics were washed with brine, dried, and condensed to yield the title compound (300 mg, 82% yield). The crude was taken to the next step without further purification. LCMS calcd for $C_8H_{10}N_3$ $[M+H]^+$: m/z=148.1; Found 148.0.

Step 2: 6-hydroxy-4,5-dimethylnicotinonitrile

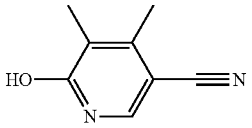

To a solution of 6-amino-4,5-dimethylnicotinonitrile (300 mg, 2.0 mmol) in sulfuric acid (2 M in water, 6.2 mL, 12.4 mmol) on ice was added a solution of sodium nitrite (515 mg, 7.5 mmol) in water (1 mL) dropwise over 1 minute. The resulting solution was allowed to warm to ambient temperature and stirred for 30 minutes. The reaction mixture was then transferred to a separatory funnel with saturated aqueous $NaHCO_3$ (150 mL) and extracted with 3:1 chloroform/IPA (3×50 mL). Combined organics were washed with brine (100 mL), dried, and condensed to yield the title compound (290 mg, 96% yield). The crude was taken to the next step without further purification. LCMS calcd for $C_8H_9N_2O$ $[M+H]^+$: m/z=149.1; Found 149.0.

Step 3: 6-(((6aR,8R)-2-chloro-6a-(difluoromethyl)-5,6,6a, 7,8,9-hexahydropyrrolo [1',2':4,5]pyrazino[2, 3-c]pyridazin-8-yl)oxy)-4,5-dimethylnicotinonitrile

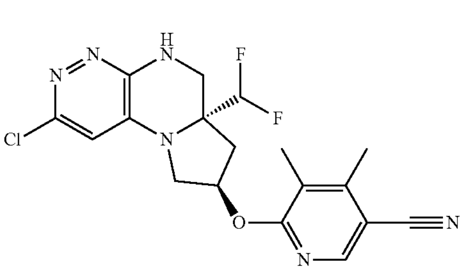 [SMILES: Cc1c(C#N)cnc(O[C@H]2CN3c4cc(Cl)nnc4NC[C@@]3(C(F)F)C2)c1C]

To a stirring solution of (6aR,8R)-2-chloro-6a-(difluoromethyl)-5,6,6a,7,8,9-hexahydropyrrolo[1',2':4,5]pyrazino [2,3-c]pyridazin-8-ol (Example 44, Step 7) (247 mg, 0.9 mmol), 6-hydroxy-4,5-dimethylnicotinonitrile (197 mg, 1.33 mmol) and polymer bound triphenylphosphine (1.6 mmol/g loading, 872 mg, 1.4 mmol) in THE (15 mL) was added DIAD (276 µL, 1.4 mmol). After stirring at 65° C. for 6 hours with little to no conversion, added DCM (15 mL), polymer bound triphenylphosphine (1.6 mmol/g loading, 339 mg, 0.6 mmol), and DIAD (110 µL, 0.63 mmol) then continued to stir at 65° C. for 18 hours. The following morning added final portions of polymer bound triphenyl phosphine (1.6 mmol/g loading, 231 mg, 0.41 mmol) and DIAD (73 µL, 0.41 mmol) and stirred 2 hours at 65° C. before cooling to ambient temperature. The reaction mixture was filtered, rinsed with THF and MeOH, and condensed under vacuum. The residue was purified using $SiO_2$ FCC 0-20% MeOH/DCM to yield the title compound (364 mg, quant. yield) as a white foam. LCMS calcd for $C_{18}H_{18}ClF_2N_6O$ $[M+H]^+$: m/z=407.1; Found 406.9.

Step 4: 6-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-4, 5-dimethylnicotinonitrile

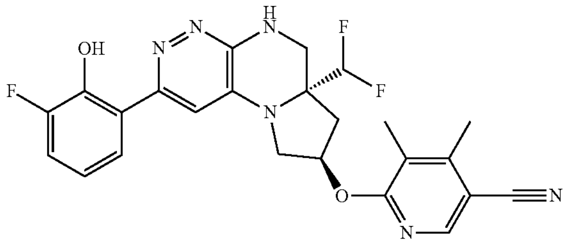 [SMILES: Cc1c(C#N)cnc(O[C@H]2CN3c4cc(-c5cccc(F)c5O)nnc4NC[C@@]3(C(F)F)C2)c1C]

A suspension of 6-(((6aR,8R)-2-chloro-6a-(difluoromethyl)-5,6,6a,7,8,9-hexahydro-pyrrolo[1',2':4,5]pyrazino[2, 3-c]pyridazin-8-yl)oxy)-4,5-dimethylnicotinonitrile (730 mg, 1.4 mmol), 3-fluoro-2-hydroxyphenylboronic acid (569 mg, 3.65 mmol), potassium carbonate (768 mg, 5.56 mmol), XPhos Pd G2 (203 mg, 0.26 mmol) in 1,4-dioxane (13 mL) and water (1.3 mL) was sparged with $N_2$ for 5 minutes, then heated to 90° C. After 3 hours, the reaction mixture was cooled to ambient temperature, filtered through celite, poured into a separatory funnel with 50 mL sat. $NaHCO_3$ (aq), and extracted with DCM (3×30 mL). The combined organics were washed with brine (30 mL), dried over sodium sulfate, and condensed to yield the title compound (400 mg, 59% yield). The crude was taken to the next step without further purification. LCMS calcd for $C_{24}H_{22}F_3N_6O_2$ $[M+H]^+$: m/z=483.2; Found 483.0.

Step 5: 6-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-4,5-dimethylnicotinaldehyde

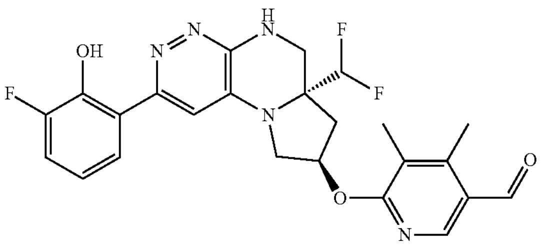

To a stirring solution of 6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-4,5-dimethylnicotinonitrile (approx. 450 mg, 0.9 mmol) in THE (19 mL) at 0° C. was added DIBAL (1M in toluene, 4.7 mL, 4.7 mmol) dropwise. The reaction was stirred on ice for 2 hours, then quenched with dropwise addition of saturated aqueous sodium potassium tartrate (3 mL). The reaction mixture was poured into a separatory funnel and extracted with DCM (3×10 mL). The combined organic layers were washed with brine, dried over sodium sulfate, and condensed at ambient temperature to yield the title compound (453 mg, quant. yield). The crude was taken to the next step without further purification. LCMS calcd for $C_{24}H_{23}F_3N_5O_3$ $[M+H]^+$: m/z=486.2; Found 486.0.

Step 6: (S)-3-(6-(4-((6-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-4,5-dimethylpyridin-3-yl)methyl)piperazin-1-yl)-1-oxoisoindolin-2-yl)piperidine-2,6-dione A solution of 6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-4,5-dimethylnicotinaldehyde (400 mg, 0.8 mmol), Intermediate 7 (615 mg, 1.7 mmol), and DIPEA (720 μL, 4.1 mmol) in DMSO (15 mL) was stirred at ambient temperature 2 hours, then sodium triacetoxyborohydride (516 mg, 2.43 mmol) was added. The reaction was stirred at 35° C. overnight, then quenched with water and MeOH, diluted in DMSO, and purified by prep-HPLC (Waters CSH-C18, 5 μm, 30×100 mm, 17.0-28.0% MeCN/water (containing 0.1% TFA) over 5 min) to give the TFA salt of the title compound (100.3 mg, 12% yield). LCMS calcd for $C_{41}H_{43}F_4N_9O_5[M+H]^+$: m/z=798.3; Found 798.2. $^1$H NMR (400 MHz, DMSO) δ 10.98 (s, 1H), 9.86 (s, 1H), 8.29 (s, 1H), 8.16 (s, 1H), 7.50 (d, J=8.3 Hz, 1H), 7.46-7.34 (m, 2H), 7.31 (dd, J=8.5, 2.3 Hz, 1H), 7.29-7.14 (m, 2H), 6.36 (t, J=55.3 Hz, 1H), 5.78 (p, J=5.6 Hz, 1H), 5.10 (dd, J=13.2, 5.1 Hz, 1H), 4.48-4.14 (m, 6H), 3.90 (dd, J=12.7, 5.0 Hz, 4H), 3.35 (s, 4H), 2.91 (td, J=13.6, 6.4 Hz, 2H), 2.60 (d, J=17.9 Hz, 1H), 2.39 (dd, J=13.2, 4.7 Hz, 1H), 2.33 (s, 3H), 2.09 (s, 3H), 1.99 (d, J=12.7 Hz, 1H), 1.18 (d, J=6.2 Hz, 2H).

Example 87: (S)-3-(6-(4-((6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-2,5-dimethylpyridin-3-yl)methyl)piperazin-1-yl)-1-oxoisoindolin-2-yl)piperidine-2,6-dione

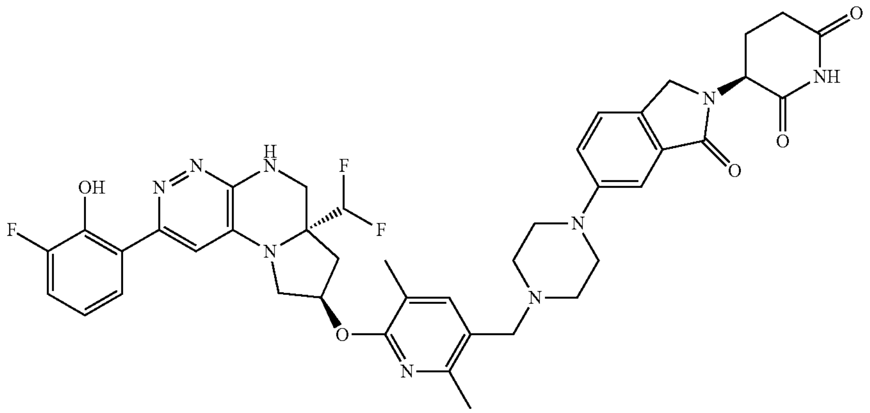 [SMILES: Cc1cc(CN2CCN(c3ccc4c(c3)C(=O)N([C@H]3CCC(=O)NC3=O)C4)CC2)c(C)nc1O[C@H]1CN2c3cc(-c4cccc(F)c4O)nnc3NC[C@@]2(C(F)F)C1]

Step 1: 3,6-dimethyl-5-vinylpyridin-2-ol

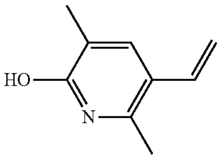

A suspension of 5-bromo-3,6-dimethylpyridin-2-ol (1.49 g, 7.4 mmol), 4,4,5,5-tetramethyl-2-vinyl-1,3,2-dioxaborolane (3.8 mL, 22.3 mmol), potassium carbonate (4.3 g, 30.8 mmol) and XPhos Pd G2 (1.1 g, 1.4 mmol) in 1,4-dioxane (60 mL) and water (6 mL) was degassed with $N_2$ for 5 minutes, then heated to 100° C. After 90 minutes, the reaction mixture was cooled to ambient temperature, filtered through celite, poured into a separatory funnel with sat. aqueous $NaHCO_3$ (100 mL), and extracted with a 3:1 mixture of chloroform/isopropanol (3×50 mL). The combined organic layers were washed with brine (50 mL), dried, and purified by $SiO_2$ FCC (0-10% MeOH/DCM) to yield the title compound (800 mg, 73% yield) as an orange solid. LCMS calcd for $C_9H_{12}NO$ $[M+H]^+$: m/z=150.1; Found 150.0.

Step 2: (6R,8R)-2-chloro-6a-(difluoromethyl)-8-((3,6-dimethyl-5-vinylpyridin-2-yl)oxy)-5,6,6a, 7,8,9-hexahydropyrrolo[1',2':4,5]pyrazino[2,3-c]pyridazine

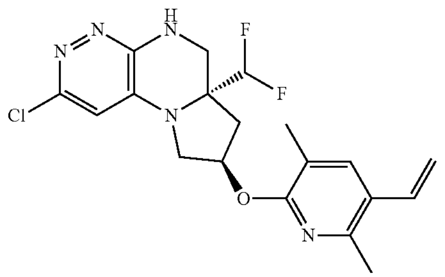 [SMILES: C=Cc1cc(C)c(O[C@H]2CN3c4cc(Cl)nnc4NC[C@@]3(C(F)F)C2)nc1C]

To a stirring suspension of (6aR,8S)-2-chloro-6a-(difluoromethyl)-5,6,6a,7,8,9-hexahydropyrrolo[1',2':4,5]pyrazino[2,3-c]pyridazin-8-ol (Example 44, Step 7, 278 mg, 1 mmol), 3,6-dimethyl-5-vinylpyridin-2-ol (225 mg, 1.51 mmol), and polymer bound triphenylphosphine (1.6 mmol/g loading, 979 mg, 1.57 mmol) in THE (15 mL) was added DIAD (311 μL, 1.58 mmol) and the reaction was heated to 65° C. After 3 hours, the reaction was allowed to cool to ambient temperature and filtered to remove the triphenylphosphine. The filtrate was condensed and purified by $SiO_2$ FCC (0-20% MeOH/DCM) to yield the title compound (93 mg, 23% yield). LCMS calcd for $C_{19}H_{21}ClF_2N_{50}$ $[M+H]^+$: m/z=408.1; Found 408.0.

Step 3: 2-((6aR,8R)-6a-(difluoromethyl)-8-((3,6-dimethyl-5-vinylpyridin-2-yl)oxy)-5,6,6a, 7,8,9-hexahydropyrrolo[1',2':4,5]pyrazino[2,3-c]pyridazin-2-yl)-6-fluorophenol

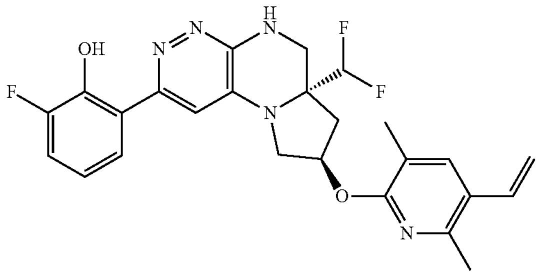 [SMILES: C=Cc1cc(C)c(O[C@H]2CN3c4cc(-c5cccc(F)c5O)nnc4NC[C@@]3(C(F)F)C2)nc1C]

A suspension of (6R,8R)-2-chloro-6a-(difluoromethyl)-8-((3,6-dimethyl-5-vinylpyridin-2-yl)oxy)-5,6,6a,7,8,9-hexahydropyrrolo[1',2':4,5]pyrazino[2,3-c]pyridazine (500 mg, 1.2 mmol), 3-fluoro-2-hydroxyphenylboronic acid (540 mg, 3.5 mmol), potassium carbonate (683 mg, 4.9 mmol), and XPhos Pd G2 (164 mg, 0.21 mmol) in 1,4-dioxane (11.1 mL) and water (1.1 mL) was degassed with $N_2$ for 1 minute, then sealed and heated to 100° C. After 90 minutes, the reaction was cooled to ambient temperature, poured into a separatory funnel with sat. $NaHCO_3$ (aq), and extracted with DCM (3×30 mL). The combined organic layers were washed with brine (30 mL), dried, and condensed to yield the title compound (592 mg, quant yield) as a dark, amber-colored oil. The crude was taken to the next step without further purification. LCMS calcd for $C_{25}H_{25}F_3N_5O_2[M+H]^+$: m/z=484.2; Found 484.0.

Step 4: 6-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-2,5-dimethylnicotinaldehyde

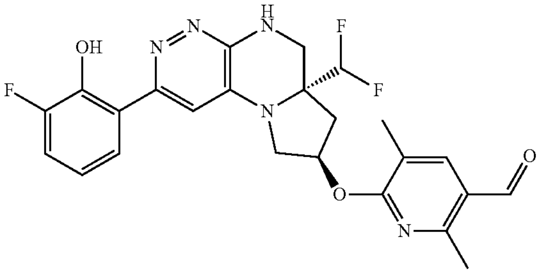 [SMILES: Cc1cc(C=O)c(C)nc1O[C@H]1CN2c3cc(-c4cccc(F)c4O)nnc3NC[C@@]2(C(F)F)C1]

Osmium tetroxide (4% in water, 525 μL, 0.08 mmol) was added to a solution of crude 2-((6aR,8R)-6a-(difluoromethyl)-8-((3,6-dimethyl-5-vinylpyridin-2-yl)oxy)-5,6,6a,7,8,9-hexahydropyrrolo[1',2':4,5]pyrazino[2,3-c]pyridazin-2-yl)-6-fluorophenol (400 mg, 0.8 mmol) and sodium periodate (527 mg, 2.5 mmol) in THE (11 mL) and water (5.5 mL) and the reaction was sealed. After stirring for 3 hours at ambient temperature, the reaction was quenched with dropwise addition of saturated aqueous sodium sulfite (4 mL) and stirred vigorously for an additional 5 minutes. The quenched reaction mixture was then transferred to a separatory funnel with sat. sodium sulfite (aq) and extracted with DCM (4×20 mL). The combined organics were washed with brine (30 mL), dried, and condensed to yield the title compound (400 mg, quant yield). The crude was taken to the next step without further purification. LCMS calcd for $C_{24}H_{23}F_3N_5O_3[M+H]^+$: m/z=486.2; Found 485.9.

Step 5: (S)-3-(6-(4-((6-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-2,5-dimethylpyridin-3-yl)methyl)piperazin-1-yl)-1-oxoisoindolin-2-yl)piperidine-2,6-dione The title compound was prepared using the procedure analogous to that described for Example 86, Step 6 using the appropriate intermediates and starting materials. LCMS calcd for $C_{41}H_{43}F_3N_9O_5[M+H]^+$: m/z=798.3; Found 798.3. $^1H$ NMR (400 MHz, DMSO) δ 10.98 (s, 1H), 9.58 (s, 1H), 8.16 (s, 1H), 7.65 (s, 1H), 7.50 (d, J=8.4 Hz, 2H), 7.40-7.24 (m, 3H), 7.18 (s, 1H), 6.94 (s, 1H), 6.35 (t, J=55.4 Hz, 2H), 5.79 (s, 2H), 5.09 (dd, J=13.3, 5.1 Hz, 1H), 4.36 (d, J=16.2 Hz, 2H), 4.28-4.13 (m, 2H), 3.90 (d, J=30.4 Hz, 4H), 3.06 (s, 2H), 2.91 (t, J=12.6 Hz, 2H), 2.09 (s, 3H), 1.99 (d, J=13.1 Hz, 2H), 1.82 (s, 1H), 1.19 (d, J=6.2 Hz, 5H).

Example 88: 3-(6-(1-((6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-5-fluoropyridin-3-yl)methyl)piperidin-4-yl)-1-oxoisoindolin-2-yl)piperidine-2,6-dione

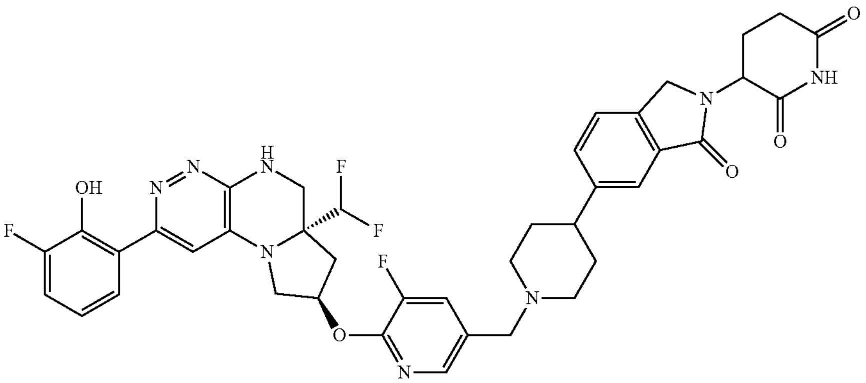 [SMILES: O=C1CCC(N2Cc3ccc(C4CCN(Cc5cnc(O[C@H]6CN7c8cc(-c9cccc(F)c9O)nnc8NC[C@@]7(C(F)F)C6)c(F)c5)CC4)cc3C2=O)C(=O)N1]

Step 1: (6aR,8R)-8-(benzyloxy)-6a-(difluoromethyl)-2-(3-fluoro-2-methoxyphenyl)-6a, 7,8,9-tetrahydropyrrolo[1',2':4,5]pyrazino[2,3-c]pyridazin-6(5H)-one

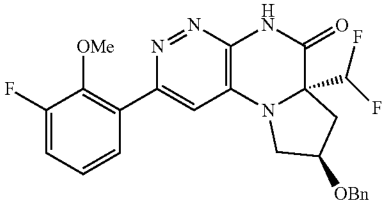 [SMILES: COc1c(F)cccc1-c1cc2c(nn1)NC(=O)[C@@]1(C(F)F)C[C@@H](OCc3ccccc3)CN21]

3-Fluoro-2-methoxyphenylboronic acid (1.34 g, 7.9 mmol), (6aR,8R)-8-(benzyloxy)-2-chloro-6a-(difluoromethyl)-6a,7,8,9-tetrahydropyrrolo[1',2':4,5]pyrazino[2,3-c]pyridazin-6(5H)-one (1.0 g, 2.63 mmol), and cesium carbonate (2.57 g, 7.9 mmol) were combined in 1,4-dioxane (14.4 mL) and water (1.39 mL) under nitrogen. The solution was sparged with $N_2$ for ~5 minutes and then chloro(2-dicyclohexylphosphino-2',6'-dimethoxy-1,1'-biphenyl)[2-(2'-amino-1,1'-biphenyl)]palladium(II) (0.19 g, 0.26 mmol) was added. The mixture was sparged under $N_2$ for ~5 min then stirred at 100° C. overnight. The reaction was cooled to RT, diluted with water, and extracted with ethyl acetate. The organics were dried over $MgSO_4$, filtered, and concentrated under reduced pressure. The crude material was purified via $SiO_2$ FCC: 20-50% ethyl acetate/hexanes to obtain (6aR,8R)-8-(benzyloxy)-6a-(difluoromethyl)-2-(3-fluoro-2-methoxy-phenyl)-6a,7,8,9-tetrahydropyrrolo[1',2':4,5]pyrazino[2,3-c]pyridazin-6(5H)-one (800 mg, 65% yield) as a colorless viscous oil. LCMS calcd for $C_{24}H_{22}F_3N_4O_3[M+H]^+$: m/z=471.2; Found: 470.9.

Step 2: (6aR,8R)-8-(benzyloxy)-6a-(difluoromethyl)-2-(3-fluoro-2-methoxyphenyl)-5,6,6a, 7,8,9-hexahydropyrrolo[1',2':4,5]pyrazino[2,3-c]pyridazine

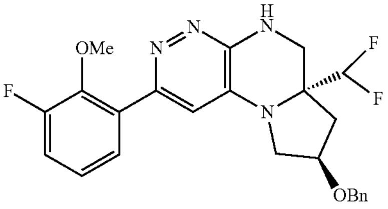 [SMILES: COc1c(F)cccc1-c1cc2c(nn1)NC[C@@]1(C(F)F)C[C@@H](OCc3ccccc3)CN21]

(6aR,8R)-8-(benzyloxy)-6a-(difluoromethyl)-2-(3-fluoro-2-methoxyphenyl)-6a,7,8,9-tetrahydropyrrolo[1',2':4,5]pyrazino[2,3-c]pyridazin-6(5H)-one (0.8 g, 1.7 mmol) was dissolved in anhydrous THE (11.3 mL). The solution was cooled to 0° C. and lithium aluminum hydride (0.19 g, 5.1 mmol) was added slowly under nitrogen and warmed to RT, stirred for 1 hour. The reaction was placed in an ice-bath, quenched very slowly with methanol (11 mL) then treated with acetic acid (1.95 mL, 34.01 mmol) and sodium cyanoborohydride (1.07 g, 17.0 mmol). The reaction was stirred at 80° C. overnight then quenched with saturated sodium bicarbonate (aq) and extracted with DCM. The combined organic layers were dried over sodium sulfate and concentrated under reduced pressure. The crude material was passed through a plug of silica gel using 10% MeOH in DCM to obtain (6aR,8R)-8-(benzyloxy)-6a-(difluoromethyl)-2-(3-fluoro-2-methoxyphenyl)-5,6,6a,7,8,9-hexahydropyrrolo[1',2':4,5]pyrazino[2,3-c]pyridazine (0.58 g, 75% yield)) as pale green foam. LCMS calcd for $C_{24}H_{24}F_3N_4O_2$ $[M+H]^+$: m/z=457.2; Found: 456.9.

Step 3: (6aR,8R)-6a-(difluoromethyl)-2-(3-fluoro-2-methoxyphenyl)-5,6,6a, 7,8,9-hexahydropyrrolo[1',2':4,5]pyrazino[2,3-c]pyridazin-8-ol

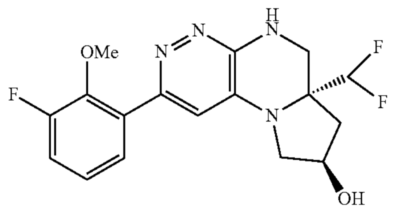 [SMILES: COc1c(F)cccc1-c1cc2c(nn1)NC[C@@]1(C(F)F)C[C@@H](O)CN21]

A solution of (6aR,8R)-8-(benzyloxy)-6a-(difluoromethyl)-2-(3-fluoro-2-methoxy-phenyl)-5,6,6a,7,8,9-hexahydropyrrolo[1',2':4,5]pyrazino[2,3-c]pyridazine (0.58 g, 1.27 mmol), in anhydrous DCM (15 mL) was cooled to −78° C. Trichloroborane (1 M in DCM, 3.8 mL, 3.8 mmol) was added slowly for 1 minute and then reaction was transferred to ice-bath and stirred for 30 minutes. The reaction was diluted water and transferred to a separatory funnel containing a saturated solution of sodium bicarbonate (aq), then extracted with 3:1 chloroform/iPrOH. The combined organic extracts were dried over sodium sulfate, concentrated under reduced pressure to give yellow material, which was purified via $SiO_2$ FCC: 0 to 20% MeOH in DCM to obtain (6aR,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-ol (80 mg, 17% yield) as off-white solid. LCMS calcd for $C_{17}H_{18}F_3N_4O_2[M+H]^+$: m/z=367.1; Found: 367.0.

Step 4: (6-(((6aR,8R)-6a-(difluoromethyl)-2-(3-fluoro-2-methoxyphenyl)-5,6,6a, 7,8,9-hexahydro-pyrrolo[1',2':4,5]pyrazino[2,3-c]pyridazine-8-yl)oxy)-5-fluoropyridin-3-yl)methanol

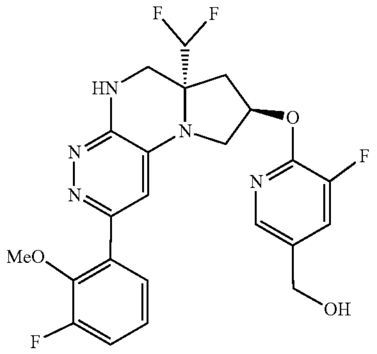 [SMILES: COc1c(F)cccc1-c1cc2c(nn1)NC[C@@]1(C(F)F)C[C@@H](Oc3ncc(CO)cc3F)CN21]

A solution of (6aR,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-ol (22 mg, 0.06 mmol) in anhydrous THE (1.1 mL) was cooled to 0° C. Sodium hydride (60% dispersion in mineral oil; 14.3 mg, 0.36 mmol) was added followed by methyl 6-chloro-5-fluoropyridine-3-carboxylate (17.0 mg, 0.09 mmol) and then reaction was stirred at RT for 30 minutes. LCMS analysis showed 20% conversion to desired product. The reaction was heated to 40° C. for an hour at which point LCMS analysis showed 80% conversion to desired product. The reaction was cooled 0° C., added sodium hydride (14.3 mg, 0.36 mmol, 3.0 equiv) and methyl 6-chloro-5-fluoropyridine-3-carboxylate (17.0 mg, 0.09 mmol, 1.0 equiv) then stirred at 40° C. for an additional 30 minutes. The reaction was cooled to 0° C. and then lithium aluminum hydride (13.6 mg, 0.36 mmol) was added and stirred at RT for 15 minutes. The reaction was quenched with MeOH and diluted with THE and transferred to separatory funnel, extracted with 3:1 chloroform/iPrOH. The combined organic layers were dried over anhydrous sodium sulfate to give a viscous oil, which was purified via $SiO_2$ FCC: 0 to 10% MeOH in DCM to obtain (6-(((6aR,8R)-6a-(difluoromethyl)-2-(3-fluoro-2-methoxyphenyl)-5,6,6a,7,8,9-hexahydropyrrolo[1',2':4,5]pyrazino[2,3-c]pyridazine-8-yl)oxy)-5-fluoropyridin-3-yl)methanol (10 mg, 32% yield) as pale brown solid. LCMS calcd for $C_{23}H_{22}F_4N_5O_3[M+H]^+$: m/z=492.1; Found: 491.9.

Step 5: 2-((6aR,8R)-8-((5-(chloromethyl)-3-fluoro-pyridin-2-yl)oxy)-6a-(difluoromethyl)-5,6,6a, 7,8,9-hexahydropyrrolo[1',2':4,5]pyrazino[2,3-c]pyridazine-2-yl)-6-fluorophenol

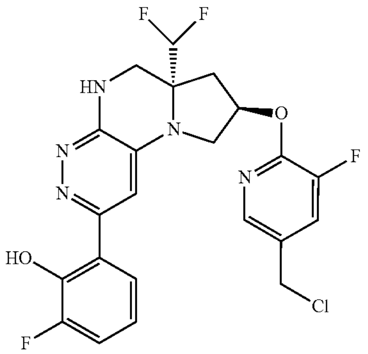 [SMILES: Oc1c(F)cccc1-c1cc2c(nn1)NC[C@@]1(C(F)F)C[C@@H](Oc3ncc(CCl)cc3F)CN21]

A solution of (6-(((6aR,8R)-6a-(difluoromethyl)-2-(3-fluoro-2-methoxyphenyl)-5,6,6a,7,8,9-hexahydropyrrolo[1',2':4,5]pyrazino[2,3-c]pyridazine-8-yl)oxy)-5-fluoropyridin-3-yl)methanol (10 mg, 0.02 mmol) in DCM (0.5 mL) was cooled to 0° C. Trichloroborane (1 M in DCM; 0.8 mL, 0.8 mmol) was added slowly and the reaction was warmed to RT and stirred for 36 h. The reaction was slowly quenched with water and transferred to a separatory funnel containing a saturated solution of potassium carbonate then extracted with 3:1 chloroform/iPrOH. The combined organic extracts were dried over sodium sulfate and concentrated under reduced pressure to give 2-((6aR,8R)-8-((5-(chloromethyl)-3-fluoropyridin-2-yl)oxy)-6a-(difluoro-methyl)-5,6,6a,7,8,9-hexahydropyrrolo[1',2':4,5]pyrazino[2,3-c]pyridazine-2-yl)-6-fluorophenol (assumed quantitative yield) as a brown oil, which was used in next step without further purification. LCMS calcd for $C_{22}H_{19}ClF_4N_5O_2$ [M+H]$^+$: m/z=496.1; Found: 496.1.

Step 6: 3-(6-(1-((6-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazine-8-yl)oxy)-5-fluoropyridin-3-yl)methyl)piperidin-4-yl)-1-oxoisoindolin-2-yl)piperidine-2,6-dione

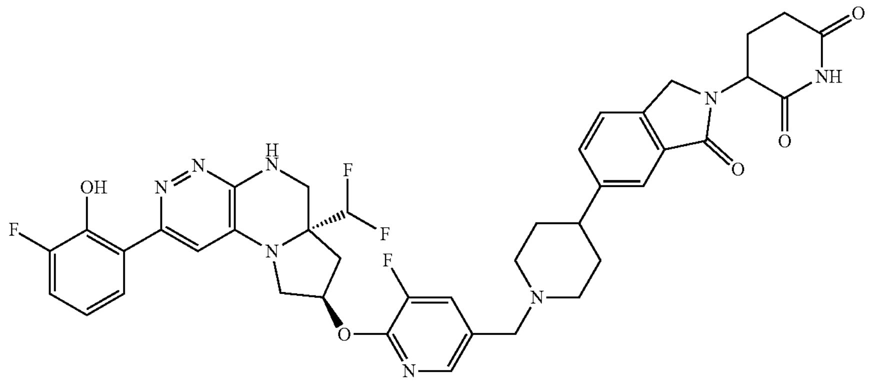 [SMILES: O=C1CCC(N2Cc3ccc(C4CCN(Cc5cnc(O[C@H]6CN7c8cc(-c9cccc(F)c9O)nnc8NC[C@@]7(C(F)F)C6)c(F)c5)CC4)cc3C2=O)C(=O)N1]

2-((6aR,8R)-8-((5-(chloromethyl)-3-fluoropyridin-2-yl)oxy)-6a-(difluoromethyl)-5,6,6a,7,8,9-hexahydropyrrolo[1',2':4,5]pyrazino[2,3-c]pyridazine-2-yl)-6-fluorophenol (22.01 mg, 0.06 mmol) and (S)-3-(1-oxo-6-(piperidin-4-yl)isoindolin-2-yl)piperidine-2,6-dione hydrochloride (20.0 mg, 0.04 mmol) in MeCN (1.6 mL) was added N,N-diisopropylethylamine (35.13 uL, 0.2 mmol) heated at 120° C. for 30 minutes. The reaction was cooled to room temperature, diluted with DMSO and filtered. The filtrate was directly purified via prep-HPLC (Waters CSH-Fluoro-Phenyl, 5 uM, 30×100 mm, 12.2-32.2% $CH_3CN$ in $H_2O$ with 0.1% TFA) over 5 minutes to give the TFA salt of the title compound (4.8 mg, 12% yield) as a white solid. LCMS calcd for $C_{40}H_{39}F_4N_8O_5[M+H]^+$: m/z=787.3; Found: 787.3.

Example 89: (S)-3-(6-(1-((6-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazine-8-yl)oxy)-5-fluoro-4-methylpyridin-3-yl)methyl)piperidin-4-yl)-1-oxoisoindolin-2-yl)piperidine-2,6-dione Step 1: 6-(((6aS,8R)-6a-(difluoromethyl)-2-(3-fluoro-2-methoxyphenyl)-5,6,6a, 7,8,9-hexahydropyrrolo[1',2':4,5]pyrazino[2,3-c]pyridazin-8-yl)oxy)-5-fluoro-4-methylnicotinonitrile

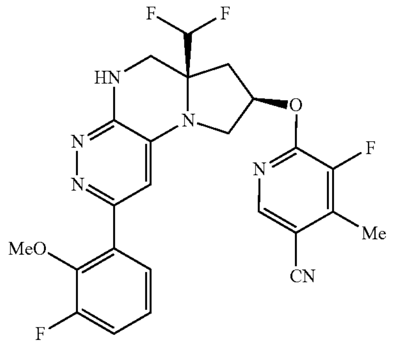

Diisopropyl azodicarboxylate (0.03 mL, 0.16 mmol) was added to a solution of (6aS,8S)-6a-(difluoromethyl)-2-(3-fluoro-2-methoxyphenyl)-5,6,6a,7,8,9-hexahydropyrrolo[1',2':4,5]pyrazino[2,3-c]pyridazin-8-ol (35.0 mg, 0.1

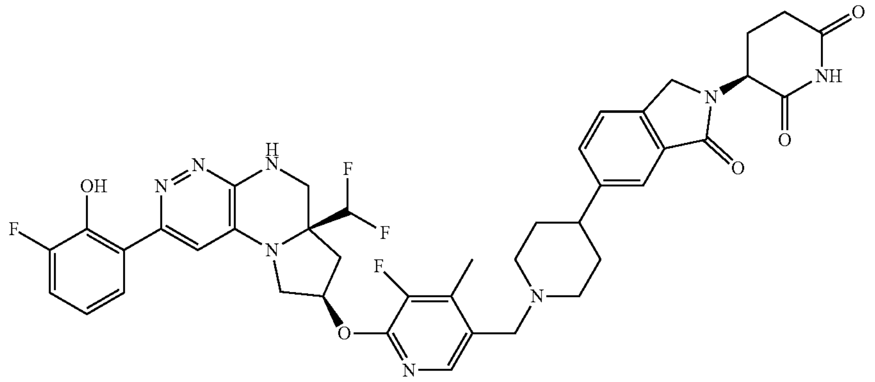 [SMILES: Cc1c(CN2CCC(c3ccc4c(c3)C(=O)N([C@H]3CCC(=O)NC3=O)C4)CC2)cnc(O[C@H]2CN3c4cc(-c5cccc(F)c5O)nnc4NC[C@]3(C(F)F)C2)c1F]

mmol), 5-fluoro-6-hydroxy-4-methylpyridine-3-carbonitrile (21.8 mg, 0.14 mmol) and triphenylphosphine (101 mg, 0.16 mmol) in THF (2.0 mL).

The reaction mixture was heated at 65° C. for 45 minutes then cooled to room temperature and directly purified via $SiO_2$ FCC: 0-10% MeOH/DCM to obtain 6-(((6aS,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-yl)oxy)-5-fluoro-4-methylnicotinonitrile (23 mg, 48% yield) as a thick viscous yellow oil. LCMS calcd for $C_{24}H_{21}F_4N_6O_2[M+H]^+$: m/z=501.2; Found: 501.0.

Step 2: 6-(((6aS,8R)-6a-(difluoromethyl)-2-(3-fluoro-2-methoxyphenyl)-5,6,6a, 7,8,9-hexahydro-pyrrolo[1',2':4,5]pyrazino[2,3-c]pyridazin-8-yl)oxy)-5-fluoro-4-methylnicotinaldehyde

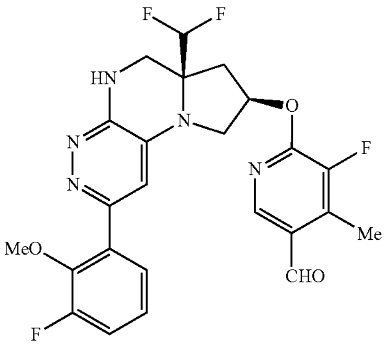 [SMILES: COc1c(F)cccc1-c1cc2c(nn1)NC[C@]1(C(F)F)C[C@@H](Oc3ncc(C=O)c(C)c3F)CN21]

6-(((6aS,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-yl)oxy)-5-fluoro-4-methylnicotinonitrile (23 mg, 0.05 mmol) in toluene (2.3 mL) was cooled to −78° C. Diisobutylaluminum hydride (1 M in toluene; 0.56 mL, 0.56 mmol) was added and the reaction was warmed to 0° C. and stirred for 30 minutes. The reaction was quenched with 1N hydrochloric acid (aq). The reaction mixture was basified to pH 9 using saturated solution of sodium bicarbonate (aq) and extracted with 3:1 chloroform/iPrOH. The combined organic extracts were dried and concentrated to give 6-(((6aS,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-yl)oxy)-5-fluoro-4-methylnicotinaldehyde (23 mg crude, assumed quant.yield) as a brown viscous oil. The reaction was carried on to the next step without further purification. LCMS calcd for $C_{24}H_{22}F_4N_5O_3[M+H]^+$: m/z=504.2; Found: 504.0.

Step 3: 6-(((6aS,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-5-fluoro-4-methylnicotinaldehyde

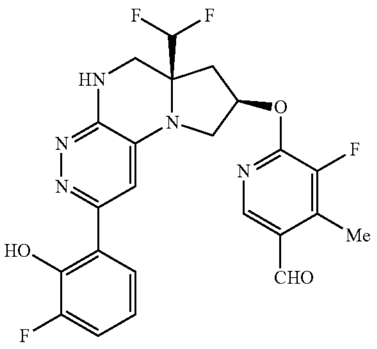 [SMILES: Cc1c(C=O)cnc(O[C@H]2CN3c4cc(-c5cccc(F)c5O)nnc4NC[C@]3(C(F)F)C2)c1F]

A solution give 6-(((6aS,8R)-6a-(difluoromethyl)-2-(3-fluoro-2-methoxyphenyl)-5,6,6a,7,8,9-hexahydropyrrolo[1',2':4,5]pyrazino[2,3-c]pyridazin-8-yl)oxy)-5-fluoro-4-methylnicotinaldehyde (23 mg, 0.04 mmol) in DCM (0.4 mL) was cooled to 0° C. Trichloroborane (1 M in DCM; 1.8 mL, 1.8 mmol) was added slowly and the reaction was warmed to RT and stirred for 36 h. The reaction was slowly quenched with water, transferred to a separatory funnel containing saturated solution of potassium carbonate (aq), and extracted with 3:1 chloroform/iPrOH. The combined organic extracts were dried over sodium sulfate, concentrated under reduced pressure to give 6-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-5-fluoro-4-methylnicotinaldehyde (22 mg crude, assumed quant. yield) as a brown oil, which was used in next step without further purification. LCMS calcd for $C_{23}H_{20}F_4N_5O_3[M+H]^+$: m/z=490.1; Found: 489.9.

Step 4: (S)-3-(6-(1-((6-(((6aS,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazine-8-yl)oxy)-5-fluoro-4-methylpyridin-3-yl)methyl)piperidin-4-yl)-1-oxoisoindolin-2-yl)piperidine-2,6-dione

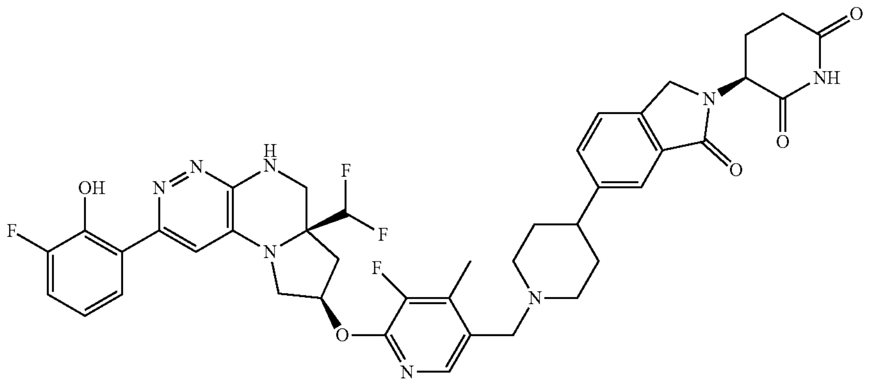 [SMILES: Cc1c(CN2CCC(c3ccc4c(c3)C(=O)N([C@H]3CCC(=O)NC3=O)C4)CC2)cnc(O[C@H]2CN3c4cc(-c5cccc(F)c5O)nnc4NC[C@]3(C(F)F)C2)c1F]

To 6-(((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-5-fluoro-4-methylnicotinaldehyde (22 mg, 0.04 mmol) and (S)-3-(1-oxo-6-(piperidin-4-yl)isoindolin-2-yl)piperidine-2,6-dione (HCl salt; 20.0 mg, 0.09 mmol) in DMSO (1.0 mL) was added N,N-Diisopropylethylamine (39.1 μL, 0.23 mmol). The reaction was stirred for 45 minutes at 35° C. then treated with sodium triacetoxyborohydride (48.0 mg, 0.23 mmol). The solution was stirred at 35° C. overnight then cooled to room temperature, filtered, and directly purified via prep-LCMS (Waters CSH-Fluoro-Phenyl, 5 uM, 30×100 mm, 10.9-30.9% $CH_3CN$ in $H_2O$ with 0.1% TFA over 5 minutes) to yield the title compound (2.0 mg, 4% yield) as a white TFA salt. LCMS calcd for $C_{41}H_{41}F_4N_8O_5[M+H]^+$: m/z=801.3; Found: 801.3.

Example 90: (S)-3-(6-(1-((6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)pyridin-3-yl)methyl)piperidin-4-yl)-1-oxoisoindolin-2-yl)piperidine-2,6-dione

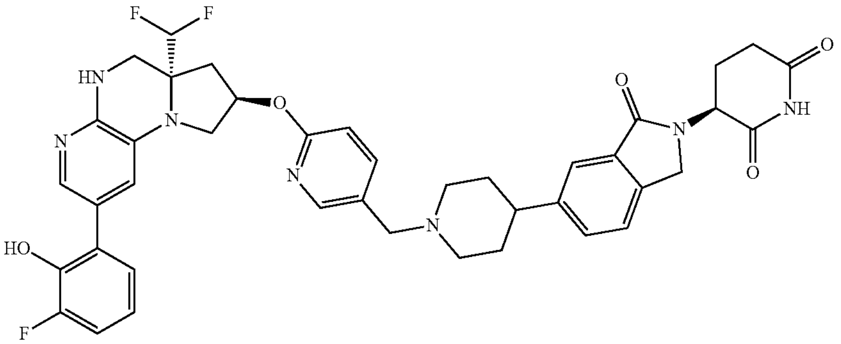 [SMILES: O=C1CC[C@H](N2Cc3ccc(C4CCN(Cc5ccc(O[C@H]6CN7c8cc(-c9cccc(F)c9O)cnc8NC[C@@]7(C(F)F)C6)nc5)CC4)cc3C2=O)C(=O)N1]

Step 1: 5-vinylpyridin-2-ol

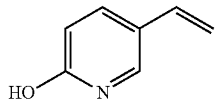

A mixture of 5-bromo-pyridin-2-ol (1.0 g, 5.8 mmol), potassium vinyltrifluoroborate (1.54 g, 11.5 mmol), cesium carbonate (5.60 g, 17.2 mmol) and chloro(2-dicyclohexylphosphino-2',6'-dimethoxy-1,1'-biphenyl)[2-(2'-amino-1,1'-biphenyl)]palladium(II) (0.414 g, 0.58 mmol) in 1,4-dioxane (18.4 mL) and water (4.6 mL) was sparged with $N_2$ for 5 minutes. The reaction was heated at 85° C. for 4 hours. The reaction was cooled to room temperature, diluted with ethyl acetate, washed with a saturated solution of brine, then dried over sodium sulfate, filtered and concentrated under reduced pressure. The crude material was purified via $SiO_2$ FCC: 0-5% MeOH/DCM to obtain 5-vinylpyridin-2-ol (208 mg, 30% yield). LCMS calcd for $C_7H_8NO$ $[M+H]^+$: m/z=122.1; Found: 121.9.

Step 1: (6aR,8R)-2-chloro-6a-(difluoromethyl)-8-((5-vinylpyridin-2-yl)oxy)-5,6,6a, 7,8,9-hexahydropyrrolo[1',2':4,5]pyrazino[2,3-c]pyridazine

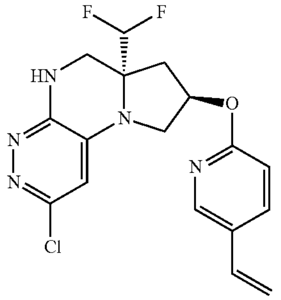 [SMILES: C=Cc1ccc(O[C@H]2CN3c4cc(Cl)nnc4NC[C@@]3(C(F)F)C2)nc1]

Diisopropyl azodicarboxylate (0.19 mL, 0.98 mmol) was added to a solution of (6aR,8S)-2-chloro-6a-(difluoromethyl)-5,6,6a,7,8,9-hexahydropyrrolo[1',2':4,5]pyrazino[2,3-c]pyridazin-8-ol (180.0 mg, 0.65 mmol), 5-ethenylpyridin-2-ol (94.6 mg, 0.78 mmol) and triphenylphosphine (205 mg, 0.78 mmol) in 1:2 THF:DCM (3 mL). The reaction mixture was stirred at 30° C. overnight. then cooled to room temperature and filtered. The filtrate was directly purified via $SiO_2$ FCC: 0-5% MeOH/DCM to obtain (6aR,8R)-2-chloro-6a-(difluoromethyl)-8-((5-vinylpyridin-2-yl)oxy)-5,6,6a,7,8,9-hexahydropyrrolo[1',2':4,5]pyrazino[2,3-c]pyridazine (247 mg, assumed quant. yield) as a thick viscous yellow oil. LCMS calcd for $C_{17}H_{17}ClF_2N_5O$ $[M+H]^+$: m/z=380.1; Found: 380.1.

Step 2: 2-((6aR,8R)-6a-(difluoromethyl)-8-((5-vinylpyridin-2-yl)oxy)-5,6,6a,7,8,9-hexahydropyrrolo[1',2':4,5]pyrazino[2,3-c]pyridazin-2-yl)-6-fluorophenol

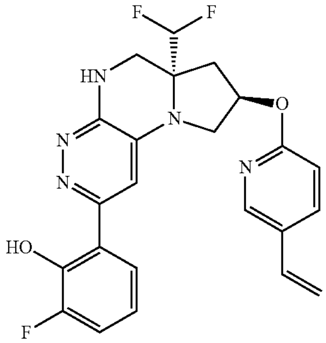 [SMILES: C=Cc1ccc(O[C@H]2CN3c4cc(-c5cccc(F)c5O)nnc4NC[C@@]3(C(F)F)C2)nc1]

To (6aR,8R)-2-chloro-6a-(difluoromethyl)-8-((5-vinylpyridin-2-yl)oxy)-5,6,6a,7,8,9-hexahydropyrrolo[1',2':4,5]pyrazino[2,3-c]pyridazine (247 mg, 0.65 mmol) in 1,4-dioxane (6.0 mL) and water (0.6 mL) was added 3-fluoro-2-hydroxyphenylboronic acid (308.0 mg, 1.97 mmol) and potassium carbonate (364.0 mg, 2.63 mmol). The solution was sparged with $N_2$ for ~2 min and then chloro(2-dicyclohexylphosphino-2',6'-dimethoxy-1,1'-biphenyl)[2-(2'-amino-1,1'-biphenyl)]palladium(II) (47.4 mg, 0.065 mmol) was added. The mixture was sparged with $N_2$ for ~2 min then stirred at 85° C. After 1 h, the reaction was cooled to RT, dried over sodium sulfate, concentrated under reduced pressure and purified via $SiO_2$ FCC: 0-5% MeOH/DCM to obtain 2-((6aR,8R)-6a-(difluoromethyl)-8-((5-vinylpyridin-2-yl)oxy)-5,6,6a,7,8,9-hexahydropyrrolo [1',2':4,5]pyrazino [2,3-c]pyridazin-2-yl)-6-fluorophenol (98.0 mg, 33%) as a pale yellow solid. LCMS calcd for $C_{23}H_{21}F_3N_5O_2[M+H]^+$: m/z=456.2; Found: 456.1.

Step 3: 6-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy) nicotinaldehyde

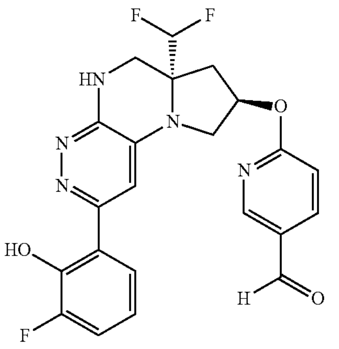 [SMILES: O=Cc1ccc(O[C@H]2CN3c4cc(-c5cccc(F)c5O)nnc4NC[C@@]3(C(F)F)C2)nc1]

Osmium tetroxide (4% in water; 0.137 mL, 0.022 mmol) and 2,6-lutidine (0.05 mL, 0.43 mmol) were added to a solution of 2-((6aR,8R)-6a-(difluoromethyl)-8-((5-vinylpyridin-2-yl)oxy)-5,6,6a,7,8,9-hexahydropyrrolo[1',2':4,5]pyrazino[2,3-c]pyridazin-2-yl)-6-fluorophenol (98.0 mg, 0.22 mmol) in 1,4-dioxane (4.5 mL) and water (1.5 mL). Sodium periodate (138 mg, 0.65 mmol) was added, and the reaction was stirred at RT for 2 hours. The reaction was poured into brine and extracted with $CHCl_3$:iPrOH (3:1). The combined organic layers were dried over $MgSO_4$, filtered and concentrated under reduced pressure to obtain crude 6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)nicotinaldehyde (98 mg, assumed quant. yield). The material was used in the following step without additional purification. LCMS calcd for $C_{22}H_{19}F_3N_5O_3[M+H]^+$: m/z=458.1; Found: 458.0.

Step 4: (S)-3-(6-(1-((6-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)pyridin-3-yl)methyl)piperidin-4-yl)-1-oxoisoindolin-2-yl)piperidine-2,6-dione

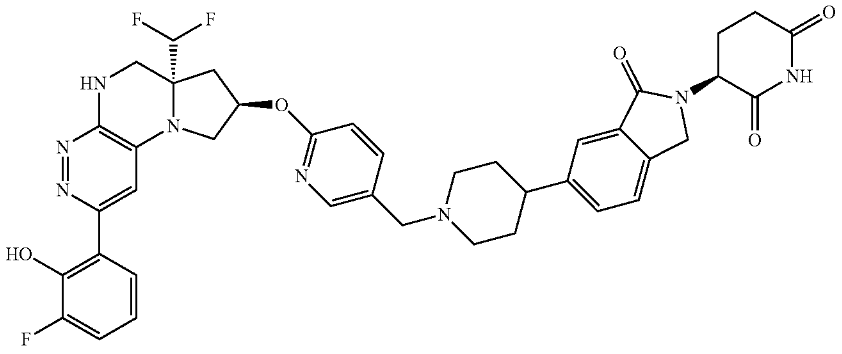 [SMILES: O=C1CC[C@H](N2Cc3ccc(C4CCN(Cc5ccc(O[C@H]6CN7c8cc(-c9cccc(F)c9O)nnc8NC[C@@]7(C(F)F)C6)nc5)CC4)cc3C2=O)C(=O)N1]

To 6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)nicotinaldehyde (98.0 mg, 0.2 mmol) and (S)-3-(1-oxo-6-(piperidin-4-yl)isoindolin-2-yl)piperidine-2,6-dione (HCl salt; 194.0 mg, 0.43 mmol) in DMSO (3.0 mL) was added N,N-diisopropylethylamine (0.187 mL, 1.07 mmol). The reaction was stirred for 45 minutes at 35° C. then treated with sodium triacetoxyborohydride (227.0 mg, 1.07 mmol). The reaction was stirred at 35° C. overnight then cooled to room temperature, filtered, and directly purified via prep-LCMS (Waters CSH-C18, 5 uM, 30×100 mm, 19.0-27.0% $CH_3CN$ in $H_2O$ with 0.2% TFA over 5 minutes) to yield the title compound (25.0 mg, 12% yield) as a white TFA salt. LCMS calcd for $C_{40}H_{40}F_3N_8O_5[M+H]^+$: m/z=769.3; Found: 769.2.

Examples 91-94

Examples 91-94 shown below in Table 8 were prepared as TFA salts by the method used in preparing Example 90, utilizing the appropriate starting materials and intermediates.

TABLE 8

| Ex. | Structure/Name | Calcd. (M + H)+ m/z | Found (M + H)+ m/z |
|---|---|---|---|
| | Example 91-94 | | |
| 91 | 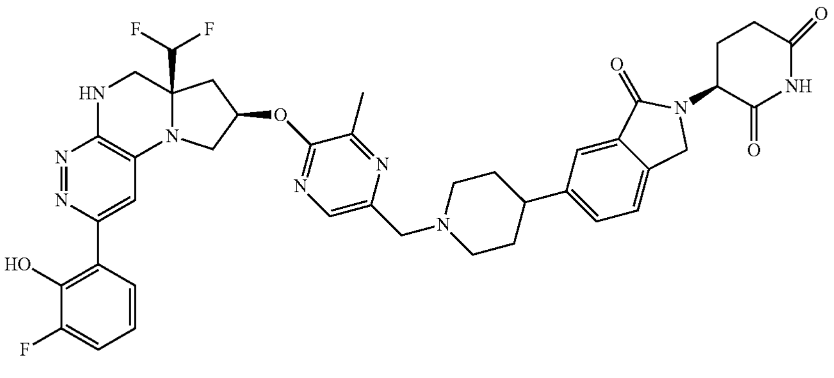 [SMILES: Cc1nc(CN2CCC(c3ccc4c(c3)C(=O)N([C@H]3CCC(=O)NC3=O)C4)CC2)cnc1O[C@H]1CN2c3cc(-c4cccc(F)c4O)nnc3NC[C@]2(C(F)F)C1] (S)-3-(6-(1-((5-(((6aS,8R)-6a-(difluoromethyl)-2-(3-fluoro-2-hydroxyphenyl)-5,6,6a,7,8,9-hexahydropyrrolo[1',2':4,5] pyrazino[2,3-c]pyridazin-8-yl)oxy)-6-methylpyrazin-2-yl)methyl)piperidin-4-yl)-1-oxoisoindolin-2-yl)piperidine-2,6-dione | 784.3 | 784.3 |
| 92 | 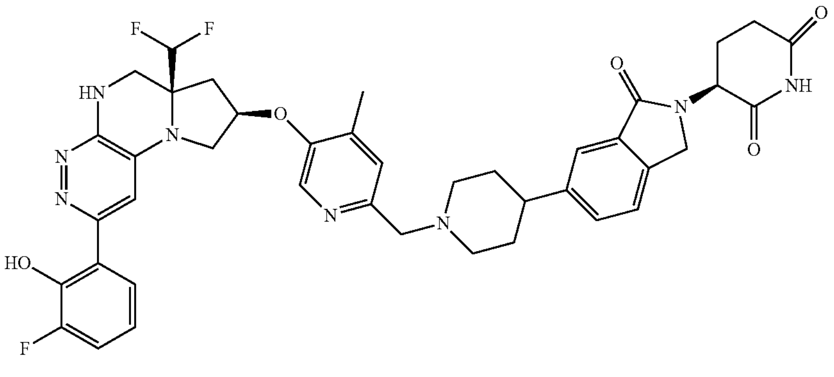 [SMILES: Cc1cc(CN2CCC(c3ccc4c(c3)C(=O)N([C@H]3CCC(=O)NC3=O)C4)CC2)ncc1O[C@H]1CN2c3cc(-c4cccc(F)c4O)nnc3NC[C@]2(C(F)F)C1] (S)-3-(6-(1-((5-(((6aS,8R)-6a-(difluoromethyl)-2-(3-fluoro-2-hydroxyphenyl)-5,6,6a,7,8,9-hexahydropyrrolo[1',2':4,5] pyrazino[2,3-c]pyridazin-8-yl)oxy)-4-methylpyridin-2-yl)methyl)piperidin-4-yl)-1-oxoisoindolin-2-yl)piperidine-2,6-dione | 783.3 | 783.4 |
| 93 | 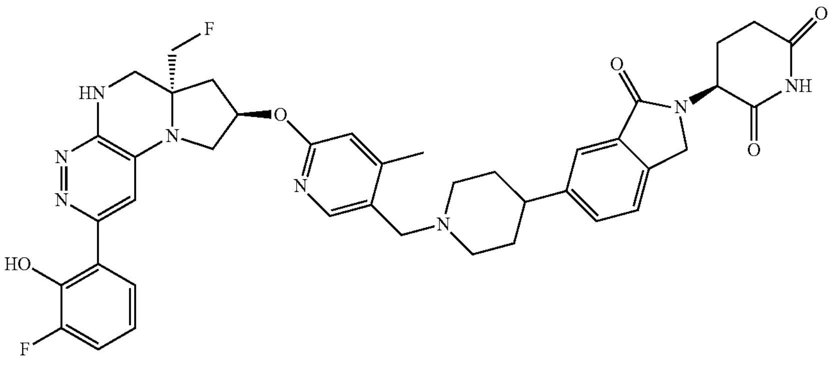 [SMILES: Cc1cc(O[C@H]2CN3c4cc(-c5cccc(F)c5O)nnc4NC[C@@]3(CF)C2)ncc1CN1CCC(c2ccc3c(c2)C(=O)N([C@H]2CCC(=O)NC2=O)C3)CC1] (S)-3-(6-(1-((6-(((6aR,8R)-2-(3-fluoro-2-hydroxyphenyl)-6a-(fluoromethyl)-5,6,6a,7,8,9-hexahydropyrrolo [1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione | 765.3 | 765.1 |

TABLE 8-continued

| Example 91-94 | | | |
|---|---|---|---|
| Ex. | Structure/Name | Calcd. (M + H)+ m/z | Found (M + H)+ m/z |
| 94 | 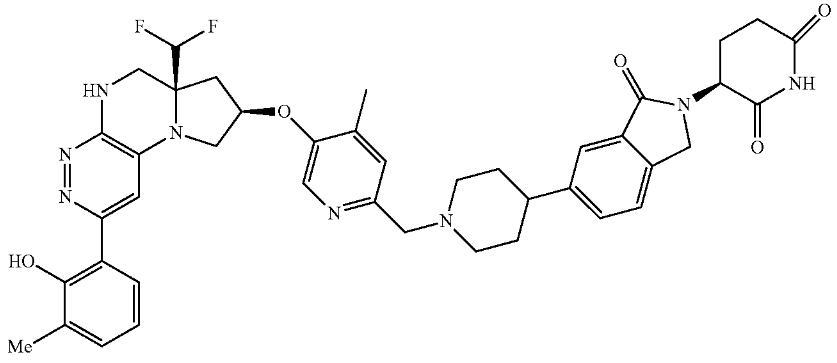 [SMILES: Cc1cc(CN2CCC(c3ccc4c(c3)C(=O)N([C@H]3CCC(=O)NC3=O)C4)CC2)ncc1O[C@H]1CN2c3cc(-c4cccc(C)c4O)nnc3NC[C@]2(C(F)F)C1] (S)-3-(6-(1-((5-(((6aS,8R)-6a-(difluoromethyl)-2-(2-hydroxy-3-methylphenyl)-5,6,6a,7,8,9-hexahydropyrrolo [1',2':4,5]pyrazino[2,3-c]pyridazin-8-yl)oxy)-4-methylpyridin-2-yl)methyl)piperidin-4-yl)-1-oxoisoindolin-2-yl)piperidine-2,6-dione | 779.3 | 779.4 |

Example 95: (S)-3-(6-(1-((5-(((6aR,8R)-6a-ethyl-2-(2-hydroxy-3-methylphenyl)-5,6,6a,7,8,9-hexahydropyrrolo[1',2':4,5]pyrazino[2,3-c]pyridazin-8-yl)oxy)-3,4-dimethylpyridin-2-yl)methyl)piperidin-4-yl)-1-oxoisoindolin-2-yl)piperidine-2,6-dion

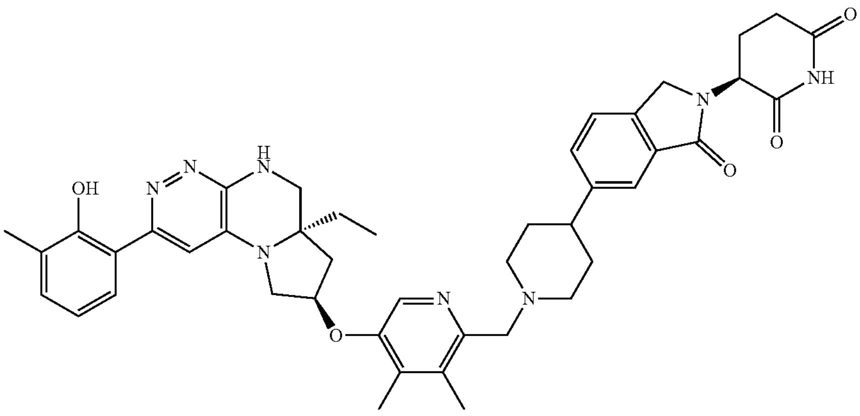 [SMILES: CC[C@@]12CNc3nnc(-c4cccc(C)c4O)cc3N1C[C@H](Oc1cnc(CN3CCC(c4ccc5c(c4)C(=O)N([C@H]4CCC(=O)NC4=O)C5)CC3)c(C)c1C)C2]

Step 1: 2,5-dibromo-3,4-dimethylpyridine

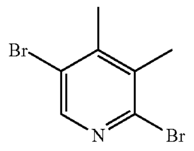

2-Amino-5-bromo-3,4-dimethylpyridine (5.0 g, 24.87 mmol) and copper(II) bromide (6.66 g, 29.84 mmol) were added to a 250 mL round-bottom flask, followed by dibromomethane (52 mL, 746 mmol). The flask was sealed with a rubber septum and the mixture was purged with nitrogen for 5 minutes. Tert-butyl nitrite (4.4 mL, 37.3 mmol) was added via a needle. The mixture was stirred at room temperature overnight, and then quenched with a 1 molar sodium hydroxide solution (40 mL).

After stirring for 30 minutes, the biphasic mixture was passed through a pad of Celite eluting with dichloromethane (50 mL). The mixture was diluted with a saturated sodium chloride solution (50 mL) and dichloromethane (50 mL). The phases were separated, and the aqueous phase was extracted with dichloromethane (2×50 mL). The combined organic phase was dried over anhydrous magnesium sulfate (~20 g), filtered, and concentrated under reduced pressure. The crude material was purified by flash silica gel column chromatography eluting with a gradient of 0-20% ethyl acetate/hexanes to obtain 2,5-dibromo-3,4-dimethylpyridine (4.48 g, 68% yield) as a white solid. LCMS calcd for $C_7H_8Br_2N$ [M+H]+: m/z=265.9; Found: 265.7.

Step 2: 5-bromo-3,4-dimethyl-2-vinylpyridine

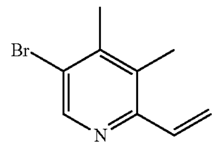

2,5-Dibromo-3,4-dimethylpyridine (2.2 g, 8.3 mmol), potassium vinyltrifluoroborate (1.22 g, 9.13 mmol), cesium carbonate (5.41 g, 16.61 mmol), 1,4-dioxane (60 mL), and water (15 mL) were added to a 250 mL round-bottom flask. The flask was sealed with a rubber septum and the mixture was sparged with nitrogen for 5 minutes. Tetrakis(triphenylphosphine)palladium(0) (960 mg, 0.83 mmol) was added. The flask was equipped with a reflux condenser, sealed with a rubber septum, and purged with nitrogen for 5 minutes. The mixture was stirred at 85° C. overnight. After cooling to room temperature, the mixture was diluted with a saturated sodium chloride solution (50 mL) and methyl tert-butyl ether (100 mL). The phases were separated. The aqueous was extracted with dichloromethane (100 mL). The combined organic phase was dried over anhydrous magnesium sulfate (~20 g), filtered, and concentrated under reduced pressure. The crude material was purified by flash silica gel column chromatography eluting with a gradient of 0-10% ethyl acetate/hexanes to obtain 5-bromo-3,4-dimethyl-2-vinylpyridine (1.66 g, 94% yield) as a white solid. LCMS calcd for $C_9H_{11}BrN$ $[M+H]^+$: m/z=212.0; Found: 211.8.

Step 3:4,5-dimethyl-6-vinylpyridin-3-ol

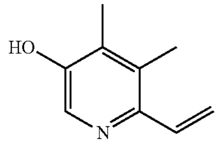

5-Bromo-3,4-dimethyl-2-vinylpyridine (1.5 g, 7.07 mmol), bis(pinacolato)diboron (2.33 g, 9.19 mmol), potassium 2,2-dimethylpropanoate (2.58 g, 18.39 mmol), and 1,4-dioxane (70 mL) were added to a 250 mL round-bottom flask. The flask was sealed with a rubber septum and the mixture was sparged with nitrogen for 5 minutes. Tris (dibenzylideneacetone)dipalladium (0) (130 mg, 0.14 mmol) and 2-dicyclohexylphosphino-2',4',6'-triisopropylbiphenyl (XPhos) (135 mg, 0.28 mmol) were added. The flask was equipped with a reflux condenser, sealed with a rubber septum, and purged with nitrogen for 5 minutes. The mixture was stirred at 95° C. overnight. After cooling to room temperature, the mixture was diluted with dichloromethane (100 mL), passed through a pad of Celite eluting with dichloromethane (100 mL), and concentrated under reduced pressure. The crude material was diluted with water (60 mL), and tetrahydrofuran (60 mL) in a 250 mL round-bottom flask. Sodium percarbonate (5.55 g, 35.4 mmol) was next added and the mixture was stirred at room temperature under air for 30 minutes. The mixture was quenched with a saturated thiosulfate solution (50 mL) and diluted with a saturated sodium chloride solution (50 mL) and ethyl acetate (100 mL). The phases were separated. The aqueous phase was extracted with dichloromethane (2×100 mL). The combined organic phase was dried over anhydrous magnesium sulfate (~10 g), filtered, and concentrated under reduced pressure. The crude material was purified by flash silica gel column chromatography eluting with a gradient of 0 to 4.5% methanol/dichloromethane. The fractions containing the product were combined and concentrated under reduced pressure. The resulting solid was triturated with 20 mL hexanes to afford 4,5-dimethyl-6-vinylpyridin-3-ol (330 mg, 31% yield) as a pale-yellow solid. LCMS calcd for $C_9H_{12}NO$ $[M+H]^+$: m/z=150.1; Found: 150.0.

Step 4: (6aR,8R)-2-chloro-8-((4,5-dimethyl-6-vinylpyridin-3-yl)oxy)-6a-ethyl-5,6,6a, 7,8,9-hexahydropyrrolo[1',2':4,5]pyrazino[2,3-c]pyridazine

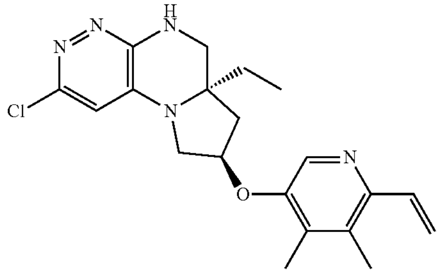 [SMILES: C=Cc1ncc(O[C@H]2CN3c4cc(Cl)nnc4NC[C@@]3(CC)C2)c(C)c1C]

(6aR,8S)-2-Chloro-6a-ethyl-5,6,6a,7,8,9-hexahydropyrrolo[1',2':4,5]pyrazino[2,3-c]pyridazin-8-ol (60.0 mg, 0.24 mmol), 4,5-dimethyl-6-vinylpyridin-3-ol (53 mg, 0.35 mmol), and triphenylphosphine (93 mg, 0.35 mmol) were added to a 8-mL vial followed by dichloromethane (2 mL) and tetrahydrofuran (1 mL). The vial was sealed with a septum cap and purged with nitrogen for 3 minutes. Diisopropyl azodicarboxylate (74 μL, 0.35 mmol) was added via a pipet with quick removal and replacement of the cap. The mixture was stirred at 30° C. overnight. The volatiles were removed under reduced pressure. The crude material was purified by preparative (Waters CSH C18, 5 μm particle size, 30×100 mm) HPLC (7.7-27.7% $CH_3CN$ in $H_2O$ with 0.1% TFA in 5 minutes) to afford (6aR,8R)-2-chloro-8-((4,5-dimethyl-6-vinylpyridin-3-yl)oxy)-6a-ethyl-5,6,6a,7,8,9-hexahydropyrrolo[1',2':4,5]pyrazino[2,3-c]pyridazine (36 mg, 40% yield) as white solid. LCMS calcd for $C_{20}H_{25}ClN_5O$ $[M+H]^+$: m/z=386.2; Found: 386.1.

Step 5: 2-((6aR,8R)-8-((4,5-dimethyl-6-vinylpyridin-3-yl)oxy)-6a-ethyl-5,6,6a,7,8,9-hexahydropyrrolo[1',2':4,5]pyrazino[2,3-c]pyridazin-2-yl)-6-methylphenol

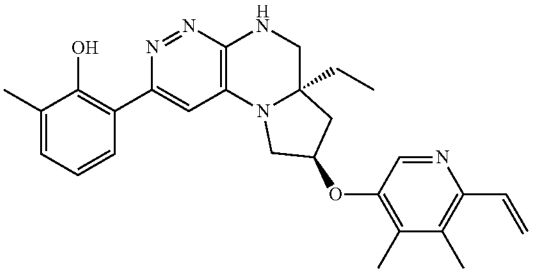 [SMILES: C=Cc1ncc(O[C@H]2CN3c4cc(-c5cccc(C)c5O)nnc4NC[C@@]3(CC)C2)c(C)c1C]

(6aR,8R)-2-Chloro-8-((4,5-dimethyl-6-vinylpyridin-3-yl)oxy)-6a-ethyl-5,6,6a,7,8,9-hexahydropyrrolo[1',2':4,5]pyrazino[2,3-c]pyridazine (30.0 mg, 0.08 mmol), 2-hydroxy-3-methylphenylboronic acid (35 mg, 0.23 mmol), potassium carbonate (43 mg, 0.31 mmol), 1,4-dioxane (1.5 mL), and water (0.3 mL) were added to a 20 mL vial equipped with a stir bar. The mixture was sparged with nitrogen for 5 minutes. Chloro(2-dicyclohexylphosphino-2',6'-dimethoxy-1,1'-biphenyl)[2-(2'-amino-1,1'-biphenyl)]palladium(II) (SPhos Pd G2) (5.6 mg, 0.01 mmol) was added. The vial was sealed with a septum cap and purged with nitrogen for 5 minutes. The mixture was stirred at 85° C. for 2 hours. After cooling to room temperature, the mixture was diluted with dichloromethane (10 mL), dried over anhydrous magnesium sulfate (~4 g), filtered, and concentrated under reduced pressure. The crude material was purified by flash silica gel column chromatography eluting with a gradient of 0-4.5% methanol/dichloromethane to afford 2-((6aR,8R)-8-((4,5-dimethyl-6-vinylpyridin-3-yl)oxy)-6a-ethyl-5,6,6a,7,8,9-hexahydropyrrolo[1',2':4,5]pyrazino[2,3-c]pyridazin-2-yl)-6-methylphenol (20 mg, 56% yield) as pale yellow film. LCMS calcd for $C_{27}H_{32}N_5O_2$ $[M+H]^+$: m/z=458.3; Found: 458.1.

Step 6: 5-(((6aR,8R)-6a-ethyl-2-(2-hydroxy-3-methylphenyl)-5,6,6a, 7,8,9-hexahydro-pyrrolo[1',2':4,5]pyrazino[2,3-c]pyridazin-8-yl)oxy)-3,4-dimethylpicolinaldehyde

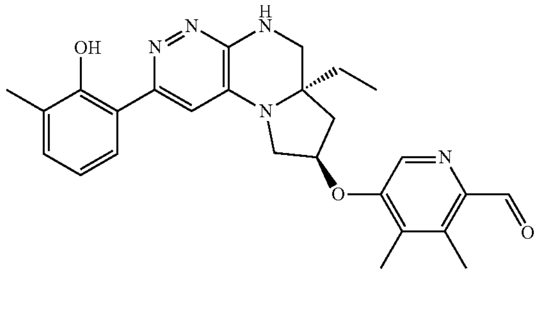 [SMILES: CC[C@@]12CNc3nnc(-c4cccc(C)c4O)cc3N1C[C@H](Oc1cnc(C=O)c(C)c1C)C2]

2-((6aR,8R)-8-((4,5-Dimethyl-6-vinylpyridin-3-yl)oxy)-6a-ethyl-5,6,6a,7,8,9-hexahydro-pyrrolo[1',2':4,5]pyrazino[2,3-c]pyridazin-2-yl)-6-methylphenol (20.0 mg, 0.04 mmol), 2,6-lutidine (10 μL, 0.09 mmol), 1,4-dioxane (1.5 mL), and water (0.5 mL) were added to a 20 mL vial charged with a stir bar. Osmium tetroxide (28 μL, 5 μmol, 4 wt % in water) and sodium periodate (28.05 mg, 0.13 mmol) were added next. The mixture was stirred at room temperature for 3 hours. The mixture was diluted with dichloromethane (10 mL), dried over anhydrous magnesium sulfate (~5 g), filtered, and concentrated under reduced pressure to afford 5-(((6aR,8R)-6a-ethyl-2-(2-hydroxy-3-methylphenyl)-5,6,6a,7,8,9-hexahydropyrrolo[1',2':4,5]pyrazino[2,3-c]pyridazin-8-yl)oxy)-3,4-dimethylpicolinaldehyde (assumed quantitative yield) as brown solid. LCMS calcd for $C_{26}H_{30}N_5O_3$ $[M+H]^+$: m/z=460.2; Found: 460.1.

Step 7: (S)-3-(6-(1-((5-(((6aR,8R)-6a-ethyl-2-(2-hydroxy-3-methylphenyl)-5,6,6a, 7,8,9-hexahydro-pyrrolo[1',2':4,5]pyrazino[2,3-c]pyridazin-8-yl)oxy)-3,4-dimethylpyridin-2-yl)methyl)piperidin-4-yl)-1-oxoisoindolin-2-yl)piperidine-2,6-dione

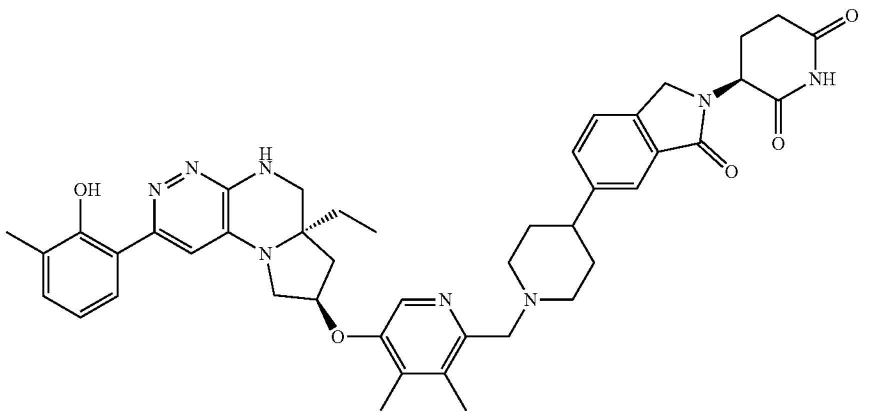 [SMILES: CC[C@@]12CNc3nnc(-c4cccc(C)c4O)cc3N1C[C@H](Oc1cnc(CN3CCC(c4ccc5c(c4)C(=O)N([C@H]4CCC(=O)NC4=O)C5)CC3)c(C)c1C)C2]

(S)-3-(1-Oxo-6-(piperidin-4-yl)isoindolin-2-yl)piperidine-2,6-dione hydrochloride (35 mg, 0.07 mmol), 5-(((6aR,8R)-6a-ethyl-2-(2-hydroxy-3-methylphenyl)-5,6,6a,7,8,9-hexahydropyrrolo[1',2':4,5]pyrazino[2,3-c]pyridazin-8-yl)oxy)-3,4-dimethylpicolinaldehyde (20.0 mg, 0.04 mmol), and dimethyl sulfoxide (1 mL) were added to a 20 mL vial charged with a stir bar, followed by N,N-diisopropylethylamine (38 μL, 0.22 mmol). The mixture was stirred for 20 minutes, and then sodium triacetoxyborohydride (46 mg, 0.22 mmol) was added. The mixture was stirred at 35° C. overnight. After cooling to room temperature, the mixture was filtered and purified by preparative (Waters CSH Phenyl-Hexyl, 5 μm particle size, 30×100 mm) HPLC (14-34% $CH_3CN$ in $H_2O$ with 0.1% TFA in 5 minutes) to afford (S)-3-(6-(1-((5-(((6aR,8R)-6a-ethyl-2-(2-hydroxy-3-methylphenyl)-5,6,6a,7,8,9-hexahydropyrrolo[1',2':4,5]pyrazino[2,3-c]pyridazin-8-yl)oxy)-3,4-dimethylpyridin-2-yl)methyl)piperidin-4-yl)-1-oxoisoindolin-2-yl)piperidine-2,6-dione (Example 95) (6.5 mg, 12% yield) as an off-white solid (TFA salt). LCMS calcd for $C_{44}H_{51}N_8O_5$ $[M+H]^+$: m/z=771.4; Found: 771.2.

Example 96: (S)-3-(6-(1-((2-(((6aS,8R)-6a-ethyl-2-(2-hydroxy-3-methylphenyl)-5,6,6a,7,8,9-hexahydropyrrolo[1',2':4,5]pyrazino[2,3-c]pyridazin-8-yl)oxy)-4,6-dimethylpyrimidin-5-yl)methyl)piperidin-4-yl)-1-oxoisoindolin-2-yl)piperidine-2,6-dione

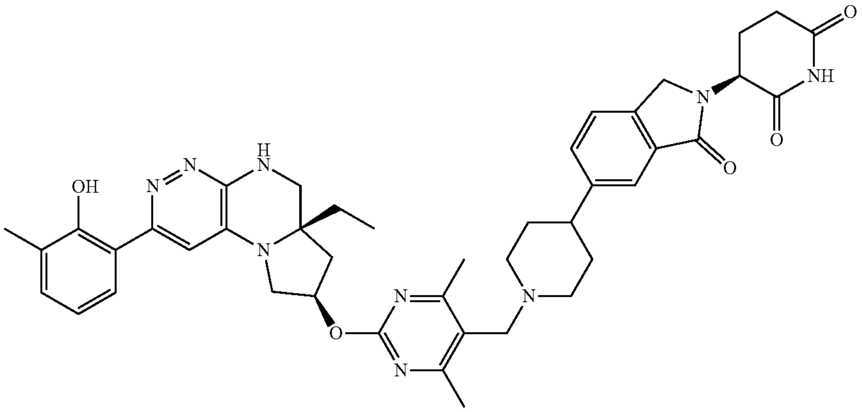 [SMILES: CC[C@]12CNc3nnc(-c4cccc(C)c4O)cc3N1C[C@H](Oc1nc(C)c(CN3CCC(c4ccc5c(c4)C(=O)N([C@H]4CCC(=O)NC4=O)C5)CC3)c(C)n1)C2]

Step 1:4,6-dimethyl-5-vinylpyridin-2(1H)-one

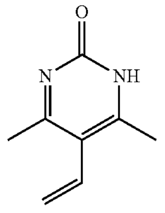

5-Bromo-4,6-dimethylpyrimidin-2-ol (830 mg, 4.09 mmol), cesium carbonate (2664 mg, 8.18 mmol), and potassium vinyltrifluoroborate (821 mg, 6.13 mmol) were added to a 40 mL vial, followed by 1,4-dioxane (27 mL) and water (3 mL). The mixture was sparged with nitrogen for 5 minutes. Chloro(2-dicyclohexylphosphino-2',6'-dimethoxy-1,1'-biphenyl)[2-(2'-amino-1,1'-biphenyl)]palladium(II) (SPhos Pd G2) (265 mg, 0.37 mmol) was added next. The vial was sealed with a septum cap and purged with nitrogen for 5 minutes. The mixture was stirred at 95° C. for 2 hours. After cooling to room temperature, additional SPhos Pd G2 (100 mg, 0.14 mmol) and potassium vinyltrifluoroborate (300 mg, 2.24 mmol) were added and the mixture was stirred overnight at 95° C. After cooling to room temperature, the mixture was diluted with dichloromethane (30 mL), ethanol (30 mL), and ethyl acetate (50 mL), dried over anhydrous magnesium sulfate (~15 g), filtered through a pad of Celite, and concentrated under reduced pressure. The crude material was purified by flash silica gel column chromatography eluting with a gradient of 0 to 14% methanol/dichloromethane to afford 4,6-dimethyl-5-vinylpyridin-2(1H)-one (423 mg, 69% yield) as a pale-yellow solid. LCMS calcd for $C_8H_{11}N_2O$ $[M+H]^+$: m/z=151.1; Found: 151.0.

Step 2: Example SRZ-2: (S)-3-(6-(1-((2-(((6aS,8R)-6a-ethyl-2-(2-hydroxy-3-methylphenyl)-5,6,6a, 7,8, 9-hexahydropyrrolo[1',2':4,5]pyrazino[2,3-c]pyridazin-8-yl)oxy)-4,6-dimethylpyrimidin-5-yl)methyl)piperidin-4-yl)-1-oxoisoindolin-2-yl)piperidine-2,6-dione

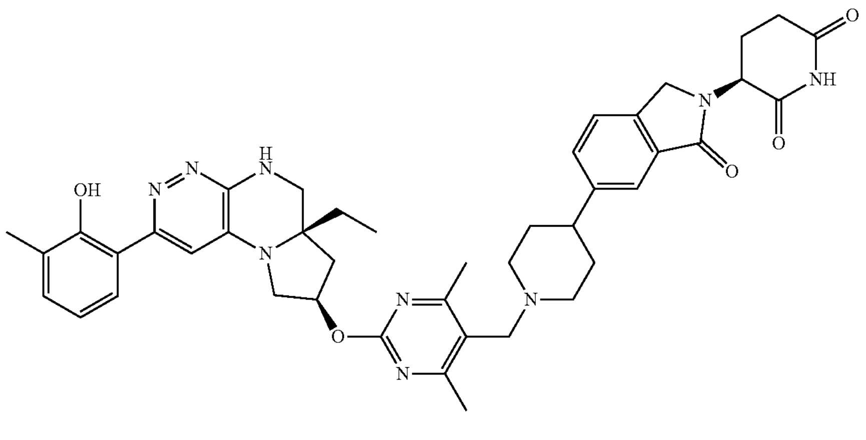 [SMILES: CC[C@]12CNc3nnc(-c4cccc(C)c4O)cc3N1C[C@H](Oc1nc(C)c(CN3CCC(c4ccc5c(c4)C(=O)N([C@H]4CCC(=O)NC4=O)C5)CC3)c(C)n1)C2]

This example was synthesized by procedures analogous to that described in Example 95, using 4,6-dimethyl-5-vinylpyrimidin-2(11)-one and (6aS,8R)-2-chloro-6a-ethyl-5,6,6a,7,8,9-hexahydropyrrolo[1',2':4,5]pyrazino[2,3-c]pyridazin-8-ol instead of 4,5-dimethyl-6-vinylpyridin-3-ol and (6aR,8R)-2-chloro-6a-ethyl-5,6,6a,7,8,9-hexahydropyrrolo[1',2':4,5]pyrazino[2,3-c]pyridazin-8-ol in Step 4. LCMS calcd for $C_{43}H_{50}N_9O_5$ $[M+H]^+$: m/z=772.4; Found: 772.2.

Example 97: (S)-3-(6-(1-((5-(((6aS,8R)-6a-ethyl-2-(2-hydroxy-3-methylphenyl)-5,6,6a,7,8,9-hexahydropyrrolo[1',2':4,5]pyrazino[2,3-c]pyridazin-8-yl)oxy)-3-methylpyridin-2-yl)methyl)piperidin-4-yl)-1-oxoisoindolin-2-yl)piperidine-2,6-dione; (PRT1008878)

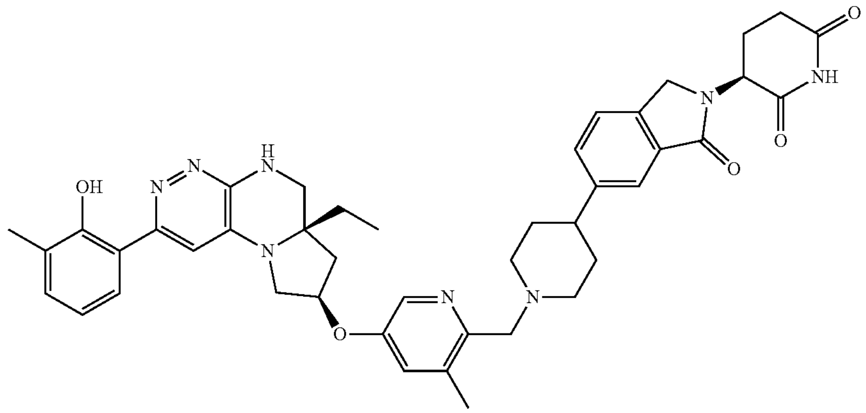 [SMILES: CC[C@]12CNc3nnc(-c4cccc(C)c4O)cc3N1C[C@H](Oc1cnc(CN3CCC(c4ccc5c(c4)C(=O)N([C@H]4CCC(=O)NC4=O)C5)CC3)c(C)c1)C2]

Step 1: 5-methyl-6-vinylpyridin-3-ol

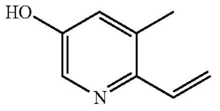

2-Bromo-5-hydroxy-3-picoline (2.0 g, 10.64 mmol), 4,4,5,5-tetramethyl-2-vinyl-1,3,2-dioxaborolane (3.28 g, 21.27 mmol), potassium carbonate (4.41 g, 31.91 mmol), 1,4-dioxane (62 mL), and water (8 mL) were added to a 250 round-bottomed flask. The flask was sparged with nitrogen for 5 minutes. Chloro(2-dicyclohexylphosphino-2',6'-dimethoxy-1,1'-biphenyl)[2-(2'-amino-1,1'-biphenyl)]palladium (II) (SPhos Pd G2) (383.3 mg, 0.53 mmol) was added next. The flask was equipped with a reflux condenser, sealed with a rubber septum, and purged with nitrogen for 5 minutes. The mixture was stirred at 100° C. overnight. After cooling to room temperature, the mixture was filtered through a pad of Celite topped with anhydrous magnesium sulfate eluting with ethyl acetate (100 mL). The volatiles were removed under reduced pressure. The crude material was purified by flash silica gel column chromatography eluting with a gradient of 15 to 50% ethyl acetate/hexanes. The resulting material was crystallized from hexanes (30 mL) to afford 5-methyl-6-vinylpyridin-3-ol (606 mg, 42% yield) as a white solid. LCMS calcd for $C_8H_{10}NO$ $[M+H]^+$: m/z=136.1; Found: 135.9.

Step 2: (S)-3-(6-(1-((5-(((6aS,8R)-6a-ethyl-2-(2-hydroxy-3-methylphenyl)-5,6,6a, 7,8,9-hexahydropyrrolo[1',2':4,5]pyrazino[2,3-c]pyridazin-8-yl)oxy)-3-methylpyridin-2-yl)methyl)piperidin-4-yl)-1-oxoisoindolin-2-yl)piperidine-2,6-dione

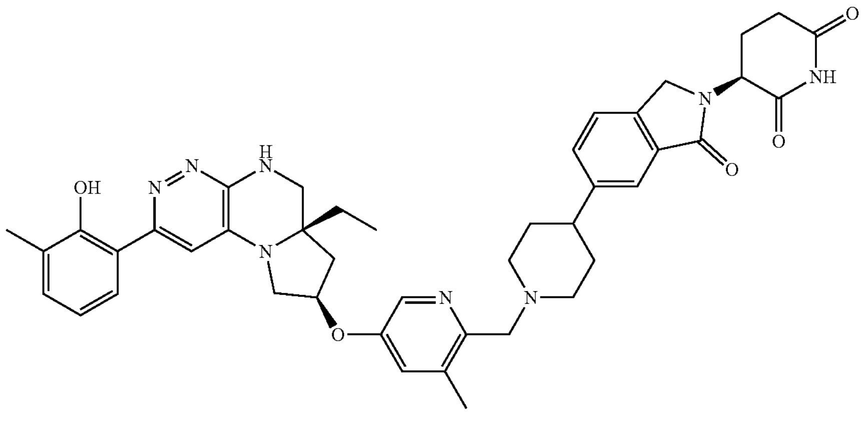 [SMILES: CC[C@]12CNc3nnc(-c4cccc(C)c4O)cc3N1C[C@H](Oc1cnc(CN3CCC(c4ccc5c(c4)C(=O)N([C@H]4CCC(=O)NC4=O)C5)CC3)c(C)c1)C2]

This example was synthesized by procedures analogous to that described in Example 95, using 5-methyl-6-vinylpyridin-3-ol and (6aS,8R)-2-chloro-6a-ethyl-5,6,6a,7,8,9-hexahydropyrrolo[1',2':4,5]pyrazino[2,3-c]pyridazin-8-ol instead of 4,5-dimethyl-6-vinylpyridin-3-ol and (6aR,8R)-2-chloro-6a-ethyl-5,6,6a,7,8,9-hexahydropyrrolo[1',2':4,5]pyrazino[2,3-c]pyridazin-8-ol in Step 4. LCMS calcd for $C_{43}H_{49}N_8O_5$ $[M+H]^+$: m/z=757.4; Found: 757.3.

Step 2: (S)-3-(6-(1-((6-(((6aS,8R)-6a-ethyl-2-(2-hydroxy-3-methylphenyl)-5,6,6a, 7,8,9-hexahydropyrrolo[1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione

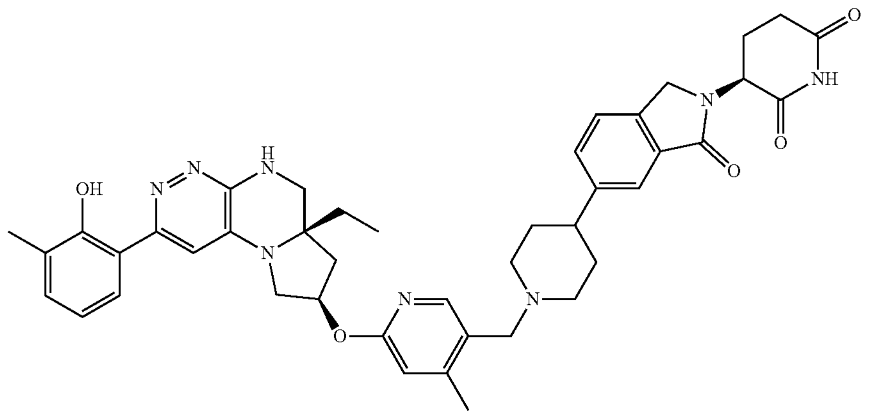 [SMILES: CC[C@]12CNc3nnc(-c4cccc(C)c4O)cc3N1C[C@H](Oc1cc(C)c(CN3CCC(c4ccc5c(c4)C(=O)N([C@H]4CCC(=O)NC4=O)C5)CC3)cn1)C2]

Step 1:4-methyl-5-vinylpyridin-2(1H)-one (Intermediate-9)

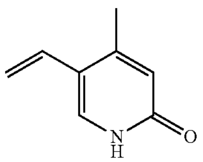

This compound was synthesized by procedures analogous to that described in Example 96, using 5-bromo-4-methylpyridin-2(1H)-one instead of 5-bromo-4,6-dimethylpyrimidin-2-ol in Step 1. LCMS calcd for $C_8H_{10}NO$ $[M+H]^+$: m/z=136.1; Found: 135.9.

Step 2: (S)-3-(6-(1-((6-(((6aS,8R)-6a-ethyl-2-(2-hydroxy-3-methylphenyl)-5,6,6a, 7,8,9-hexahydropyrrolo[1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione

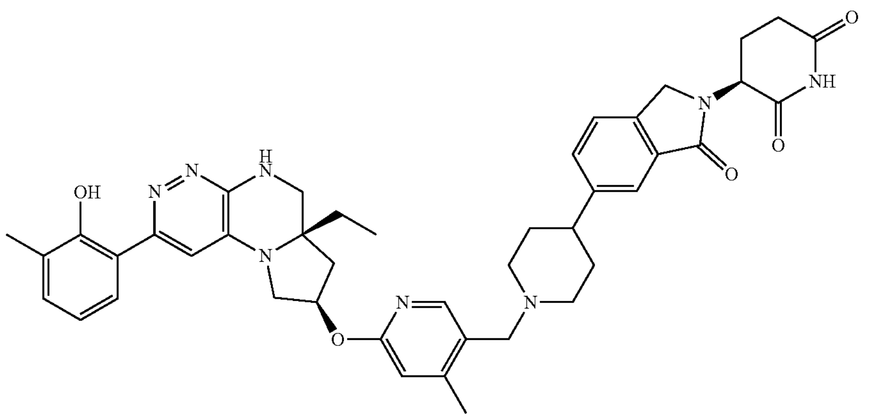 [SMILES: CC[C@]12CNc3nnc(-c4cccc(C)c4O)cc3N1C[C@H](Oc1cc(C)c(CN3CCC(c4ccc5c(c4)C(=O)N([C@H]4CCC(=O)NC4=O)C5)CC3)cn1)C2]

This example was synthesized by procedures analogous to that described in Example 95, using 4-methyl-5-vinylpyridin-2(1H)-one and (6aS,8R)-2-chloro-6a-ethyl-5,6,6a,7,8,9-hexahydro-pyrrolo[1',2':4,5]pyrazino[2,3-c]pyridazin-8-ol instead of 4,5-dimethyl-6-vinylpyridin-3-ol and (6aR,8R)-2-chloro-6a-ethyl-5,6,6a,7,8,9-hexahydropyrrolo[1',2':4,5]pyrazino[2,3-c]pyridazin-8-ol in Step 4. LCMS calcd for $C_{43}H_{49}N_8O_5$ [M+H]$^+$: m/z=757.4; Found: 757.3.

Example 99: (S)-3-(6-(1-((3-chloro-5-(((6aS,8R)-2-(3-chloro-2-hydroxyphenyl)-6a-ethyl-5,6,6a,7,8,9-hexahydropyrrolo[1',2':4,5]pyrazino[2,3-c]pyridazin-8-yl)oxy)pyridin-2-yl)methyl)piperidin-4-yl)-1-oxoisoindolin-2-yl)piperidine-2,6-dione

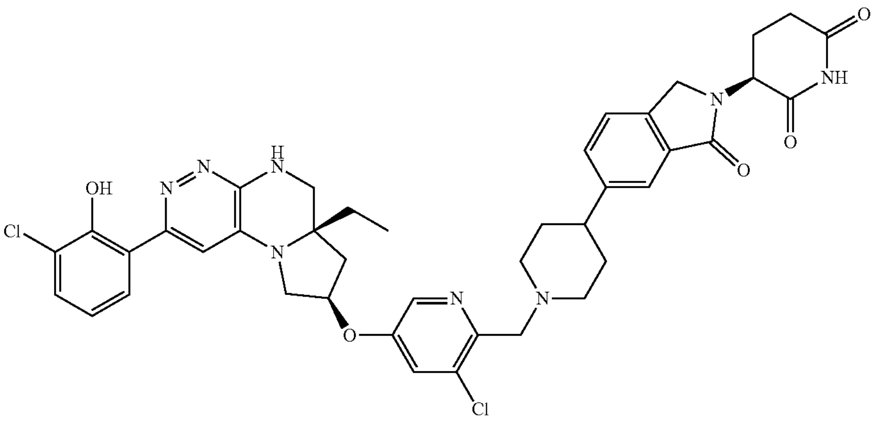 [SMILES: CC[C@]12CNc3nnc(-c4cccc(Cl)c4O)cc3N1C[C@H](Oc1cnc(CN3CCC(c4ccc5c(c4)C(=O)N([C@H]4CCC(=O)NC4=O)C5)CC3)c(Cl)c1)C2]

Step 1: 5-chloro-6-vinylpyridin-3-ol

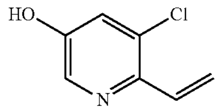

2-Bromo-3-chloro-5-hydroxypyridine (428.92 mg, 2.06 mmol), cesium carbonate (1005.7 mg, 3.09 mmol), and potassium vinyltrifluoroborate (303.2 mg, 2.26 mmol) were added to a 40 mL vial, followed by 1,4-dioxane (12 mL) and water (2 mL). The mixture was sparged with nitrogen for 5 minutes. Tetrakis(triphenylphosphine)palladium(0) (237.8 mg, 0.21 mmol) was added. The vial was sealed with a septum cap and purged with nitrogen for 5 minutes. The mixture was stirred at 95° C. overnight. After cooling to room temperature, the mixture was diluted with ethyl acetate (30 mL) and a saturated sodium chloride solution (20 mL). The phases were separated. The aqueous phase was extracted with a 3:1 mixture chloroform/isopropanol (3×20 mL). The combined organic phase was dried over anhydrous magnesium sulfate, filtered, concentrated under reduced pressure, and purified by flash silica gel column chromatography eluting with a gradient of 0 to 8% methanol/dichloromethane to afford 5-chloro-6-vinylpyridin-3-ol (125 mg 39% yield) as a pale-yellow solid. LCMS calcd for $C_7H_7ClNO$ [M+H]$^+$: m/z=156.0; Found: 155.9.

Step 2: 2-chloro-6-((6aS,8R)-8-((5-chloro-6-vinylpyridin-3-yl)oxy)-6a-ethyl-5,6,6a, 7,8,9-hexahydropyrrolo[1',2':4,5]pyrazino[2,3-c]pyridazin-2-yl)phenol

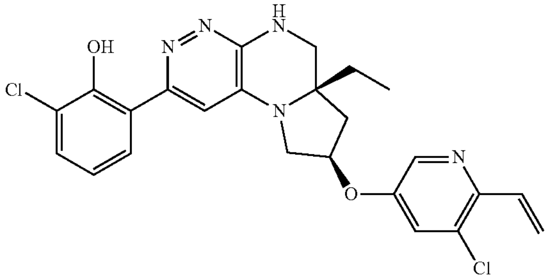 [SMILES: C=Cc1ncc(O[C@H]2CN3c4cc(-c5cccc(Cl)c5O)nnc4NC[C@]3(CC)C2)cc1Cl]

(6aS,8R)-2-Chloro-8-((5-chloro-6-vinylpyridin-3-yl)oxy)-6a-ethyl-5,6,6a,7,8,9-hexahydropyrrolo[1',2':4,5]pyrazino[2,3-c]pyridazine (13.0 mg, 0.03 mmol), 3-chloro-2-hydroxyphenyl boronic acid (11.42 mg, 0.07 mmol), potassium carbonate (13.74 mg, 0.1 mmol), 1,4-dioxane (1.2 mL), and water (0.2 mL) were added to a 8 mL vial equipped with a stir bar. The mixture was sparged with nitrogen for 5 minutes. Tetrakis(triphenylphosphine)palladium(0) (3.8 mg, 0.003 mmol) was added. The vial was sealed with a septum cap and purged with nitrogen for 5 minutes. The mixture was stirred at 95° C. overnight. After cooling to room temperature, the mixture was diluted with dimethyl sulfoxide (4 mL) and purified by preparative (Waters CSH C18, 5 μm particle size, 30×100 mm) HPLC (32.6-52.6% $CH_3CN$ in $H_2O$ with 0.1% TFA in 5 minutes) to afford 2-chloro-6-((6aR,8R)-8-((5-chloro-6-vinylpyridin-3-yl)oxy)-6a-ethyl-5,6,6a,7,8,9-hexahydropyrrolo[1',2':4,5]pyrazino[2,3-c]pyridazin-2-yl)phenol (5 mg, 31% yield) as pale yellow film. LCMS calcd for $C_{24}H_{24}Cl_2N_5O_2$ [M+H]$^+$: m/z=484.1; Found: 484.0.

Step 3: (S)-3-(6-(1-((3-chloro-5-(((6aS,8R)-2-(3-chloro-2-hydroxyphenyl)-6a-ethyl-5,6,6a, 7,8,9-hexahydropyrrolo[1',2':4,5]pyrazino[2,3-c]pyridazin-8-yl)oxy)pyridin-2-yl)methyl)piperidin-4-yl)-1-oxoisoindolin-2-yl)piperidine-2,6-dione

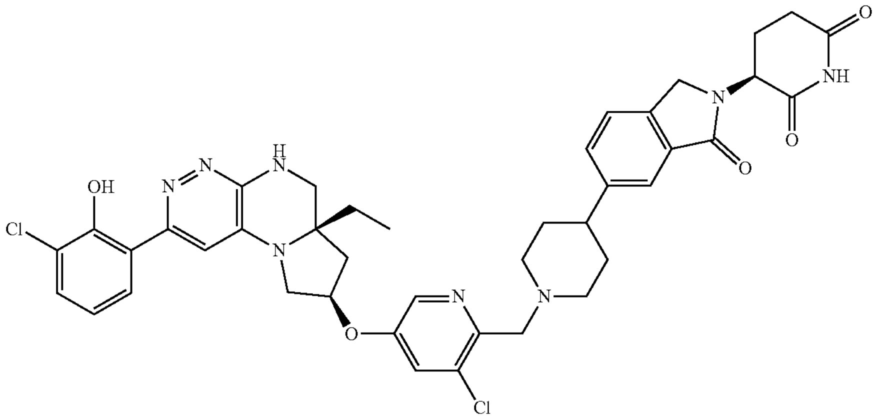 [SMILES: CC[C@]12CNc3nnc(-c4cccc(Cl)c4O)cc3N1C[C@H](Oc1cnc(CN3CCC(c4ccc5c(c4)C(=O)N([C@H]4CCC(=O)NC4=O)C5)CC3)c(Cl)c1)C2]

This example was synthesized by procedures analogous to that described in Example 95, using 2-chloro-6-((6aS,8R)-8-((5-chloro-6-vinylpyridin-3-yl)oxy)-6a-ethyl-5,6,6a,7,8,9-hexahydropyrrolo[1',2':4,5]pyrazino[2,3-c]pyridazin-2-yl)phenol instead of 2-((6aR,8R)-8-((4,5-dimethyl-6-vinylpyridin-3-yl)oxy)-6a-ethyl-5,6,6a,7,8,9-hexahydropyrrolo[1',2':4,5]pyrazino[2,3-c]pyridazin-2-yl)-6-methylphenol in Step 6. LCMS calcd for $C_{41}H_{43}Cl_2N_8O_5$ $[M+H]^+$: m/z=797.3; Found: 797.2.

Example 100: (S)-3-(6-(1-((6-(((6aR,8R)-2-(3-chloro-2-hydroxyphenyl)-6a-ethyl-5,6,6a,7,8,9-hexahydropyrrolo[1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione

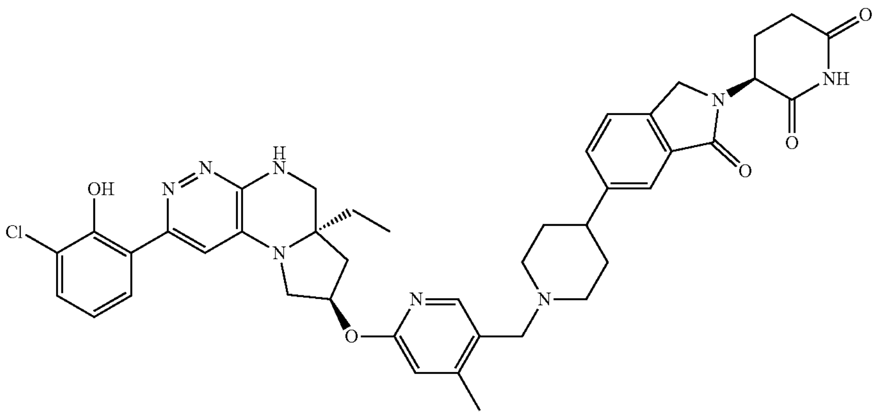 [SMILES: CC[C@@]12CNc3nnc(-c4cccc(Cl)c4O)cc3N1C[C@H](Oc1cc(C)c(CN3CCC(c4ccc5c(c4)C(=O)N([C@H]4CCC(=O)NC4=O)C5)CC3)cn1)C2]

This example was synthesized by procedures analogous to that described in Example 99, using 4-methyl-5-vinylpyridin-2(1H)-one and (6aR,8R)-2-chloro-6a-ethyl-8-((4-methyl-5-vinylpyridin-2-yl)oxy)-5,6,6a,7,8,9-hexahydropyrrolo[1',2':4,5]pyrazino[2,3-c]pyridazine instead of 5-chloro-6-vinylpyridin-3-ol and (6aS,8R)-2-chloro-6a-ethyl-8-((4-methyl-5-vinylpyridin-2-yl)oxy)-5,6,6a,7,8,9-hexahydropyrrolo[1',2':4,5]pyrazino[2,3-c]pyridazine in Step 2. LCMS calcd for $C_{42}H_{46}ClN_8O_5[M+H]^+$: m/z=777.3; Found: 777.3. $^1H$ NMR (400 MHz, DMSO-$d_6$) δ 10.99 (s, 1H), 9.27 (s, 1H), 8.30 (s, 1H), 8.12 (s, 1H), 7.63-7.47 (m, 4H), 7.02-6.90 (m, 2H), 6.83 (s, 1H), 5.78 (s, 1H), 5.10 (dd, J=13.3, 5.1 Hz, 1H), 4.46-4.29 (m, 5H), 4.13 (dd, J=13.8, 5.9 Hz, 2H), 3.86-3.74 (m, 2H), 3.75-3.63 (m, 2H), 3.28-3.16 (m, 2H), 3.10 (d, J=11.8 Hz, 1H), 3.07-2.85 (m, 2H), 2.78-2.56 (m, 2H), 2.42 (s, 3H), 2.10-1.85 (m, 5H), 1.67-1.51 (m, 2H), 0.91 (t, J=7.4 Hz, 3H).

Example 101: (S)-3-(6-(1-((5-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-3-fluoropyridin-2-yl)methyl)piperidin-4-yl)-1-oxoisoindolin-2-yl)piperidine-2,6-dione

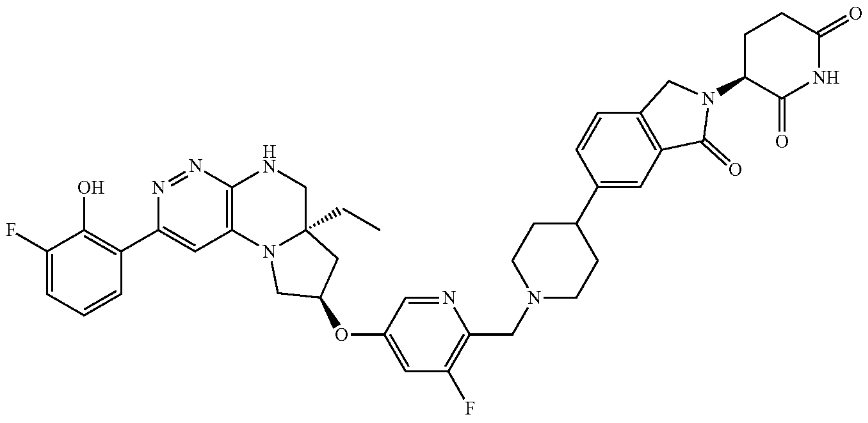 [SMILES: CC[C@@]12CNc3nnc(-c4cccc(F)c4O)cc3N1C[C@H](Oc1cnc(CN3CCC(c4ccc5c(c4)C(=O)N([C@H]4CCC(=O)NC4=O)C5)CC3)c(F)c1)C2]

Step 1: 5-fluoro-6-vinylpyridin-3-ol (Intermediate-12)

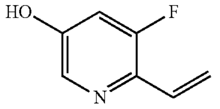

This compound was synthesized by procedures analogous to that described in Example 96, using 6-bromo-5-fluoropyridin-3-ol instead of 5-bromo-4,6-dimethylpyrimidin-2-ol in Step 1. LCMS calcd for $C_7H_7FNO$ $[M+H]^+$: m/z=140.0; Found: 139.9.

Step 2: (S)-3-(6-(1-((5-(((6aR,8R)-6a-ethyl-2-(3-fluoro-2-hydroxyphenyl)-5,6,6a, 7,8,9-hexahydropyrrolo[1',2':4,5]pyrazino[2,3-c]pyridazin-8-yl)oxy)-3-fluoropyridin-2-yl)methyl)piperidin-4-yl)-1-oxoisoindolin-2-yl)piperidine-2,6-dione

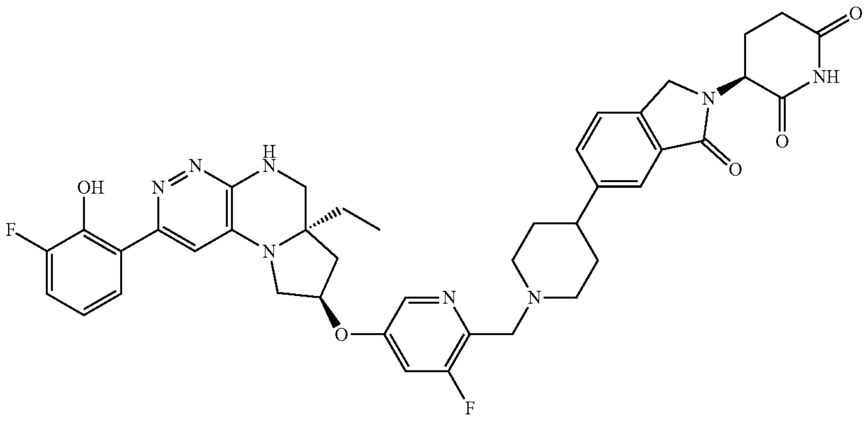 [SMILES: CC[C@@]12CNc3nnc(-c4cccc(F)c4O)cc3N1C[C@H](Oc1cnc(CN3CCC(c4ccc5c(c4)C(=O)N([C@H]4CCC(=O)NC4=O)C5)CC3)c(F)c1)C2]

This example was synthesized by procedures analogous to that described in Example 95, using 5-fluoro-6-vinylpyridin-3-ol instead of 4,5-dimethyl-6-vinylpyridin-3-ol in Step 4, and (3-fluoro-2-hydroxyphenyl)boronic acid instead of (2-hydroxy-3-methylphenyl)boronic acid in Step 5. LCMS calcd for $C_{41}H_{42}F_3N_8O_5[M+H]^+$: m/z=765.3; Found: 765.3.

Example 102: (S)-3-(6-(1-((2-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-4,6-dimethylpyrimidin-5-yl)methyl)piperidin-4-yl)-1-oxoisoindolin-2-yl)piperidine-2,6-dione

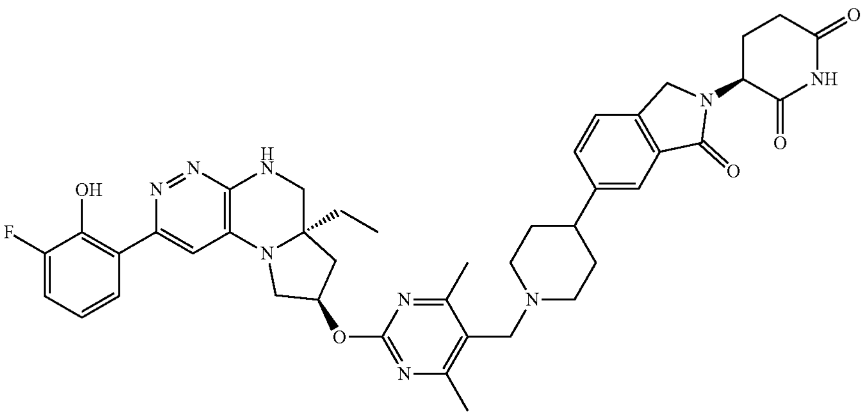 [SMILES: CC[C@@]12CNc3nnc(-c4cccc(F)c4O)cc3N1C[C@H](Oc1nc(C)c(CN3CCC(c4ccc5c(c4)C(=O)N([C@H]4CCC(=O)NC4=O)C5)CC3)c(C)n1)C2]

This example was synthesized by procedures analogous to that described in Example 95, using 4,6-dimethyl-5-vinylpyrimidin-2(1H)-one instead of 4,5-dimethyl-6-vinylpyridin-3-ol in Step 4, and (3-fluoro-2-hydroxyphenyl)boronic acid instead of (2-hydroxy-3-methylphenyl) boronic acid in Step 5. LCMS calcd for $C_{42}H_{47}FN_9O_5$[M+H]$^+$: m/z=776.4; Found: 776.2.

Example 103: (S)-3-(6-(1-((5-(((6aS,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)pyrazin-2-yl)methyl)piperidin-4-yl)-1-oxoisoindolin-2-yl)piperidine-2,6-dione 5-Bromopyrazin-2-ol (1.25 g, 7.14 mmol), copper(I) iodide (136 mg, 0.71 mmol), and tributyl(vinyl)tin (4.08 g, 12.86 mmol) were added to a 40 mL vial, followed by acetonitrile (34 mL). The vial was sealed with a septum cap. The mixture was sparged with nitrogen for 5 minutes. Tetrakis(triphenylphosphine)palladium(0) (826 mg, 0.71 mmol) was added with quick removal and replacement of the cap. The vial was purged with nitrogen for 3 minutes. The mixture was then stirred at 80° C. overnight. While hot, the mixture was passed through Celite eluting with acetonitrile (100 mL). The volatiles were removed under reduced

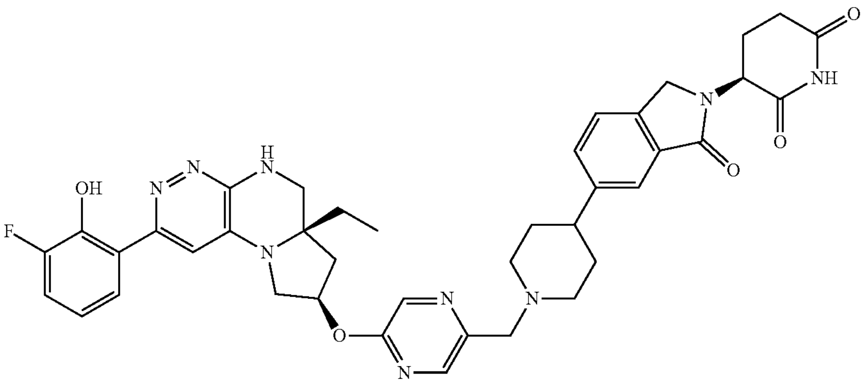 [SMILES: CC[C@]12CNc3nnc(-c4cccc(F)c4O)cc3N1C[C@H](Oc1cnc(CN3CCC(c4ccc5c(c4)C(=O)N([C@H]4CCC(=O)NC4=O)C5)CC3)cn1)C2]

Step 1: 5-vinylpyrazin-2(1H)-one (Intermediate-13)

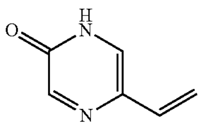

pressure. The crude material was purified by flash silica gel column chromatography eluting with a gradient of 0 to 8% methanol/dichloromethane. The resulting solid was triturated with a 1:5 mixture of methyl tert-butyl ether/hexanes (30 mL) to afford 5-vinylpyrazin-2(1H)-one (582 mg, 67% yield) as a light-yellow solid. LCMS calcd for $C_6H_7N_2O$ [M+H]$^+$: m/z=123.1; Found: 122.9.

Step 2: (S)-3-(6-(1-((5-(((6aS,8R)-6a-ethyl-2-(3-fluoro-2-hydroxyphenyl)-5,6,6a, 7,8,9-hexahydropyrrolo[1',2':4,5]pyrazino[2,3-c]pyridazin-8-yl)oxy)pyrazin-2-yl)methyl)piperidin-4-yl)-1-oxoisoindolin-2-yl)piperidine-2,6-dione

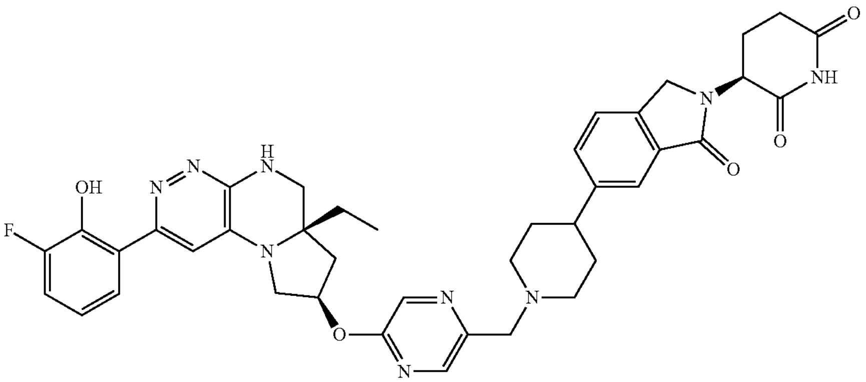 [SMILES: CC[C@]12CNc3nnc(-c4cccc(F)c4O)cc3N1C[C@H](Oc1cnc(CN3CCC(c4ccc5c(c4)C(=O)N([C@H]4CCC(=O)NC4=O)C5)CC3)cn1)C2]

This example was synthesized by procedures analogous to that described in Example 95, using 5-vinylpyrazin-2(1H)-one and (6aS,8R)-2-chloro-6a-ethyl-5,6,6a,7,8,9-hexahydropyrrolo [1',2':4,5]pyrazino[2,3-c]pyridazin-8-ol instead of 4,5-dimethyl-6-vinylpyridin-3-ol and (6aR,8R)-2-chloro-6a-ethyl-5,6,6a,7,8,9-hexahydropyrrolo[1',2':4,5]pyrazino [2,3-c]pyridazin-8-ol in Step 4, and (3-fluoro-2-hydroxyphenyl)boronic acid instead of (2-hydroxy-3-methylphenyl) boronic acid in step 5. LCMS calcd for $C_{40}H_{43}FN_9O_5[M+H]^+$: m/z=748.3; Found: 748.1.

Example 104: (S)-3-(6-(1-((5-(((6aS,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-3-methylpyridin-2-yl)methyl)piperidin-4-yl)-1-oxoisoindolin-2-yl)piperidine-2,6-dione

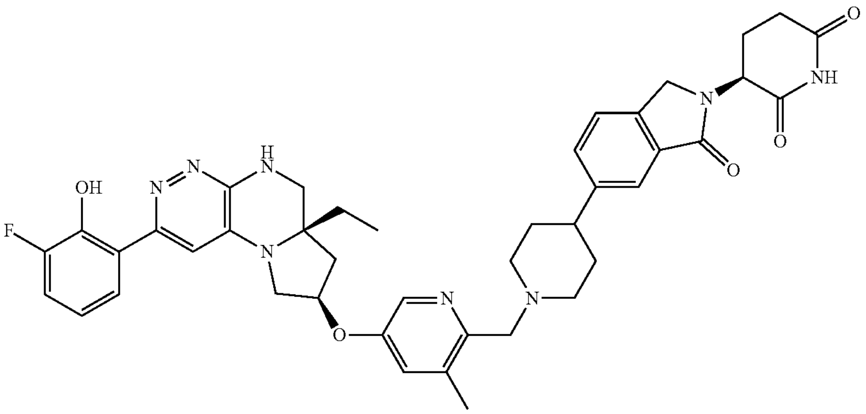 [SMILES: CC[C@]12CNc3nnc(-c4cccc(F)c4O)cc3N1C[C@H](Oc1cnc(CN3CCC(c4ccc5c(c4)C(=O)N([C@H]4CCC(=O)NC4=O)C5)CC3)c(C)c1)C2]

This example was synthesized by procedures analogous to that described in Example 95, using 5-methyl-6-vinylpyridin-3-ol and (6aS,8R)-2-chloro-6a-ethyl-5,6,6a,7,8,9-hexahydro-pyrrolo[1',2':4,5]pyrazino[2,3-c]pyridazin-8-ol instead of 4,5-dimethyl-6-vinylpyridin-3-ol and (6aR,8R)-2-chloro-6a-ethyl-5,6,6a,7,8,9-hexahydropyrrolo[1',2':4,5]pyrazino[2,3-c]pyridazin-8-ol in Step 4, and (3-fluoro-2-hydroxyphenyl)boronic acid instead of (2-hydroxy-3-methylphenyl) boronic acid in Step 5. LCMS calcd for $C_{42}H_{46}FN_8O_5[M+H]^+$: m/z=761.4; Found: 761.2.

Example 105: (S)-3-(6-(1-((2-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-4-methylpyrimidin-5-yl)methyl)piperidin-4-yl)-1-oxoisoindolin-2-yl)piperidine-2,6-dione

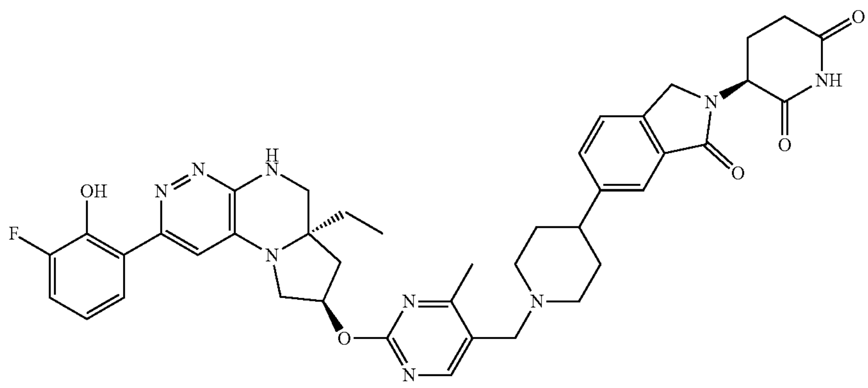 [SMILES: CC[C@@]12CNc3nnc(-c4cccc(F)c4O)cc3N1C[C@H](Oc1ncc(CN3CCC(c4ccc5c(c4)C(=O)N([C@H]4CCC(=O)NC4=O)C5)CC3)c(C)n1)C2]

Step 1:4-methyl-5-vinylpyrimidin-2(1H)-one

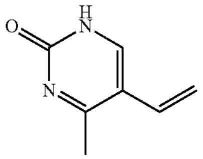

5-Bromo-2-chloro-4-methylpyrimidine (1.00 g, 4.82 mmol) and hydrochloric acid (4.0 mL, 24.1 mmol, 6 M) were added to a 20 mL vial. The vial was sealed with a septum cap and the mixture was stirred at 95° C. for 4 hours. After cooling to room temperature, the mixture was transferred to a 50 mL round-bottom flask, diluted with water (10 mL), and basified by slow addition of potassium carbonate (~5 g) to pH~10. 4,4,5,5-tetramethyl-2-vinyl-1,3,2-dioxaborolane (1.48 g, 9.64 mmol) and 1,4-dioxane (50 mL) were added. The mixture was sparged with nitrogen for 5 minutes. Chloro(2-dicyclohexylphosphino-2',6'-dimethoxy-1,1'-biphenyl)[2-(2'-amino-1,1'-biphenyl)]palladium(II) (SPhos Pd G2) (347.35 mg, 0.48 mmol) was added. The flask was equipped with a reflux condenser, sealed with a rubber septum, and purged with nitrogen for 5 minutes. The mixture was stirred at reflux overnight. After cooling to room temperature, the mixture was diluted with ethyl acetate (100 mL) and filtered through a pad of Celite. The phases were separated. The aqueous phase was extracted with a 3:1 mixture chloroform/isopropanol (3×50 mL). The combined organic phase was dried over anhydrous magnesium sulfate (~10 g), filtered, concentrated under reduced pressure, and purified by flash silica gel column chromatography eluting with a gradient of 0 to 10% methanol/dichloromethane to afford 4-methyl-5-vinylpyrimidin-2(1H)-one (340 mg, 52% yield). LCMS calcd for $C_7H_9N_2O$ $[M+H]^+$: m/z=137.1; Found: 136.9.

Step 2: (S)-3-(6-(1-((2-(((6aR,8R)-6a-ethyl-2-(3-fluoro-2-hydroxyphenyl)-5,6,6a, 7,8,9-hexahydropyrrolo[1',2':4,5]pyrazino[2,3-c]pyridazin-8-yl)oxy)-4-methylpyrimidin-5-yl)methyl)piperidin-4-yl)-1-oxoisoindolin-2-yl)piperidine-2,6-dione

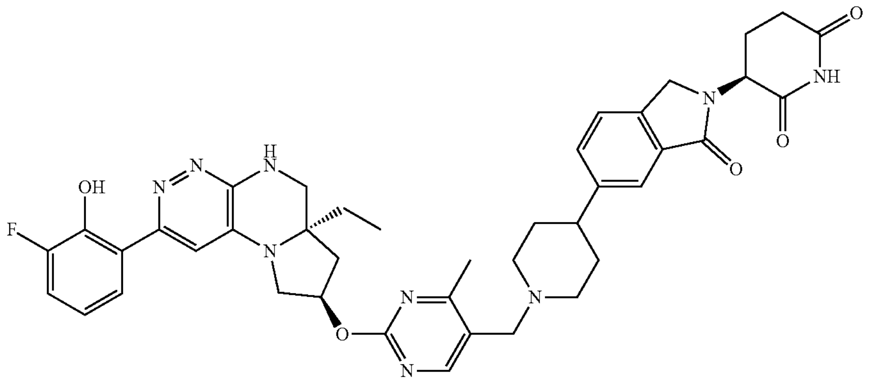 [SMILES: CC[C@@]12CNc3nnc(-c4cccc(F)c4O)cc3N1C[C@H](Oc1ncc(CN3CCC(c4ccc5c(c4)C(=O)N([C@H]4CCC(=O)NC4=O)C5)CC3)c(C)n1)C2]

This example was synthesized by procedures analogous to that described in Example 95, using 4-methyl-5-vinylpyrimidin-2(1H)-one instead of 4,5-dimethyl-6-vinylpyridin-3-ol in Step 4, and (3-fluoro-2-hydroxyphenyl)boronic acid instead of (2-hydroxy-3-methylphenyl)boronic acid in Step 5. LCMS calcd for $C_{41}H_{45}FN_9O_5$[M+H]$^+$: m/z=762.4; Found: 762.2. $^1$H NMR (400 MHz, DMSO-$d_6$) δ 14.33 (s, 1H), 10.99 (s, 1H), 9.57 (s, 1H), 8.66 (s, 1H), 8.22 (s, 1H), 7.64-7.48 (m, 2H), 7.45-7.29 (m, 1H), 6.96 (d, J=17.1 Hz, 1H), 5.76 (s, 1H), 5.23-4.95 (m, 1H), 4.56-4.03 (m, 4H), 3.90 (d, J=13.4 Hz, 2H), 3.73-3.68 (m, 1H), 3.32-3.06 (m, 3H), 2.93 (dd, J=24.8, 12.2 Hz, 2H), 2.73 (dd, J=13.7, 6.6 Hz, 1H), 2.51 (m, 19H), 2.13-1.83 (m, 4H), 1.63 (dt, J=14.5, 7.7 Hz, 2H), 0.91 (t, J=7.4 Hz, 2H).

Example 106: 3-(6-(1-((6-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione palladium(II) (SPhos Pd G2) (17.0 mg, 0.02 mmol) was added with quick removal and replacement of the cap and purging with nitrogen continued for 5 minutes. The mixture was stirred at 75° C. overnight. After cooling to room temperature, the mixture was diluted with ethyl acetate (20 mL) and a saturated sodium chloride solution (10 mL). The phases were separated. The aqueous phase was extracted with dichloromethane (3×10 mL). The combined organic phase was dried over anhydrous magnesium sulfate (~5 g), filtered, concentrated under reduced pressure, and purified by flash silica gel column chromatography, eluting with a gradient of 0-20% methanol/dichloromethane to afford ((6aR,8R)-6a-ethyl-2-(3-fluoro-2-methoxyphenyl)-5,6,6a,7,8,9-hexahydropyrrolo[1',2':4,5]pyrazino[2,3-c]pyridazin-8-ol (156 mg, 96% yield) as a white solid. LCMS calcd for $C_{18}H_{22}FN_4O_2$[M+H]$^+$: m/z=345.2; Found: 345.0.

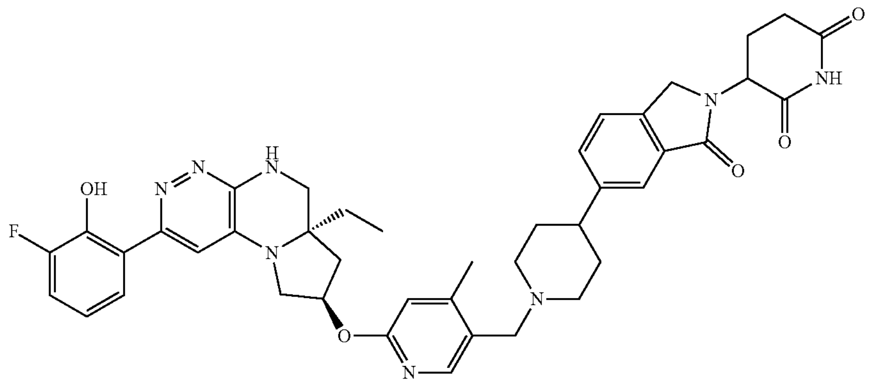 [SMILES: CC[C@@]12CNc3nnc(-c4cccc(F)c4O)cc3N1C[C@H](Oc1cc(C)c(CN3CCC(c4ccc5c(c4)C(=O)N(C4CCC(=O)NC4=O)C5)CC3)cn1)C2]

Step 1: ((6aR,8R)-6a-ethyl-2-(3-fluoro-2-methoxyphenyl)-5,6,6a, 7,8,9-hexahydropyrrolo [1',2':4,5] pyrazino[2,3-c]pyridazin-8-ol

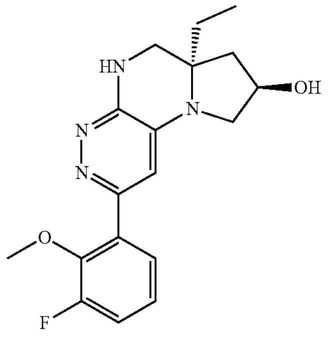 [SMILES: CC[C@@]12CNc3nnc(-c4cccc(F)c4OC)cc3N1C[C@H](O)C2]

(6aR,8R)-2-Chloro-6a-ethyl-5,6,6a,7,8,9-hexahydropyrrolo[1',2':4,5]pyrazino[2,3-c]pyridazin-8-ol (120.5 mg, 0.47 mmol), 3-fluoro-2-methoxyphenylboronic acid (160.8 mg, 0.95 mmol), potassium carbonate (196.1 mg, 1.42 mmol), 1,4-dioxane (4 mL), and water (0.5 mL) were added to a 2-dram vial equipped with a stir bar. The vial was sealed with a septum cap and the mixture was sparged with nitrogen for 3 minutes. Chloro(2-dicyclohexylphosphino-2',6'-dimethoxy-1,1'-biphenyl)[2-(2'-amino-1,1'-biphenyl)]

Step 2: 6-(((6aR,8R)-6a-ethyl-2-(3-fluoro-2-methoxyphenyl)-5,6,6a, 7,8,9-hexahydro-pyrrolo[1',2':4,5]pyrazino[2,3-c]pyridazin-8-yl)oxy)-4-methylnicotinate

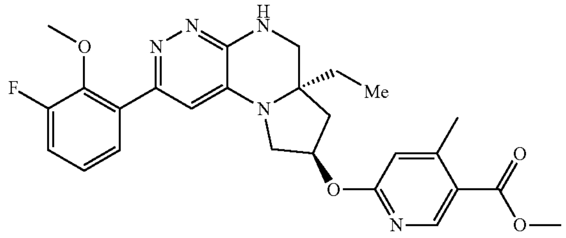 [SMILES: CC[C@@]12CNc3nnc(-c4cccc(F)c4OC)cc3N1C[C@H](Oc1cc(C)c(C(=O)OC)cn1)C2]

((6aR,8R)-6a-Ethyl-2-(3-fluoro-2-methoxyphenyl)-5,6,6a,7,8,9-hexahydropyrrolo [1',2':4,5]pyrazino[2,3-c]pyridazin-8-ol (40.0 mg, 0.12 mmol), and 1-methylpyrrolidin-2-one (NMP) (2 mL) were added to a 1-dram vial equipped with a stir bar. The vial was sealed with a septum cap and the mixture was sparged with nitrogen for 5 minutes. Sodium hydride (5.58 mg, 0.14 mmol) was added with quick removal and replacement of the cap. The vial was purged with nitrogen for 5 minutes and the mixture was stirred at 50° C. for 10 minutes. After cooling to room temperature, methyl 6-fluoro-4-methylpyridine-3-carboxylate (23.58 mg, 0.14 mmol) was added with quick removal and replacement of the cap, and the mixture was stirred at 35° C. for 90 minutes. The mixture was diluted with ethyl acetate (5 ml) and water (5 ml). The phases were separated. The aqueous phase was extracted with ethyl acetate (10 ml). The combined organic phase was washed with water (10 ml), dried over anhydrous magnesium sulfate (~5 g), concentrated under reduced pressure, and purified by flash silica gel column chromatography eluting with a gradient of 0-10% methanol/dichloromethane to afford methyl 6-(((6aR,8R)-6a-ethyl-2-(3-fluoro-2-methoxyphenyl)-5,6,6a,7,8,9-hexahydropyrrolo[1',2':4,5]pyrazino[2,3-c]pyridazin-8-yl)oxy)-4-methylnicotinate (60 mg, 91% yield) as pale-yellow film. LCMS calcd for $C_{26}H_{29}FN_5O_4$[M+H]$^+$: m/z=494.2; Found: 494.0.

Step 3: (6-(((6aR,8R)-6a-ethyl-2-(3-fluoro-2-methoxyphenyl)-5,6,6a, 7,8,9-hexahydro-pyrrolo[1', 2':4,5]pyrazino[2,3-c]pyridazin-8-yl)oxy)-4-methylpyridin-3-yl)methanol

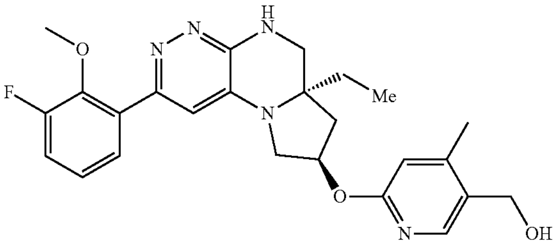 [SMILES: CC[C@@]12CNc3nnc(-c4cccc(F)c4OC)cc3N1C[C@H](Oc1cc(C)c(CO)cn1)C2]

Methyl 6-(((6aR,8R)-6a-ethyl-2-(3-fluoro-2-methoxyphenyl)-5,6,6a,7,8,9-hexahydro-pyrrolo[1',2':4,5]pyrazino[2,3-c]pyridazin-8-yl)oxy)-4-methylnicotinate (60.0 mg, 0.12 mmol) was added to a 2-dram vial, followed by tetrahydrofuran (2 mL). The vial was placed in a water/ice bath, and then lithium aluminum hydride (0.36 mL, 0.36 mmol, 1 M in tetrahydrofuran) was added dropwise and the mixture was stirred at 0° C. for 30 minutes. The reaction was quenched by slow addition of methanol (1 mL). The mixture was next poured into water (20 mL) and extracted with dichloromethane (3×20 mL). The combined organic layer was washed with a saturated sodium chloride solution (10 mL), dried over anhydrous magnesium sulfate, filtered, and concentrated under reduced pressure to afford (6-(((6aR, 8R)-6a-ethyl-2-(3-fluoro-2-methoxyphenyl)-5,6,6a,7,8,9-hexahydropyrrolo[1',2':4,5]pyrazino[2,3-c]pyridazin-8-yl)oxy)-4-methylpyridin-3-yl)methanol (55 mg, 97% yield) as a pale-yellow solid. LCMS calcd for $C_{25}H_{29}FN_5O_3$ [M+H]$^+$: m/z=466.2; Found: 465.9.

Step 4: 2-((6aR,8R)-8-((5-(chloromethyl)-4-methylpyridin-2-yl)oxy)-6a-ethyl-5,6,6a, 7,8,9-hexahydropyrrolo[1',2':4,5]pyrazino[2,3-c]pyridazin-2-yl)-6-fluorophenol

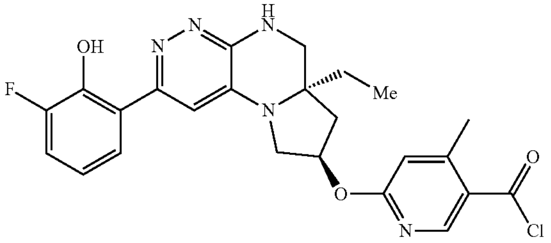 [SMILES: CC[C@@]12CNc3nnc(-c4cccc(F)c4O)cc3N1C[C@H](Oc1cc(C)c(C(=O)Cl)cn1)C2]

(6-(((6aR,8R)-6a-Ethyl-2-(3-fluoro-2-methoxyphenyl)-5,6,6a,7,8,9-hexahydropyrrolo [1',2':4,5]pyrazino[2,3-c]pyridazin-8-yl)oxy)-4-methylpyridin-3-yl)methanol (50 mg, 0.11 mmol) was added to a 20 mL vial, followed by dichloromethane (3 mL). The vial was sealed with a septum cap and boron trichloride (2.9 mL, 2.91 mmol, 1 M in dichloromethane) was added via a needle. The mixture was stirred at room temperature overnight. The vial was then placed in a water/ice bath and the mixture was quenched by slow addition of water, neutralized with a sodium bicarbonate solution (40 mL), and extracted with dichloromethane (3×20 mL). The combined organic phase was washed with a saturated sodium chloride solution (10 mL), dried over anhydrous magnesium sulfate (~10 g), filtered, and concentrated under reduced pressure to afford 2-((6aR,8R)-8-((5-(chloromethyl)-4-methylpyridin-2-yl)oxy)-6a-ethyl-5,6,6a,7,8,9-hexahydropyrrolo[1',2':4,5]pyrazino[2,3-c]pyridazin-2-yl)-6-fluorophenol (assumed quantitative) as pale-yellow film. LCMS calcd for $C_{24}H_{26}ClFN_5O_2$ [M+H]$^+$: m/z=470.2; Found: 469.9.

Step 6: 3-(6-(1-((6-(((6aR,8R)-6a-ethyl-2-(3-fluoro-2-hydroxyphenyl)-5,6,6a, 7,8,9-hexahydropyrrolo [1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione 2-((6aR,8R)-8-((5-(Chloromethyl)-4-methylpyridin-2-yl)oxy)-6a-ethyl-5,6,6a,7,8,9-hexahydropyrrolo[1',2':4,5]pyrazino[2,3-c]pyridazin-2-yl)-6-fluorophenol (20 mg, 0.047 mmol), (S)-3-(1-oxo-6-(piperidin-4-yl)isoindolin-2-yl)piperidine-2,6-dione hydrochloride (15.48 mg, 0.047 mmol), acetonitrile (2 mL), and N,N-diisopropylethylamine (37.06 μL, 0.21 mmol) were added to a 2-dram vial. The vial was sealed with a Teflon-coated cap and the mixture was stirred at 120° C. for 30 minutes. The mixture was cooled to room temperature, diluted with dimethyl sulfoxide (8 mL), filtered, and purified by preparative (Waters CSH Fluoro-Phenyl, 5 μm particle size, 30×100 mm) HPLC (12.8-32.8% $CH_3CN$ in $H_2O$ with 0.1% TFA in 5 minutes) to afford 3-(6-(1-((6-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione (2.2 mg, 5% yield) as a colorless film (TFA salt, mixture of diastereomers). LCMS calcd for $C_{42}H_{46}FN_8O_5$[M+H]$^+$: m/z=761.4; Found: 761.6.

SMARCA2 HiBiT and SMARCA4 HiBiT Degradation Assay

Preparation of SMARCA2/4-HiBiT Knock-In Cells

HiBiT peptide knock-in of SMARCA2 in LgBiT expressing HEK293T cells was performed by CRISPR-mediated tagging system as described Promega. The homozygous HiBiT knock-in on c-terminus SMARCA2 was confirmed by sanger sequence. SMARCA2-HiBiT knock-in Hela monoclonal cell (CS302366) and SMARCA4-HiBiT knock-in Hela monoclonal cell (CS3023226) were purchased from Promega. The heterozygous HiBiT-knock-in was confirmed by sanger sequence in both SMARCA2-HiBiT and SMARCA4-HiBiT monoclonal cells.

SMARCA2 HiBiT and SMARCA4 HiBiT Degradation Assay in HeLa Cells

Dispense 10 ul aliquot of prepared Hela-SMARCA2-HiBiT or Hela-SMARCA4-HiBiT cells (1:1 ratio of cells: Trypan Blue (#1450013, Bio-Rad)) onto cell counting slide (#145-0011, Bio-Rad) and obtain cell density and cell viability using cell counter (TC20, Bio-Rad). Remove appropriate volume of resuspended cells from culture flask to accommodate 2500 cells/well @ 20 μL/well. Transfer Hela-HiBiT cells to 50 mL conical (#430290, Corning). Spin down at 1000 rpm for 5 min using tabletop centrifuge (SPINCHRON 15, Beckman). Discard supernatant and resuspend cell pellet in modified EMEM (#30-2003, ATCC) cell culture media containing 10% FBS (F2422-500ML, Sigma), and 1× Penicillin/Streptomycin (200 g/L) (30-002-CI, Corning) to a cell density of 125,000 cells/mL. Dispense 20 μLof resuspended Hela-HiBit cells per well in 384-well TC treated plate (#12-565-343, Thermo Scientific) using standard cassette (#50950372, Thermo Scientific) on Multidrop Combi (#5840310, Thermo Scientific) inside laminar flow cabinet.

Compounds were dissolved in DMSO to make 10 mM stock and 3-fold series dilutions were further conducted keeping the highest concentration 10 μM. Dispense test compounds onto plates using digital liquid dispenser (D300E, Tecan). Incubate plates in humidified tissue culture incubator @37° C. for 18 hours. Add 20 μL of prepared Nano-Glo® HiBiT Lytic detection buffer (N3050, Promega) to each well of 384-well plate using small tube cassette (#24073295, Thermo Scientific) on Multidrop Combi, incubate @ RT for 30-60 min. Read plates on microplate reader (Envision 2105, PerkinElmer) using 384 well Ultra-Sensitive luminescence mode. Raw data files and compound information reports are swept into centralized data lake and deconvoluted using automated scripts designed by TetraScience, Inc. Data analysis, curve-fitting and reporting done in Dotmatics Informatics Suite using Screening Ultra module.

Results are summarized below in Table 9. In Table 4, A=DC50<0.1 μM; B=0.1 μM≤DC50<1 μM and C=DC50>1 μM. In Table 4, A=Dmax>75% and B=50%<Dmax≤75% and C=Dmax<50%.

TABLE 9

| Biological Data | | | | |
|---|---|---|---|---|
| Example | SMARCA2 $DC_{50}$ (nM) | SMARCA2 $D_{max}$ % | SMARCA4 $DC_{50}$ (nM) | SMARCA4 $D_{max}$ % |
| 1 | A | A | A | A |
| 2 | A | A | A | A |
| 3 | A | A | A | B |
| 4 | A | A | A | A |
| 5 | A | A | A | A |
| 6 | A | A | A | A |
| 7 | A | A | A | B |
| 8 | A | A | A | A |
| 9 | A | A | A | B |
| 10 | A | A | C | B |
| 11 | A | A | A | B |
| 12 | A | A | A | A |
| 13 | A | A | A | A |
| 14 | A | A | A | A |
| 15 | A | A | C | B |
| 16 | A | B | A | B |
| 17 | A | A | C | C |
| 18 | A | A | A | A |
| 19 | A | A | A | B |
| 20 | A | A | C | C |
| 21 | A | A | A | A |
| 22 | A | A | A | A |
| 23 | A | A | A | B |
| 24 | A | B | C | C |
| 25 | A | A | A | A |
| 26 | A | A | A | A |
| 27 | A | A | A | B |
| 28 | A | A | A | B |
| 29 | A | A | A | B |
| 30 | A | A | A | A |
| 31 | A | A | A | A |
| 32 | A | A | A | B |
| 33 | A | A | A | A |
| 34 | A | B | C | C |
| 35 | C | B | C | C |
| 36 | A | A | A | A |
| 37 | A | A | A | A |
| 38 | A | A | C | C |
| 39 | C | NA | C | NA |
| 40 | A | A | B | C |
| 41 | A | A | B | C |
| 42 | A | A | C | C |
| 43 | A | A | C | C |
| 44 | A | A | B | C |
| 45 | A | B | C | C |
| 46 | A | A | A | A |
| 47 | A | A | A | A |
| 48 | A | B | B | C |
| 49 | A | A | B | C |
| 50 | A | A | A | B |
| 51 | A | A | C | C |
| 52 | A | A | C | C |
| 53 | A | A | A | A |
| 54 | A | A | A | B |
| 55 | A | A | A | B |
| 56 | A | A | A | B |
| 57 | A | A | B | C |
| 58 | A | A | C | C |
| 59 | A | A | A | B |
| 60 | A | A | A | B |
| 61 | A | A | A | B |
| 62 | A | A | B | C |
| 63 | A | A | A | A |
| 64 | A | A | B | C |
| 65 | A | A | B | C |
| 66 | A | A | A | B |
| 67 | A | A | C | C |
| 68 | A | A | C | C |
| 69 | A | A | A | A |
| 70 | A | A | A | B |
| 71 | A | A | C | C |
| 72 | A | A | B | C |
| 73 | A | A | A | B |
| 74 | A | A | A | A |
| 75 | A | A | B | C |
| 76 | A | A | A | A |
| 77 | A | A | C | C |
| 78 | A | A | C | C |
| 79 | A | A | A | B |
| 80 | A | A | A | B |
| 81 | A | A | B | C |
| 82 | A | A | A | B |

TABLE 9-continued

| Biological Data | | | | |
|---|---|---|---|---|
| Example | SMARCA2 $DC_{50}$ (nM) | SMARCA2 $D_{max}$ % | SMARCA4 $DC_{50}$ (nM) | SMARCA4 $D_{max}$ % |
| 83 | A | A | A | A |
| 84 | A | A | B | C |
| 85 | A | A | A | B |
| 86 | A | A | B | C |
| 87 | A | A | B | C |
| 88 | A | A | B | C |
| 89 | A | A | A | A |
| 90 | A | A | C | C |
| 91 | A | A | A | B |
| 92 | A | A | A | B |
| 93 | A | A | C | C |
| 94 | A | B | C | C |
| 95 | A | A | C | C |
| 96 | A | A | B | C |
| 97 | A | A | A | B |
| 98 | A | A | A | A |
| 99 | A | A | A | B |
| 100 | A | A | B | C |
| 101 | A | A | B | C |
| 102 | A | A | C | C |
| 103 | A | A | A | B |
| 104 | A | A | A | B |
| 105 | A | A | B | C |
| 106 | A | A | B | C |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A compound of Formula (I):

(I)

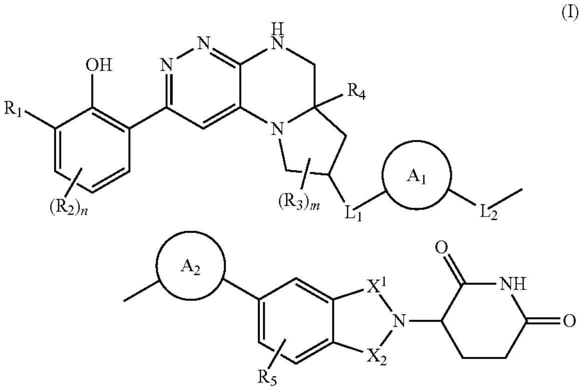

or a pharmaceutically acceptable salt thereof; wherein $R_1$ is halo, $C_{1-6}$ alkyl, or $C_{1-6}$ haloalkyl;

each $R_2$ is independently H, D, or F;

each $R_3$ is independently H, D, $C_{1-6}$ alkyl, $C_{1-6}$ haloalkyl, $C_{3-6}$ heterocycloalkyl or $C_{3-6}$ cycloalkyl;

n is 1, 2 or 3;

m is 1, 2, 3, or 4;

$R_4$ is H, D, $C_{1-6}$ alkyl, $C_{1-6}$ alkoxyalkyl, $C_{3-6}$ cycloalkyl, or $C_{1-6}$ haloalkyl;

$R_5$ is H, D, or F;

$L_1$ is a bond, O, S, S(O), $SO_2$, $NR_3$, $C(R_3)_2$ or CO;

$L_2$ is a bond, O, S, S(O), $SO_2$, $NR_3$, $C(R_3)_2$ or CO;

ring $A_1$ is a 6 membered aryl group or a 5-6 membered heteroaryl group;

ring $A_2$ is a 3-7 membered cycloalkyl group or a 4-7-membered heterocycloalkyl group;

$X_1$ is $CH_2$, CO, CH-CH (when $X_2$=CO), or N═CH (when $X_2$=CO);

$X_2$ is $CH_2$, CO, CH═CH (when $X_1$=CO), or N═CH (when $X_1$=CO);

wherein the alkyl group, haloalkyl group, cycloalkyl group, alkoxyalkyl group, aryl group, heteroaryl group or heterocycloalkyl group is optionally substituted by one or more $R^f$ groups;

each $R^f$ is independently D, oxo, halogen, $C_1$-$C_8$ alkoxy, $C_1$-$C_8$alkyl, $C_{1-6}$ haloalkyl, $C_{1-6}$ haloalkoxy, —OH, -CN, —$NO_2$, —$C_2$-$C_6$ alkenyl, —$C_2$-$C_6$ alkynyl, $C_{6-10}$ aryl, $C_{5-12}$ heteroaryl, $C_{3-8}$ cycloalkyl, $C_{3-8}$ cycloalkenyl, $C_{3-8}$ heterocycloalkyl, $C_{3-8}$ heterocycloalkenyl, —$OR^a$, —$SR^a$, —$NR^cR^d$, —$NR^aR^c$, —$C(O)R^b$, —OC(O)$R^b$, —$C(O)OR^b$, —$C(O)NR^cR^d$, —$S(O)R^b$, —$S(O)_2NR^cR^d$, —S(O) (═$NR^b$)$R^b$, —SF5, —P(O)$R^bR^b$, —$P(O)R^cR^d$, —$P(O)(OR^b)(OR^b)$, —B(OR)$(OR^d)$, —$S(O)_2R^b$, —$C(O)NR^bOR^b$, —$S(O)_2OR^b$, —$OS(O)_2OR^b$, or -$OPO(OR^b)(OR^b)$; wherein said $C_1$-$C_8$ alkyl is optionally substituted by 1-6 groups selected from D, halogen, —OH, -CN, —$OR^a$, —$SR^a$, —$NR^aR^d$, or $NR^cR^a$, each $R^a$ is independently H, D, —$C(O)R^b$, —$C(O)OR^c$, —$C(O)NR^cR^d$, —C(═$NR^b$)$NR^bR^c$, —C(=NORD)$NR^bR^c$, —C(═NCN)$NR^bR^c$, —$P(OR^c)_2$, —P(O)$R^cR^b$, —$P(O)R^cR^d$, —$P(O)OR^cOR^b$, —$S(O)R^b$, —$S(O)NR^cR^d$, —$S(O)_2R^b$, —$S(O)_2NR^cR^d$, $SiRb_3$, —$C_1$-$C_{10}$ alkyl, —$C_2$-$C_{10}$ alkenyl, —$C_2$-$C_{10}$ alkynyl, $C_{6-10}$ aryl, $C_{3-8}$ cycloalkyl, $C_{3-8}$ cycloalkenyl, $C_{5-12}$ heteroaryl, $C_{3-8}$ heterocycloalkyl, or $C_{3-8}$ heterocycloalkenyl;

each $R^b$, is independently H, D, —$C_1$-$C_6$ alkyl, —$C_2$-$C_6$ alkenyl, —$C_2$-$C_6$ alkynyl, $C_{6-10}$ aryl, $C_{3-8}$ cycloalkyl, $C_{3-8}$ cycloalkenyl, $C_{5-12}$ heteroaryl, $C_{3-8}$ heterocycloalkyl, or $C_{3-8}$ heterocycloalkenyl;

each $R^c$ or $R^d$ is independently H, D, —$C_1$-$C_{10}$ alkyl, —$C_2$-$C_6$ alkenyl, —$C_2$-$C_6$ alkynyl, —$OC_1$-$C_6$ alkyl, —O-cycloalkyl, $C_{6-10}$ aryl, $C_{5-12}$ heteroaryl, $C_{3-8}$ cycloalkyl, $C_{3-8}$ cycloalkenyl, $C_{3-8}$ heterocycloalkyl, or $C_{3-8}$ heterocycloalkenyl;

or $R^c$ and $R^d$, together with the atom to which they are both attached, form a monocyclic or multicyclic heterocycloalkyl, or a monocyclic or multicyclic heterocycloalkenyl group.

2. The compound according to claim 1, wherein $R_1$ is halo.

3. The compound according to claim 1, wherein $R_1$ is F.

4. The compound according to claim 1, wherein n is 1.

5. The compound according to claim 1, wherein n is 2.

6. The compound according to claim 1, wherein n is 3.

7. The compound according to claim 1, wherein each $R_2$ is F.

8. The compound according to claim 1, wherein each $R_2$ is H.

9. The compound according to claim 1, wherein m is 1.

10. The compound according to claim 1, wherein m is 2.

11. The compound according to claim 1, wherein m is 3.

12. The compound according to claim 1, wherein m is 4.

13. The compound according to claim 1, wherein each $R_3$ is H.

14. The compound according to claim 1, wherein $R_4$ is H.

15. The compound according to claim 1, wherein $R_4$ is D.

16. The compound according to claim 1, wherein $R_4$ is $C_{1-6}$ alkyl.

17. The compound according to claim 1, wherein $R_4$ is methyl.

18. The compound according to claim 1, wherein $R_5$ is H.

19. The compound according to claim 1, wherein $L_1$ is O.

20. The compound according to claim 1, wherein $L_1$ is $NR_3$.

21. The compound according to claim 1, wherein $L_1$ is S.

22. The compound according to claim 1, wherein $L_2$ is CO.

23. The compound according to claim 1, wherein $L_2$ is $C(R_3)_2$.

24. The compound according to claim 1, wherein $L_2$ is a methylene group.

25. The compound according to claim 1, wherein ring $A_1$ is a 6 membered aryl group.

26. The compound according to claim 25, wherein ring $A_1$ is a phenyl group.

27. The compound according to claim 1, wherein ring $A_1$ is a 5-6-membered heteroaryl group.

28. The compound according to claim 27, wherein ring $A_1$ is a pyridine group.

29. The compound according to claim 1, wherein ring $A_2$ is a 4-7-membered heterocycloalkyl group.

30. The compound according to claim 29, wherein ring $A_2$ is a piperidine group or a piperazine group.

31. The compound according to claim 1, wherein $X_1$ is $CH_2$.

32. The compound according to claim 1, wherein $X_1$ is CO.

33. The compound according to claim 1, wherein $X_2$ is $CH_2$.

34. The compound according to claim 1, wherein $X_2$ is CO.

35. The compound according to claim 1 that is a compound of formula IIa or formula IIb:

(IIa)

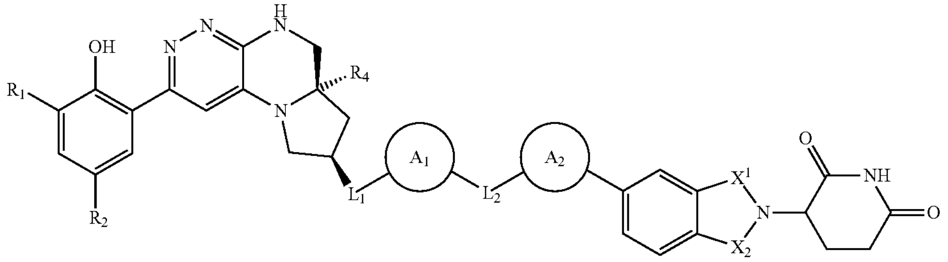

(IIb)

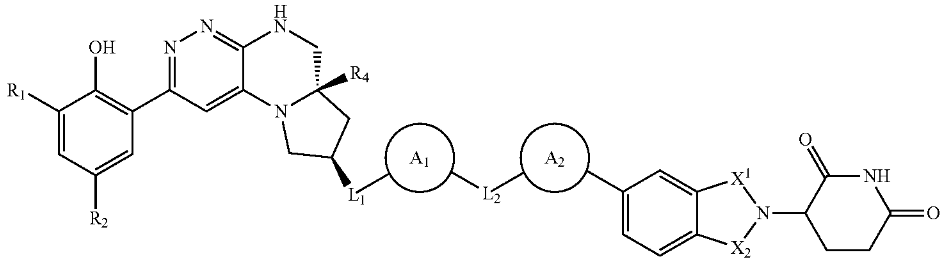

or a pharmaceutically acceptable salt thereof.

36. The compound according to claim 1 that is a compound of formula IIIa or formula IIIb:

(IIIa)

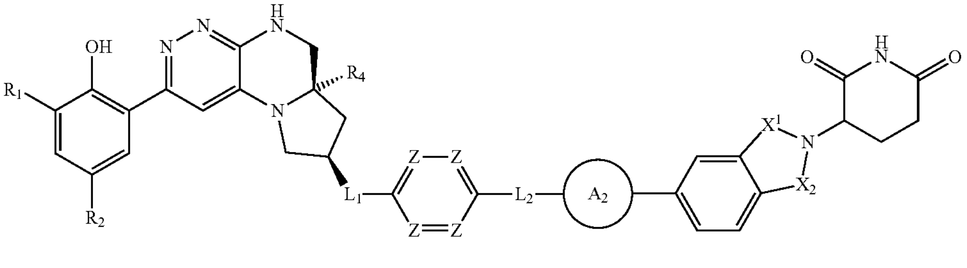

-continued (IIIb)

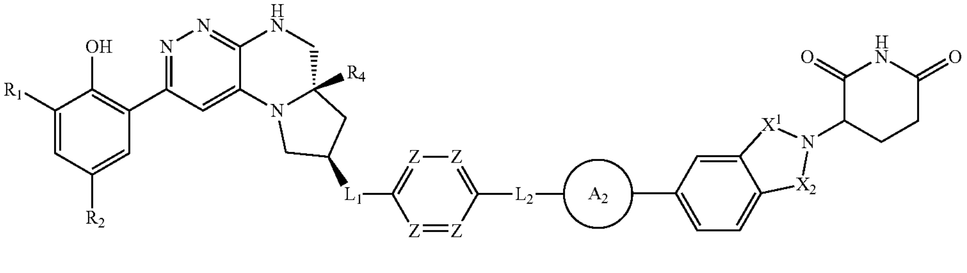

or a pharmaceutically acceptable salt thereof; wherein each Z is independently N or $CR_6$; and each $R_6$ is independently H, D, halo, —CN, $C_{1-6}$ alkyl, $C_{1-6}$ alkoxy, $C_{1-6}$ haloalkyl, $C_{1-6}$ haloalkoxy, or $C_{3-6}$ cycloalkyl.

37. The compound according to claim 36, wherein at least one Z is N.

38. The compound according to claim 36, wherein at least two Z are N.

39. The compound according to claim 36, wherein at least one Z is $CR_6$.

40. The compound according to claim 36, wherein at least two Z are $CR_6$.

41. The compound according to claim 36, wherein at least one $R_6$ is H.

42. The compound according to claim 36, wherein at least one $R_6$ is $C_{1-6}$ alkyl.

43. The compound according to claim 42, wherein at least one $R_6$ is methyl.

44. The compound according to claim 36 that is a compound of formula IVa or formula IVb:

(IVa)

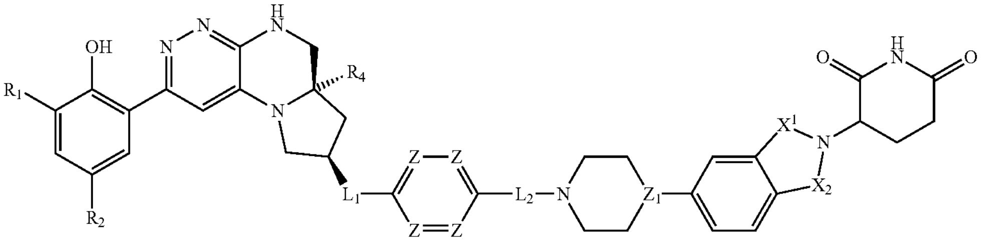

(IVb)

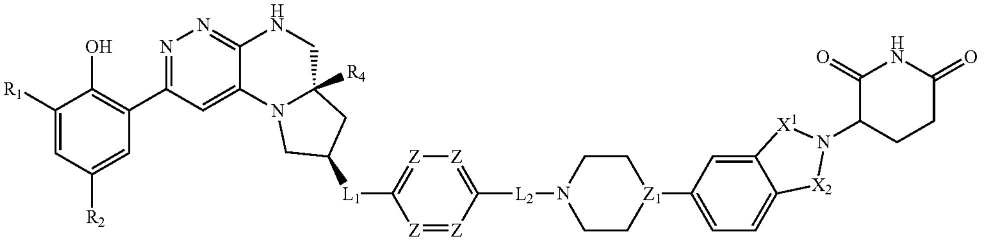

or a pharmaceutically acceptable salt thereof; wherein $Z_1$ is N or $CR_6$.

45. The compound according to claim 44, wherein $Z_1$ is N.

46. The compound according to claim 44, wherein $Z_1$ is $CR_6$.

47. The compound according to claim 36 that is a compound of formula Va or formula Vb:

(Va)

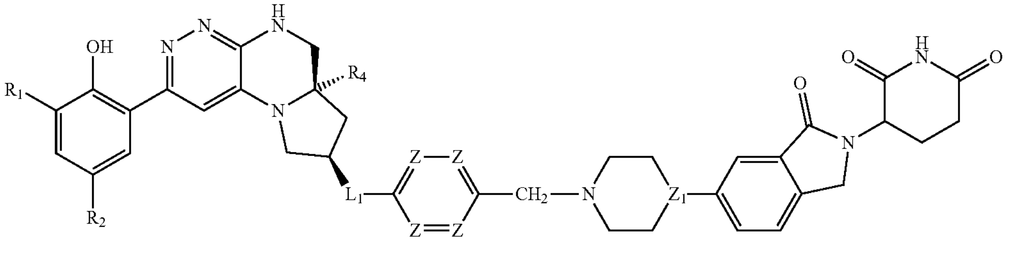

-continued
(Vb)
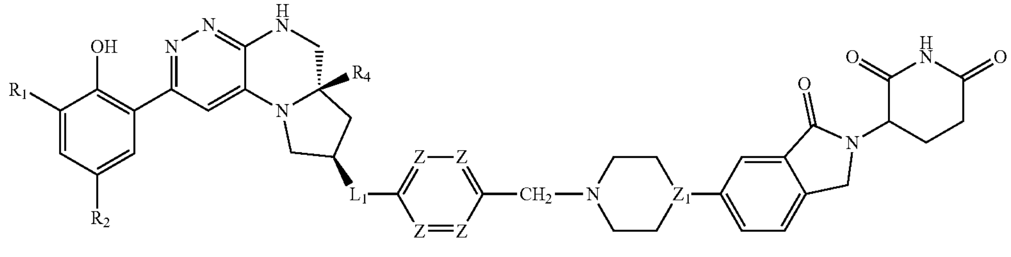
or a pharmaceutically acceptable salt thereof.
48. The compound according to claim 36 that is a compound of formula VIa or formula VIb:
(VIa)
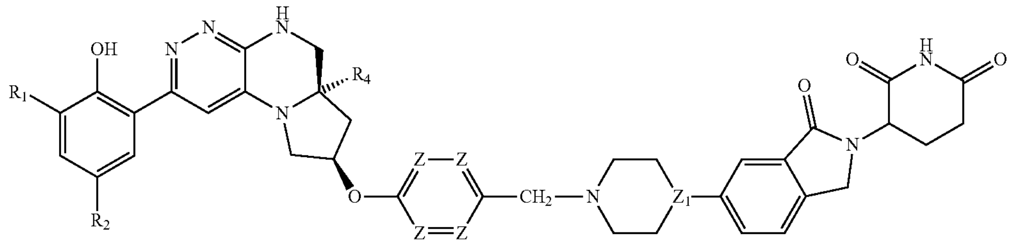
(VIb)
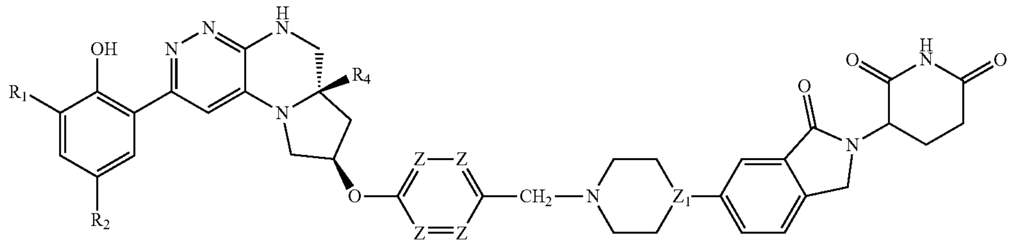
or a pharmaceutically acceptable salt thereof.
49. The compound according to claim 36 that is a compound of formula VIIa or formula VIIb:
(VIIa)
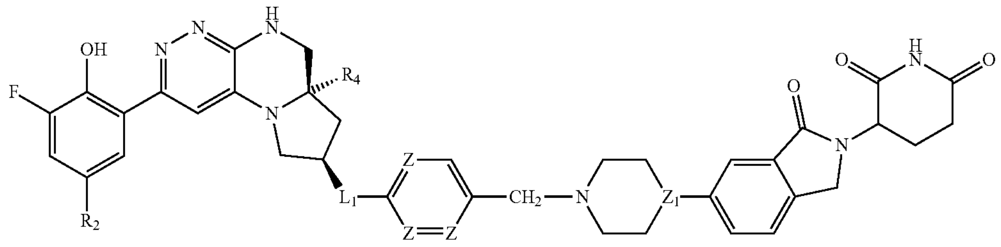
(VIIb)
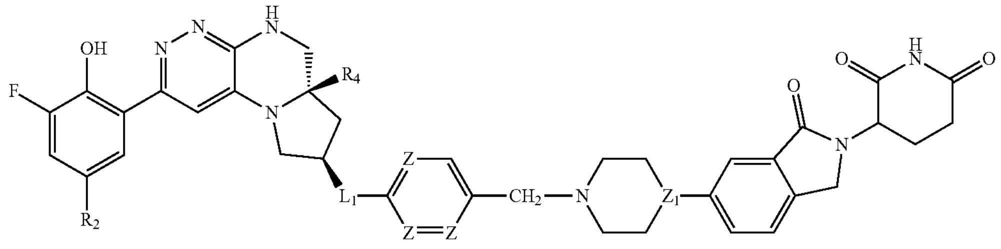
or a pharmaceutically acceptable salt thereof.

50. A compound according to claim 1 that is:

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)benzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-3-methylbenzyl)piperazin-1-yl)-1-oxoisoindolin-2-yl)piperidine-2,6-dione;

3-(6-(4-((5-(((6aR,8R)-2-(3,5-difluoro-2-hydroxyphenyl)-5,6,6a, 7,8,9-hexahydro-pyrrolo[11,2':4,5]pyrazino[2,3-c]pyridazin-8-yl)oxy) pyridin-2-yl)methyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-3-fluorobenzyl)piperazin-1-yl)-1-oxoisoindolin-2-yl)piperidine-2,6-dione;

3-(6-(4-(4-(((6aR,8R)-2-(3-fluoro-2-hydroxyphenyl)-5,6,6a,7,8,9-hexahydro-pyrrolo[11,2':4,5]pyrazino[2,3-c]pyridazin-8-yl)oxy)benzyl)piperazin-1-yl)-1-oxoisoindolin-2-yl)piperidine-2,6-dione;

3-(6-(4-(3-chloro-4-(((6aR,8R)-2-(3,5-difluoro-2-hydroxyphenyl)-5,6,6a, 7,8,9-hexahydropyrrolo[1',2':4,5]pyrazino[2,3-c]pyridazin-8-yl)oxy)benzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[11,2':4,5]pyrazino[2,3-c]pyridazin-8-yl)oxy)-2-methylbenzyl)piperazin-1-yl)-1-oxoisoindolin-2-yl)piperidine-2,6-dione;

3-(6-(4-(4-(((6aR,8R)-2-(3-chloro-2-hydroxyphenyl)-5,6,6a,7,8,9-hexahydro-pyrrolo[1',2':4,5]pyrazino[2,3-c]pyridazin-8-yl)oxy)benzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-2,5-dimethylbenzyl)piperazin-1-yl)-1-oxoisoindolin-2-yl)piperidine-2,6-dione;

3-(6-(4-(4-(((6aR,8R)-2-(3-chloro-2-hydroxyphenyl)-5,6,6a,7,8,9-hexahydro-pyrrolo[11,2':4,5]pyrazino[2,3-c]pyridazin-8-yl)oxy)-2-methylbenzyl)piperazin-1-yl)-1-oxoisoindolin-2-yl)piperidine-2,6-dione;

3-(6-(4-(4-(((6aR,8R)-2-(3-fluoro-2-hydroxyphenyl)-5,6,6a,7,8,9-hexahydro-pyrrolo[11,2':4,5]pyrazino[2,3-c]pyridazin-8-yl)oxy)-2-methylbenzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-2-methoxybenzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-2-fluorobenzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-3-isopropylbenzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-2-(trifluoromethyl)benzyl)piperazin-1-yl)-] oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[11,2':4,5]pyrazino[2,3-c]pyridazin-8-yl)oxy)-2-isopropylbenzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[11,2':4,5]pyrazino[2,3-c]pyridazin-8-yl)oxy)-2,6-dimethylbenzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[11,2':4,5]pyrazino[2,3-c]pyridazin-8-yl)oxy)-2,3-dimethylbenzyl)piperazin-1-yl)-1-oxoisoindolin-2-yl)piperidine-2,6-dione;

3-(6-(4-(4-(((6aR,8R)-2-(3-chloro-5-fluoro-2-hydroxyphenyl)-5,6,6a,7,8,9-hexahydro-pyrrolo[1',2':4,5]pyrazino[2,3-c]pyridazin-8-yl)oxy)-2-methylbenzyl)piperazin-1-yl)-1-oxoisoindolin-2-yl)piperidine-2,6-dione;

3-(6-(4-(4-(((6aR,8R)-2-(2-hydroxy-3-methylphenyl)-5,6,6a,7,8,9-hexahydro-pyrrolo[1',2':4,5]pyrazino[2,3-c]pyridazin-8-yl)oxy)-2-methylbenzyl)piperazin-1-yl)-1-oxoisoindolin-2-yl)piperidine-2,6-dione;

3-(6-(4-(4-(((6aR,8R)-2-(3-chloro-2-hydroxyphenyl)-5,6,6a,7,8,9-hexahydro-pyrrolo[1',2':4,5]pyrazino[2,3-c]pyridazin-8-yl)oxy)-2-methoxybenzyl)piperazin-1-yl)-1-oxoisoindolin-2-yl)piperidine-2,6-dione;

3-(6-(4-(4-(((6aR,8R)-2-(3-chloro-5-fluoro-2-hydroxyphenyl)-5,6,6a,7,8,9-hexahydropyrrolo[1',2':4,5]pyrazino[2,3-c]pyridazin-8-yl)oxy)benzyl)piperazin-1-yl)-1-oxoisoindolin-2-yl)piperidine-2,6-dione;

3-(6-(4-(4-(((6aR,8R)-2-(2-hydroxy-3-methylphenyl)-5,6,6a,7,8,9-hexahydro-pyrrolo[1',2':4,5]pyrazino[2,3-c]pyridazin-8-yl)oxy)benzyl)piperazin-1-yl)-1-oxoisoindolin-2-yl)piperidine-2,6-dione;

3-(6-(4-(4-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-2-(trifluoromethoxy)benzyl)piperazin-1-yl)-1-oxoisoindolin-2-yl)piperidine-2,6-dione;

(S)-3-(6-(4-(4-(((6aR,8R)-2-(3-chloro-2-hydroxyphenyl)-5,6,6a,7,8,9-hexahydro-pyrrolo[1',2':4,5]pyrazino[2,3-c]pyridazin-8-yl)oxy)benzyl)piperazin-1-yl)-1-oxoisoindolin-2-yl)piperidine-2,6-dione;

3-(6-(4-((2-(((6aR,8R)-2-(3,5-difluoro-2-hydroxyphenyl)-5,6,6a,7,8,9-hexahydro-pyrrolo[11,2':4,5]pyrazino[2,3-c]pyridazin-8-yl)thio) pyrimidin-5-yl)methyl)piperazin-1-yl)-1-oxoisoindolin-2-yl)piperidine-2,6-dione;

3-(6-(4-((6-(((6aR,8R)-2-(3,5-difluoro-2-hydroxyphenyl)-5,6,6a, 7,8,9-hexahydro-pyrrolo[11,2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione;

(S)-3-(6-(4-((6-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione;

(S)-3-(6-(1-((6-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione;

(S)-3-(6-(4-((6-(((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)oxy)-2-methylpyridin-3-yl)methyl)piperazin-1-yl)-1-oxoisoindolin-2-yl)piperidine-2,6-dione;

3-(6-(4-((6-(((6aR,8R)-2-(3,5-difluoro-2-hydroxyphenyl)-5,6,6a,7,8,9-hexahydro-pyrrolo[11,2':4,5]

pyrazino[2,3-c]pyridazin-8-yl)oxy)-5-methylpyridin-3-yl)methyl)piperazin-1-yl)-1-oxoisoindolin-2-yl)piperidine-2,6-dione;

3-(6-(4-(4-((((6aR,8R)-2-(3,5-difluoro-2-hydroxyphenyl)-5,6,6a,7,8,9-hexahydro-pyrrolo[11,2':4,5]pyrazino[2,3-c]pyridazin-8-yl)thio)benzyl)piperazin-1-yl)-1-oxoisoindolin-2-yl)piperidine-2,6-dione;

3-(6-(4-((6-((((6aR,8R)-2-(3,5-difluoro-2-hydroxyphenyl)-5,6,6a, 7,8,9-hexahydro-pyrrolo[11,2':4,5]pyrazino[2,3-c]pyridazin-8-yl)oxy) pyridin-3-yl)methyl)piperazin-1-yl)-1-oxoisoindolin-2-yl)piperidine-2,6-dione;

3-(6-(4-(((3R,5S)-4-((6aR,8R)-2-(3-fluoro-2-hydroxyphenyl)-5,6,6a,7,8,9-hexahydro-pyrrolo[11,2':4,5]pyrazino[2,3-c]pyridazine-8-carbonyl)-3,5-dimethylpiperazin-1-yl)methyl) piperidin-1-yl)-1-oxoisoindolin-2-yl)piperidine-2,6-dione;

3-(6-(4-((6-((((6aR,8R)-2-(3-fluoro-2-hydroxyphenyl)-5,6,6a,7,8,9-hexahydro-pyrrolo[1',2':4,5]pyrazino[2,3-c]pyridazin-8-yl) (methyl) amino) pyridin-3-yl)methyl)piperazin-1-yl)-1-oxoisoindolin-2-yl)piperidine-2,6-dione;

3-(6-(4-(4-((((6aS,8R)-2-(3-fluoro-2-hydroxyphenyl)-5,6,6a,7,8,9-hexahydropyrrolo [1',2':4,5]pyrazino[2,3-c]pyridazin-8-yl)oxy)-2-methylbenzyl)piperazin-1-yl)-1-oxoisoindolin-2-yl)piperidine-2,6-dione;

3-(6-(1-(4-((((6aS,8R)-2-(3-fluoro-2-hydroxyphenyl)-5,6,6a,7,8,9-hexahydropyrrolo [1',2':4,5]pyrazino[2,3-c]pyridazin-8-yl)oxy)-2-methylbenzyl)piperidin-4-yl)-1-oxoisoindolin-2-yl)piperidine-2,6-dione;

(S)-3-(6-(4-((6-((((6aR,8R)-2-(3,5-difluoro-2-hydroxyphenyl)-5,6,6a,7,8,9-hexahydro-pyrrolo[1',2':4,5]pyrazino[2,3-c]pyridazin-8-yl)thio)-4-methylpyridin-3-yl)methyl)piperazin-1-yl)-1-oxoisoindolin-2-yl)piperidine-2,6-dione;

3-(6-(4-((4-((((6aR,8R)-2-(3,5-difluoro-2-hydroxyphenyl)-5,6,6a, 7,8,9-hexahydropyrrolo [1',2':4,5]pyrazino[2,3-c]pyridazin-8-yl)oxy)-1H-pyrazol-1-yl)methyl)piperidin-1-yl)-1-oxoisoindolin-2-yl)piperidine-2,6-dione;

or a pharmaceutically acceptable salt thereof.

51. A compound that is:

3-(6-(4-((5-((((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-6-methylpyrazin-2-yl)methyl)piperazin-1-yl)-1-oxoisoindolin-2-yl)piperidine-2,6-dione;

3-(6-(4-((2-((((6aS,8R)-6a-(Difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-4,6-dimethylpyrimidin-5-yl)methyl)piperazin-1-yl)-1-oxoisoindolin-2-yl)piperidine-2,6-dione;

3-(6-(4-((2-((((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy) pyrimidin-5-yl)methyl)piperazin-1-yl)-1-oxoisoindolin-2-yl)piperidine-2,6-dione;

(S)-3-(6-(4-((6-((((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy) pyridin-3-yl)methyl)piperazin-1-yl)-1-oxoisoindolin-2-yl)piperidine-2,6-dione;

(S)-3-(6-(4-((6-((((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-5-ethylpyridin-3-yl)methyl)piperazin-1-yl)-1-oxoisoindolin-2-yl)piperidine-2,6-dione;

(S)-3-(6-(4-((5-((((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-3-fluoro-4-methylpyridin-2-yl)methyl)piperazin-1-yl)-1-oxoisoindolin-2-yl)piperidine-2,6-dione;

(S)-3-(6-(4-((5-((((6aS,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-3,4-dimethylpyridin-2-yl)methyl)piperazin-1-yl)-1-oxoisoindolin-2-yl)piperidine-2,6-dione;

(S)-3-(6-(4-((6-((((6aS,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-5-ethylpyridin-3-yl)methyl)piperazin-1-yl)-1-oxoisoindolin-2-yl)piperidine-2,6-dione;

(S)-3-(6-(4-((5-((((6aS,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-3,6-dimethylpyrazin-2-yl)methyl)piperazin-1-yl)-1-oxoisoindolin-2-yl)piperidine-2,6-dione;

(S)-3-(6-(4-((5-((((6aS,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy) pyridin-2-yl)methyl)piperazin-1-yl)-1-oxoisoindolin-2-yl)piperidine-2,6-dione;

3-(6-(4-((2-((((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-4-isopropylpyrimidin-5-yl)methyl)piperazin-1-yl)-1-oxoisoindolin-2-yl)piperidine-2,6-dione;

3-(6-(4-((5-((((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-3-methylpyrazin-2-yl)methyl)piperazin-1-yl)-1-oxoisoindolin-2-yl)piperidine-2,6-dione;

3-(6-(4-((5-((((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy) pyrazin-2-yl)methyl)piperazin-1-yl)-1-oxoisoindolin-2-yl)piperidine-2,6-dione;

3-(6-(4-((6-((((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-5-methoxypyridin-3-yl)methyl)piperazin-1-yl)-1-oxoisoindolin-2-yl)piperidine-2,6-dione;

3-(6-(4-((6-((((6aS,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-5-fluoropyridin-3-yl)methyl)piperazin-1-yl)-1-oxoisoindolin-2-yl)piperidine-2,6-dione;

3-(6-(4-((6-((((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione;

3-(6-(4-((6-((((6aR,8R)-6a-Ethyl-2-(3-fluoro-2-hydroxyphenyl)-5,6,6a,7,8,9-hexahydropyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione;

(S)-3-(6-(4-((5-((((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-3-methylpyrazin-2-yl)methyl)piperazin-1-yl)-1-oxoisoindolin-2-yl)piperidine-2,6-dione;

(S)-3-(6-(4-((6-((((6aR,8R)-2-(3-Fluoro-2-hydroxyphenyl)-6a-(fluoromethyl)-5,6,6a,7,8,9-hexahydropyrrolo

[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione;

5-((4~ (2-((S)-2,6-dioxopiperidin-3-yl)-3-oxoisoindolin-5-yl)piperazin-1-yl)methyl)-2-(((6aR,8R)-6a-ethyl-2-(3-fluoro-2-hydroxyphenyl)-5,6,6a,7,8,9-hexahydropyrrolo[1',2':4,59pyrazino[2,3-c]pyridazin-8-yl)oxy)-6-methylnicotinonitrile;

3-(6-(4-((6-(((6aR,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)thio)-4-methylpyridin-3-yl)methyl)piperazin-1-yl)-1-oxoisoindolin-2-yl)piperidine-2,6-dione;

3-(6-(4-((6-(((6aR,8R)-6a-ethyl-2-(3-fluoro-2-hydroxyphenyl)-5,6,6a, 7,8,9-hexahydropyrrolo[1',2':4,5]pyrazino[2,3-c]pyridazin-8-yl)oxy)-5-fluoro-4-methylpyridin-3-yl)methyl)piperazin-1-yl)-1-oxoisoindolin-2-yl)piperidine-2,6-dione;

3-(6-(4-((6-(((6aR,8R)-6a-ethyl-2-(3-fluoro-2-hydroxyphenyl)-5,6,6a, 7,8,9-hexahydropyrrolo[1',2':4,5]pyrazino[2,3-c]pyridazin-8-yl)oxy)-2,4-dimethylpyridin-3-yl)methyl)piperazin-1-yl)-1-oxoisoindolin-2-yl)piperidine-2,6-dione;

3-(6-(4-((6-(((6aR,8R)-2-(3,5-difluoro-2-hydroxyphenyl)-6a-ethyl-5,6,6a, 7,8,9-hexahydropyrrolo[1',2':4,5]pyrazino[2,3-c]pyridazin-8-yl)oxy) pyridin-3-yl)methyl)piperazin-1-yl)-1-oxoisoindolin-2-yl)piperidine-2,6-dione;

(S)-3-(6-(4-((5-(((6aR,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-6-methylpyrazin-2-yl)methyl)piperazin-1-yl)-1-oxoisoindolin-2-yl)piperidine-2,6-dione;

(S)-3-(6-(1-((5-(((6aR,8R)-2-(3-Fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-6-methylpyrazin-2-yl)methyl)piperidin-4-yl)-1-oxoisoindolin-2-yl)piperidine-2,6-dione;

(S)-3-(6-(4-((5-(((6aS,8R)-2-(3-fluoro-2-hydroxyphenyl)-6a-(fluoromethyl)-5,6,6a,7,8,9-hexahydropyrrolo[1',2':4,5]pyrazino[2,3-c]pyridazin-8-yl)oxy)-6-methylpyrazin-2-yl)methyl)piperazin-1-yl)-1-oxoisoindolin-2-yl)piperidine-2,6-dione;

(S)-3-(6-(4-((6-ethyl-5-(((6aR,8R)-2-(3-fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy) pyrazin-2-yl)methyl)piperazin-1-yl)-1-oxoisoindolin-2-yl)piperidine-2,6-dione;

(S)-3-(6-(1-((6-ethyl-5-(((6aR,8R)-2-(3-fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy) pyrazin-2-yl)methyl)piperidin-4-yl)-1-oxoisoindolin-2-yl)piperidine-2,6-dione;

(S)-3-(6-(4-((5-fluoro-6-(((6aS,8R)-2-(3-fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy)-2-methylpyridin-3-yl)methyl)piperazin-1-yl)-1-oxoisoindolin-2-yl)piperidine-2,6-dione;

3-(6-(4-((5-fluoro-6-(((6aR,8R)-2-(3-fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy) pyridin-3-yl)methyl)piperazin-1-yl)-1-oxoisoindolin-2-yl)piperidine-2,6-dione;

(S)-3-(6-(4-((5-fluoro-6-(((6aR,8R)-2-(3-fluoro-2-hydroxyphenyl)-6a-(fluoromethyl)-5,6,6a, 7,8,9-hexahydropyrrolo[1',2':4,5]pyrazino[2,3-c]pyridazin-8-yl)oxy)-4-methylpyridin-3-yl)methyl)piperazin-1-yl)-1-oxoisoindolin-2-yl)piperidine-2,6-dione;

(S)-3-(6-(4-((5-(((6aR,8R)-6a-Ethyl-2-(3-fluoro-2-hydroxyphenyl)-5,6,6a,7,8,9-hexahydropyrrolo[1',2':4,5]pyrazino[2,3-c]pyridazin-8-yl) oxy)-3-fluoropyridin-2-yl)methyl)piperazin-1-yl)-1-oxoisoindolin-2-yl)piperidine-2,6-dione;

(S)-3-(5-(4-((5-(((6aS,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-3-(trifluoromethyl)pyridin-2-yl)methyl)piperazin-1-yl)-1-oxoisoindolin-2-yl)piperidine-2,6-dione;

(S)-3-(5-(4-((5-(((6aS,8R)-6a-ethyl-2-(3-fluoro-2-hydroxyphenyl)-5,6,6a,7,8,9-hexahydropyrrolo[1',2':4,5]pyrazino[2,3-c]pyridazin-8-yl)oxy)-3-methylpyridin-2-yl)methyl)piperazin-1-yl)-1-oxoisoindolin-2-yl)piperidine-2,6-dione;

(S)-3-(6-(4-((2-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4,6-dimethylpyrimidin-5-yl)methyl)piperazin-1-yl)-1-oxoisoindolin-2-yl)piperidine-2,6-dione;

5-((4-(2-((S)-2,6-dioxopiperidin-3-yl)-3-oxoisoindolin-5-yl)piperazin-1-yl)methyl)-2-(((6aS,8R)-2-(3-fluoro-2-hydroxyphenyl)-6a-methyl-5,6,6a, 7,8,9-hexahydropyrrolo[1',2':4,59pyrazino[2,3-c]pyridazin-8-yl)oxy)isonicotinonitrile;

(S)-3-(6-(1-((2-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4-methylpyrimidin-5-yl)methyl)piperidin-4-yl)-1-oxoisoindolin-2-yl)piperidine-2,6-dione;

(S)-3-(6-(1-((2-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-4,6-dimethylpyrimidin-5-yl)methyl)piperidin-4-yl)-1-oxoisoindolin-2-yl)piperidine-2,6-dione;

(S)-3-(6-(4-((5-(((6aS,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy) pyrazin-2-yl)methyl)piperazin-1-yl)-1-oxoisoindolin-2-yl)piperidine-2,6-dione;

(S)-3-(6-(4-((5-(((6aS,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-3,6-dimethylpyridin-2-yl)methyl)piperazin-1-yl)-1-oxoisoindolin-2-yl)piperidine-2,6-dione;

(S)-3-(6-(4-((5-(((6aR,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-3-methylpyridin-2-yl)methyl)piperazin-1-yl)-1-oxoisoindolin-2-yl)piperidine-2,6-dione;

(S)-3-(6-(4-((5-(((6aS,8R)-2-(3-fluoro-2-hydroxyphenyl)-6a-methyl-5,6,6a, 7,8,9-hexahydropyrrolo[1',2':4,5]pyrazino[2,3-c]pyridazin-8-yl)oxy)-3-methylpyridin-2-yl)methyl)piperazin-1-yl)-1-oxoisoindolin-2-yl)piperidine-2,6-dione;

(S)-3-(6-(4-((6-(((6aS,8R)-2-(3-fluoro-2-hydroxyphenyl)-6a-methyl-5,6,6a,7,8,9-hexahydropyrrolo[1',2':4,5]pyrazino[2,3-c]pyridazin-8-yl)oxy)-5-methylpyridin-3-yl)methyl)piperazin-1-yl)-1-oxoisoindolin-2-yl)piperidine-2,6-dione;

3-(6-(4-((6-(((6aR,8R)-6a-(difluoromethyl)-2-(3-fluoro-2-hydroxyphenyl)-5,6,6a,7,8,9-hexahydropyrrolo[1',2':4,5]pyrazino[2,3-c]pyridazin-8-yl)oxy)-5-fluoropyridin-3-yl)methyl)piperazin-1-yl)-1-oxoisoindolin-2-yl)piperidine-2,6-dione;

3-(6-(4-((5-chloro-6-(((6aR,8R)-6a-(difluoromethyl)-2-(3-fluoro-2-hydroxyphenyl)-5,6,6a, 7,8,9-hexahydro-pyrrolo[1',2':4,5]pyrazino[2,3-c]pyridazin-8-yl)oxy) pyridin-3-yl)methyl)piperazin-1-yl)-1-oxoisoindolin-2-yl)piperidine-2,6-dione;

(S)-3-(6-(4-((6-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-4,5-dimethylpyridin-3-yl)methyl)piperazin-1-yl)-1-oxoisoindolin-2-yl)piperidine-2,6-dione;

(S)-3-(6-(4-((6-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-2,5-dimethylpyridin-3-yl)methyl)piperazin-1-yl)-1-oxoisoindolin-2-yl)piperidine-2,6-dione;

3-(6-(1-((6-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-5-fluoro-pyridin-3-yl)methyl)piperidin-4-yl)-1-oxoisoindolin-2-yl)piperidine-2,6-dione;

(S)-3-(6-(1-((6-(((6aS,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazine-8-yl)oxy)-5-fluoro-4-methylpyridin-3-yl)methyl)piperidin-4-yl)-1-oxoisoindolin-2-yl)piperidine-2,6-dione;

(S)-3-(6-(1-((6-(((6aR,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy) pyridin-3-yl)methyl)piperidin-4-yl)-1-oxoisoindolin-2-yl) piperidine-2,6-dione;

(S)-3-(6-(1-((5-(((6aS,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-6-methylpyrazin-2-yl)methyl)piperidin-4-yl)-1-oxoisoindolin-2-yl)piperidine-2,6-dione;

(S)-3-(6-(1-((5-(((6aS,8R)-6a-(difluoromethyl)-2-(3-fluoro-2-hydroxyphenyl)-5,6,6a, 7,8,9-hexahydropyrrolo[1',2':4,5]pyrazino[2,3-c]pyridazin-8-yl)oxy)-4-methylpyridin-2-yl)methyl)piperidin-4-yl)-1-oxoisoindolin-2-yl)piperidine-2,6-dione;

(S)-3-(6-(1-((6-(((6aR,8R)-2-(3-fluoro-2-hydroxyphenyl)-6a-(fluoromethyl)-5,6,6a,7,8,9-hexahydropyrrolo [1',2':4,5]pyrazino[2,3-c]pyridazin-8-yl)oxy)-4-methylpyridin-3-yl)methyl)piperidin-4-yl)-1-oxoisoindolin-2-yl)piperidine-2,6-dione;

(S)-3-(6-(1-((5-(((6aS,8R)-6a-(difluoromethyl)-2-(2-hydroxy-3-methylphenyl)-5,6,6a, 7,8,9-hexahydropyrrolo[1',2':4,5]pyrazino[2,3-c]pyridazin-8-yl)oxy)-4-methylpyridin-2-yl)methyl)piperidin-4-yl)-1-oxoisoindolin-2-yl)piperidine-2,6-dione;

(S)-3-(6-(1-((5-(((6aR,8R)-6a-ethyl-2-(2-hydroxy-3-methylphenyl)-5,6,6a,7,8,9-hexahydropyrrolo[1',2':4,5]pyrazino[2,3-c]pyridazin-8-yl)oxy)-3,4-dimethylpyridin-2-yl)methyl)piperidin-4-yl)-1-oxoisoindolin-2-yl)piperidine-2,6-dione;

(S)-3-(6-(1-((2-(((6aS,8R)-6a-ethyl-2-(2-hydroxy-3-methylphenyl)-5,6,6a,7,8,9-hexahydropyrrolo[1',2':4,5]pyrazino[2,3-c]pyridazin-8-yl)oxy)-4,6-dimethylpyrimidin-5-yl)methyl)piperidin-4-yl)-1-oxoisoindolin-2-yl)piperidine-2,6-dione;

(S)-3-(6-(1-((5-(((6aS,8R)-6a-ethyl-2-(2-hydroxy-3-methylphenyl)-5,6,6a,7,8,9-hexahydropyrrolo[1',2':4,5]pyrazino[2,3-c]pyridazin-8-yl)oxy)-3-methylpyridin-2-yl)methyl)piperidin-4-yl)-1-oxoisoindolin-2-yl) piperidine-2,6-dione;

(S)-3-(6-(1-((3-chloro-5-(((6aS,8R)-2-(3-chloro-2-hydroxyphenyl)-6a-ethyl-5,6,6a,7,8,9-hexahydropyrrolo [1',2':4,5]pyrazino[2,3-c]pyridazin-8-yl)oxy) pyridin-2-yl)methyl)piperidin-4-yl)-1-oxoisoindolin-2-yl) piperidine-2,6-dione;

(S)-3-(6-(1-((6-(((6aR,8R)-2-(3-chloro-2-hydroxyphenyl)-6a-ethyl-5,6,6a,7,8,9-hexahydropyrrolo[11,2':4,5] pyrazino[2,3-c]pyridazin-8-yl)oxy)-4-methylpyridin-3-yl)methyl)piperidin-4-yl)-1-oxoisoindolin-2-yl) piperidine-2,6-dione;

(S)-3-(6-(1-((5-(((6aR,8R)-6a-ethyl-2-(3-fluoro-2-hydroxyphenyl)-5,6,6a,7,8,9-hexahydropyrrolo[1',2':4,5] pyrazino[2,3-c]pyridazin-8-yl)oxy)-3-fluoropyridin-2-yl)methyl)piperidin-4-yl)-1-oxoisoindolin-2-yl) piperidine-2,6-dione;

(S)-3-(6-(1-((2-(((6aR,8R)-6a-ethyl-2-(3-fluoro-2-hydroxyphenyl)-5,6,6a, 7,8,9-hexahydropyrrolo[1',2':4,5] pyrazino[2,3-c]pyridazin-8-yl)oxy)-4,6-dimethylpyrimidin-5-yl)methyl)piperidin-4-yl)-1-oxoisoindolin-2-yl)piperidine-2,6-dione;

(S)-3-(6-(1-((5-(((6aS,8R)-6a-ethyl-2-(3-fluoro-2-hydroxyphenyl)-5,6,6a,7,8,9-hexahydropyrrolo[1',2':4,5] pyrazino[2,3-c]pyridazin-8-yl)oxy) pyrazin-2-yl) methyl)piperidin-4-yl)-1-oxoisoindolin-2-yl) piperidine-2,6-dione;

(S)-3-(6-(1-((5-(((6aS,8R)-6a-ethyl-2-(3-fluoro-2-hydroxyphenyl)-5,6,6a,7,8,9-hexahydropyrrolo[1',2':4,5] pyrazino[2,3-c]pyridazin-8-yl)oxy)-3-methylpyridin-2-yl)methyl)piperidin-4-yl)-1-oxoisoindolin-2-yl) piperidine-2,6-dione;

(S)-3-(6-(1-((2-(((6aR,8R)-6a-ethyl-2-(3-fluoro-2-hydroxyphenyl)-5,6,6a,7,8,9-hexahydropyrrolo[1',2':4,5] pyrazino[2,3-c]pyridazin-8-yl)oxy)-4-methylpyrimidin-5-yl)methyl)piperidin-4-yl)-1-oxoisoindolin-2-yl) piperidine-2,6-dione;

3-(6-(1-((6-(((6aR,8R)-6a-ethyl-2-(3-fluoro-2-hydroxyphenyl)-5,6,6a,7,8,9-hexahydropyrrolo[1',2':4,5] pyrazino[2,3-c]pyridazin-8-yl)oxy)-4-methylpyridin-3-yl)methyl)piperidin-4-yl)-1-oxoisoindolin-2-yl) piperidine-2,6-dione;

or a pharmaceutically acceptable salt thereof.

52. The compound of claim 1, in the form of a pharmaceutically acceptable salt.

53. A pharmaceutical composition comprising a compound according to claim 1, or a pharmaceutically acceptable salt thereof, and a pharmaceutically acceptable excipient.

54. A method of treating cancer in a subject in need thereof comprising administering to the subject a compound of claim 1 or a pharmaceutical composition comprising the compound.

55. The method of claim 54, wherein the cancer is SMARCA4 deleted cancer.

56. The method according to claim 54, wherein the cancer is squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas; benign and malignant melanomas; myeloproliferative diseases; sarcomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas.

57. The method according to claim 54, wherein the cancer is T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

58. The method of claim 56 wherein the lung cancer is SMARCA4 deficient non-small cell lung cancer.

59. A method of degrading a SMARCA protein comprising contacting the SMARCA protein with a compound of claim 1 or a pharmaceutical composition comprising the compound.

60. The method of claim 56 wherein the malignant lymphomas are Burkitt's lymphoma and Non-Hodgkin's lymphoma; and the sarcomas are Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas.

61. The compound of claim 1 that is:

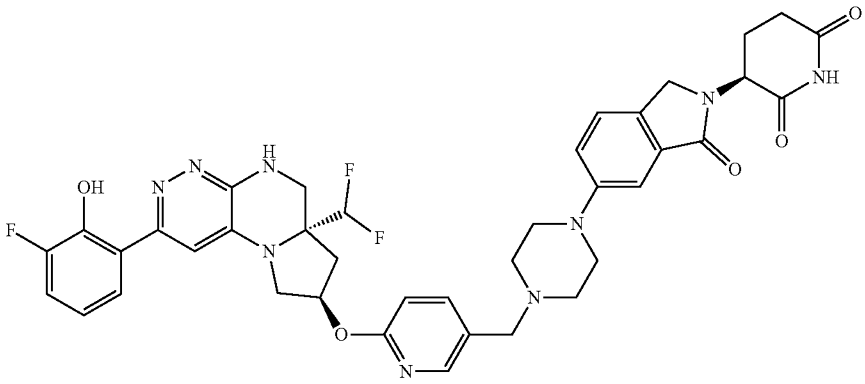 [SMILES: O=C1CC[C@H](N2Cc3ccc(N4CCN(Cc5ccc(O[C@H]6CN7c8cc(-c9cccc(F)c9O)nnc8NC[C@@]7(C(F)F)C6)nc5)CC4)cc3C2=O)C(=O)N1]

or a pharmaceutically acceptable salt thereof.

62. The compound of claim 61 that is:

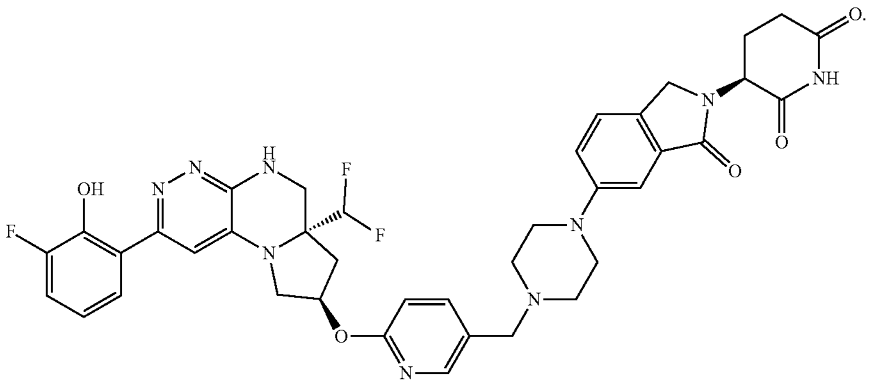 [SMILES: O=C1CC[C@H](N2Cc3ccc(N4CCN(Cc5ccc(O[C@H]6CN7c8cc(-c9cccc(F)c9O)nnc8NC[C@@]7(C(F)F)C6)nc5)CC4)cc3C2=O)C(=O)N1]

63. A pharmaceutical composition comprising a compound according to claim 61, or a pharmaceutically acceptable salt thereof, and a pharmaceutically acceptable excipient.

64. A method of treating cancer in a subject in need thereof comprising administering to the subject a compound of claim 61 or a pharmaceutical composition comprising the compound.

65. The method of claim 64, wherein the cancer is SMARCA4 deleted cancer; or wherein the cancer is squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas; benign and malignant melanomas; myeloproliferative diseases; sarcomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas; or wherein the cancer is T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML; or wherein the lung cancer is SMARCA4 deficient non-small cell lung cancer.

66. The method of claim 65, wherein the malignant lymphomas are Burkitt's lymphoma and Non-Hodgkin's lymphoma; and the sarcomas are Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas.

* * * * *